(12) United States Patent
Haketa et al.

(10) Patent No.: US 9,887,367 B2
(45) Date of Patent: Feb. 6, 2018

(54) HETEROCYCLIC COMPOUND, MATERIAL FOR ORGANIC ELECTROLUMINESCENT ELEMENTS USING SAME, ORGANIC ELECTROLUMINESCENT ELEMENT USING SAME, AND ELECTRONIC DEVICE

(71) Applicant: IDEMITSU KOSAN CO., LTD., Chiyoda-ku (JP)

(72) Inventors: Tasuku Haketa, Chiba (JP); Masahiro Kawamura, Chiba (JP); Kazuki Nishimura, Sodegaura (JP); Yumiko Mizuki, Basel (CH)

(73) Assignee: IDEMITSU KOSAN CO., LTD., Chiyoda-ku (JP)

(*) Notice: Subject to any disclaimer, the term of this patent is extended or adjusted under 35 U.S.C. 154(b) by 160 days.

(21) Appl. No.: 14/767,395

(22) PCT Filed: Mar. 28, 2014

(86) PCT No.: PCT/JP2014/059374
§ 371 (c)(1),
(2) Date: Aug. 12, 2015

(87) PCT Pub. No.: WO2014/157708
PCT Pub. Date: Oct. 2, 2014

(65) Prior Publication Data
US 2016/0005977 A1    Jan. 7, 2016

(30) Foreign Application Priority Data

Mar. 29, 2013  (JP) .................................. 2013-075294

(51) Int. Cl.
*H01L 51/00*    (2006.01)
*C07D 491/147*   (2006.01)
(Continued)

(52) U.S. Cl.
CPC ...... *H01L 51/0071* (2013.01); *C07D 491/147* (2013.01); *C07D 495/14* (2013.01);
(Continued)

(58) Field of Classification Search
None
See application file for complete search history.

(56) References Cited

U.S. PATENT DOCUMENTS

2004/0019097 A1   1/2004  Maeda et al.
2006/0211793 A1   9/2006  Maeda et al.
2014/0353640 A1   12/2014 Haketa et al.

FOREIGN PATENT DOCUMENTS

JP    2003-272865 A    9/2003
JP    2003-300981 A    10/2003
(Continued)

OTHER PUBLICATIONS

Machine English translation of Je et al. (KR 10-2011-0011579). Mar. 16, 2017.*

(Continued)

*Primary Examiner* — J. L. Yang
(74) *Attorney, Agent, or Firm* — Oblon, McClelland, Maier & Neustadt, L.L.P.

(57) ABSTRACT

A heterocyclic compound in which three 5-membered rings are fused to a benzene ring and a saturated or unsaturated ring is further fused to each of the 5-membered rings is a novel material, which is useful as a material for organic electroluminescence devices for the production of organic electroluminescence devices and electronic equipment.

22 Claims, 1 Drawing Sheet

(51) Int. Cl.
  *C07D 495/14* (2006.01)
  *H05B 33/20* (2006.01)
  *H01L 51/50* (2006.01)

(52) U.S. Cl.
  CPC ...... *H01L 51/0052* (2013.01); *H01L 51/0054* (2013.01); *H01L 51/0067* (2013.01); *H01L 51/0072* (2013.01); *H01L 51/0074* (2013.01); *H01L 51/0085* (2013.01); *H05B 33/20* (2013.01); *H01L 51/0087* (2013.01); *H01L 51/5016* (2013.01)

(56) References Cited

FOREIGN PATENT DOCUMENTS

| | | |
|---|---|---|
| JP | 2004-224755 A | 8/2004 |
| JP | 2004-224773 A | 8/2004 |
| JP | 2004-224774 A | 8/2004 |
| JP | 2006-135146 A | 5/2006 |
| KR | 10-2011-0011579 | 2/2011 |
| KR | 10-2014-0000611 A | 1/2014 |
| WO | 2002/032903 A1 | 4/2002 |
| WO | 2009/136595 A1 | 11/2009 |
| WO | 2010/151011 A1 | 12/2010 |
| WO | 2012/141273 A1 | 10/2012 |

OTHER PUBLICATIONS

International Search Report dated Jun. 3, 2014 in PCT/JP2014/059374 filed Mar. 28, 2014.
Korean Office Action dated May 19, 2016 in Patent Application No. 10-2015-7021540 (without English Translation).

\* cited by examiner

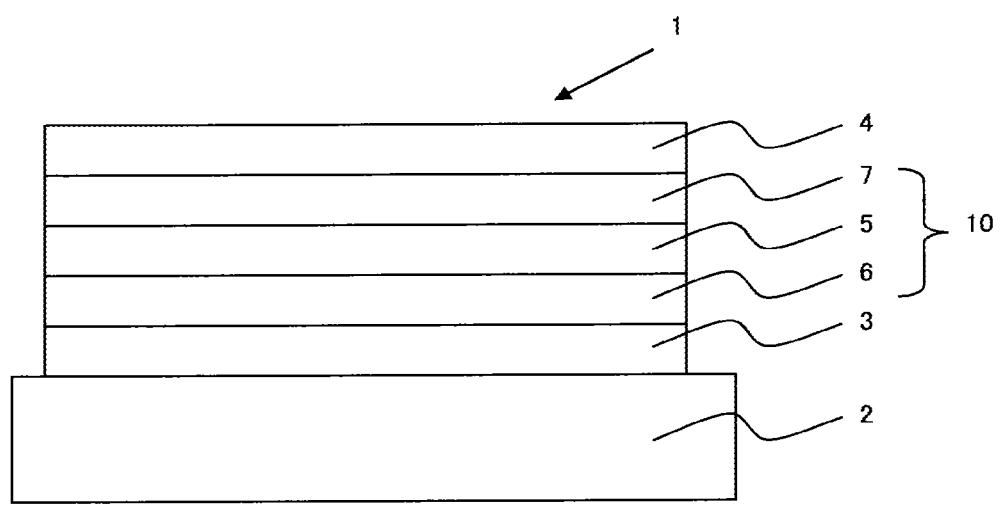

HETEROCYCLIC COMPOUND, MATERIAL FOR ORGANIC ELECTROLUMINESCENT ELEMENTS USING SAME, ORGANIC ELECTROLUMINESCENT ELEMENT USING SAME, AND ELECTRONIC DEVICE

TECHNICAL FIELD

The present invention relates to heterocyclic compounds, materials for organic electroluminescence devices including the compounds, and organic electroluminescence devices and electronic equipment each employing the materials.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode each into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary colors, red, green, and blue, has been made most actively, and the intensive research has been made to improve their properties.

Patent Documents 1 to 4 disclose compounds in which three indene structures or indole structure are fused to a benzene ring as the materials for organic EL devices.

However, in view of further improving the device performance, it has been still demanded in the field of organic EL devices to develop a new material.

PRIOR ART

Patent Documents

Patent Document 1: JP 2006-135146A
Patent Document 2: WO 2009/136595
Patent Document 3: KR 2011-0011579A
Patent Document 4: WO 2012/141273

SUMMARY OF THE INVENTION

Problems to be Solved by the Invention

The present invention has been made to solve the above problems and an object of the invention is to provide a new material useful for organic EL devices.

Means for Solving the Problem

Patent Documents 1 to 4 disclose only a compound in which three indene structures are fused to a benzene ring in the same orientation or a compound in which three indole structures are fused to a benzene ring.

As a result of extensive research, the inventors have found that a compound different from the above compounds, in which three 5-membered rings are fused to the same benzene ring and a saturated or unsaturated ring is further fused to each of the 5-membered rings, is useful as a material for organic EL devices.

In an aspect of the present invention, the flowing items (1) to (4) are provided:

(1) a heterocyclic compound represented by formula (1):

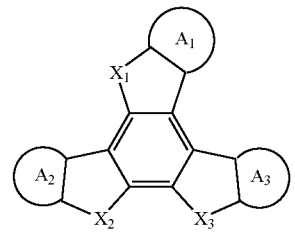

(1)

wherein:
each of $A_1$ to $A_3$ independently represents a saturated or unsaturated ring and each of $A_1$ to $A_3$ may independently have a substituent;
each of $X_1$ to $X_3$ independently represents a linking group represented by any of formulae (2) to (5), provided that one or two of $X_1$ to $X_3$ are represented by formula (2) and the rest is represented by any of formulae (3) to (5):

(2)

(3)

(4)

(5)

wherein each of $Y_1$ to $Y_3$ independently represents a hydrogen atom or a substituent; $Y_2$ and $Y_3$ may be bonded to each other to form a ring structure; each of $Y_1$ to $Y_3$ may be bonded to the substituent of each of $A_1$ to $A_3$ to form a ring structure; and when $X_2$ is represented by formula (2) or (3) and $X_3$ is represented by (2) or (3), $Y_1$ to $Y_3$ in $X_2$ and $X_3$ may be bonded to each other to form a ring structure;

(2) a material for organic electroluminescence devices which comprises the heterocyclic compound of item (1);

(3) an organic electroluminescence device which comprises an organic thin film layer between a cathode and an anode, wherein the organic thin film layer comprises one or more layers and comprises a light emitting layer, and at least one layer of the organic thin film layer comprises the heterocyclic compound of item (1); and (4) an electronic equipment comprising the organic electroluminescence device of item (3).

Effects of the Invention

The present invention provides a novel material useful as a material for organic EL devices and an organic EL device comprising the material.

BRIEF DESCRIPTION OF THE DRAWINGS

The FIGURE is a schematic illustration showing an example of the structure of an organic electroluminescence device (also referred to as "organic EL device") according to an embodiment of the invention.

MODE FOR CARRYING OUT THE INVENTION

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ. "YY" is larger than "XX" and each of "XX" and "YY" represents an integer of 1 or more.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ. "YY" is larger than "XX" and each of "XX" and "YY" represents an integer of 1 or more.

The term of "unsubstituted group ZZ" referred to by "a substituted or unsubstituted group ZZ" used herein means the group ZZ wherein no hydrogen atom is substituted by a substituent.

The definition of "hydrogen atom" used herein includes isotopes different in the neutron numbers, i.e., light hydrogen (protium), heavy hydrogen (deuterium), and tritium.

The number of "ring carbon atoms" referred to herein means the number of the carbon atoms included in the atoms which are members forming the ring itself of a compound in which a series of atoms is bonded to form the ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The optional substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; a mono- or di-substituted amino group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth) acryloyl group; an epoxy group; and an oxetanyl group.

The optional substituent may be further substituted with an optional substituent mentioned above. The optional substituents may be bonded to each other to form a ring.

Heterocyclic Compound

The heterocyclic compound of the invention is represented by formula (1):

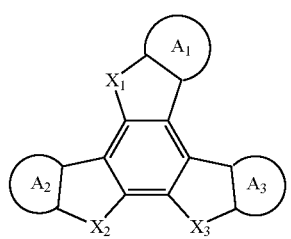

(1)

wherein:

each of $A_1$ to $A_3$ independently represents a saturated or unsaturated ring and each of $A_1$ to $A_3$ may independently have a substituent;

each of $X_1$ to $X_3$ independently represents a linking group represented by any of formulae (2) to (5), provided that one or two of $X_1$ to $X_3$ are represented by formula (2) and the rest is represented by any of formulae (3) to (5):

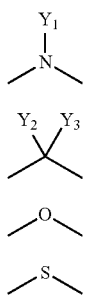

(2)

(3)

(4)

(5)

wherein each of $Y_1$ to $Y_3$ independently represents a hydrogen atom or a substituent; $Y_2$ and $Y_3$ may be bonded to each other to form a ring structure; each of $Y_1$ to $Y_3$ may be bonded to the substituent of each of $A_1$ to $A_3$ to form a ring structure; and when $X_2$ is represented by formula (2) or (3) and $X_3$ is represented by (2) or (3), $Y_1$ to $Y_3$ in $X_2$ and $X_3$ may be bonded to each other to form a ring structure Preferably, each of $A_1$ to $A_3$ independently represents a substituted or unsubstituted, 5-, 6- or 7-membered ring, and more preferably, all of $A_1$ to $A_3$ represent substituted or unsubstituted 6-membered rings.

The heterocyclic compound of the invention is preferably represented by formula (6):

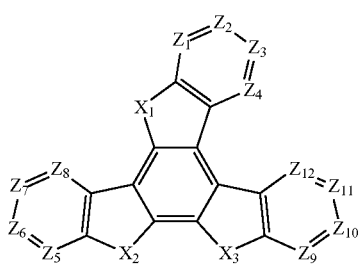

(6)

wherein:

$X_1$ to $X_3$ are as defined above;

each of $Z_1$ to $Z_{12}$ independently represents C(R) or a nitrogen atom;

each R independently represents a hydrogen atom or a substituent; and when two or more of $Z_1$ to $Z_{12}$ have substituents, the substituents may be bonded to each other to form a ring structure.

The optional substituent of $A_1$ to $A_3$, the substituent represented by each of $Y_1$ to $Y_3$ of formulae (2) and (3), and the substituent represented by R of formula (6) are independently selected preferably from the group (A), more preferably from the group (B), still more preferably from the group (C), and particularly preferably from the group (D).

The group (A) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 ring carbon atoms; a disubstituted phosphoryl group having a substituent selected from a substituted or unsubstituted alkyl group having 1 to 50 carbon atoms and a substituted or unsubstituted aryl group having 6 to 50 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl- or aryl-substituted carbonyl group; a carboxyl group; a vinyl group; a (meth)acryloyl group; an epoxy group; and an oxetanyl group.

The group (B) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 ring carbon atoms; a substituted or unsubstituted alkyl group having 1 to 50 carbon atoms; and a substituted or unsubstituted aryl group having 6 to 50 ring carbon atoms.

The group (C) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; and a nitro group.

The group (D) consists of a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a halogen atom; and a cyano group.

Examples of the alkyl group having 1 to 50, preferably 1 to 18, more preferably 1 to 8 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, an octadecyl group, a tetracosanyl group, and a tetracontanyl group. Preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), a dodecyl group (inclusive of isomeric groups), a tridecyl group, a tetradecyl group, and an octadecyl group. More preferred examples include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), and an octyl group (inclusive of isomeric groups).

Examples of the cycloalkyl group having 3 to 50, preferably 3 to 10, more preferably 3 to 8, still more preferably 5 or 6 ring carbon atoms include a cyclopropyl group, a cyclobutyl group, a cyclopentyl group, a cyclohexyl group, a cycloheptyl group, a cyclooctyl group, and an adamantyl group, with a cyclopentyl group and a cyclohexyl group being preferred.

Examples of the aryl group having 6 to 50, preferably 6 to 25, more preferably 6 to 18 ring carbon atoms include a phenyl group, a naphthyl group, a naphthylphenyl group, a biphenylyl group, a terphenylyl group, an acenaphthylenyl group, an anthryl group, a benzanthryl group, an aceanthryl group, a phenanthryl group, a benzophenanthryl group, a phenalenyl group, a fluorenyl group, a 9,9'-spirobifluorenyl group, a benzofluorenyl group, a dibenzofluorenyl group, a picenyl group, a pentaphenyl group, a pentacenyl group, a pyrenyl group, a chrysenyl group, a benzochrysenyl group, a s-indacenyl group, an as-indacenyl group, a fluoranthenyl group, a benzofluoranthenyl group, a tetracenyl group, a triphenylenyl group, a benzotriphenylenyl group, a perylenyl group, a coronyl group, and a dibenzanthryl group. Preferred are a phenyl group, a naphthyl group, a biphenylyl group, a terphenylyl group, a phenanthryl group, a fluorenyl group, a fluoranthenyl group, and a triphenylenyl group.

Examples of the arylene group having 6 to 50, preferably 6 to 25, more preferably 6 to 18 ring carbon atoms include those derived from the above aryl group by removing one hydrogen atom.

The heteroaryl group having 5 to 50, preferably 5 to 24, more preferably 5 to 13 ring atoms include at least one, preferably 1 to 5, more preferably 1 to 3, and still more preferably 1 or 2 hetero atoms, for example, a nitrogen atom, a sulfur atom, an oxygen atom, and a phosphorus atom. Examples thereof include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isooxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a benzacridinyl group, a dibenzacridinyl group, a phenanthrolinyl group, a phenazinyl group, a phenothiazinyl group, a phenoxazinyl group, an azatriphenylenyl group, a diazatriphenylenyl group, a xanthenyl group, an azacarbazolyl group, an azadibenzofuranyl group, an azadibenzothiophenyl group, a benzofuranobenzothiophenyl group, a benzothienobenzothiophenyl group, a dibenzofuranonaphthyl group, a dibenzothienonaphthyl group, and a dinaphthothienothiophenyl group. Preferred are a pyridyl group, a pyrimidinyl group, a pyrazinyl group, a triazinyl group, an indolyl group, a benzofuranyl group, a benzothiophenyl group, a quinolyl group, an isoquinolyl group, a quinazolinyl group, a quinoxalinyl group, a benzimidazolyl group, a dibenzofuranyl group, a dibenzothiophenyl group, a carbazolyl group, a phenanthridinyl group, a phenanthrolinyl group, and a diazatriphenylenyl group.

In addition, examples of the heteroaryl group having 5 to 50 ring atoms preferably include mono-valent groups derived from the following compounds by removing one hydrogen atom:

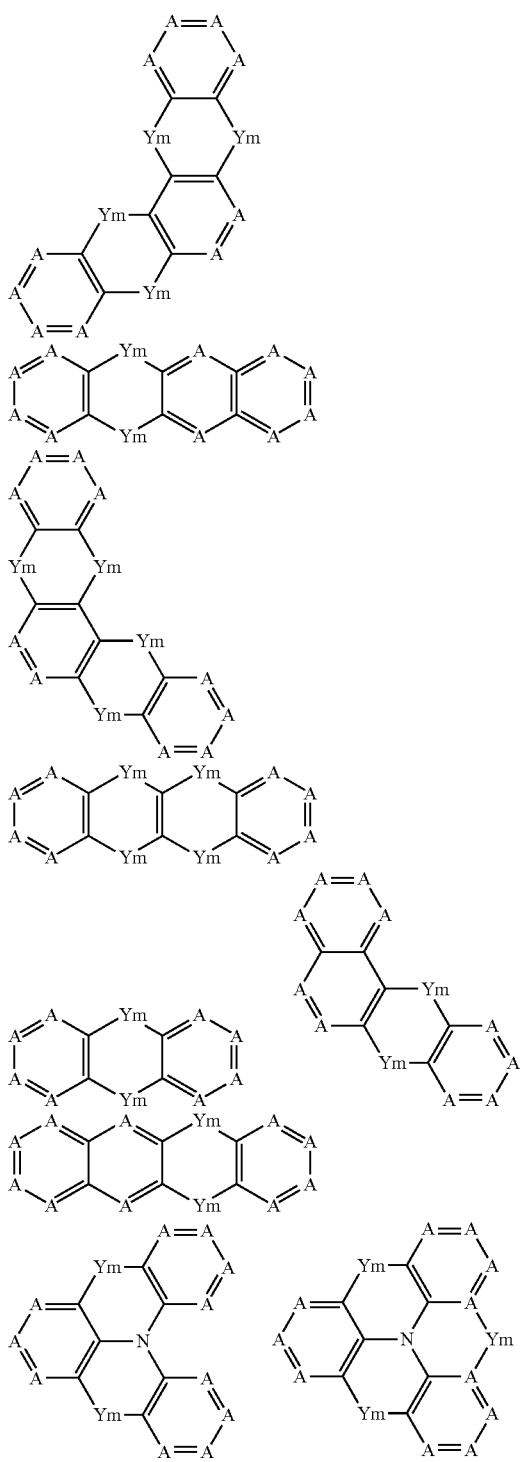

wherein:

each A independently represents $CR^{100}$ or a nitrogen atom;

each $R^{100}$ independently represents a hydrogen atom or a substituent;

each Y independently represents $C(R^{101})(R^{102})$, an oxygen atom, a sulfur atom, or $N(R^{103})$;

each of $R^{101}$, $R^{102}$ and $R^{103}$ independently represents a hydrogen atom or a substituent; and m independently represents 0 or 1, and $Y_0$ represents a single bond.

The substituent referred to above is selected from those mentioned above.

In the aralkyl group having 7 to 51 total carbon atoms, examples of an aryl group having 6 to 50, preferably 6 to 25, more preferably 6 to 18 ring carbon atoms are the same as those mentioned above.

In the mono- or di-substituted amino group, examples of an alkyl group having 1 to 50, preferably 1 to 18, more preferably 1 to 8 carbon atoms and an aryl group having 6 to 50, preferably 6 to 25, more preferably 6 to 18 ring carbon atoms are the same as those mentioned above.

In the alkoxy group having 1 to 50 carbon atoms, examples of an alkyl group having 1 to 50, preferably 1 to 18, more preferably 1 to 8 carbon atoms are the same as those mentioned above.

In the aryloxy group having 6 to 50 ring carbon atoms, examples of an aryl group having 6 to 50, preferably 6 to 25, more preferably 6 to 18 ring carbon atoms are the same as those mentioned above.

In the mono-, di- or tri-substituted silyl group, examples of an alkyl group having 1 to 50, preferably 1 to 18, more preferably 1 to 8 carbon atoms and an aryl group having 6 to 50, preferably 6 to 25, more preferably 6 to 18 ring carbon atoms are the same as those mentioned above.

Examples of the haloalkyl group having 1 to 50, preferably 1 to 18, more preferably 1 to 8 carbon atoms include those obtained by replacing one or more hydrogen atoms of the alkyl groups mentioned above with a halogen atom, such as a fluorine atom, a chlorine atom, a bromine atom and an iodine atom.

In the substituted sulfonyl group, examples of an alkyl group having 1 to 50, preferably 1 to 18, more preferably 1 to 8 carbon atoms and an aryl group having 6 to 50, preferably 6 to 25, more preferably 6 to 18 ring carbon atoms are the same as those mentioned above.

In the di-substituted phosphoryl group, examples of an alkyl group having 1 to 50, preferably 1 to 18, more preferably 1 to 8 carbon atoms and an aryl group having 6 to 50, preferably 6 to 25, more preferably 6 to 18 ring carbon atoms are the same as those mentioned above.

The disubstituted phosphoryl group is preferably represented by formula (P):

$$-P(=O)Ar_{p1}Ar_{p2} \quad (P)$$

wherein each of $Ar_{p1}$ and $Ar_{p2}$ independently represents a substituted or unsubstituted aryl group having 6 to 50 ring carbon atoms.

Examples of the aryl group having 6 to 50 ring carbon atoms represented by $Ar_{p1}$ and $Ar_{p2}$ of formula (P) are the same as those mentioned above with respect to formula (1).

The saturated ring represented by each of $A_1$ to $A_3$ of formula (1) is preferably an aliphatic hydrocarbon ring having 5 to 50, preferably 3 to 6, and more preferably 5 or 6 ring carbon atom.

The unsaturated ring represented by each of $A_1$ to $A_3$ of formula (1) is preferably an aromatic hydrocarbon ring having 6 to 50, preferably 6 to 24, and more preferably 6 to 18 ring carbon atoms or an aromatic heterocyclic ring having 5 to 50, preferably 5 to 24, and more preferably 5 to 13 ring atoms.

The ring structure formed from each of $Y_1$ to $Y_3$ of formula (1) by bonding to the substituent of $A_1$ to $A_3$, the ring structure formed from $Y_1$ to $Y_3$ by bonding to each other, and the ring structure formed from the substituents of two or more of $Z_1$ to $Z_{12}$ by bonding to each other are selected from the saturated or unsaturated ring mentioned above with respect to $A_1$ to $A_3$.

Examples of the aliphatic hydrocarbon ring having 5 to 50 ring carbon atoms include a cyclopropane ring, a cyclobutane ring, a cyclopentane ring, a cyclohexane ring, a cycloheptane ring, a cyclooctane ring, and an adamantane ring, with a cyclopentane ring and a cyclohexane ring being preferred.

Examples of the aromatic hydrocarbon ring having 6 to 50 ring carbon atoms include a benzene ring, a naphthalene ring, an anthracene ring, a benzanthracene ring, a phenanthrene ring, a benzophenanthrene ring, a fluorene ring, a benzofluorene ring, a dibenzofluorene ring, a picene ring, a tetracene ring, a pentacene ring, a pyrene ring, a chrysene ring, a benzochrysene ring, a s-indacene ring, an as-indacene ring, a fluoranthene ring, a benzofluoranthene ring, a triphenylene ring, a benzotriphenylene ring, a perylene ring, a coronene ring, and a dibenzanthracene ring. Preferred are a benzene ring, a naphthalene ring, a phenanthrene ring, a benzophenanthrene ring, a fluorene ring, a benzofluorene ring, a fluoranthene ring, a benzofluoranthene ring, and a triphenylene ring.

Examples of the aromatic heterocyclic ring having 5 to 50 ring atoms include a pyrrole ring, a pyrazole ring, an isoindole ring, a benzofuran ring, a benzothiophene ring, an isobenzofuran ring, a dibenzothiophene ring, an isoquinoline ring, a cinnoline ring, a quinoxaline ring, a phenanthridine ring, a phenanthroline ring, a pyridine ring, a pyrazine ring, a pyrimidine ring, a pyridazine ring, a triazine ring, an imidazopyridine ring, an indole ring, an indazole ring, a quinoline ring, a quinazoline ring, an acridine ring, a pyrrolidine ring, a dioxane ring, a piperidine ring, a morpholine ring, a piperazine ring, a carbazole ring, a furan ring, a thiophene ring, an oxazole ring, an oxadiazole ring, a benzoxazole ring, a thiazole ring, a thiadiazole ring, a benzothiazole ring, a triazole ring, an imidazole ring, a benzimidazole ring, a pyran ring, a dibenzofuran ring, a benzo[c]dibenzofuran ring, a purine ring, a benzacridine ring, and a dibenzacridine ring. Preferred are a benzofuran ring, a benzothiophene ring, a dibenzothiophene ring, an isoquinoline ring, a quinoxaline ring, a phenanthridine ring, a phenanthroline ring, a pyridine ring, a pyrimidine ring, a triazine ring, an indole ring, a quinoline ring, a quinazoline ring, a carbazole ring, a benzimidazole ring, and a dibenzofuran ring. More preferred are a dibenzothiophene ring, a pyridine ring, a pyrimidine ring, a triazine ring, a quinazoline ring, a carbazole ring, a benzimidazole ring, and a dibenzofuran ring.

In the present invention, a heterocyclic compound wherein the substituent is a ring-containing group is preferred, a heterocyclic compound wherein the substituent represented by $Y_1$ to $Y_3$ of formulae (2) and (3) is a ring-containing group is more preferred, and a heterocyclic compound wherein at least one of $X_1$ to $X_3$ is represented by formula (2) and $Y_1$ of formula (2) is a ring-containing group is more preferred.

A material for organic EL devices which comprises a heterocyclic compound having the ring-containing group exhibits an effect of, for example, making an organic thin film which comprises the material more uniform and more densified.

Examples of the ring-containing group include those having a group selected from a substituted or unsubstituted cycloalkyl group having 5 to 50, preferably 3 to 6, and more preferably 5 or 6 ring carbon atoms; a substituted or unsubstituted aryl group having 6 to 50, preferably 6 to 24, and more preferably 6 to 18 ring carbon atoms; an aralkyl group having 7 to 51 carbon atoms in total, which includes a substituted or unsubstituted aryl group having 6 to 50, preferably 6 to 24, and more preferably 6 to 18 ring carbon atoms; a mono- or di-arylamino group having a substituted or unsubstituted aryl group having 6 to 50, preferably 6 to 24, and more preferably 6 to 18 ring carbon atoms; an aryloxy group having a substituted or unsubstituted aryl group having 6 to 50, preferably 6 to 24, and more preferably 6 to 18 ring carbon atoms; a mono-, di- or tri-arylsilyl group having a substituted or unsubstituted aryl group having 6 to 50, preferably 6 to 24, and more preferably 6 to 18 ring carbon atoms; a substituted or unsubstituted heteroaryl group having 5 to 50, preferably 5 to 24, and more preferably 5 to 13 ring atoms; a sulfonyl group substituted with a substituted or unsubstituted aryl group having 6 to 50, preferably 6 to 24, and more preferably 6 to 18 ring carbon atoms; and a phosphonyl group substituted with a substituted or unsubstituted aryl group having 6 to 50, preferably 6 to 24, and more preferably 6 to 18 ring carbon atoms. Preferred are those including a substituted or unsubstituted aryl group having 6 to 50 ring carbon atoms, a substituted or unsubstituted heteroaryl group having 5 to 50 ring atoms, or a mono- or di-arylamino group having a substituted or unsubstituted aryl group having 6 to 50 ring carbon atoms. The details of the above groups are the same as those mentioned above.

The ring-containing group may be a group having a ring-containing group thereon. Examples of such a group are those as mentioned above.

The ring-containing group is preferably represented by formula (7), more preferably represented by formula (7a), and still more preferably represented by formula (7b).

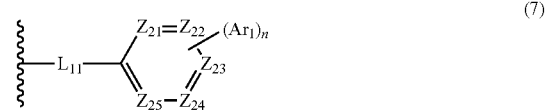

(7)

In formula (7), each of $Z_{21}$ to $Z_{25}$ independently represents $C(R_1)$ or a nitrogen atom;

each $R_1$ independently represents a hydrogen atom, a substituent, or a bond to $Ar_1$;

each $Ar_1$ independently represents a hydrogen atom or a substituent, preferably a substituted or unsubstituted aryl group having 6 to 50 ring carbon atoms or a substituted or unsubstituted heteroaryl group having 5 to 50 ring atoms;

$L_{11}$ represents a single bond, a substituted or unsubstituted divalent aromatic hydrocarbon group (arylene group) having 6 to 60 ring carbon atoms, or a substituted or unsubstituted divalent heterocyclic group (heteroarylene group) having 3 to 60 ring atoms; and n represents an integer of 0 to 5.

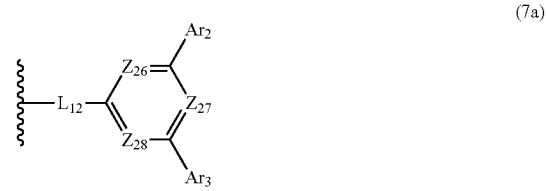

(7a)

In formula (7a), each of $Z_{26}$ to $Z_{28}$ independently represents $C(R_1)$ or a nitrogen atom;

each $R_1$ independently represents a hydrogen atom or a substituent;

each of $Ar_2$ and $Ar_3$ independently represents a hydrogen atom or a substituent, preferably a substituted or unsubstituted aryl group having 6 to 50 ring carbon atoms or a substituted or unsubstituted heteroaryl group having 5 to 50 ring atoms; and $L_{12}$ represents a single bond, a substituted or unsubstituted divalent aromatic hydrocarbon group (arylene group) having 6 to 60 ring carbon atoms, or a substituted or unsubstituted divalent heterocyclic group (heteroarylene group) having 3 to 60 ring atoms.

At least one of $Z_{26}$ to $Z_{28}$ is preferably a nitrogen atom.

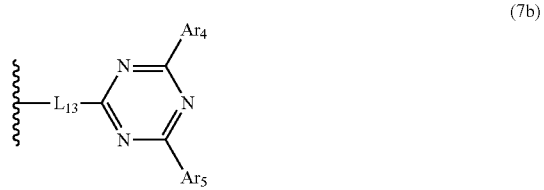

(7b)

In formula (7b), each of $Ar_4$ and $Ar_5$ independently represents a hydrogen atom or a substituent, preferably a substituted or unsubstituted aryl group having 6 to 50 ring carbon atoms or a substituted or unsubstituted heteroaryl group having 5 to 50 ring atoms, and more preferably a substituted or unsubstituted aryl group having 6 to 18 ring carbon atoms or a substituted or unsubstituted heteroaryl group having 5 to 13 ring atoms; and $L_{13}$ represents a single bond, a substituted or unsubstituted divalent aromatic hydrocarbon group (arylene group) having 6 to 60 ring carbon atoms, or a substituted or unsubstituted divalent heterocyclic group (heteroarylene group) having 3 to 60 ring atoms.

In the present invention, a heterocyclic compound wherein one of $X_1$ to $X_3$ of formula (1) and (6) is represented by formula (2), and $Y_1$ of formula (2) is represented by formula (7), (7a) or (7b) is particularly preferred.

A group represented by formula (8) is also preferred as the ring-containing group:

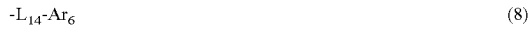

(8)

wherein:

$Ar_6$ represents a substituted or unsubstituted aryl group having 6 to 50 ring carbon atoms or a substituted or unsubstituted heteroaryl group having 5 to 50 ring atoms; and $L_{14}$ represents a single bond, a substituted or unsubstituted divalent aromatic hydrocarbon group (arylene group) having 6 to 60 ring carbon atoms, or a substituted or unsubstituted divalent heterocyclic group (heteroarylene group) having 3 to 60 ring atoms.

Examples of the aryl group having 6 to 50 ring carbon atoms represented by $Ar_6$ of formula (8) are the same as those mentioned above with respect to formula (1). Examples of the heteroaryl group having 5 to 50 ring atoms represented by $Ar_6$ of formula (8) are the same as those mentioned above with respect to formula (1).

Examples of $L_{14}$ of formula (8) are the same as those mentioned above with respect to $L_{11}$ of formula (7).

$Ar_6$ of formula (8) is particularly preferably a phenyl group, a naphthyl group, a biphenylyl group, a terphenylyl group, a phenanthryl group, a benzophenanthryl group, fluorenyl group, a benzofluorenyl group, a chrysenyl group, a benzochrysenyl group, a fluoranthenyl group, a triphenylenyl group, a pyridyl group, a pyrimidinyl group, a pyrazinyl group, a triazinyl group, an indolyl group, a benzofuranyl group, a benzothiophenyl group, a quinolyl group, an isoquinolyl group, a quinazolinyl group, a quinoxalinyl group, a benzimidazolyl group, a dibenzofuranyl group, a dibenzothiophenyl group, a carbazolyl group, a phenanthridinyl group, a phenanthrolinyl group, or a diazatriphenylenyl group.

$L_{14}$ of formula (8) is particularly preferably a single bonde, a phenylene group, a naphthylene group, a biphenylene group, a terphenylene group, a phenanthrylene group, or a fluorenylene group.

Material for Organic Electroluminescence Devices

The material for organic electroluminescence devices comprises the heterocyclic compound mentioned above. The content of the heterocyclic compound in the material for organic electroluminescence devices is, but not particularly limited, 1% by mass or more, preferably 10% by mass or more, more preferably 50% by mass or more, still more preferably 80% by mass or more, and particularly preferably 90% by mass or more.

The material for organic EL devices of the invention is useful as a material for producing an organic EL device and may be used, for example, in a light emitting layer of a fluorescent emitting unit as a host material or a dopant material and in a light emitting layer of a phosphorescent emitting unit as a host material. In addition, in either a fluorescent emitting unit or a phosphorescent emitting unit, the material for organic EL devices of the invention is also useful as a material for an anode-side organic thin film layer which is formed between an anode and a light emitting layer and a material for a cathode-side organic thin film layer which is formed between a cathode and a light emitting layer, i.e., also useful as a material for a hole transporting layer, a hole injecting layer, an electron transporting layer, an electron injecting layer, a hole blocking layer, and an electron blocking layer.

The "emission unit" referred to herein is the smallest unit for emitting light by the recombination of injected holes and injected electrons, which comprises one or more organic layers wherein at least one layer is a light emitting layer.

Examples of the heterocyclic compound represented by formula (1) or (6) are shown below, although not limited thereto.

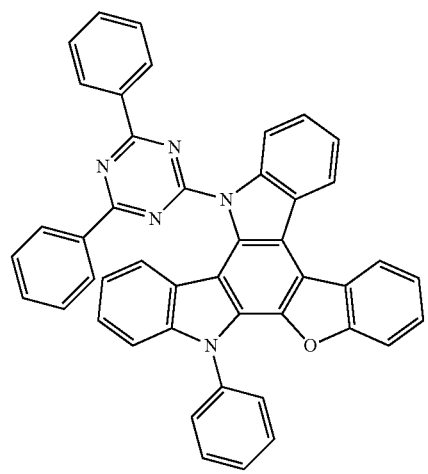

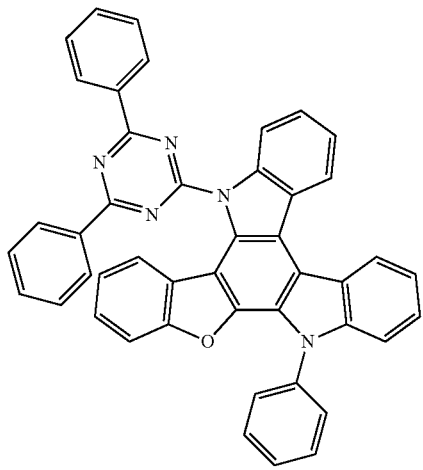
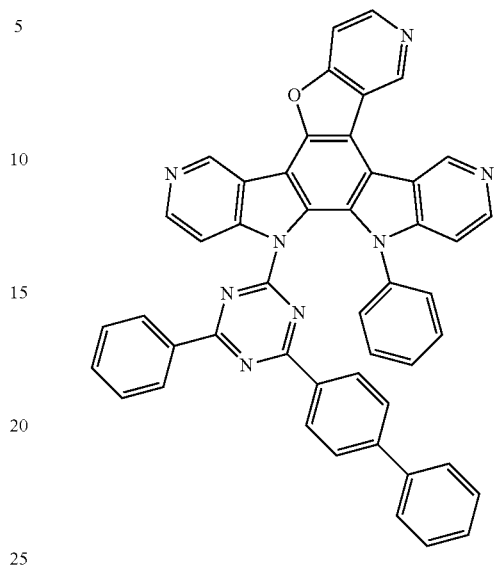
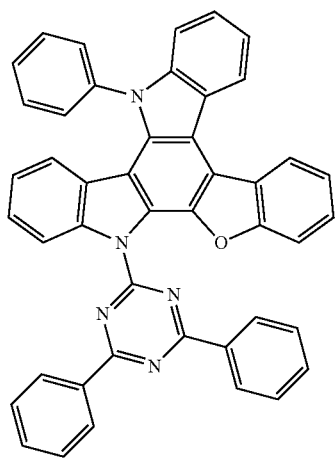
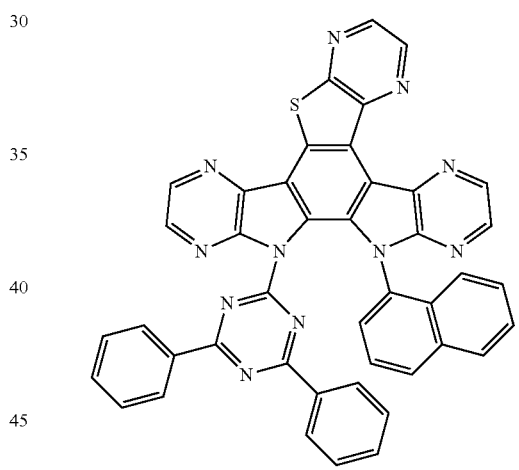
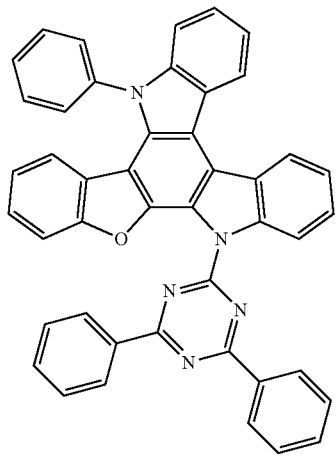
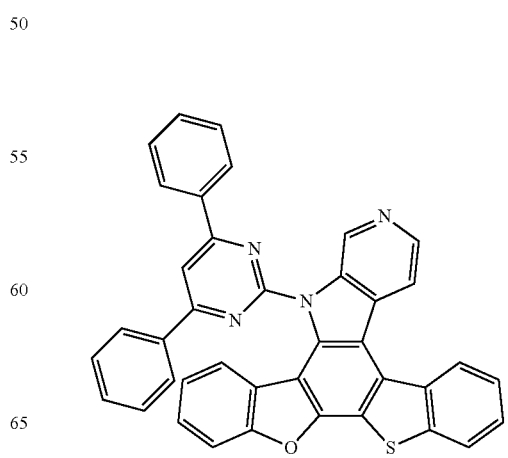

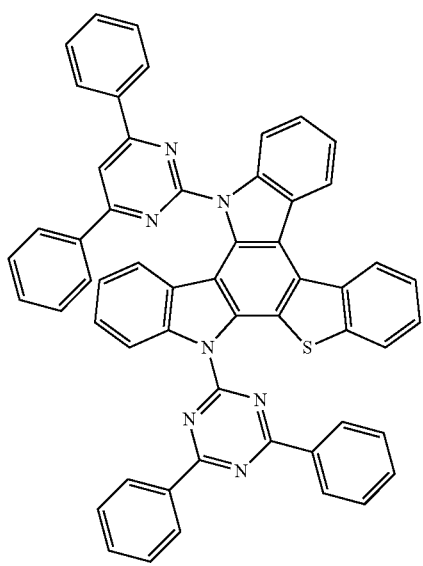
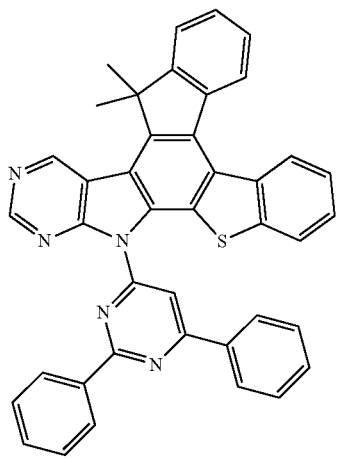
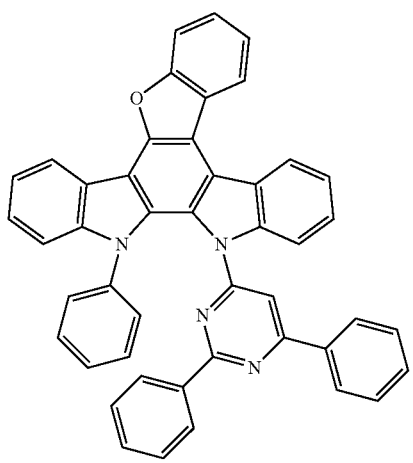
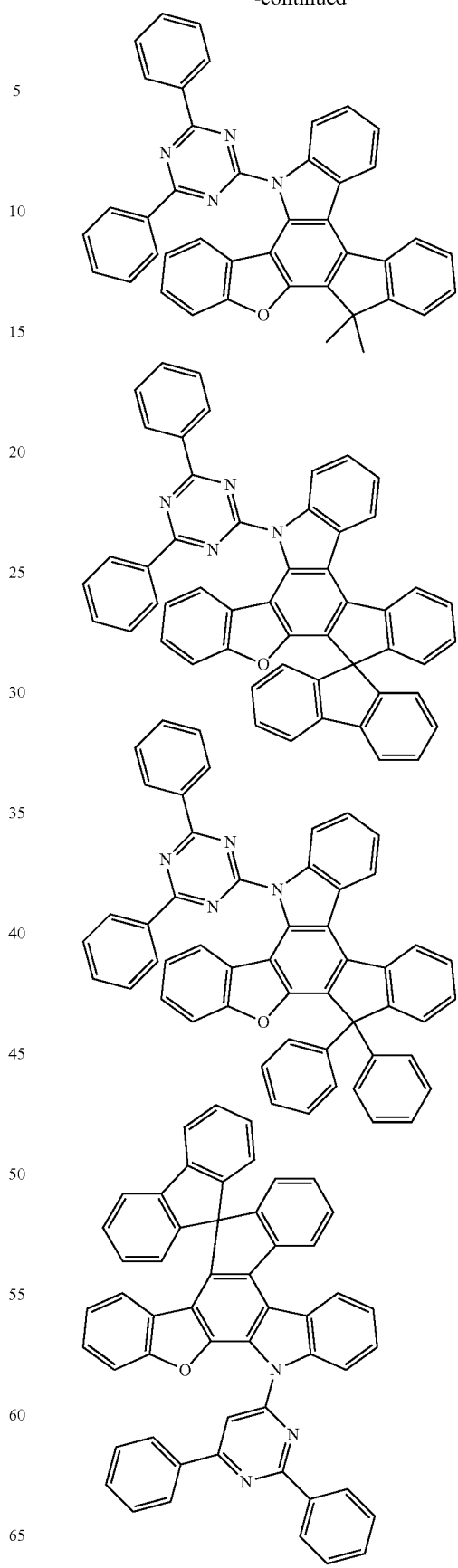

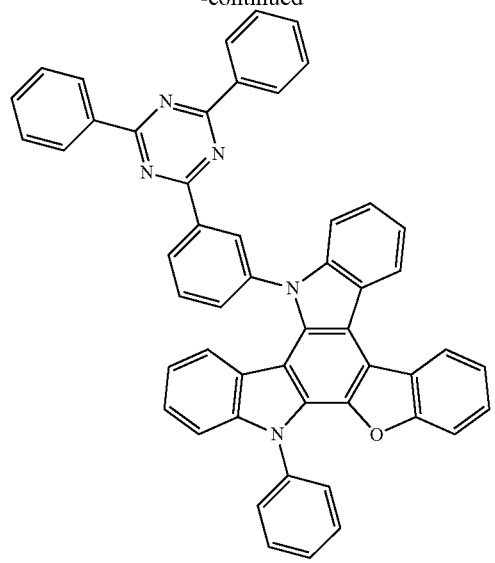
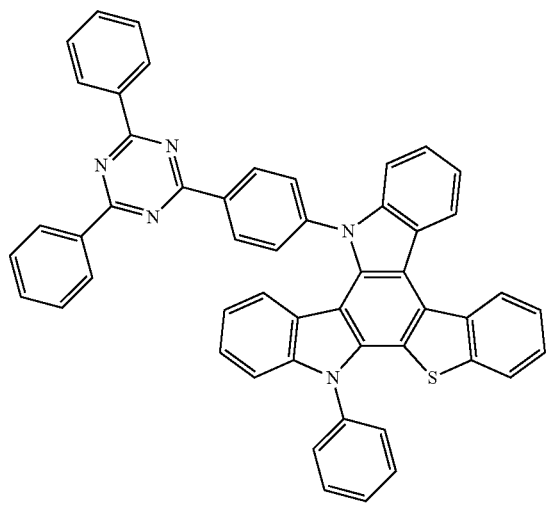
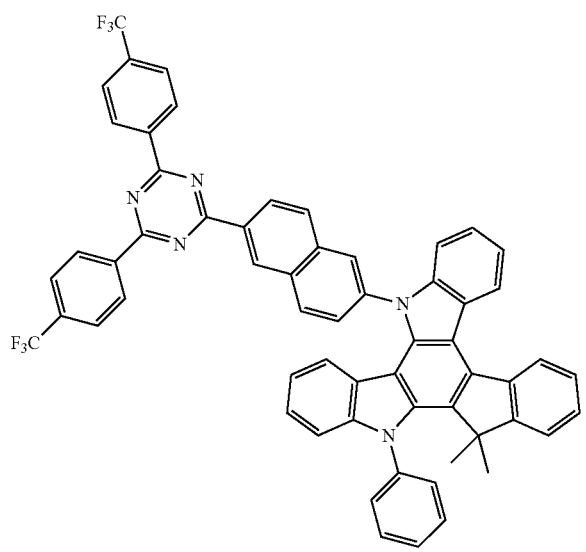
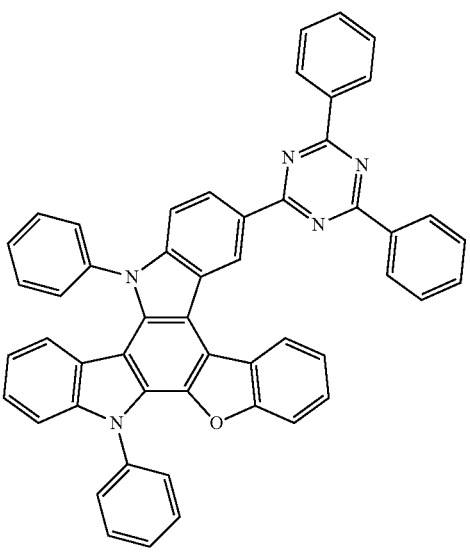
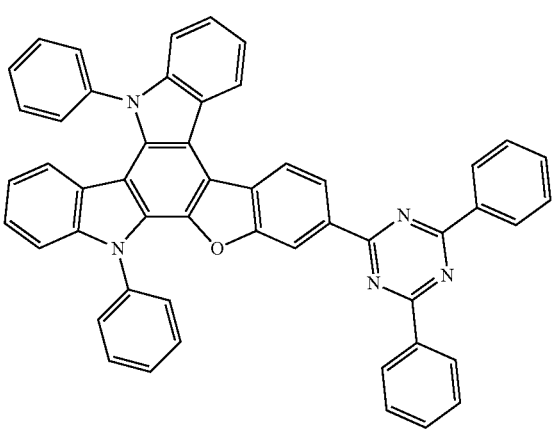
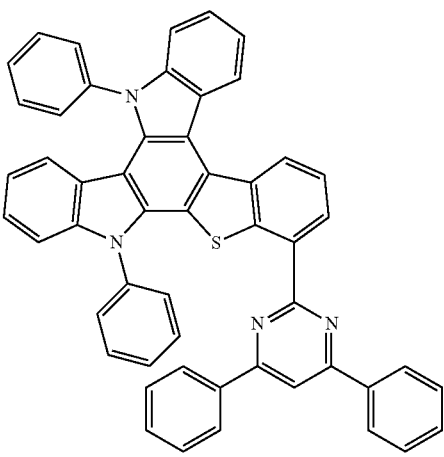

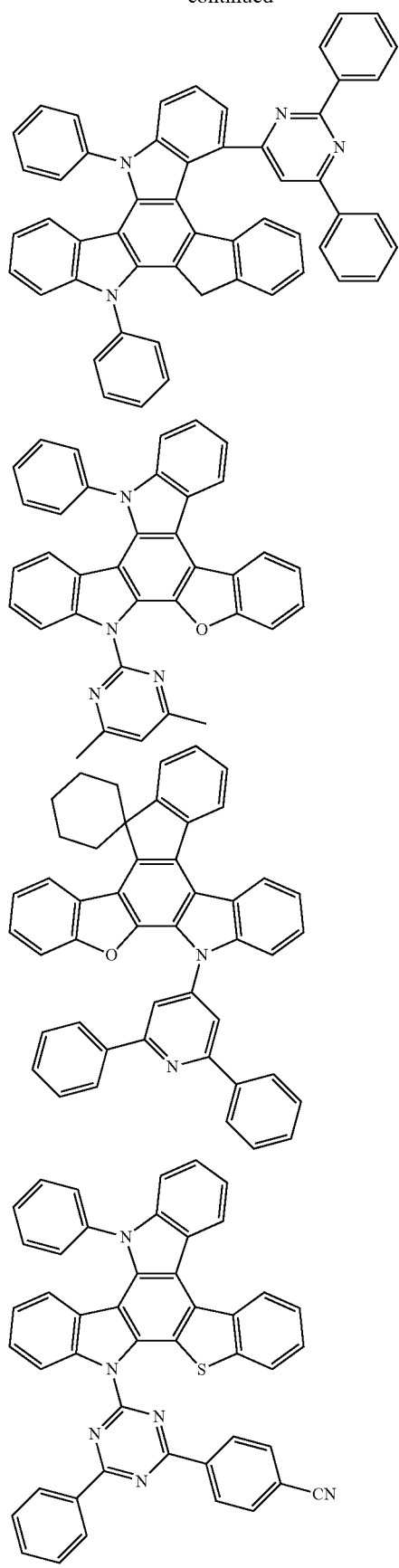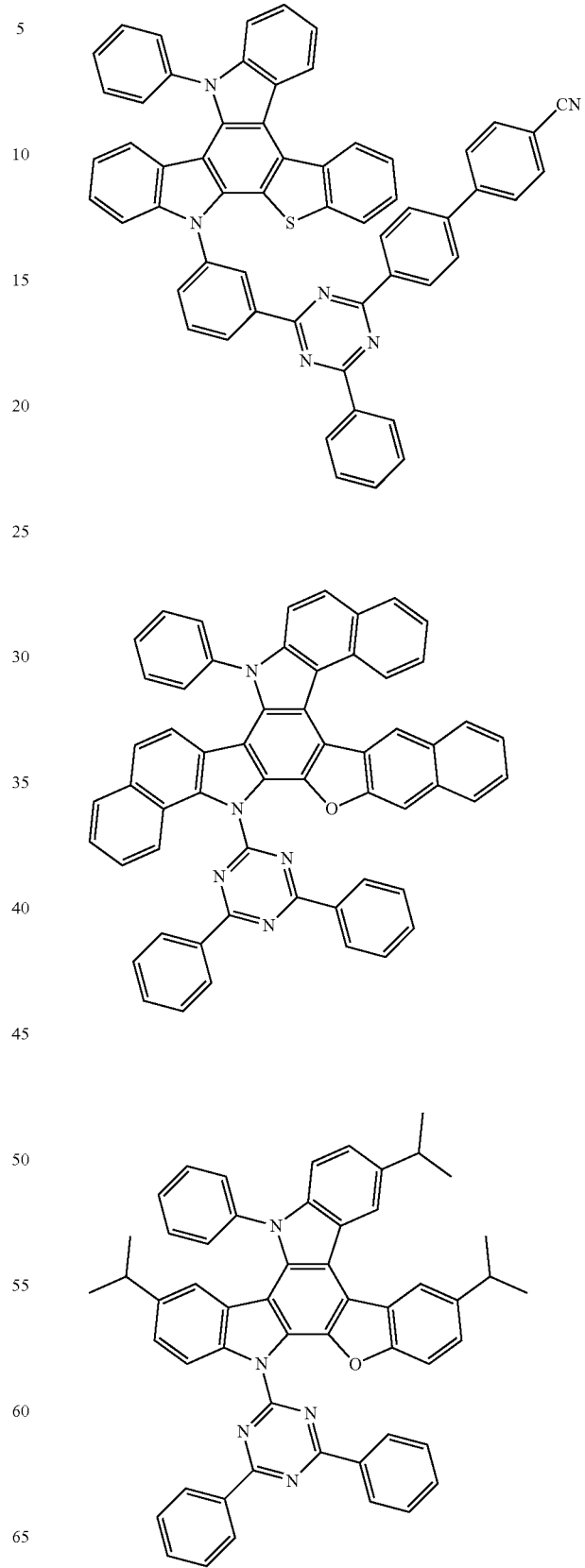

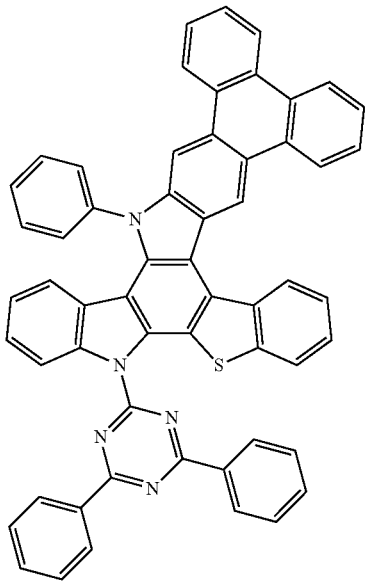
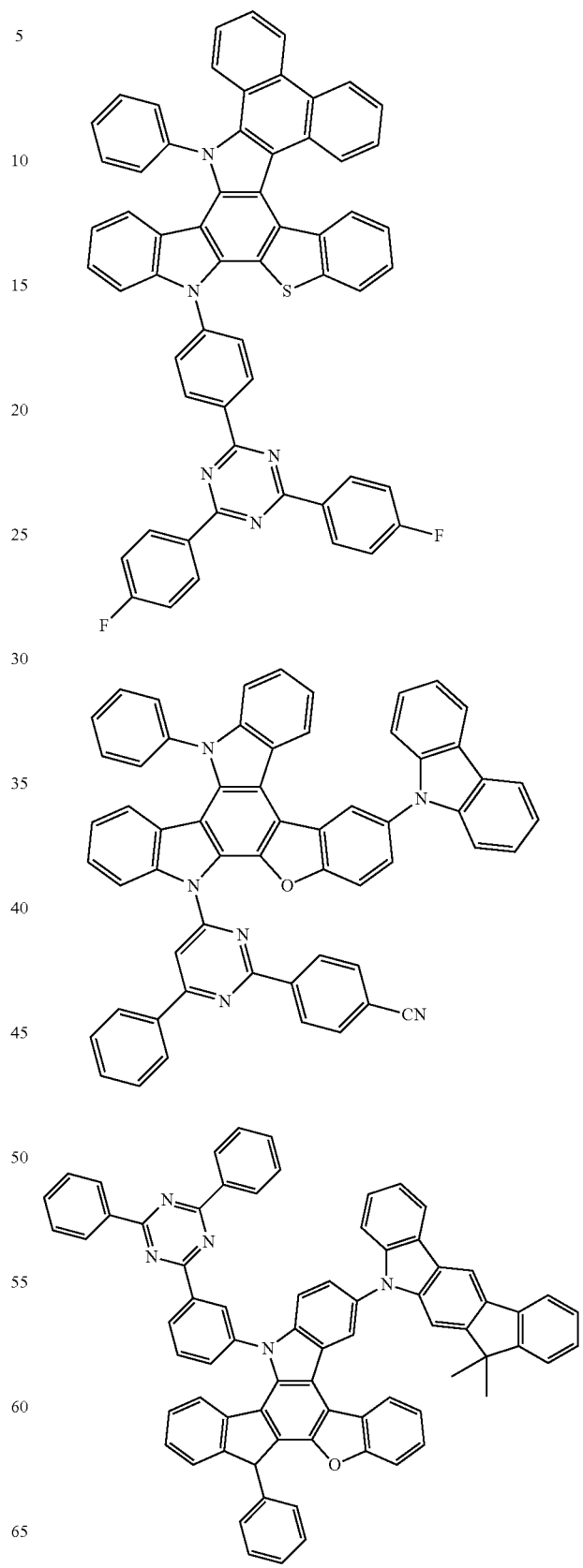

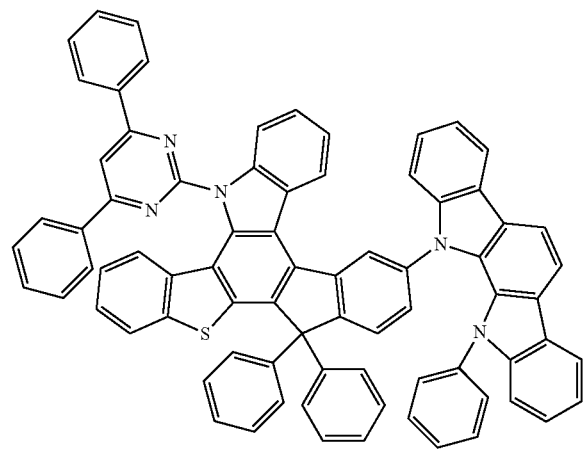
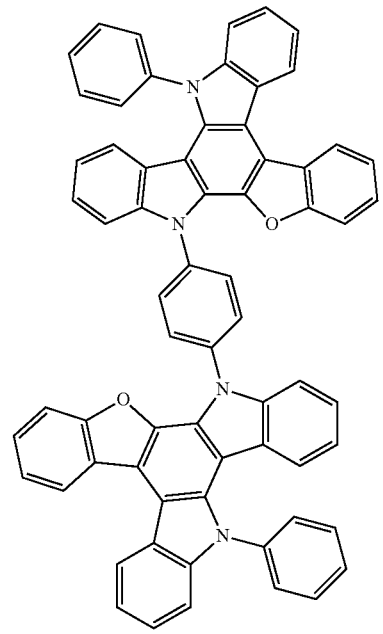
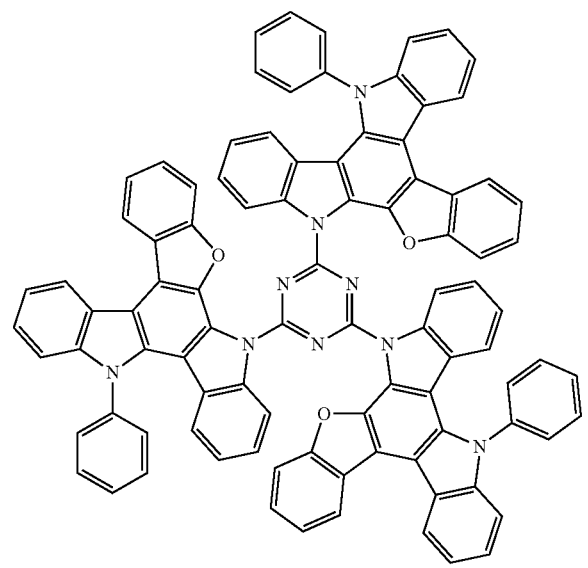
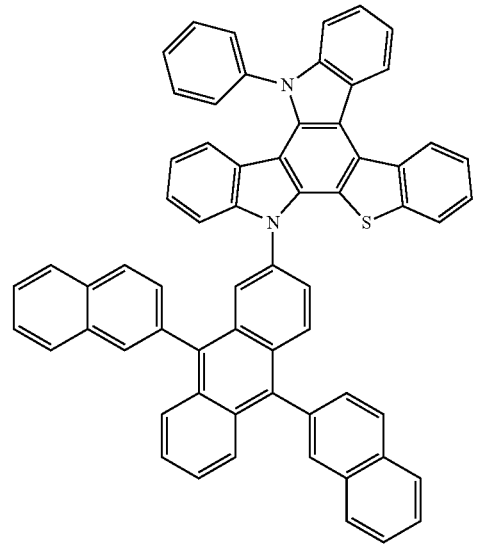
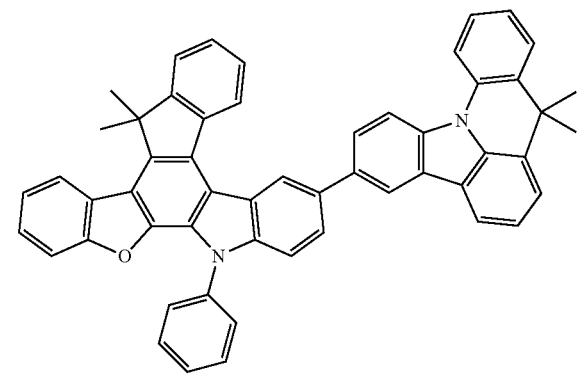
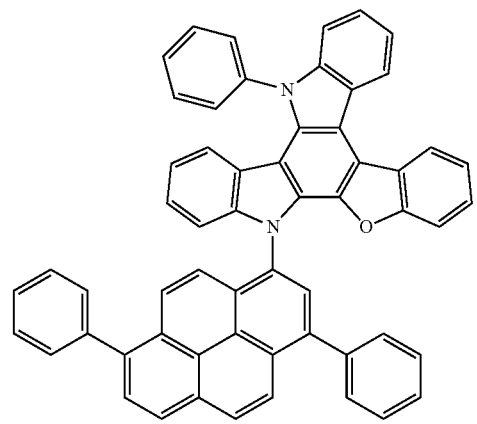

27
-continued
28
-continued
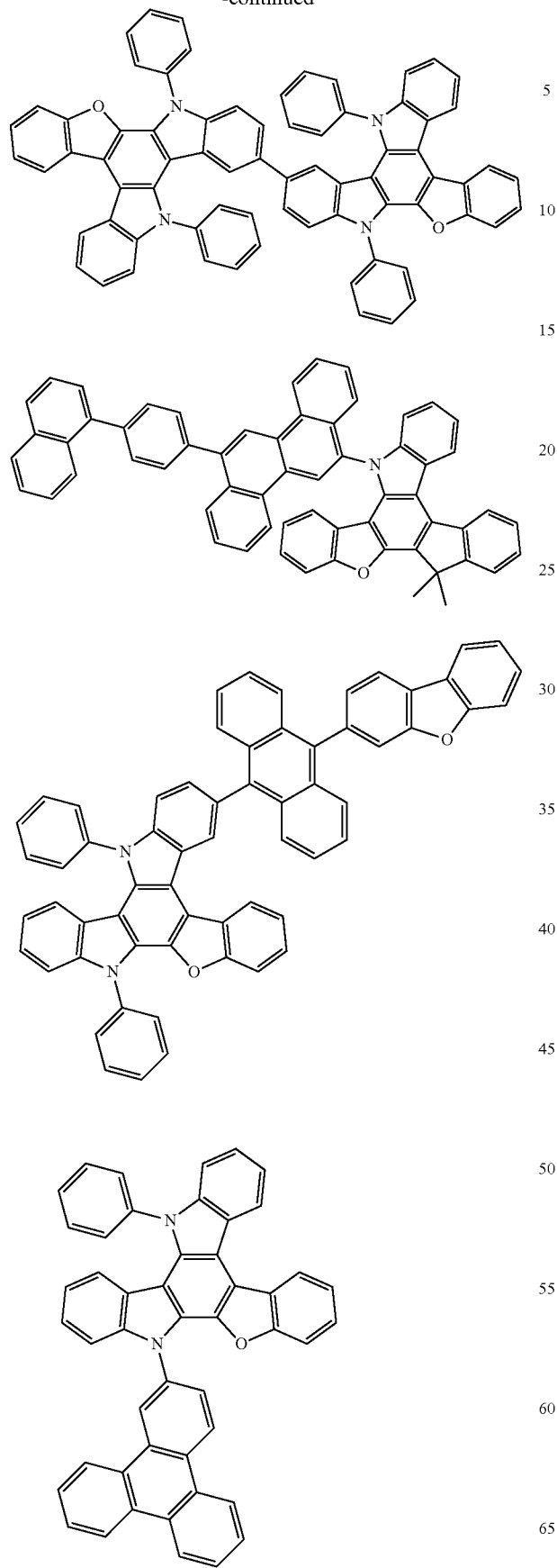
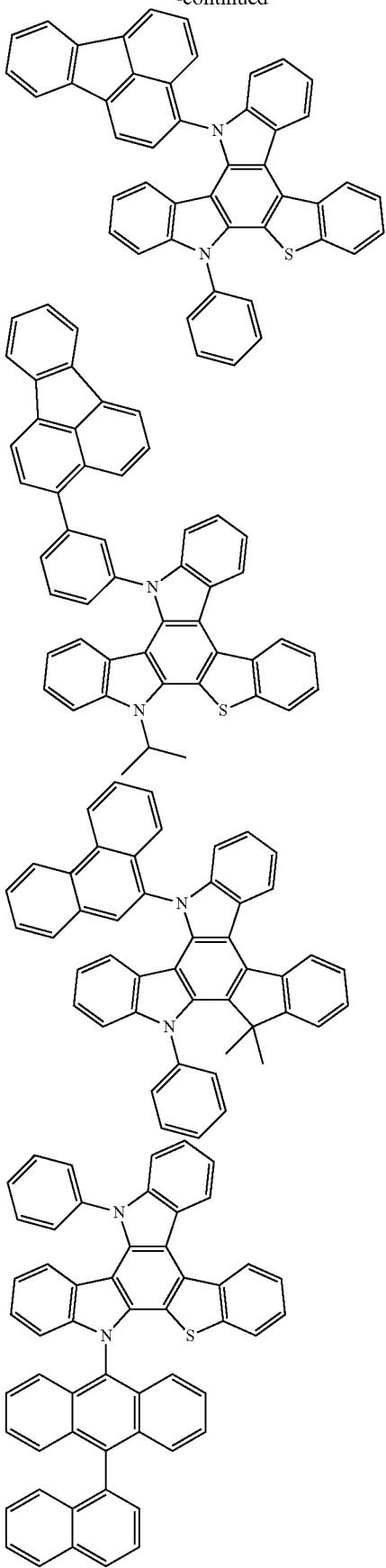

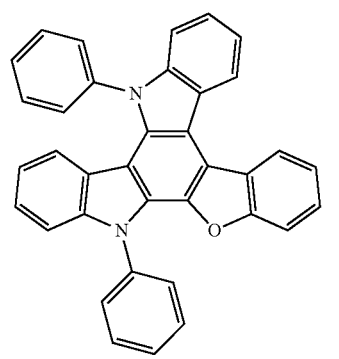
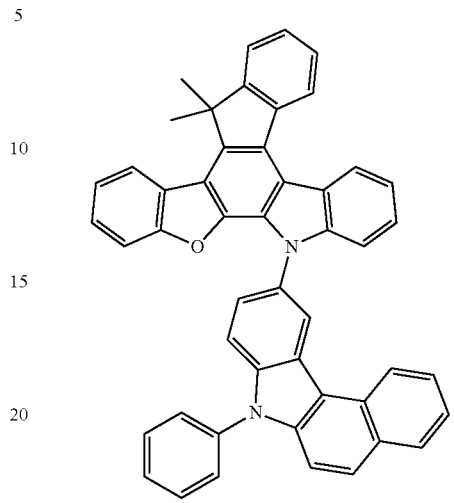
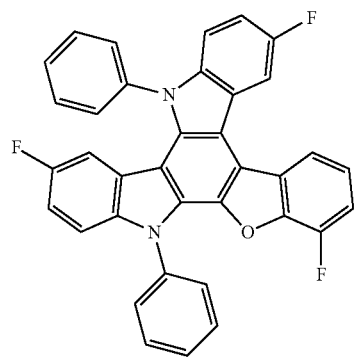
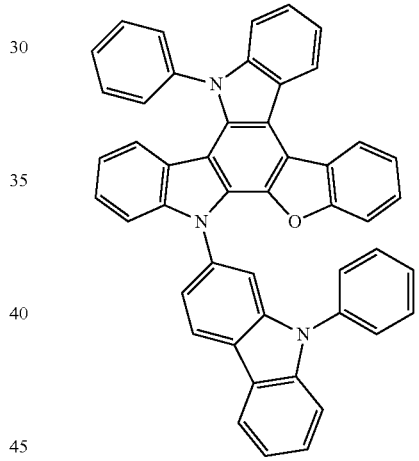
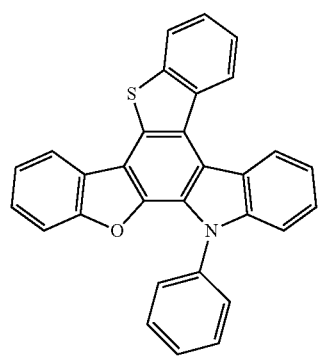
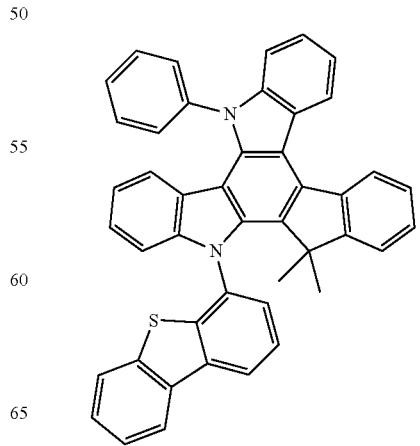
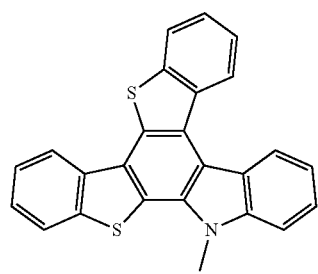

31
-continued
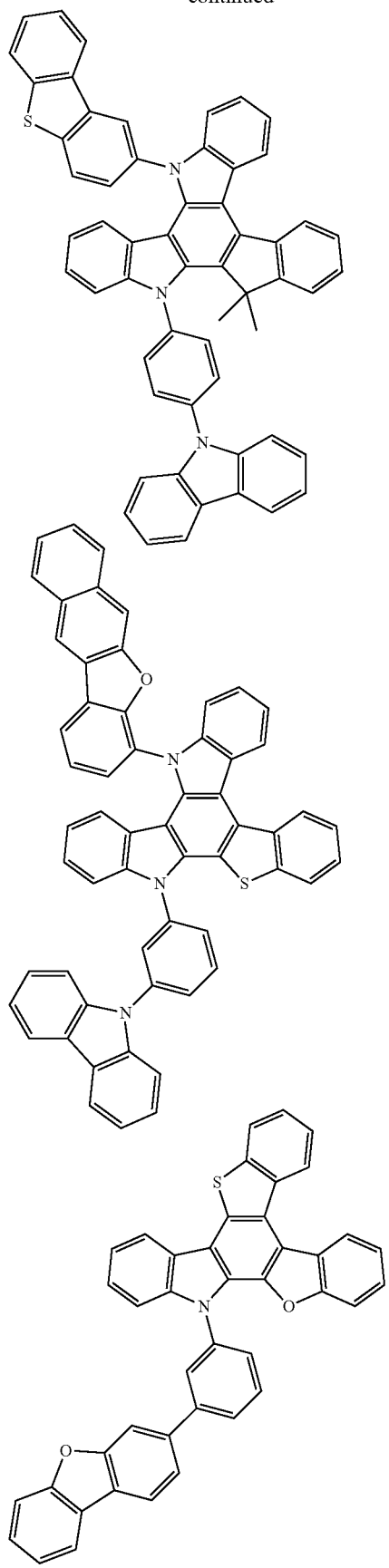
32
-continued
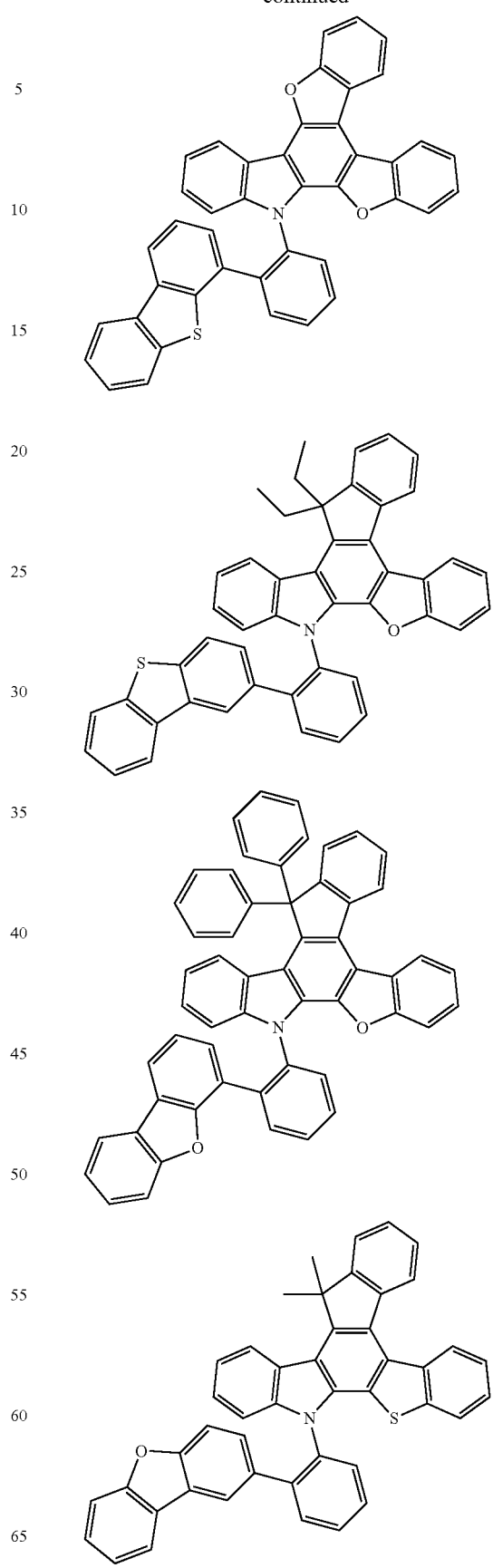

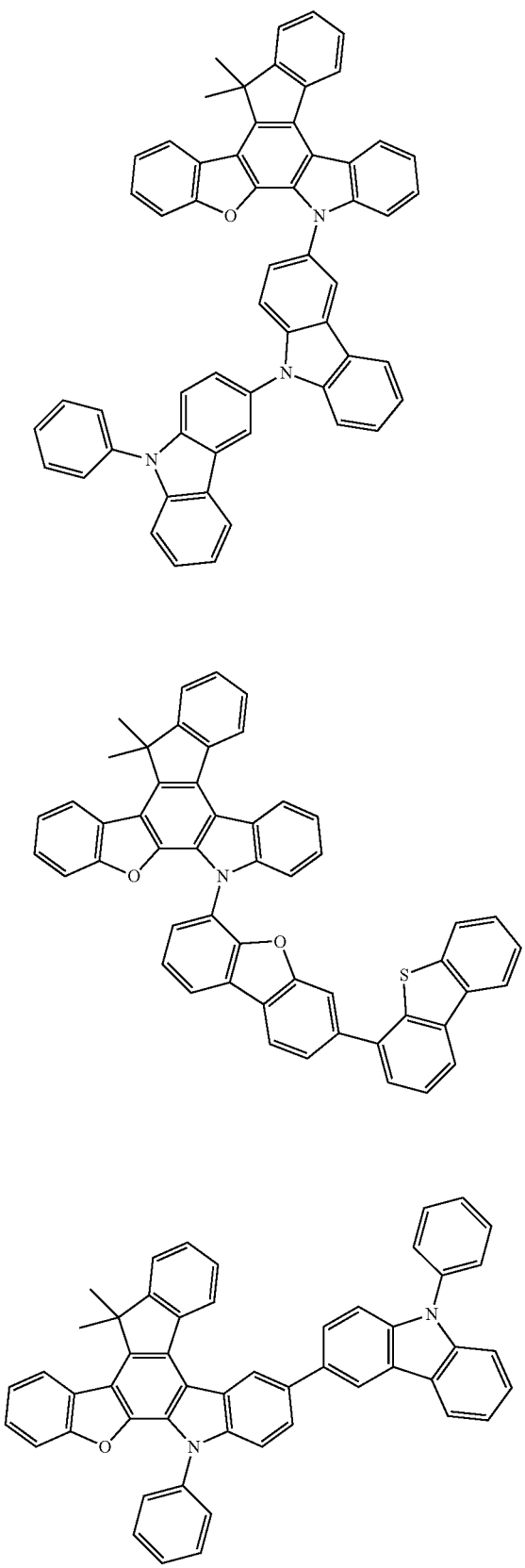
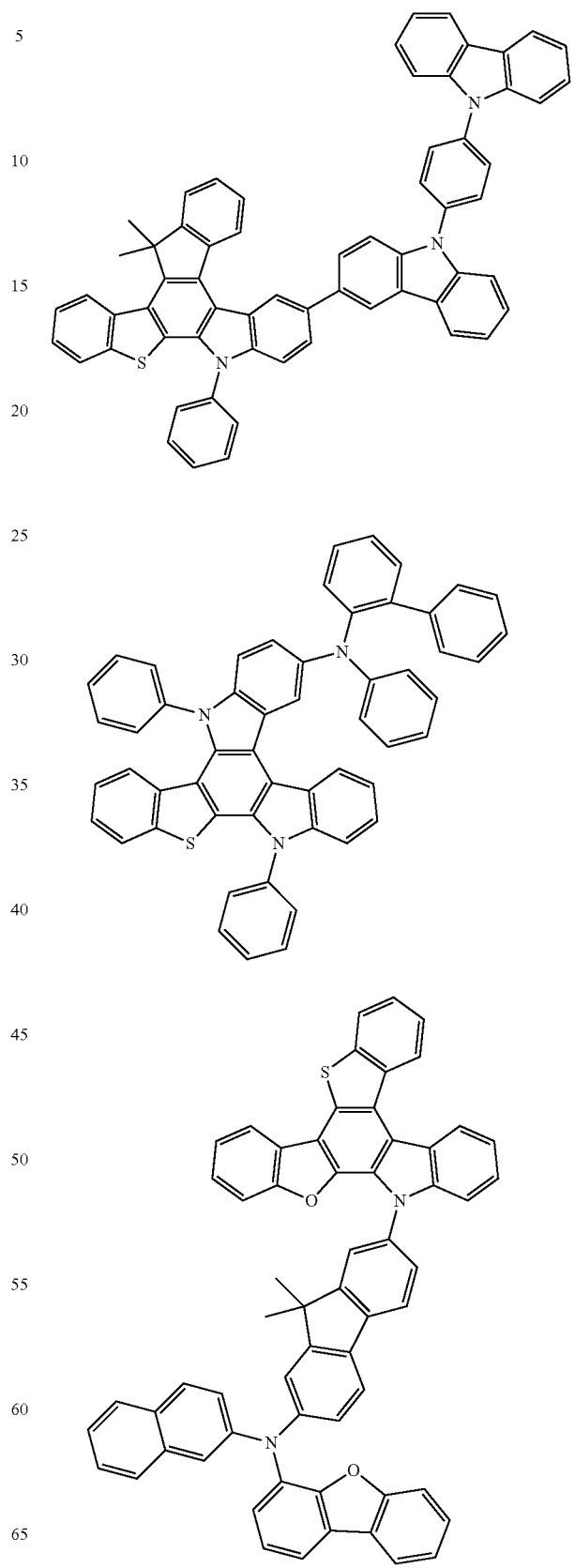

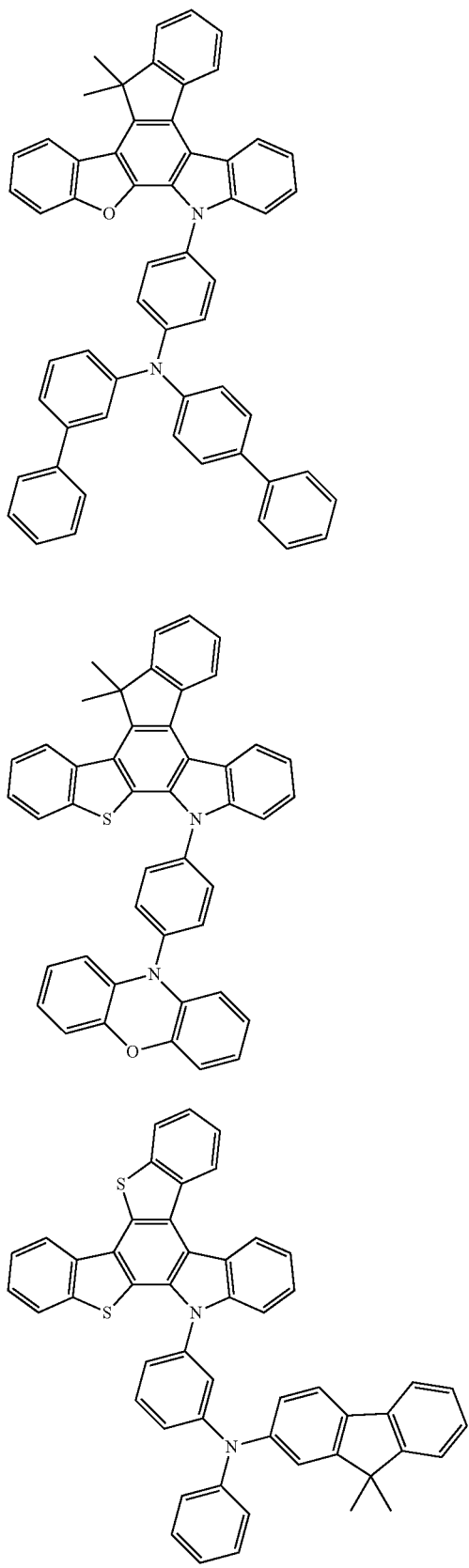
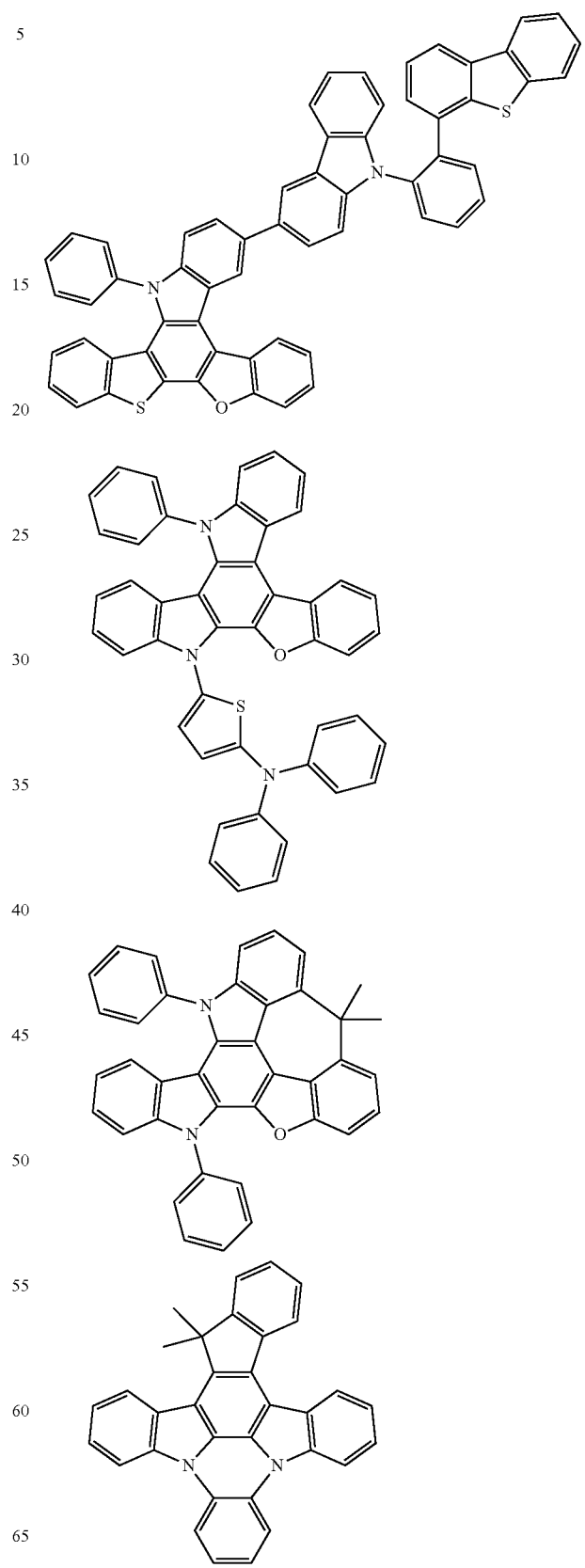

37
-continued
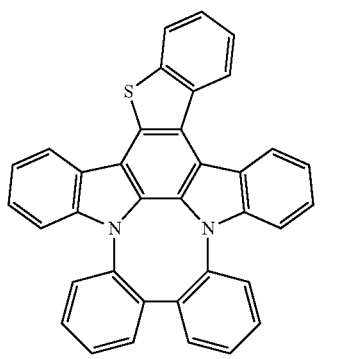
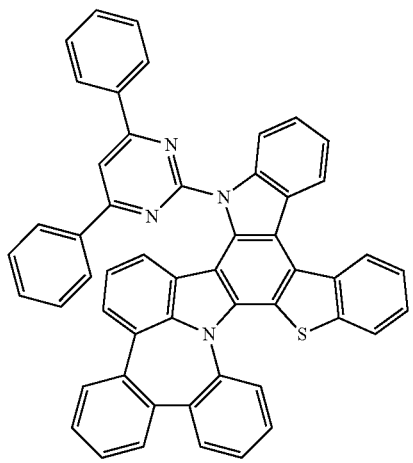
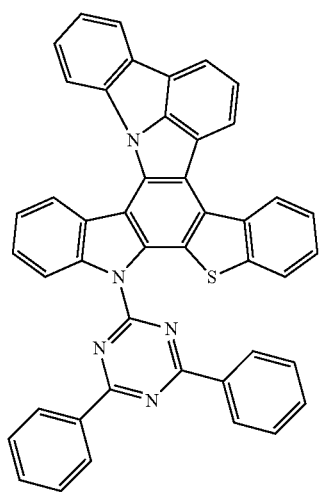
38
-continued
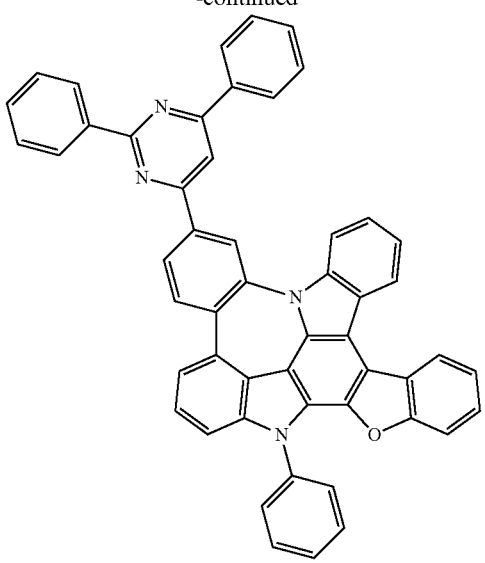
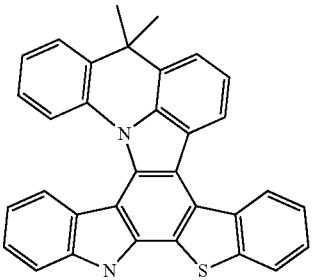
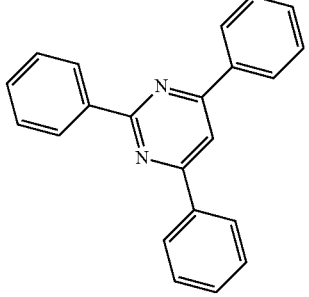
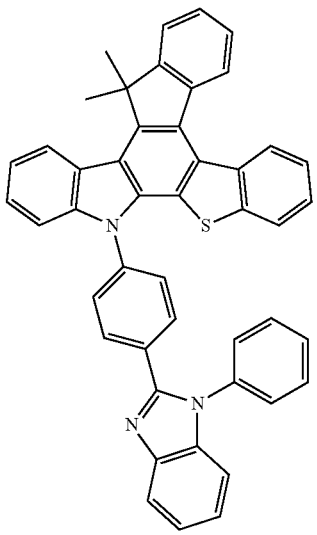

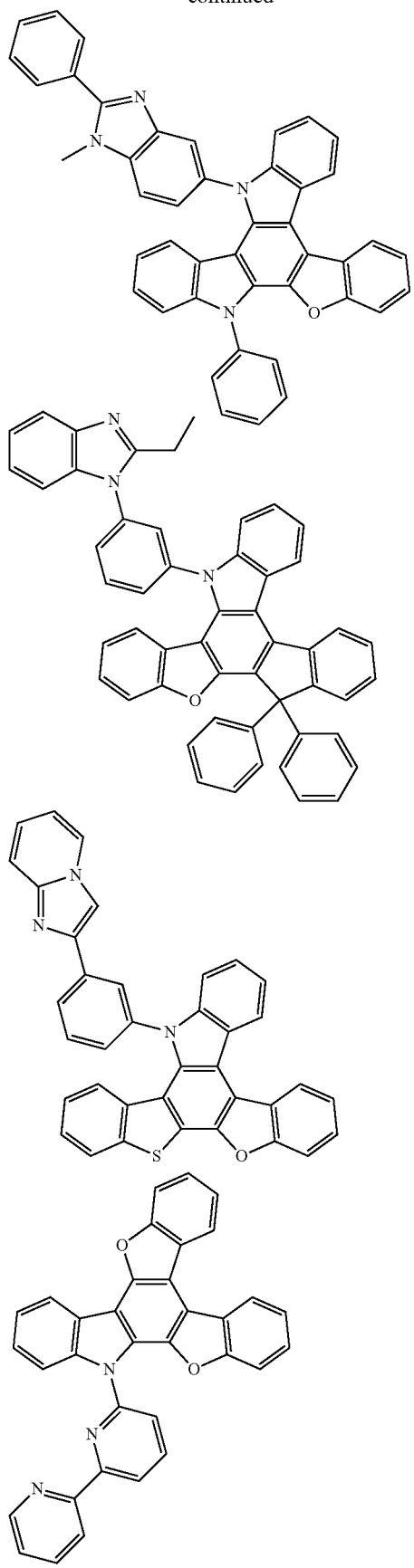
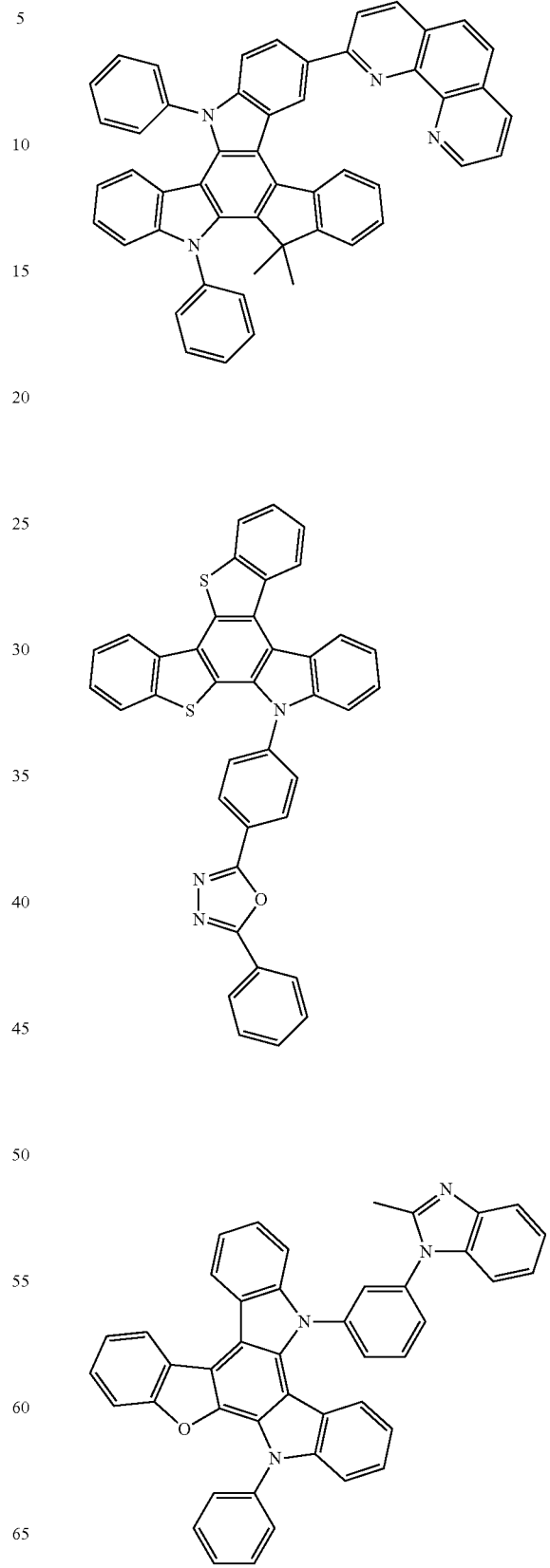

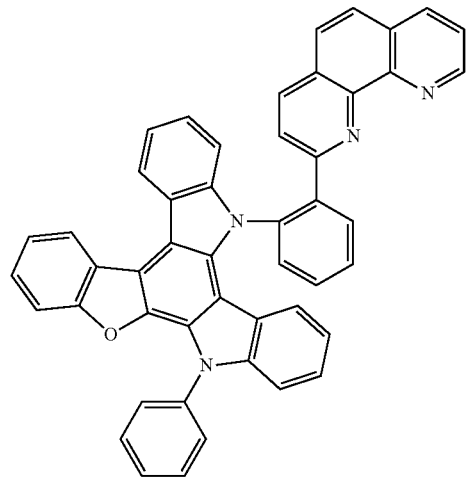
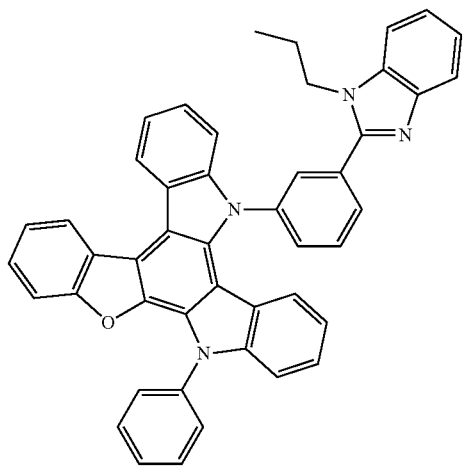
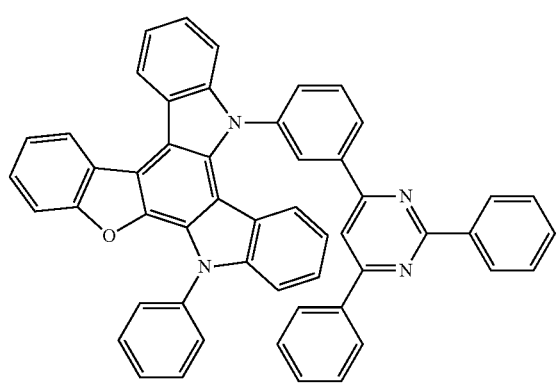
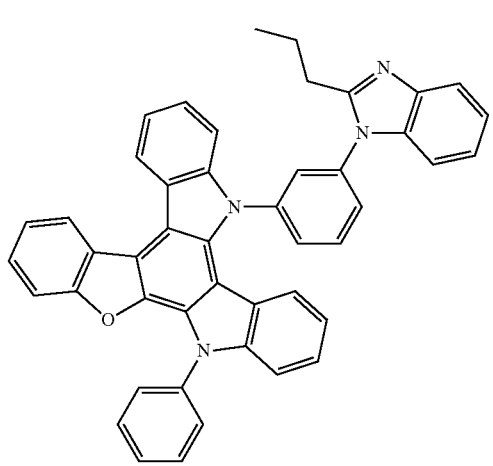
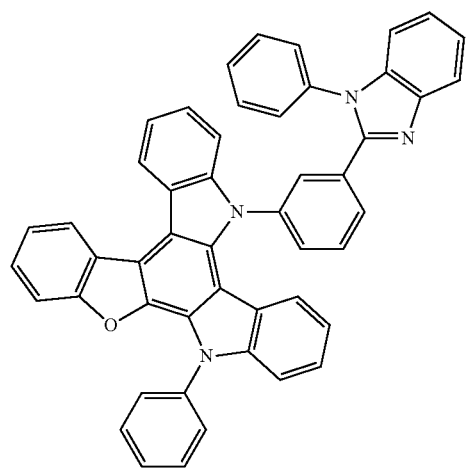
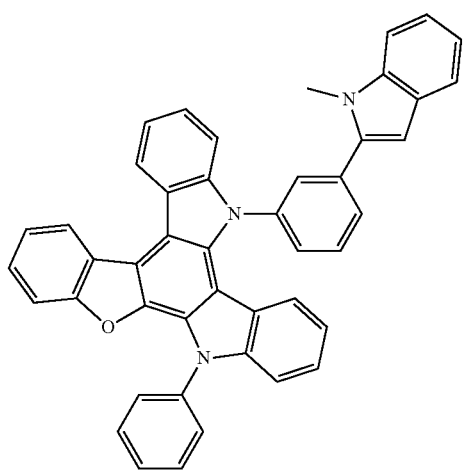

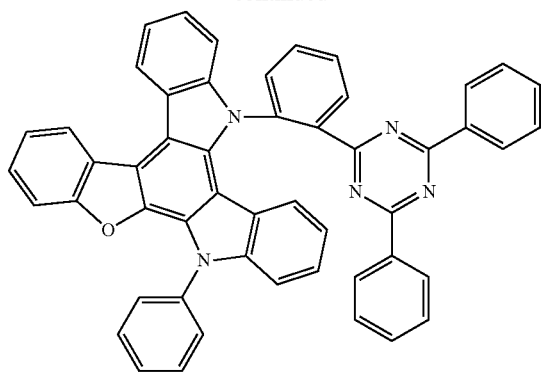
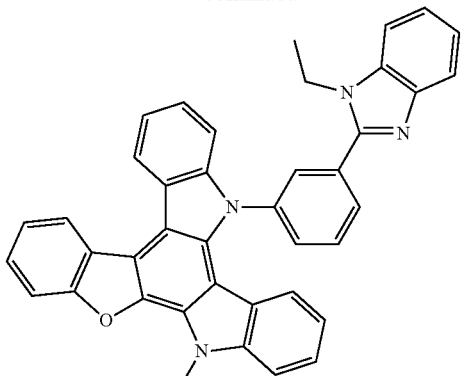
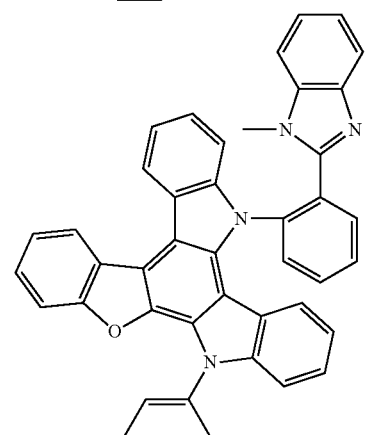
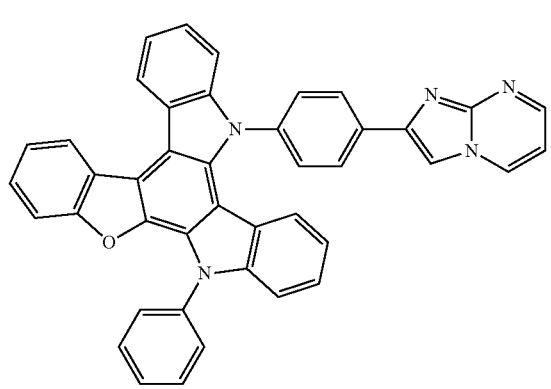
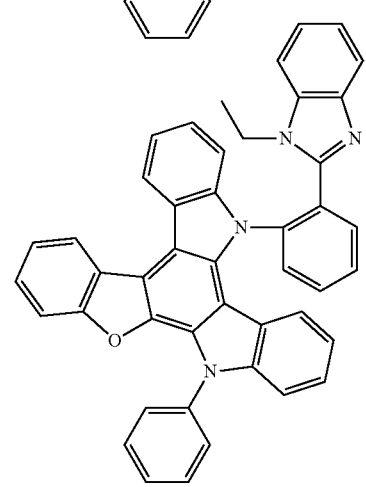
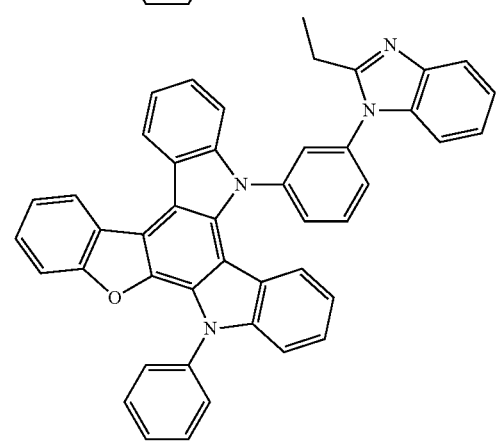

45
-continued
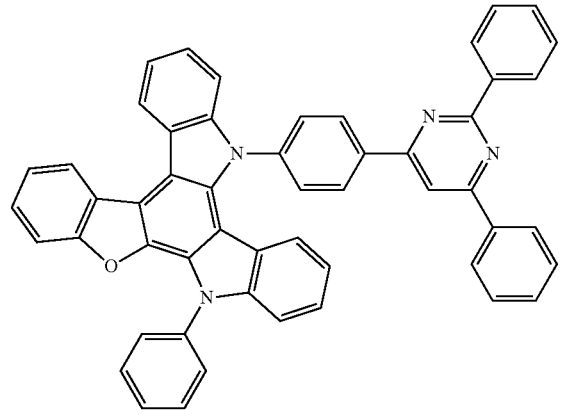
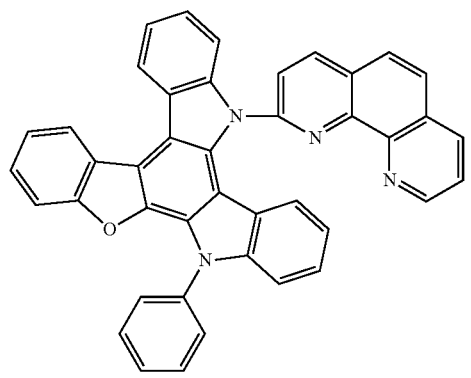
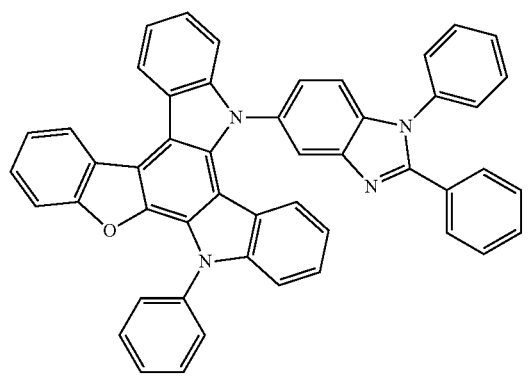
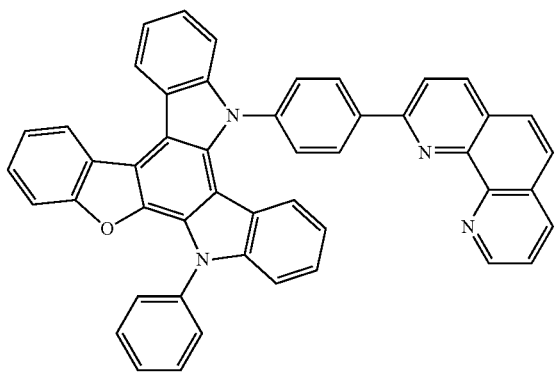
46
-continued
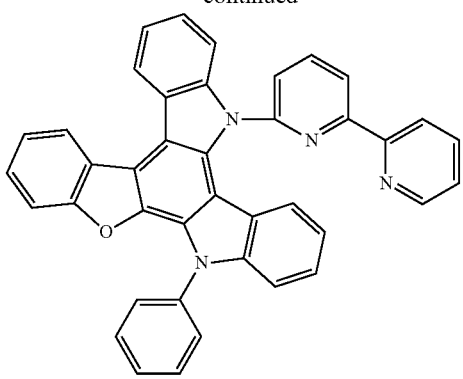
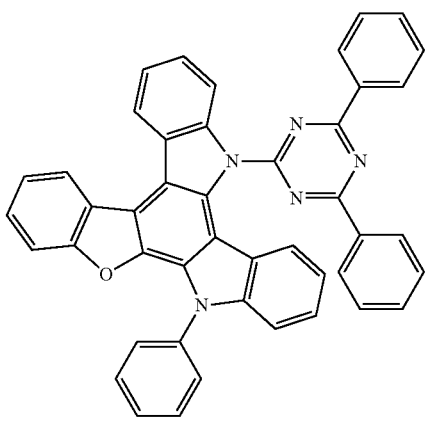
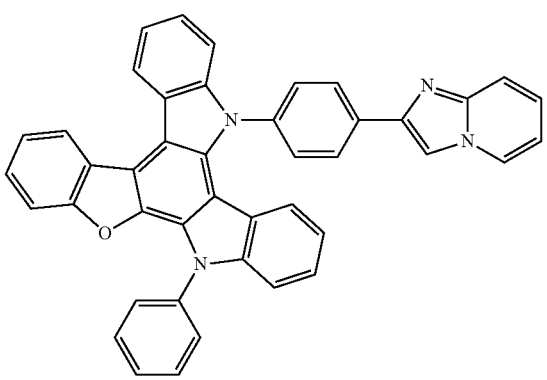
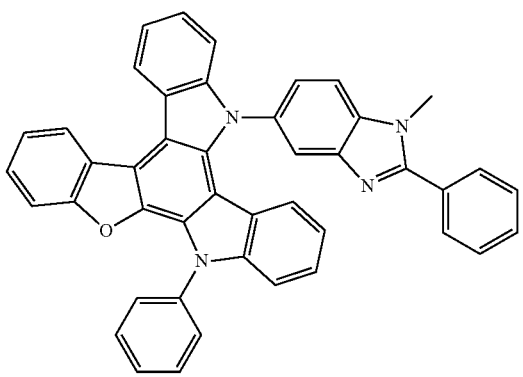

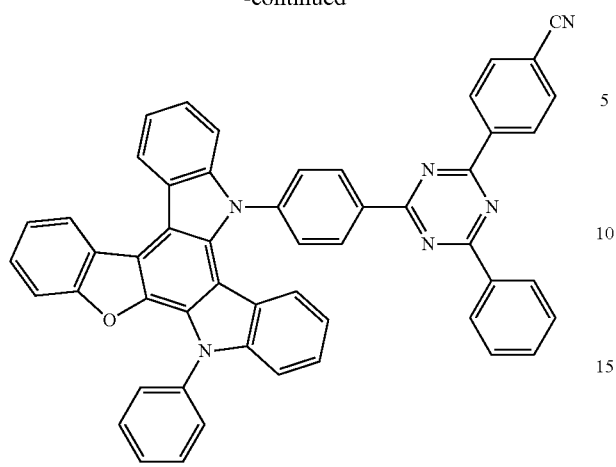
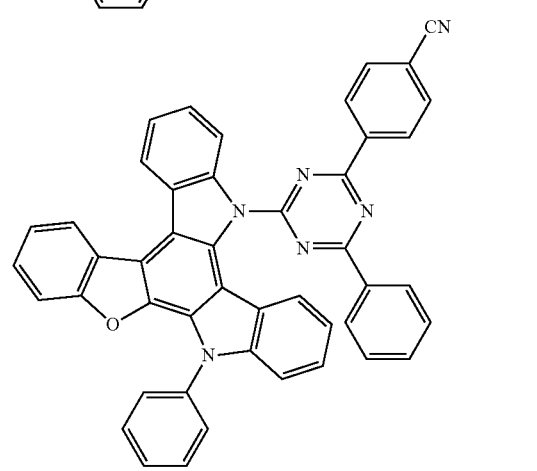
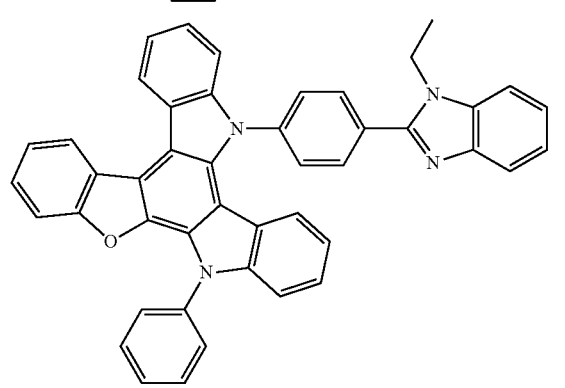
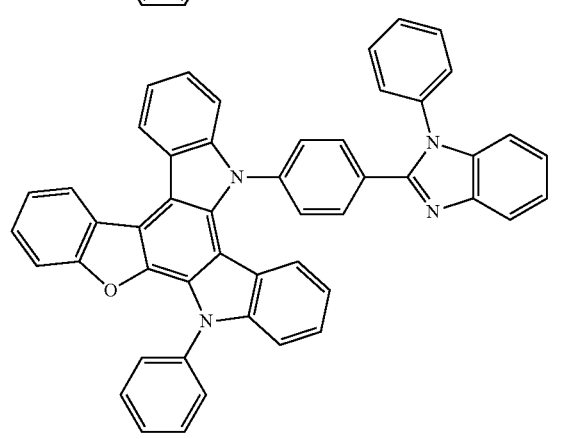
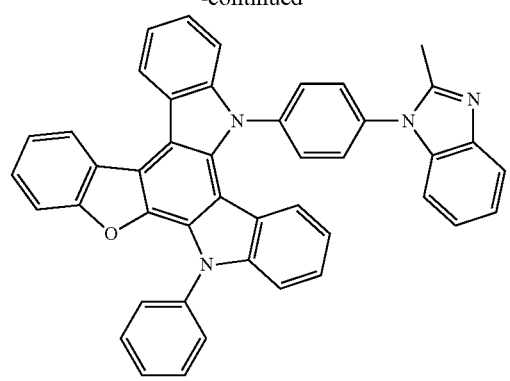
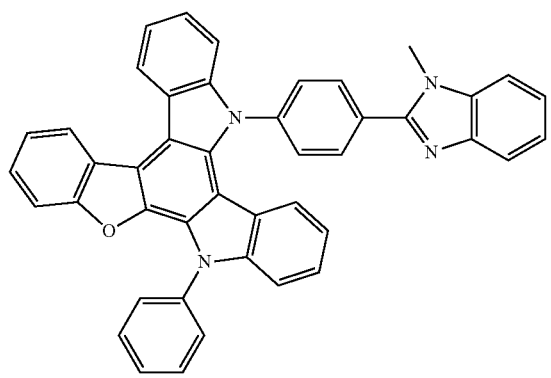
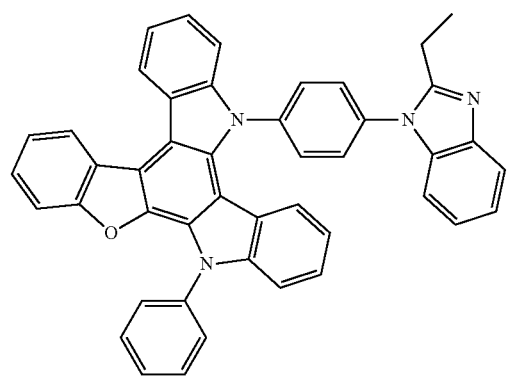
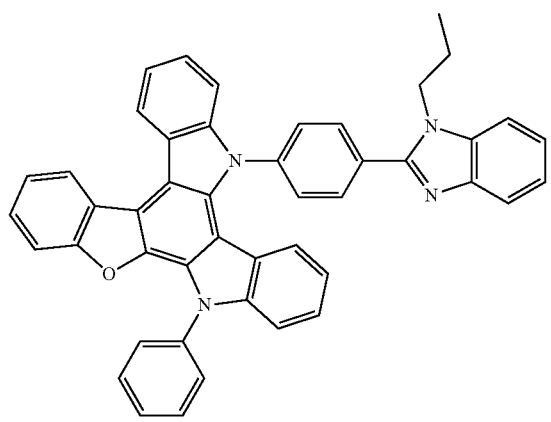

49
-continued
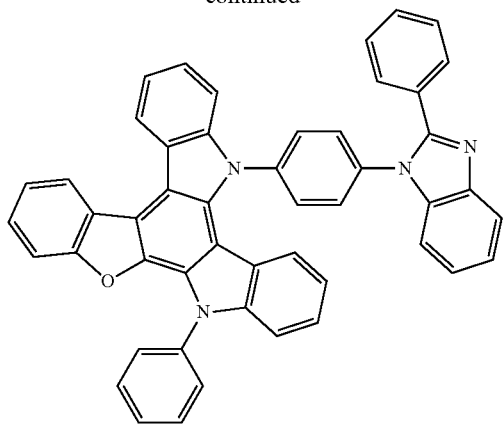
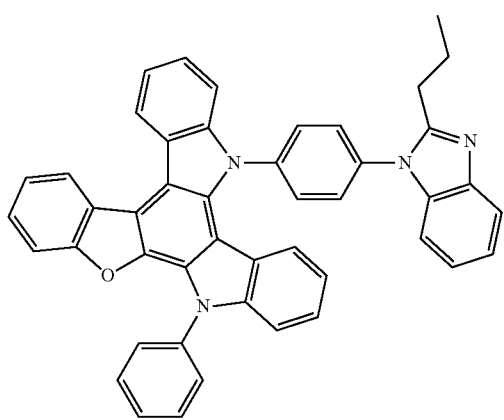
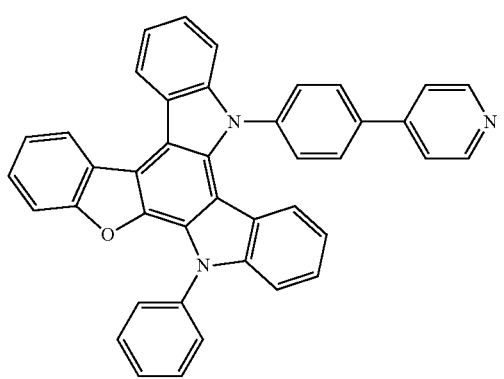
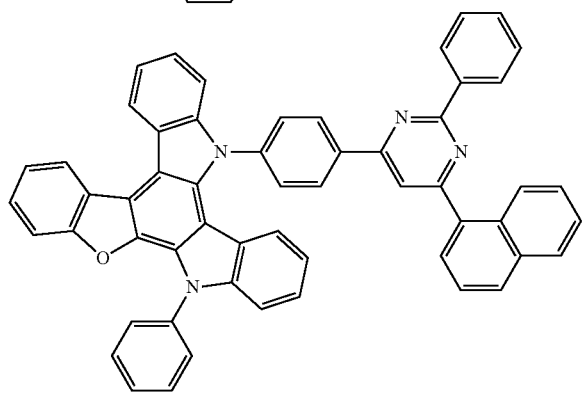
50
-continued
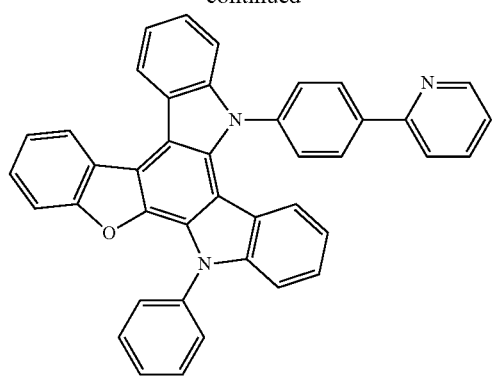
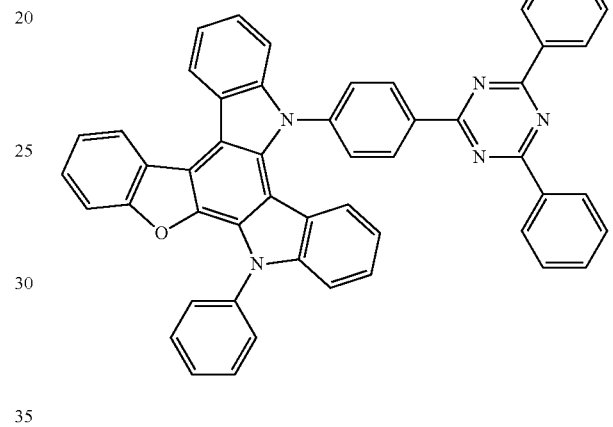
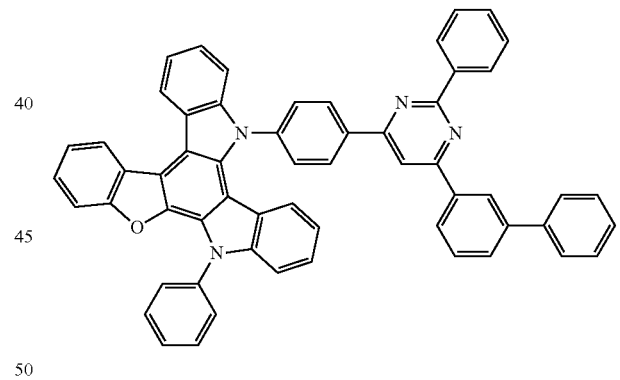
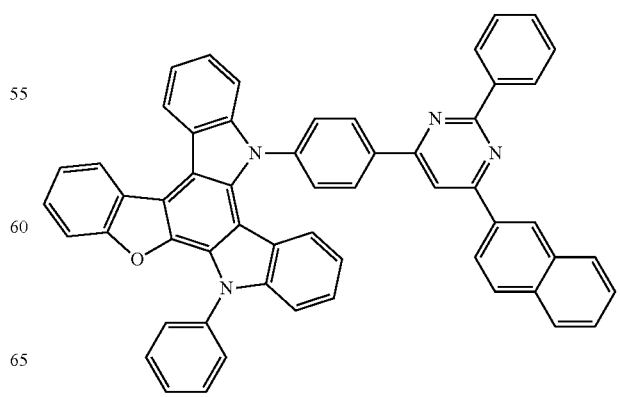

51
-continued
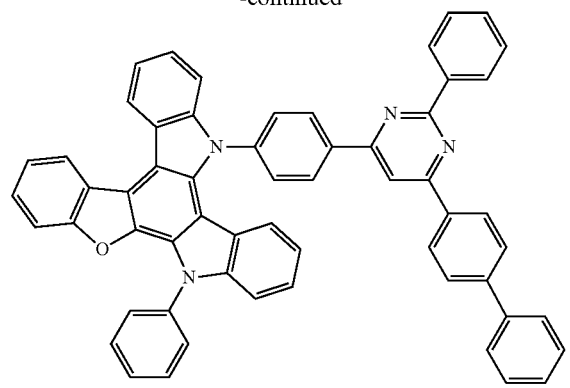
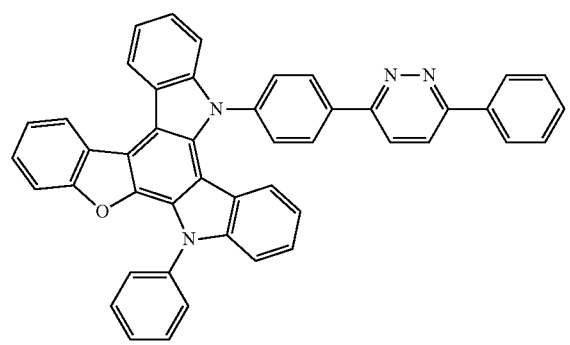
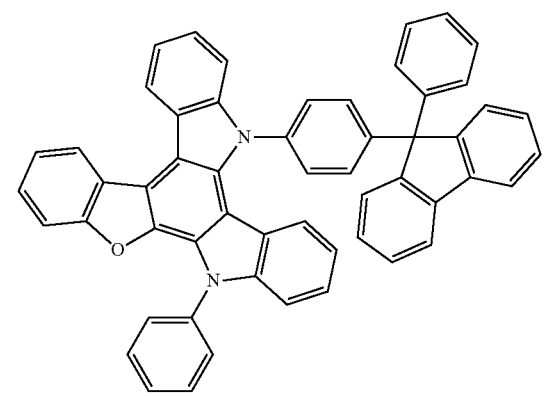
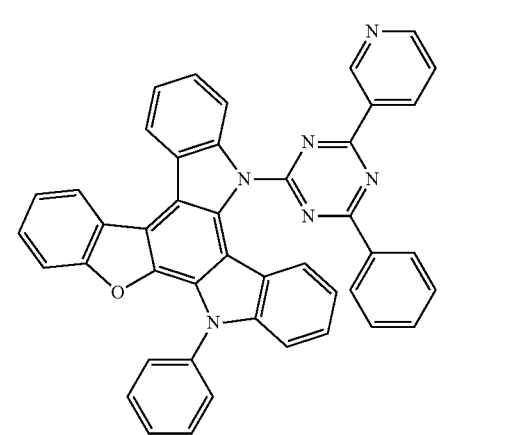
52
-continued
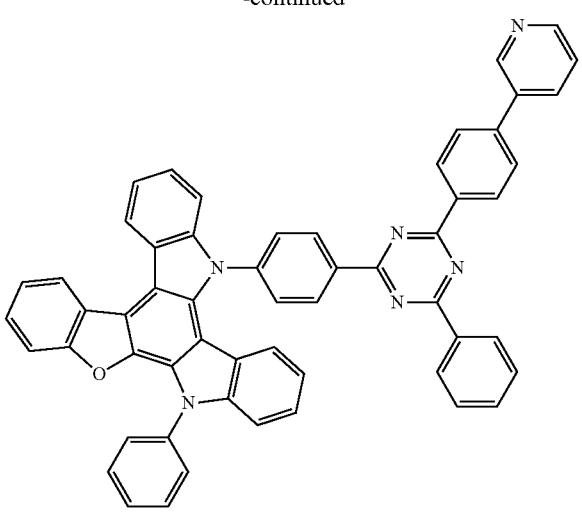

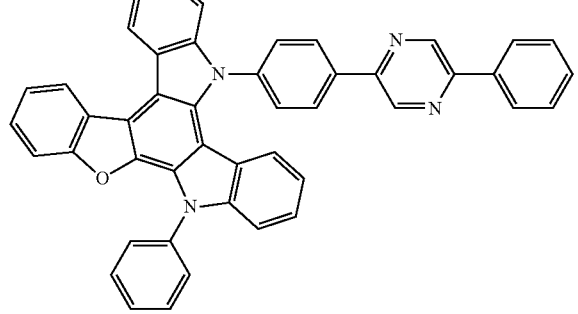
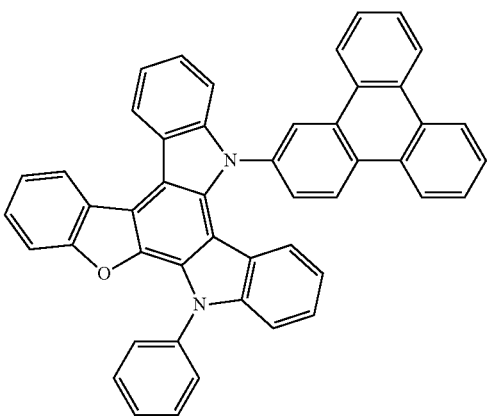

53
-continued
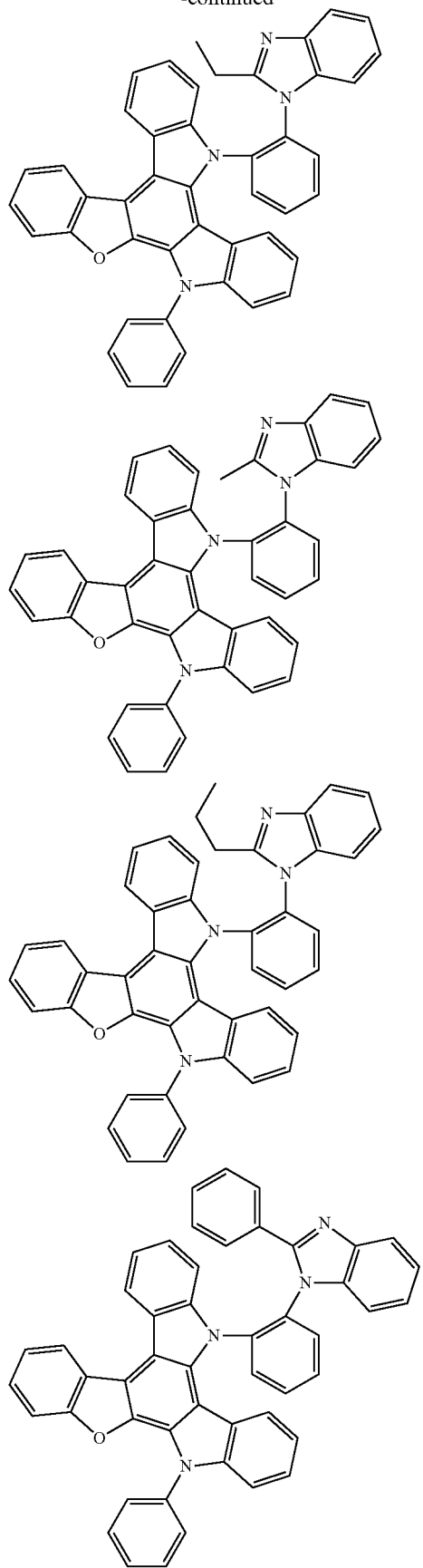
54
-continued
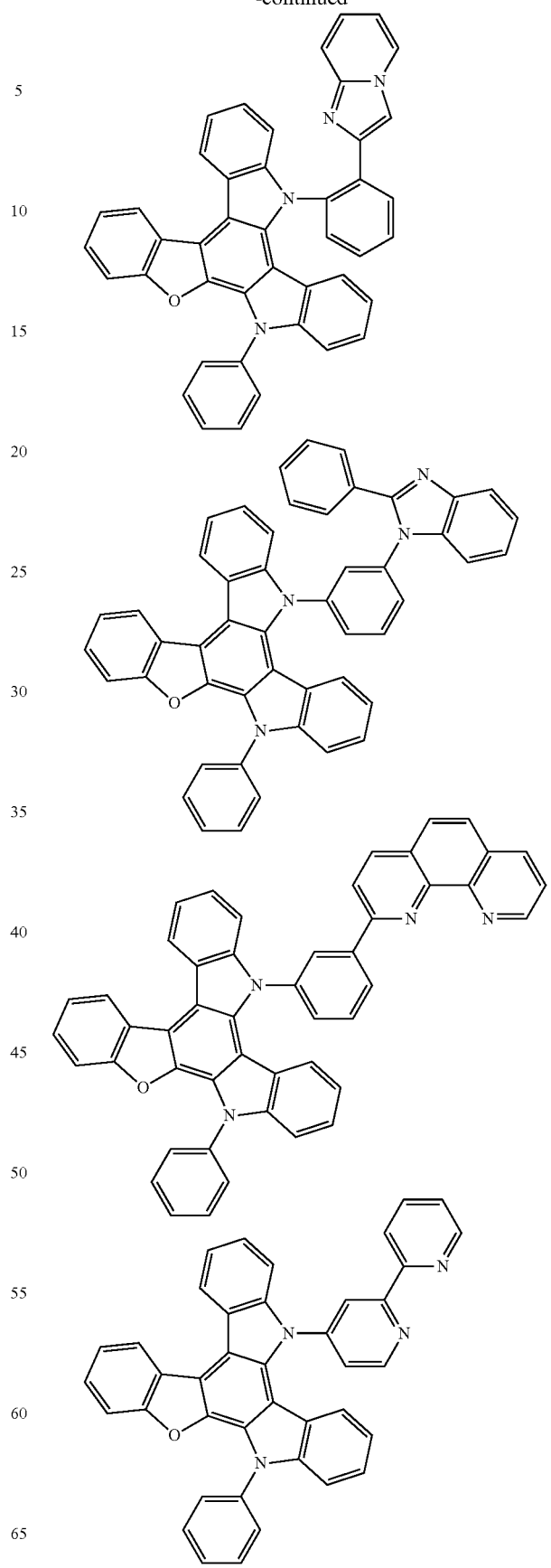

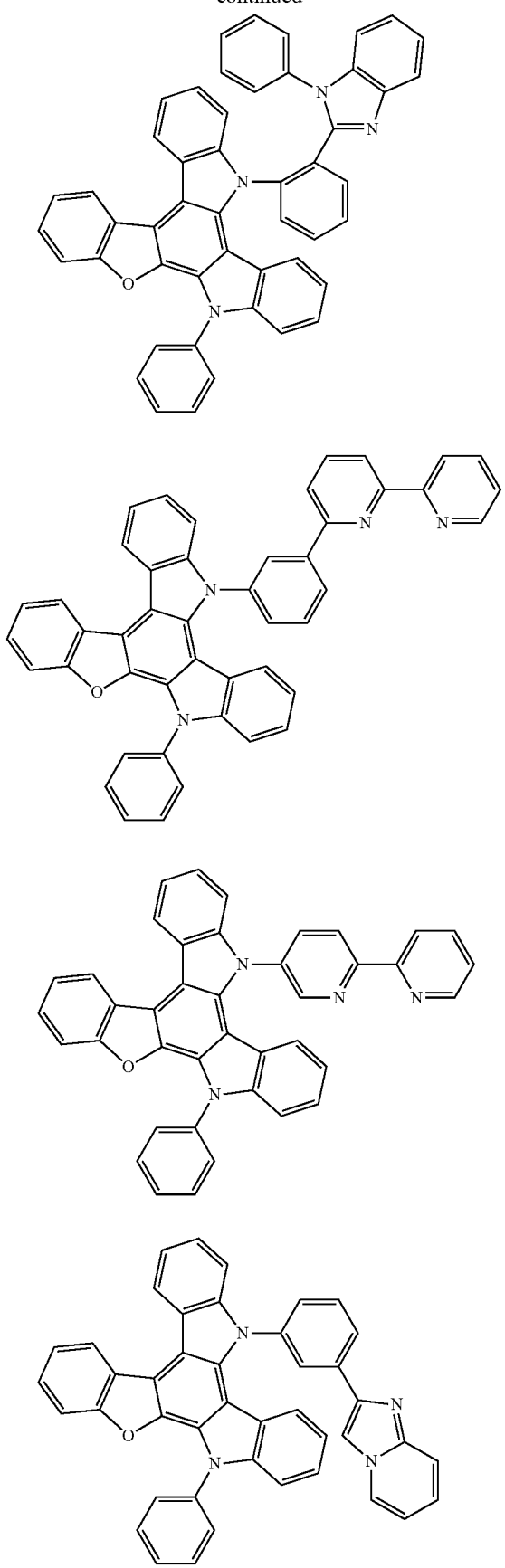

57
-continued
58
-continued
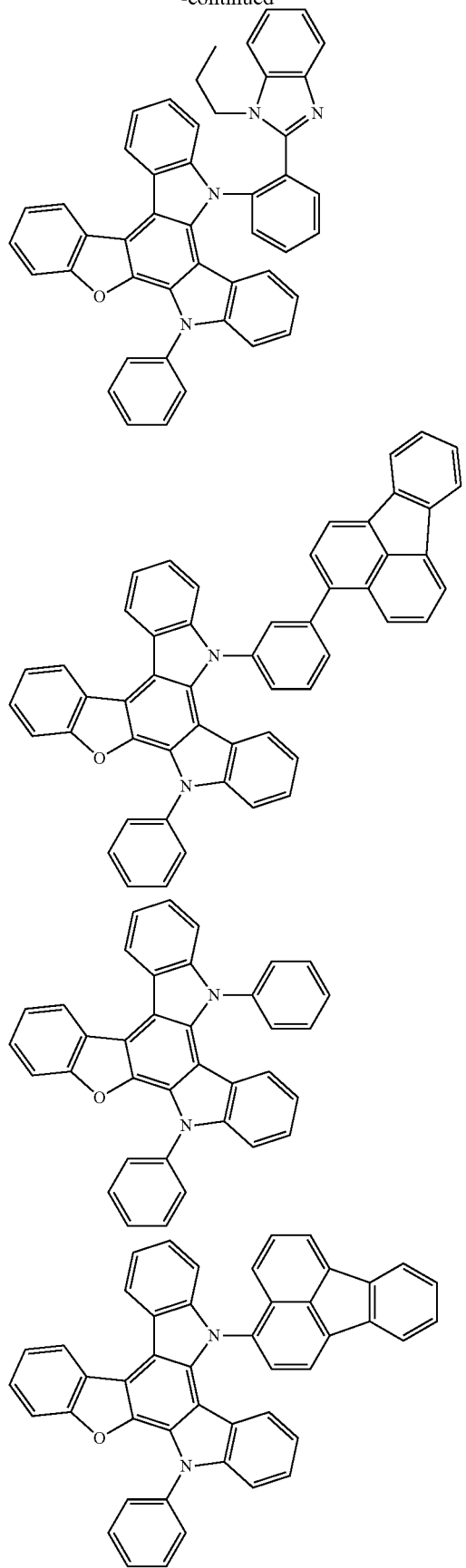
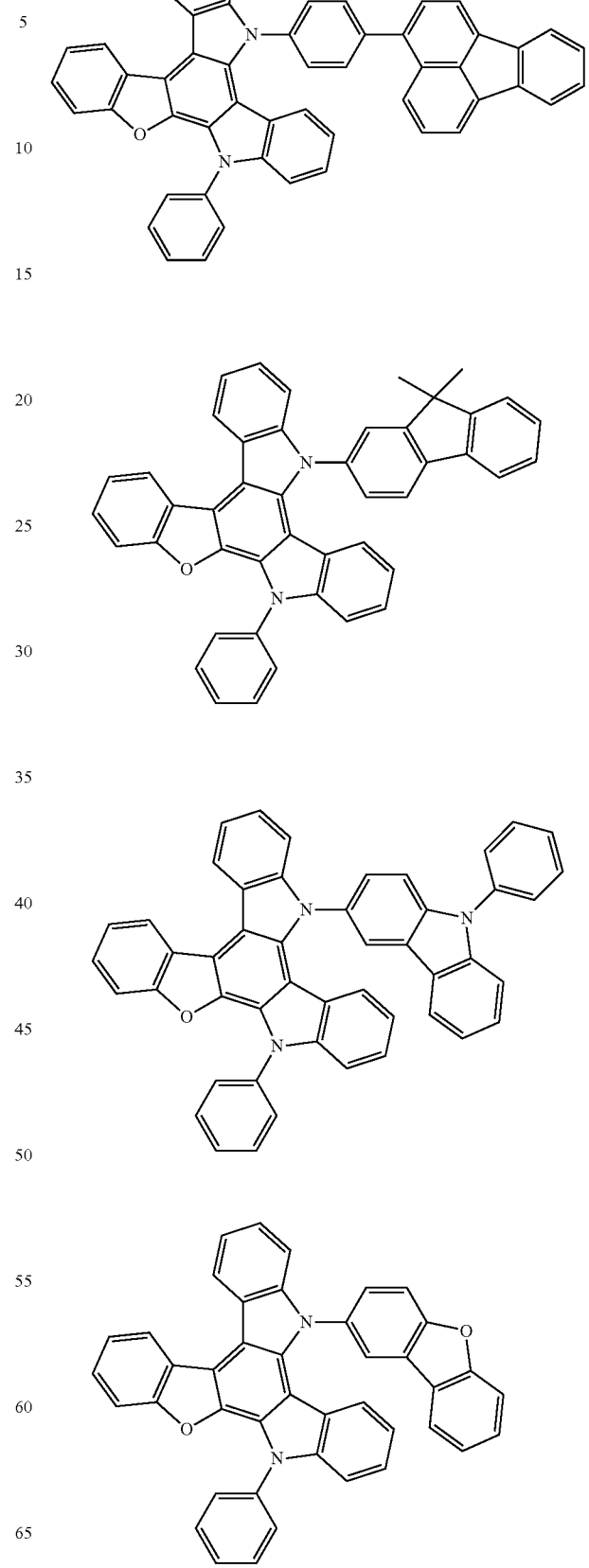

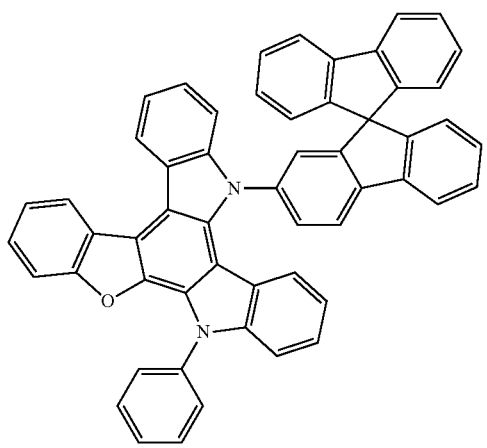
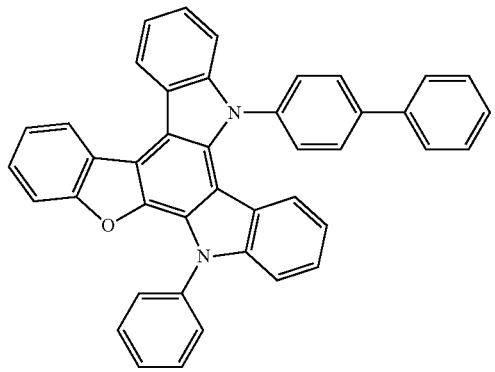
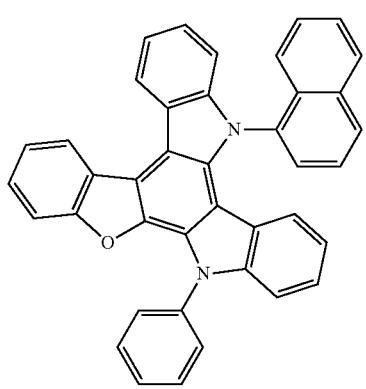
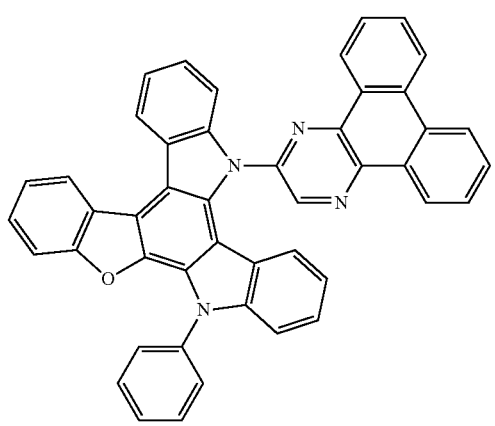
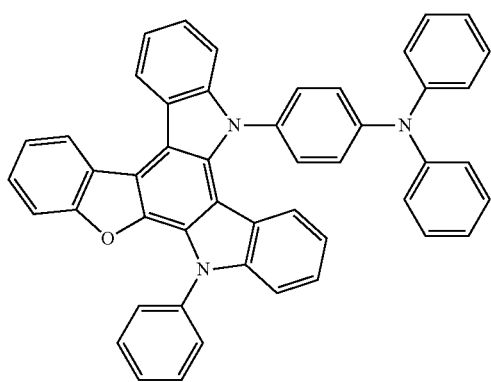
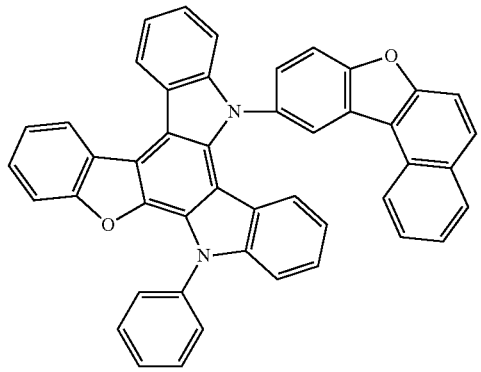
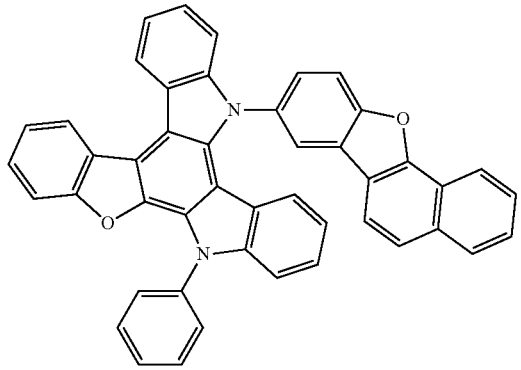
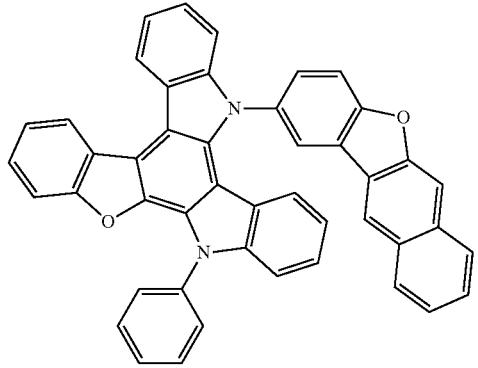

61
-continued
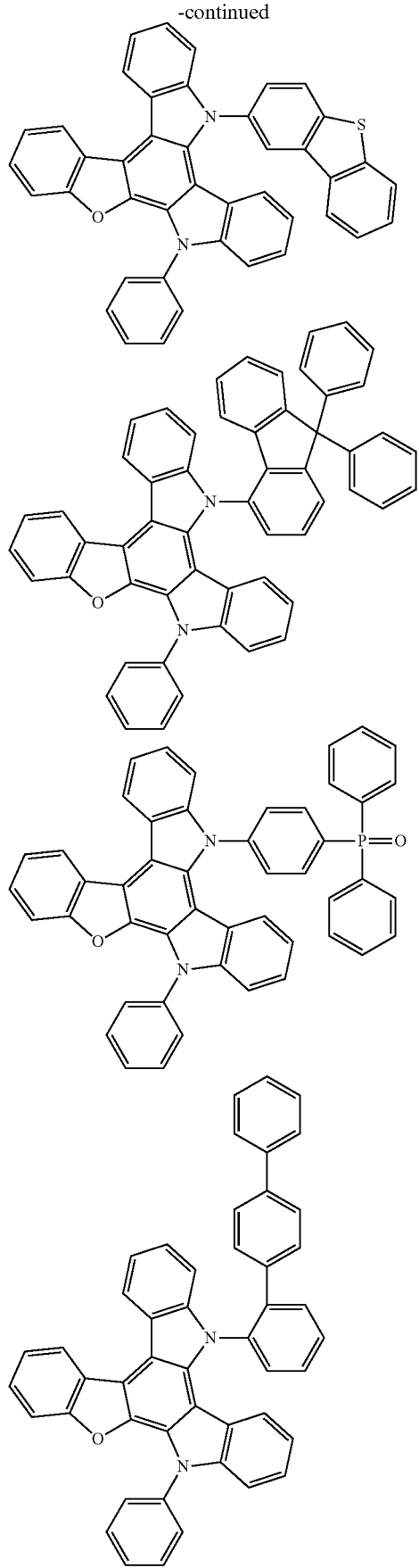
62
-continued
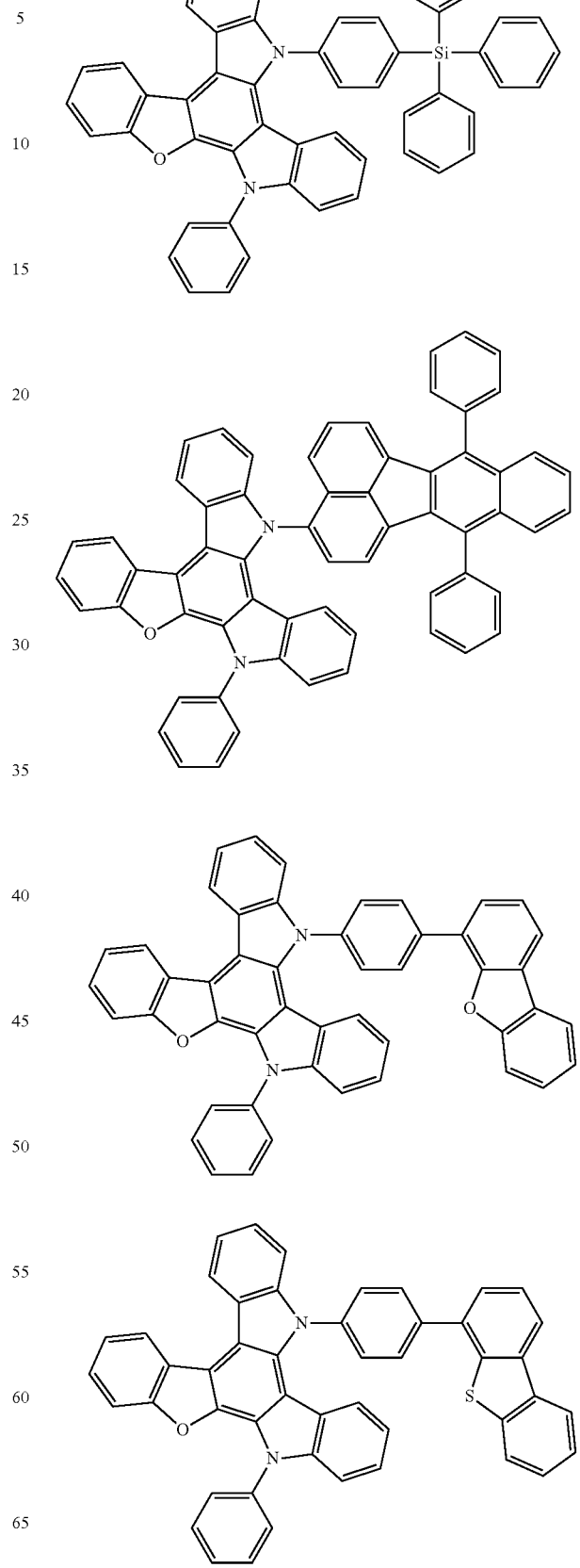

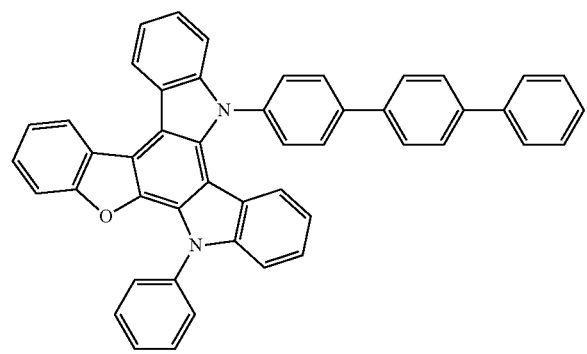
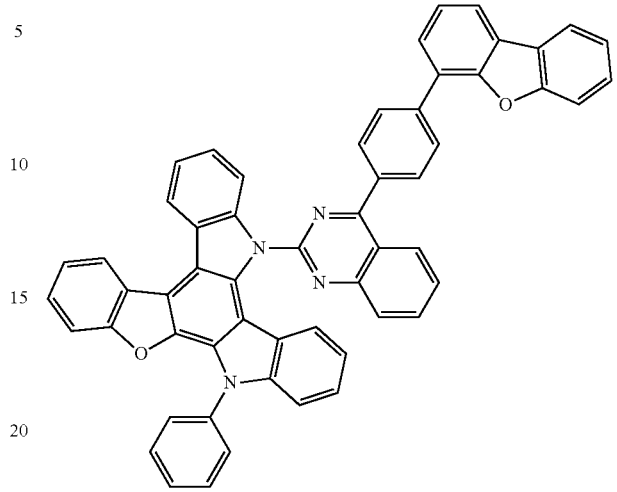
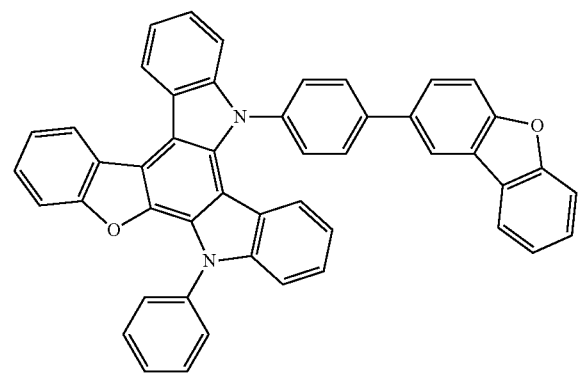
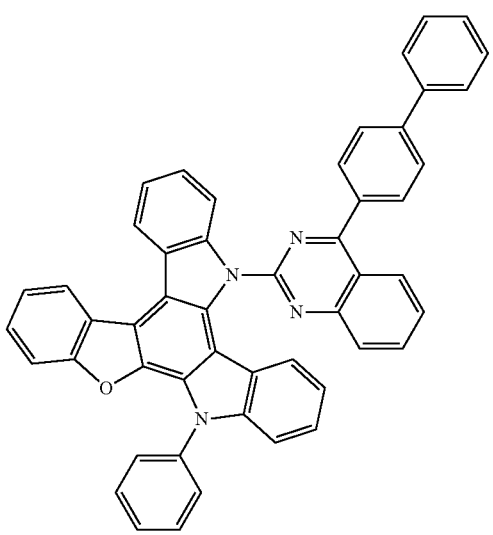
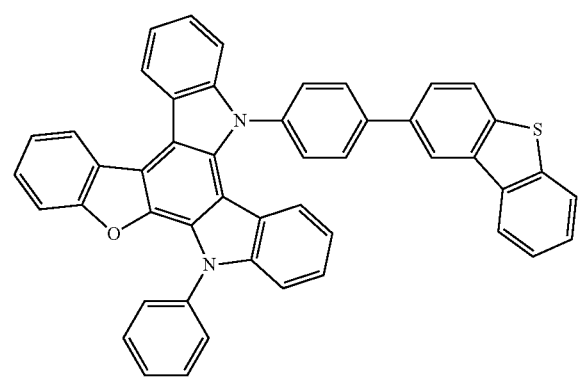
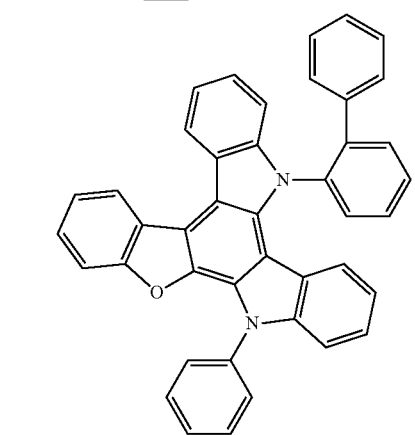
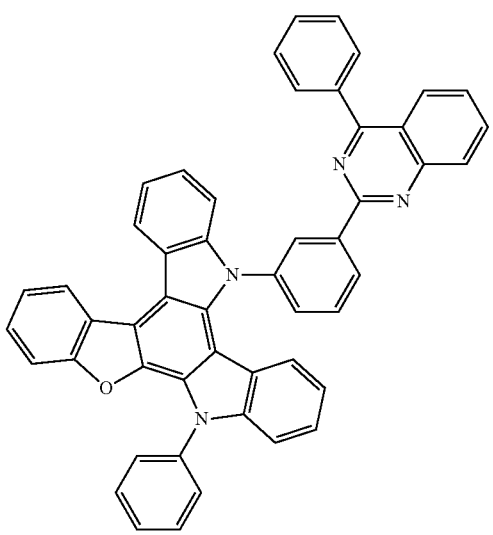

65
-continued
66
-continued
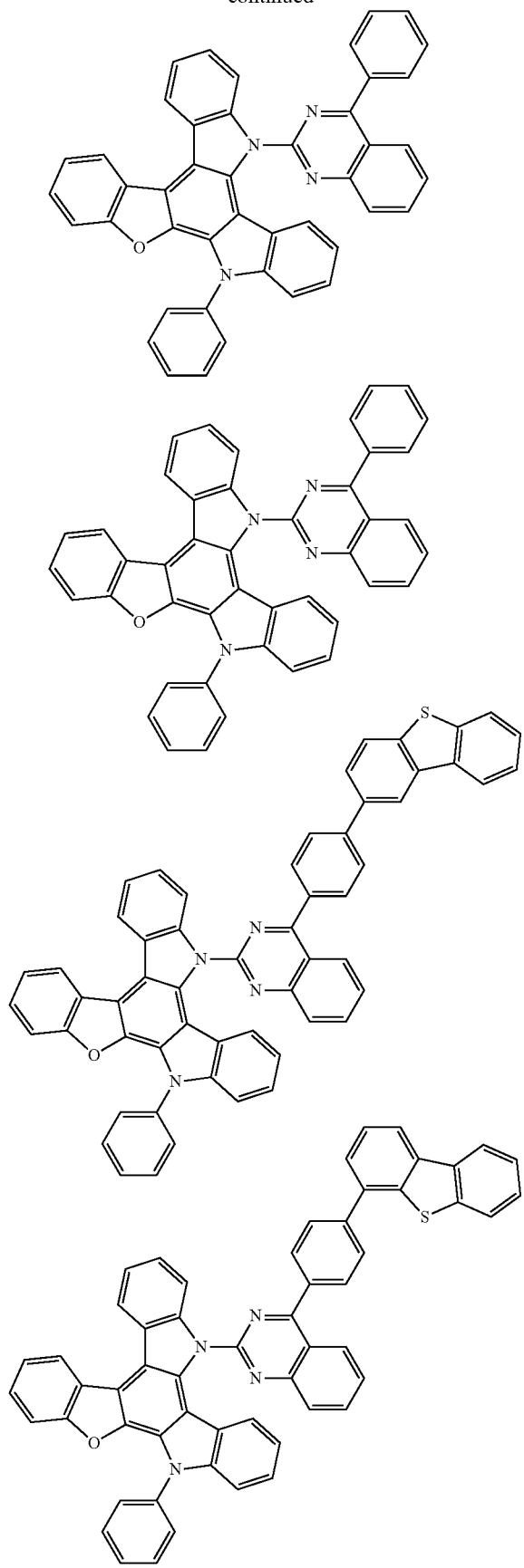
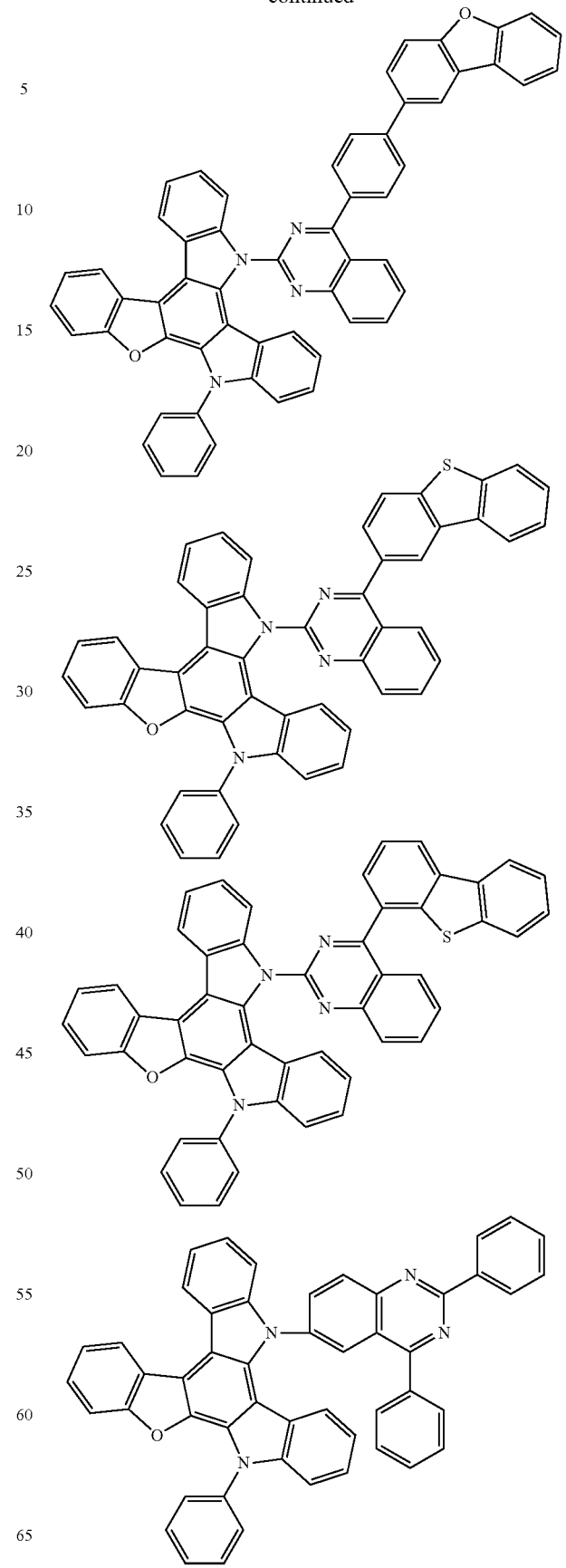

67
-continued
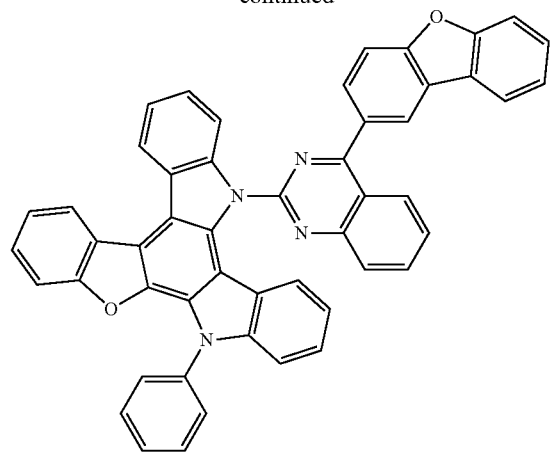
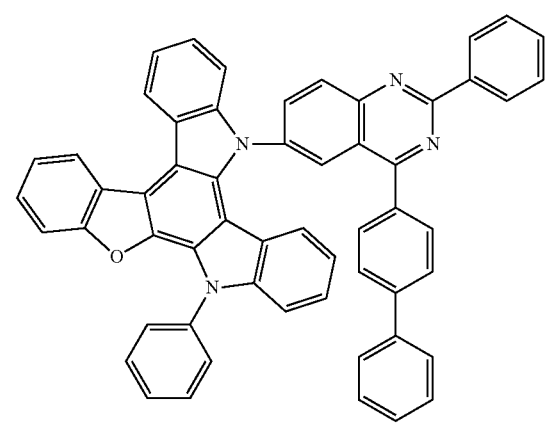
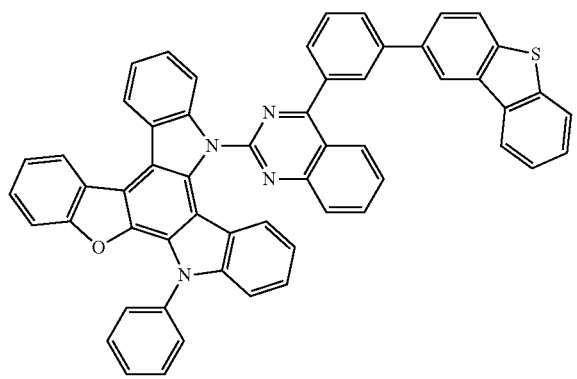
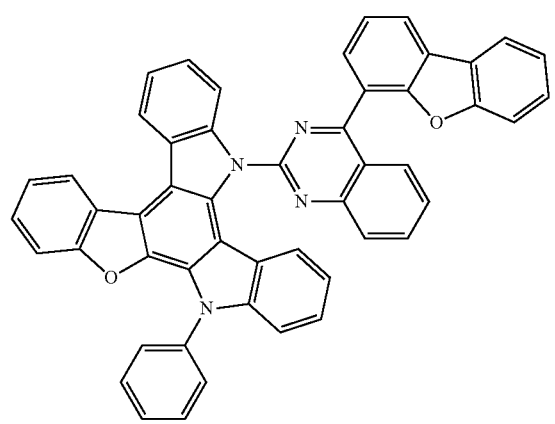
68
-continued
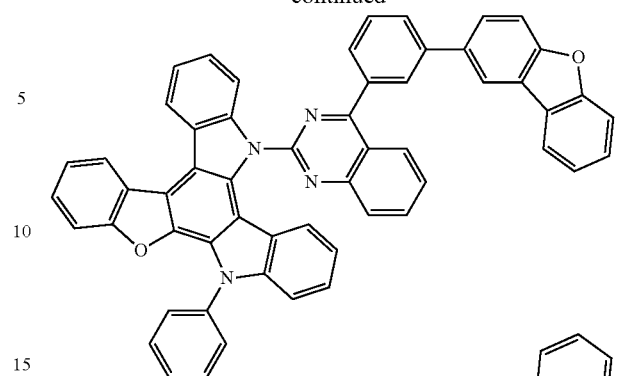
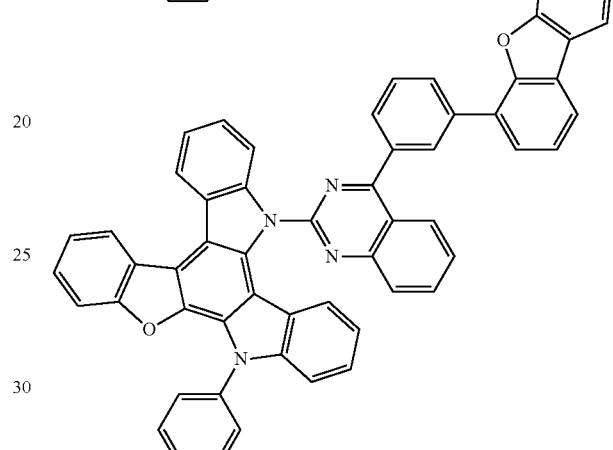
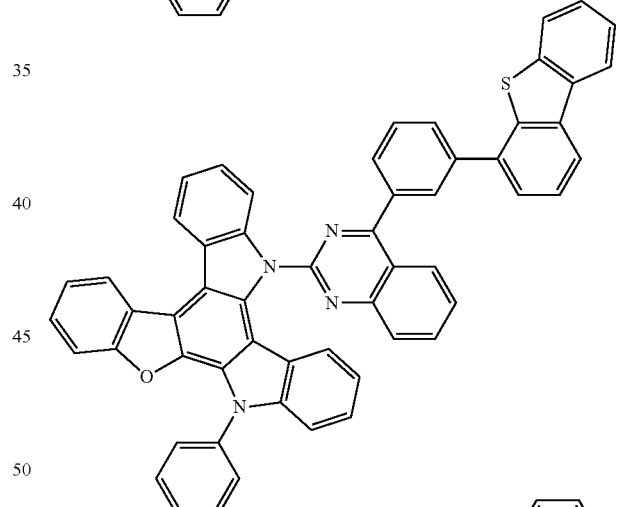
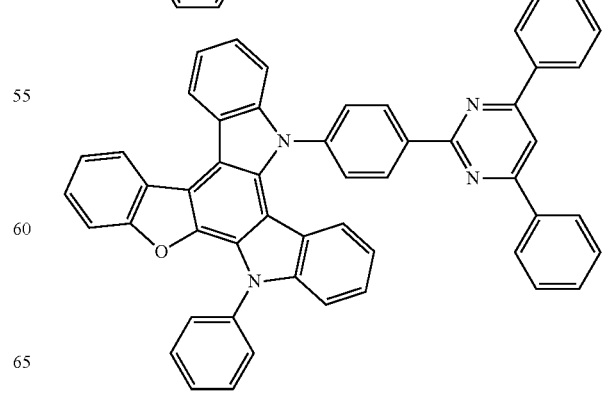

69
-continued
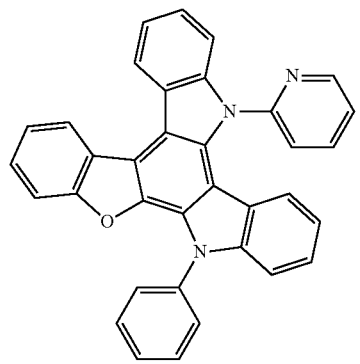
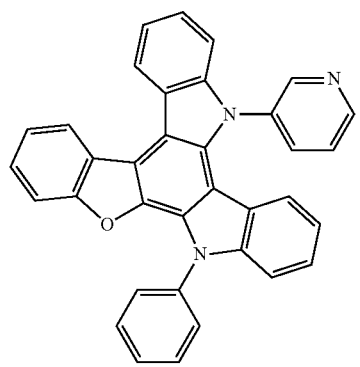
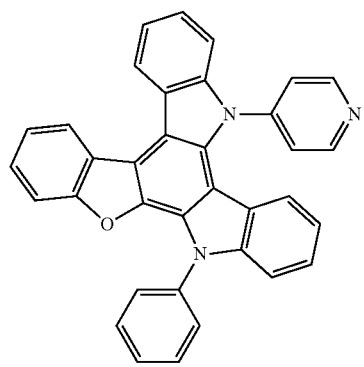
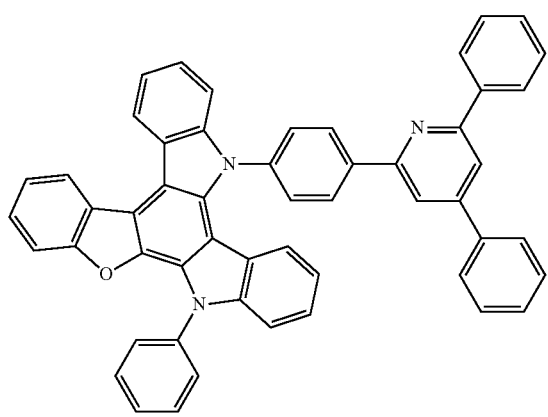
70
-continued
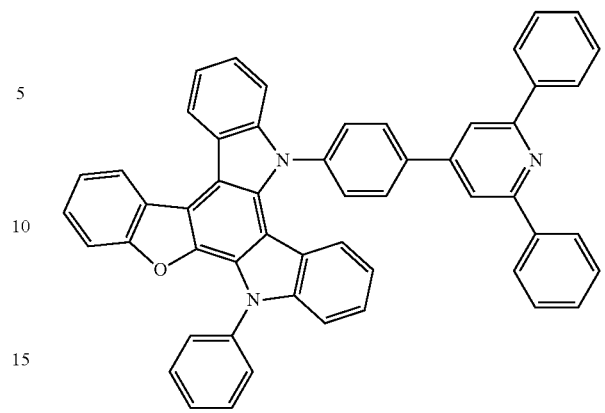
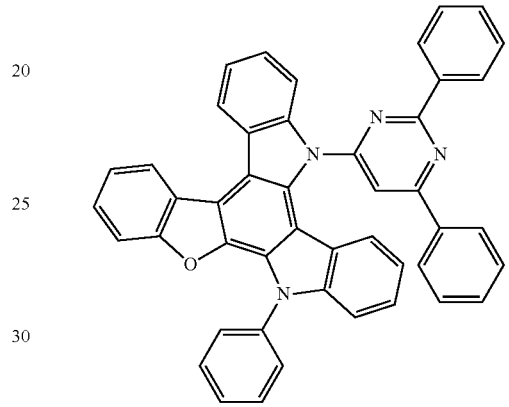
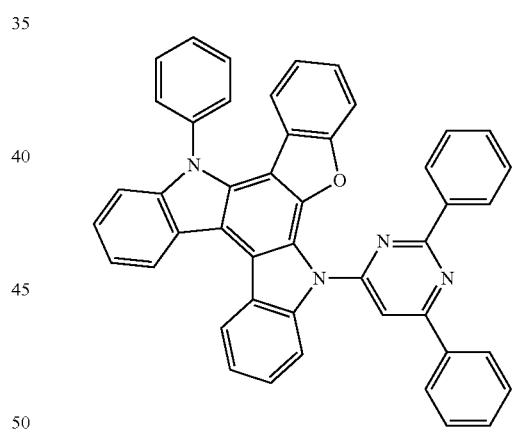
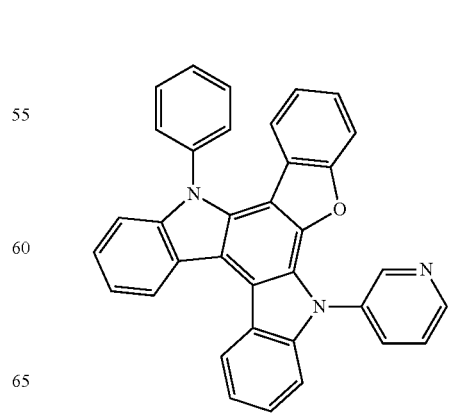

71
-continued
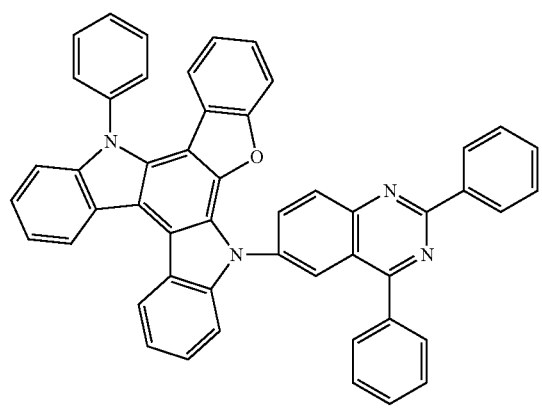
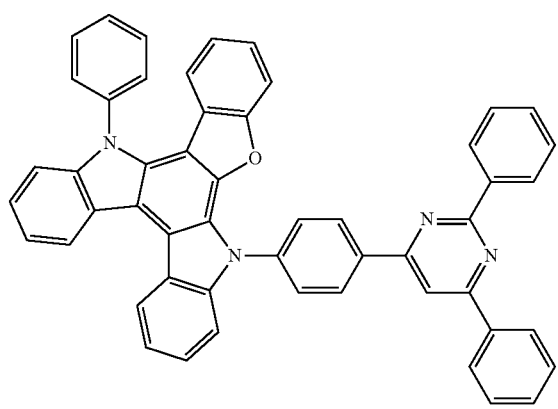
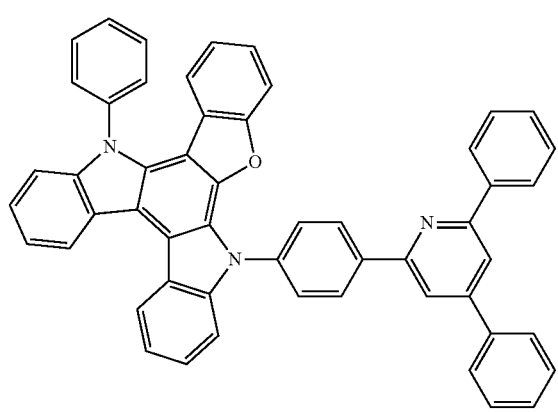
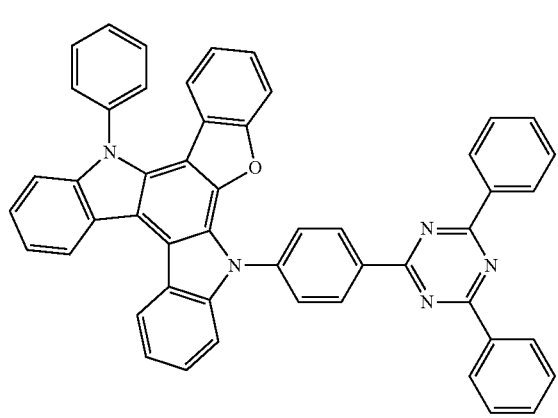
72
-continued
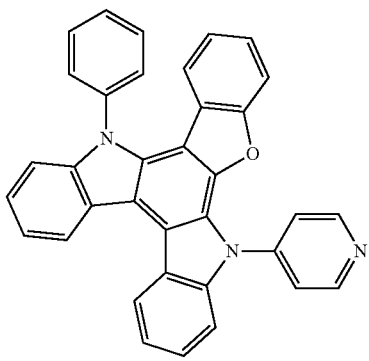
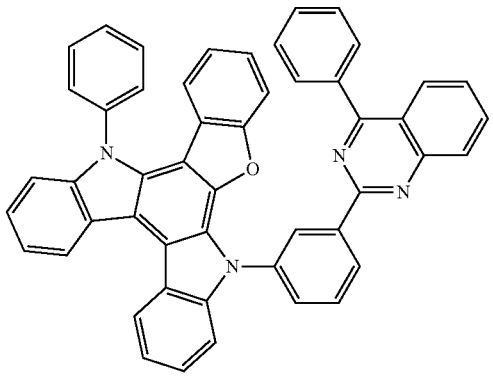
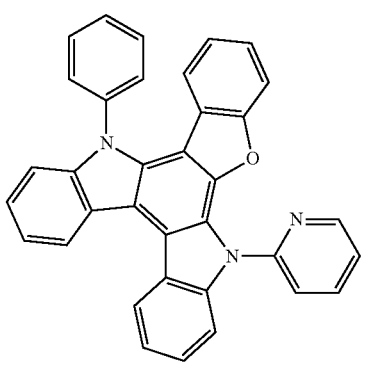
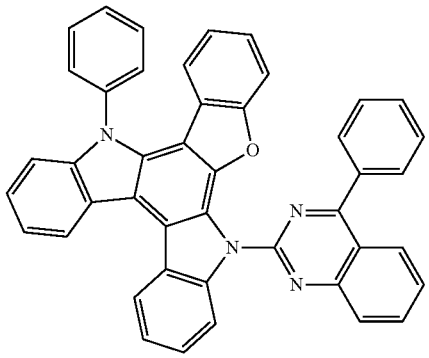

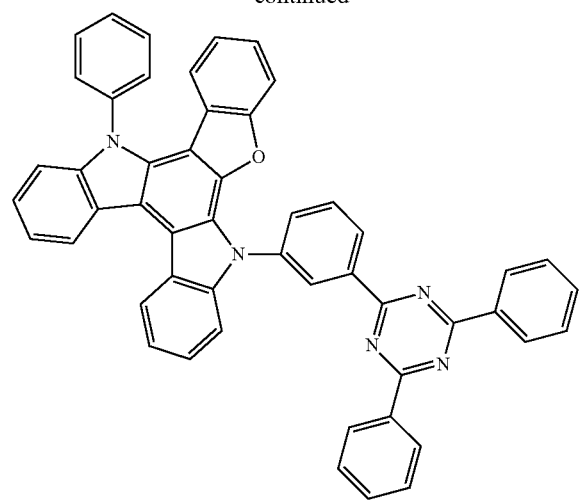
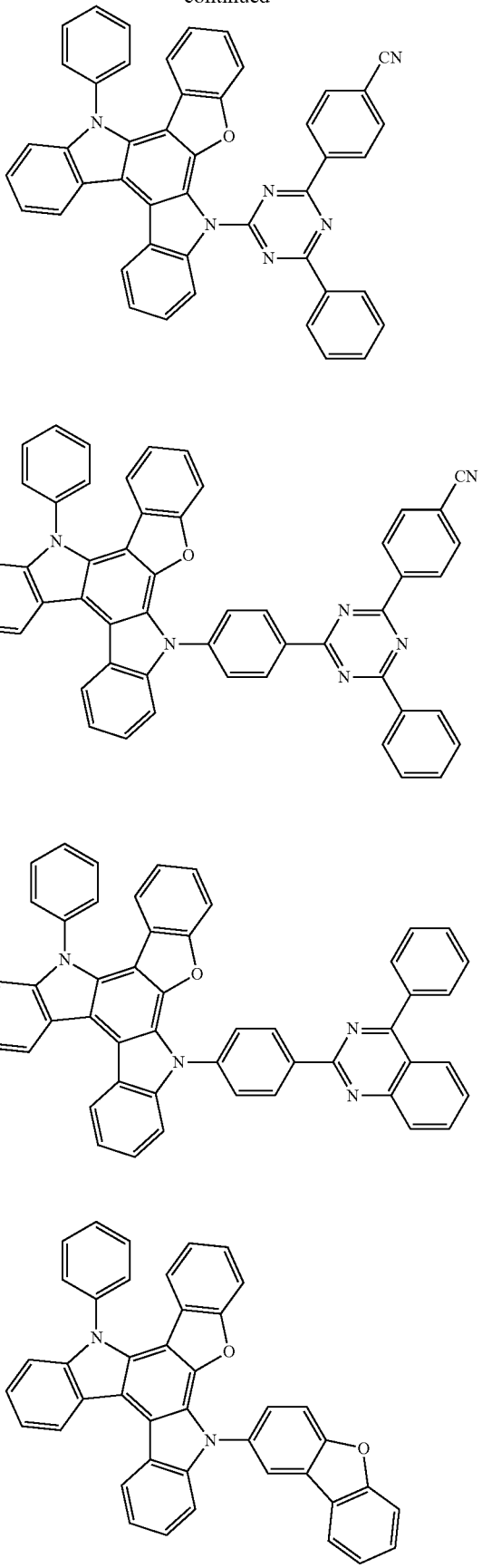

75
-continued
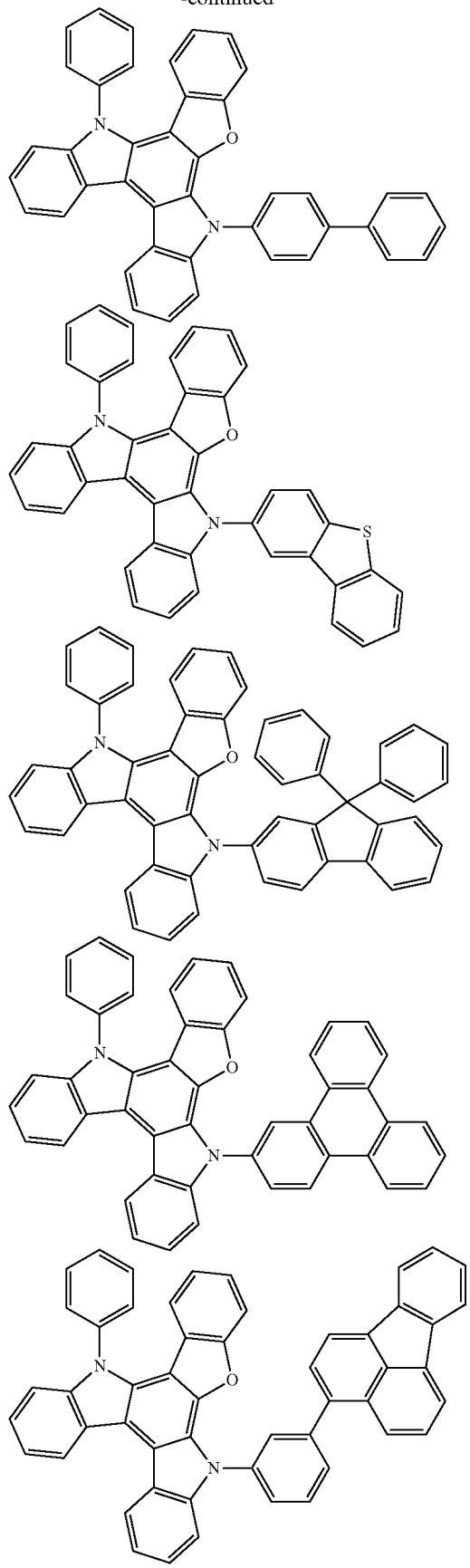
76
-continued
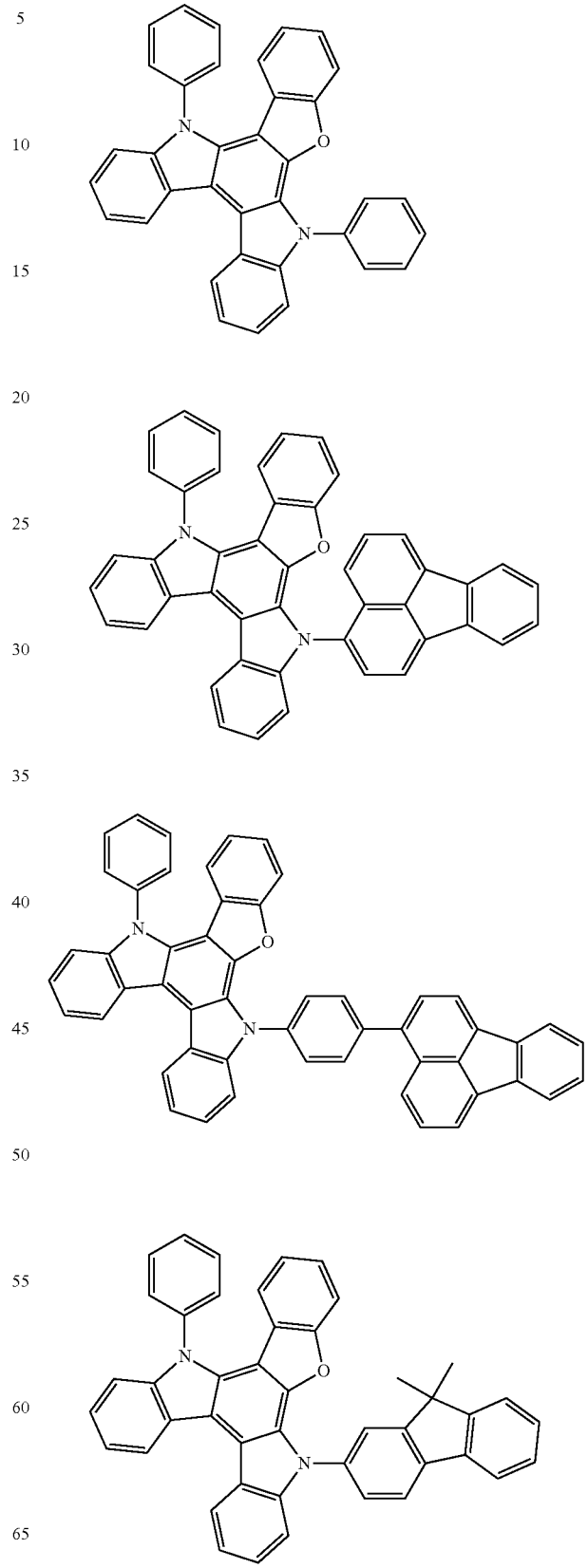

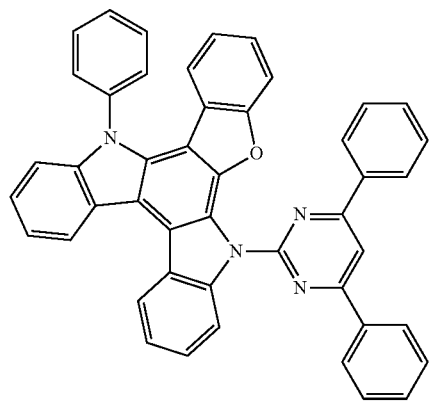
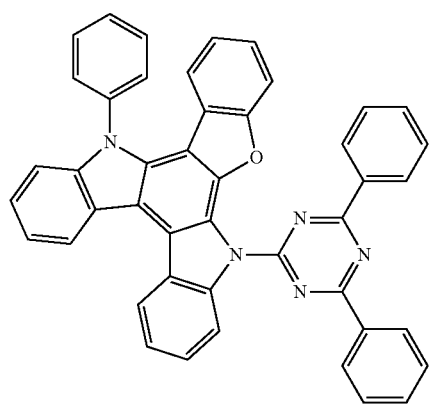
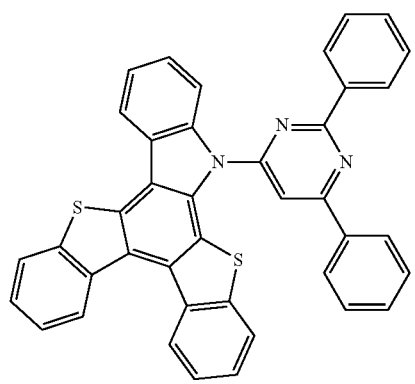
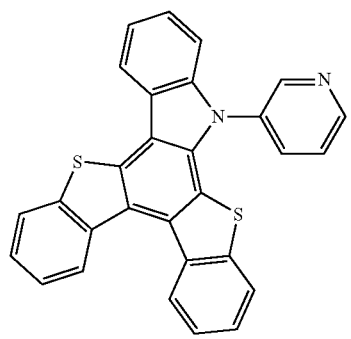
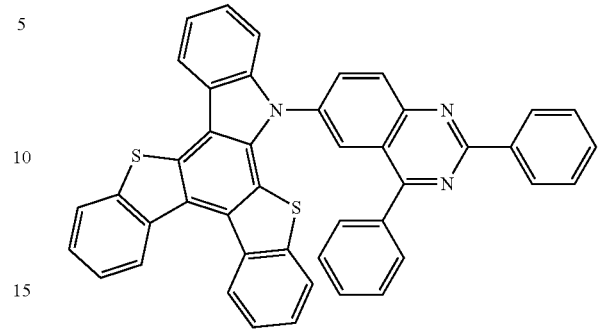
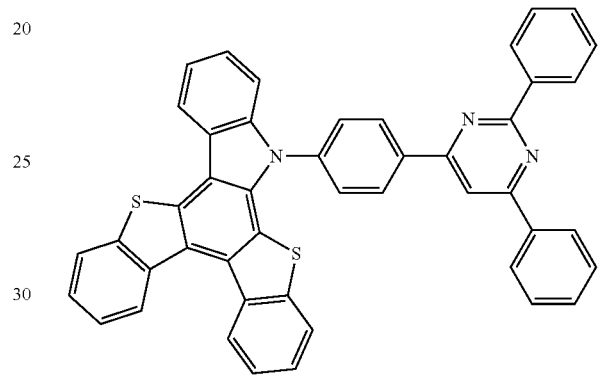
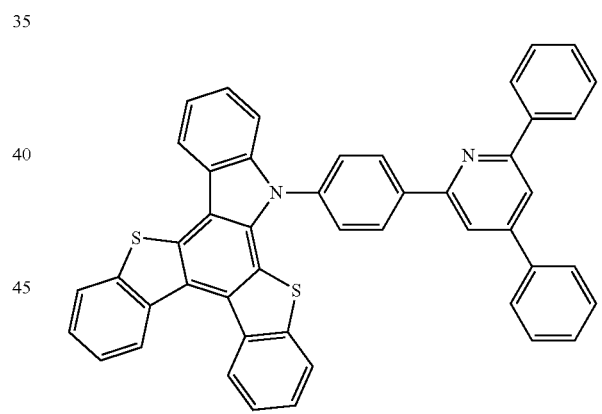

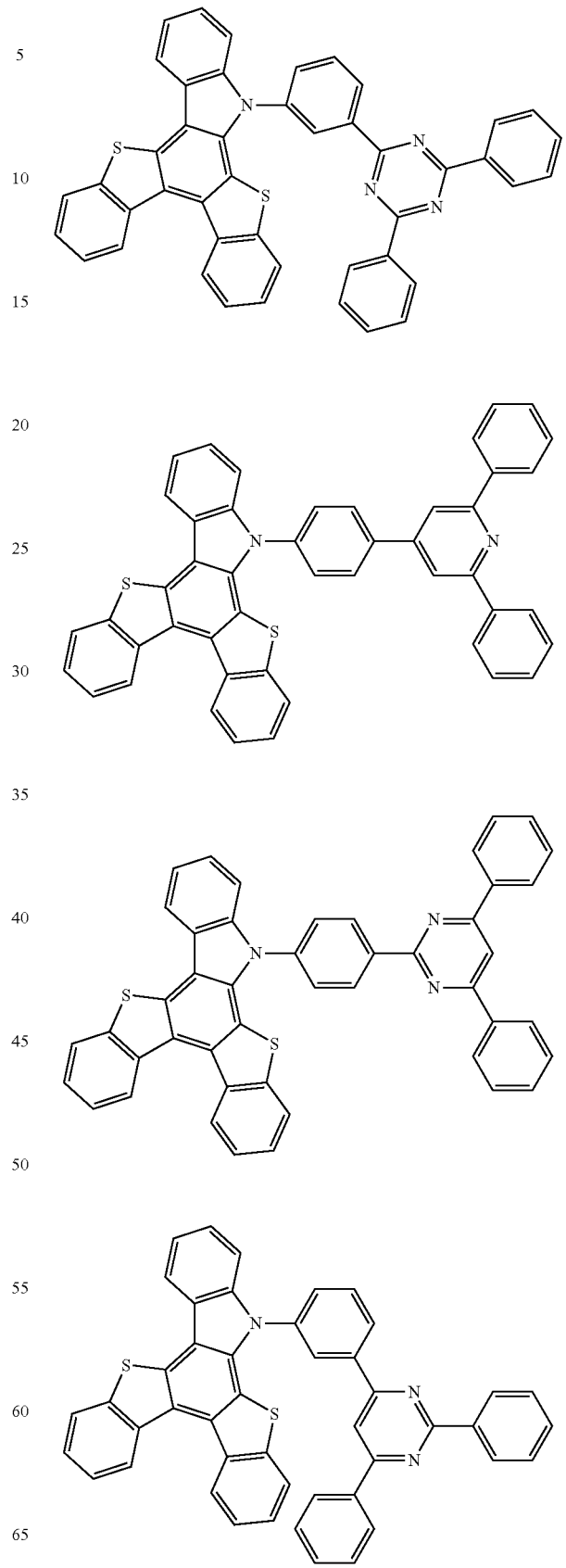

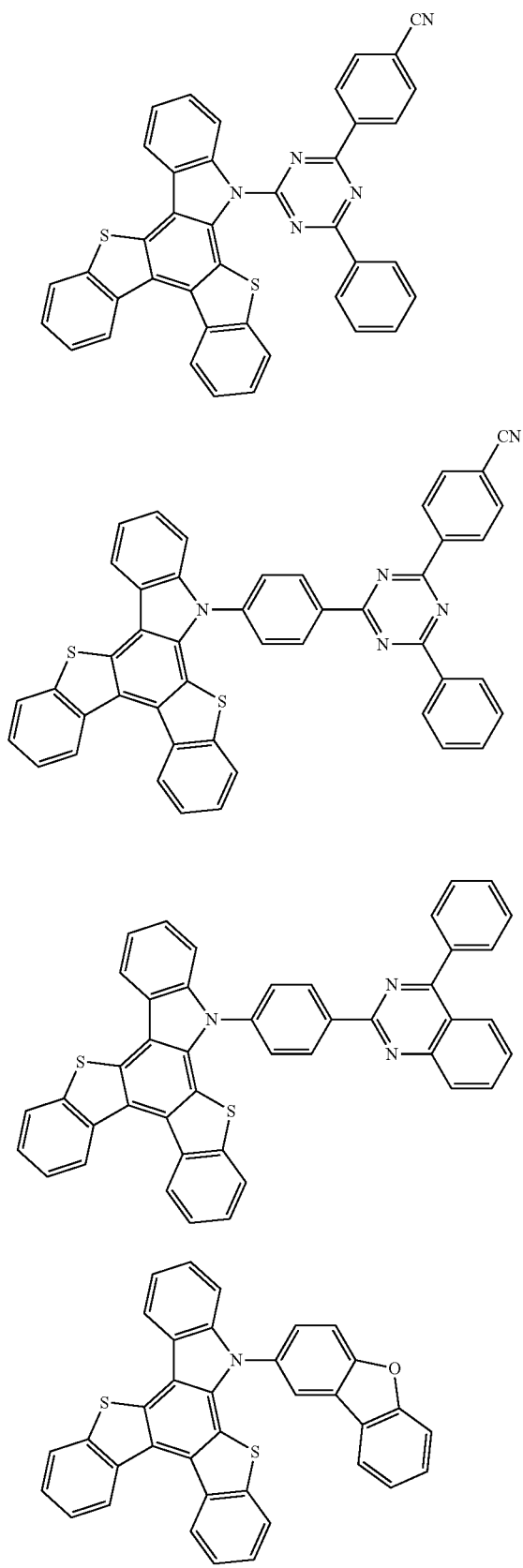
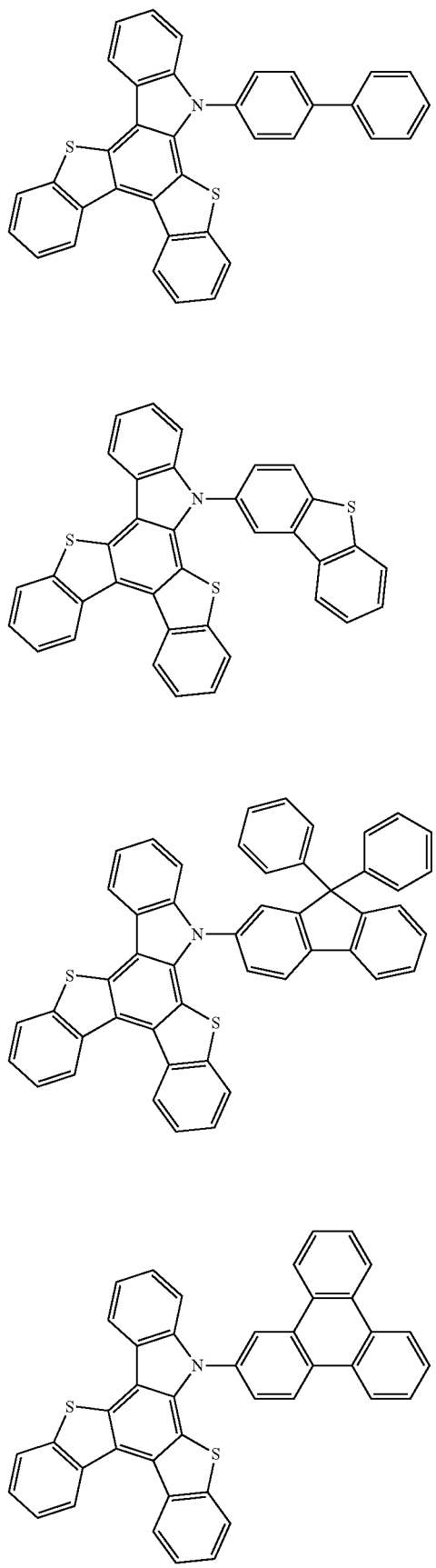

83
-continued
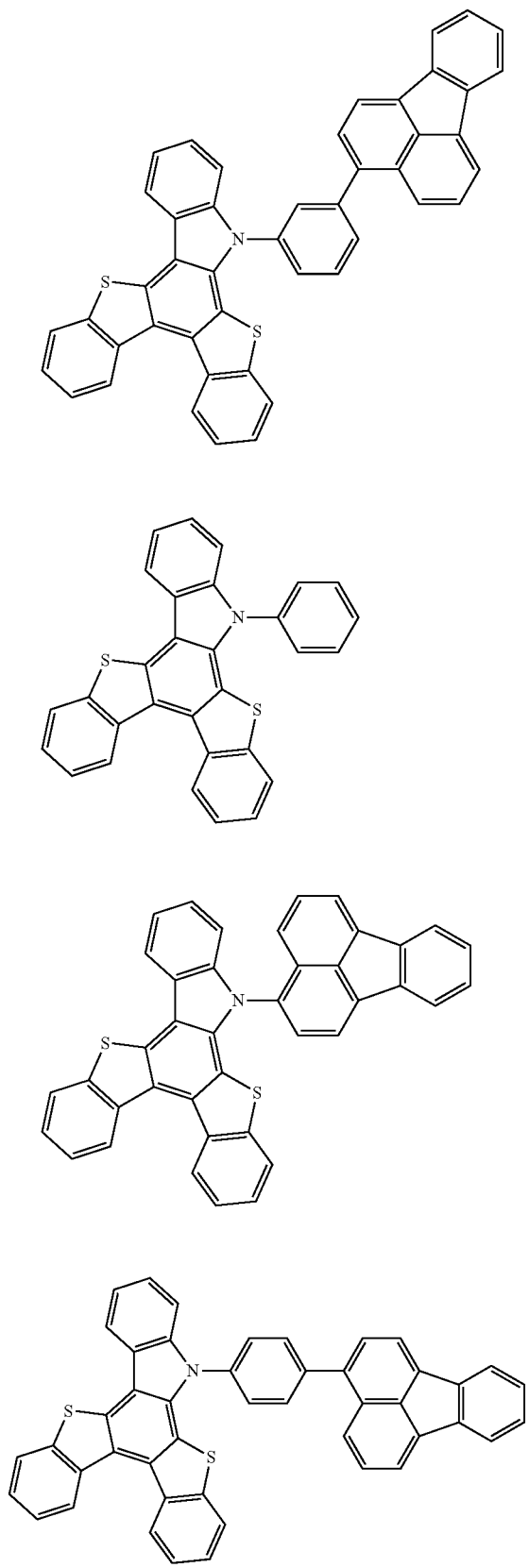
84
-continued
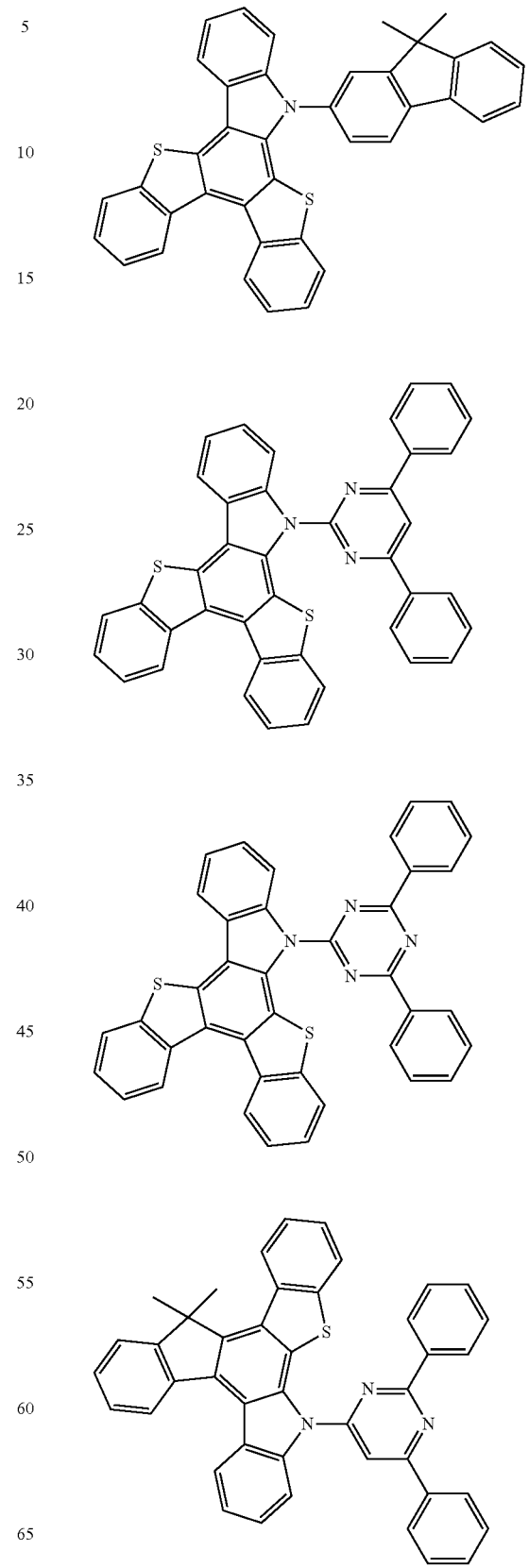

-continued
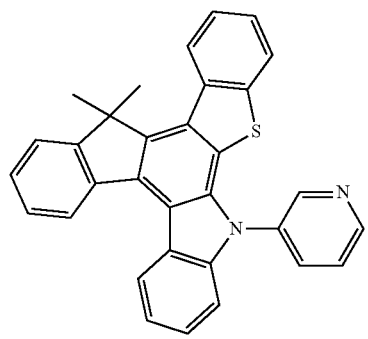
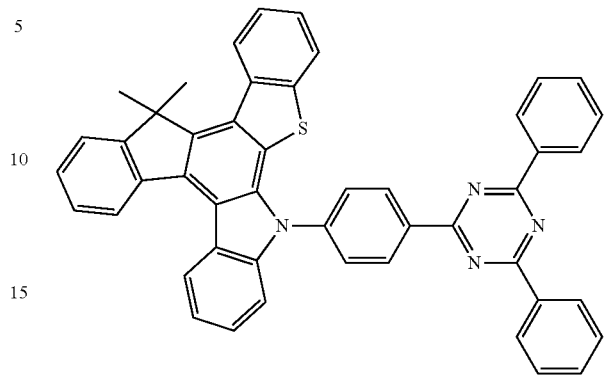
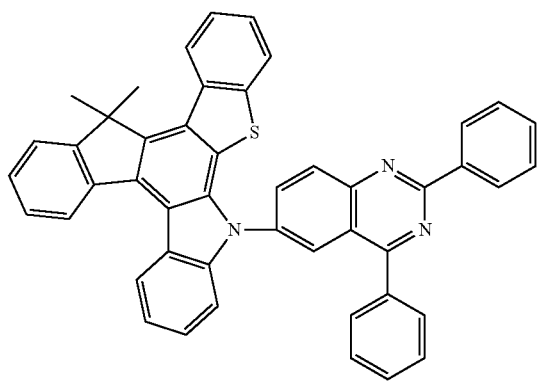
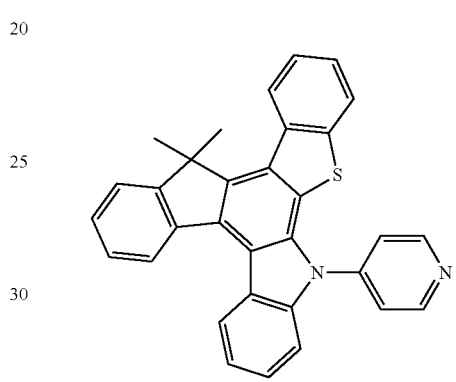
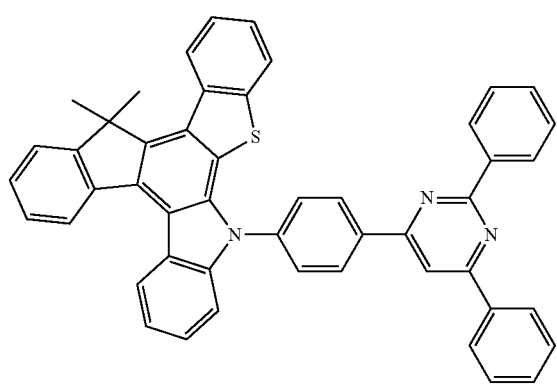
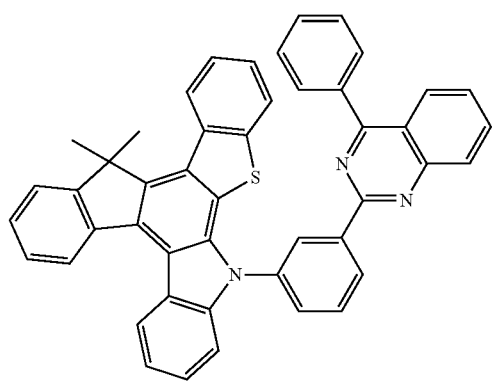
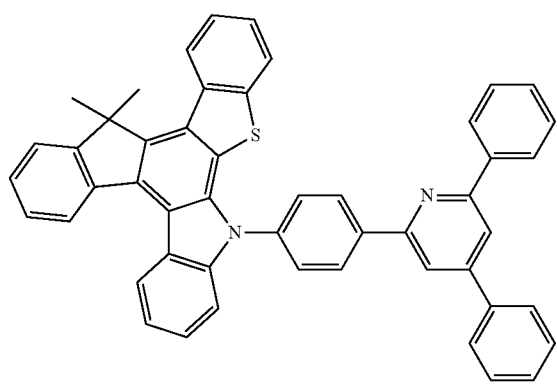

87
-continued
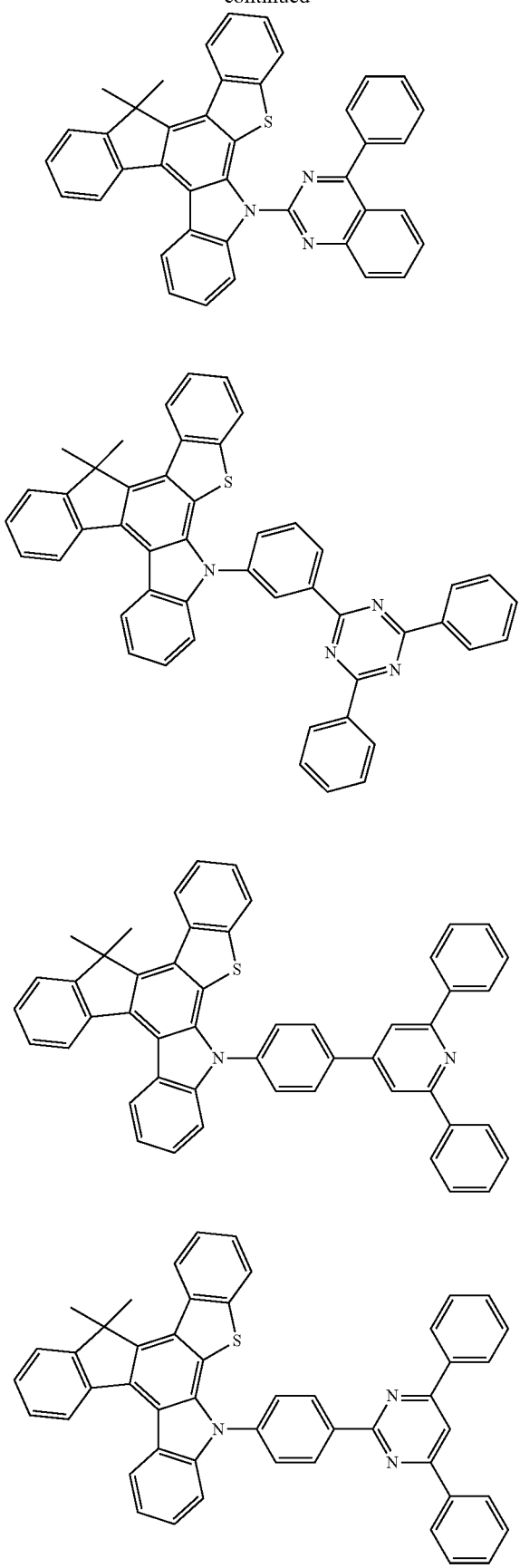
88
-continued
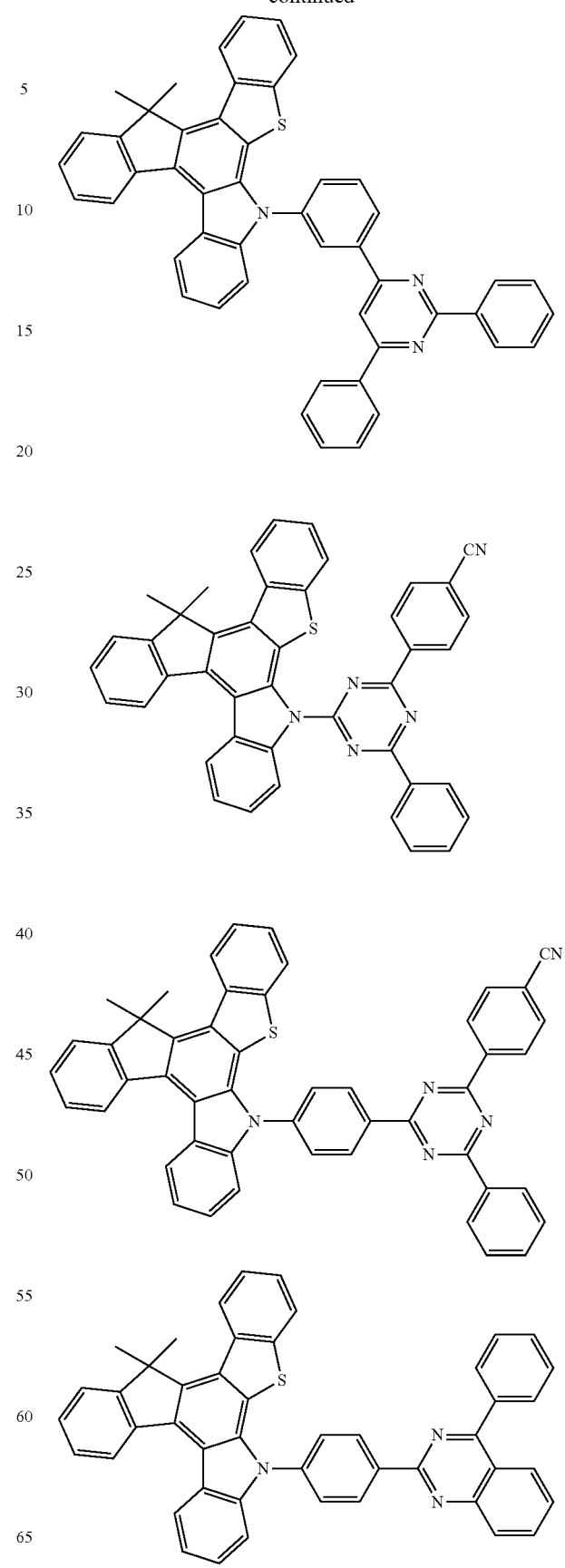

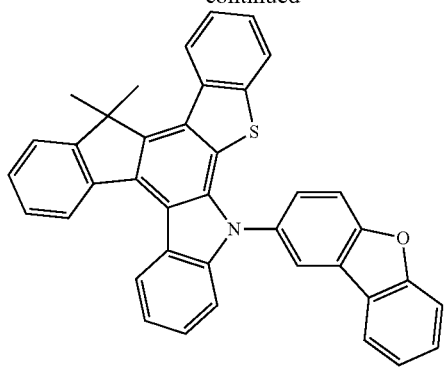
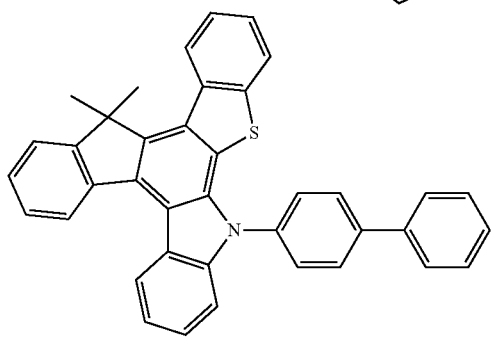
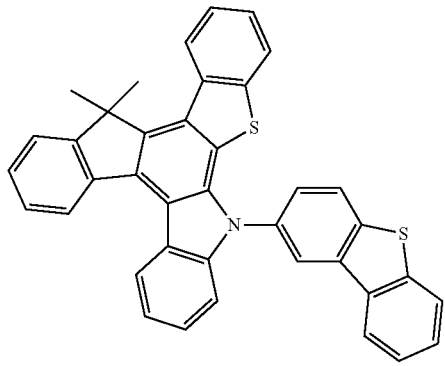
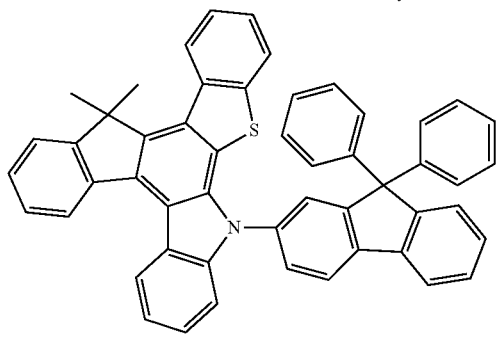
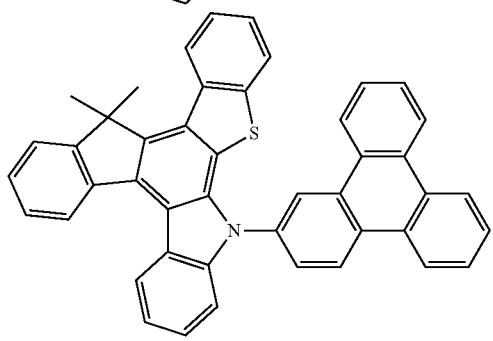
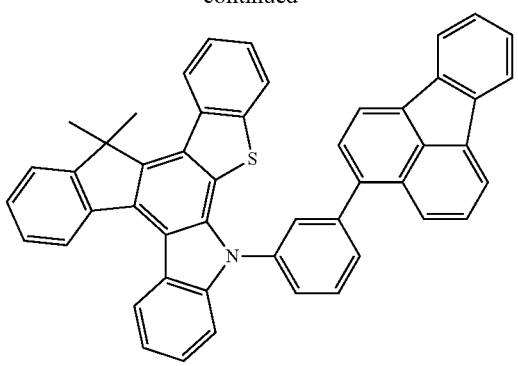
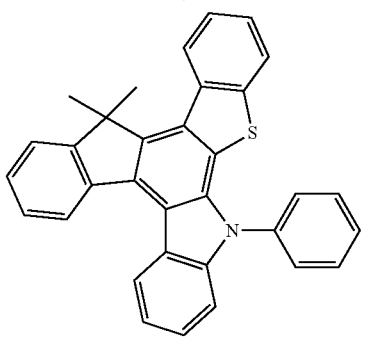
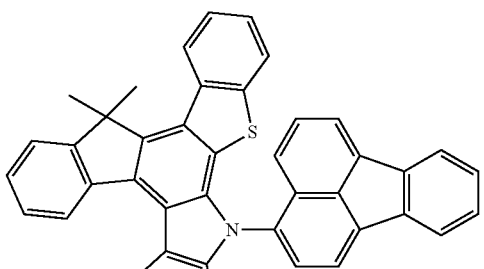
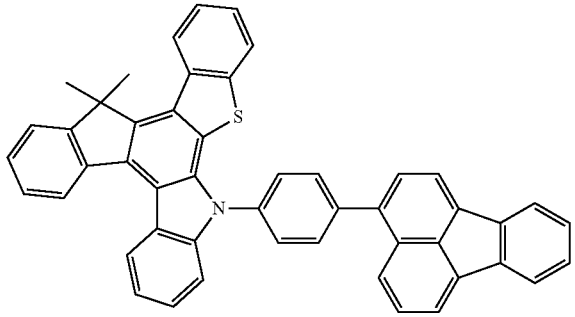

91
-continued
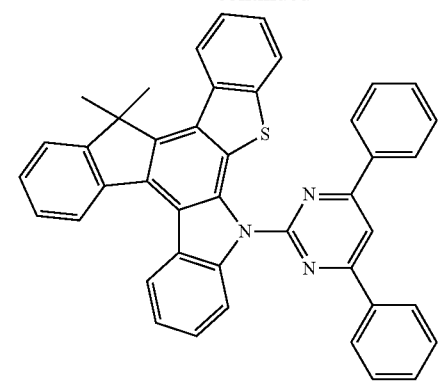
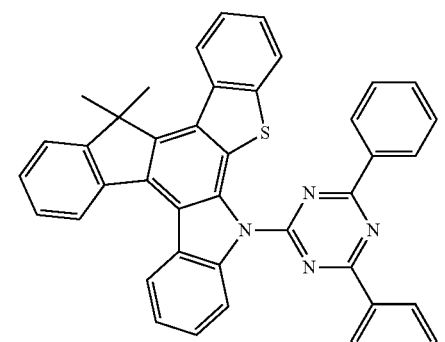
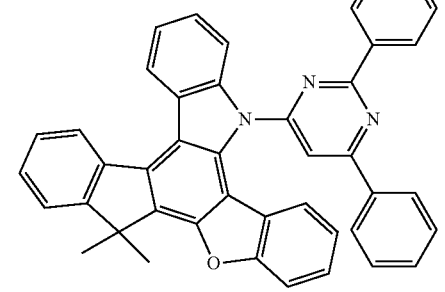
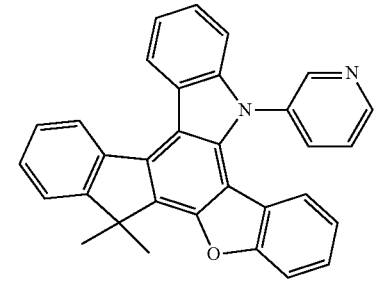
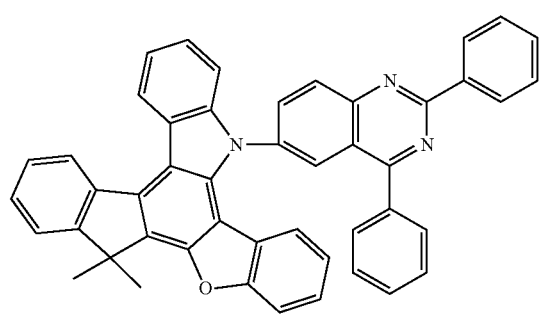
92
-continued
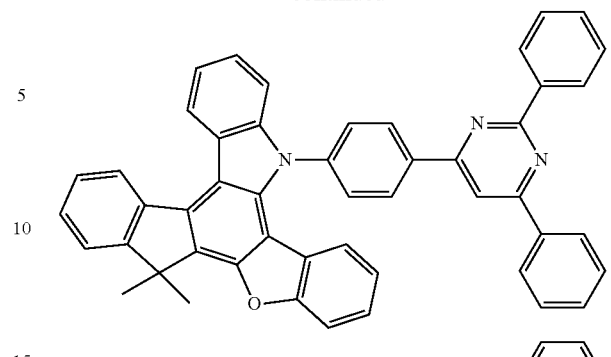
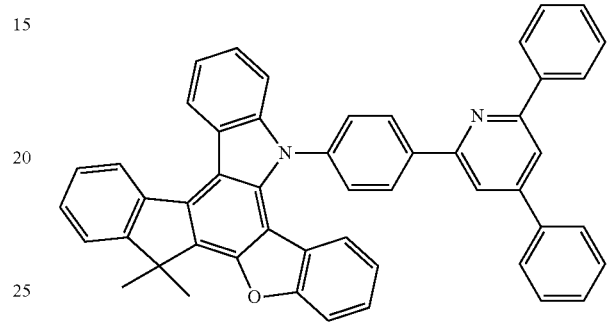
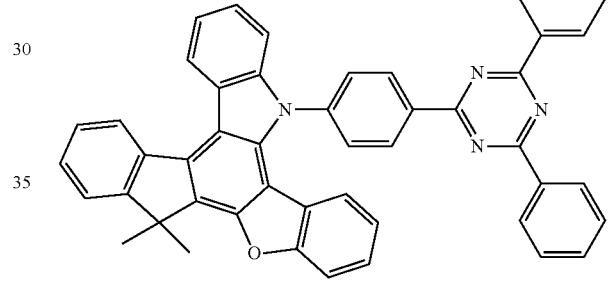
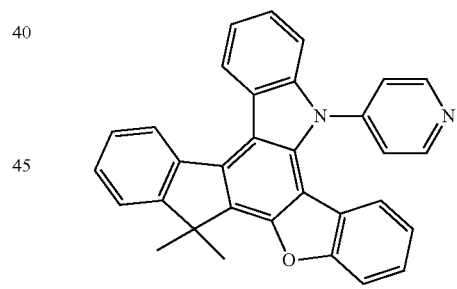
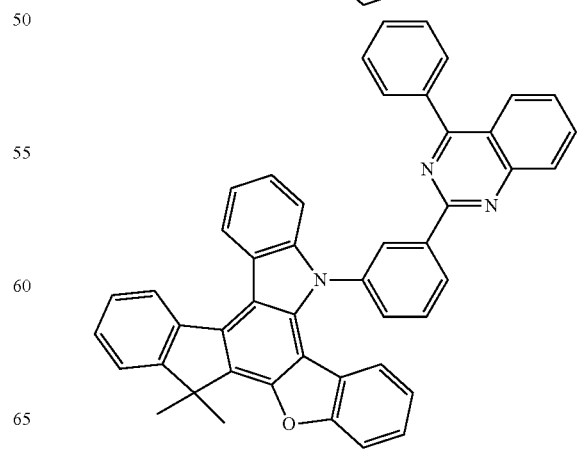

93
-continued
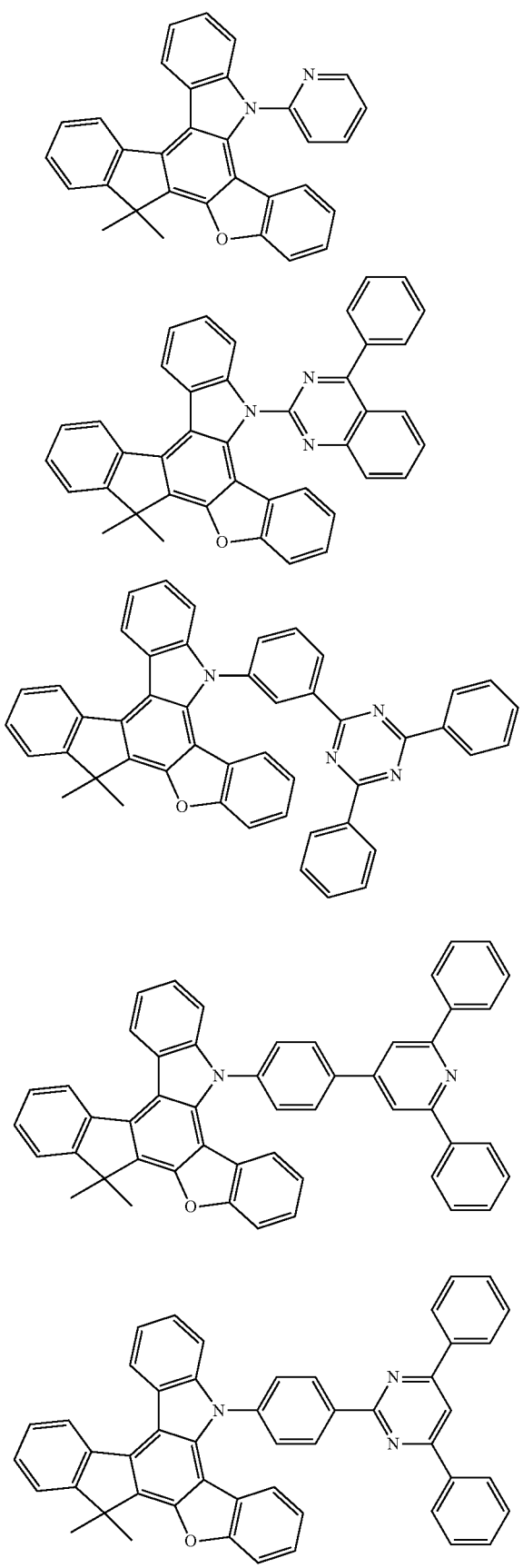
94
-continued
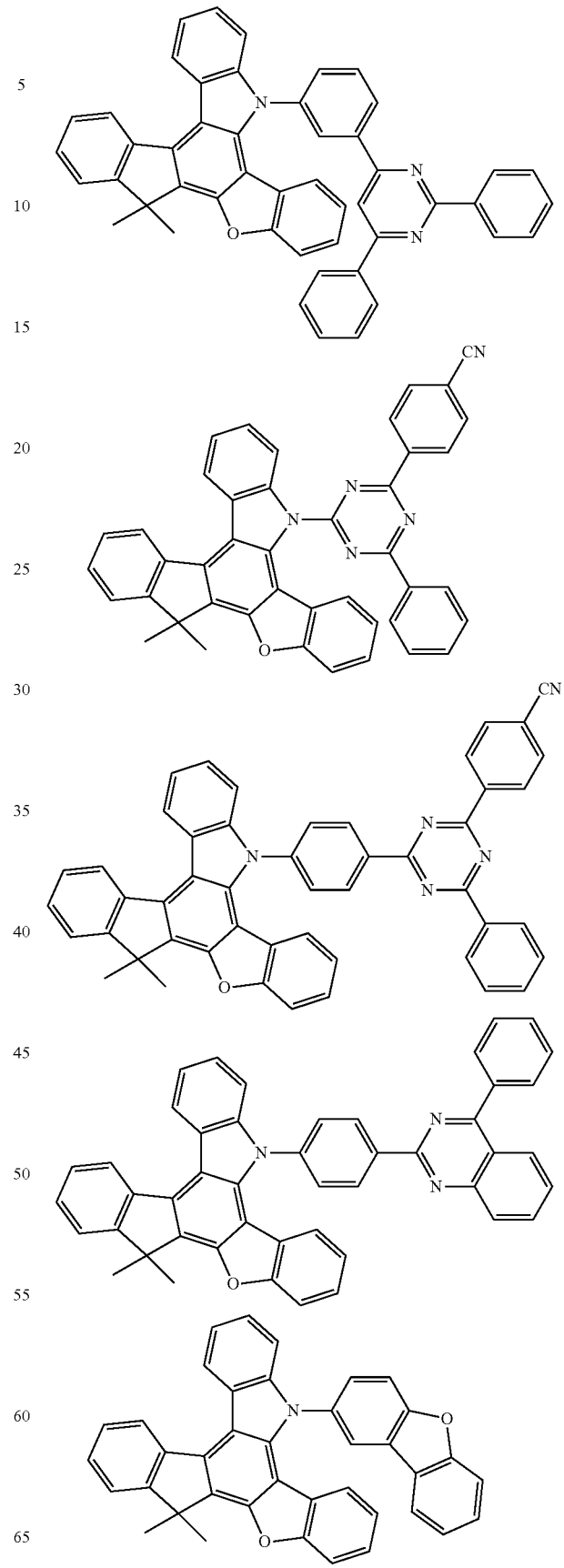

95
-continued
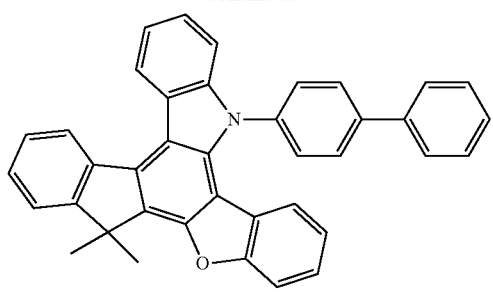
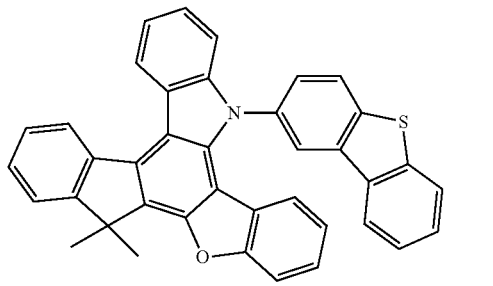
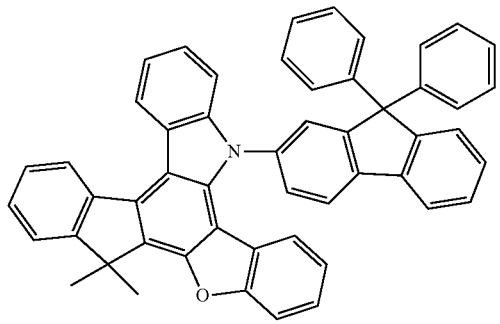
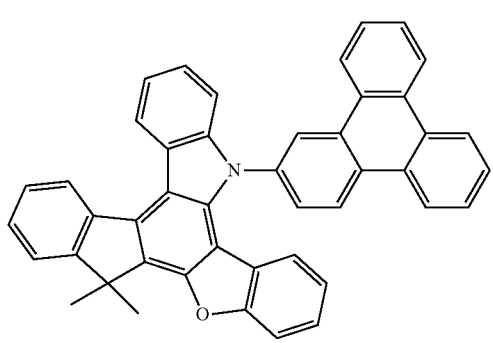
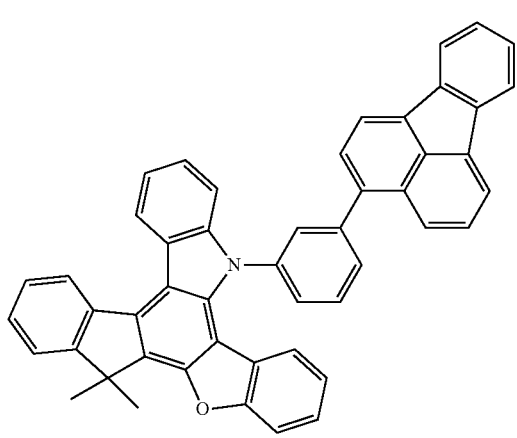
96
-continued
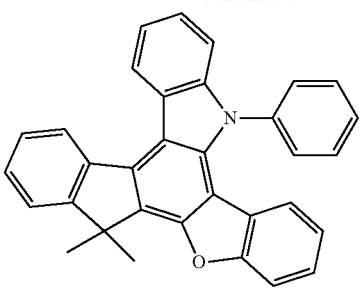
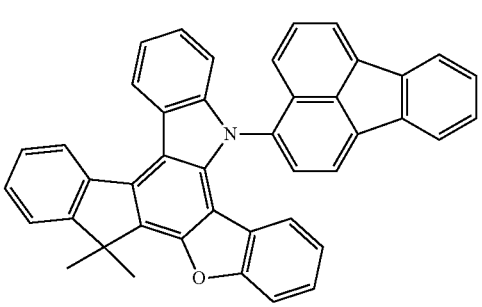
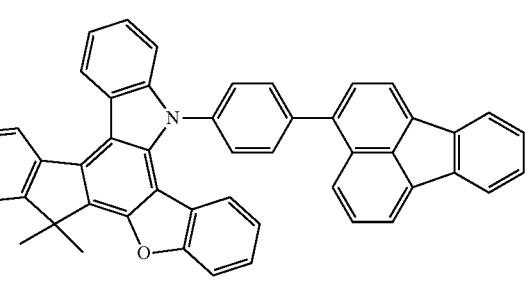
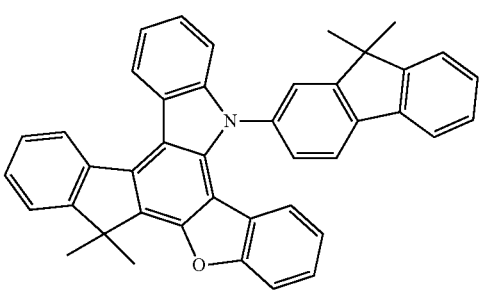
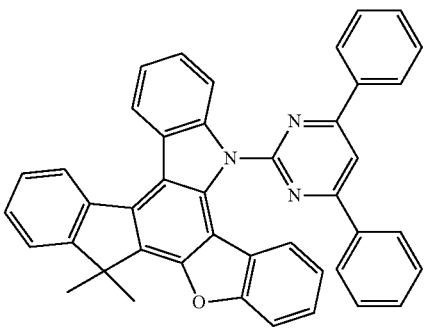

97
-continued
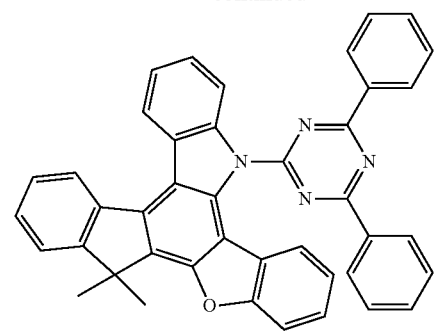
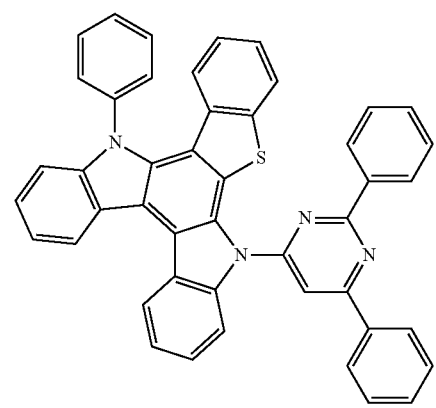
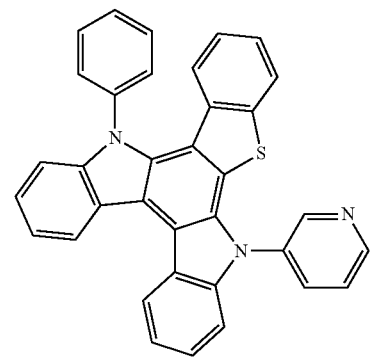
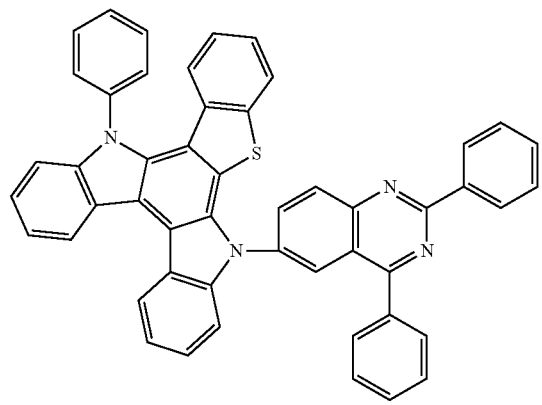
98
-continued
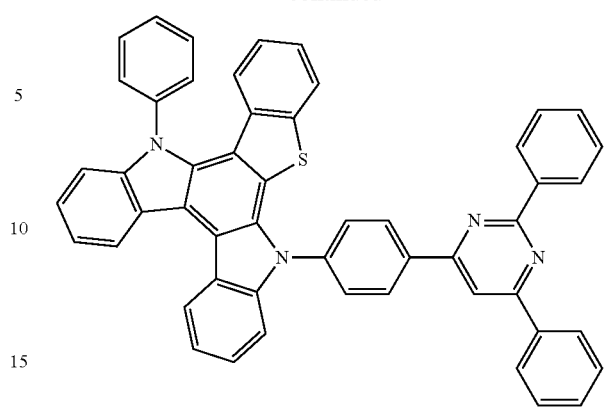
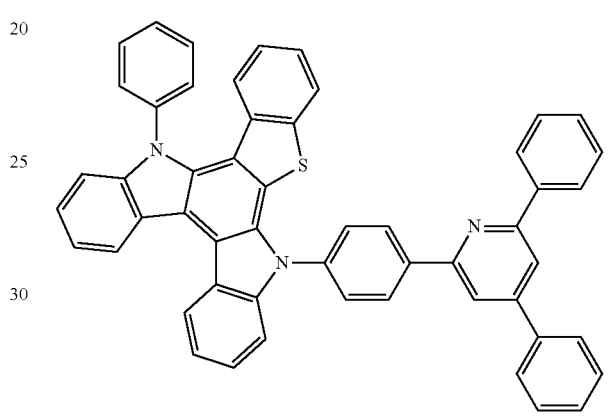
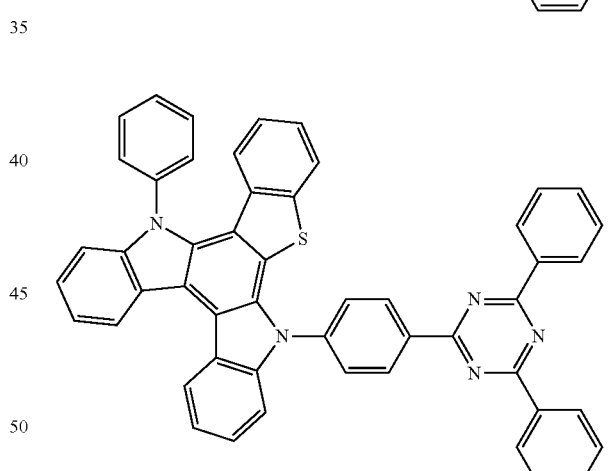
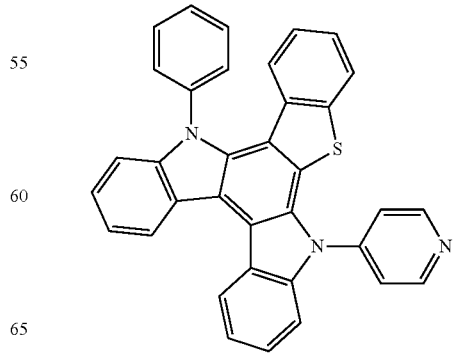

99
-continued
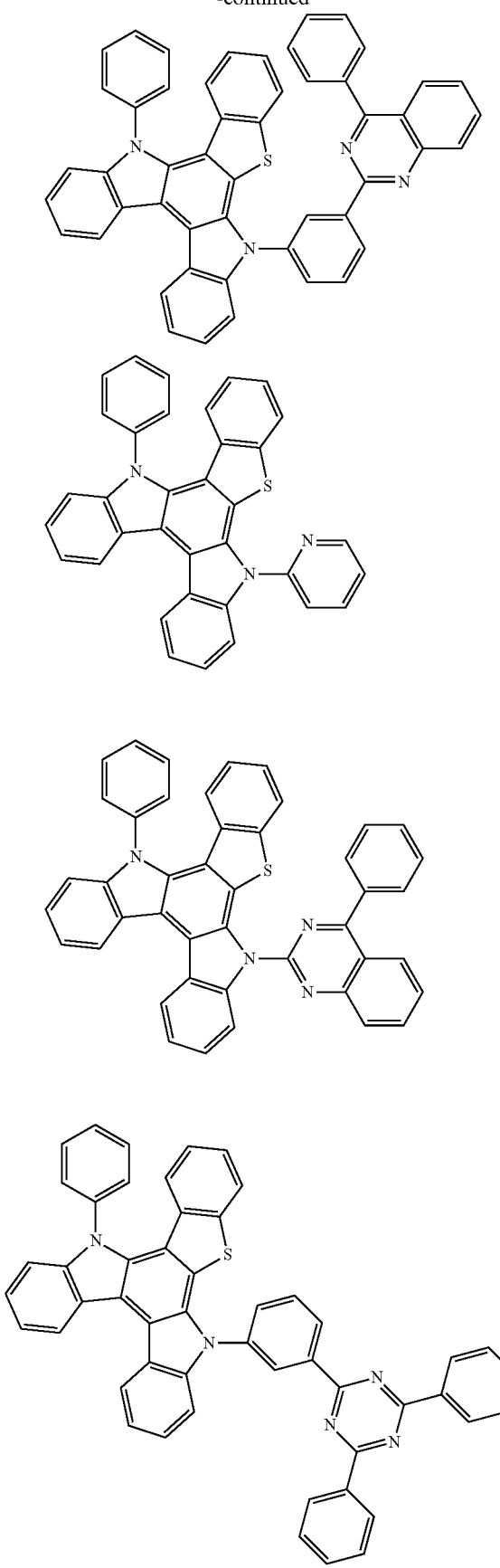
100
-continued
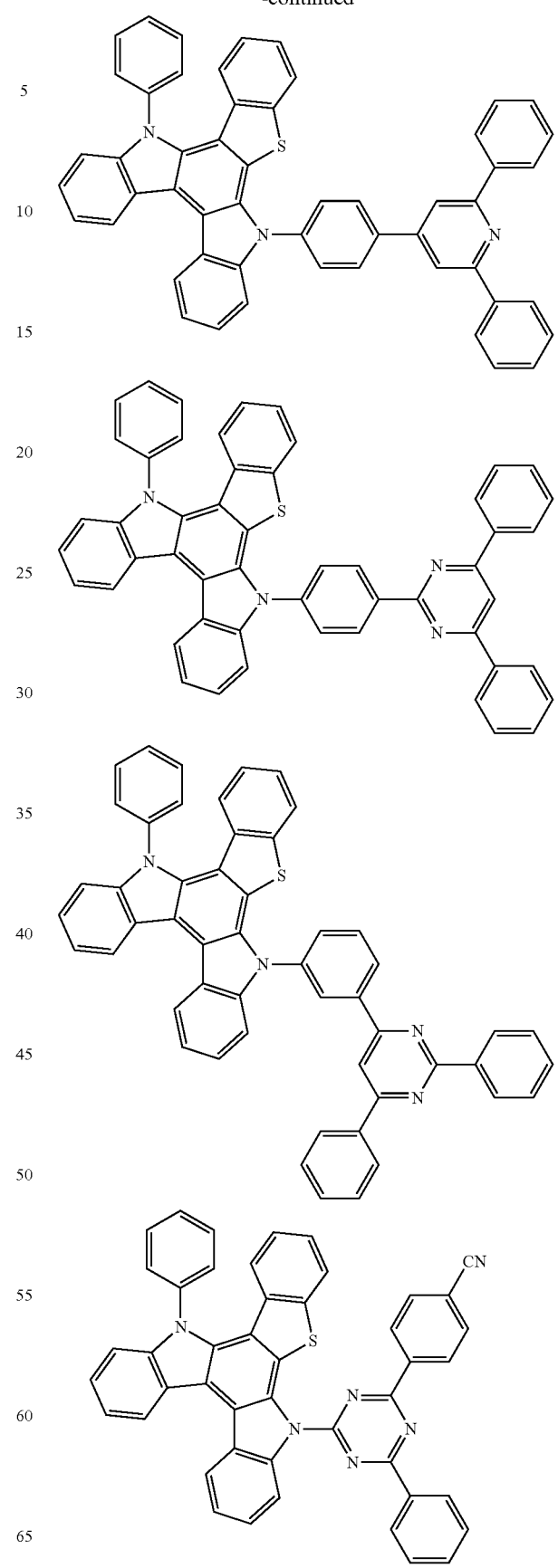

101
-continued
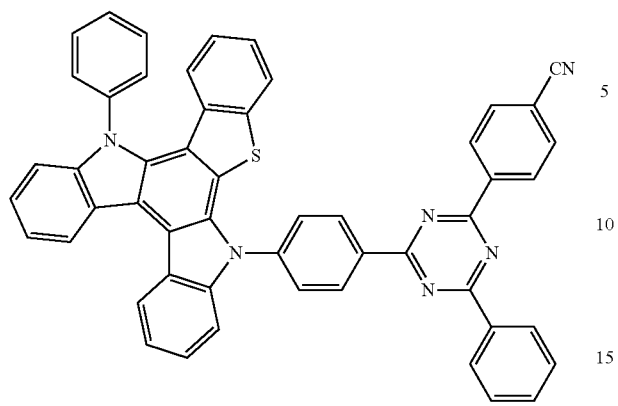
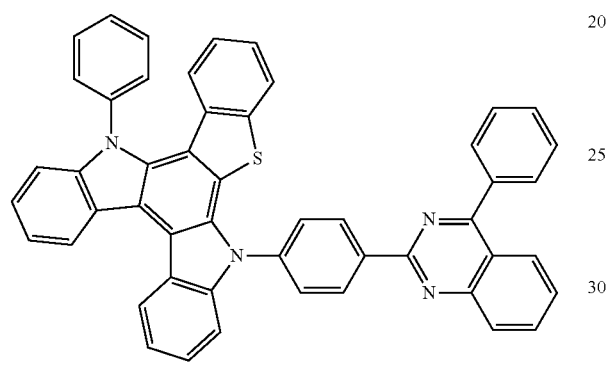
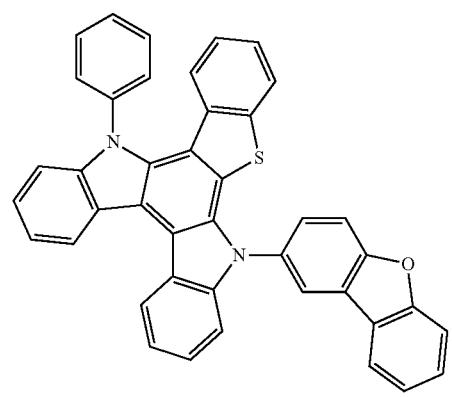
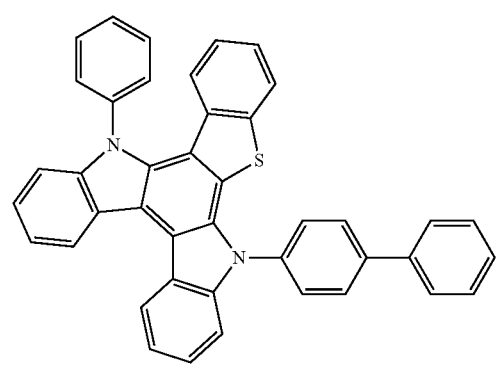
102
-continued
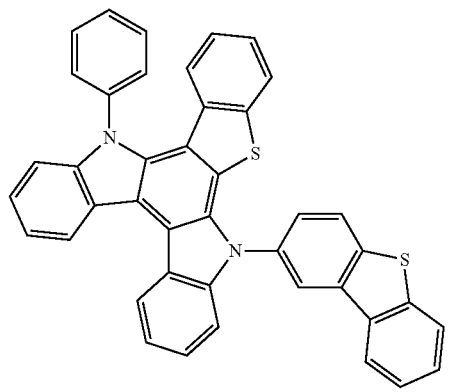
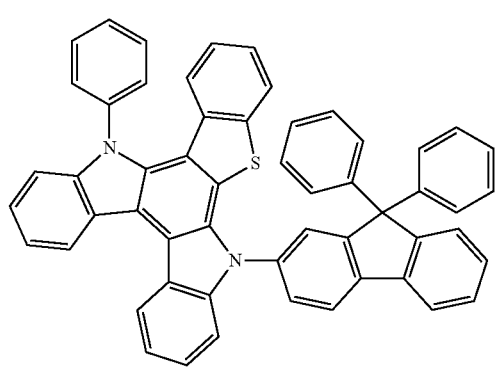
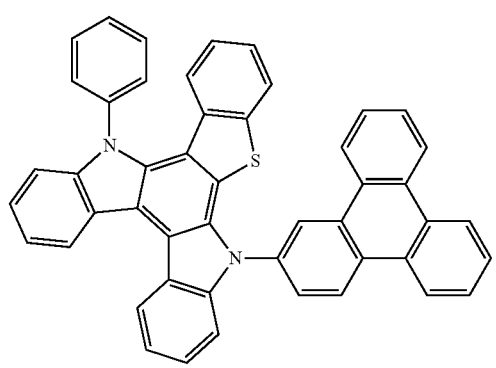
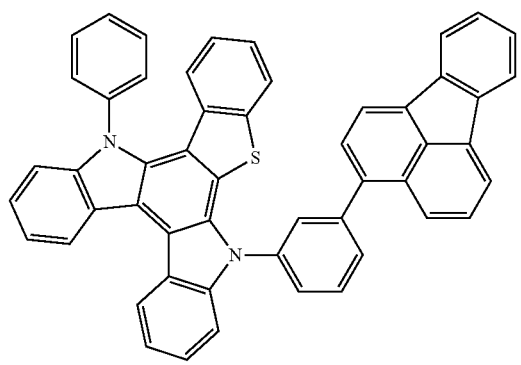

103
-continued
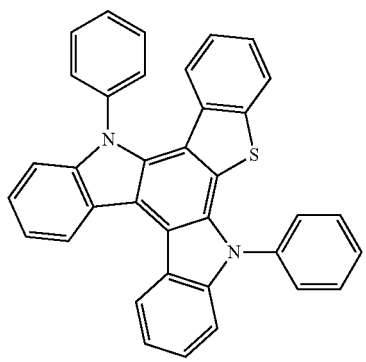
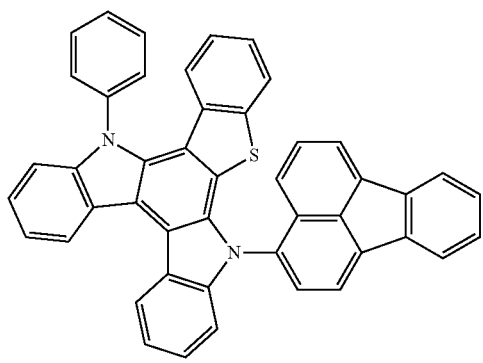
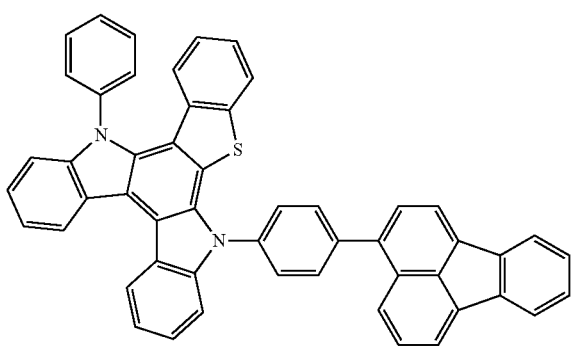
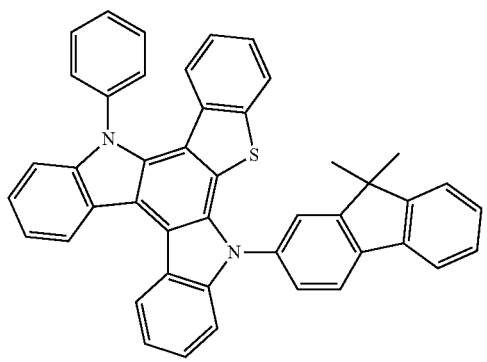
104
-continued
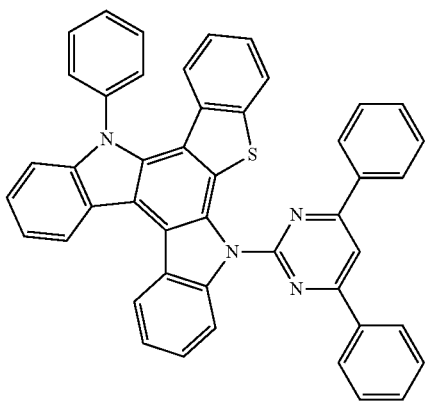
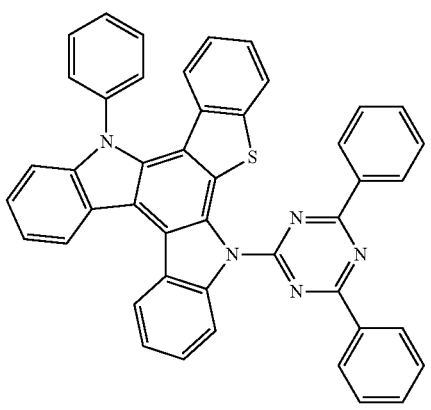
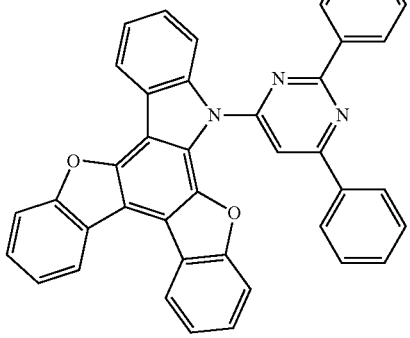
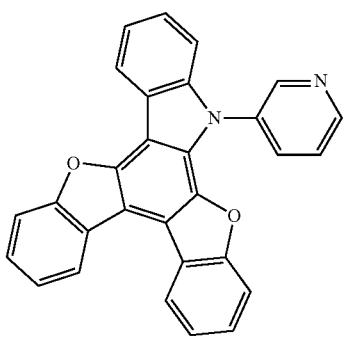

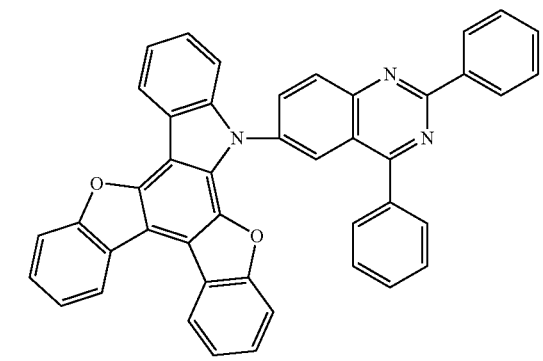
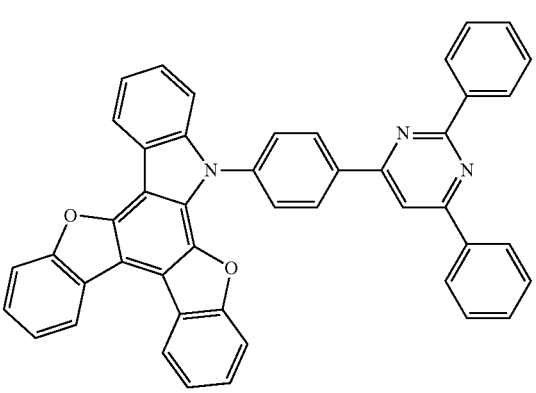
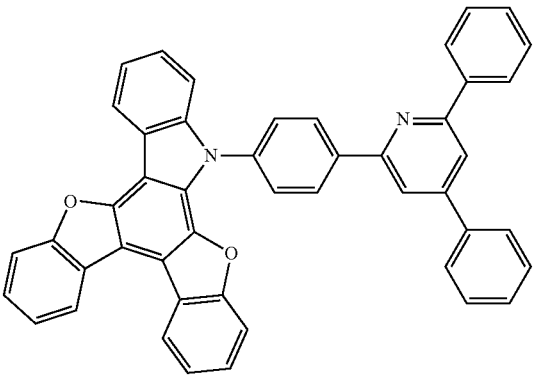
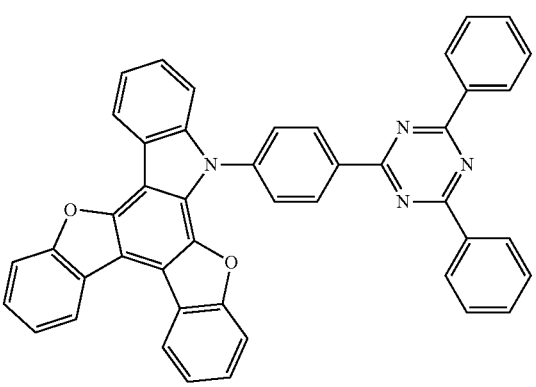
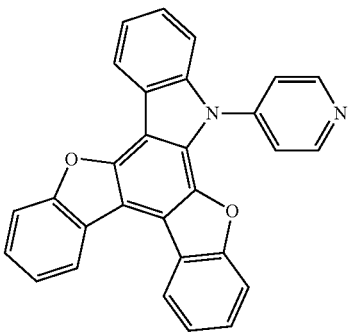
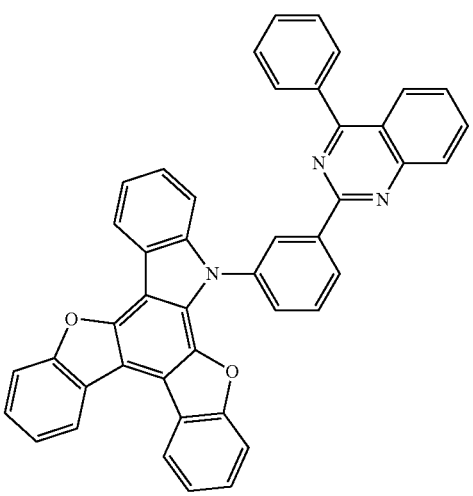
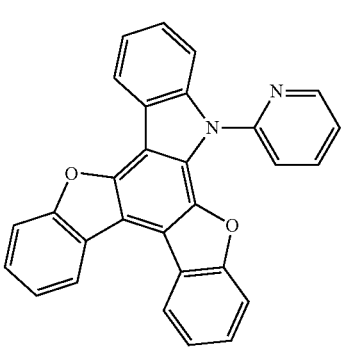
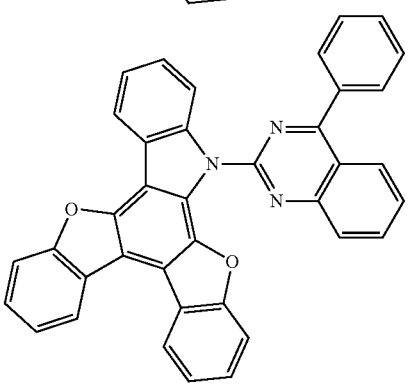

107
-continued
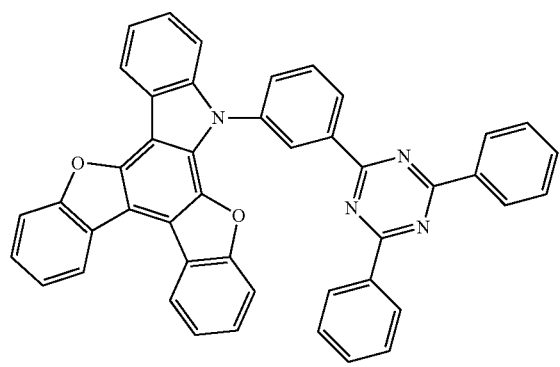
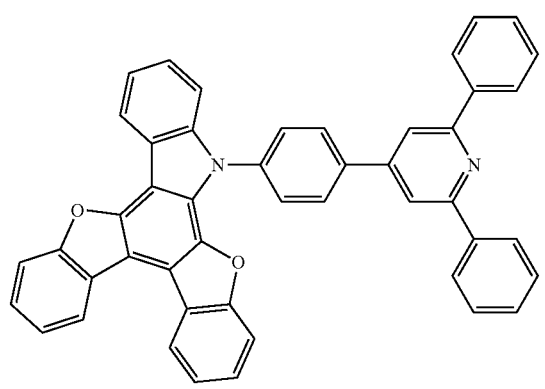
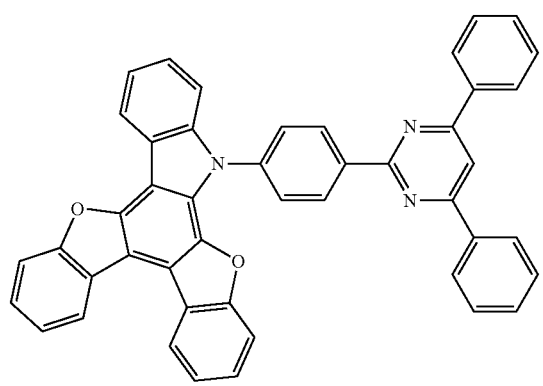
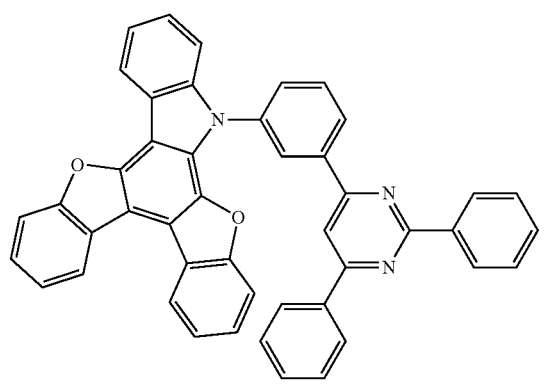
108
-continued
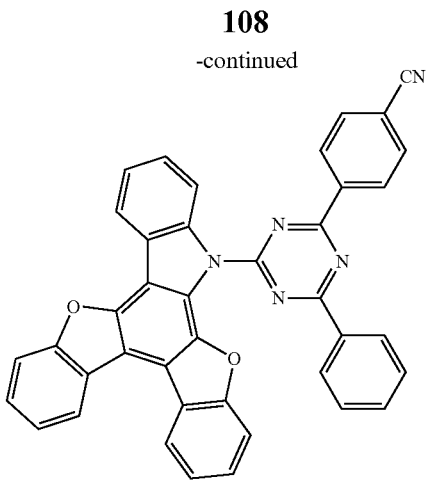
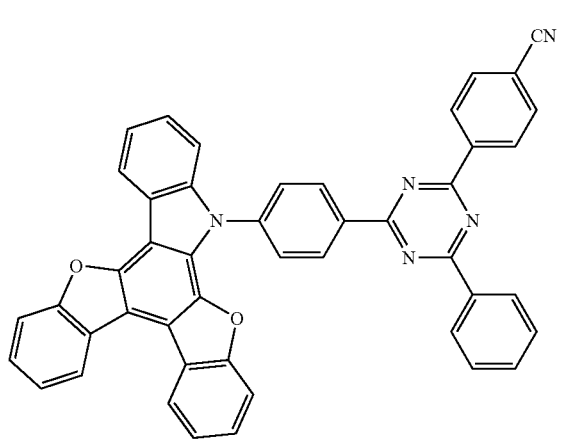
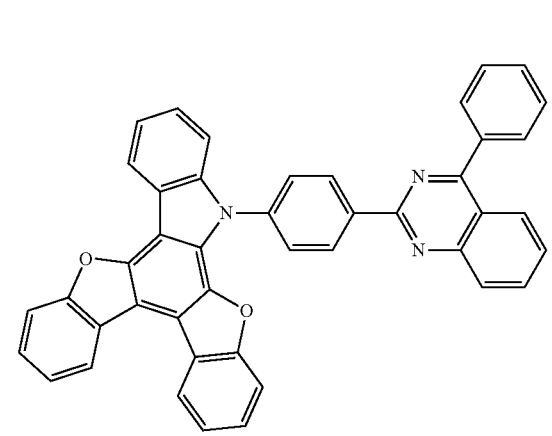
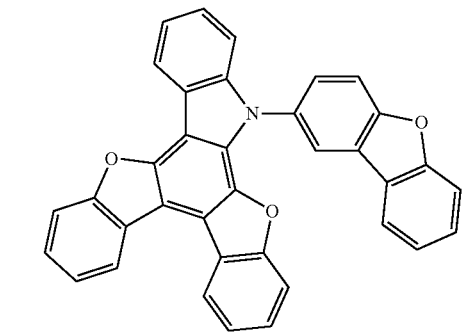

109
-continued
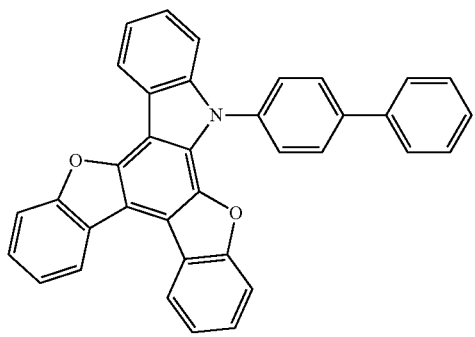
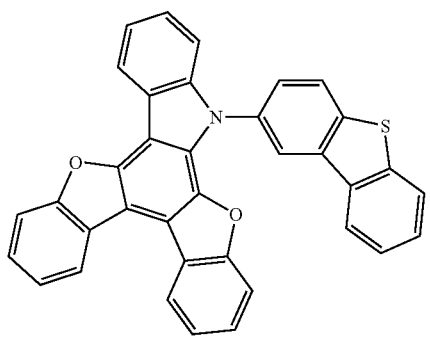
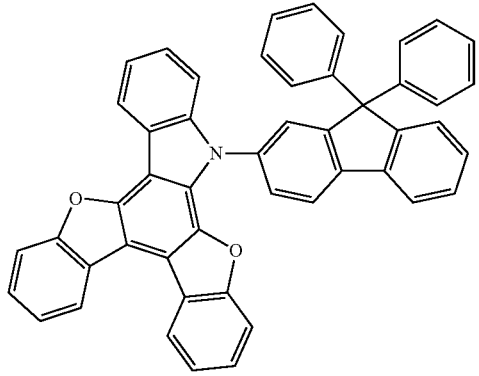
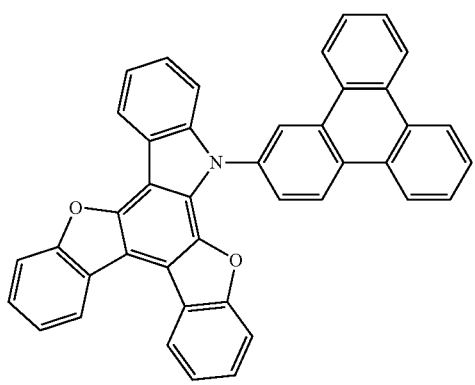
110
-continued
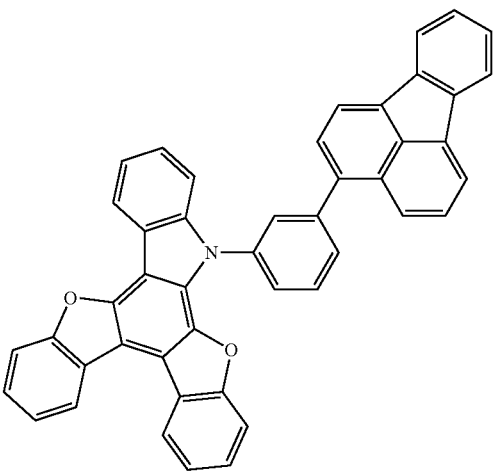
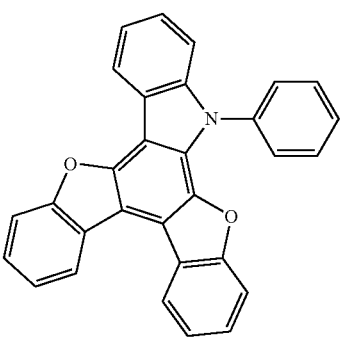
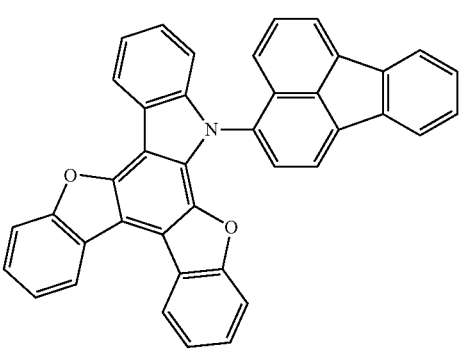
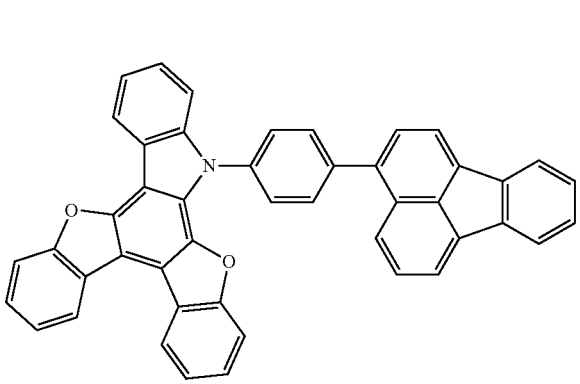

111
-continued
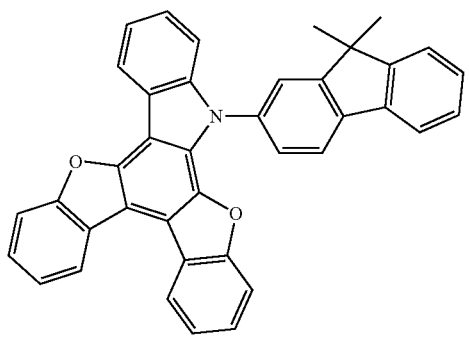
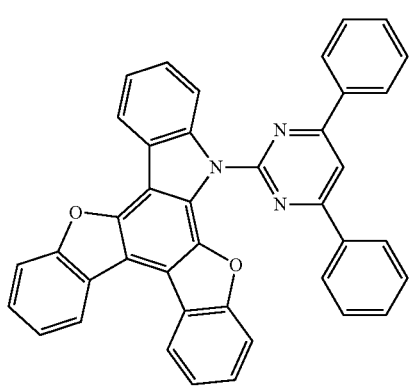
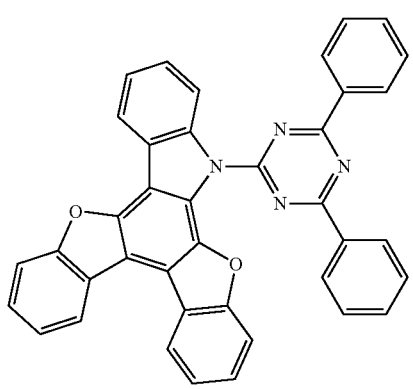
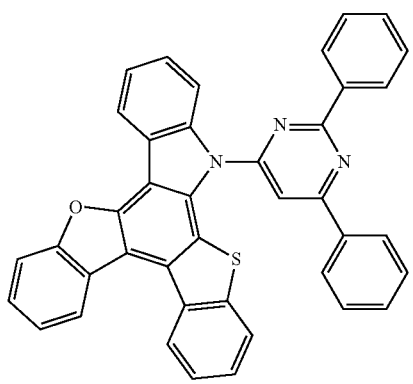
112
-continued
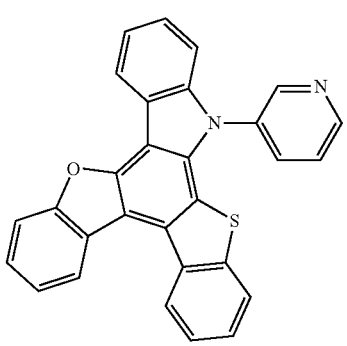
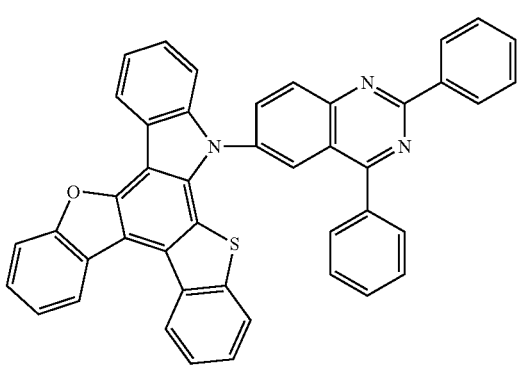
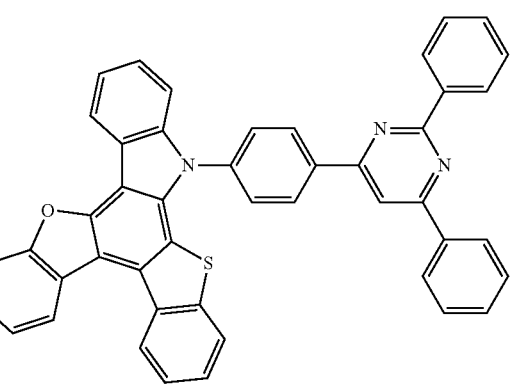
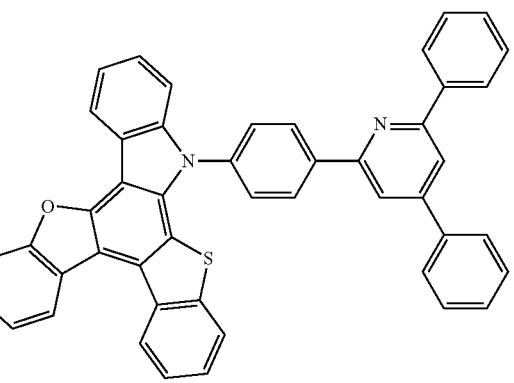

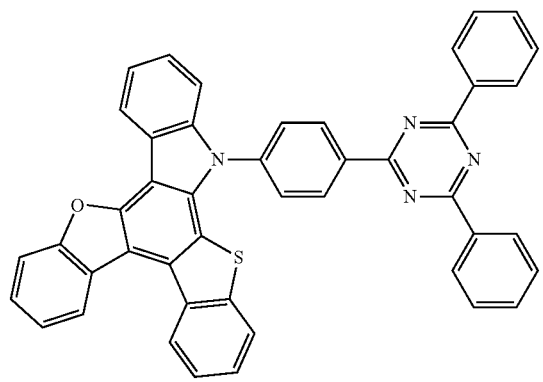
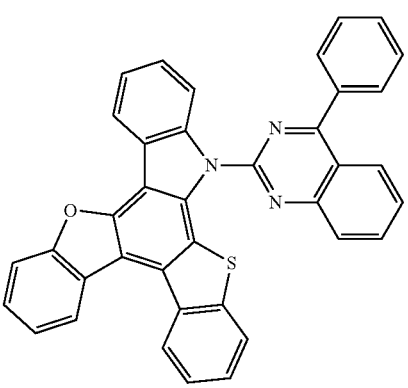
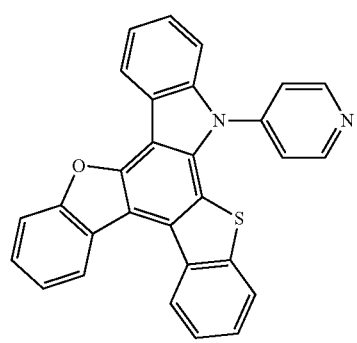
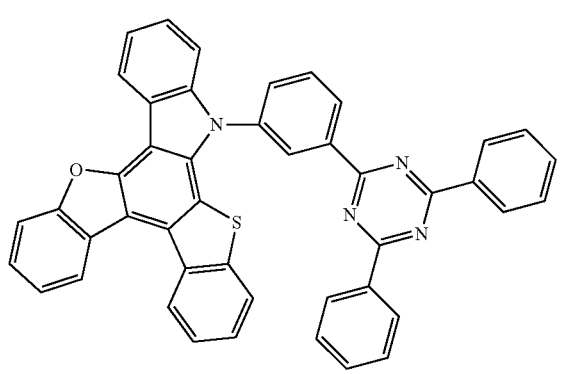
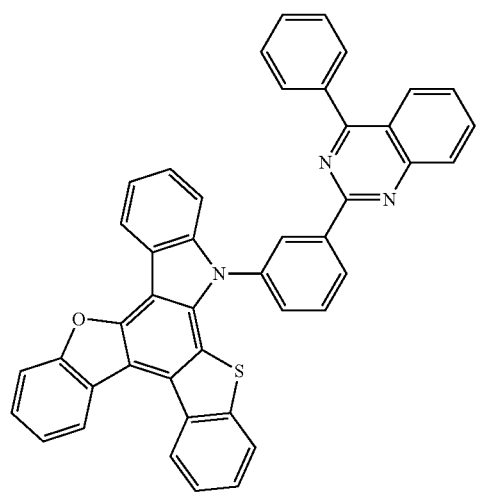
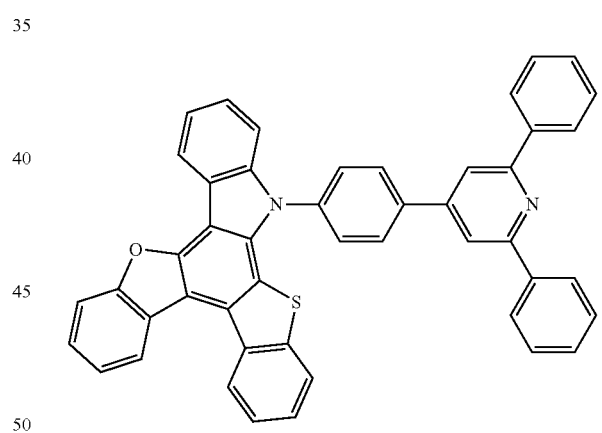
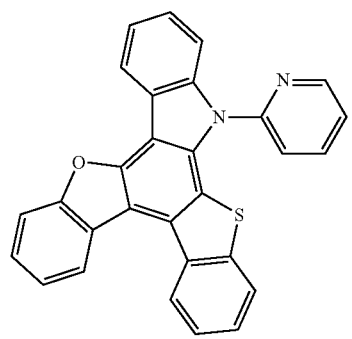
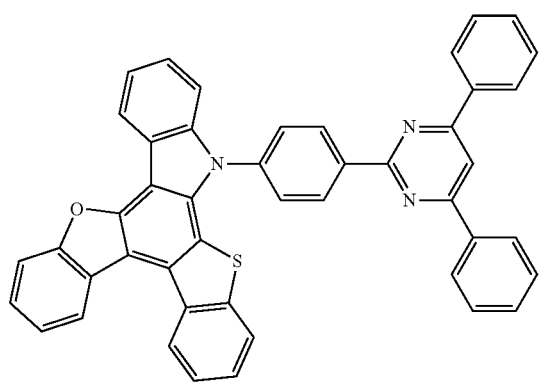

115
-continued
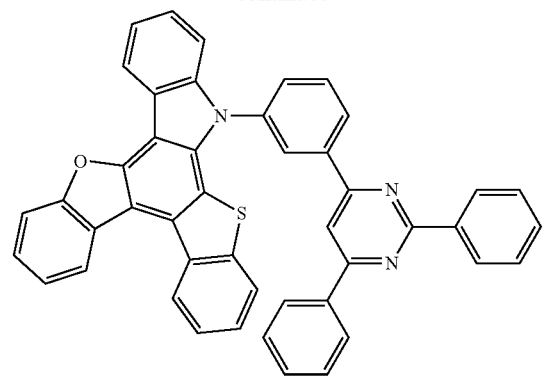
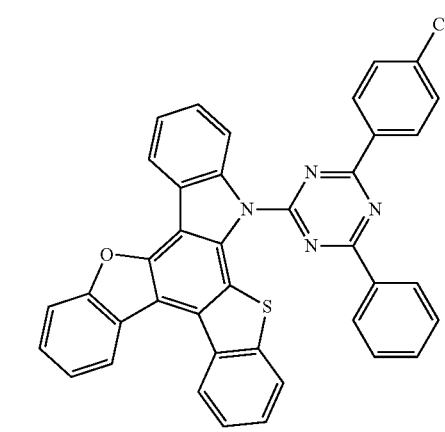
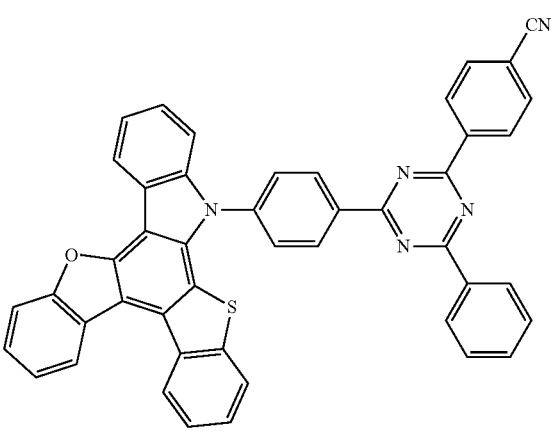
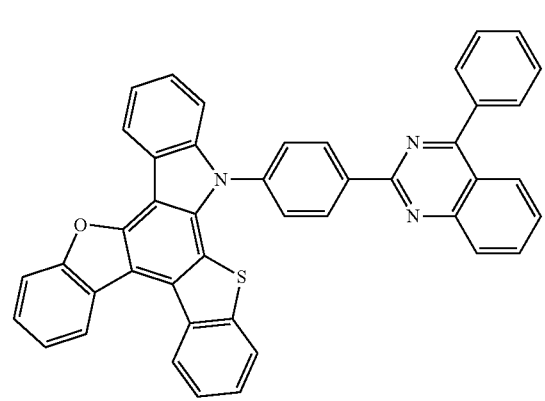
116
-continued
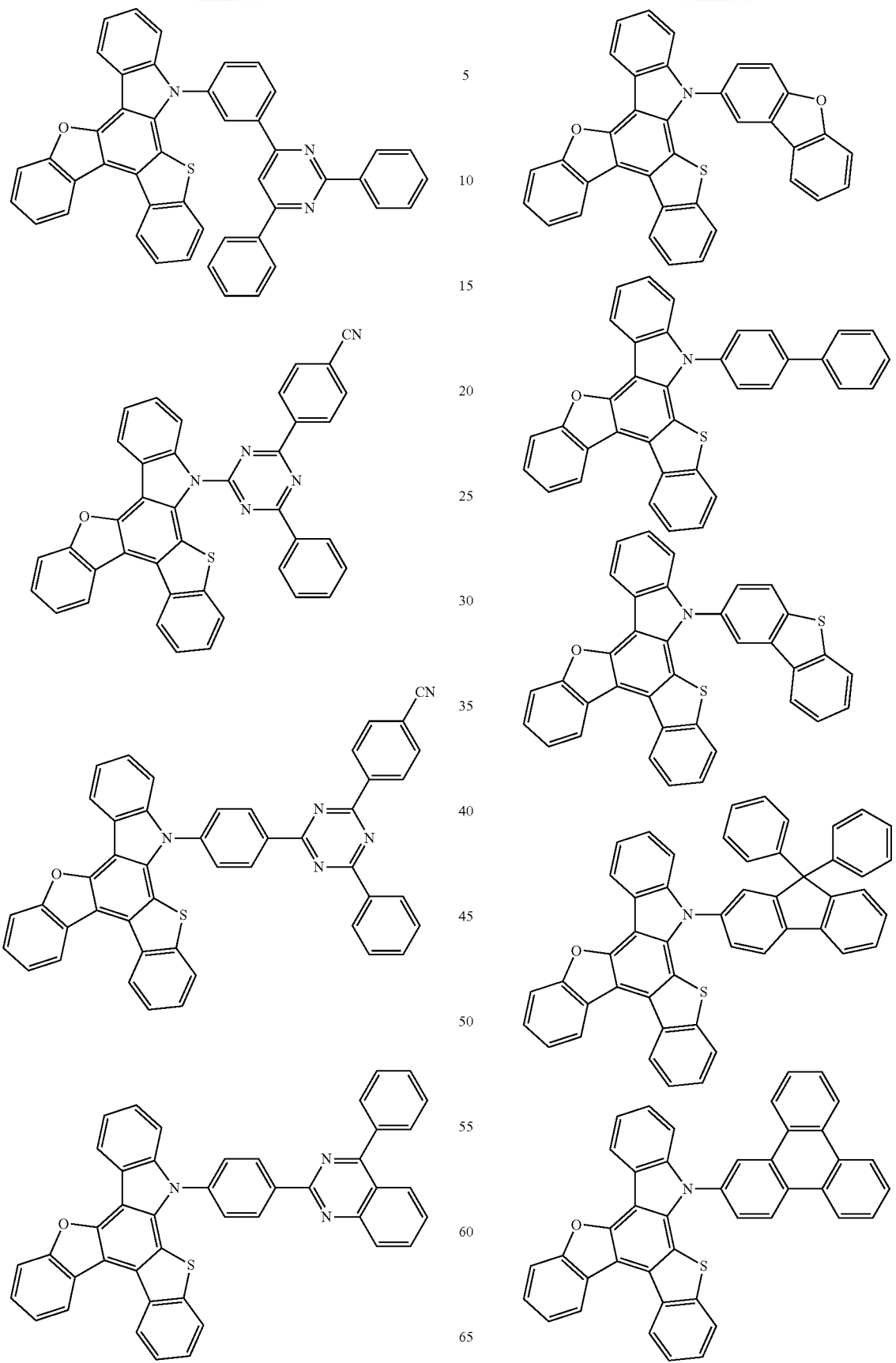

117
-continued
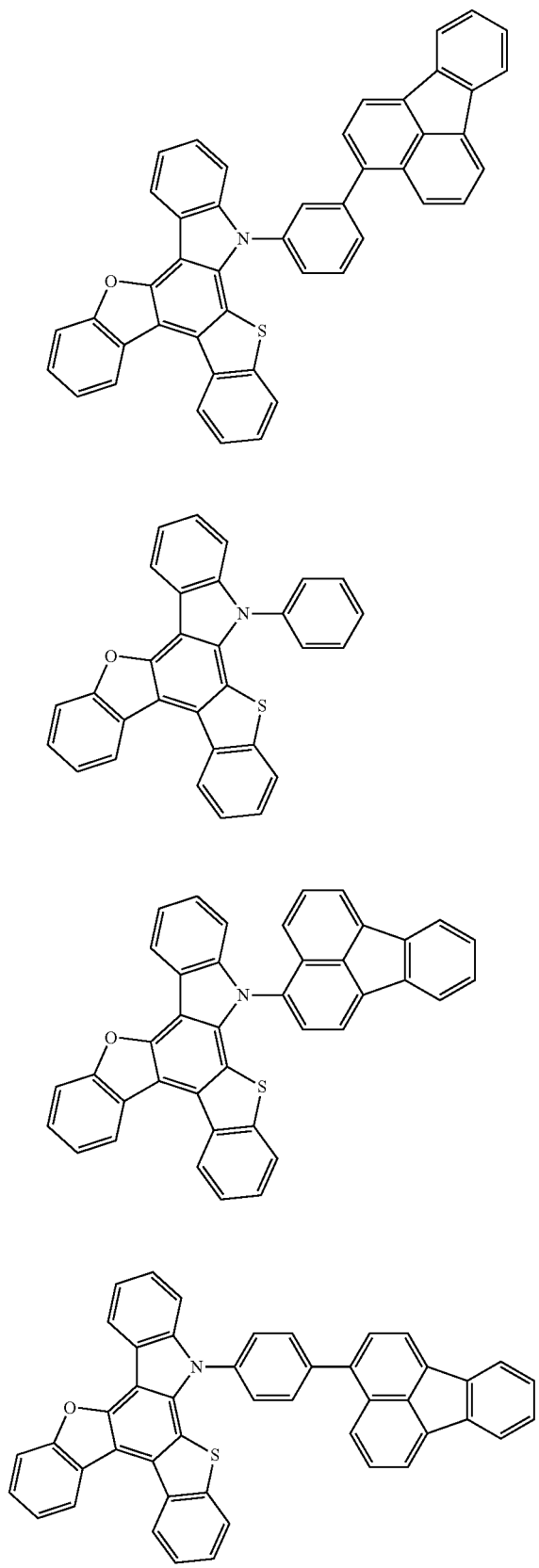
118
-continued
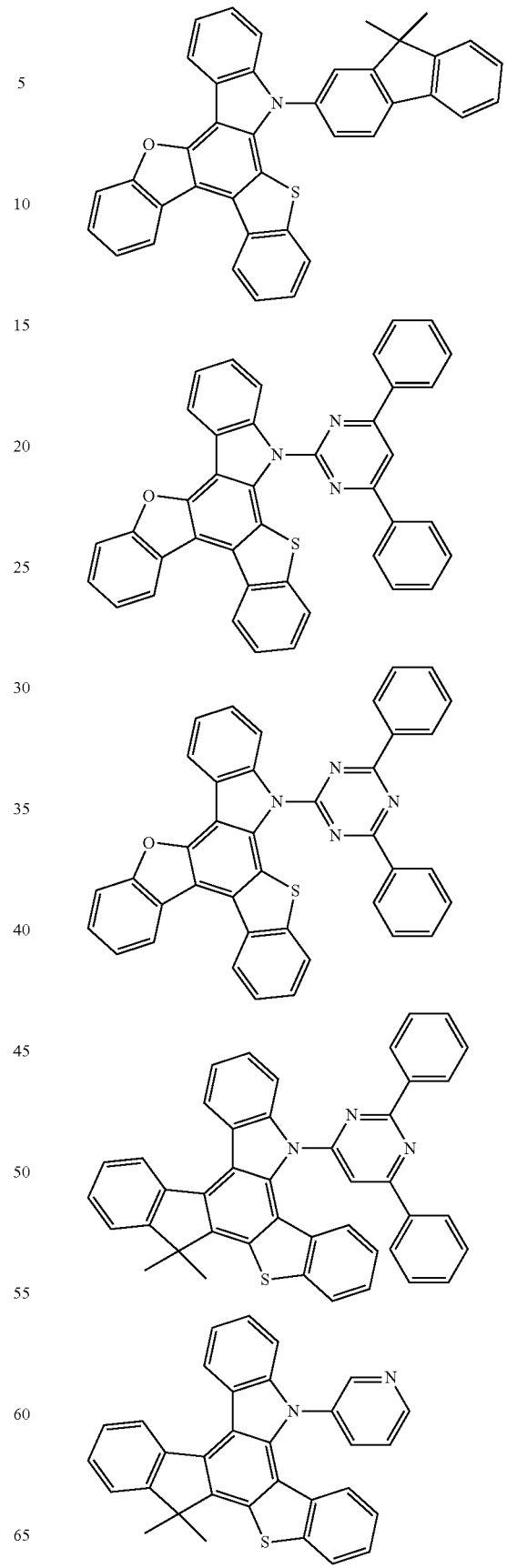

119
-continued
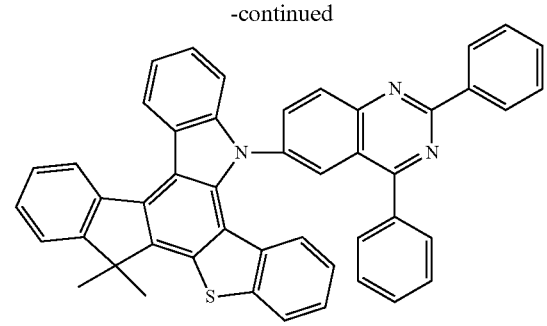
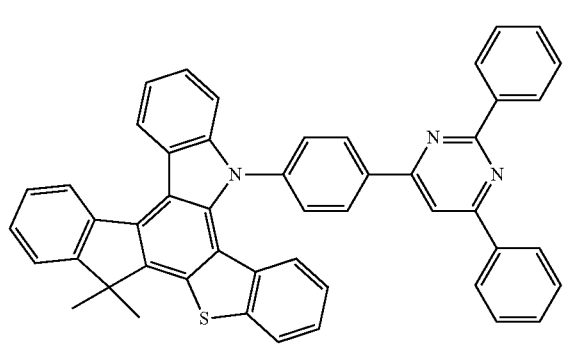
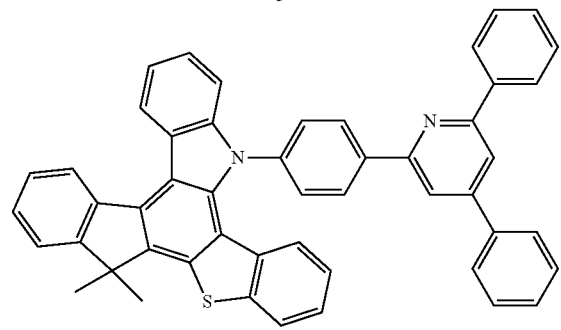
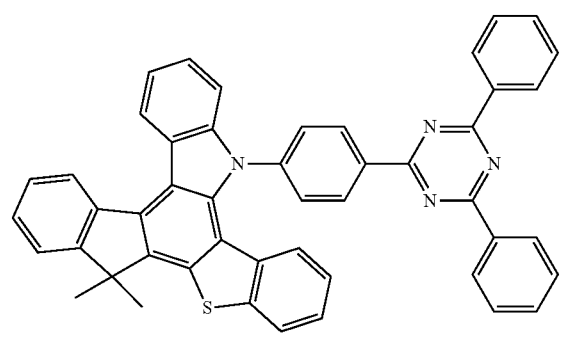
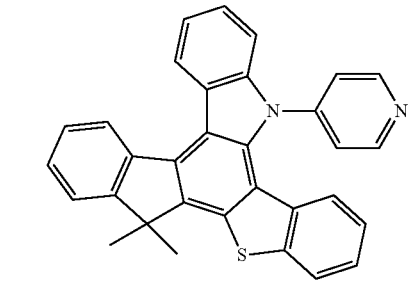
120
-continued
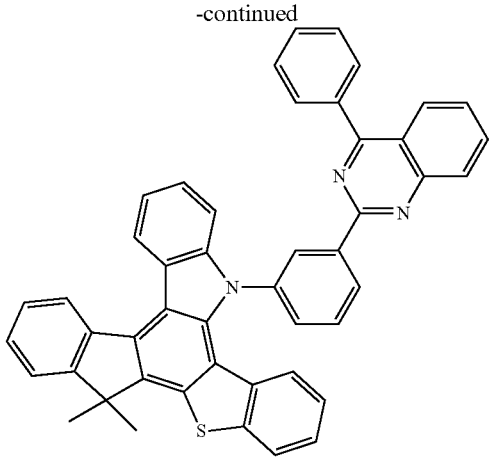
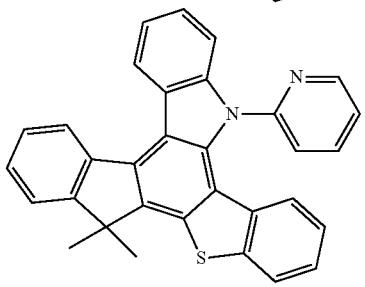
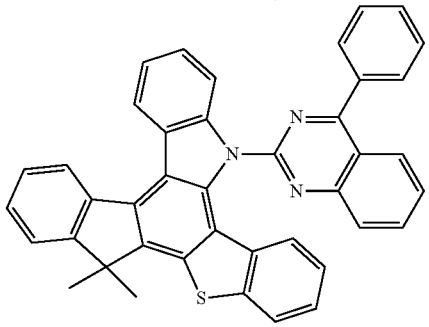
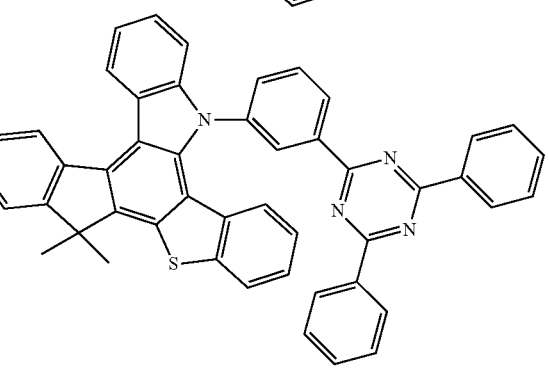
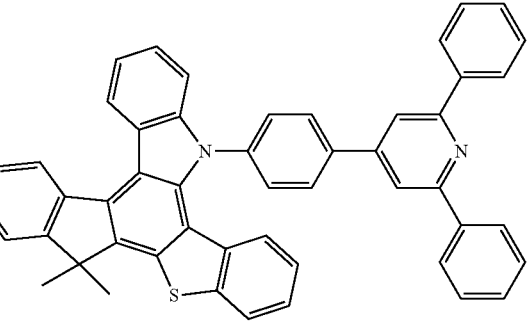

121
-continued
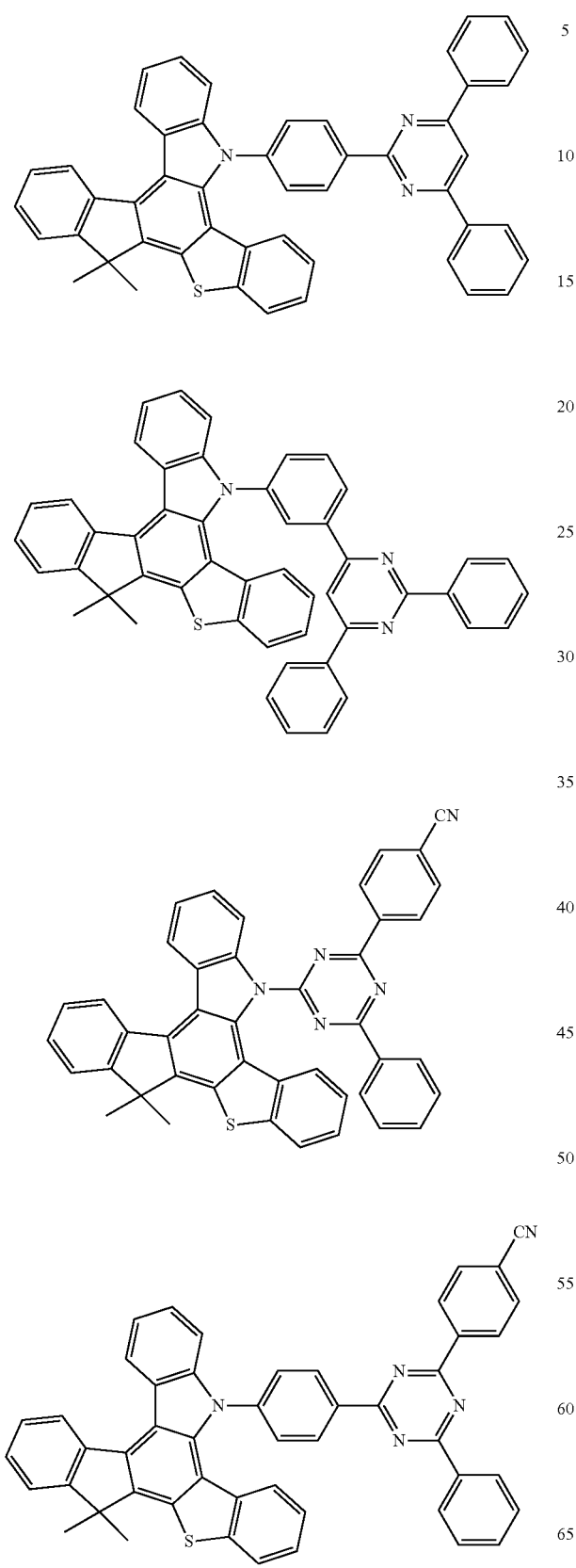
122
-continued
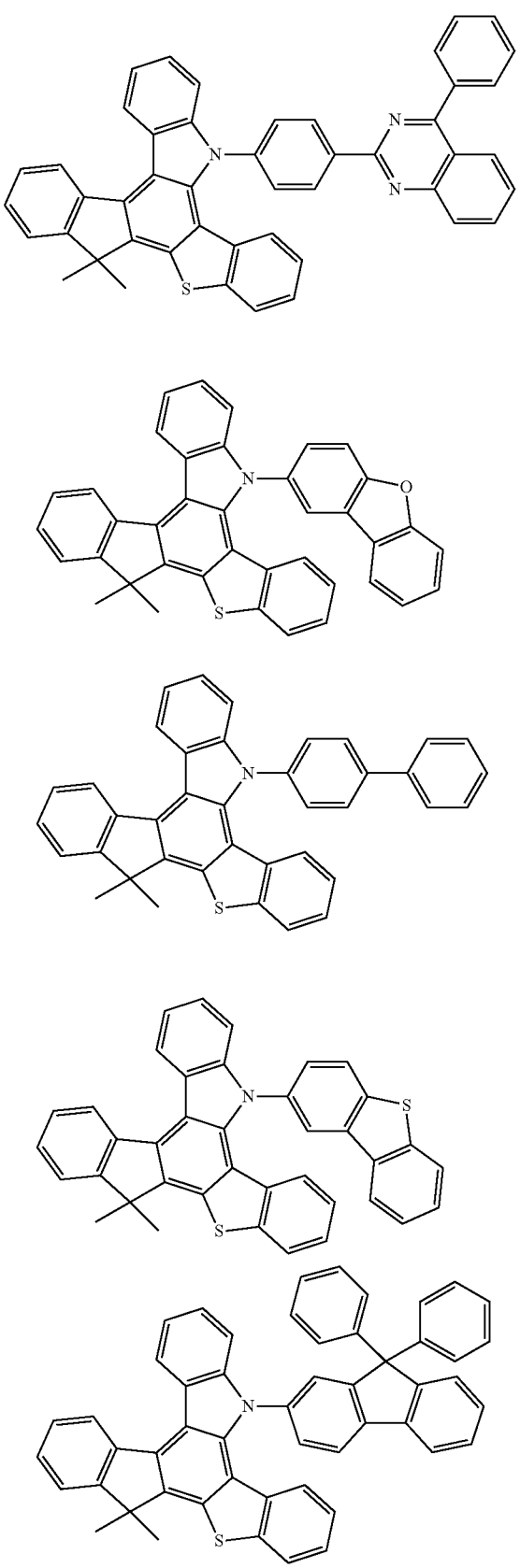

123
-continued
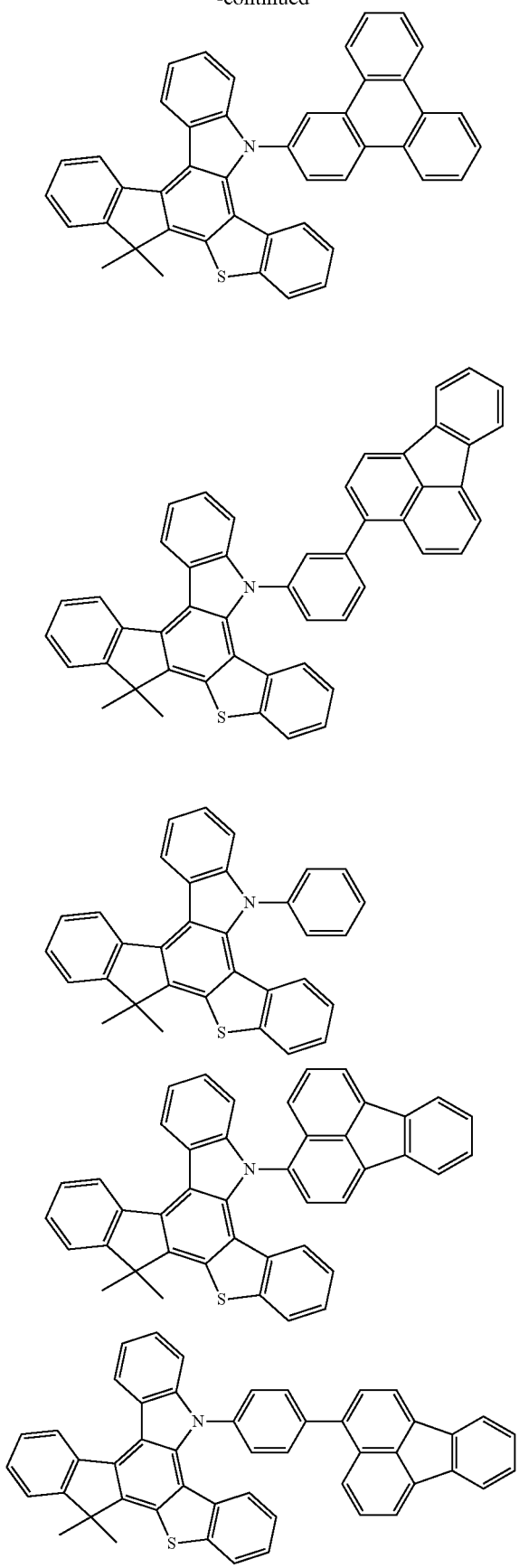
124
-continued
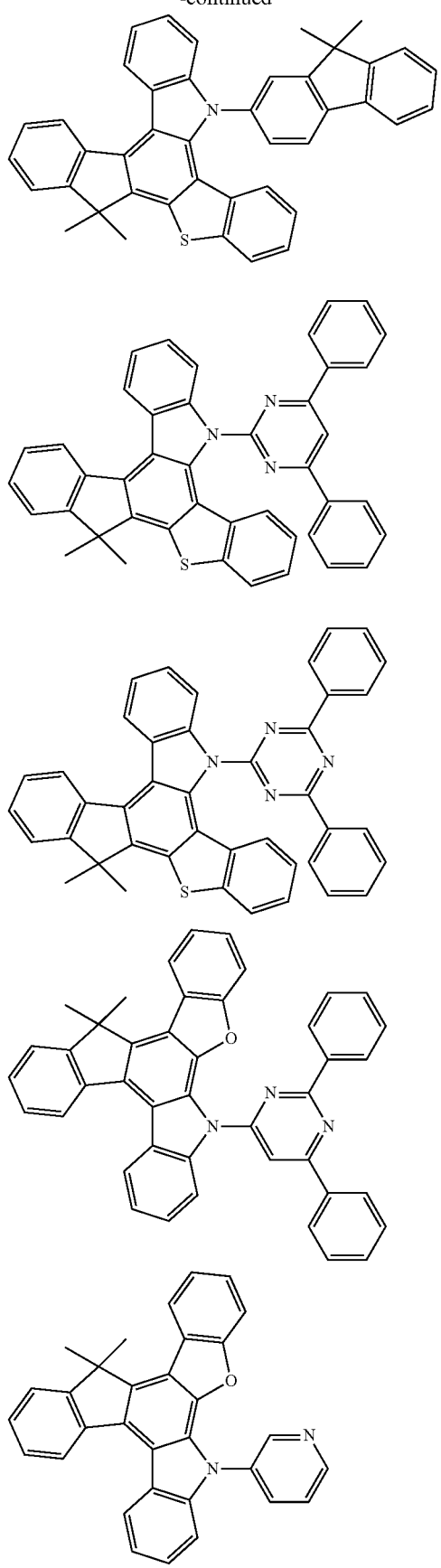

125
-continued
126
-continued
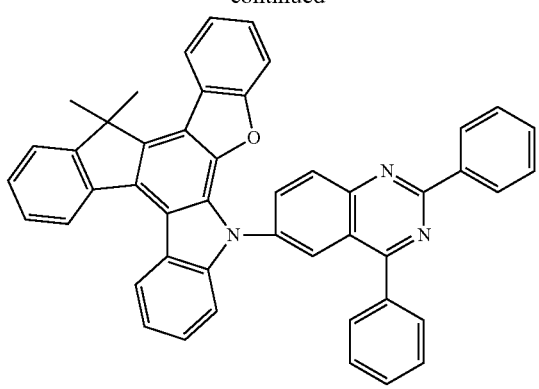
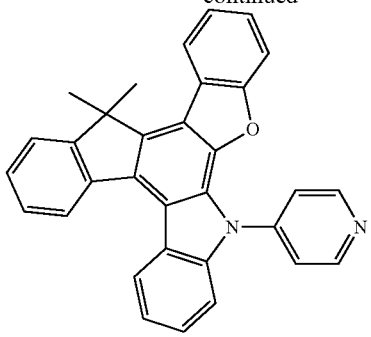
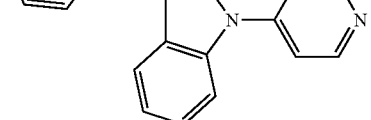
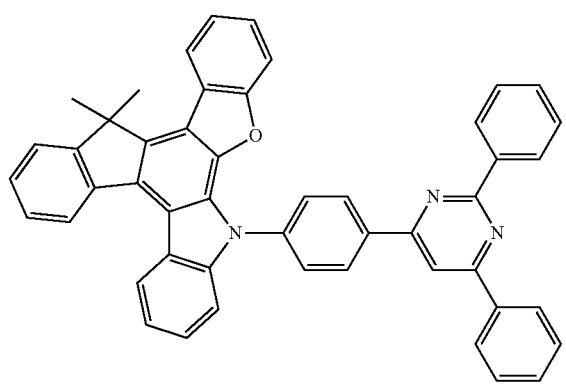
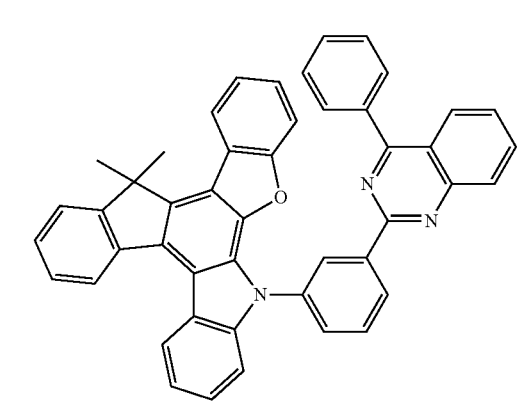
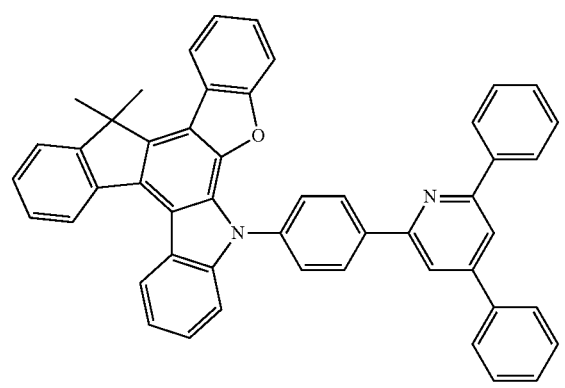
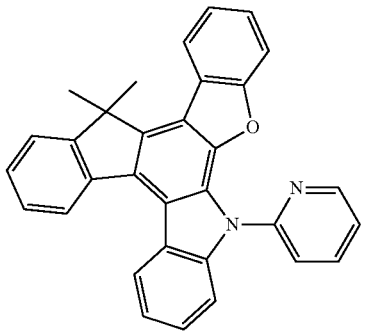
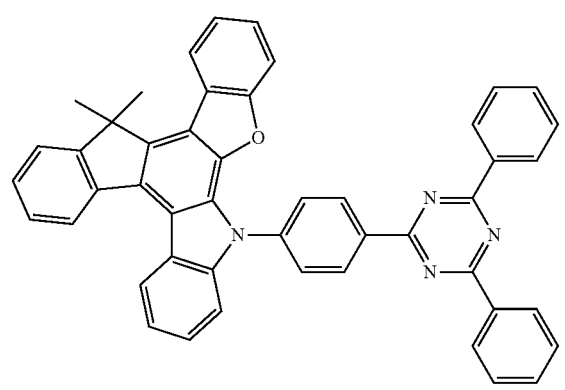
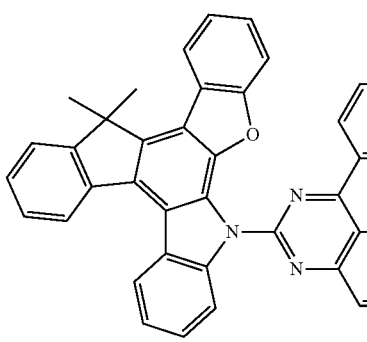

127
-continued
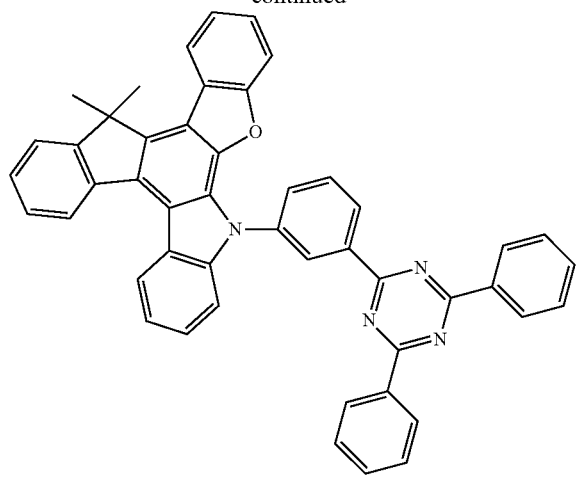
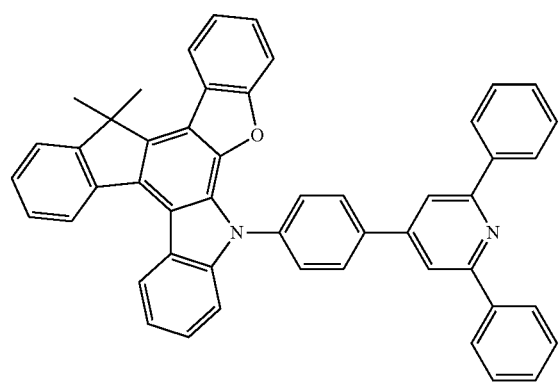
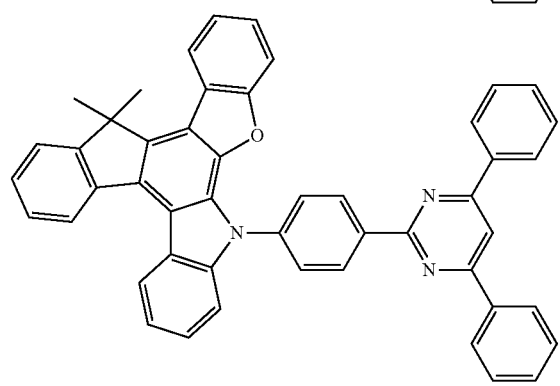
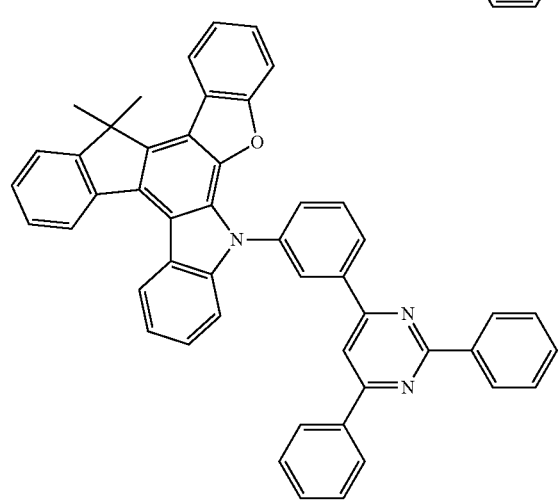
128
-continued
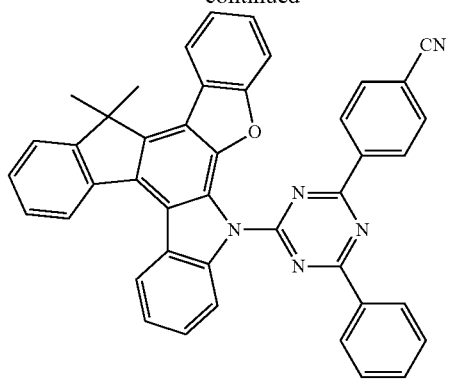
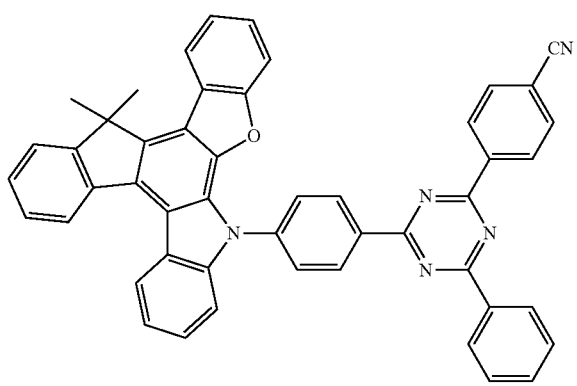
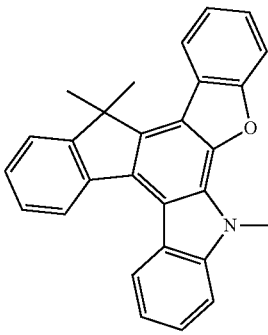
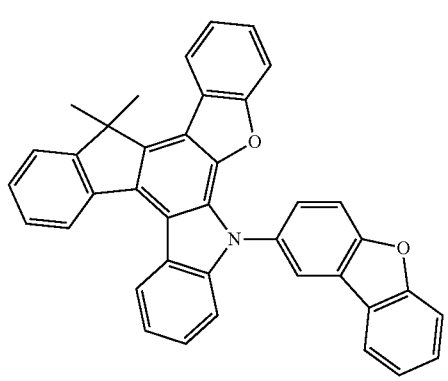

-continued
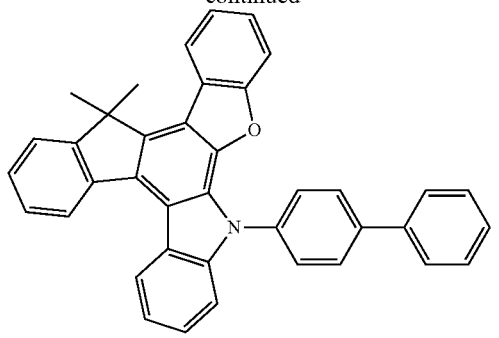
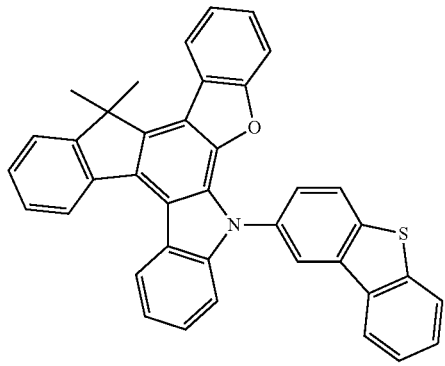
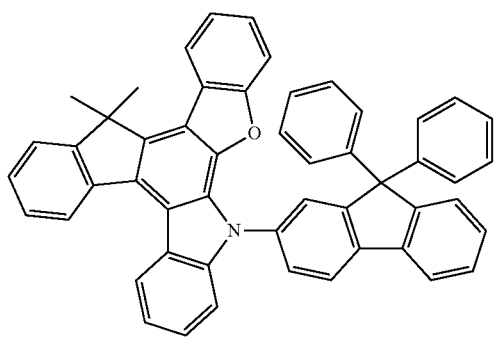
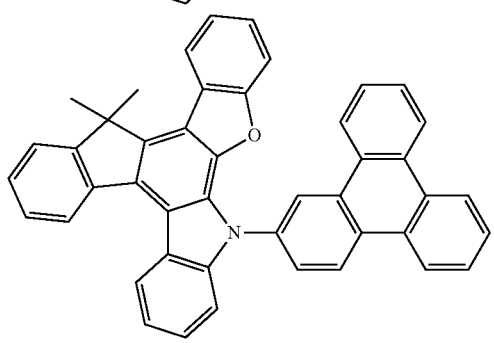
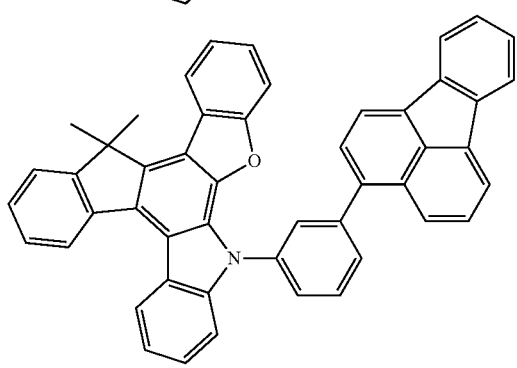
-continued
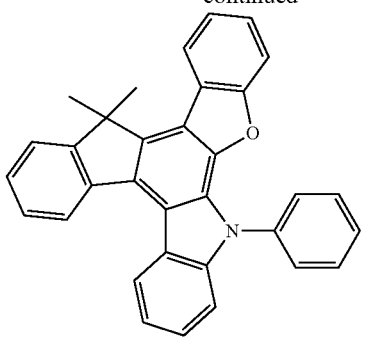
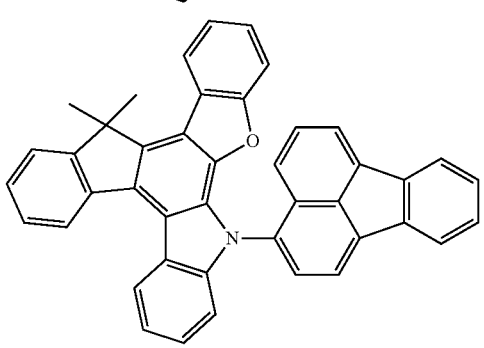
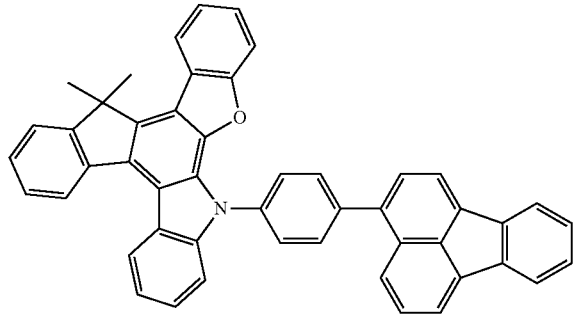
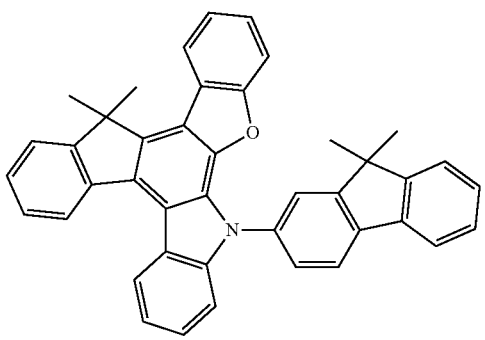
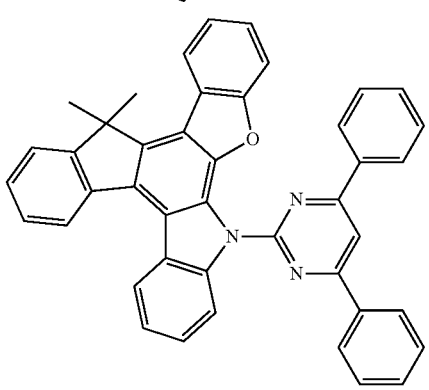

131
-continued
132
-continued
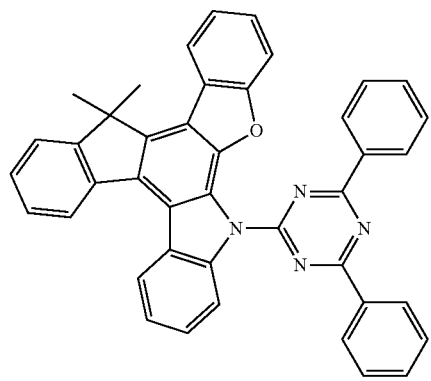
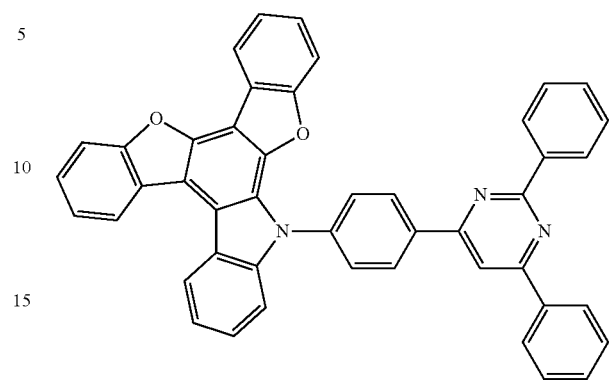
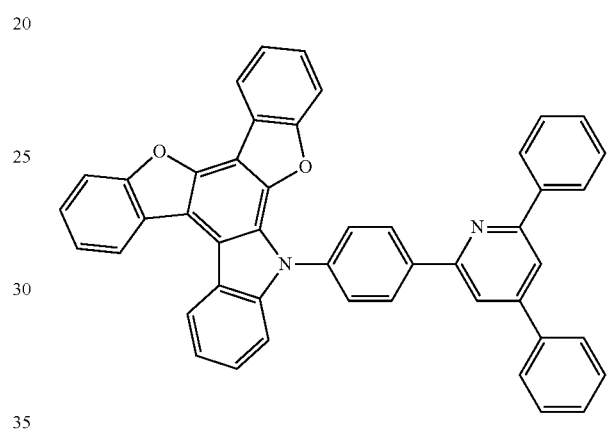
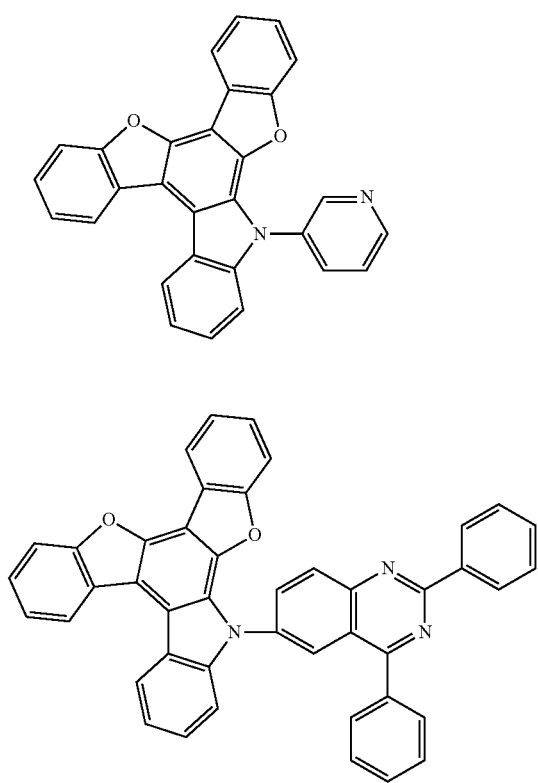

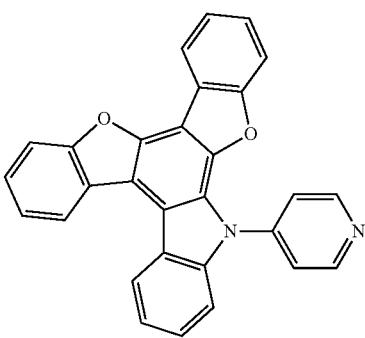

133
-continued
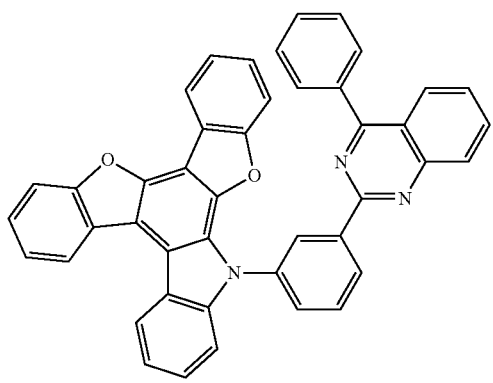
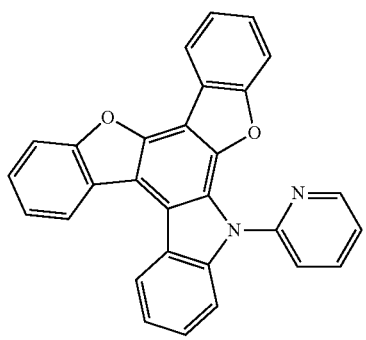
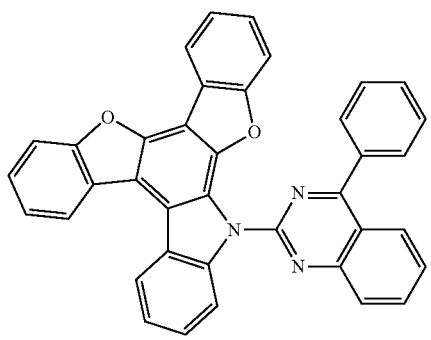
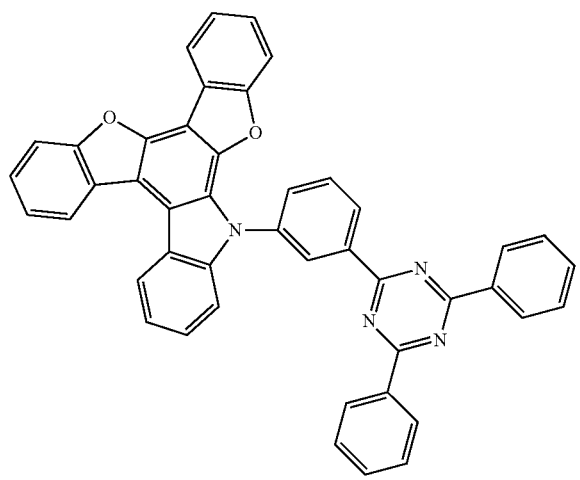
134
-continued
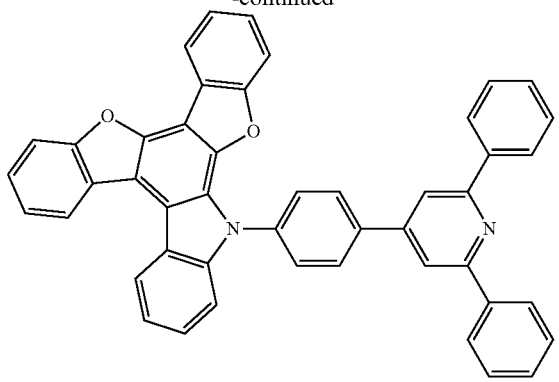
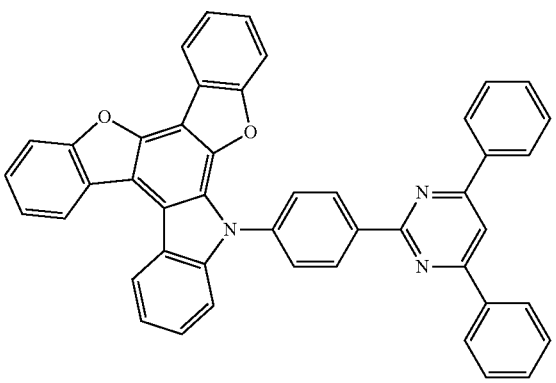
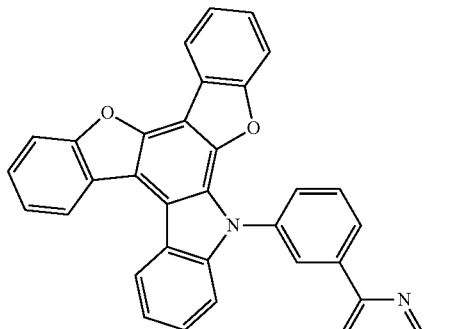
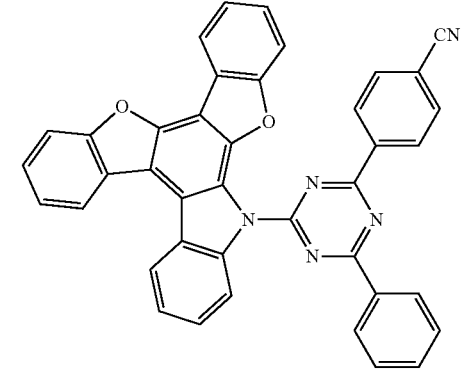

-continued
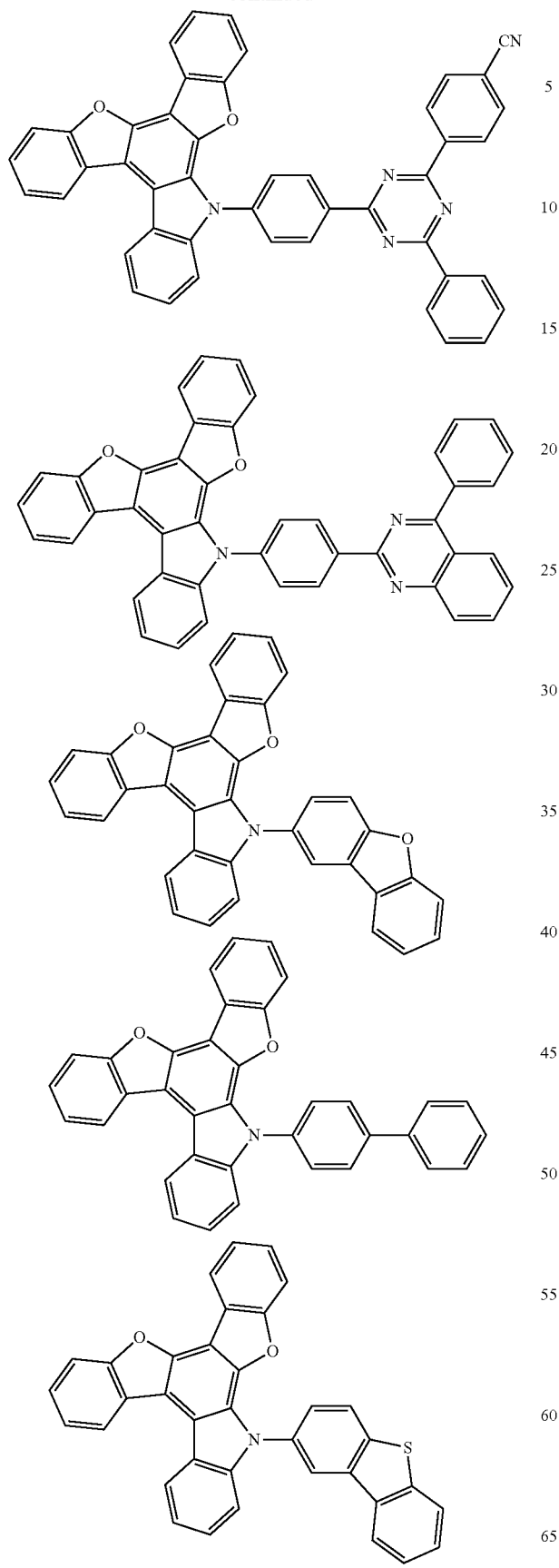
-continued
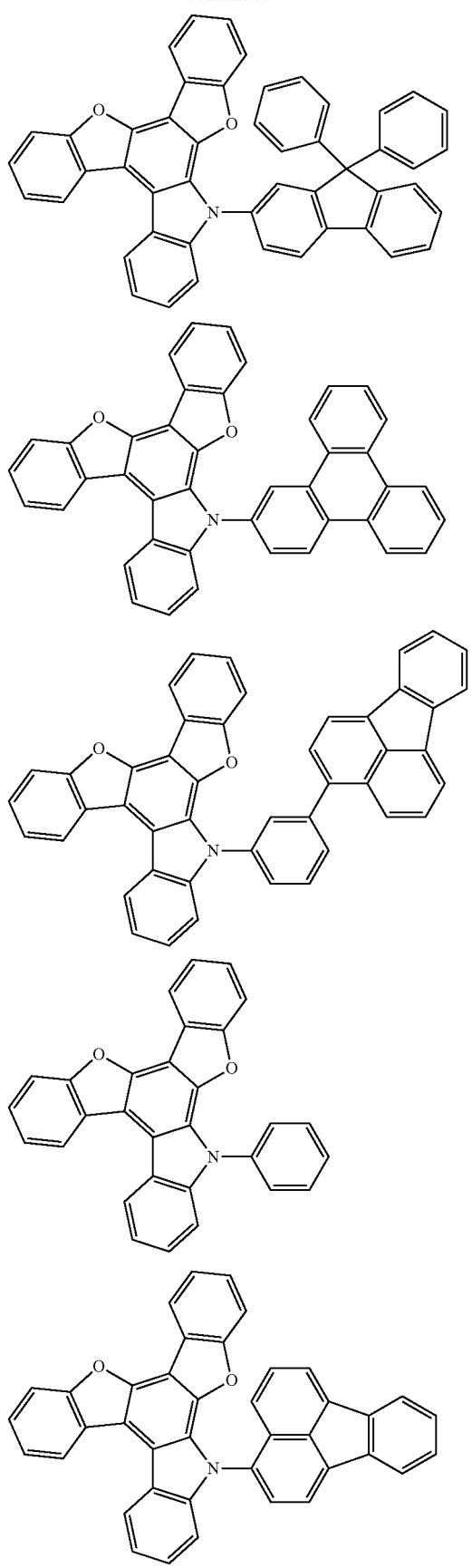

137
-continued
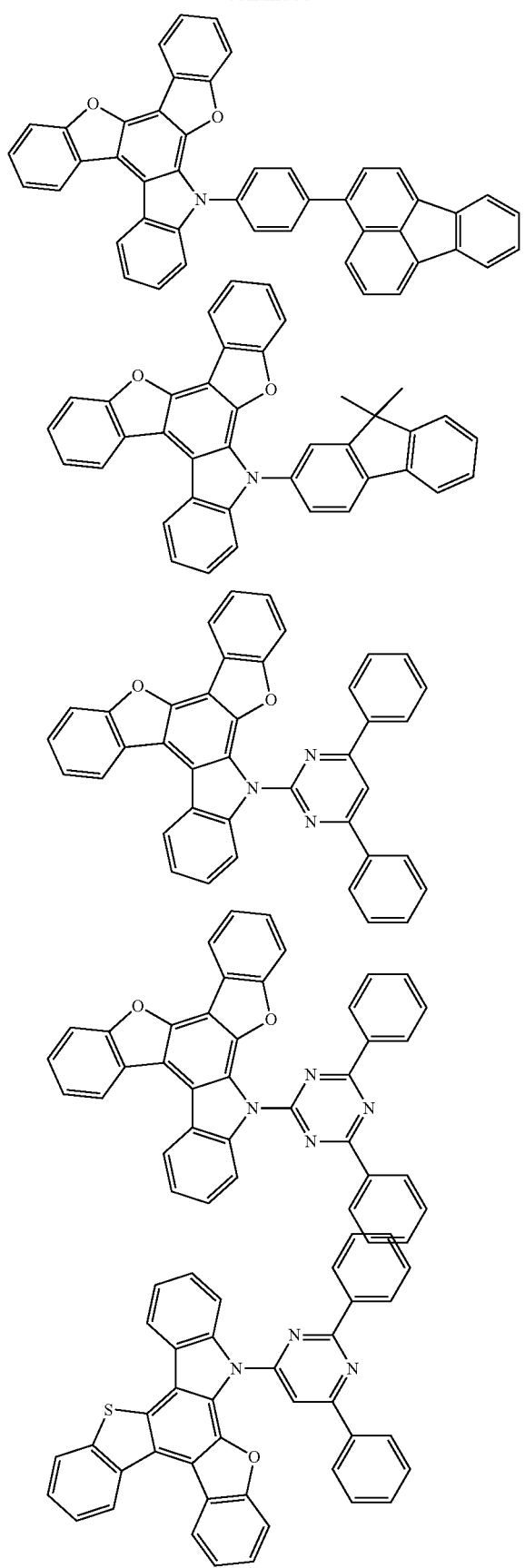
138
-continued
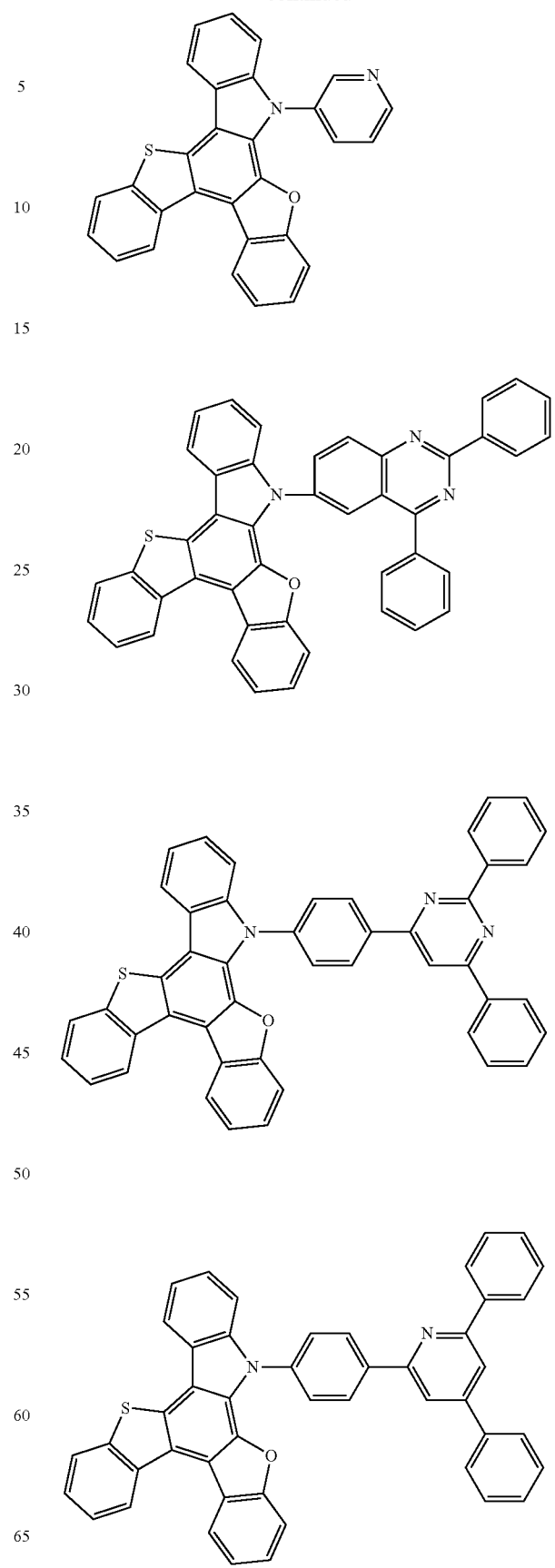

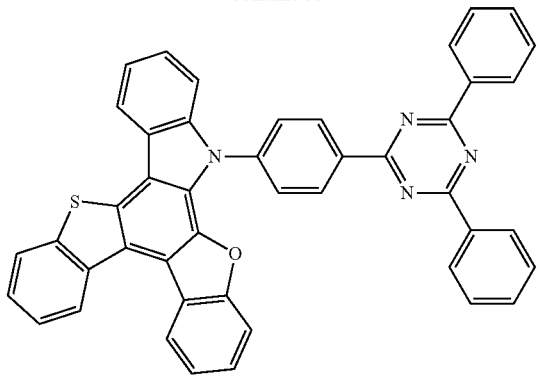
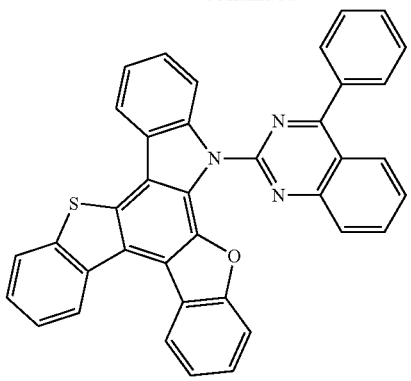
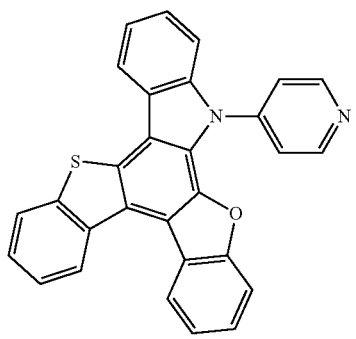
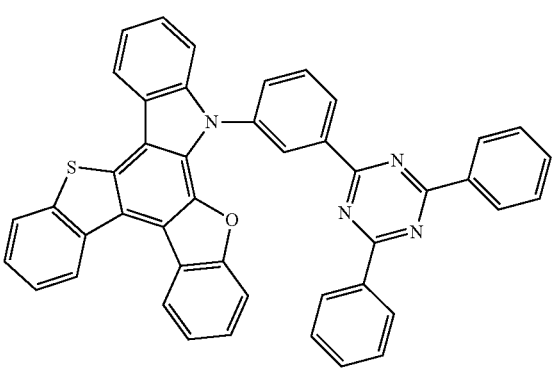
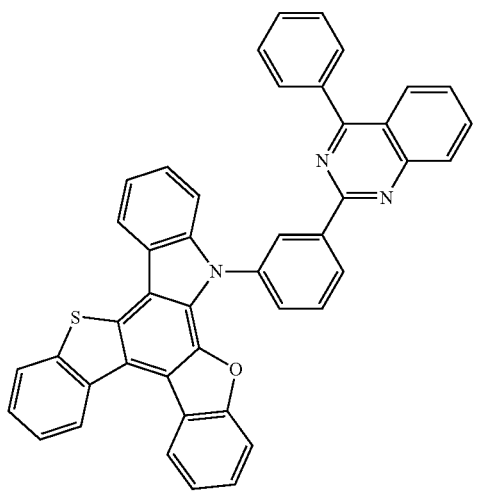
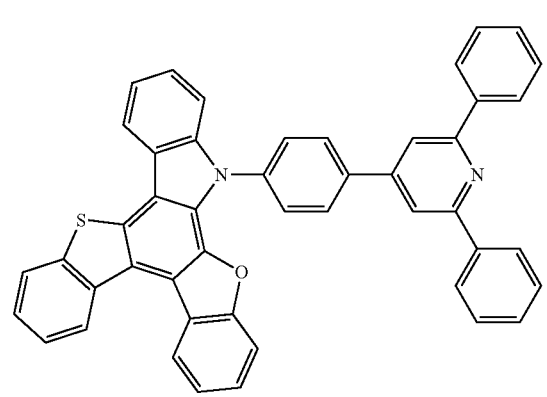
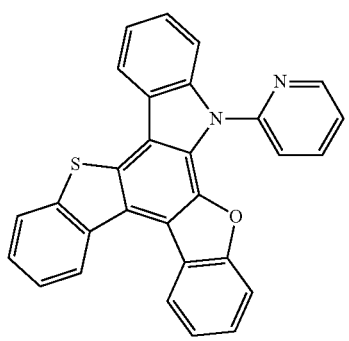
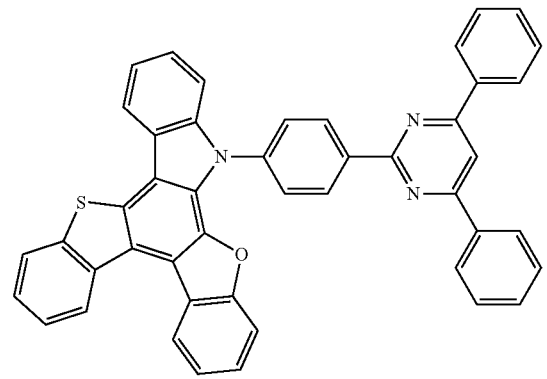

141
-continued
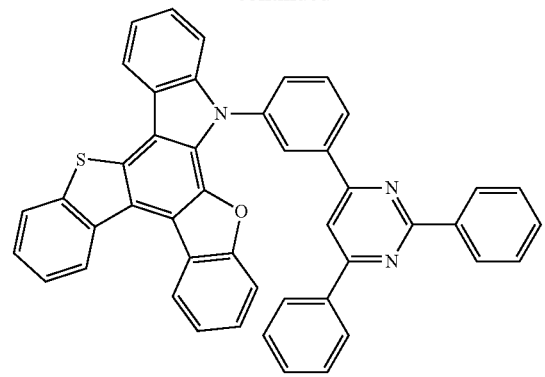
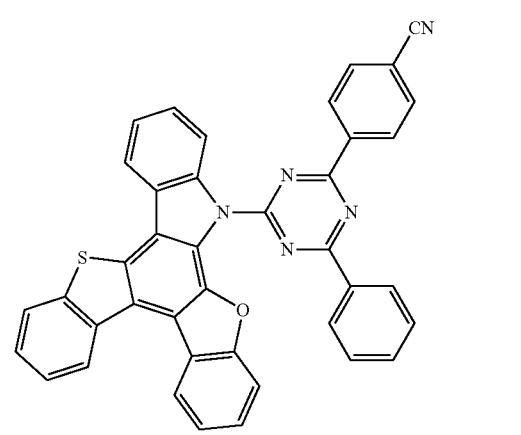
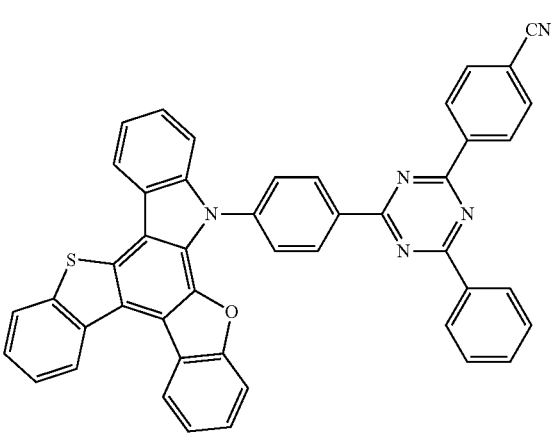
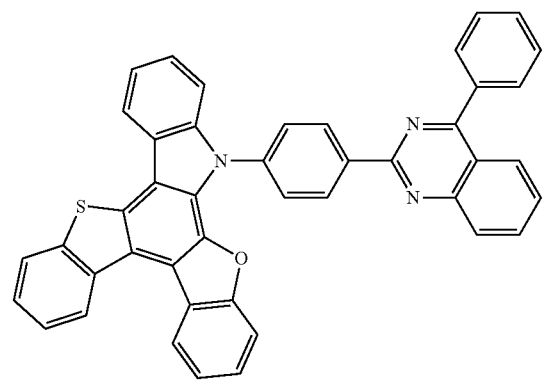
142
-continued
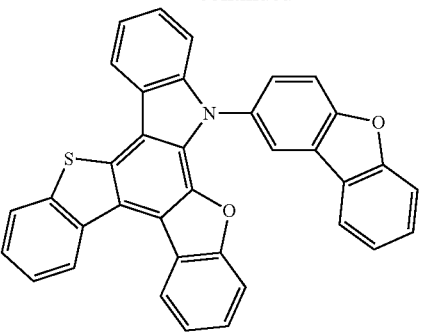
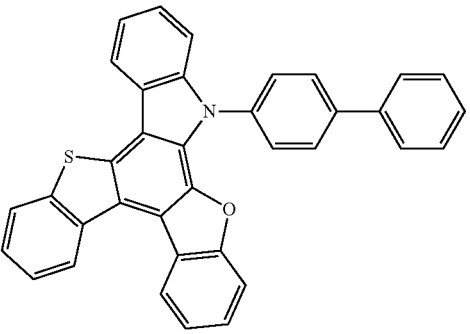
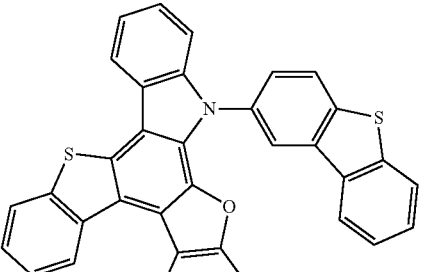
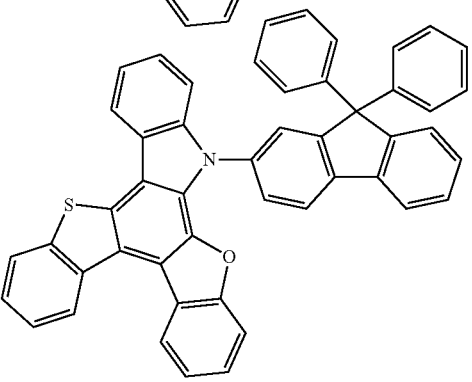
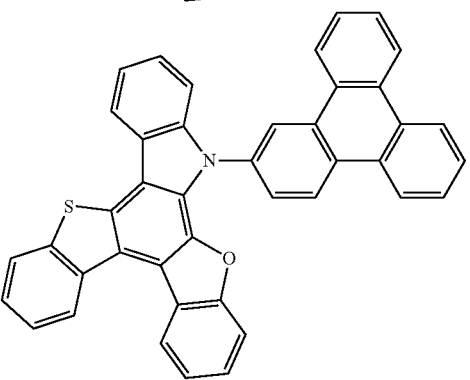

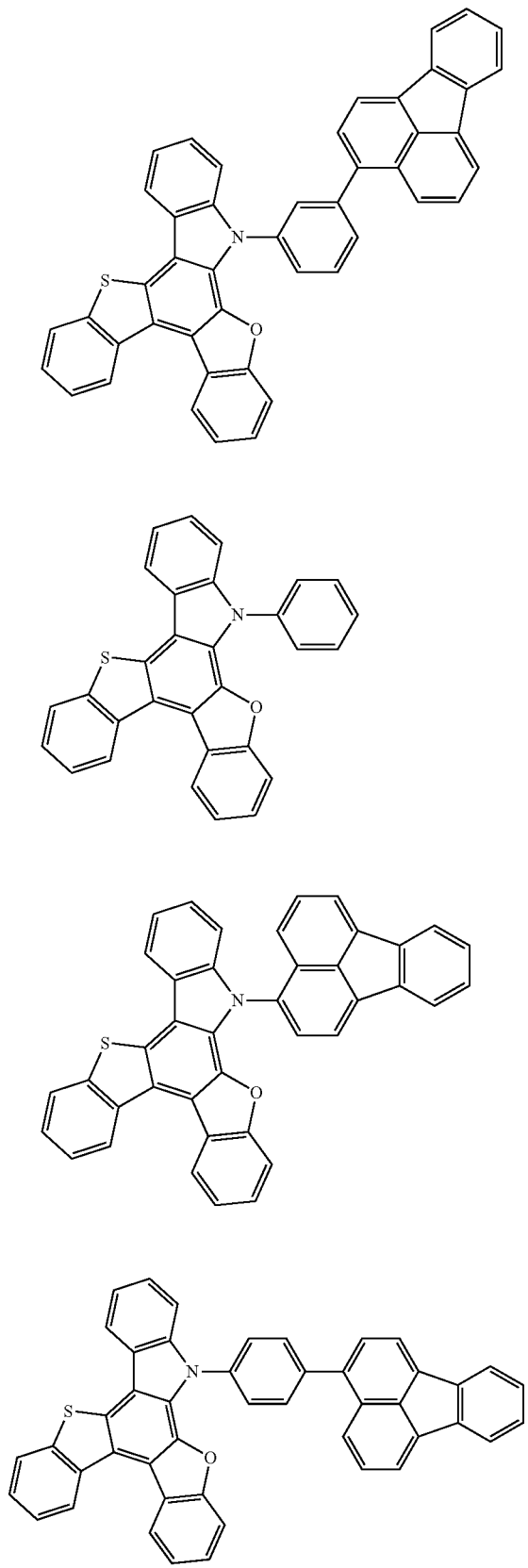
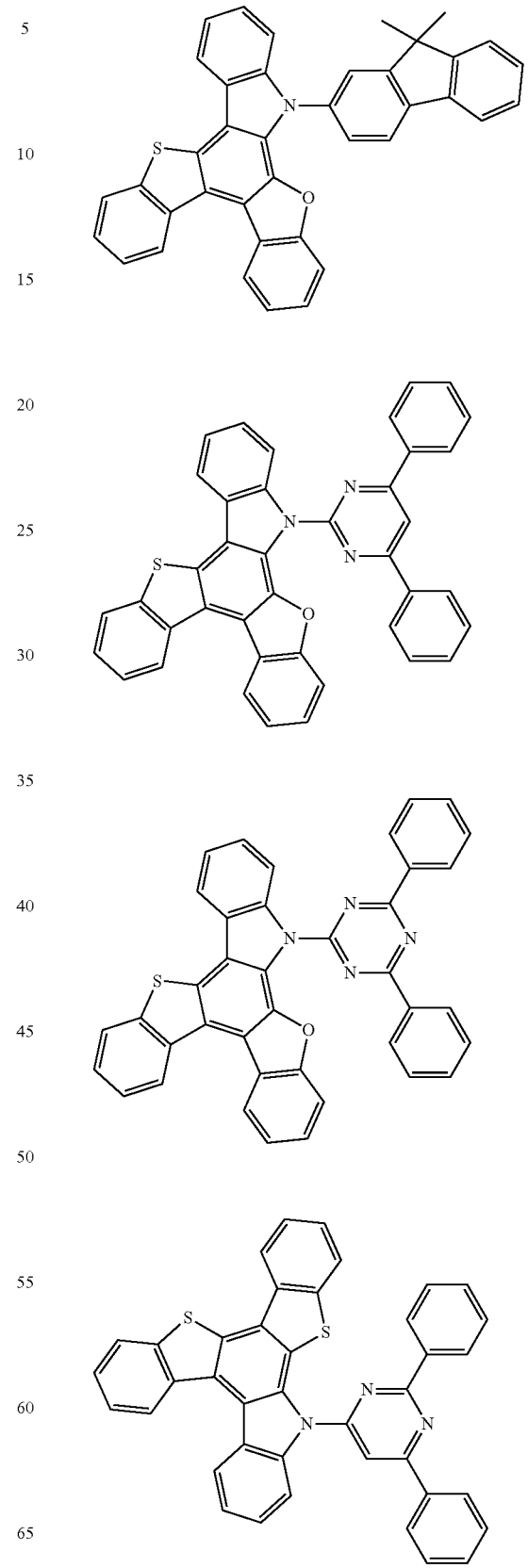

-continued
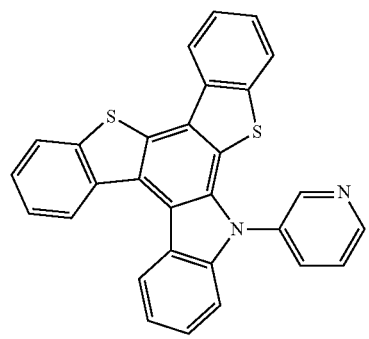
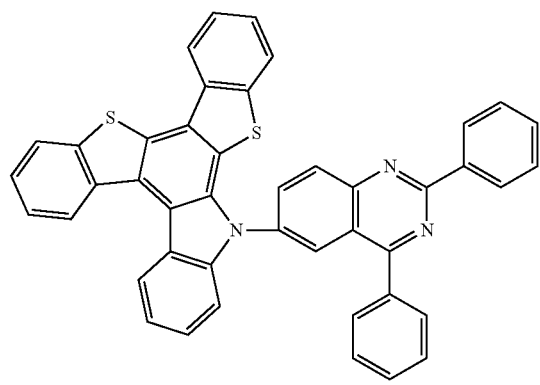
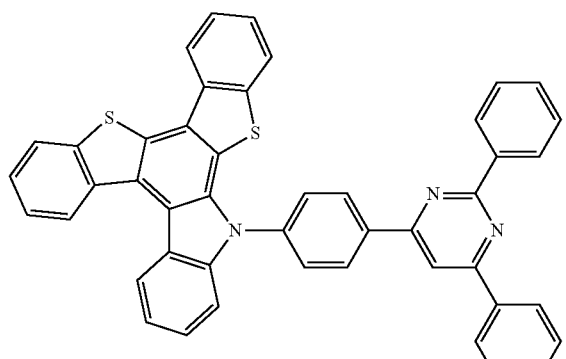
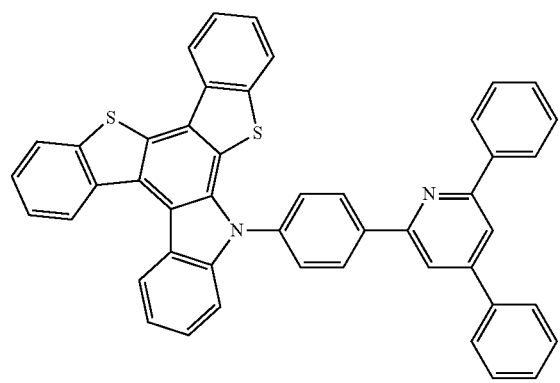
-continued
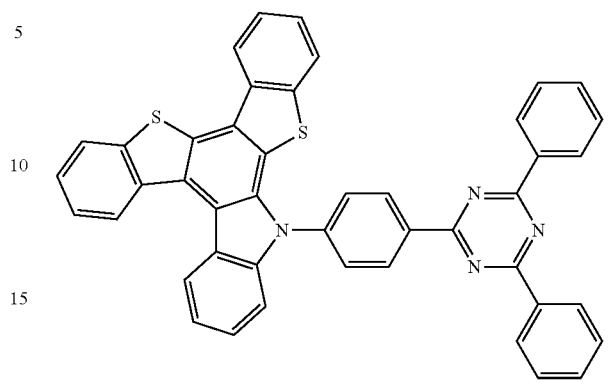
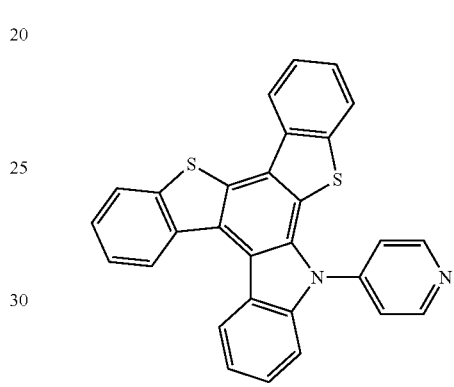
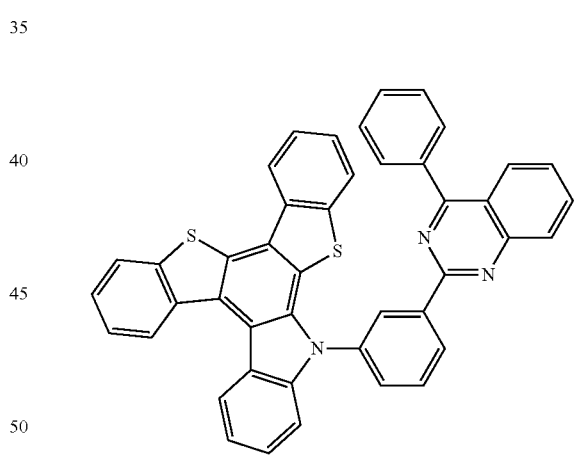
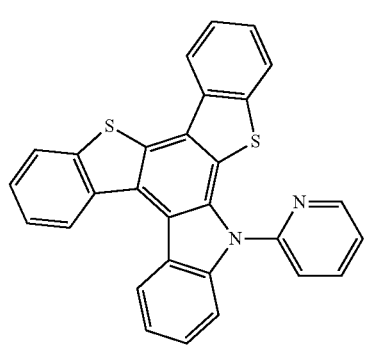

147
-continued
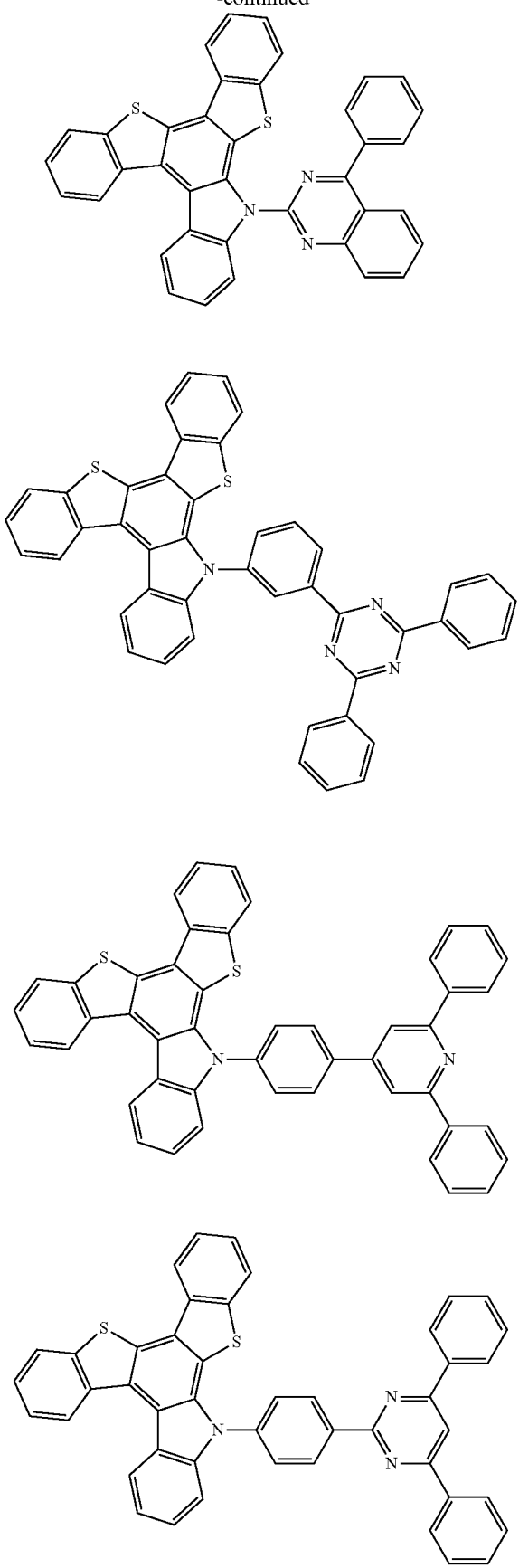
148
-continued
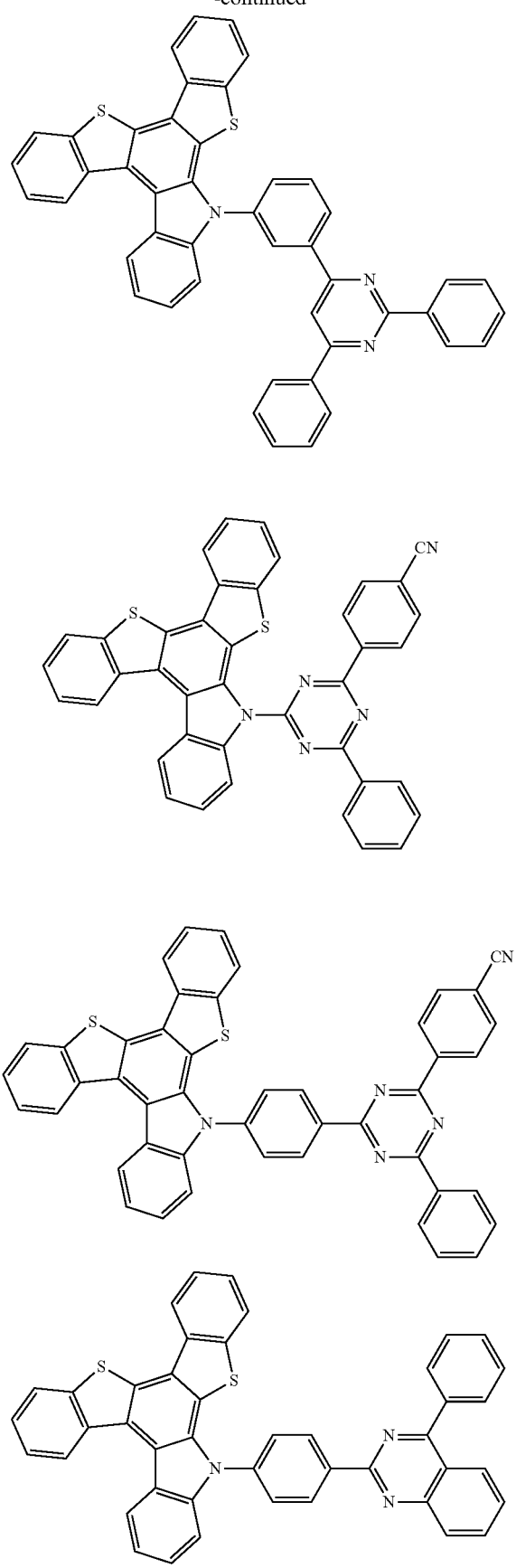

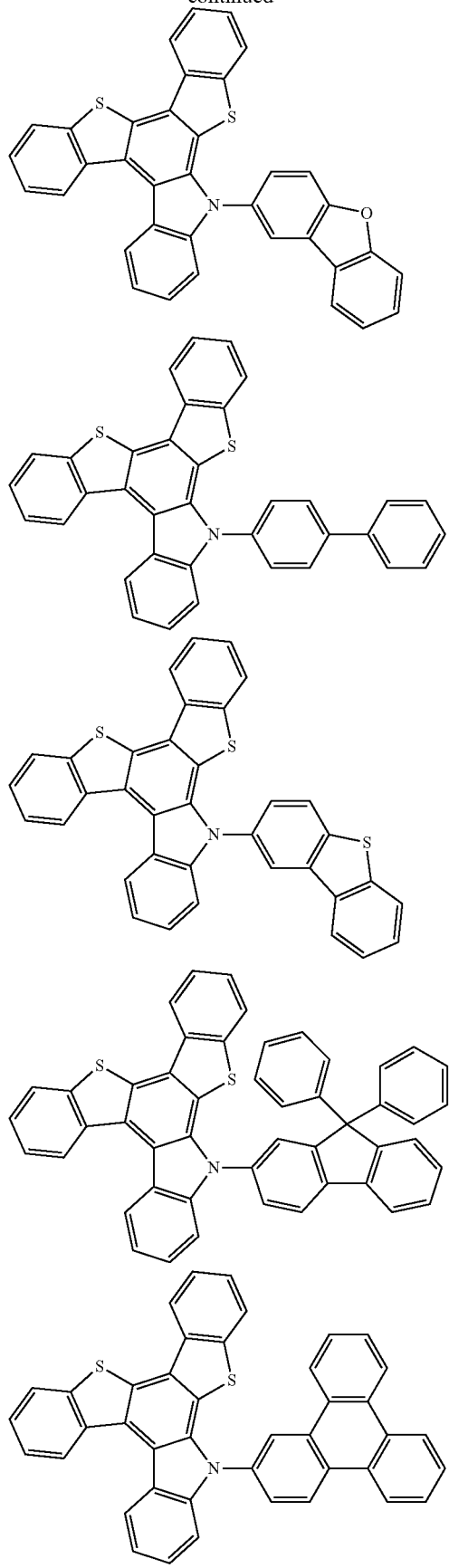
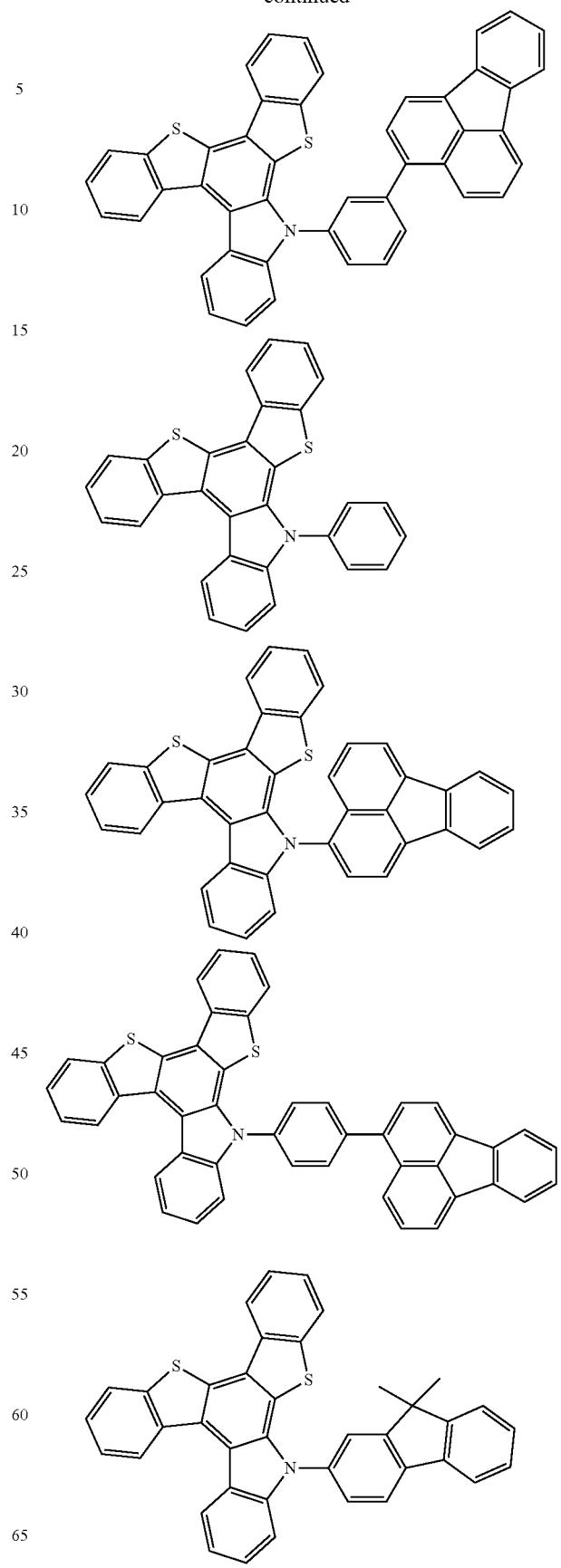

151
-continued
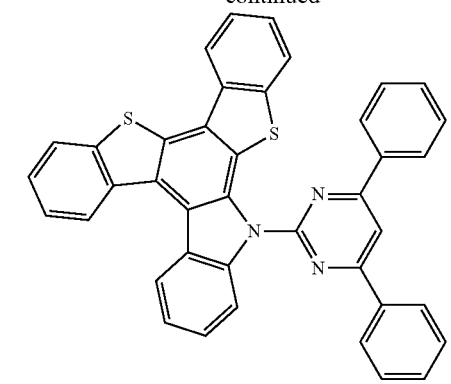
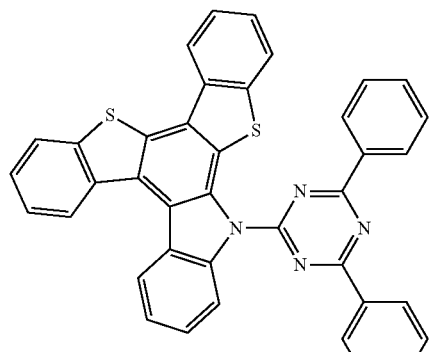
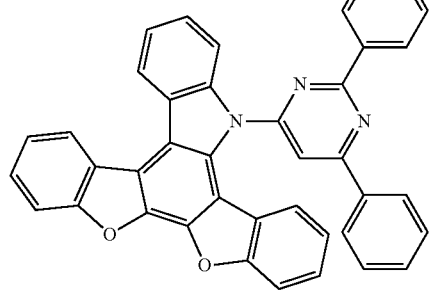
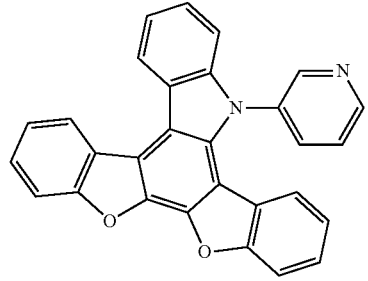
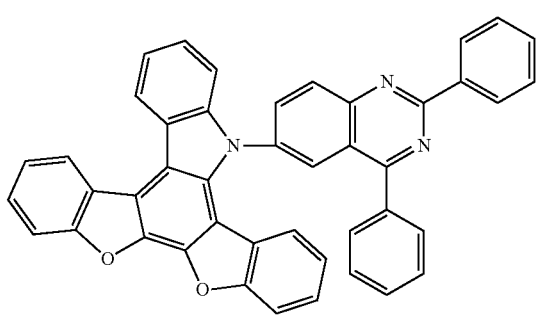
152
-continued
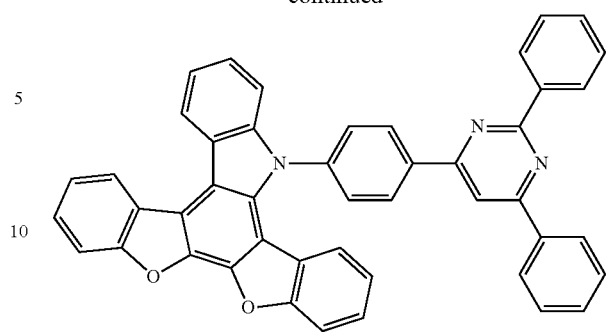
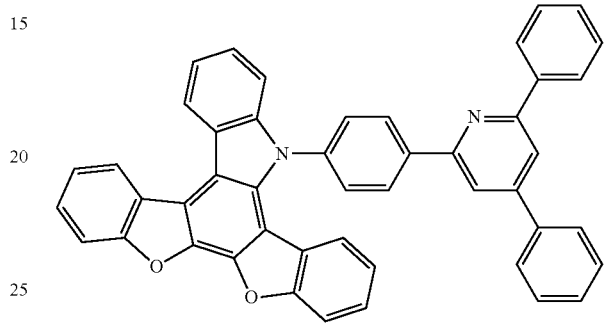
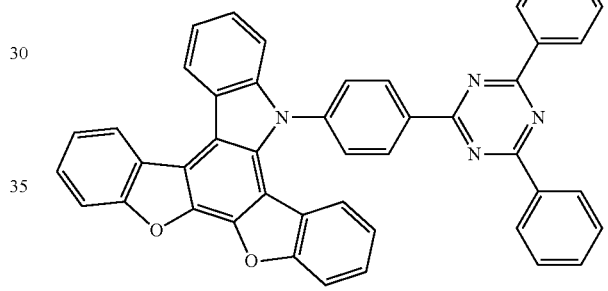
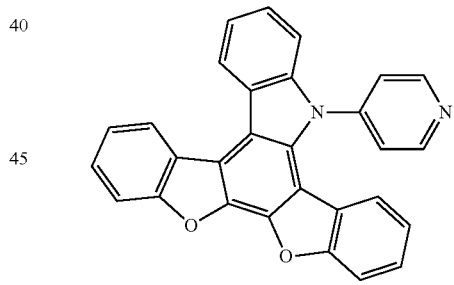
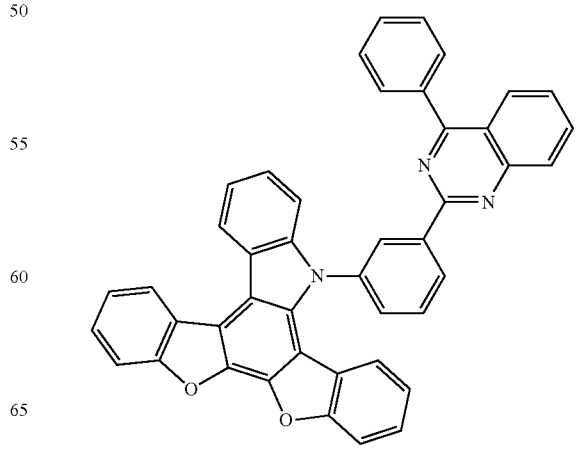

153
-continued
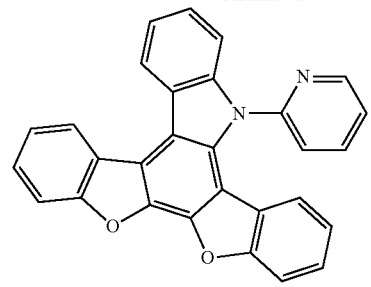
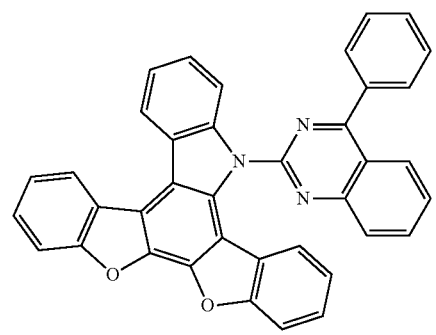
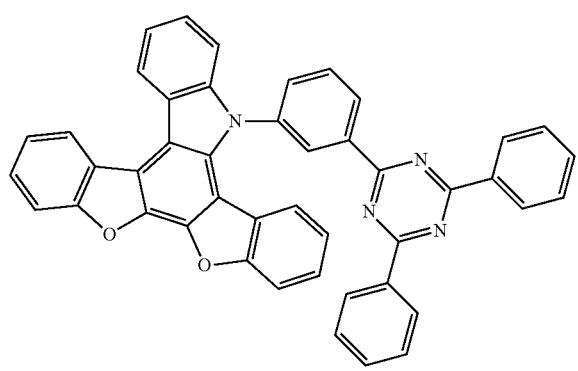
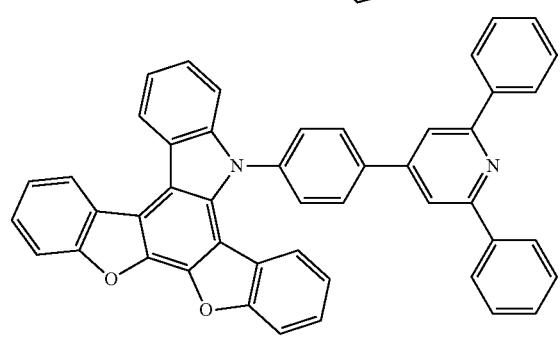
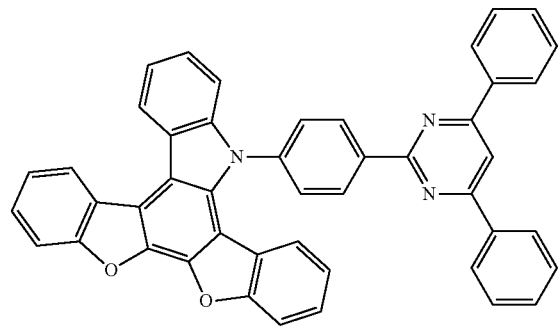
154
-continued
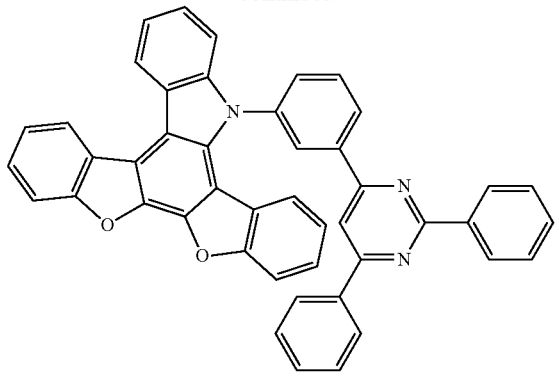
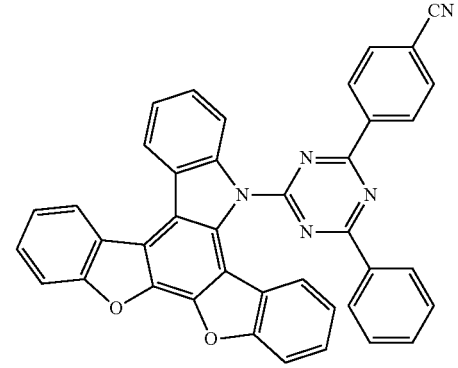
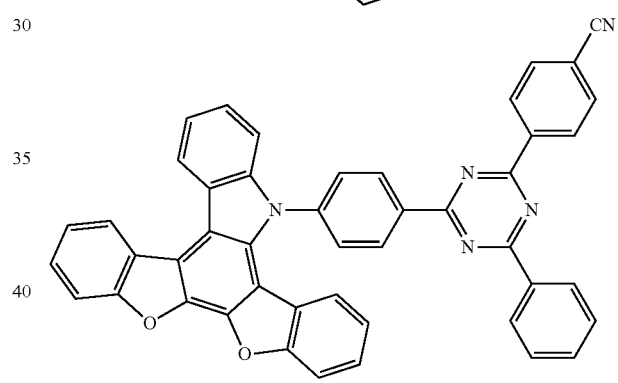
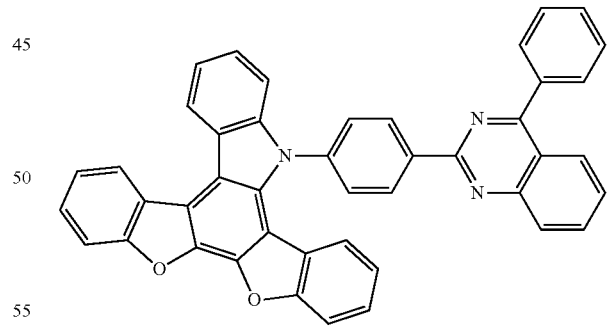
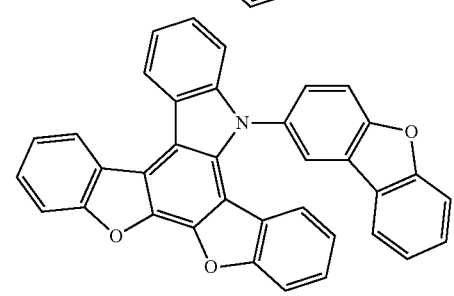

155
-continued
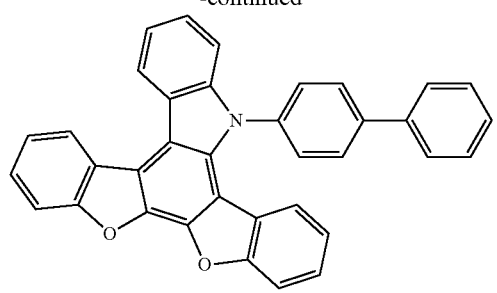
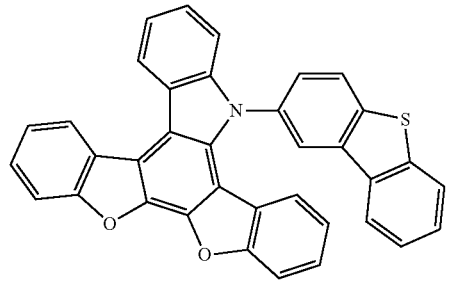
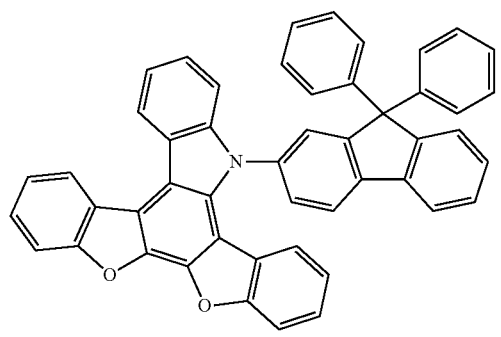
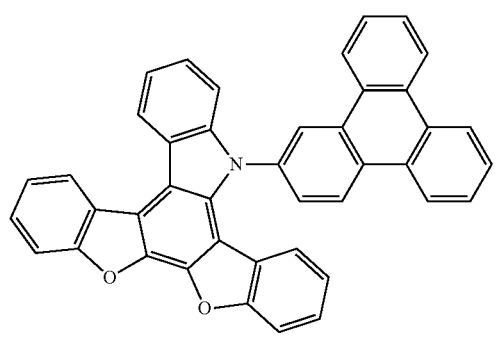
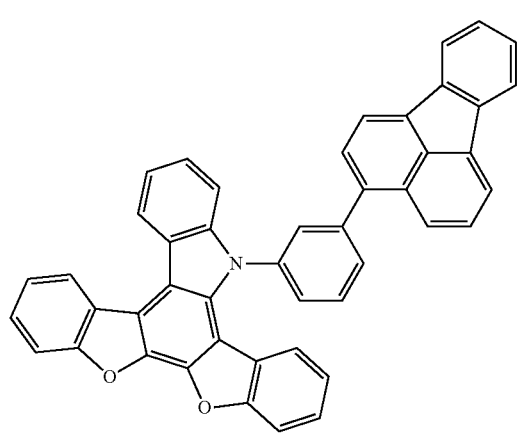
156
-continued
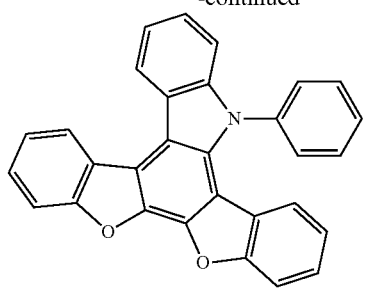
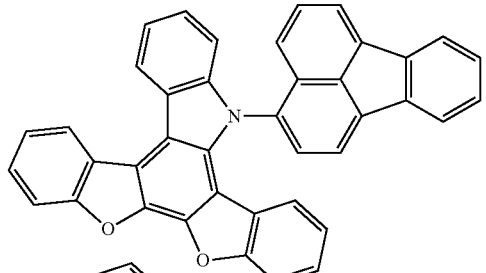
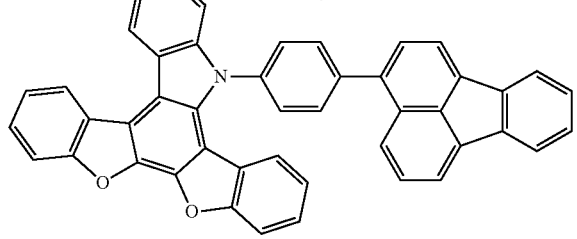
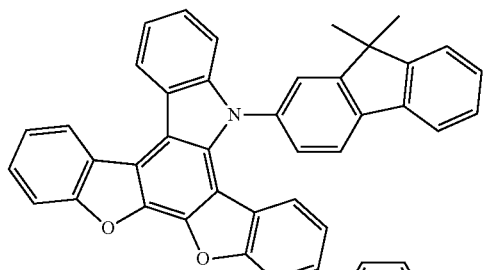
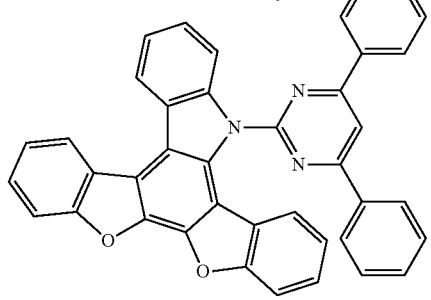
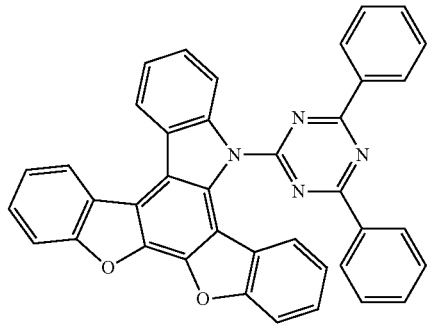

157
-continued
158
-continued
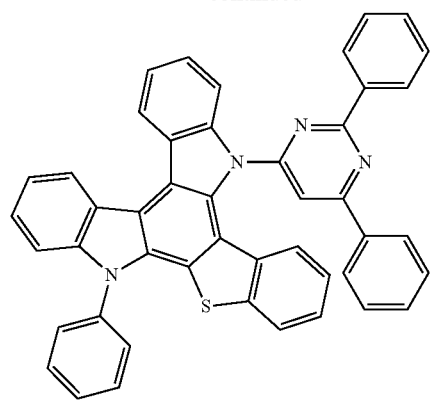
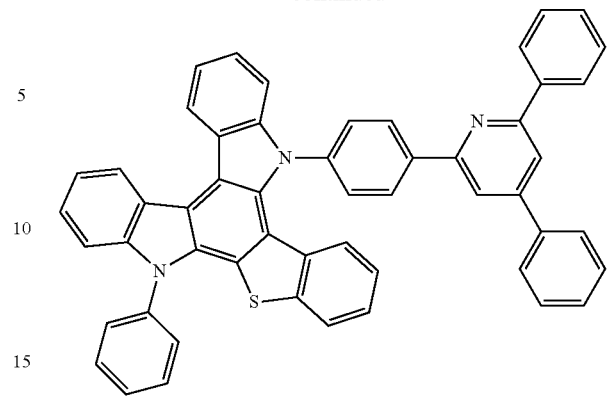
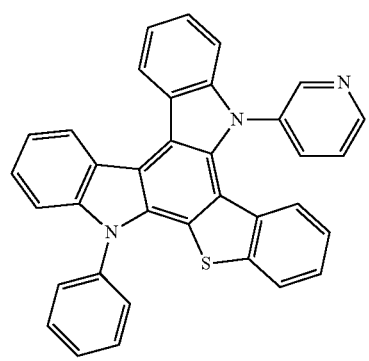
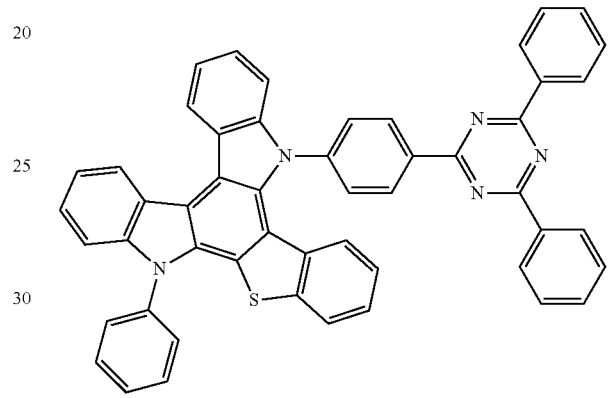
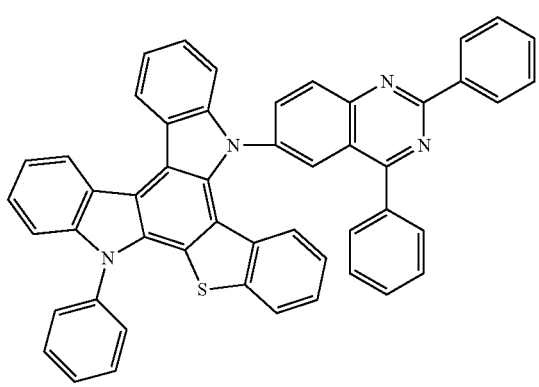
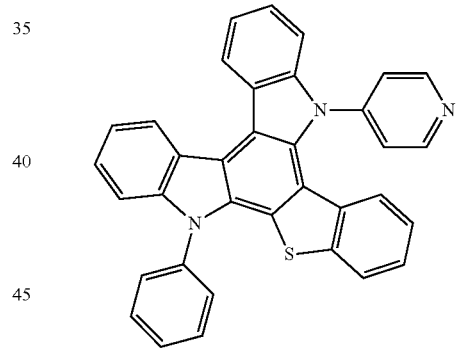
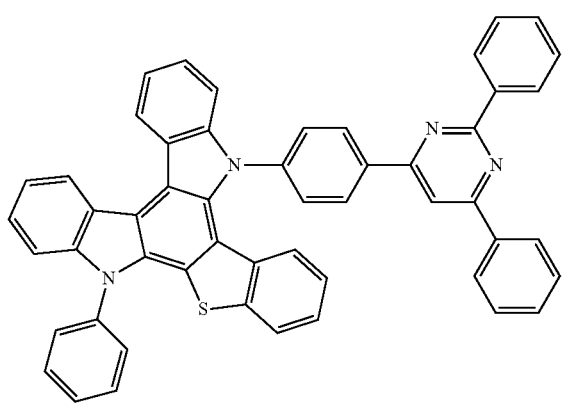
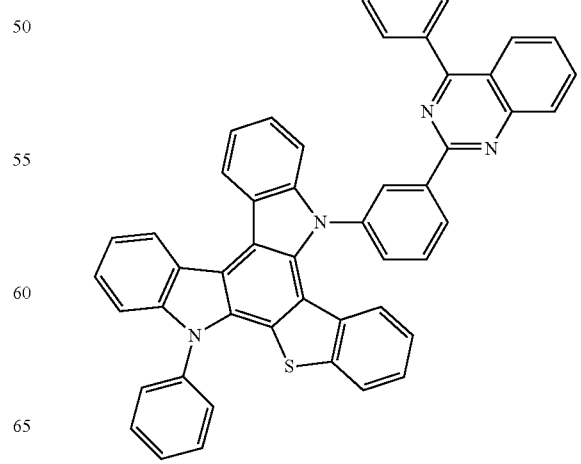

159
-continued
160
-continued
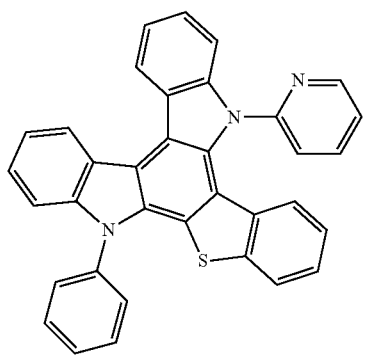
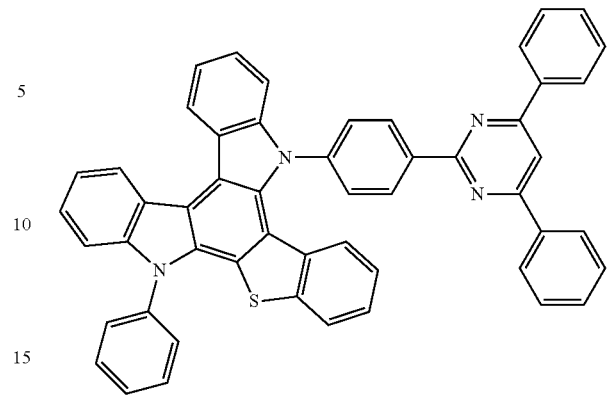
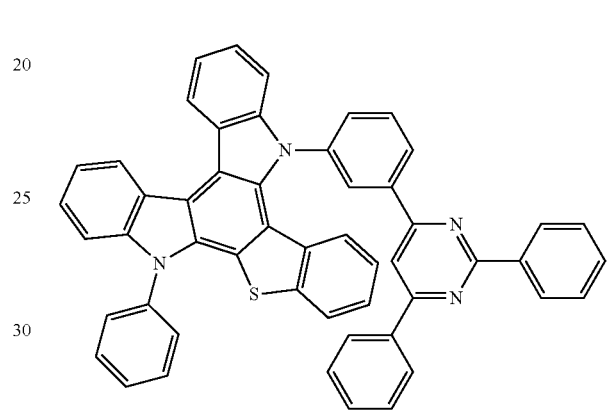
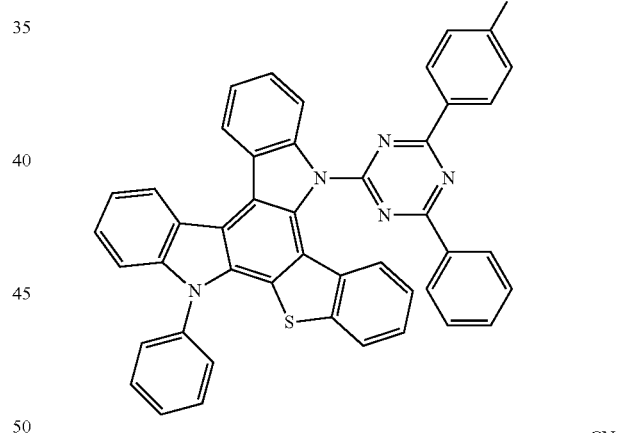
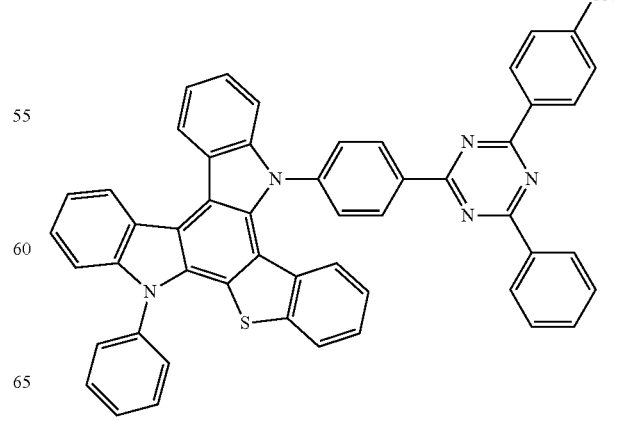

161
-continued
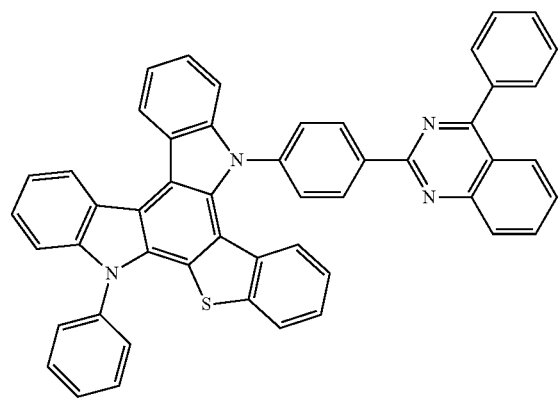
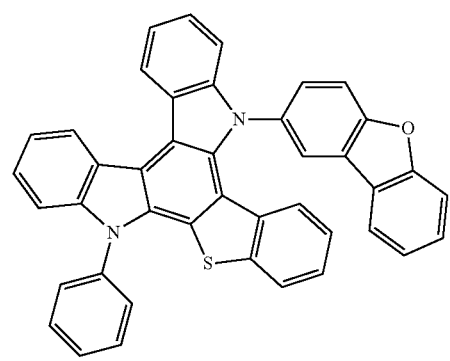
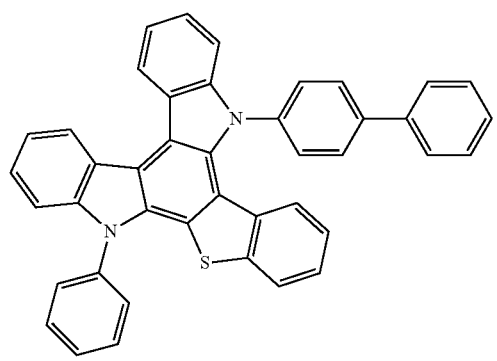
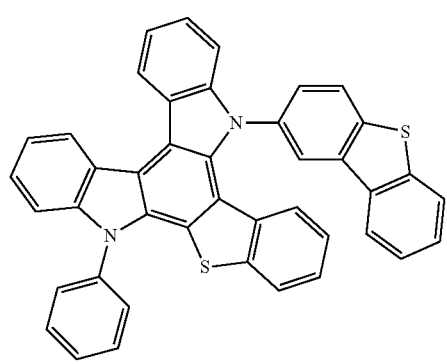
162
-continued
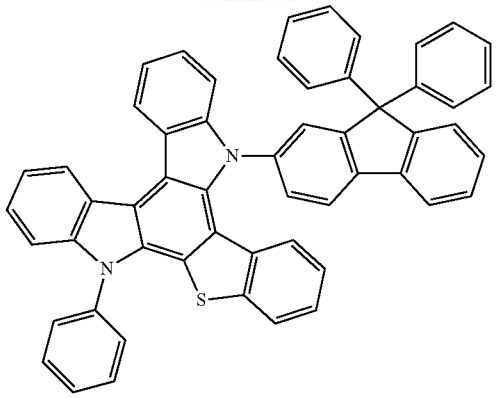
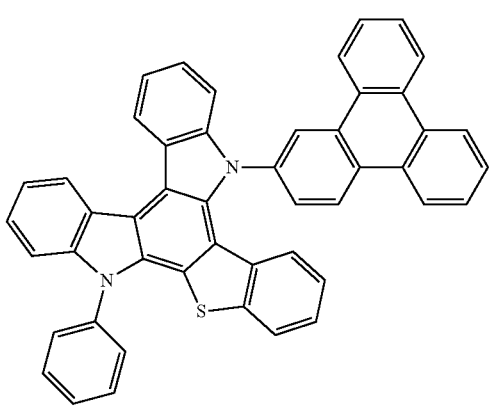
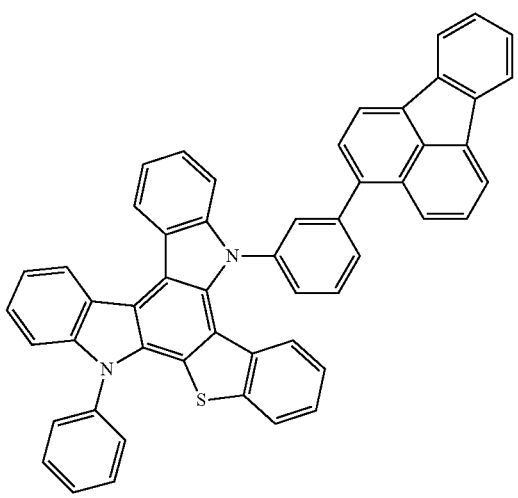
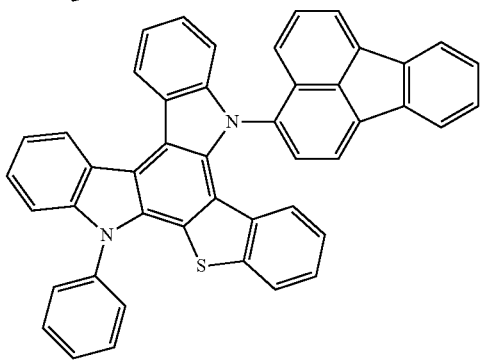

163
-continued
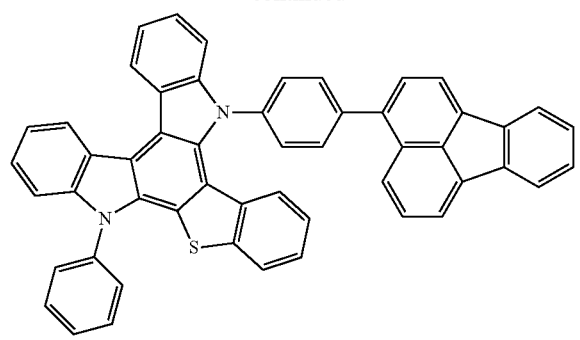
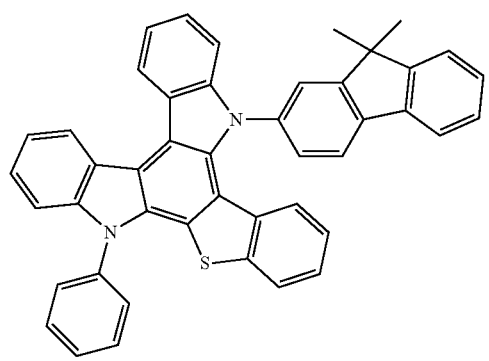
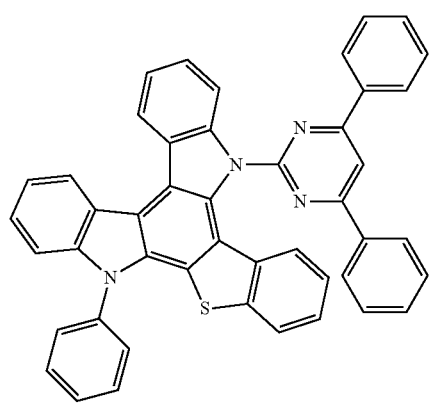
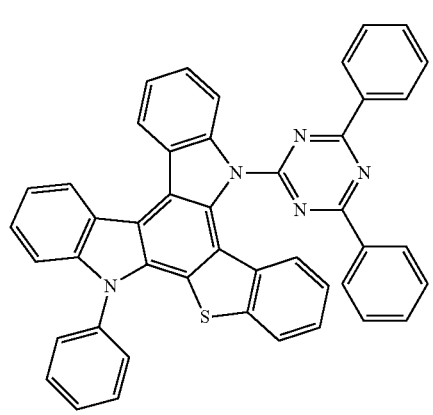
164
-continued
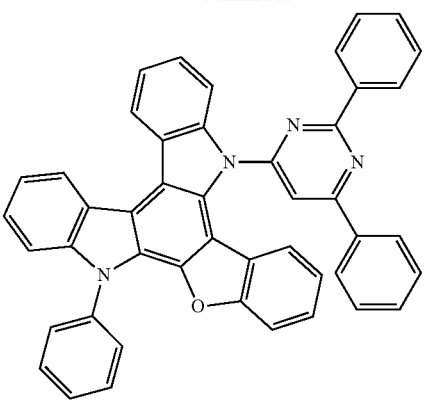
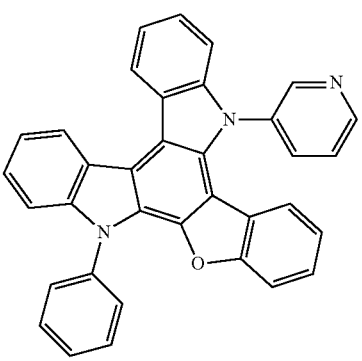
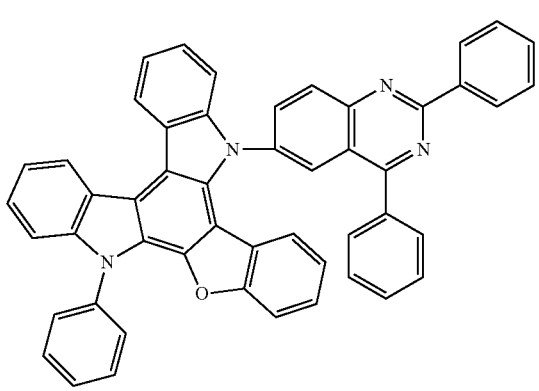
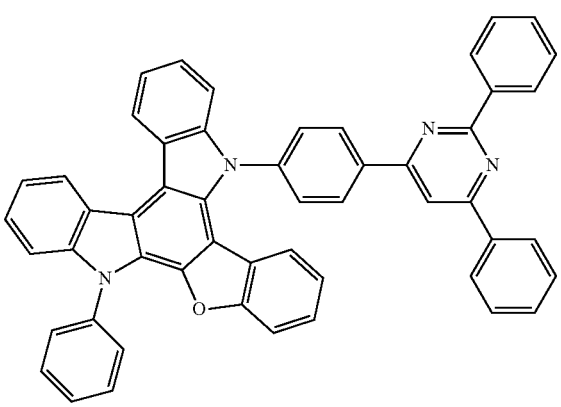

165
-continued
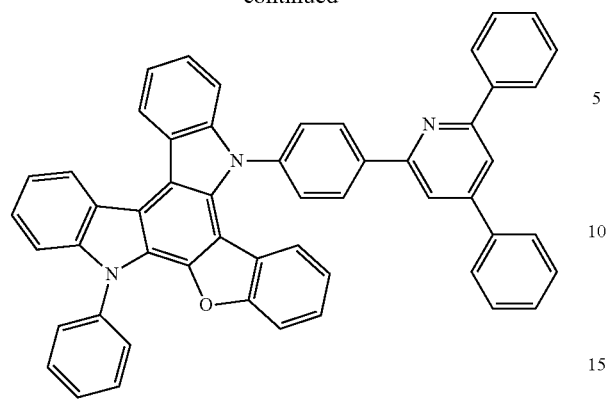
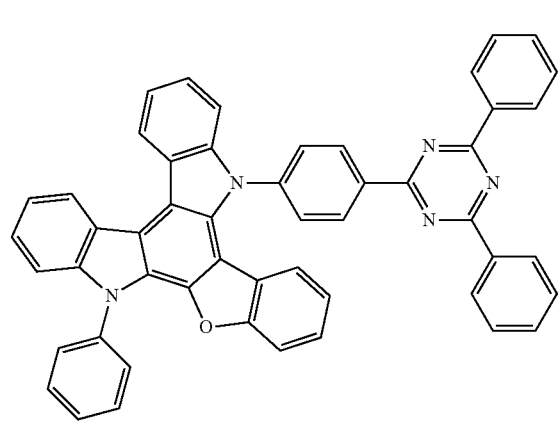
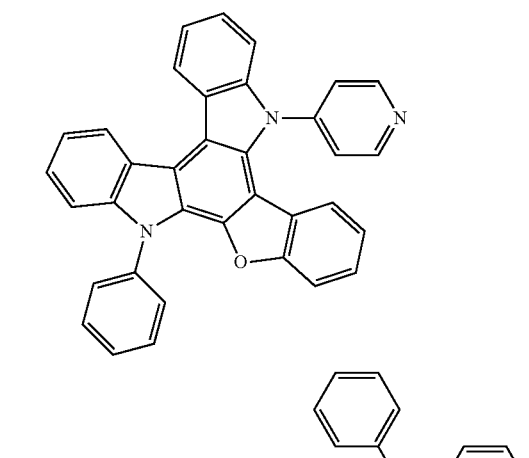
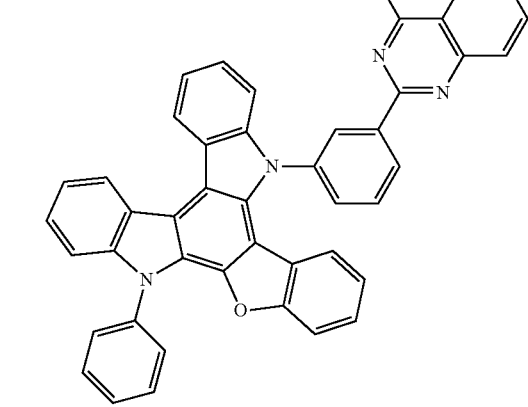
166
-continued
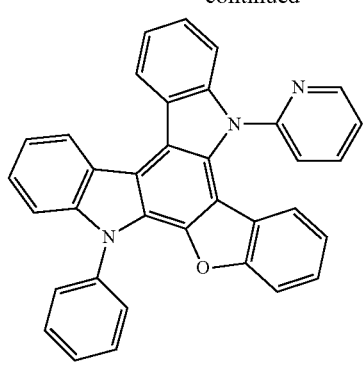
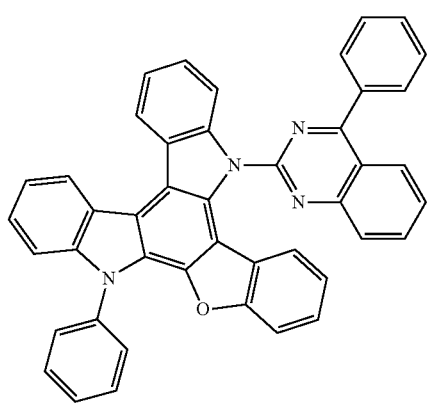
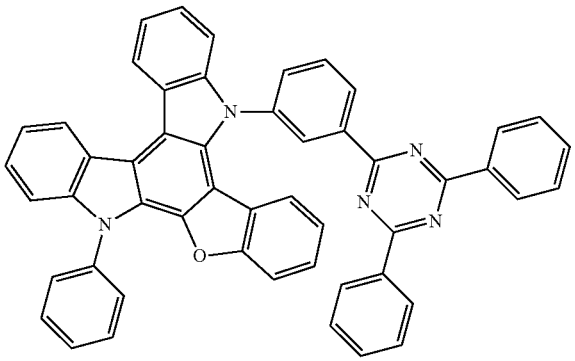
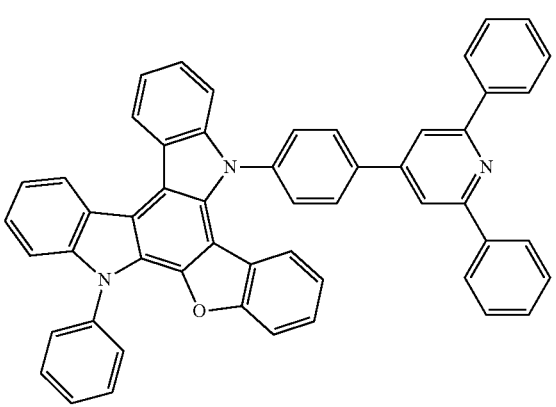

167
-continued
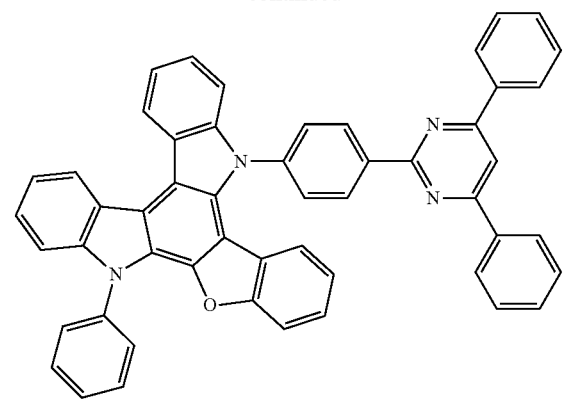
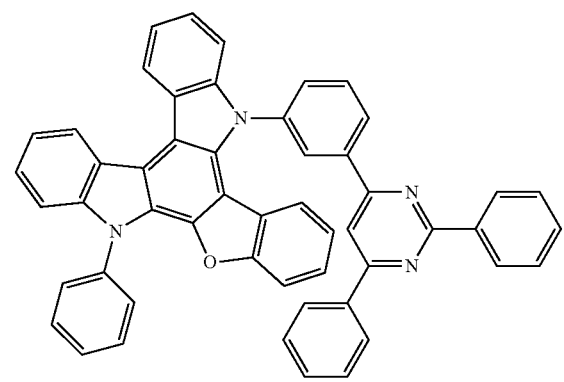
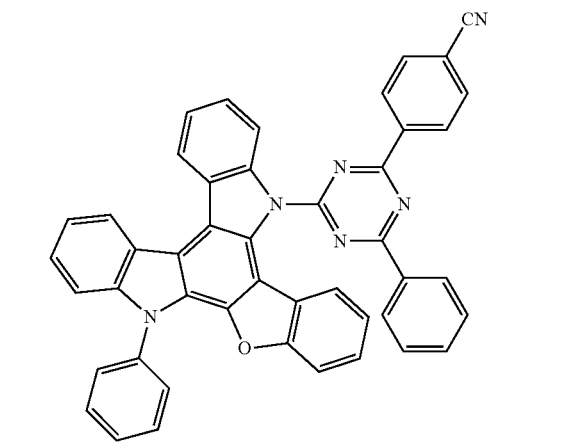
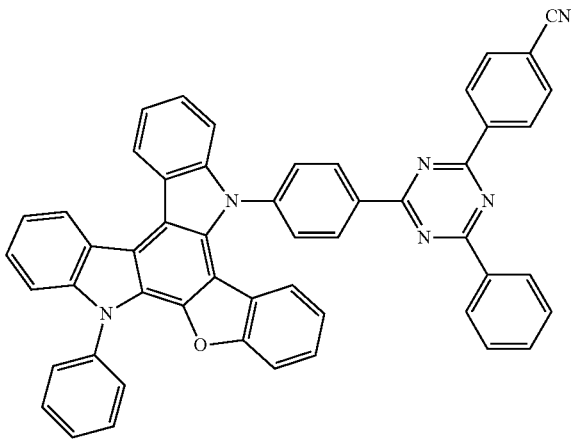
168
-continued
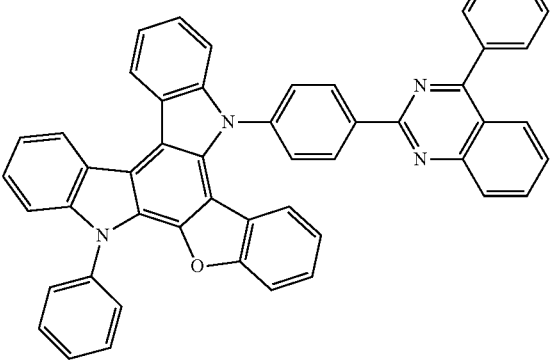
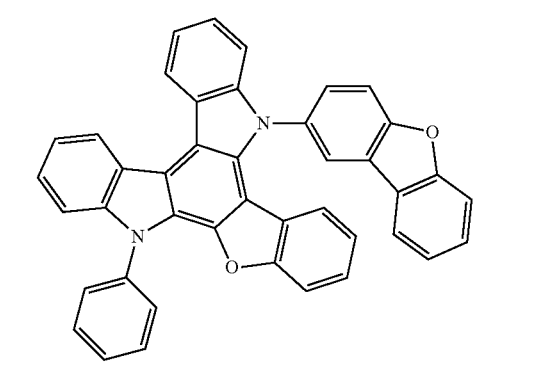
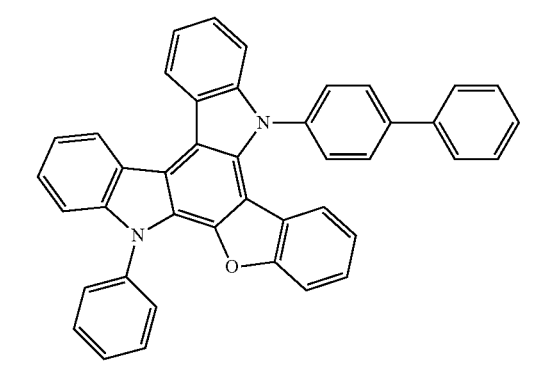
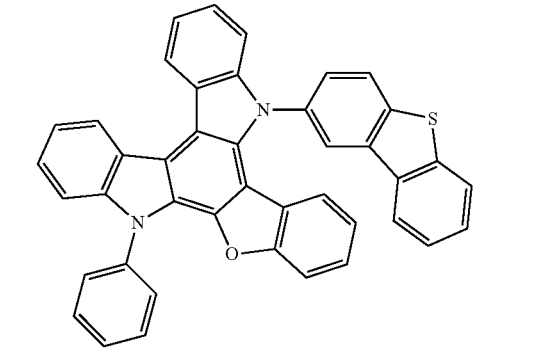

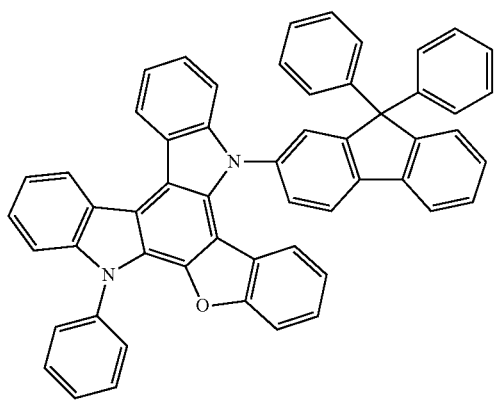
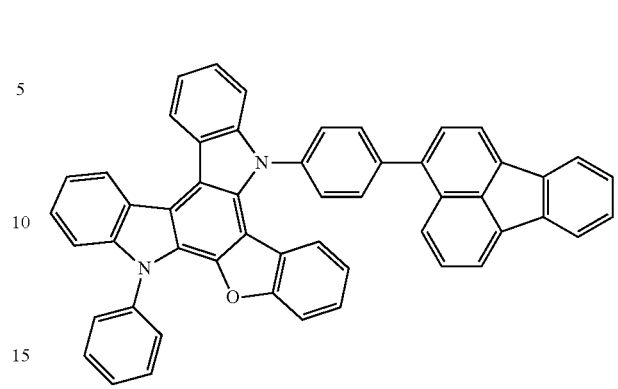
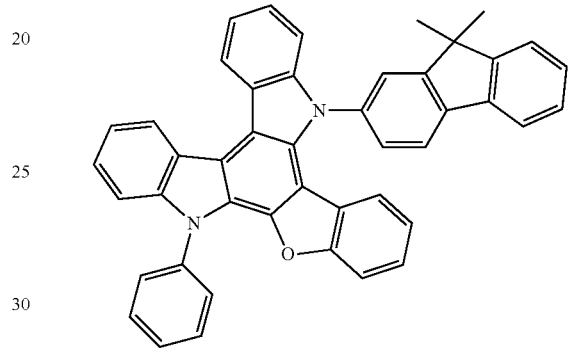
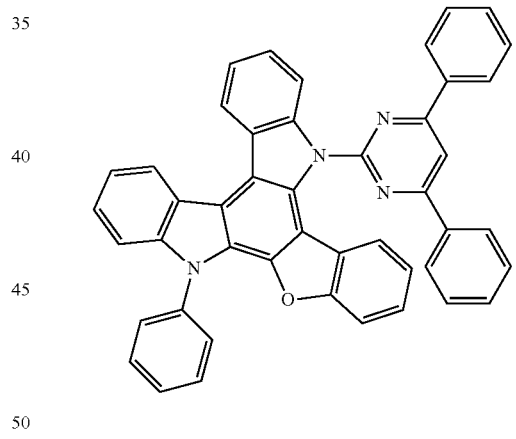
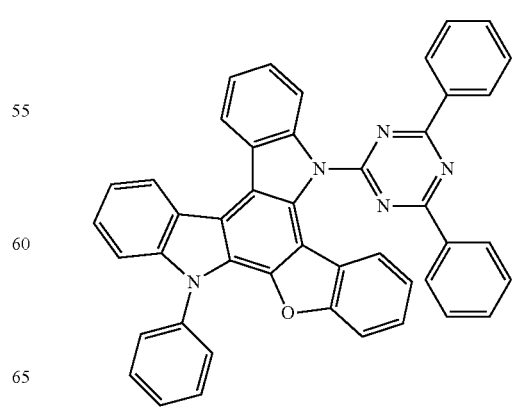

171
-continued
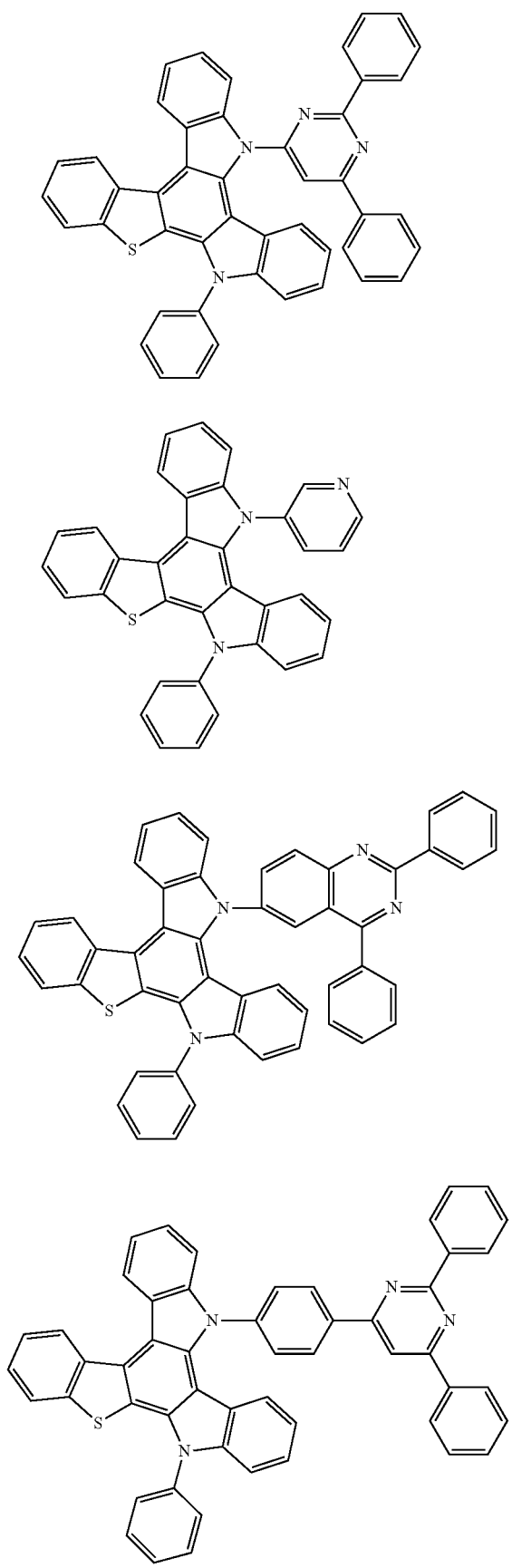
172
-continued
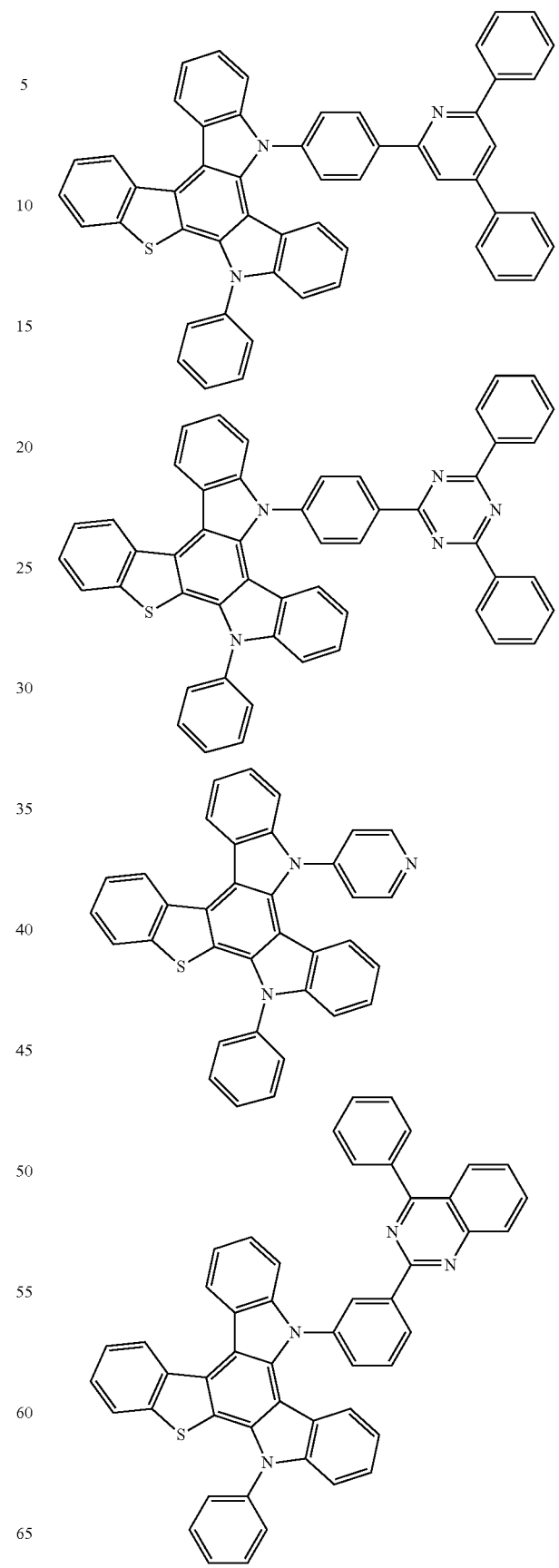

173
-continued
174
-continued
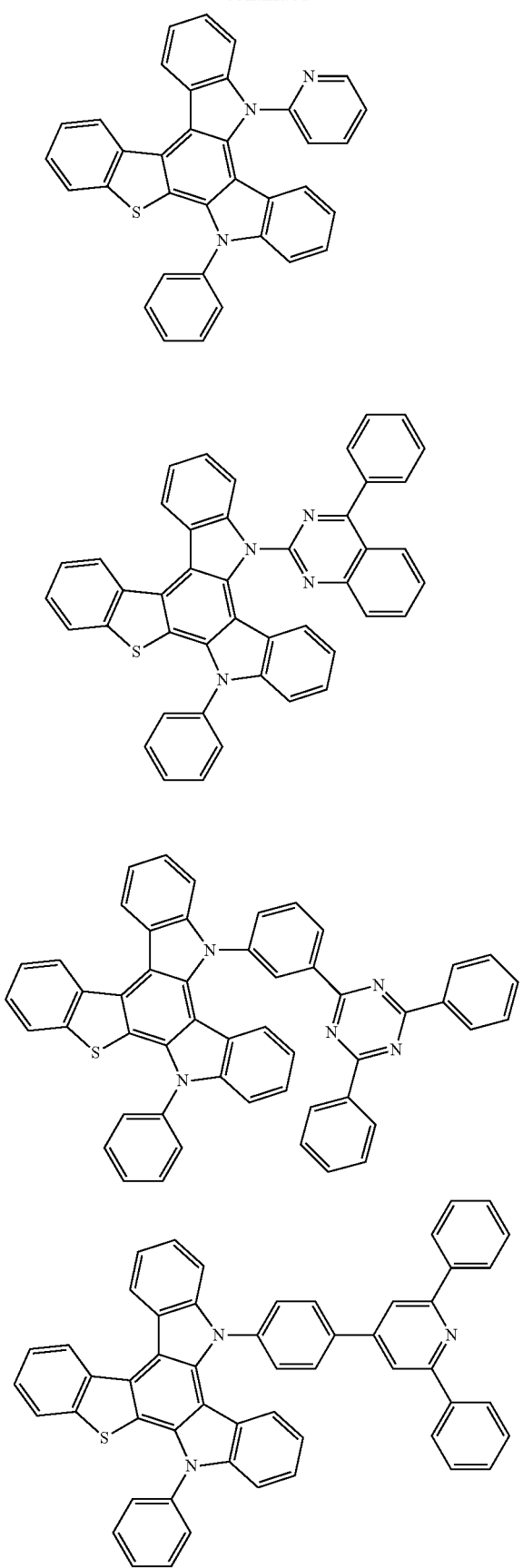
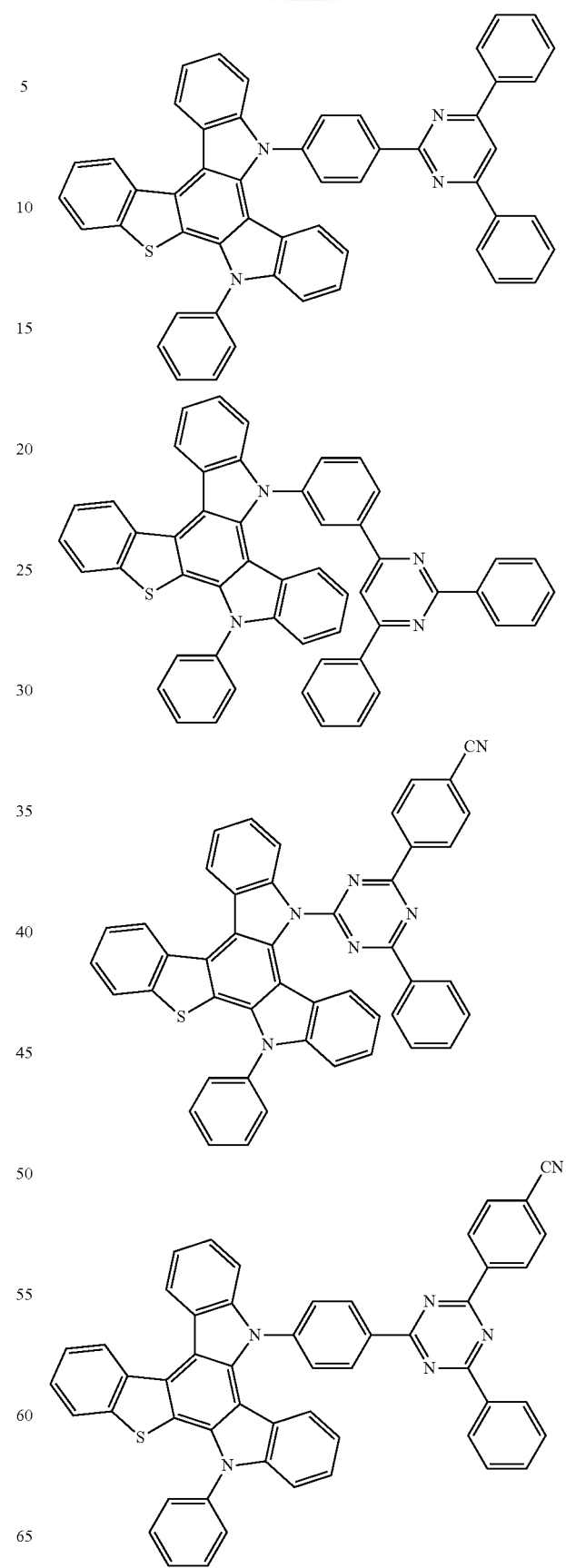

-continued
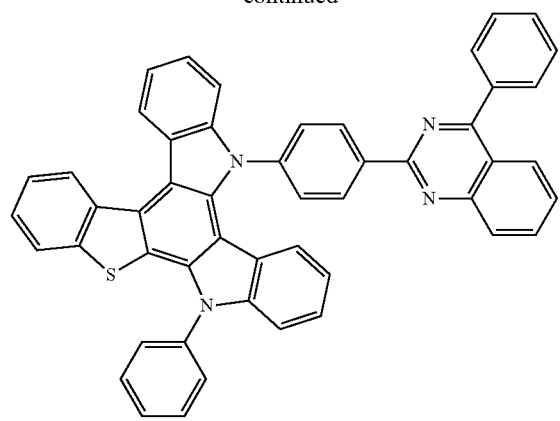
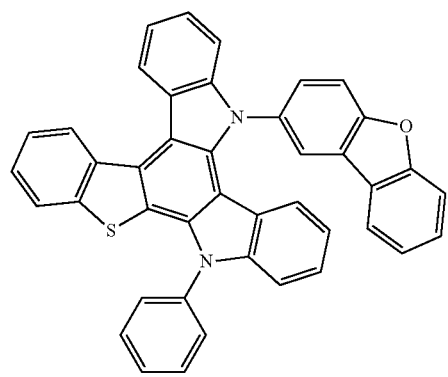
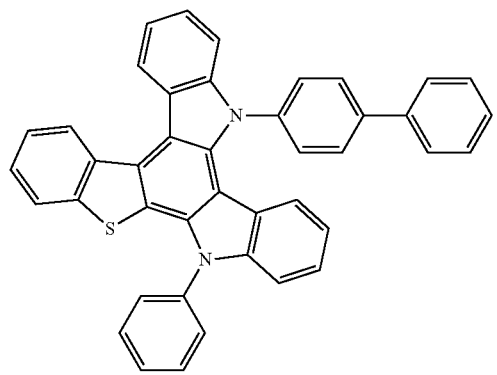
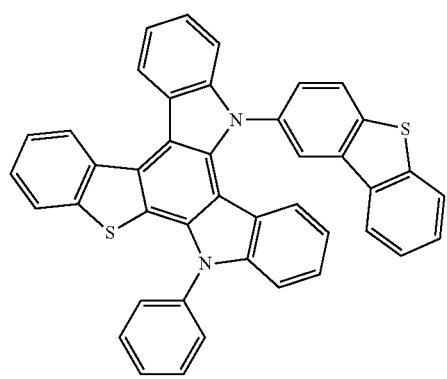
-continued
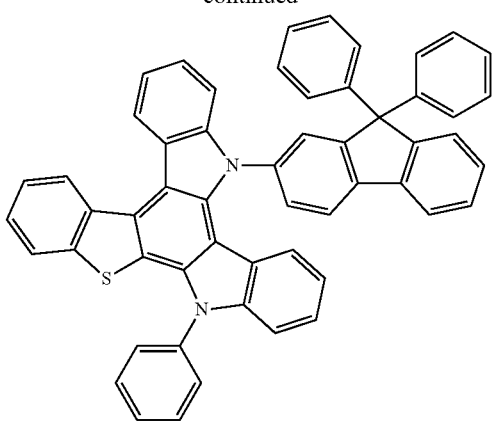
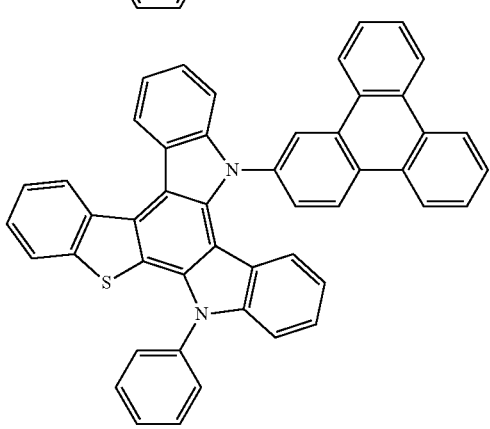
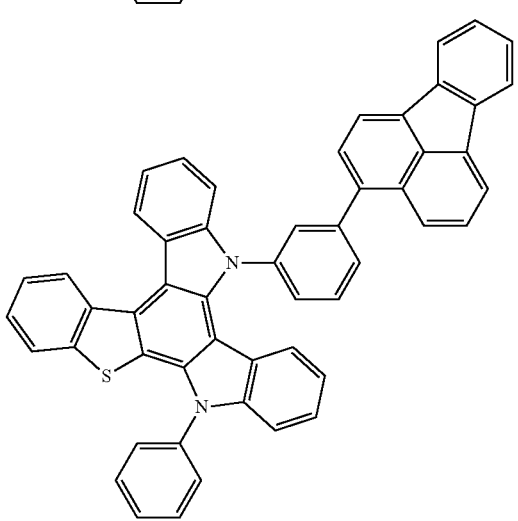
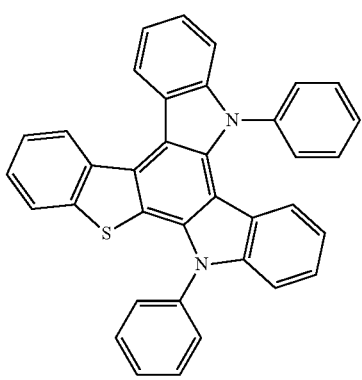

177
-continued
178
-continued
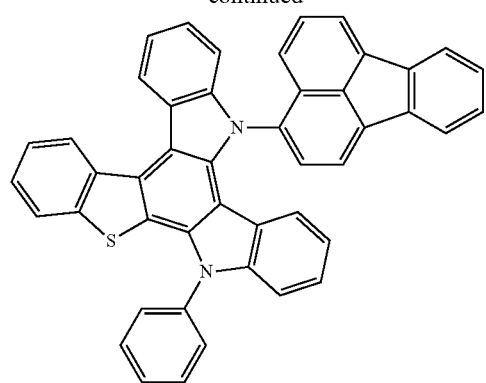
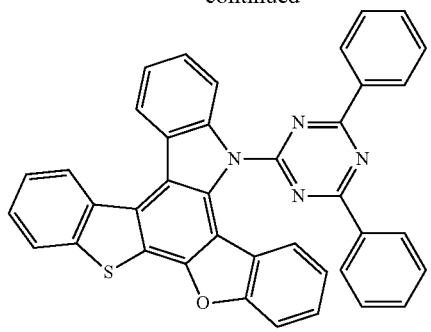
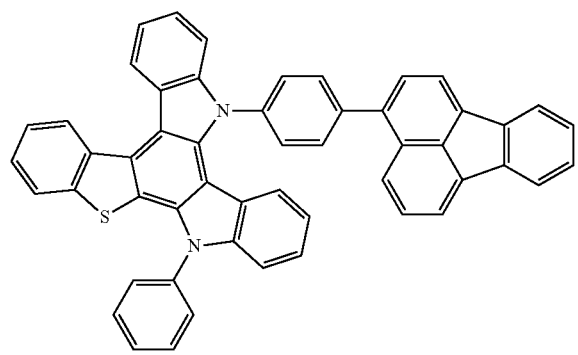
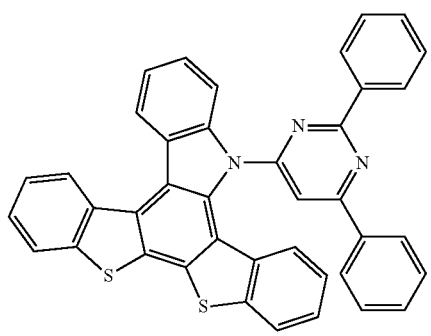
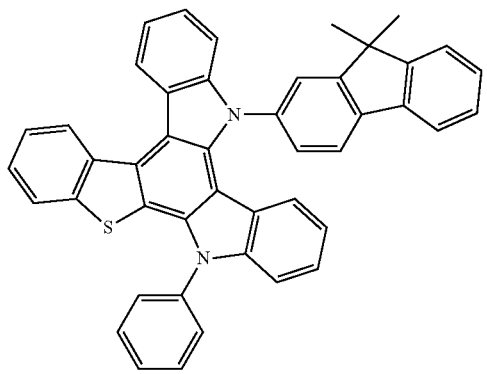
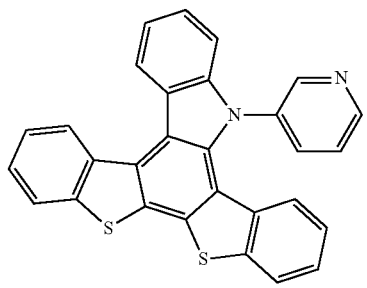
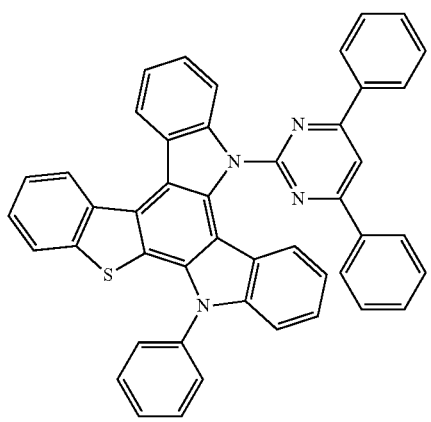
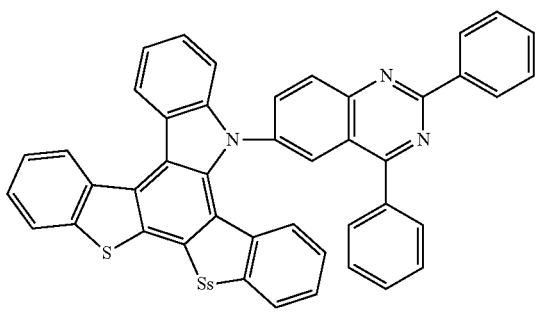
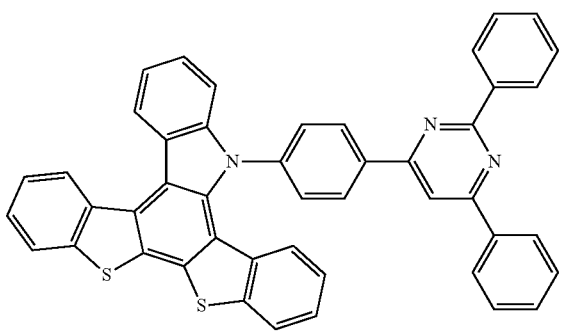

179
-continued
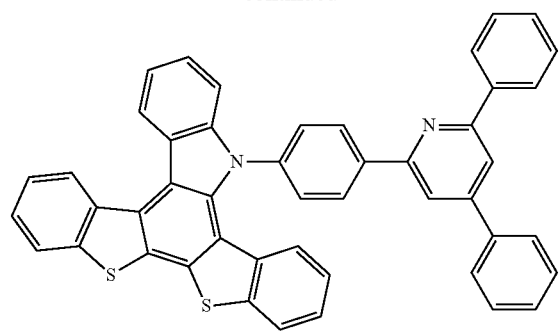
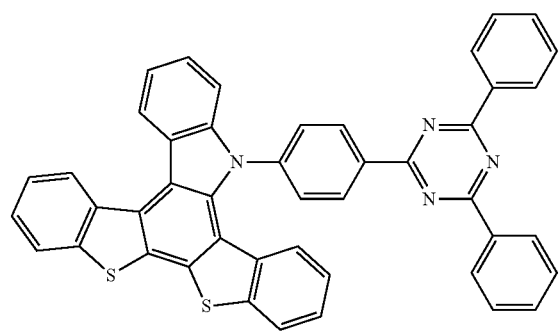
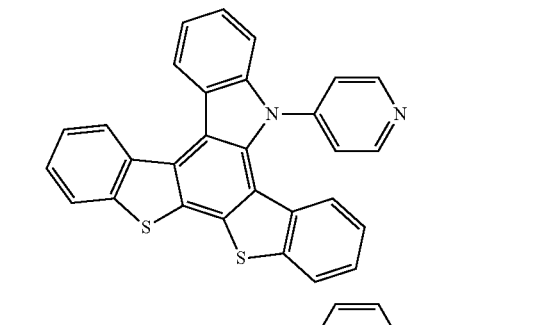
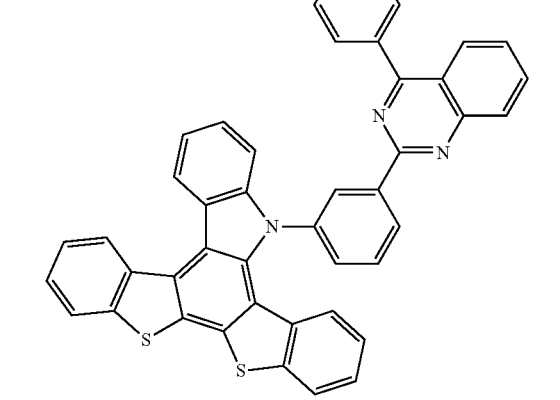
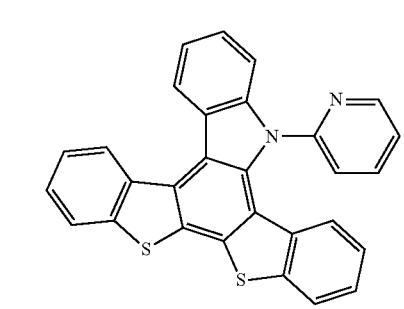
180
-continued
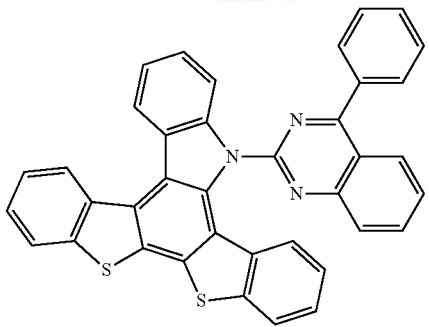
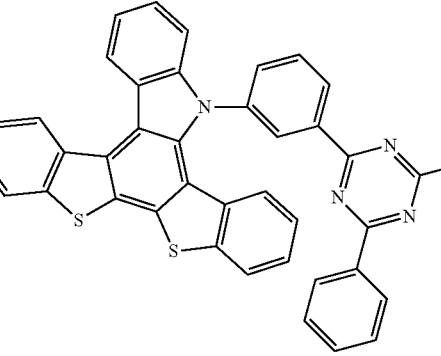
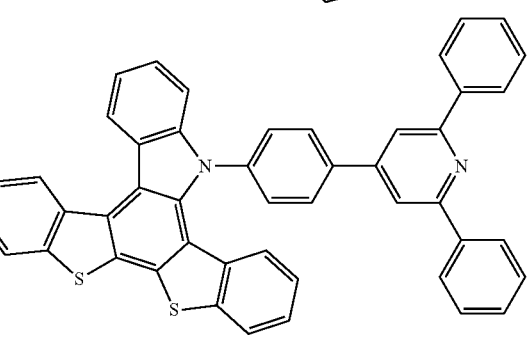
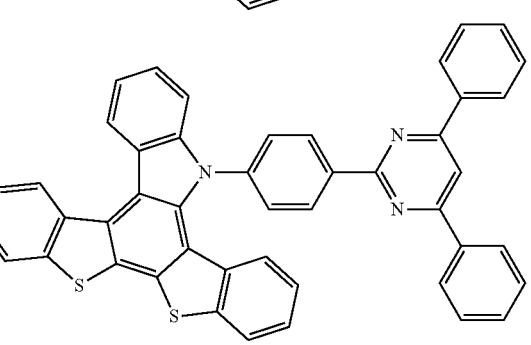
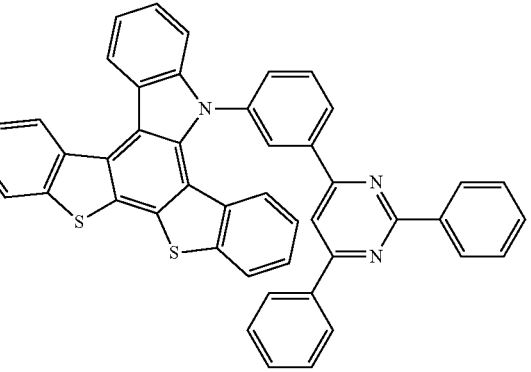

-continued
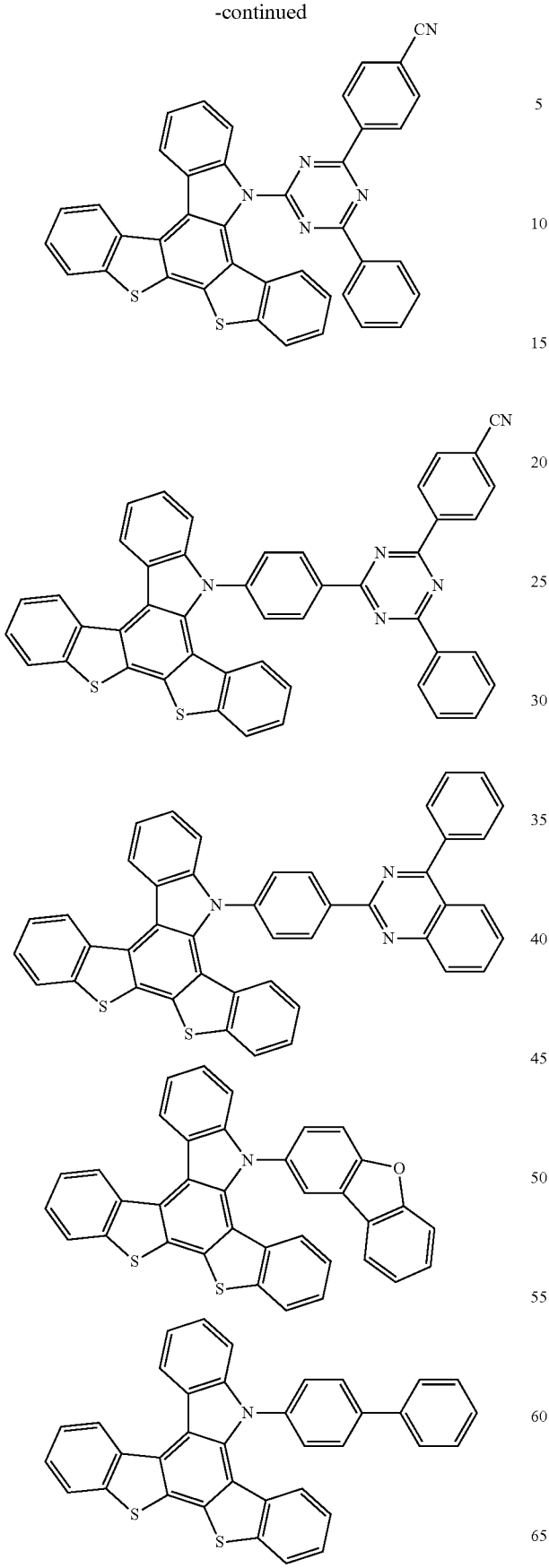
-continued
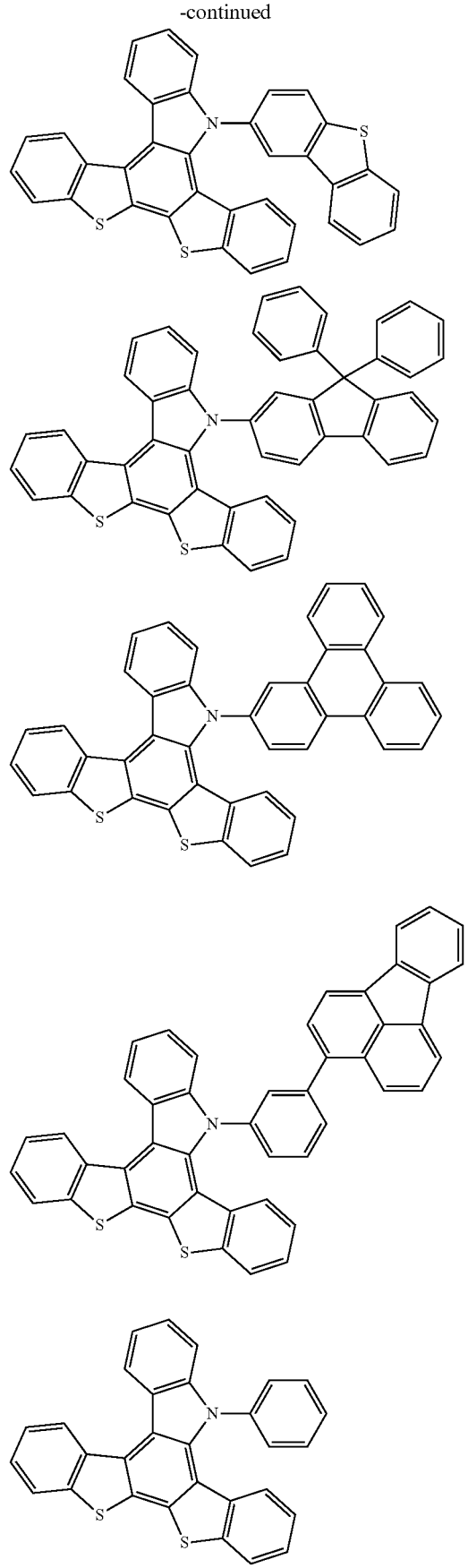

183
-continued
184
-continued
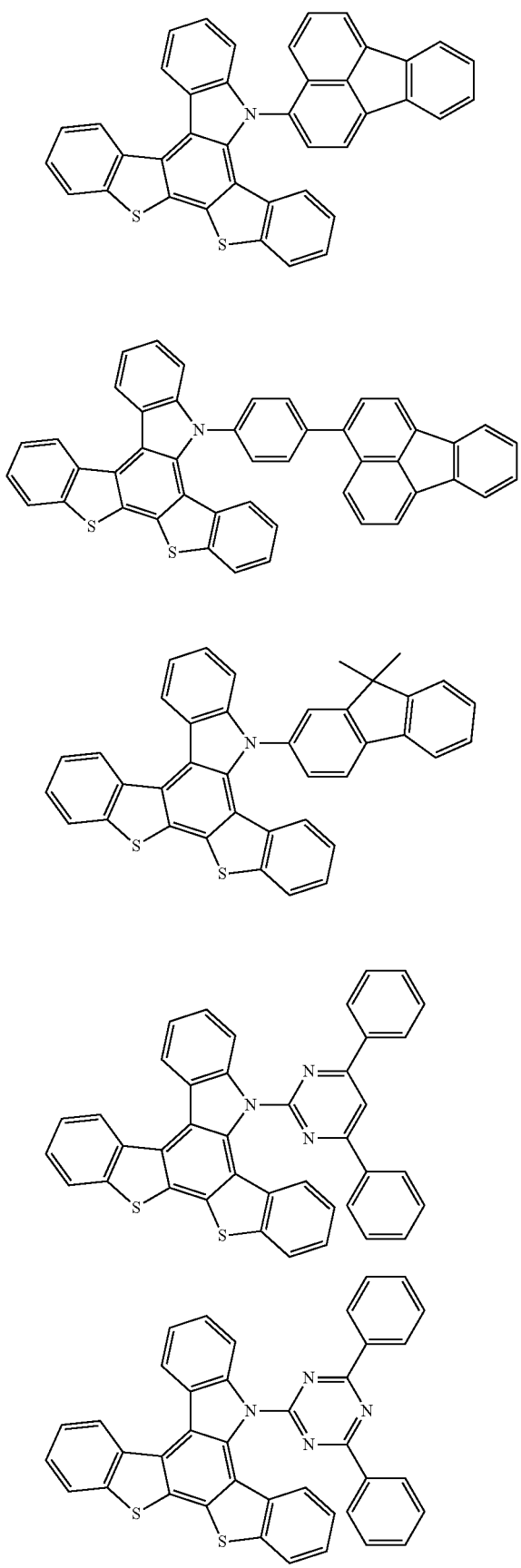
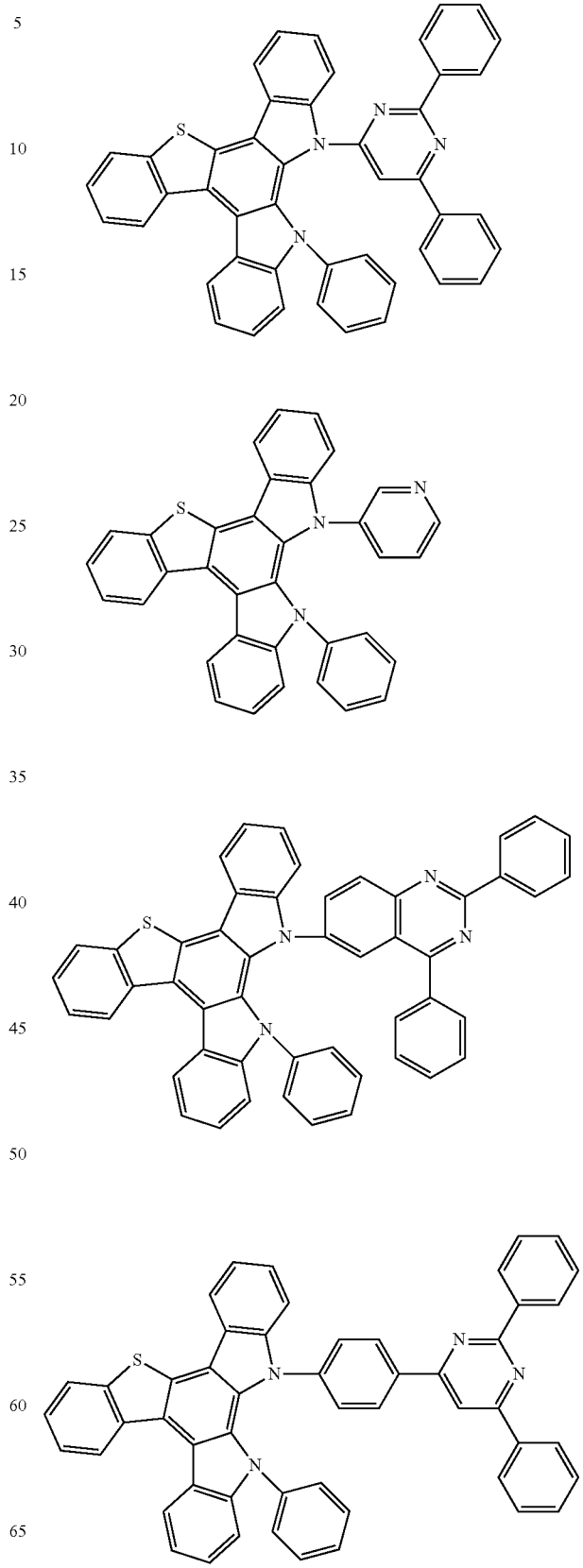

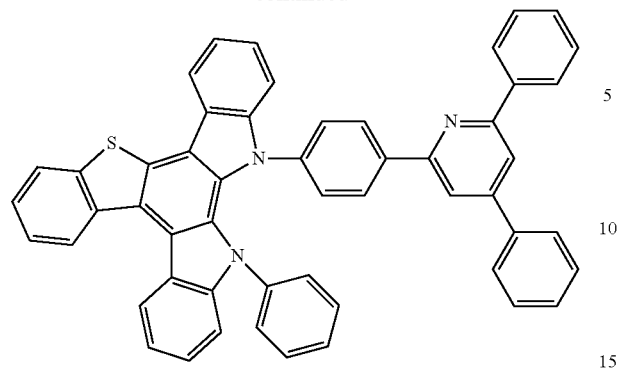
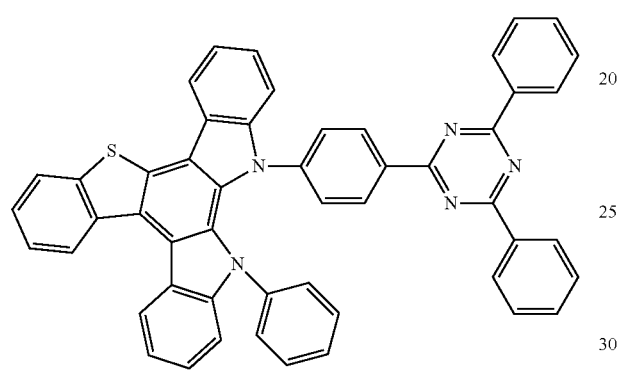
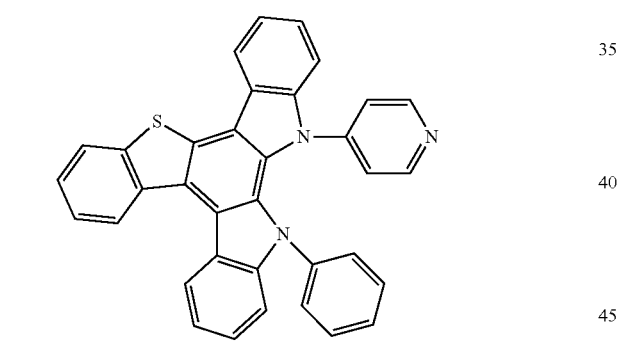
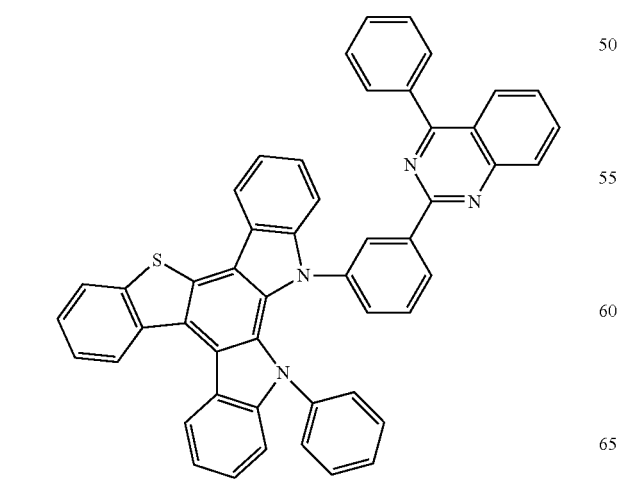
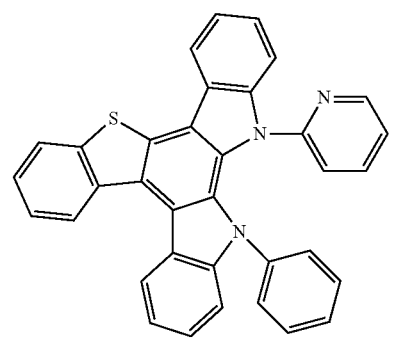
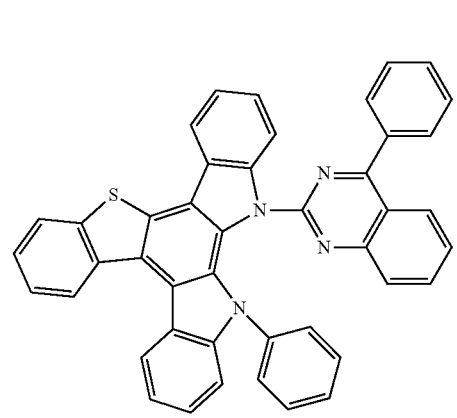
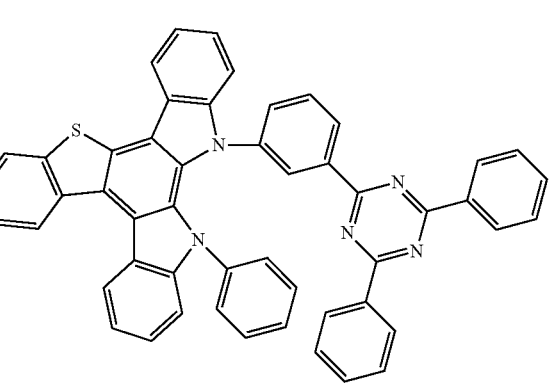
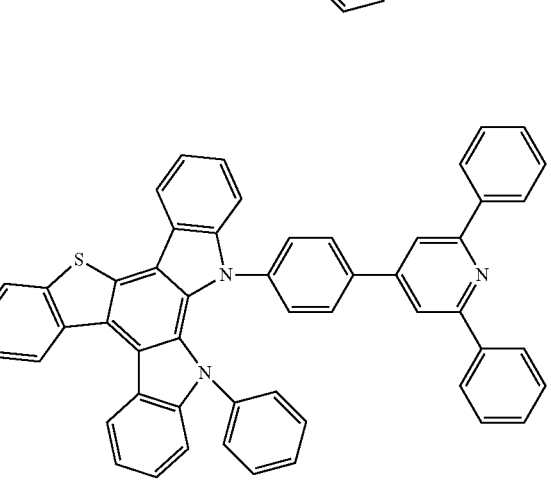

187
-continued
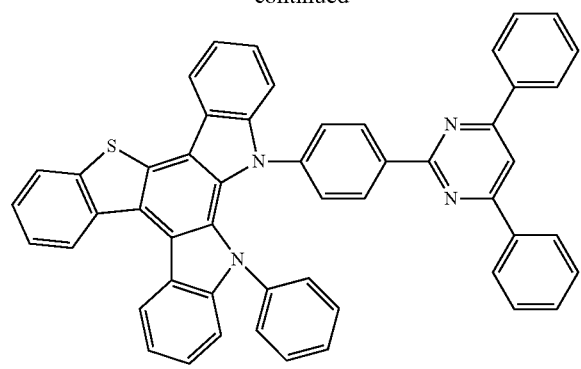
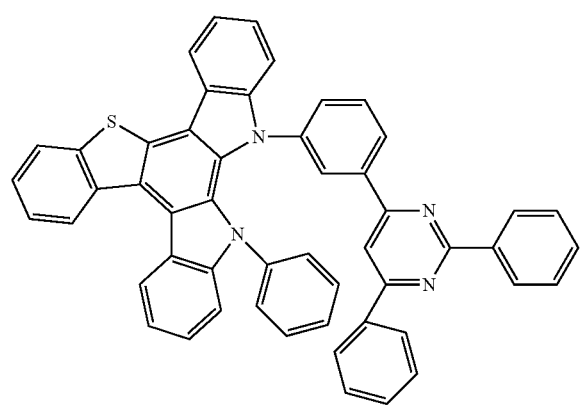
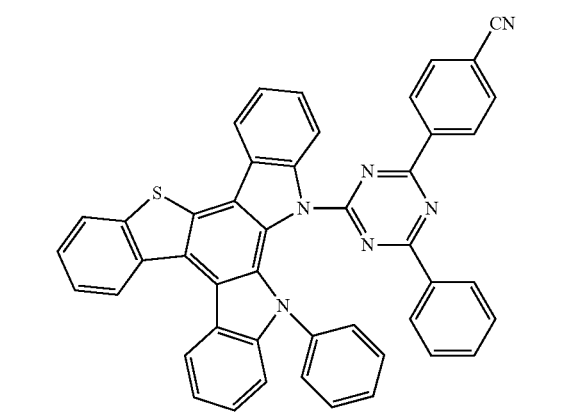
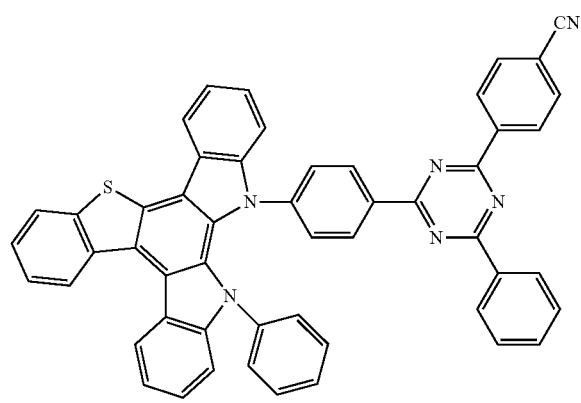
188
-continued
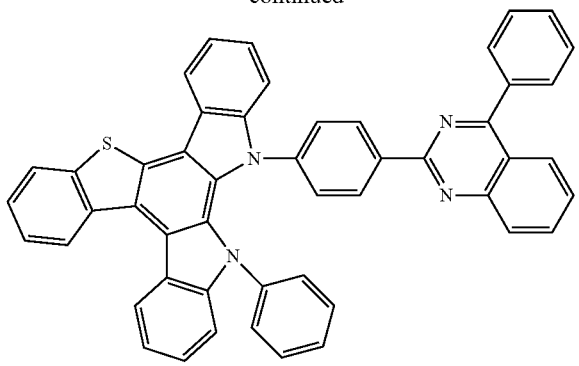
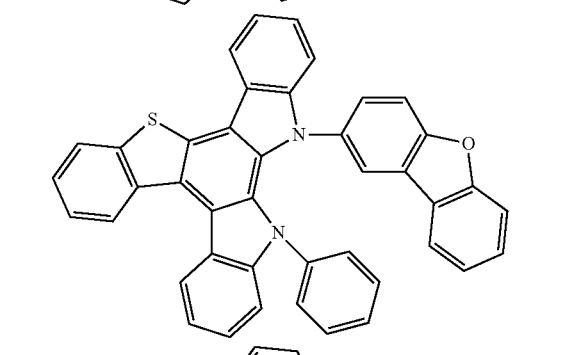
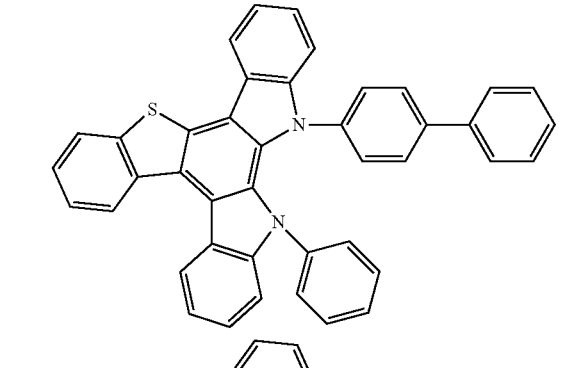
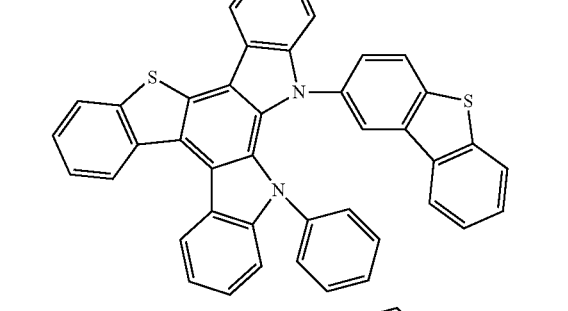
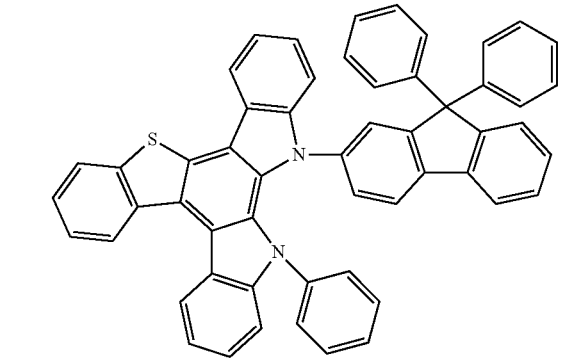

189
-continued
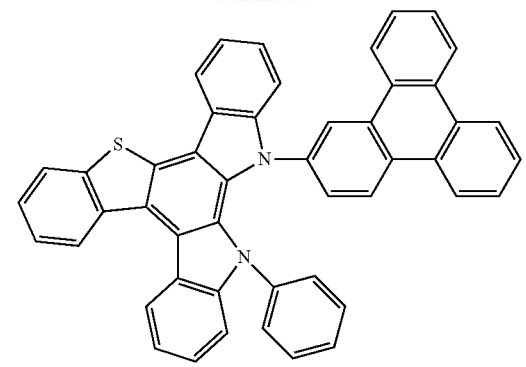
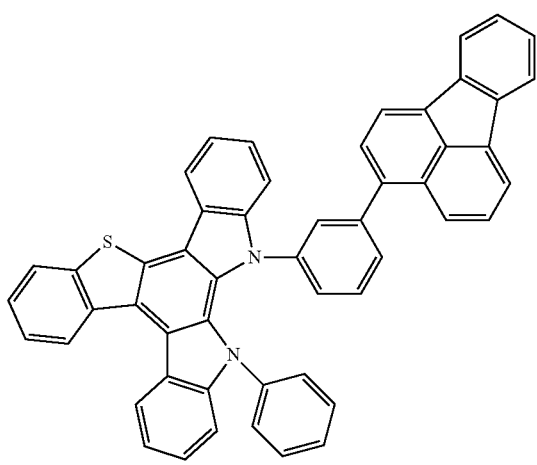
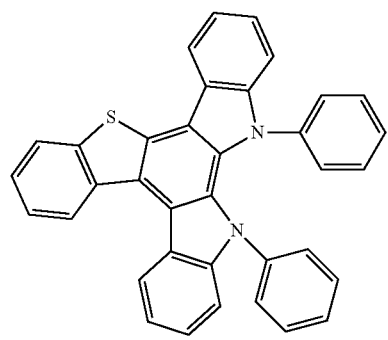
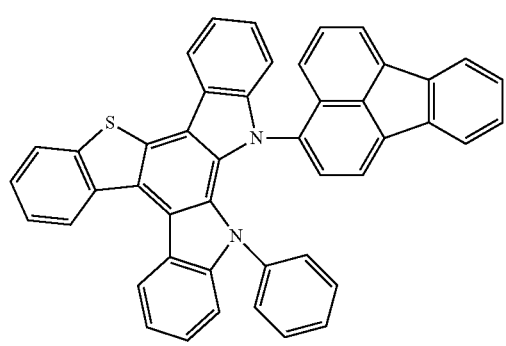
190
-continued
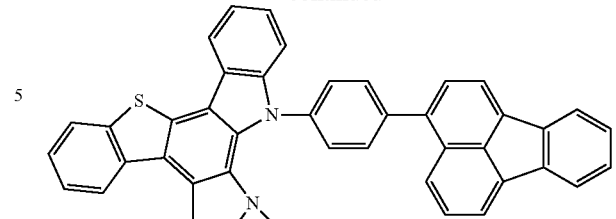
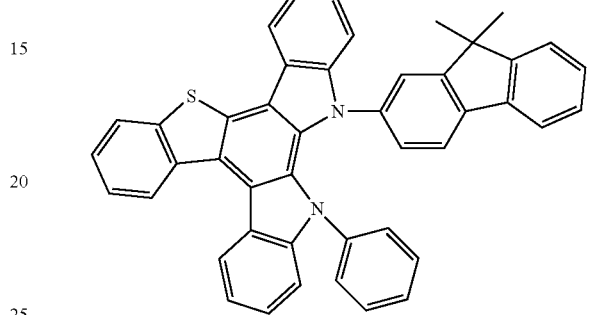
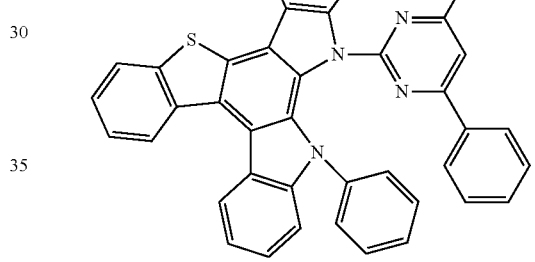
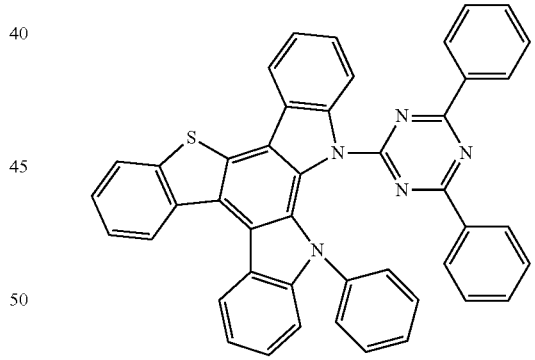

-continued
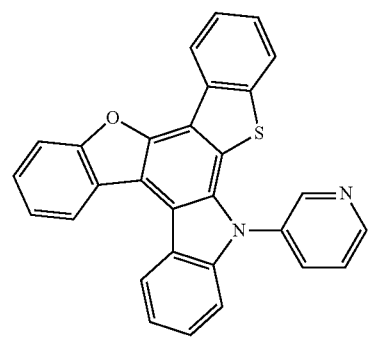
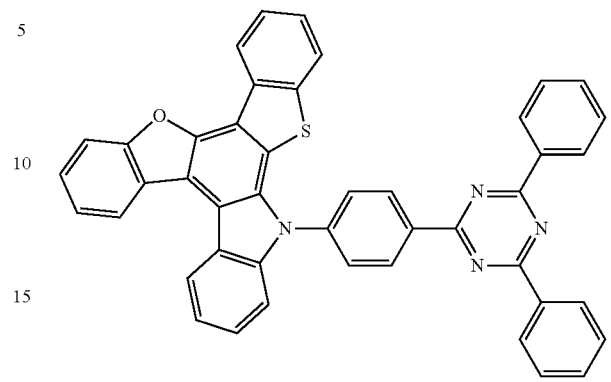
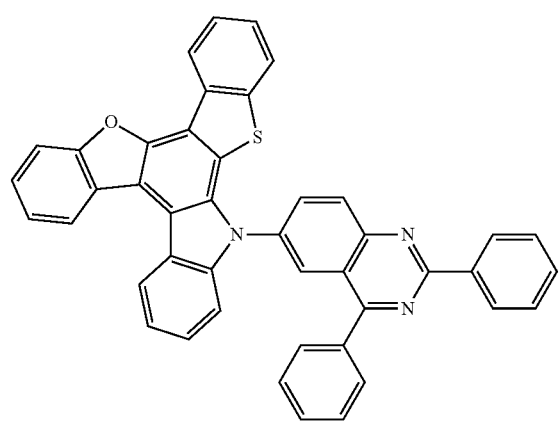
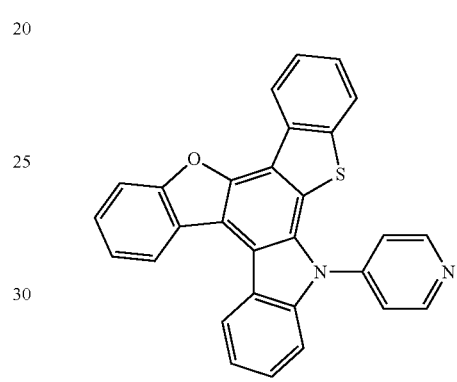
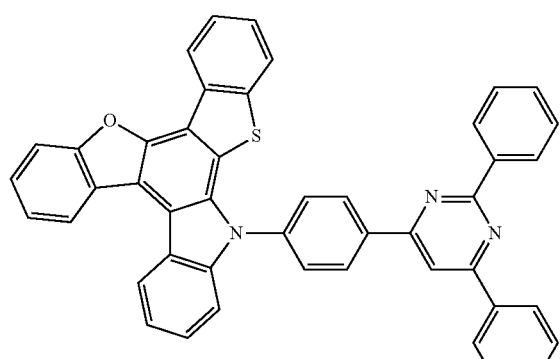
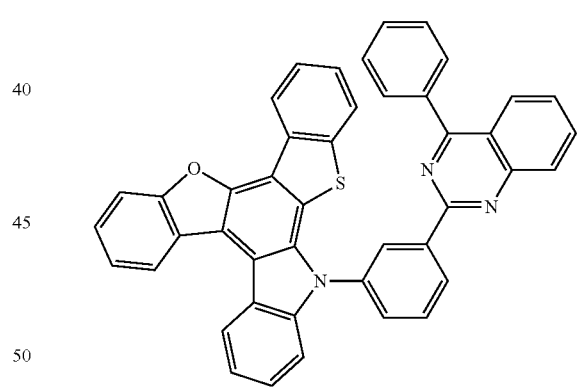
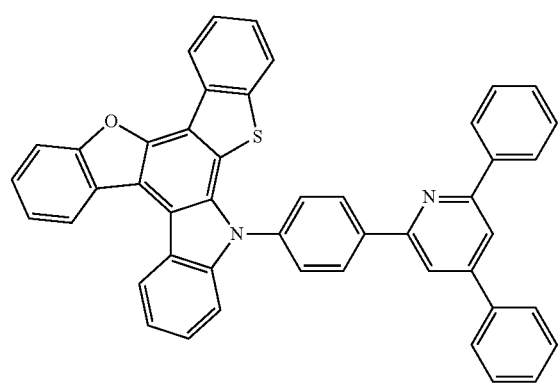
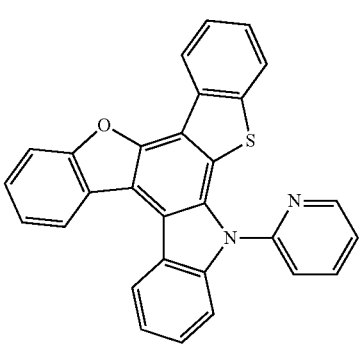

193
-continued
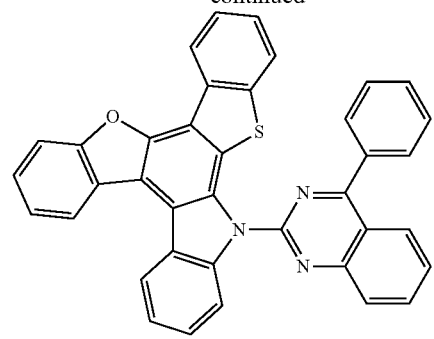
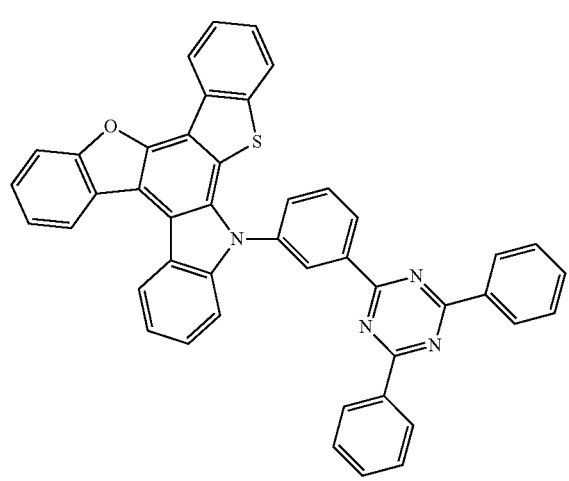
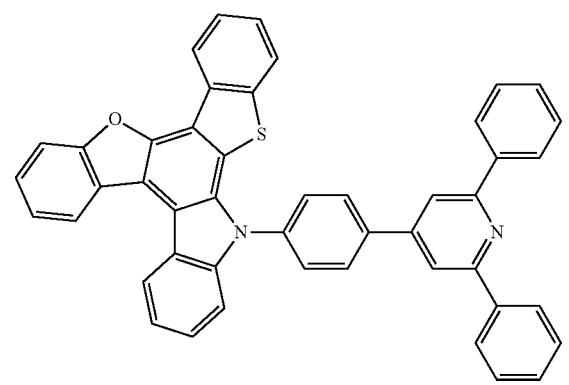
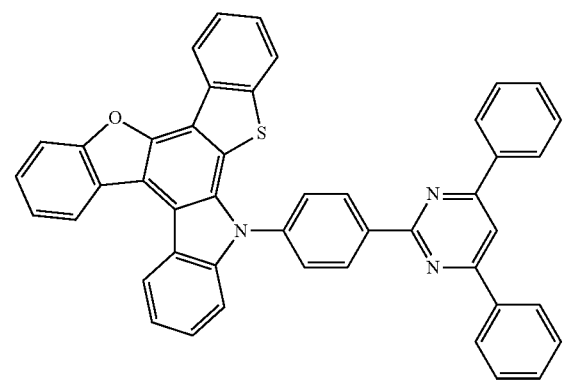
194
-continued
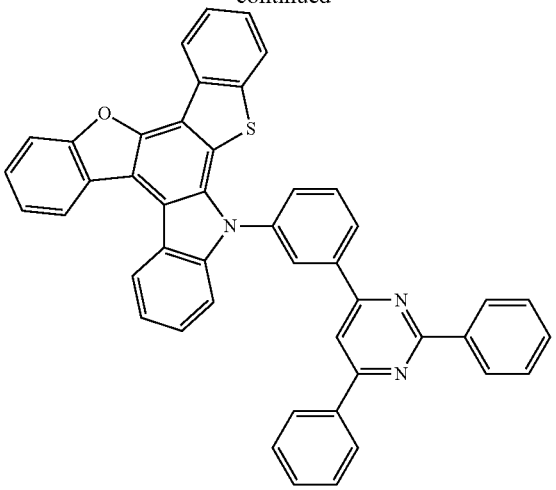
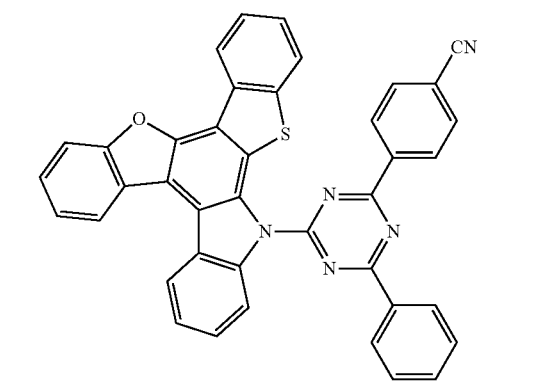
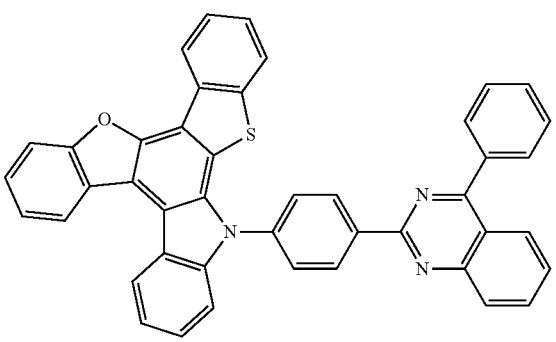

195
-continued
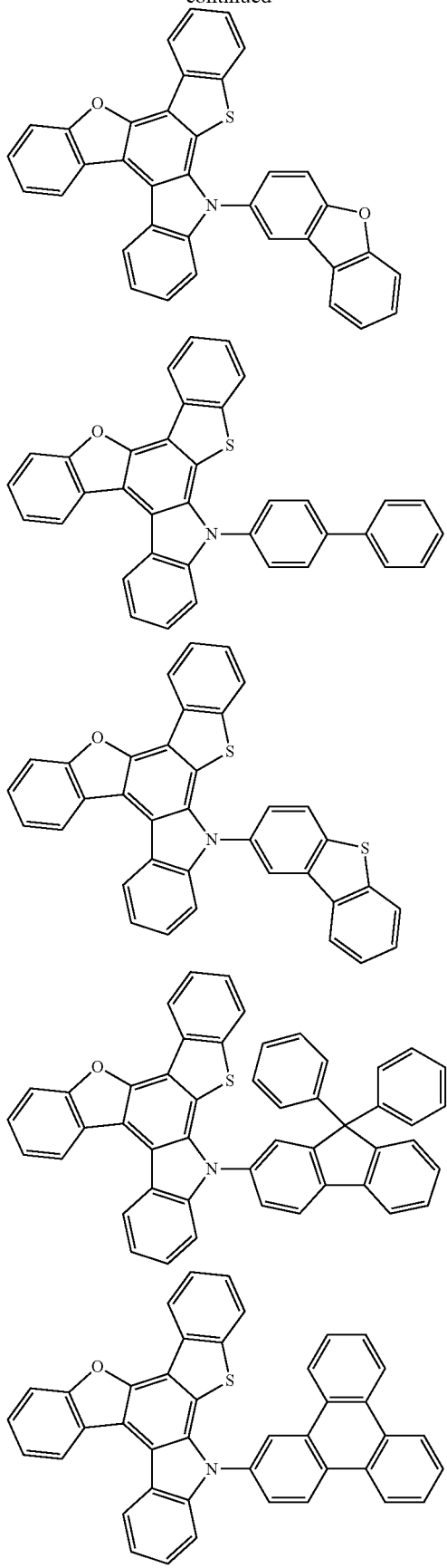
196
-continued
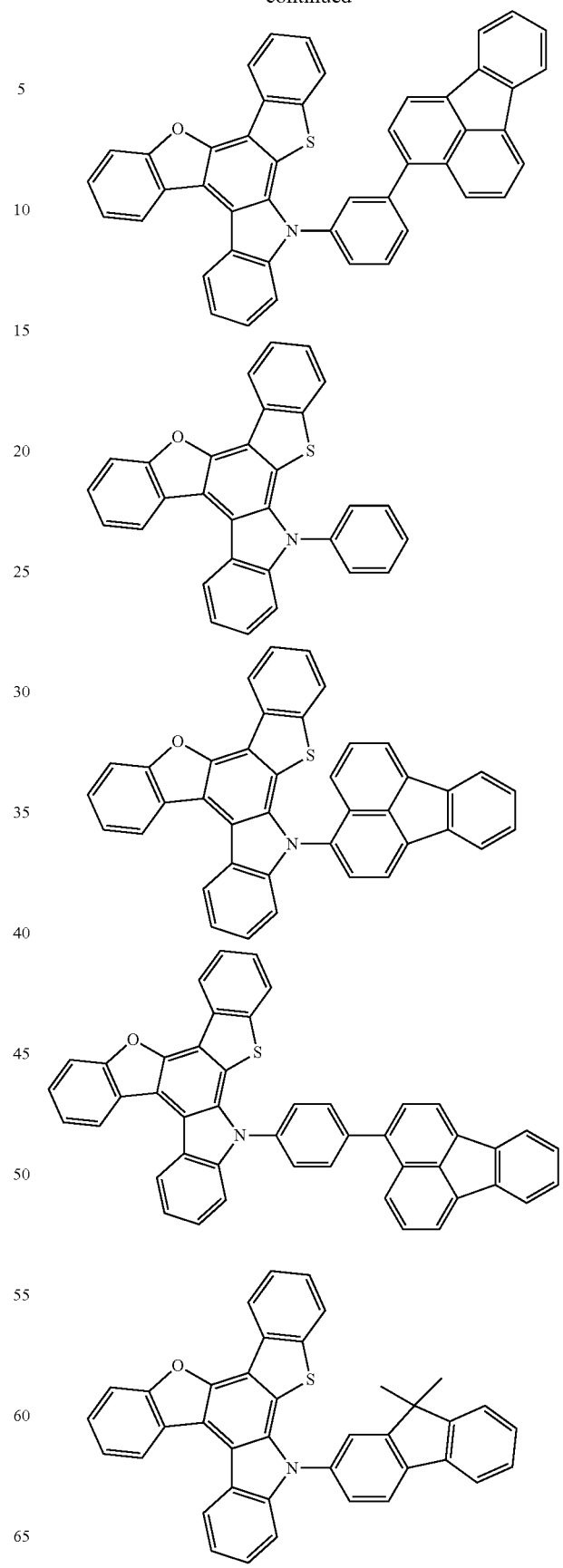

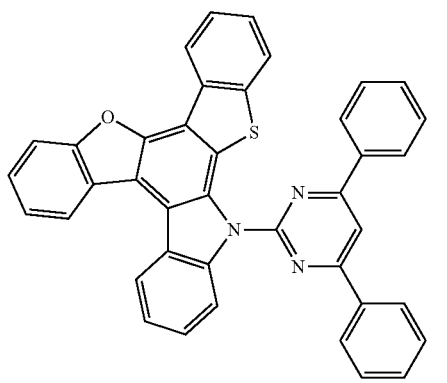
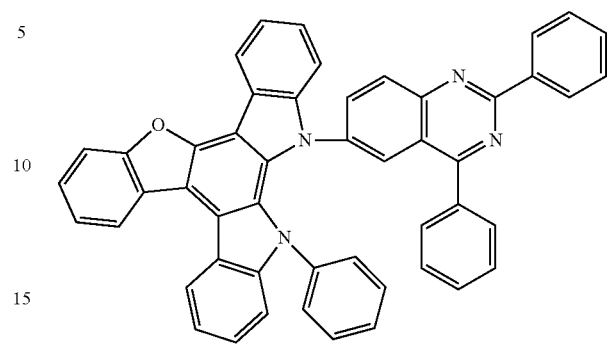
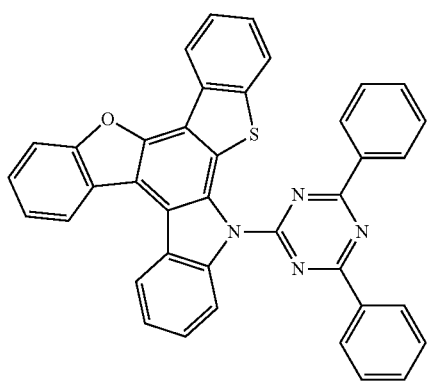
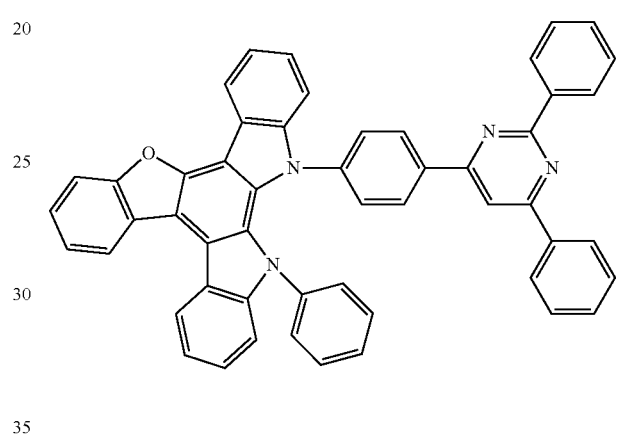
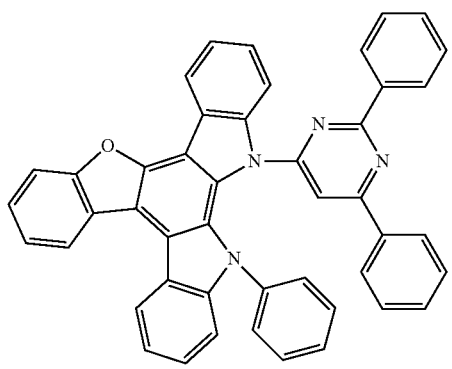
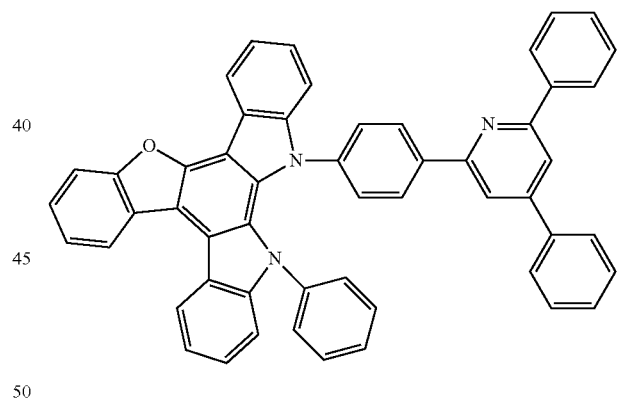
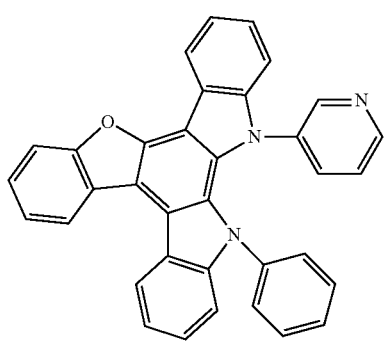
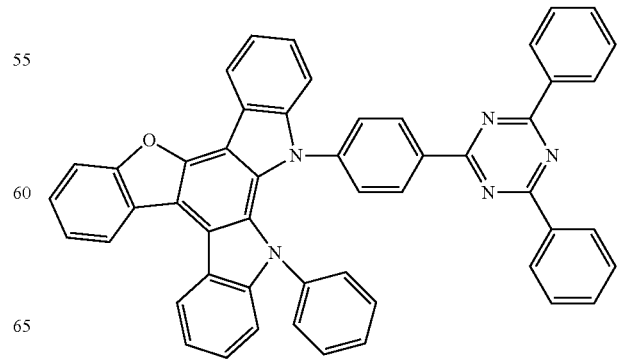

| 199 | 200 |
|---|---|
| -continued | -continued |
| 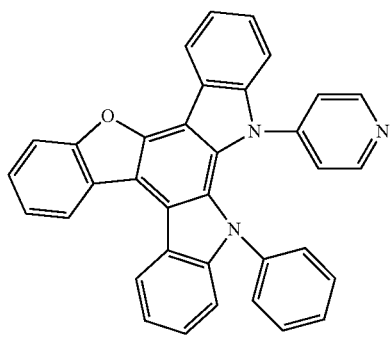 | 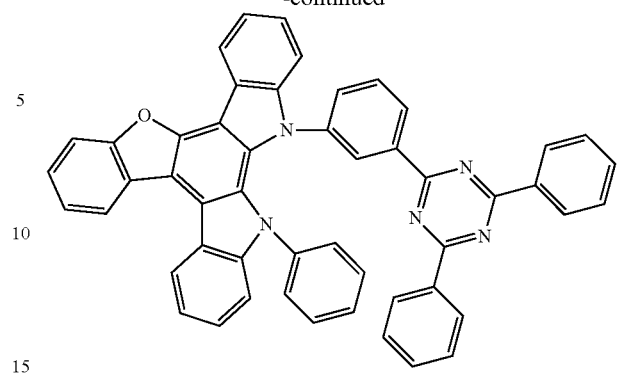 |
| 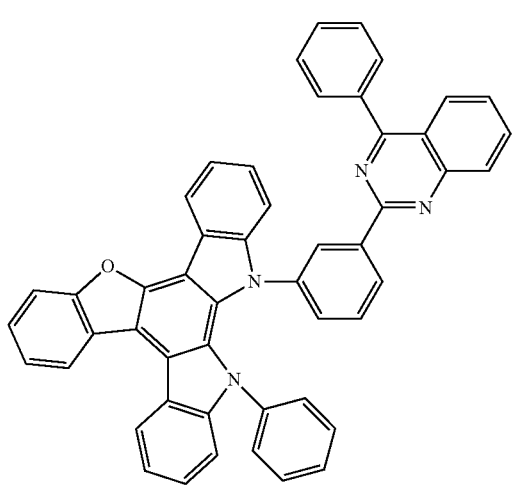 | 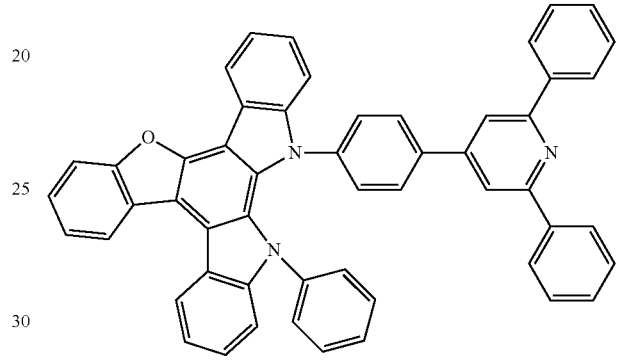 |
| 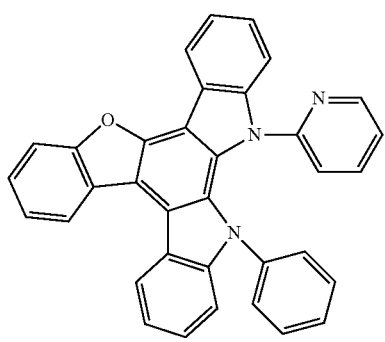 | 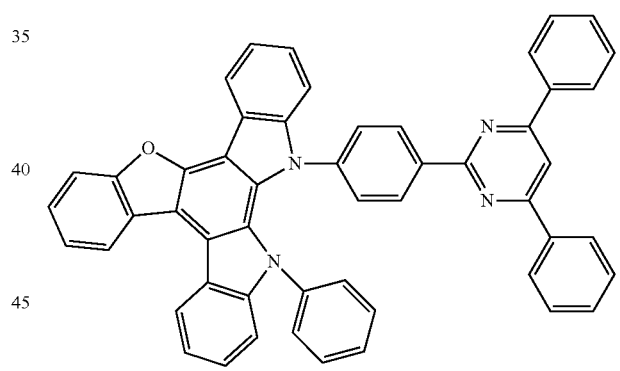 |
| 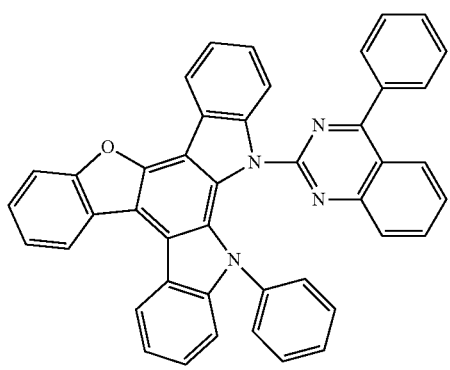 | 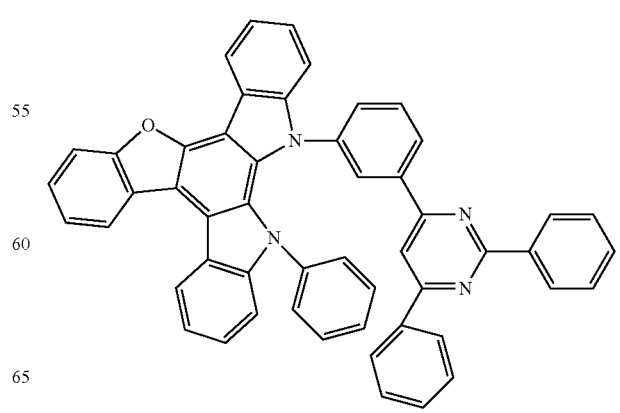 |

201
-continued
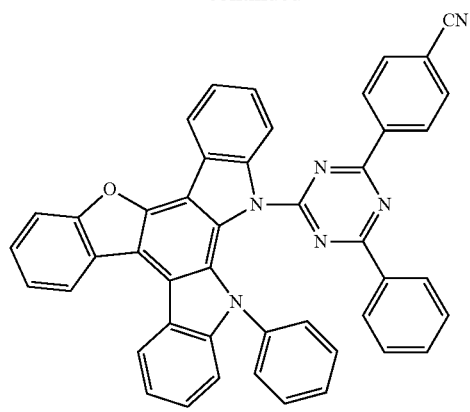
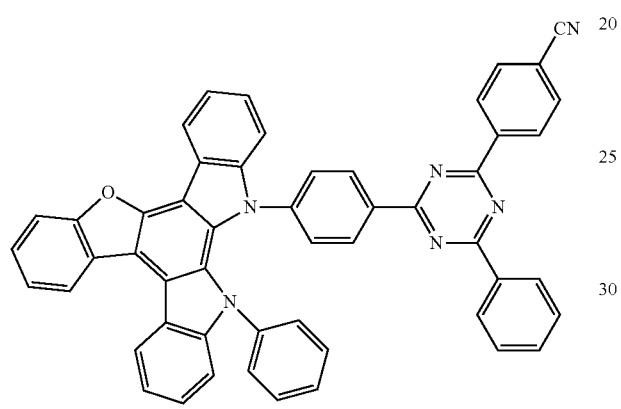
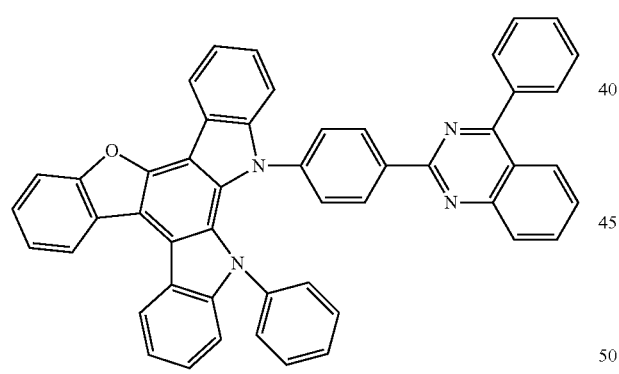
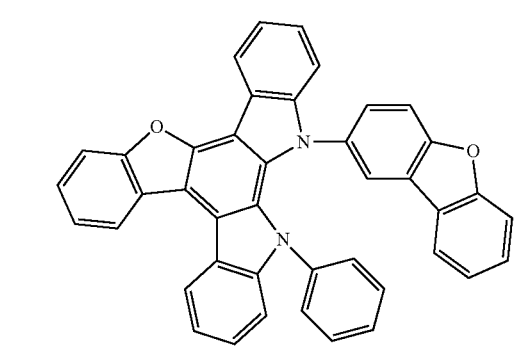
202
-continued
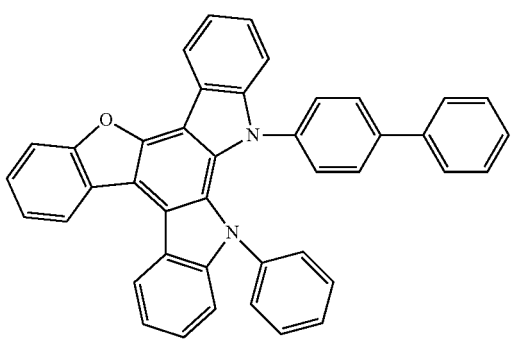
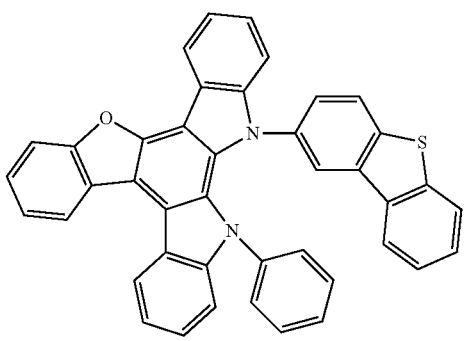
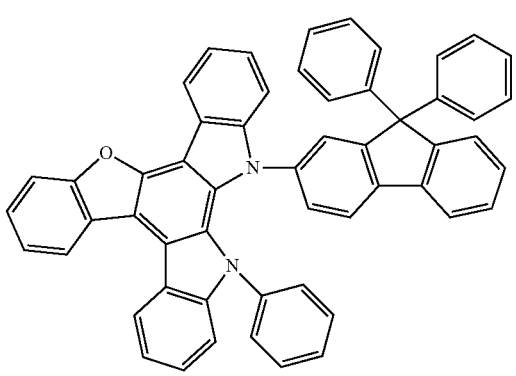
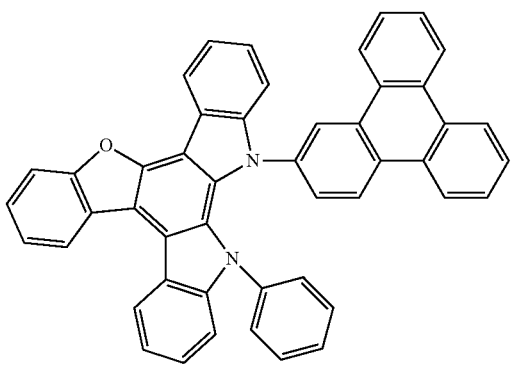

203
-continued
204
-continued
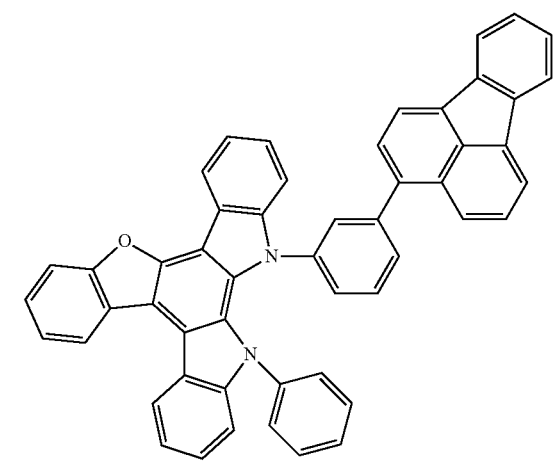
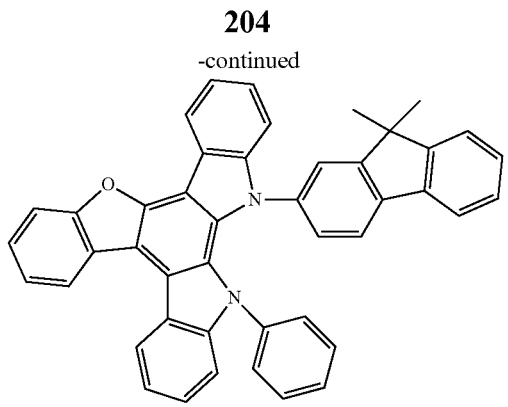
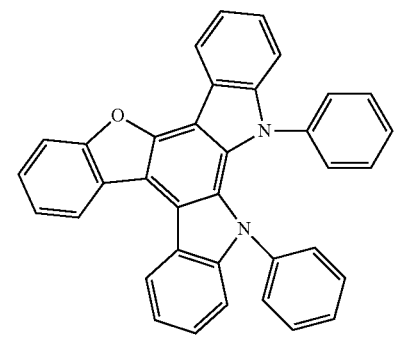
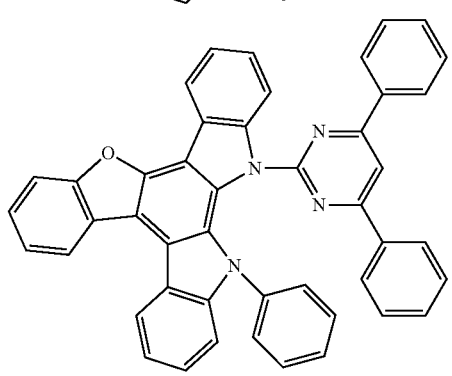
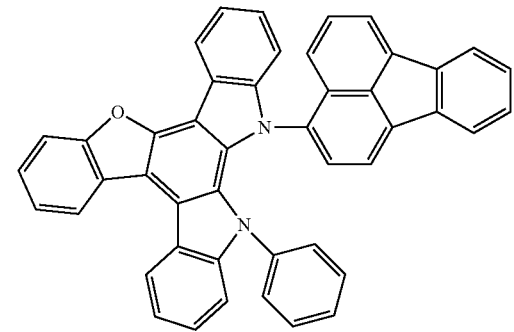
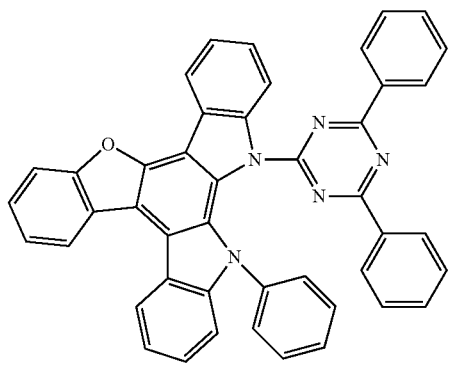
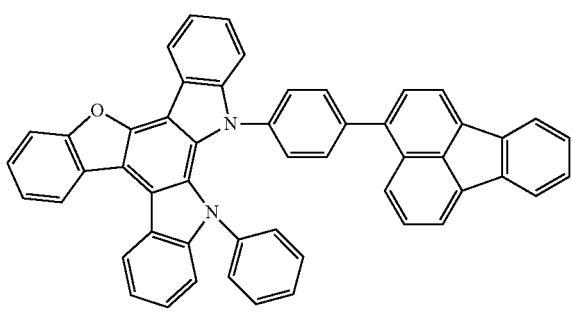
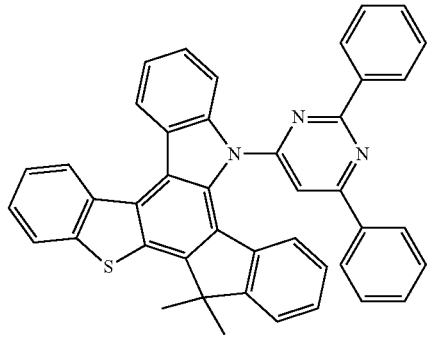
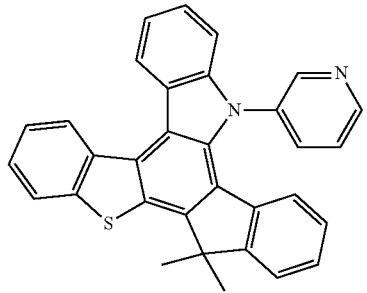

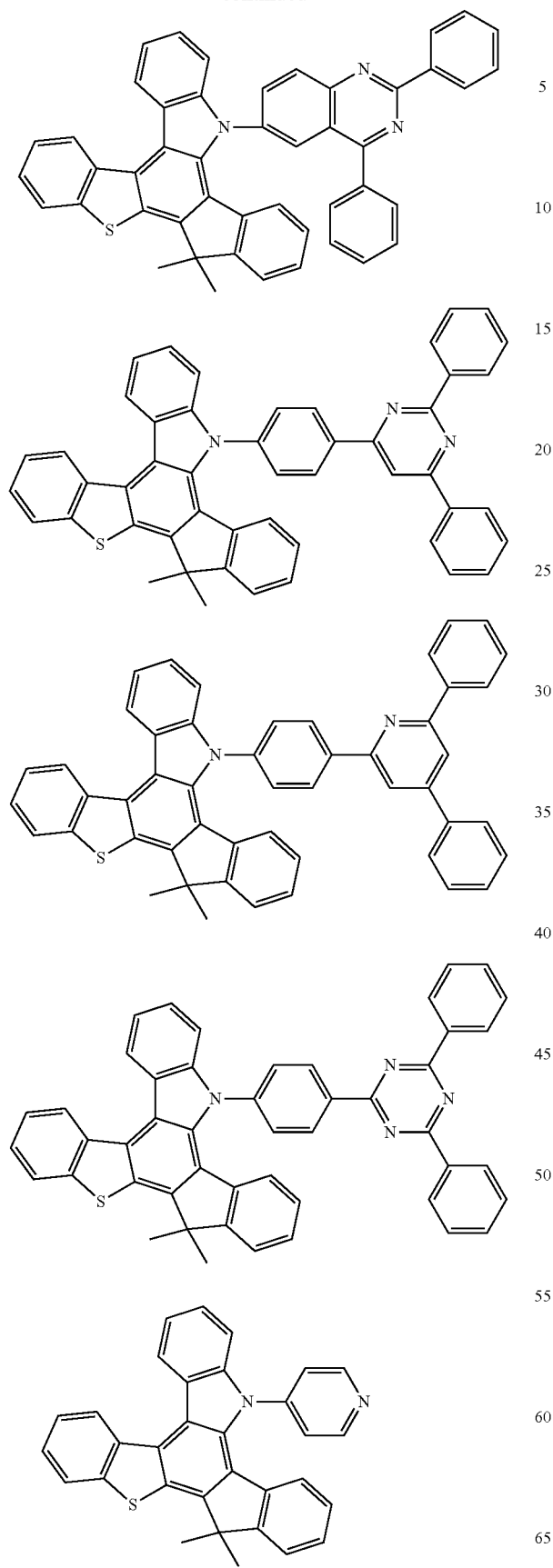

US 9,887,367 B2
207
-continued
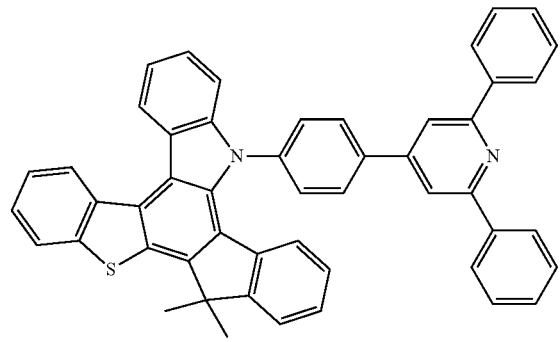
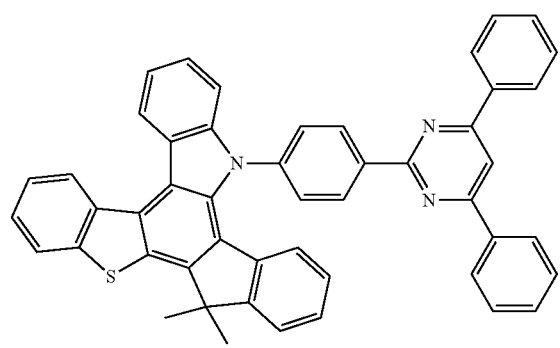
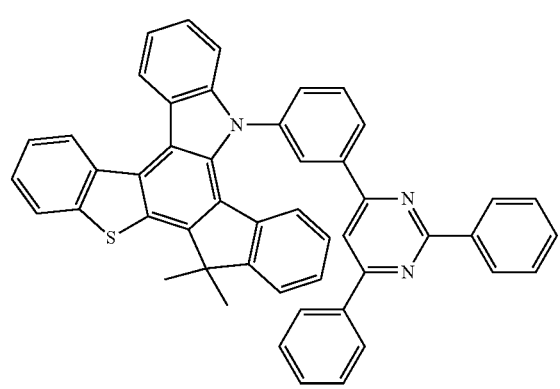
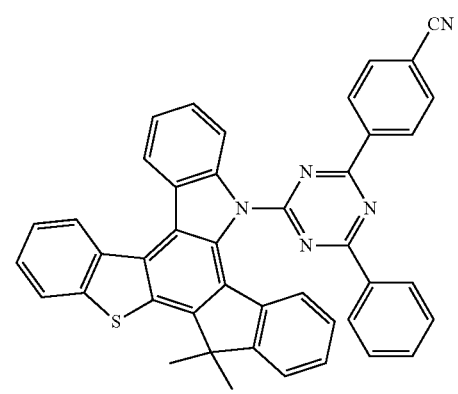
208
-continued
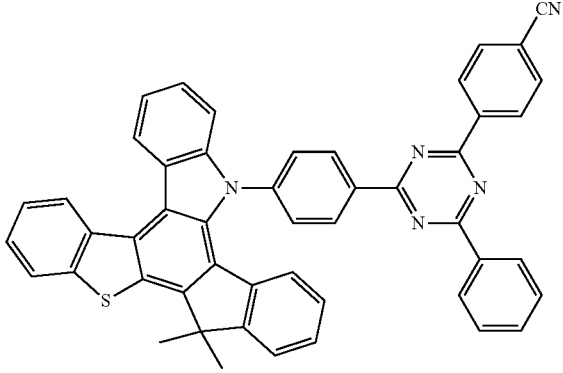
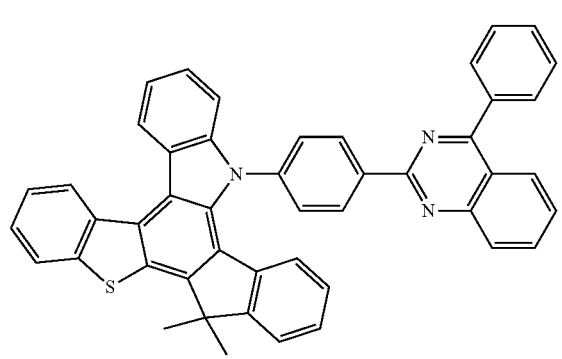
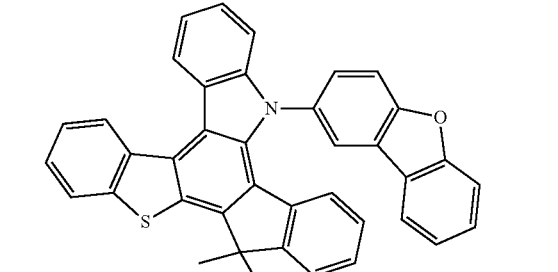
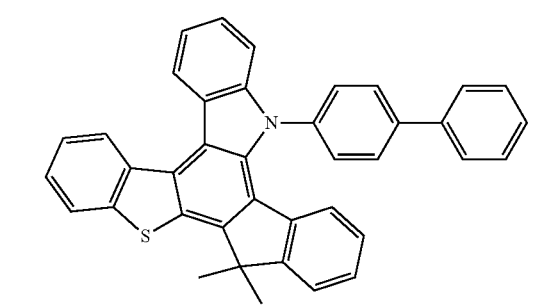
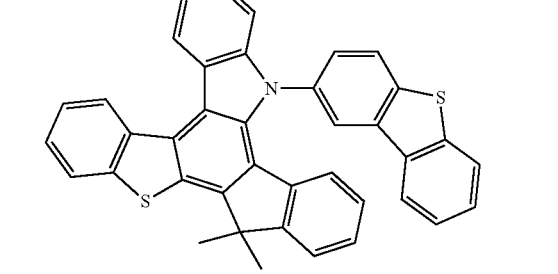

209
-continued
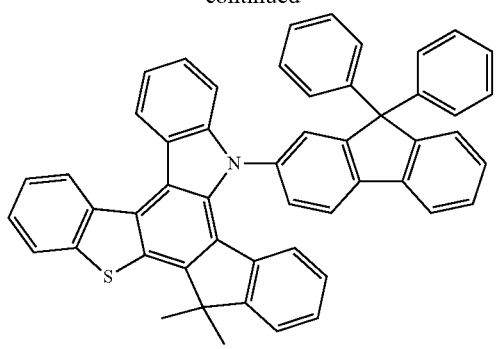
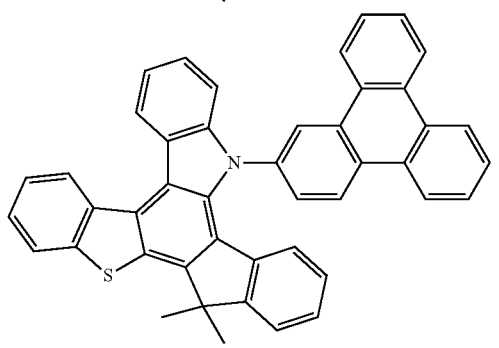
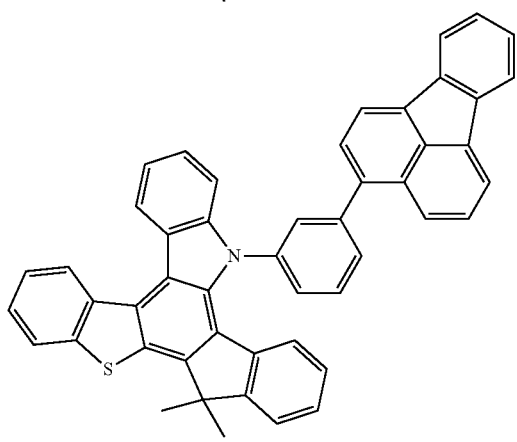
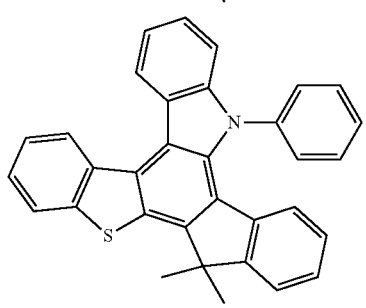
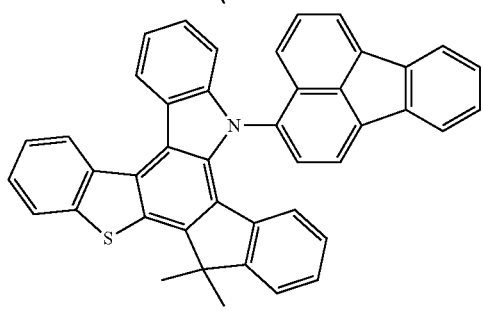
210
-continued
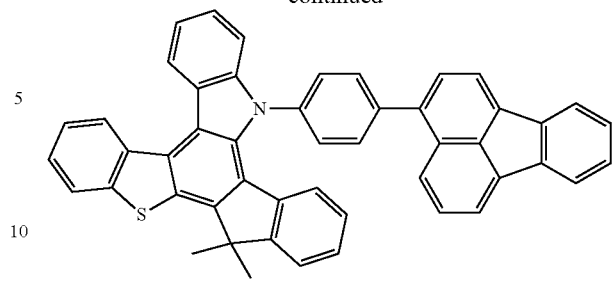
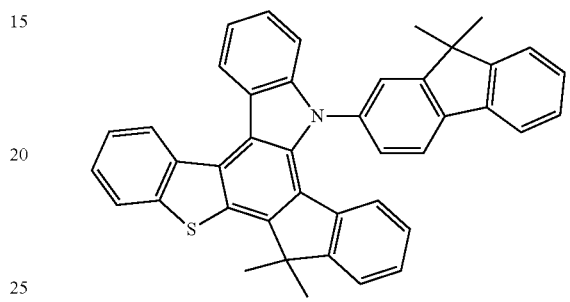
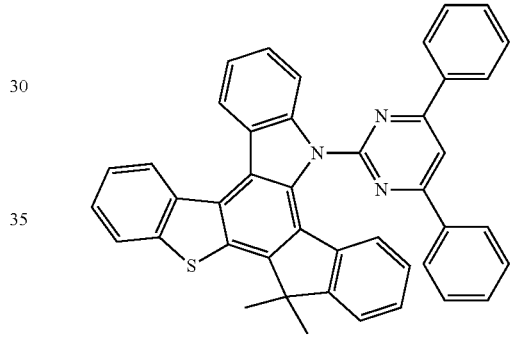
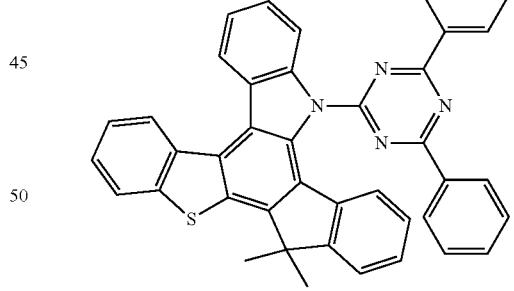
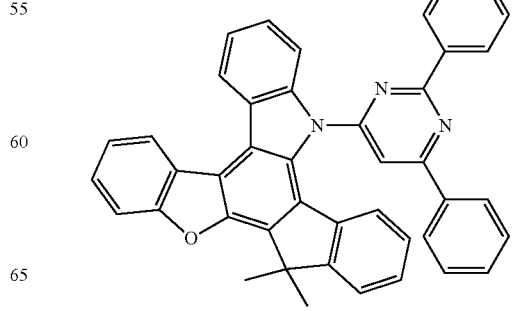

211
-continued
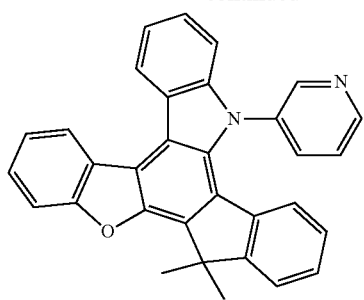
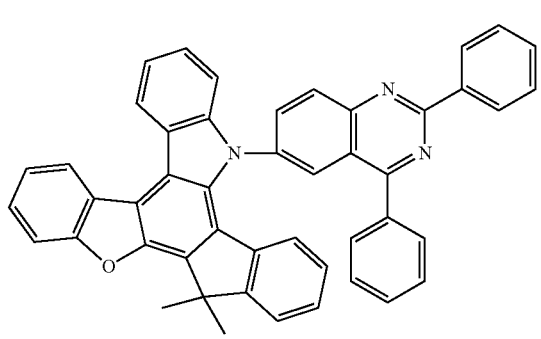
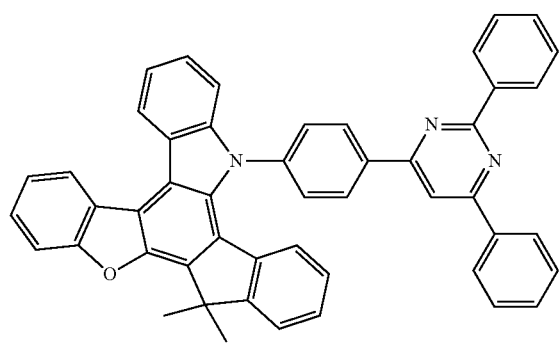
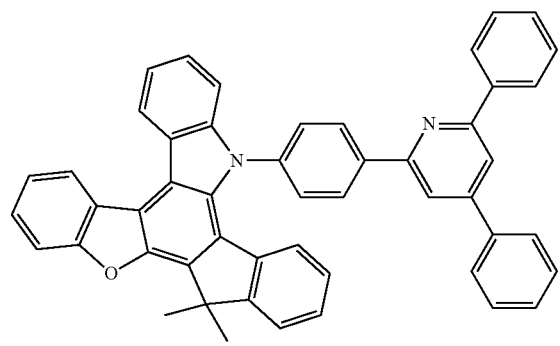
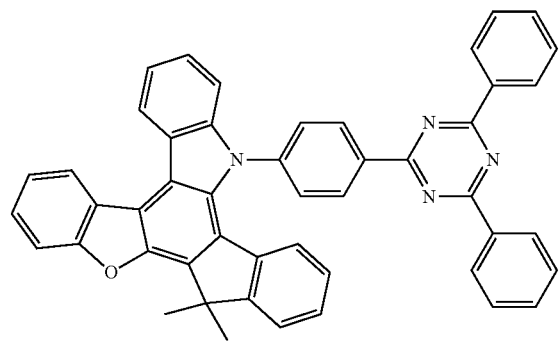
212
-continued
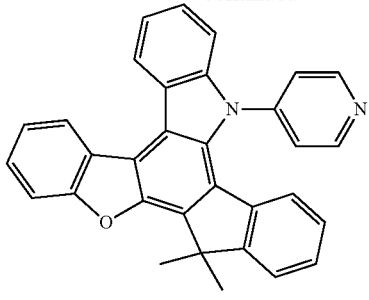
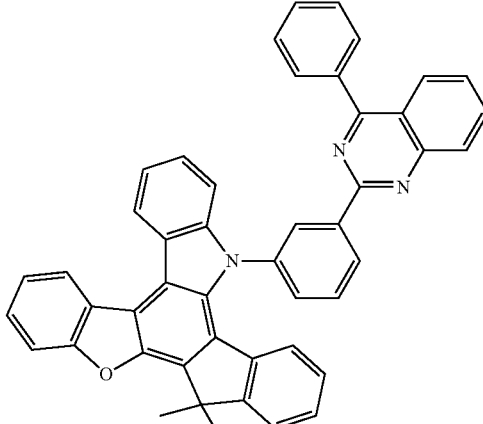
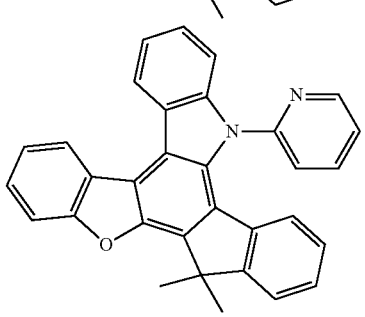
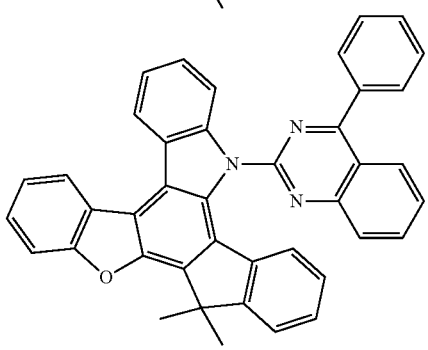
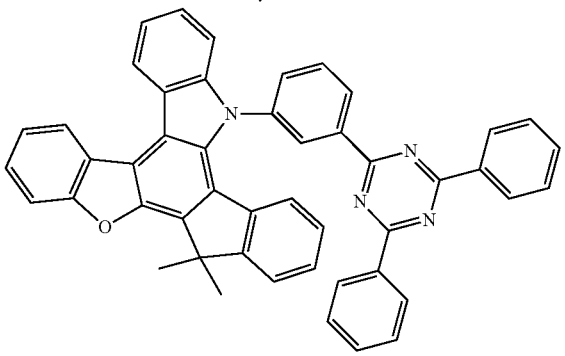

213
-continued
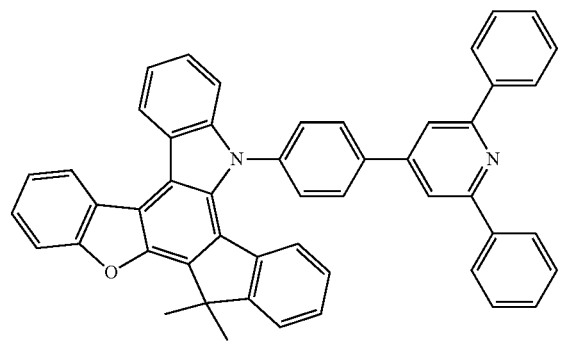
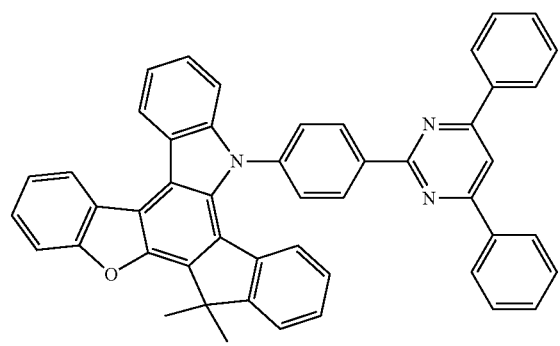
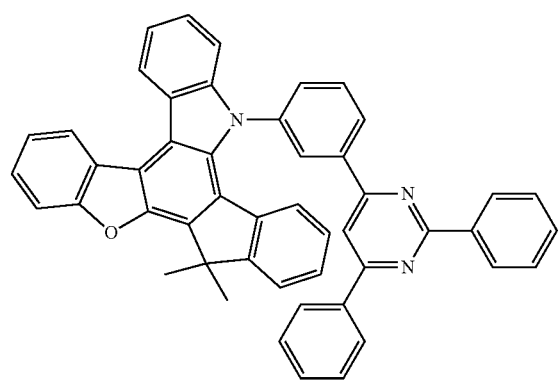
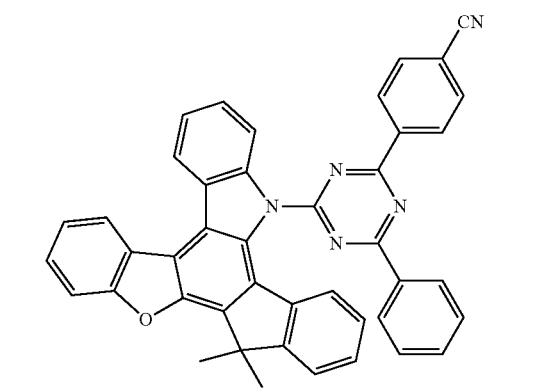
214
-continued
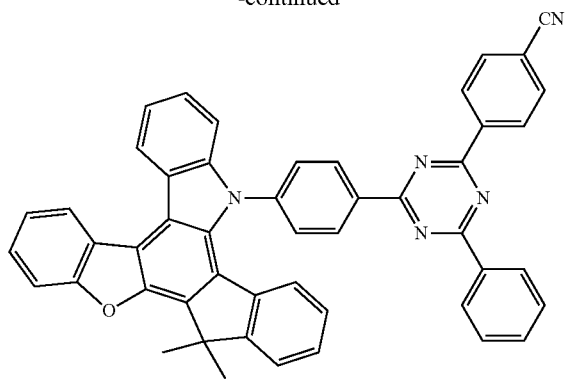
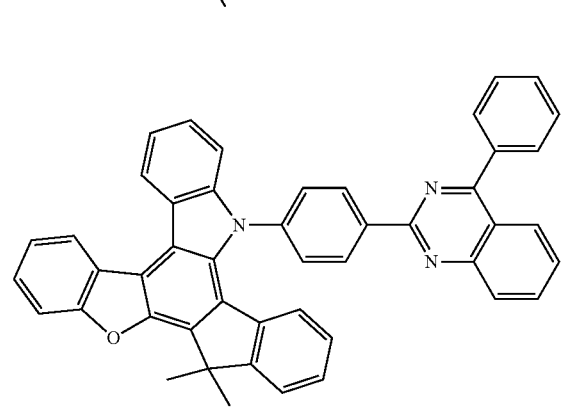
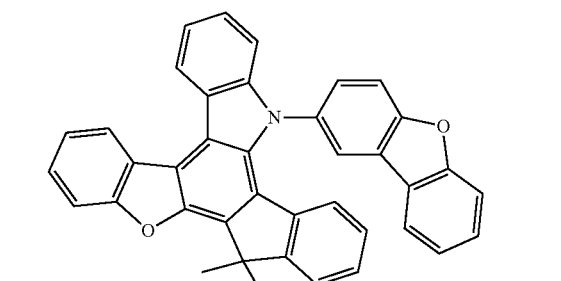
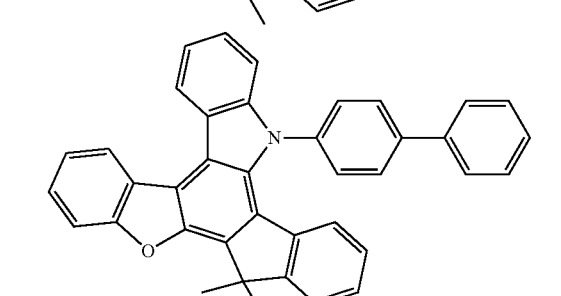
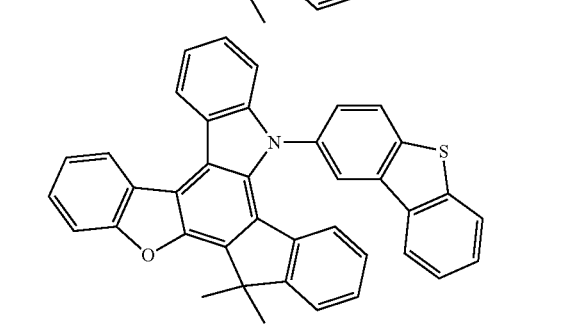

215
-continued
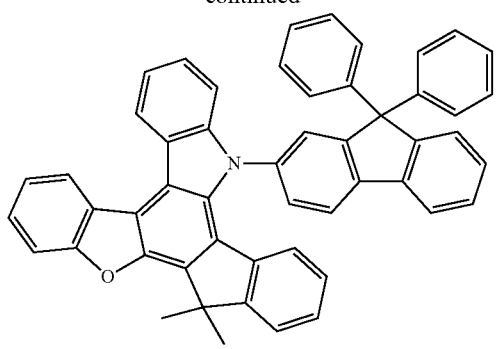
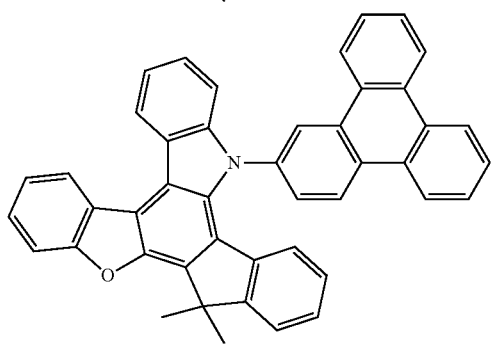
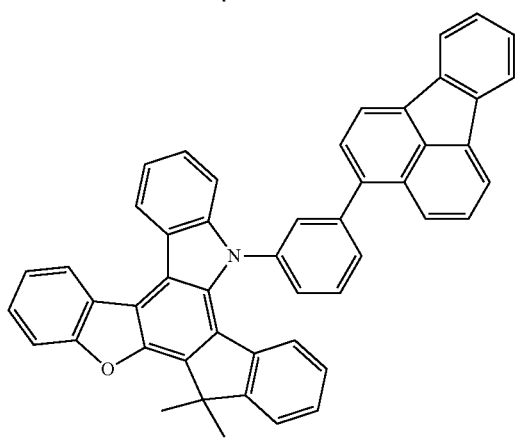
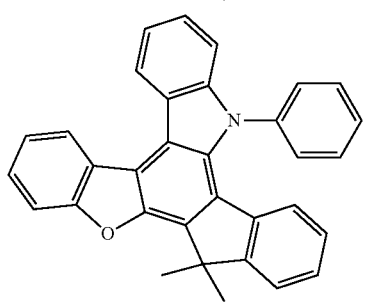
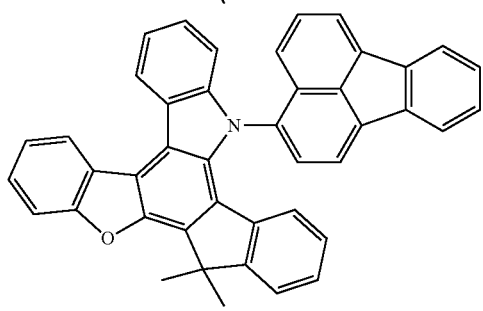
216
-continued
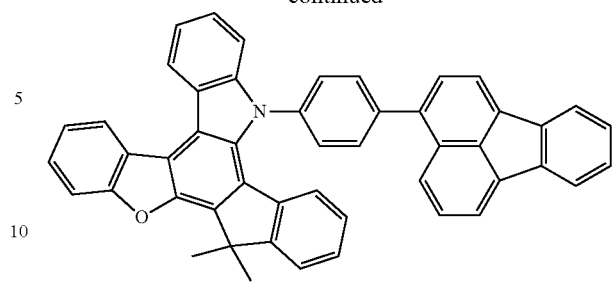
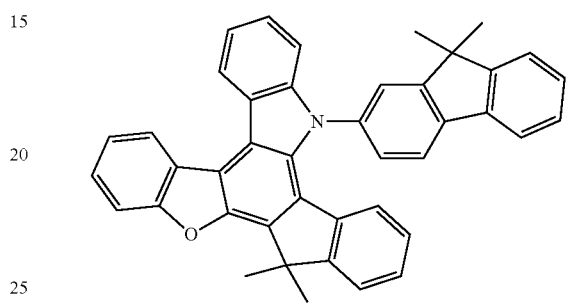
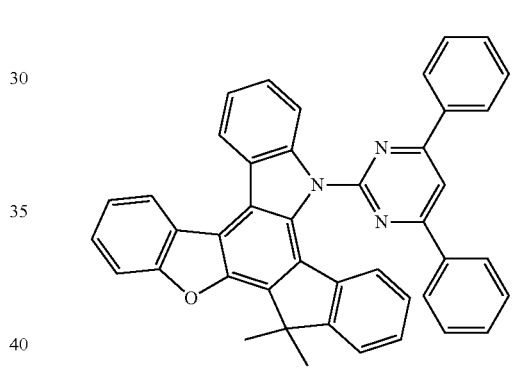
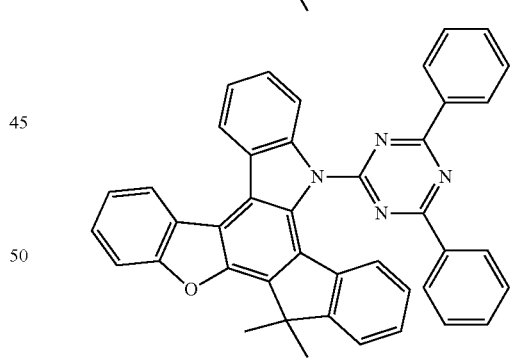
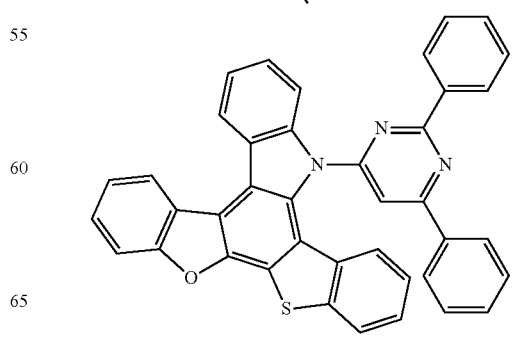

217
-continued
218
-continued
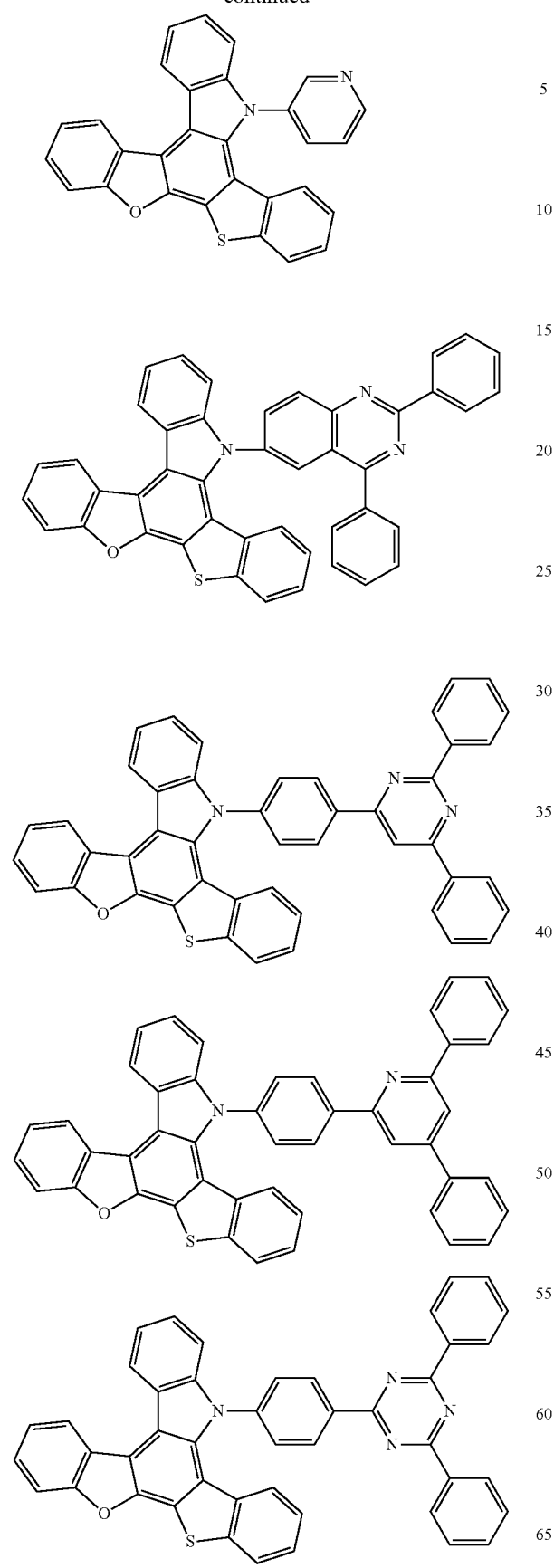
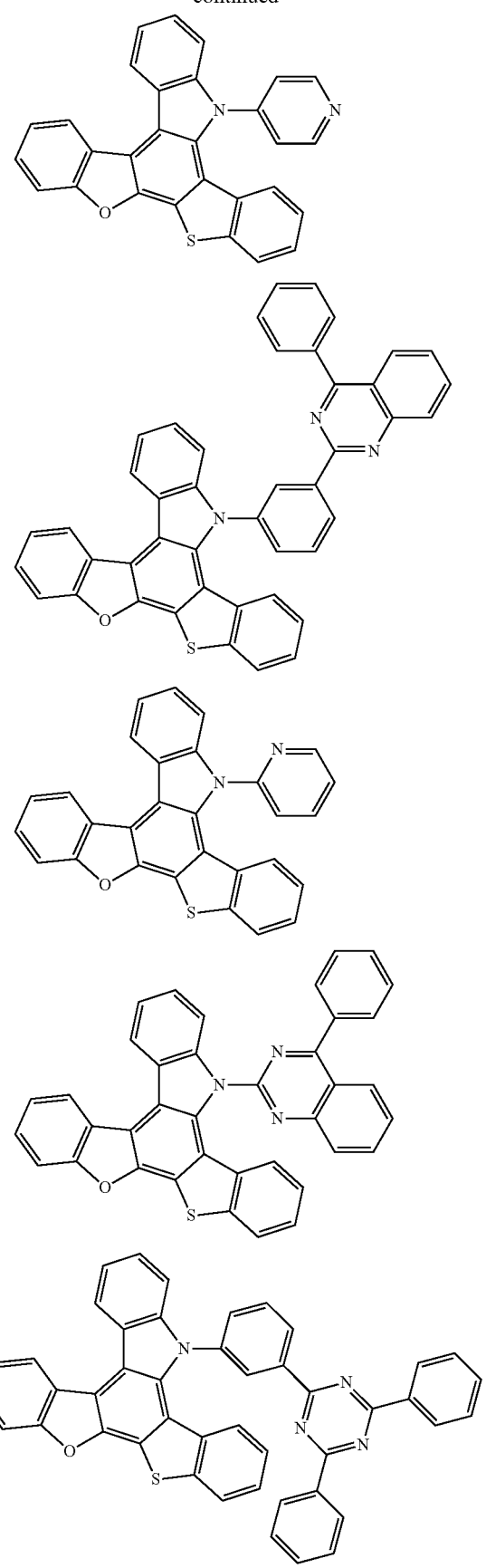

219
-continued
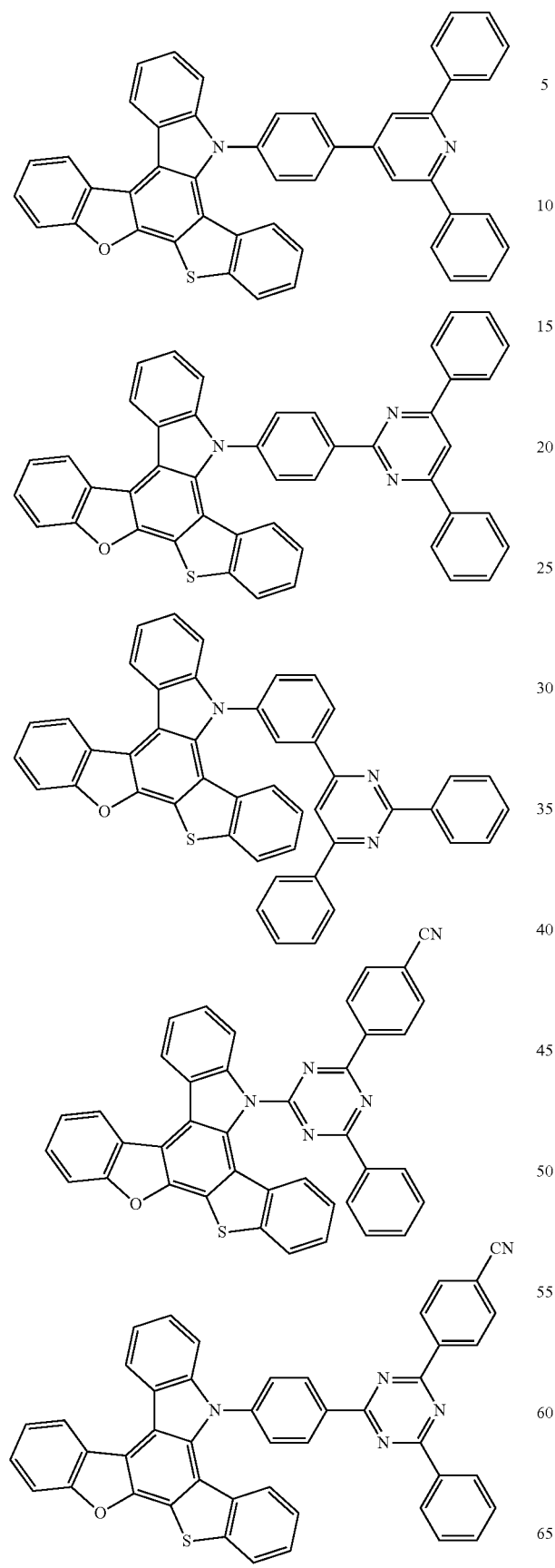
220
-continued
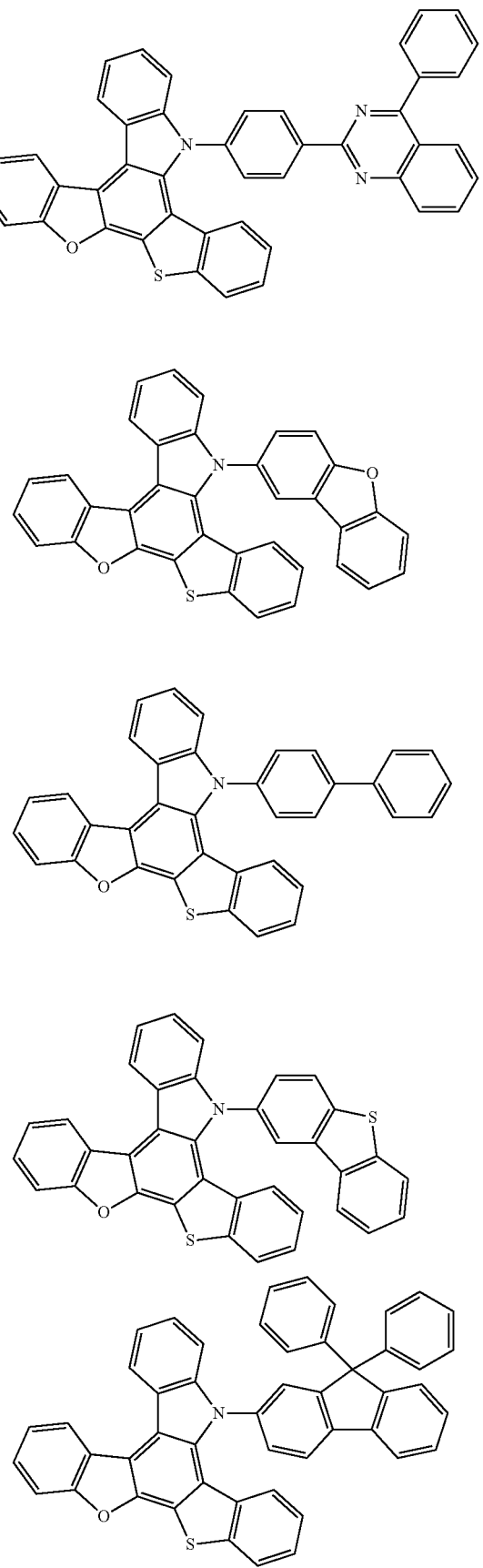

221
-continued
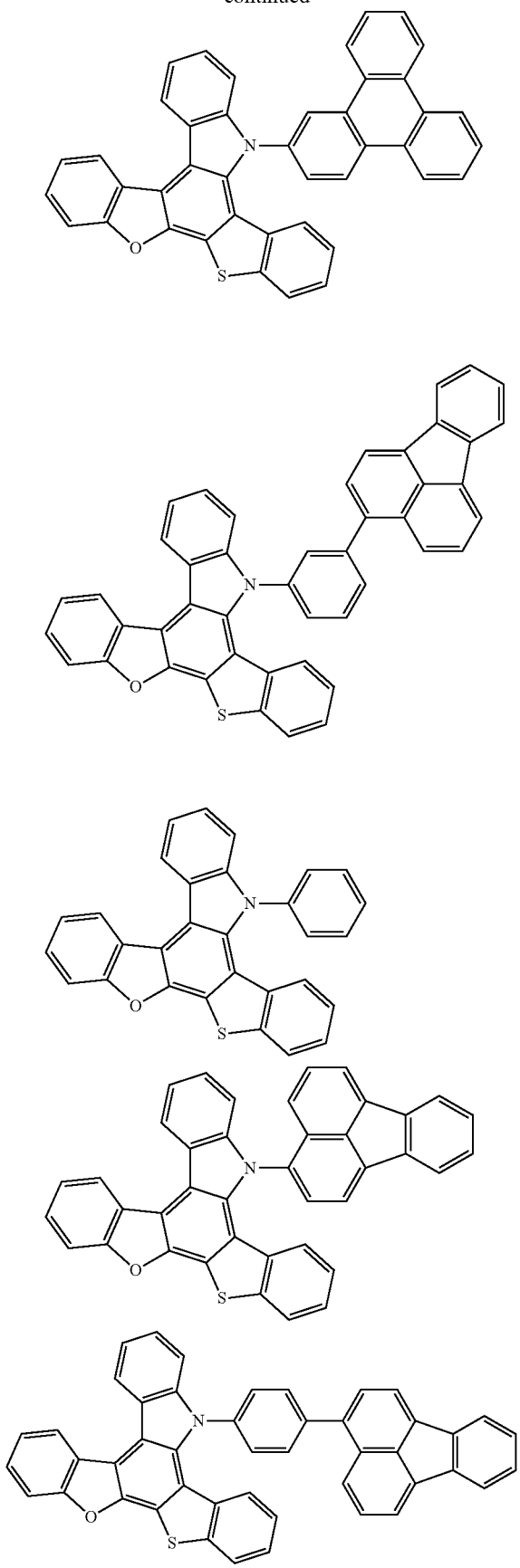
222
-continued
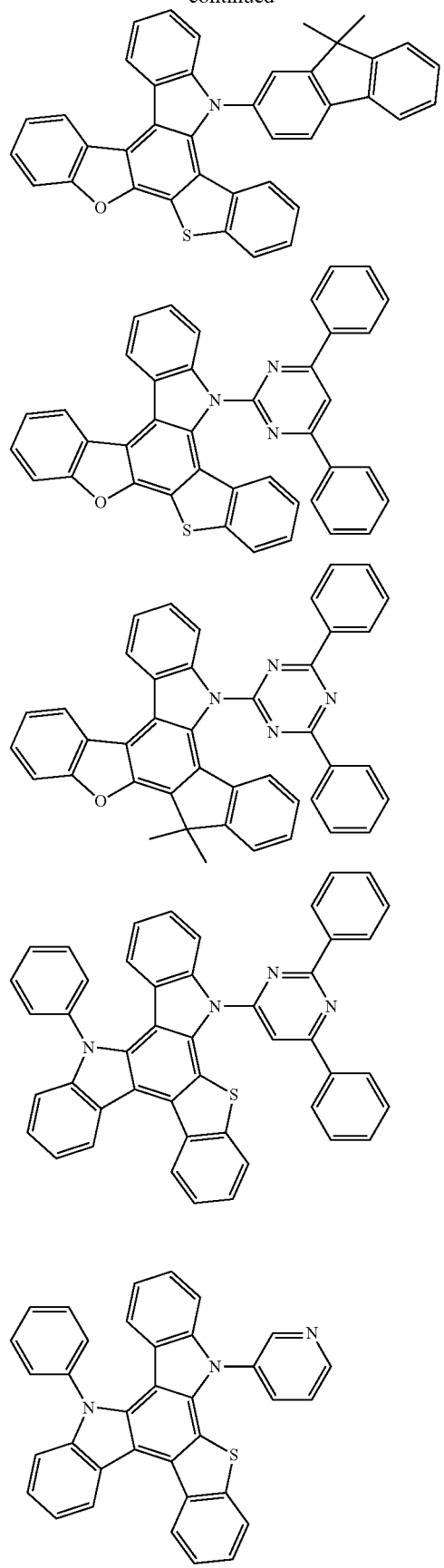

223
-continued
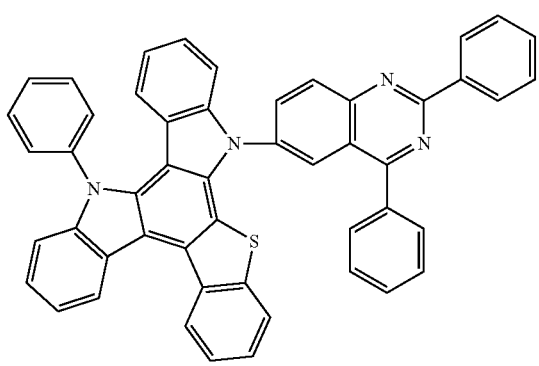
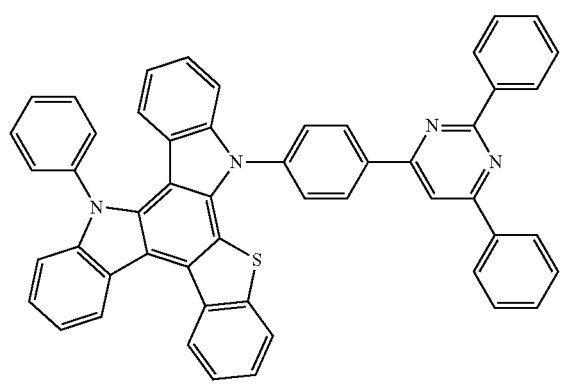
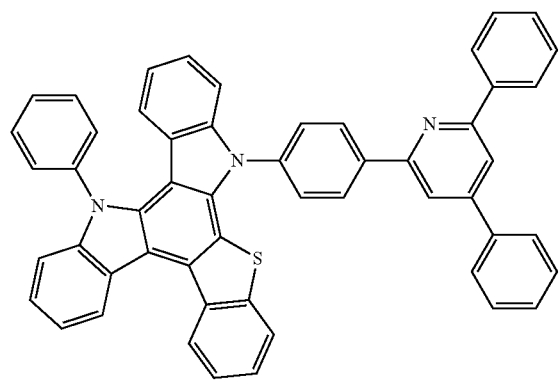
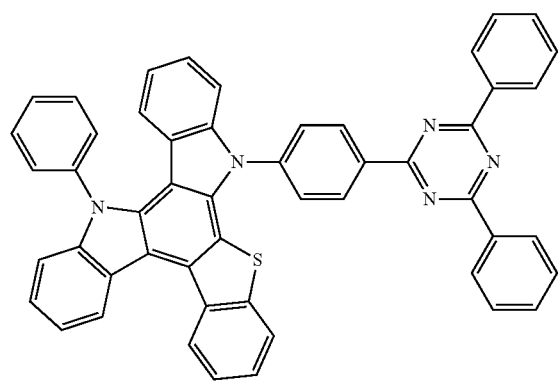
224
-continued
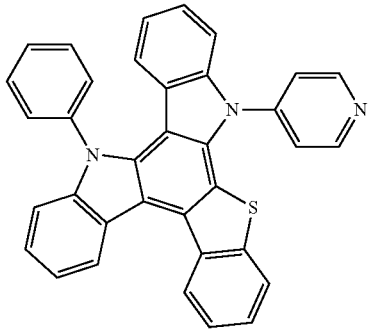
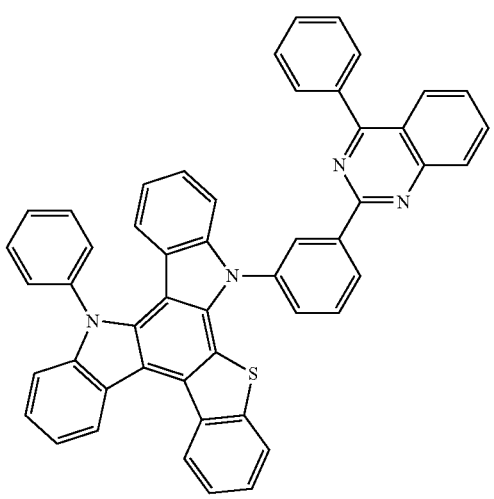
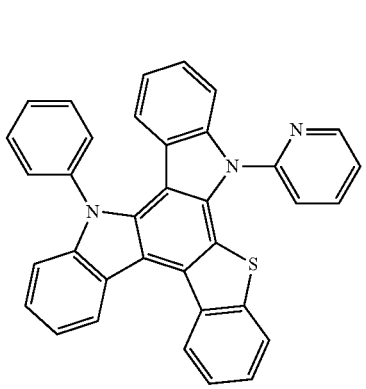
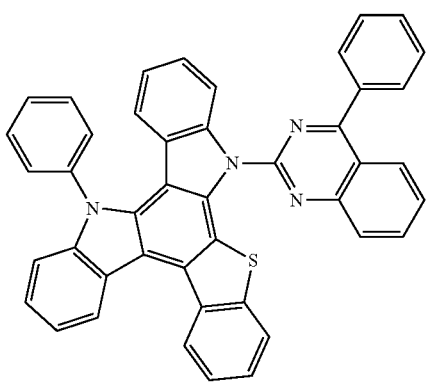

225
-continued
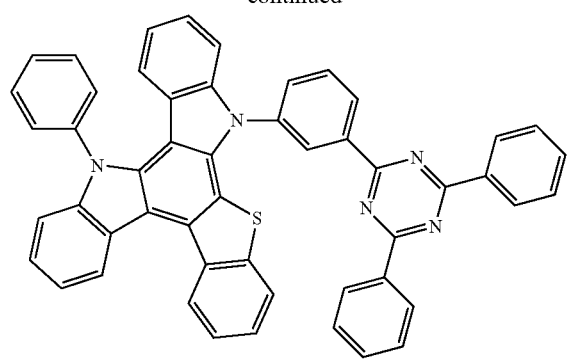
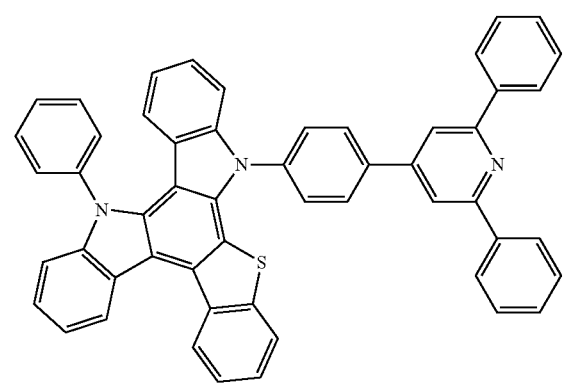
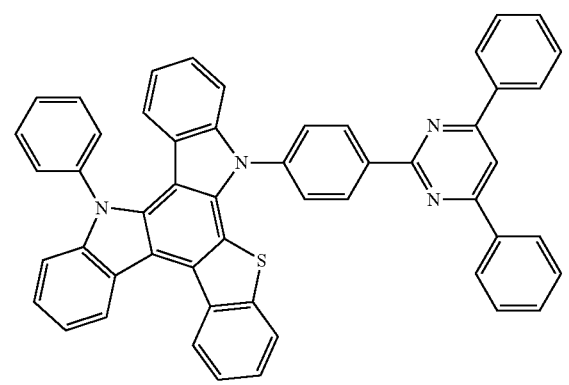
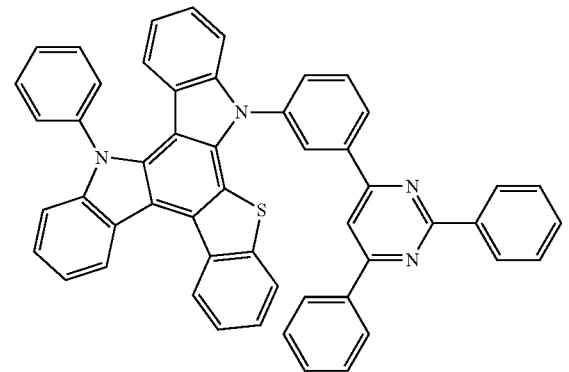
226
-continued
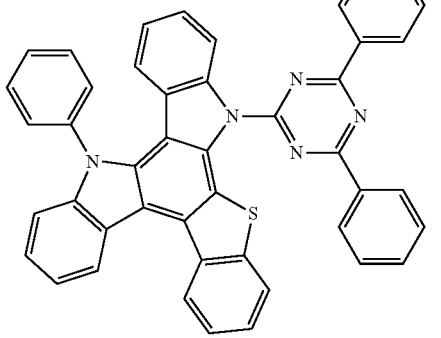
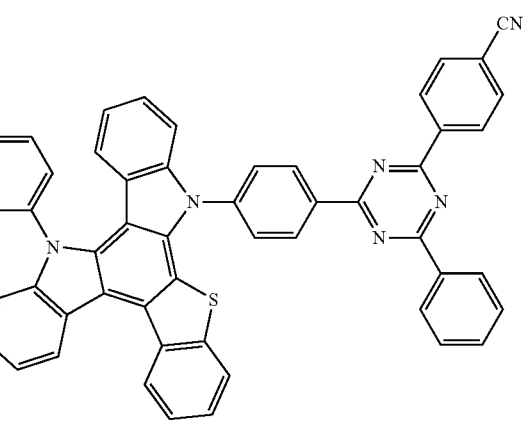
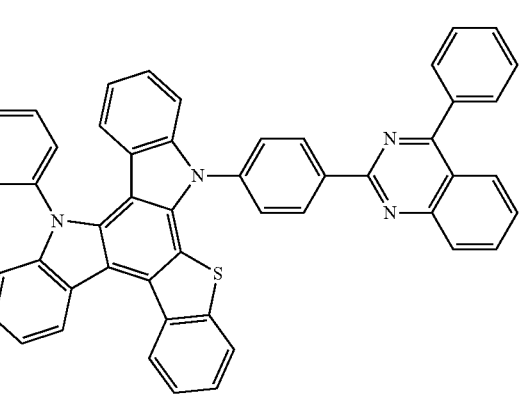
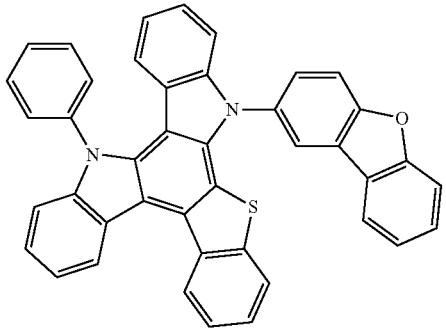

227
-continued
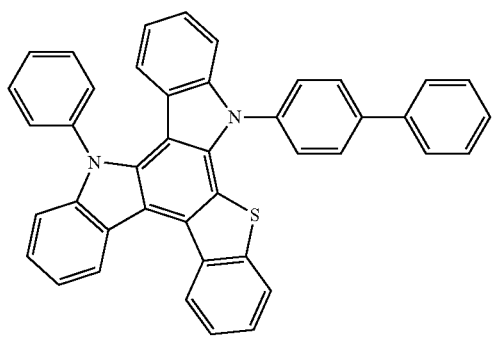
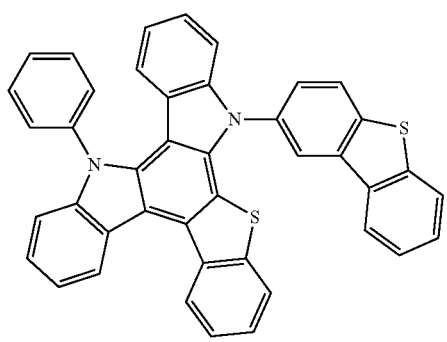
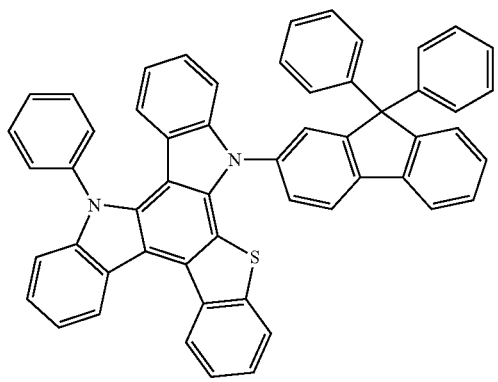
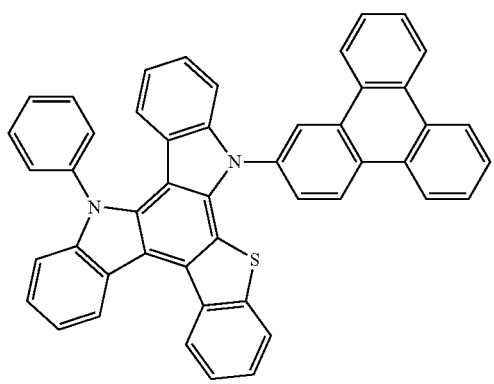
228
-continued
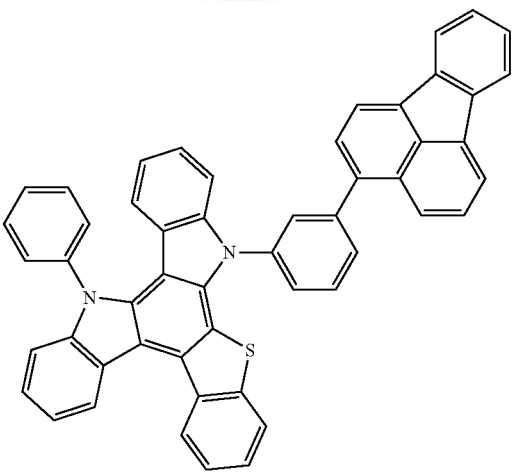
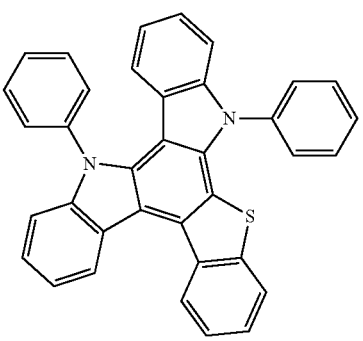
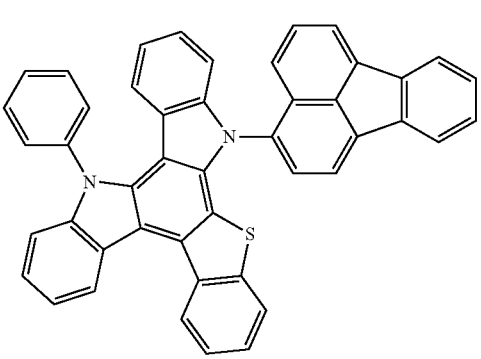
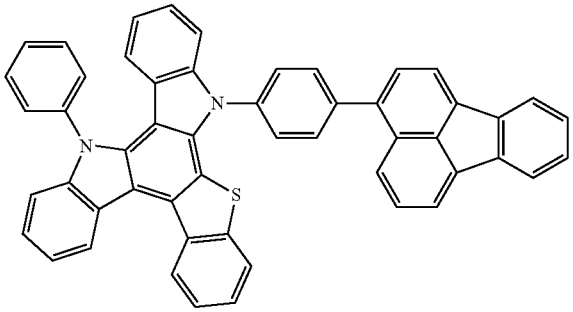

| 229 -continued | 230 -continued |
|---|---|
| 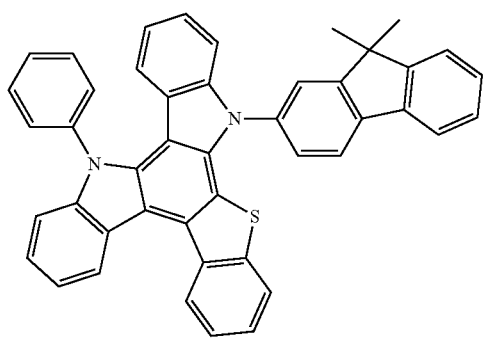 | 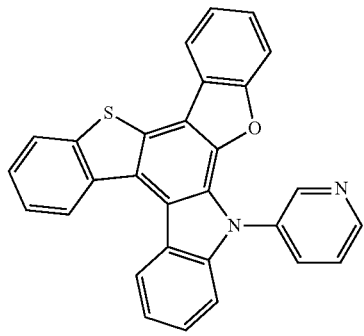 |
| 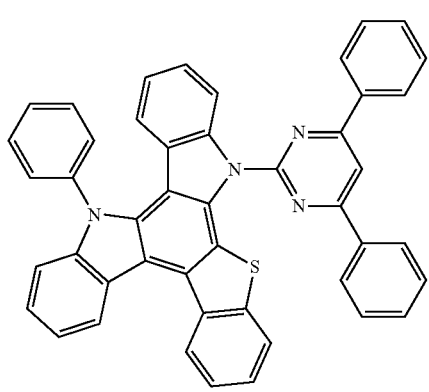 | 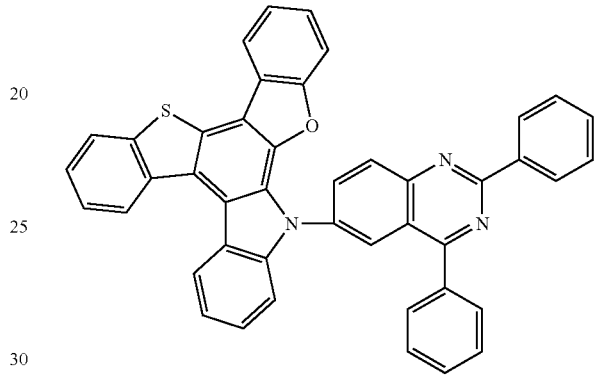 |
| 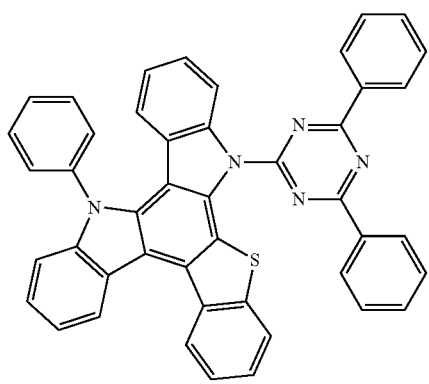 | 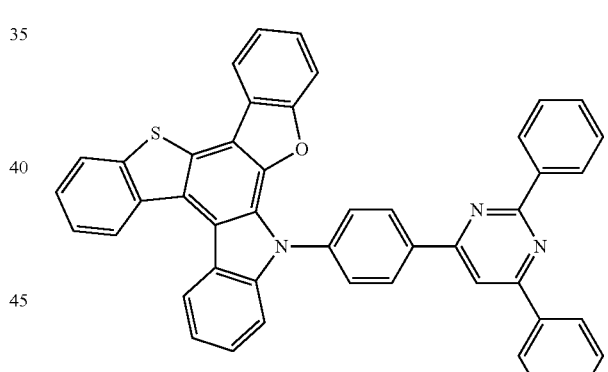 |
| 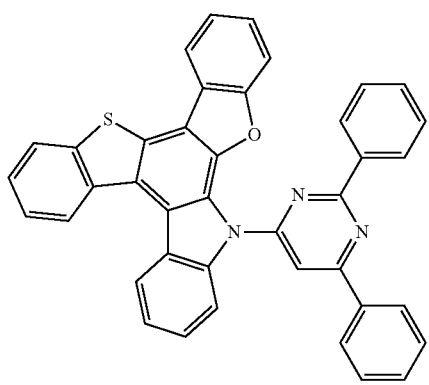 | 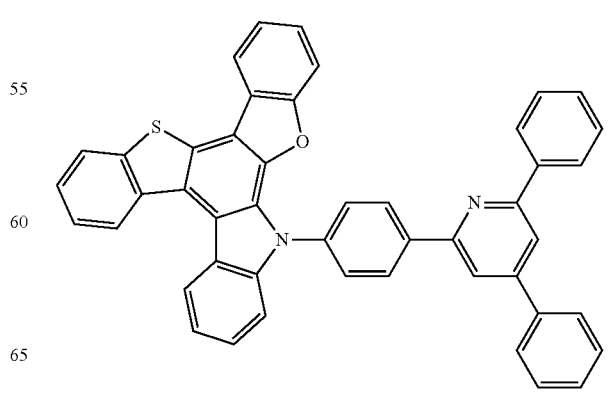 |

231
-continued
232
-continued
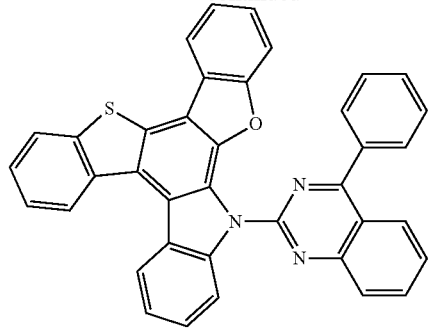
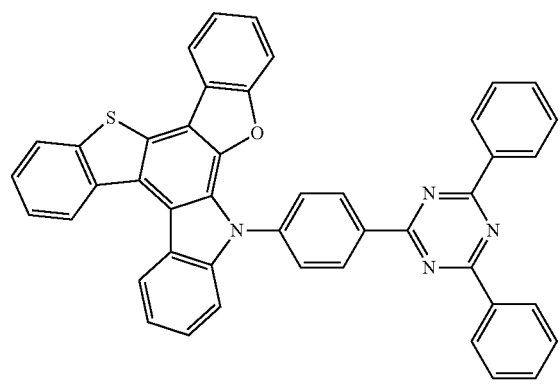
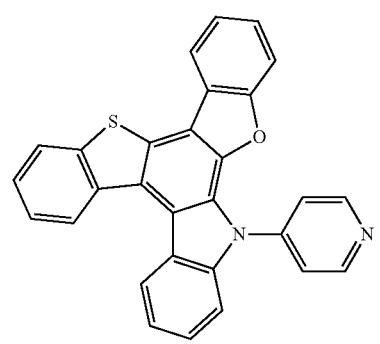
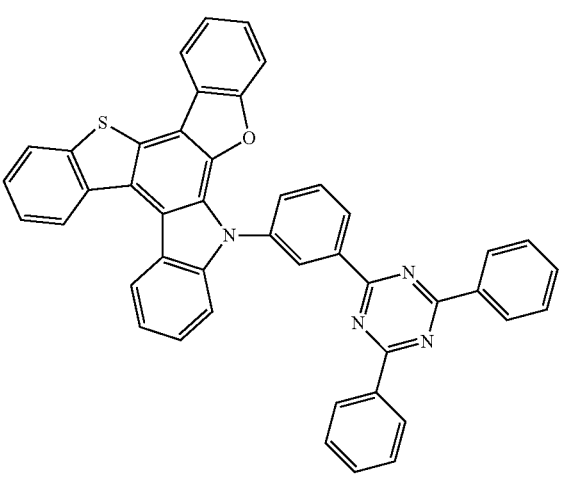
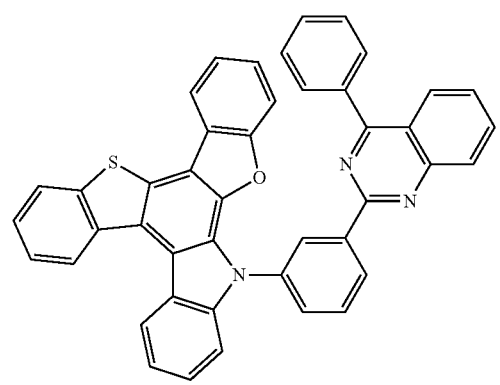
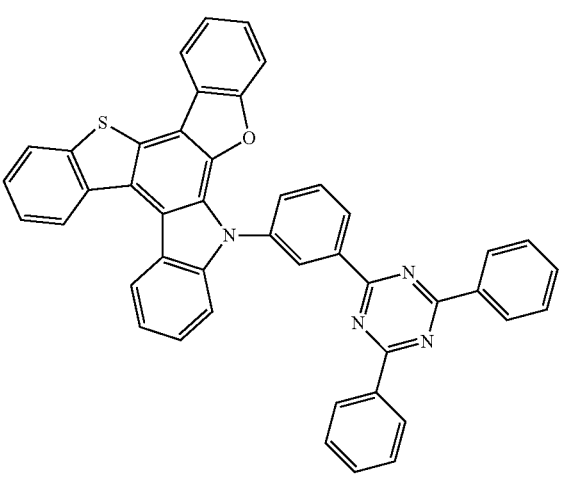
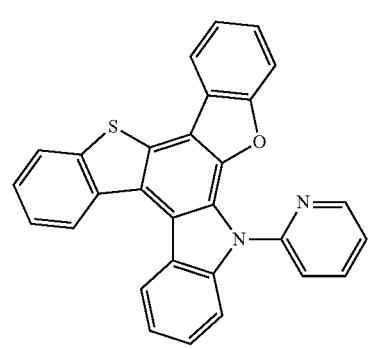
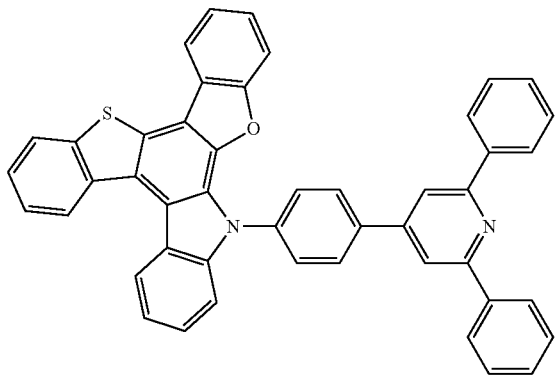
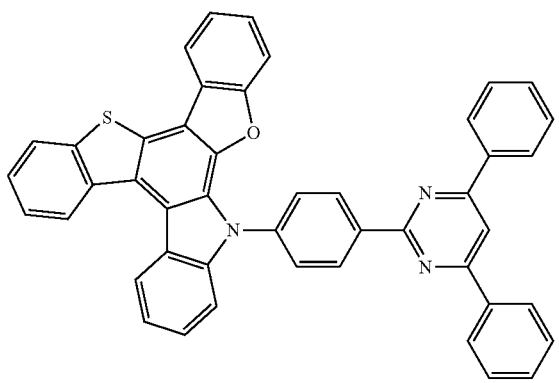

233
-continued
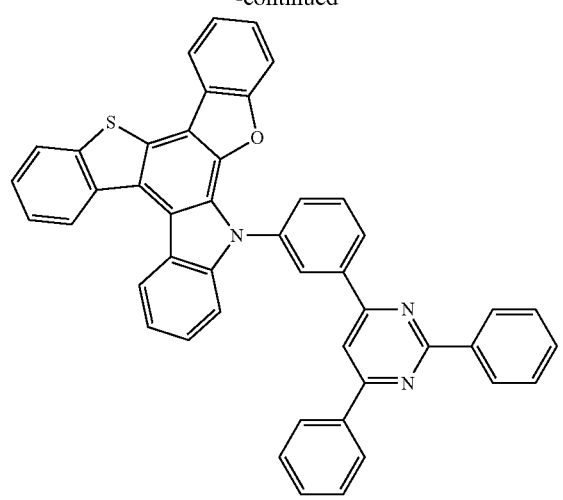
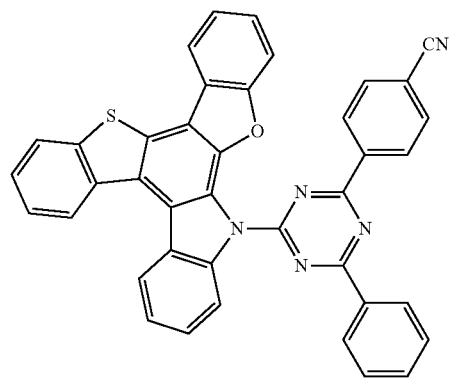
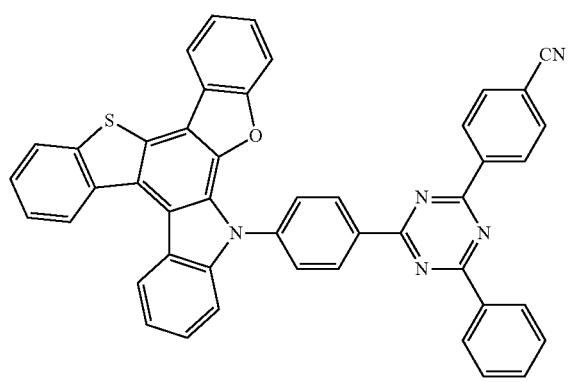
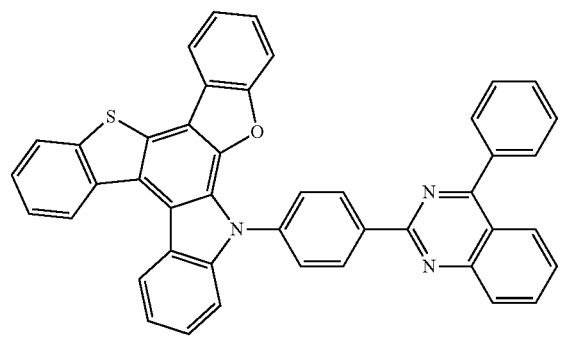
234
-continued
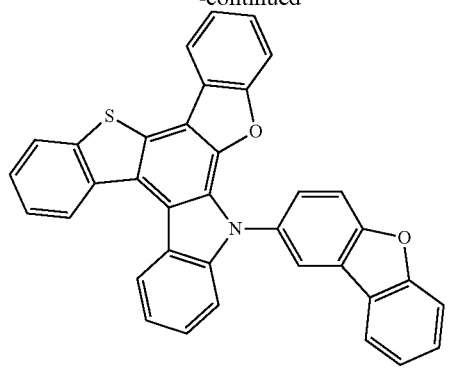
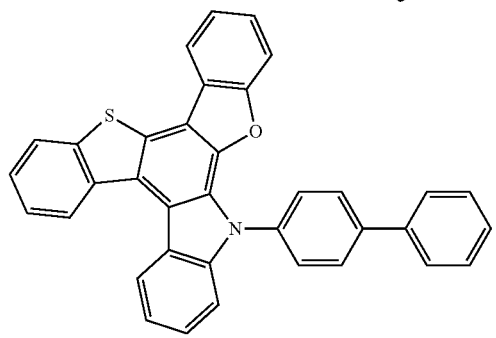
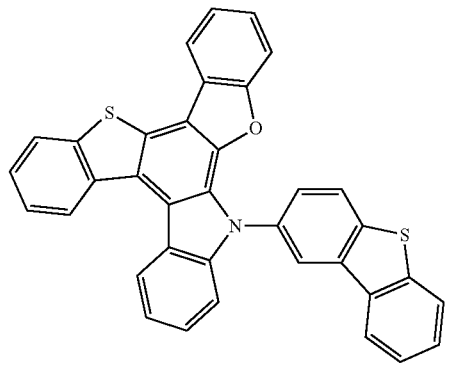
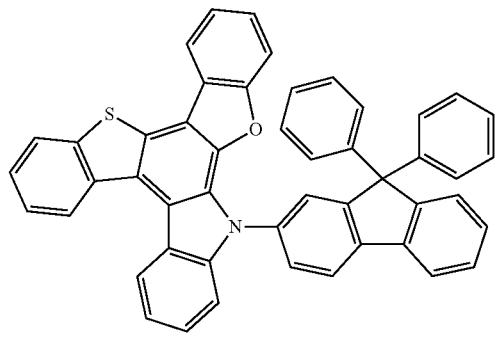
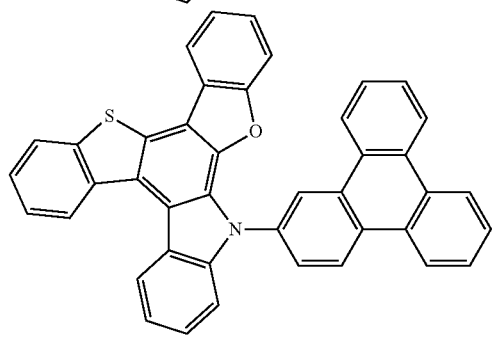

235
-continued
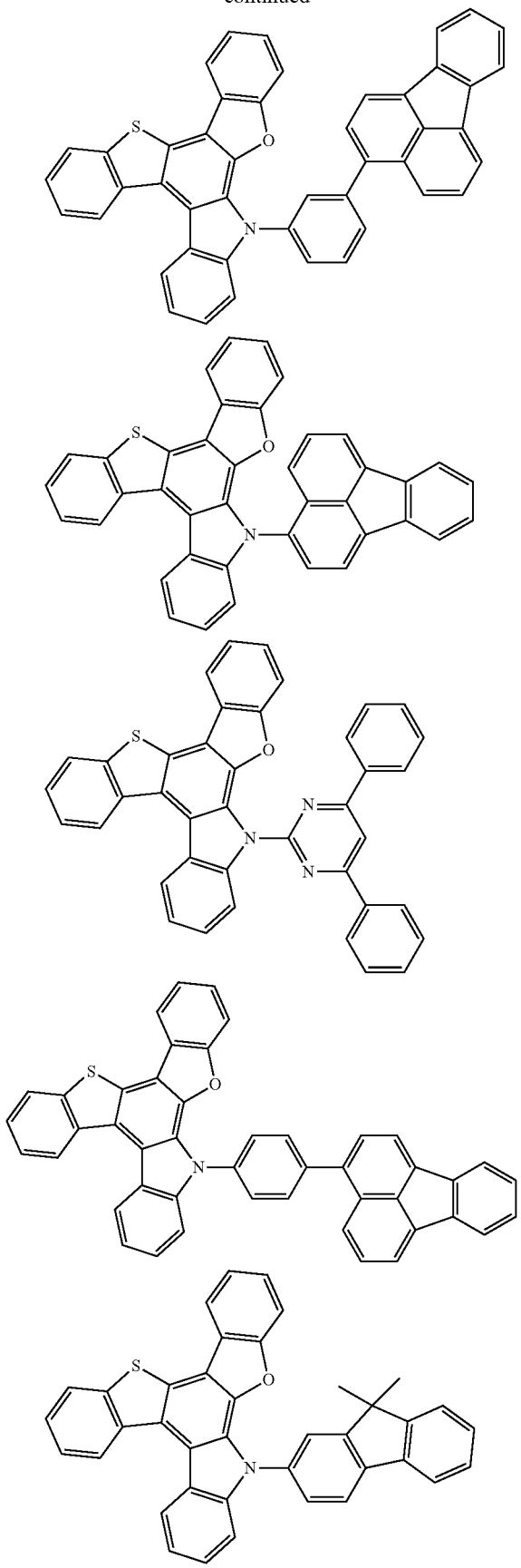
236
-continued
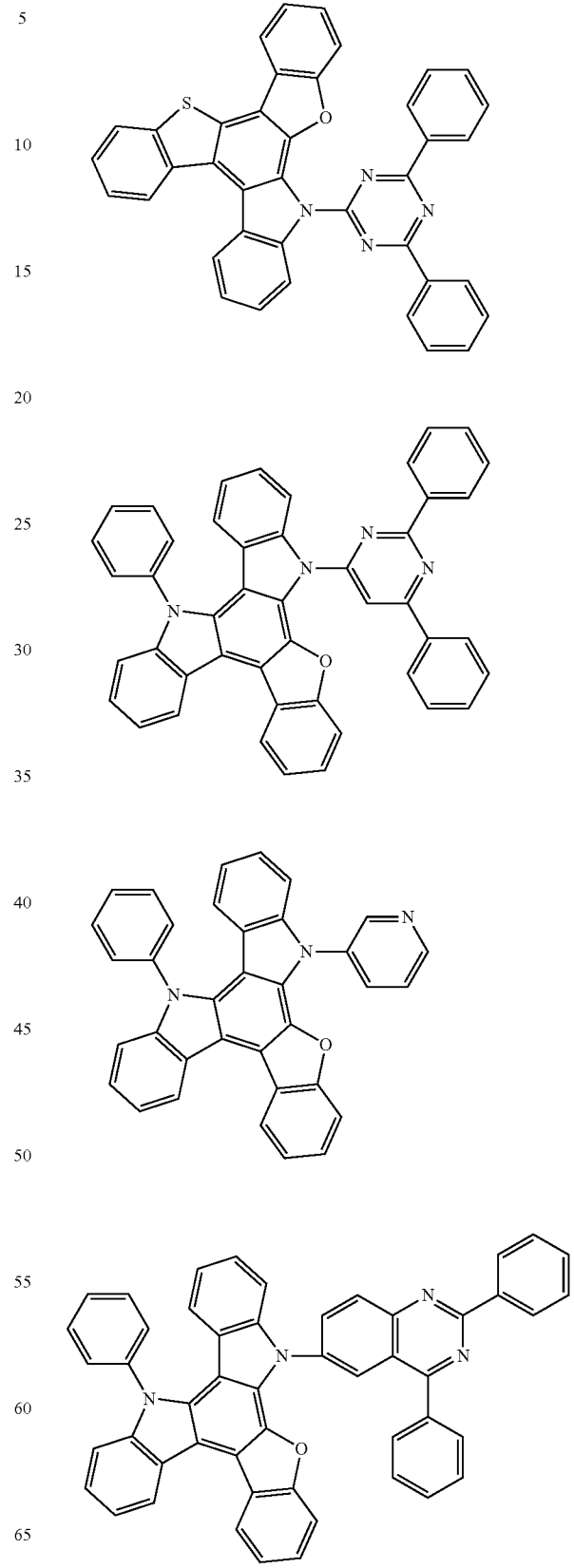

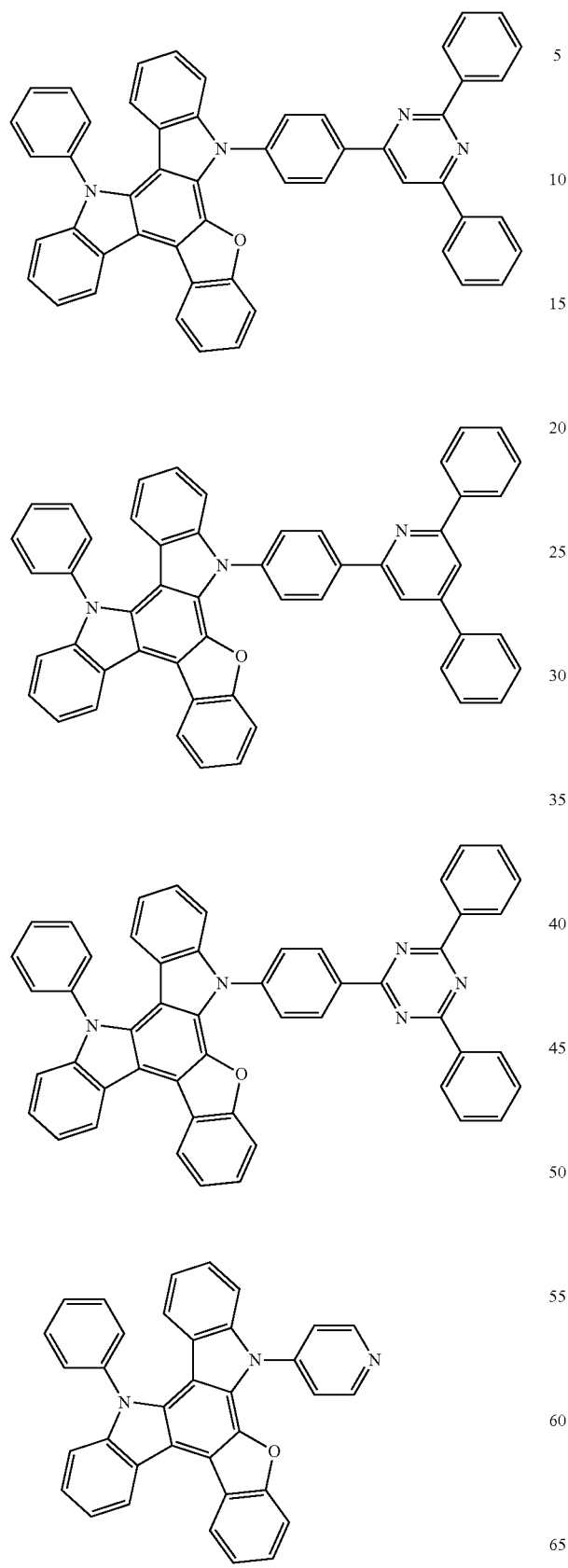
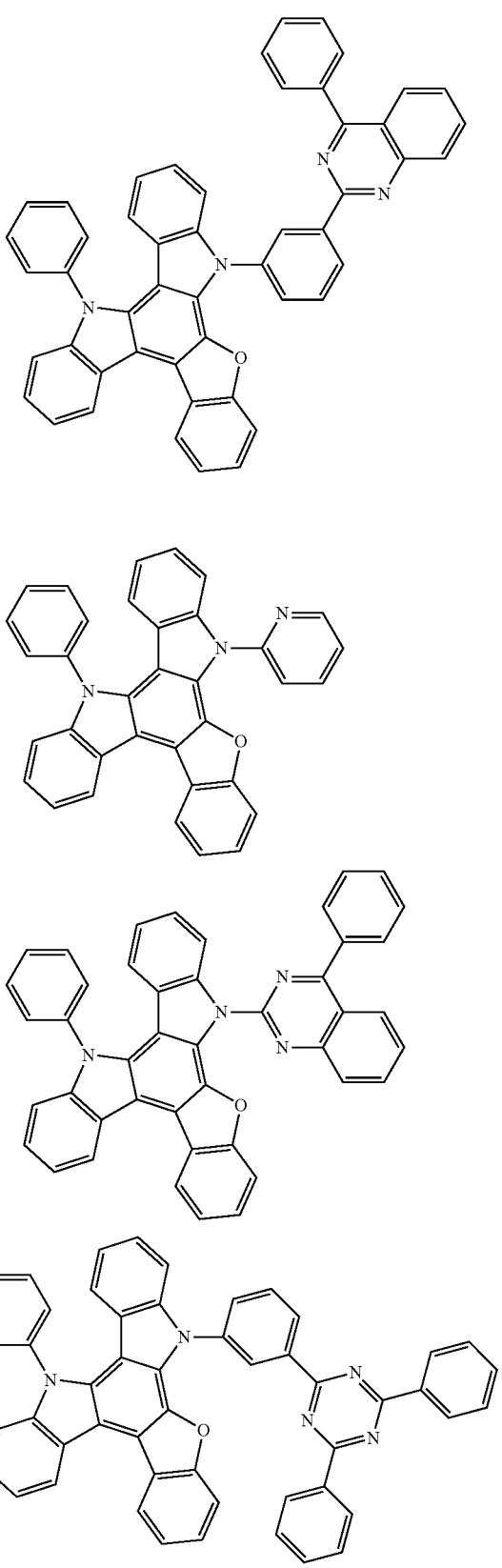

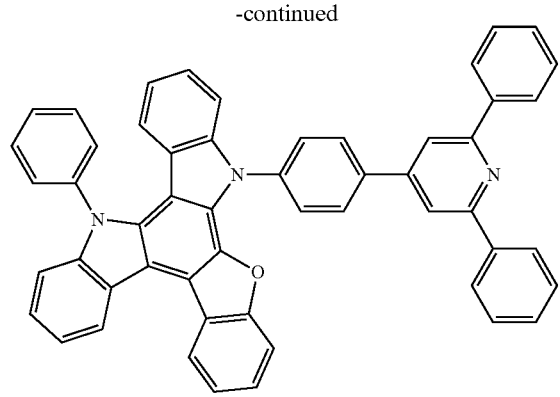
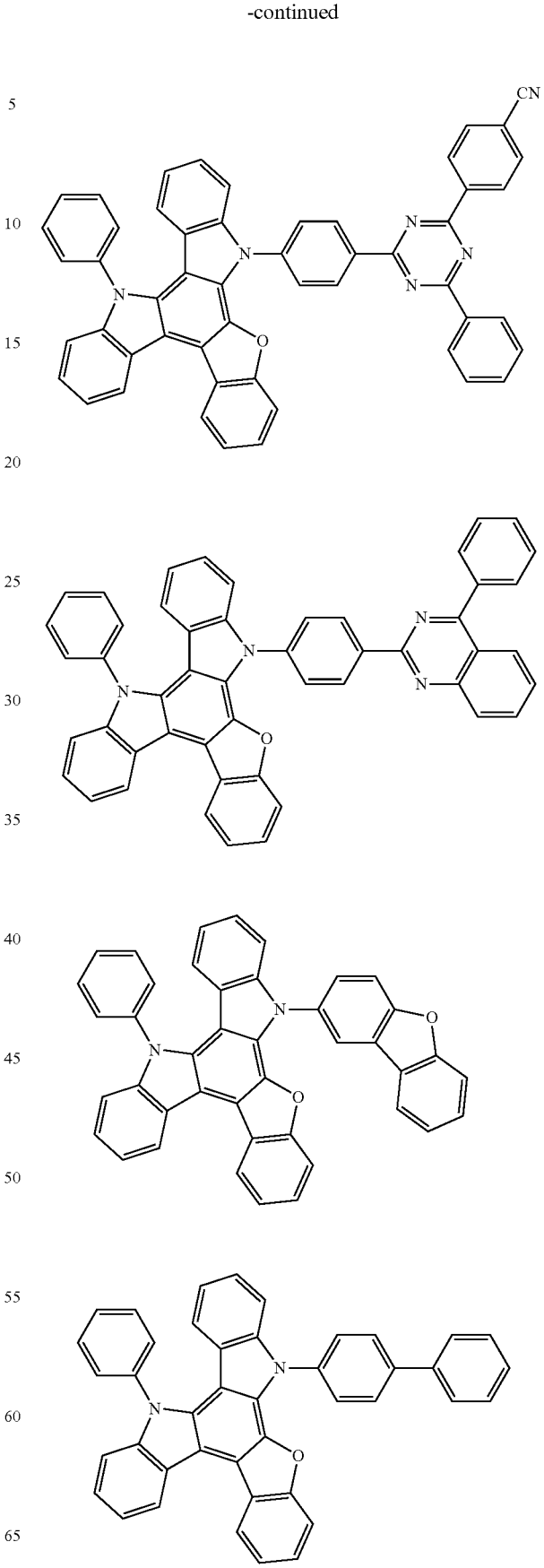

241
-continued
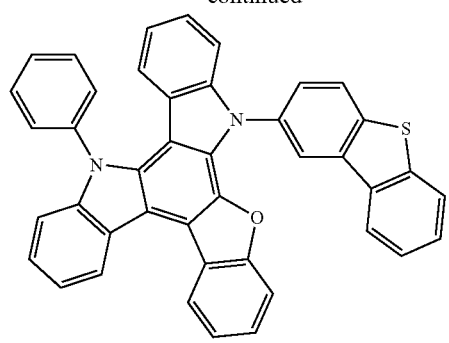
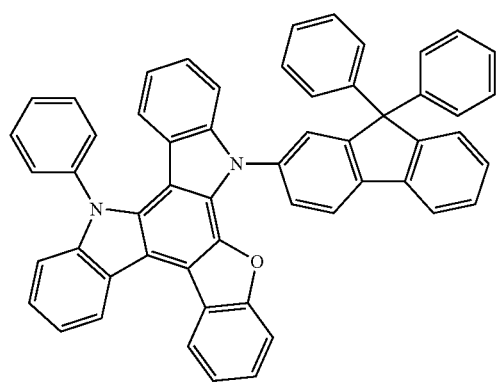
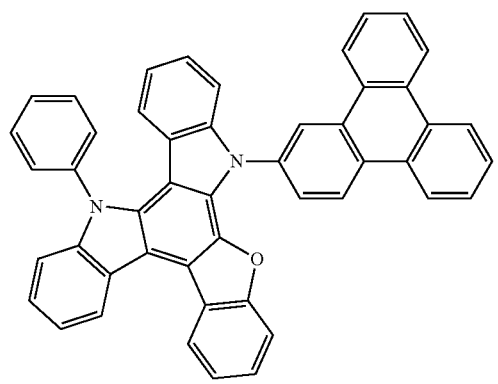
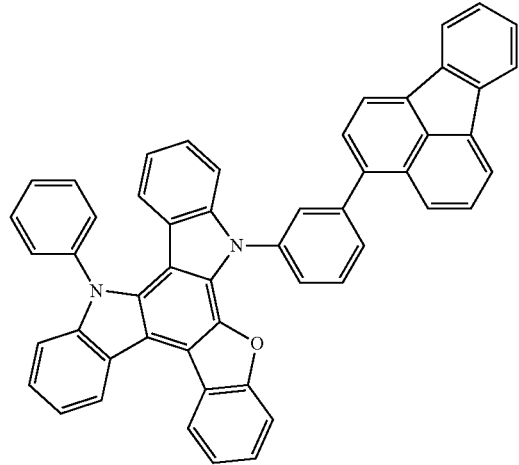
242
-continued
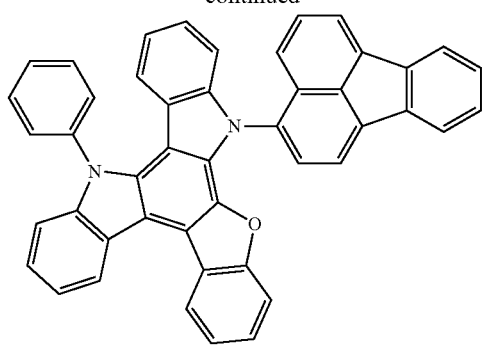
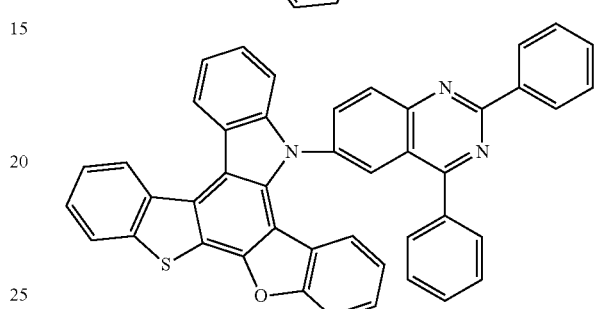
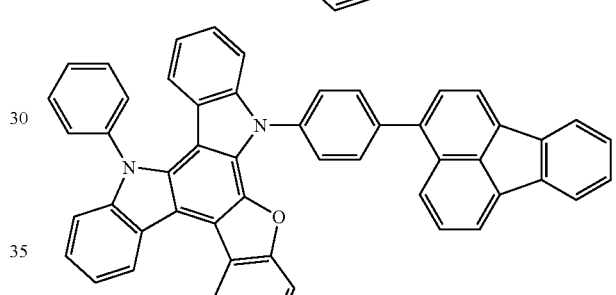
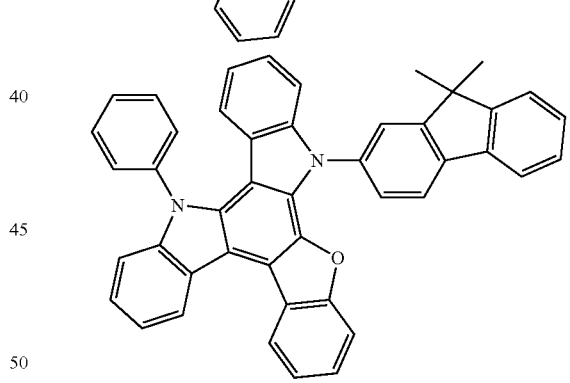
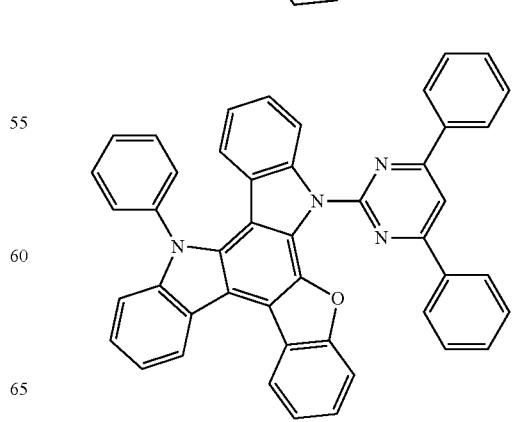

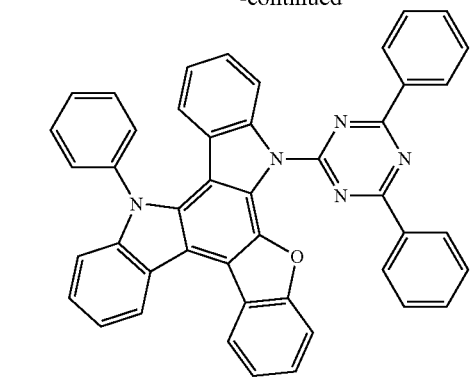
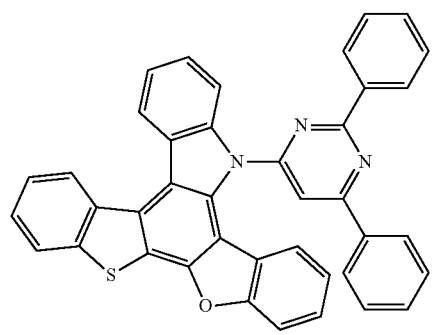
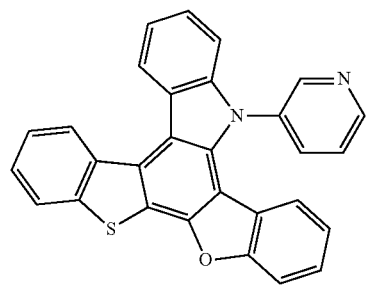
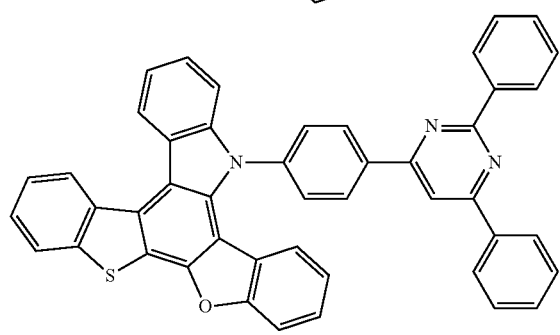
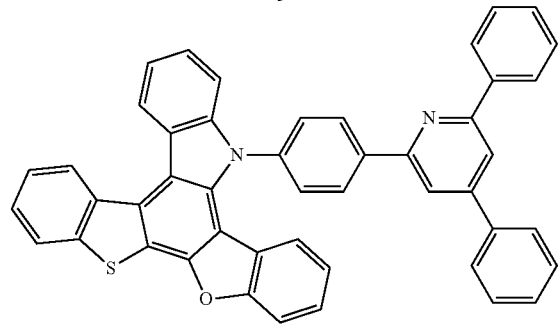
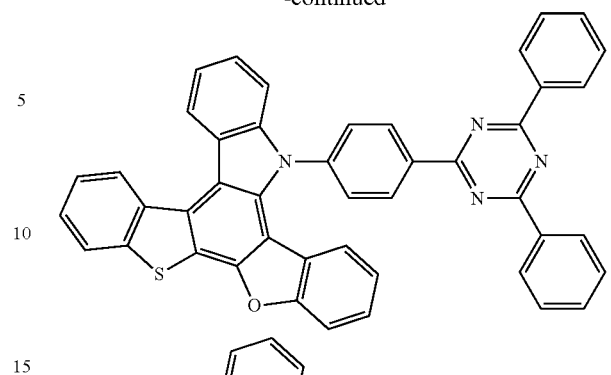
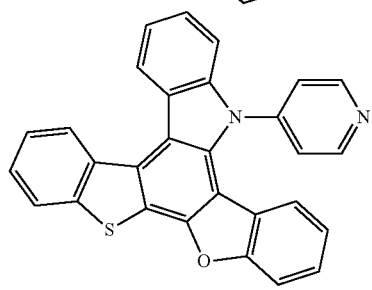
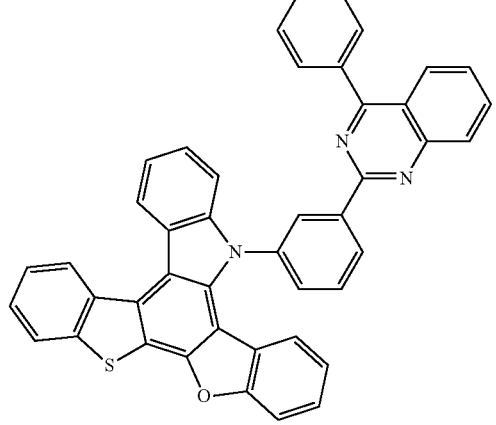
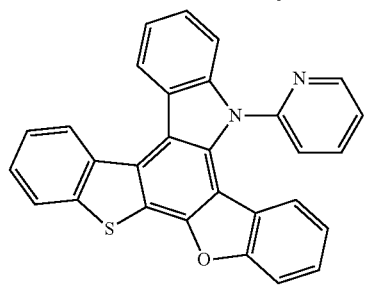
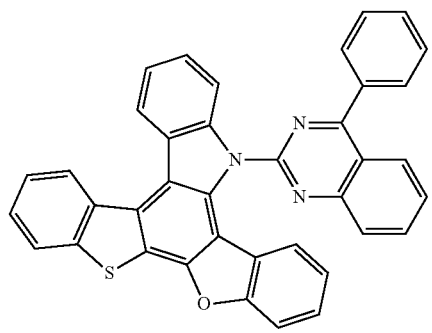

245
-continued
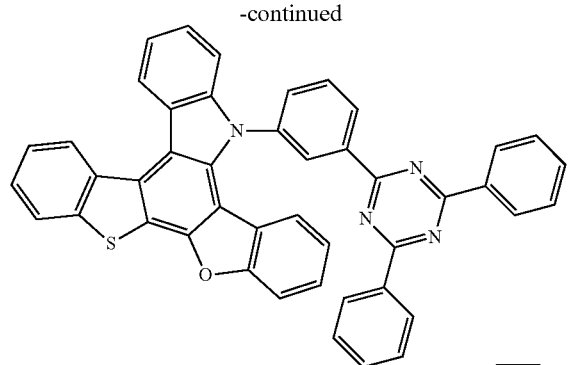
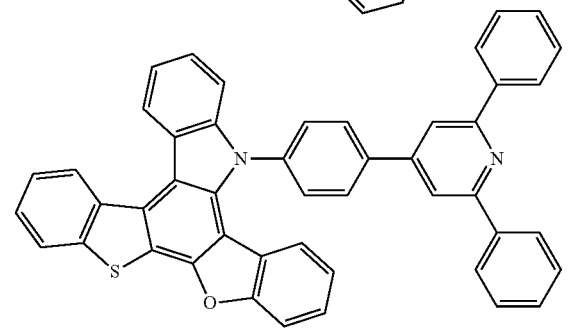
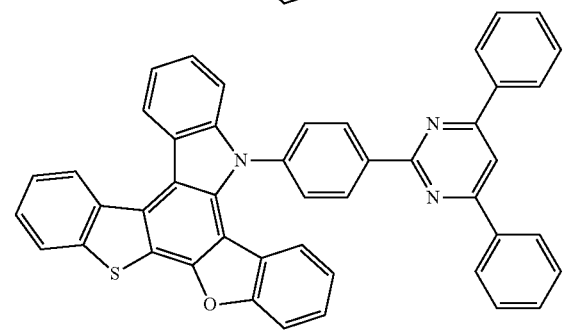
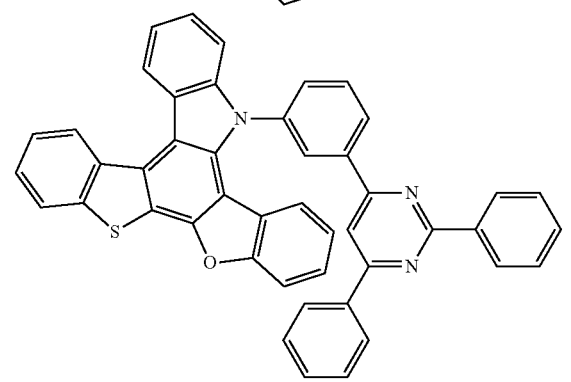
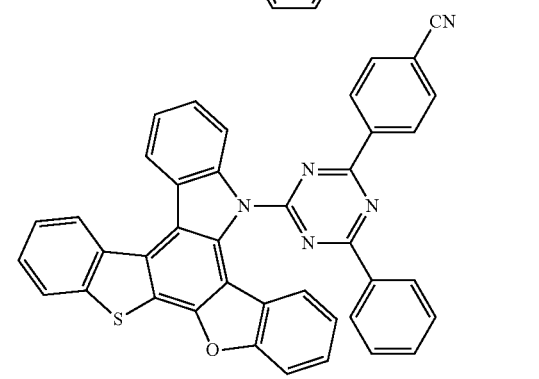
246
-continued
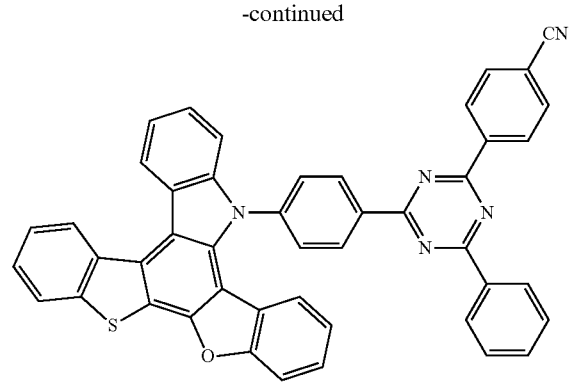
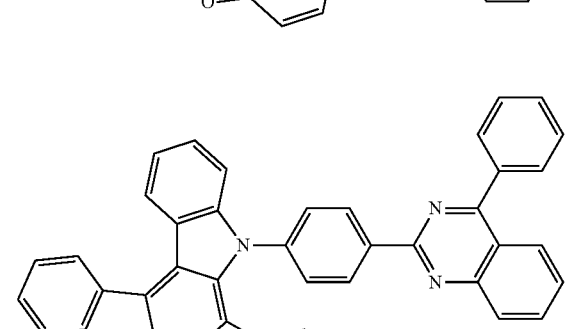
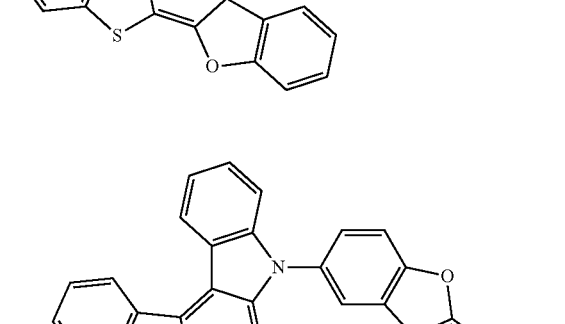
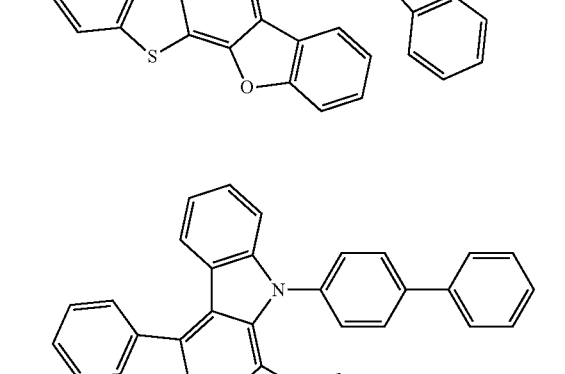
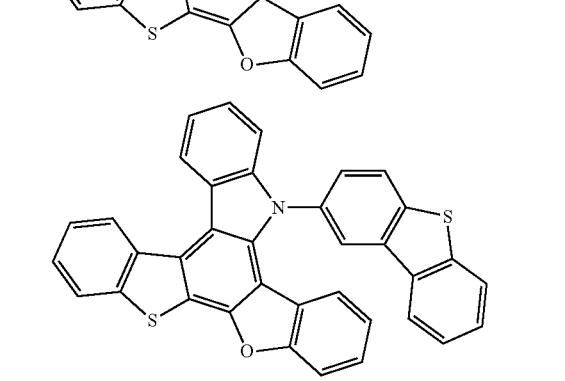

247
-continued
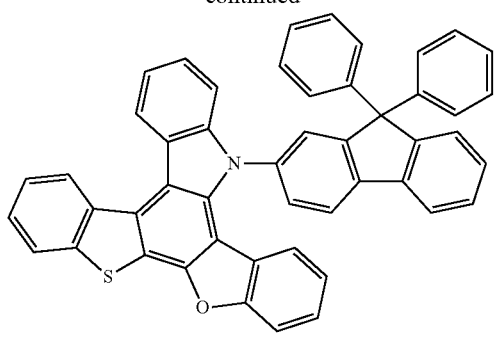
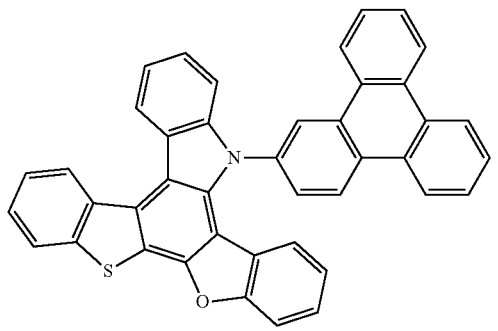
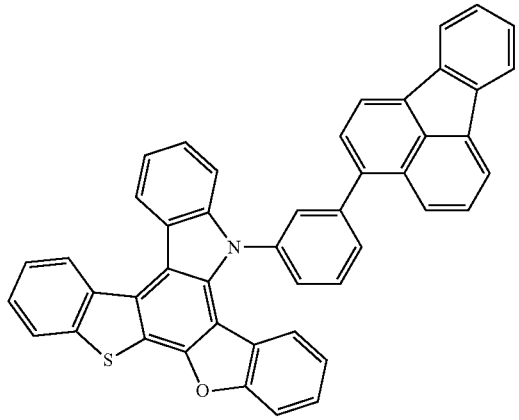
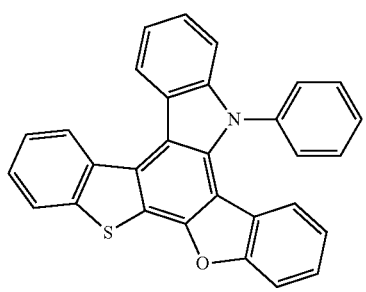
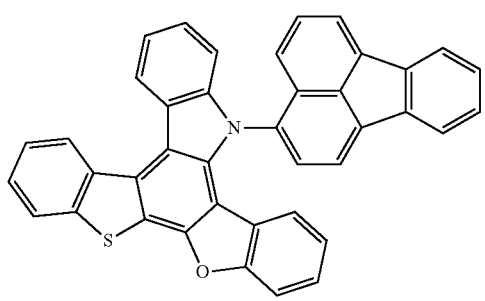
248
-continued
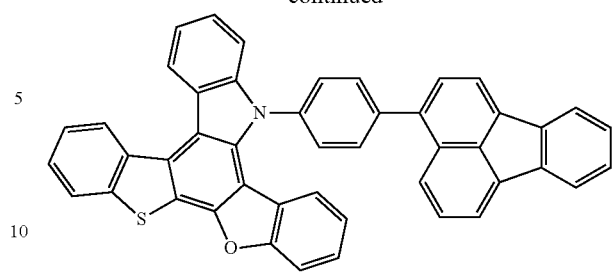
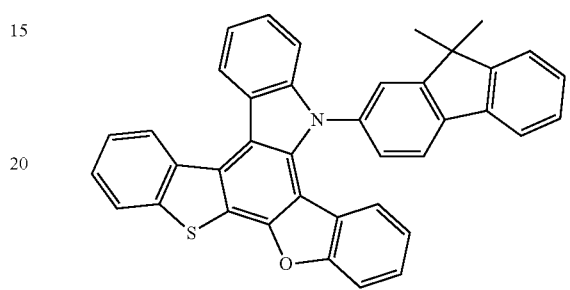
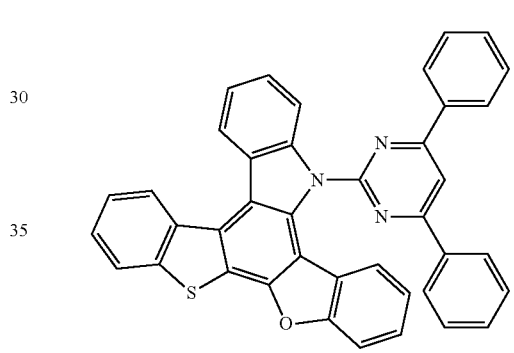
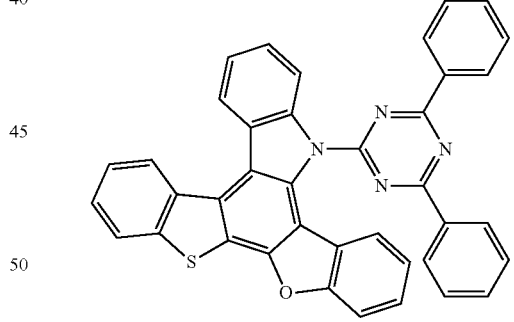
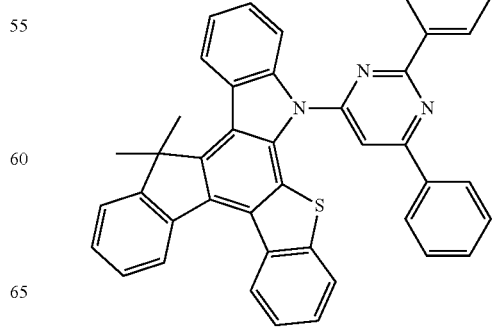

249
-continued
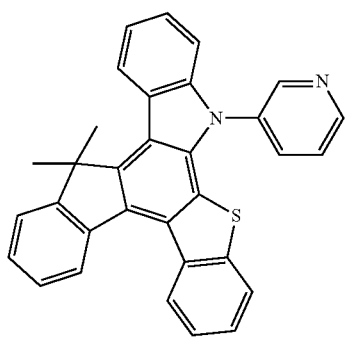
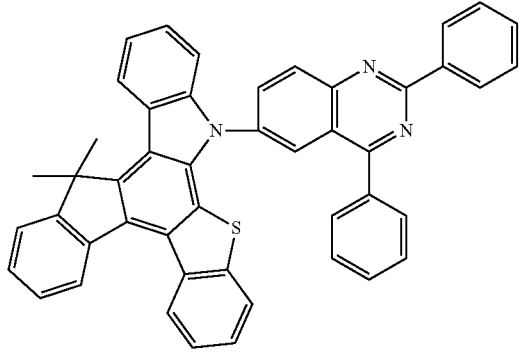
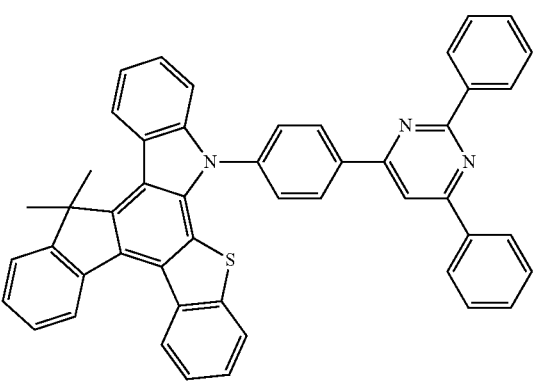
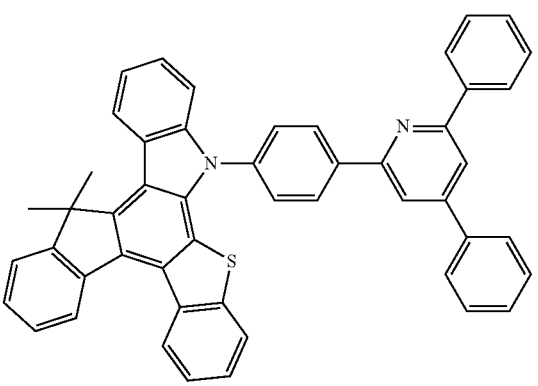
250
-continued
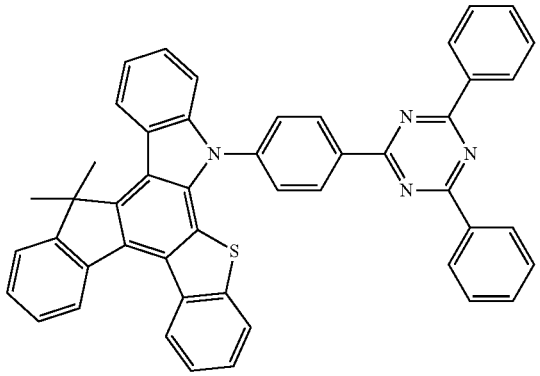
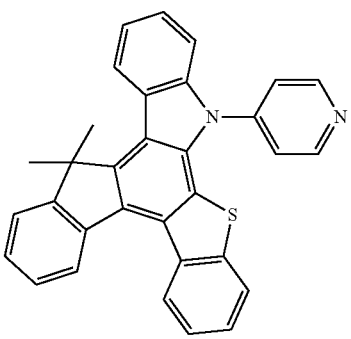
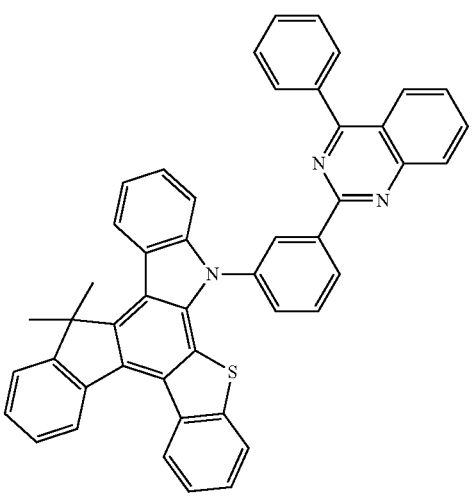
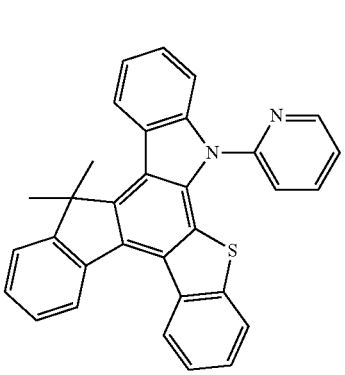

251
-continued
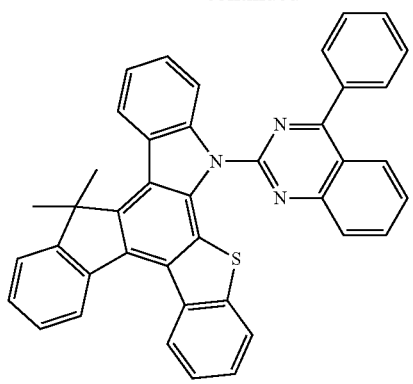
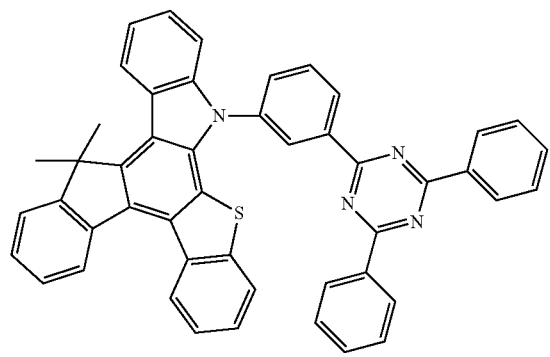
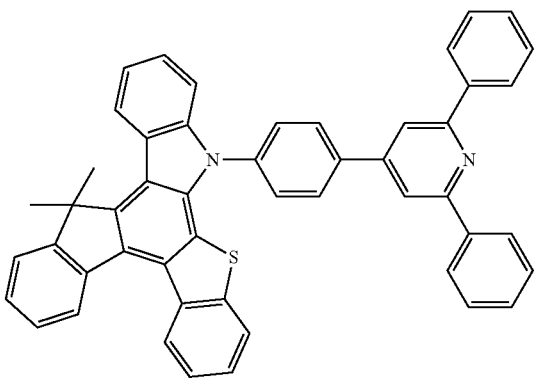
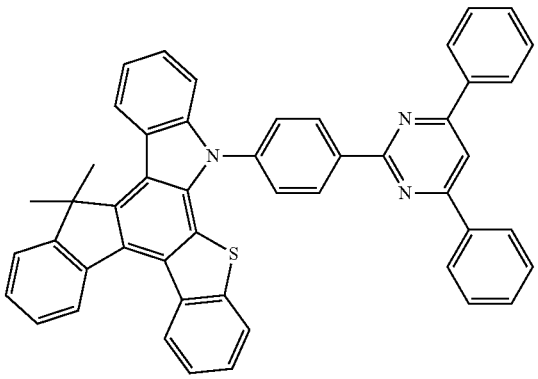
252
-continued
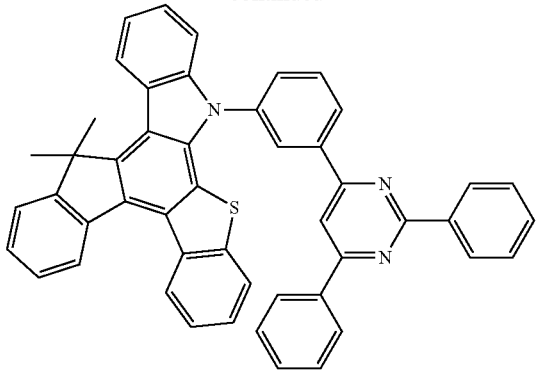
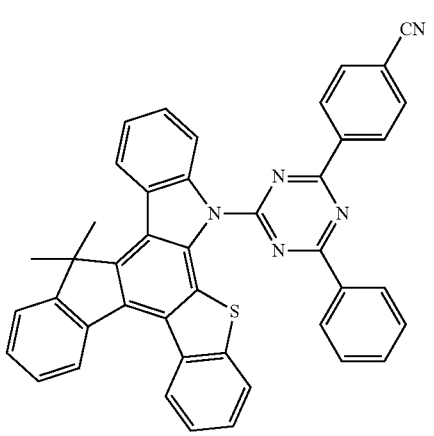
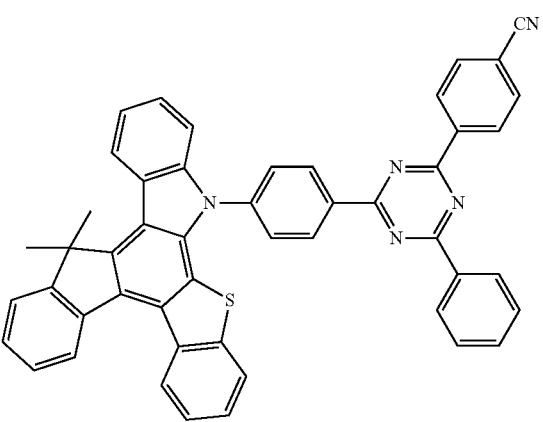
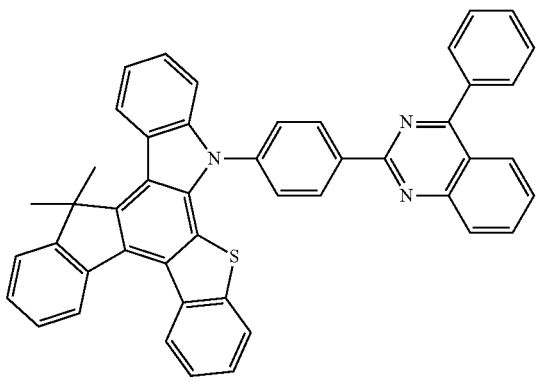

253
-continued
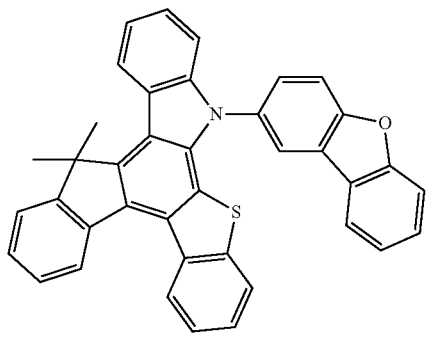
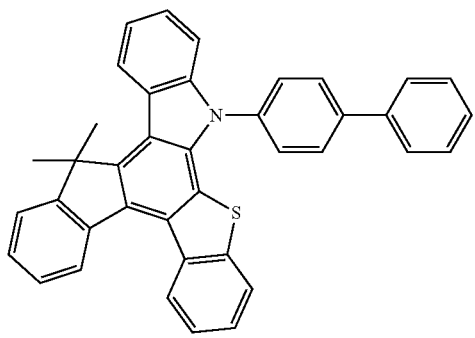
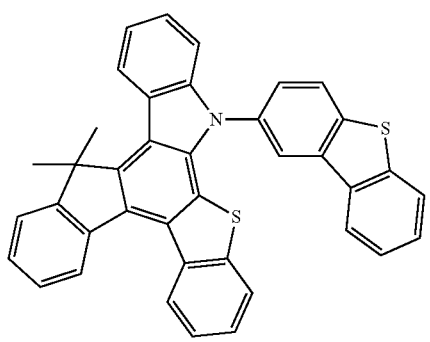
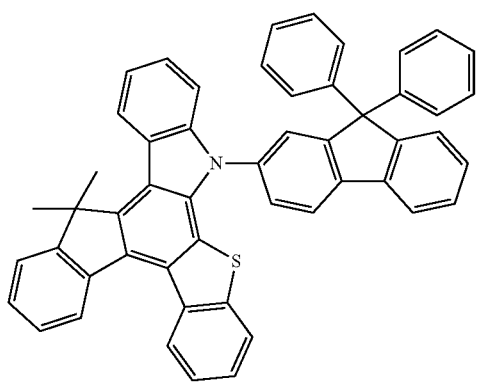
254
-continued
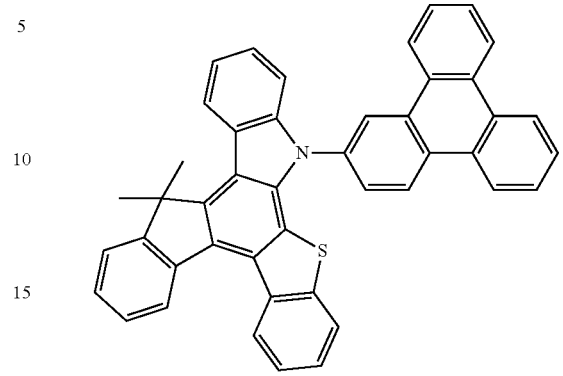
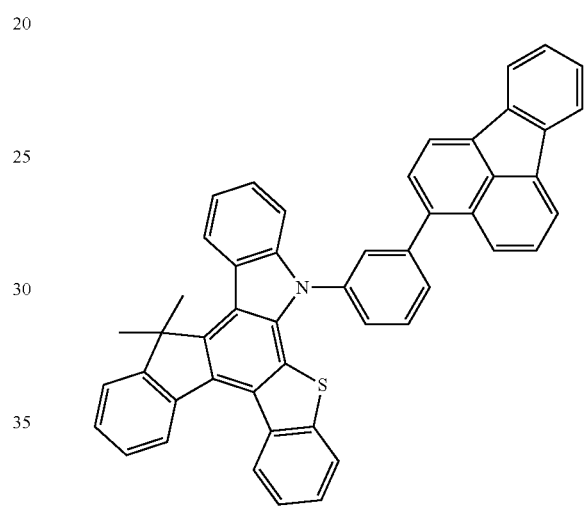
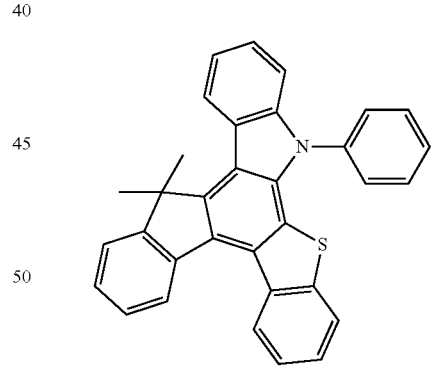
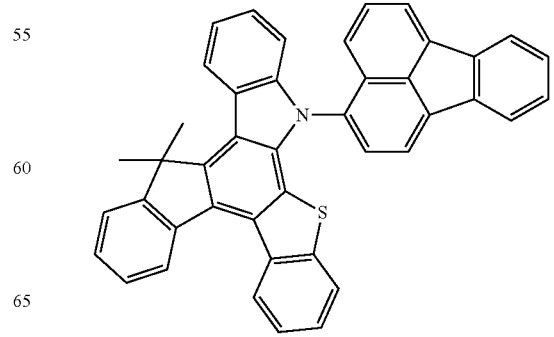

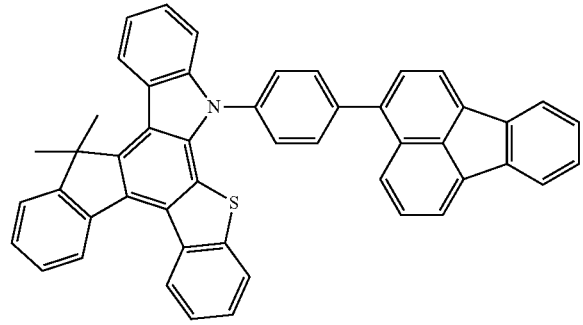
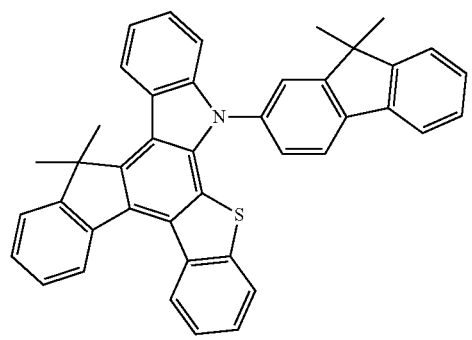
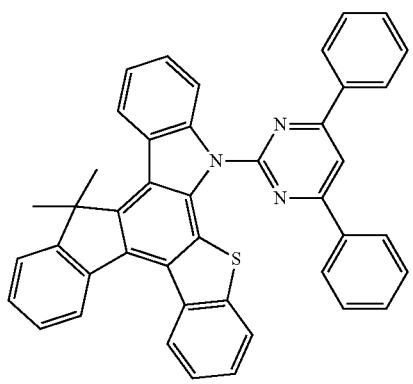
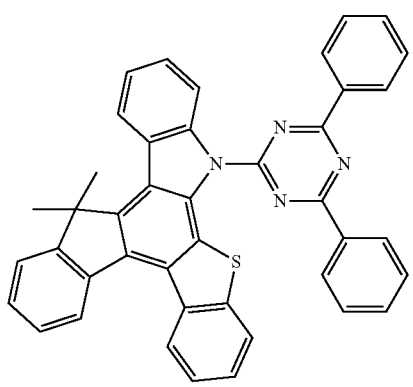
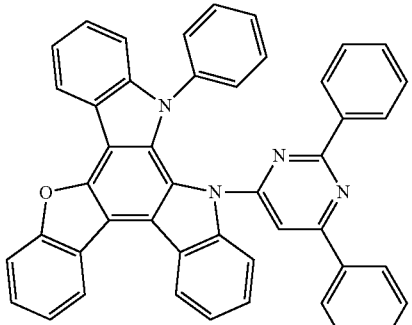
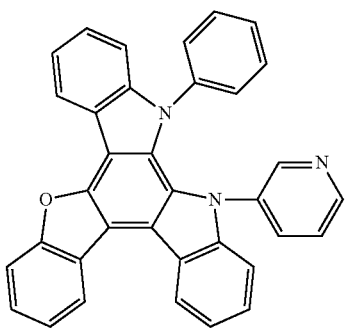
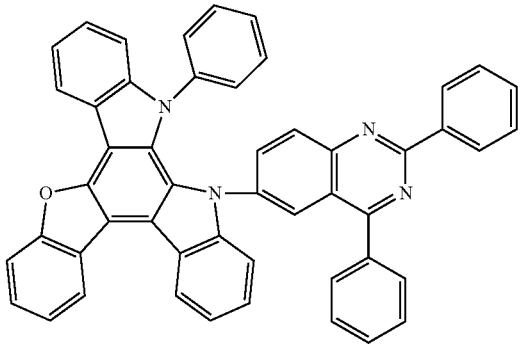
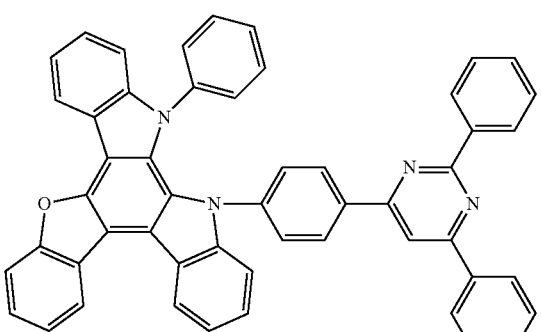
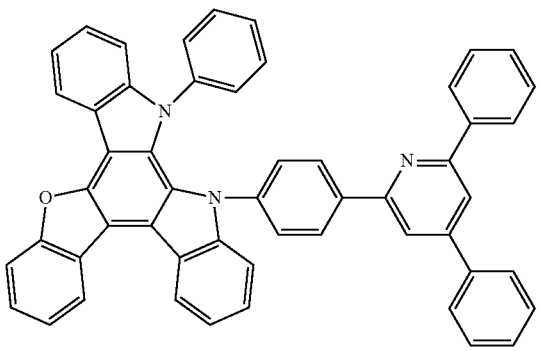

257
-continued
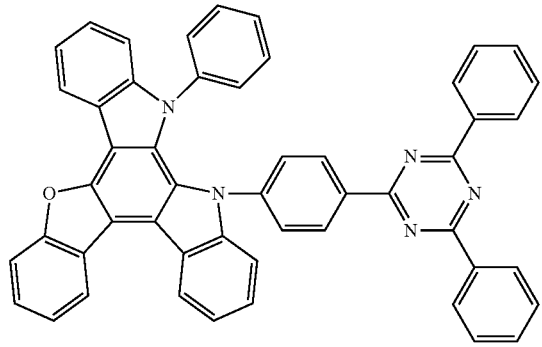
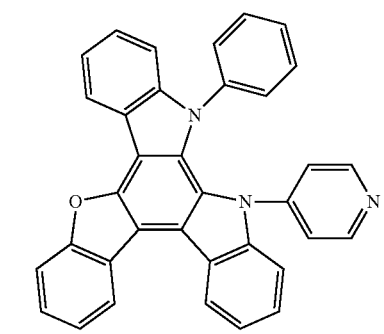
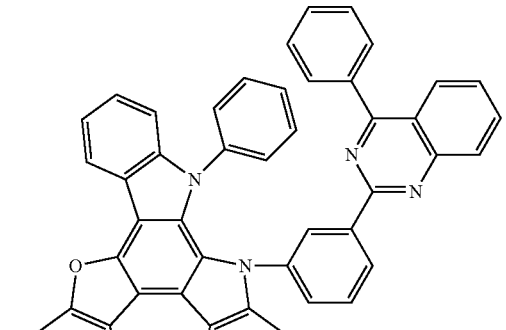
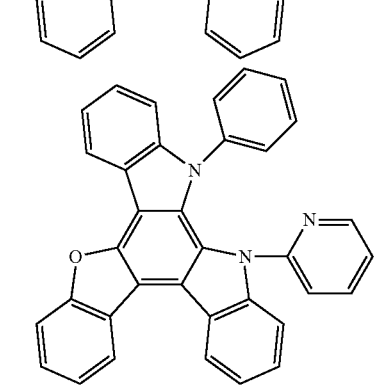
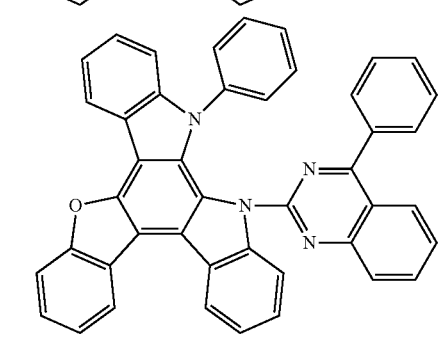
258
-continued
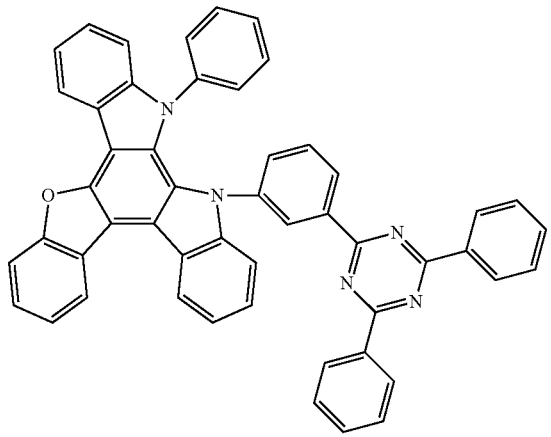
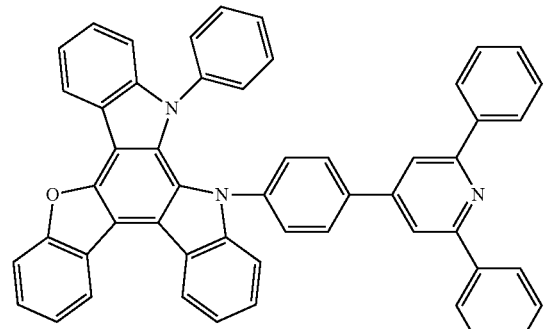
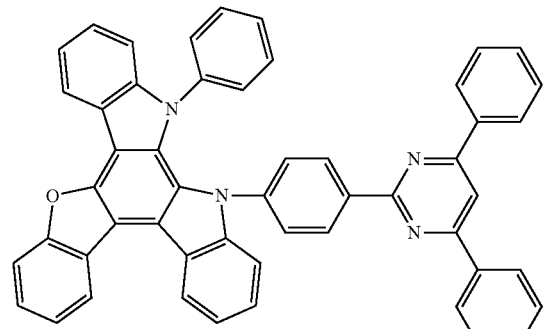
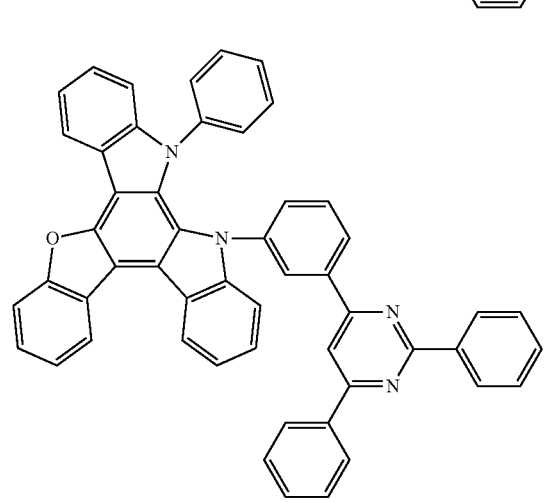

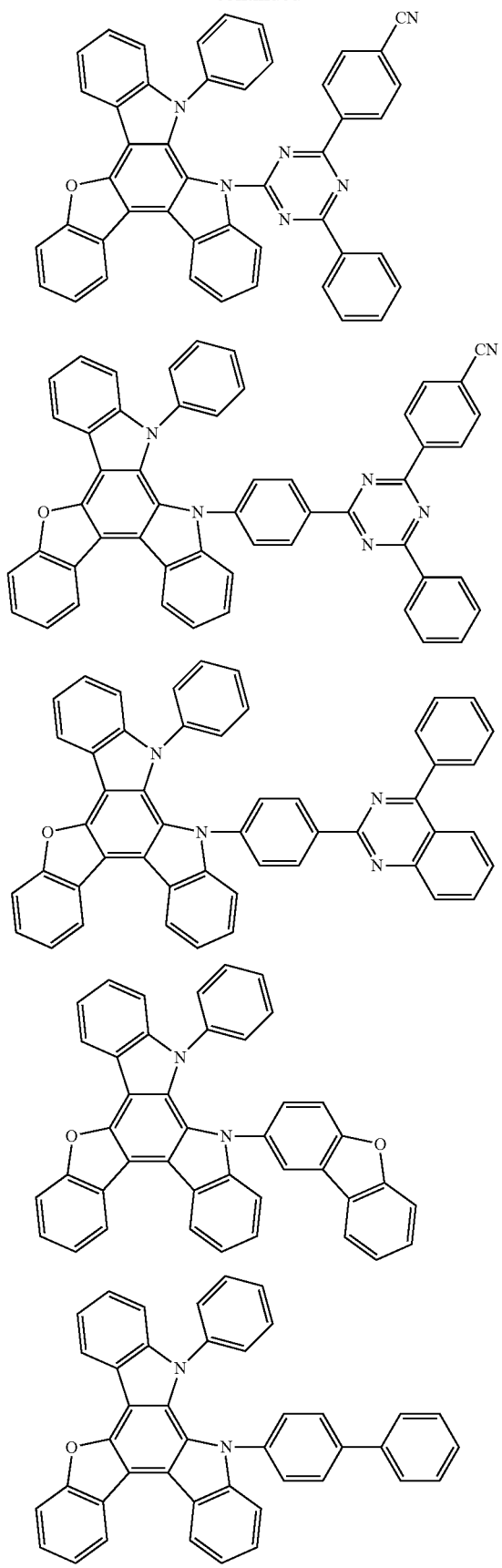
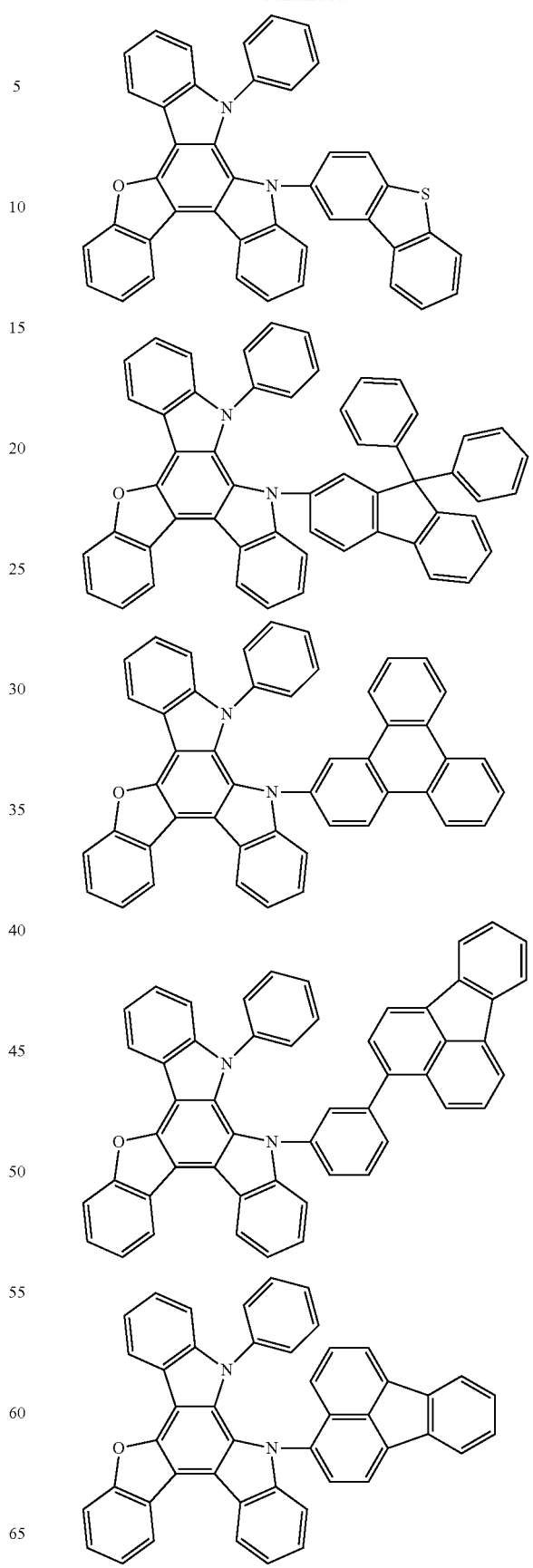

261
-continued
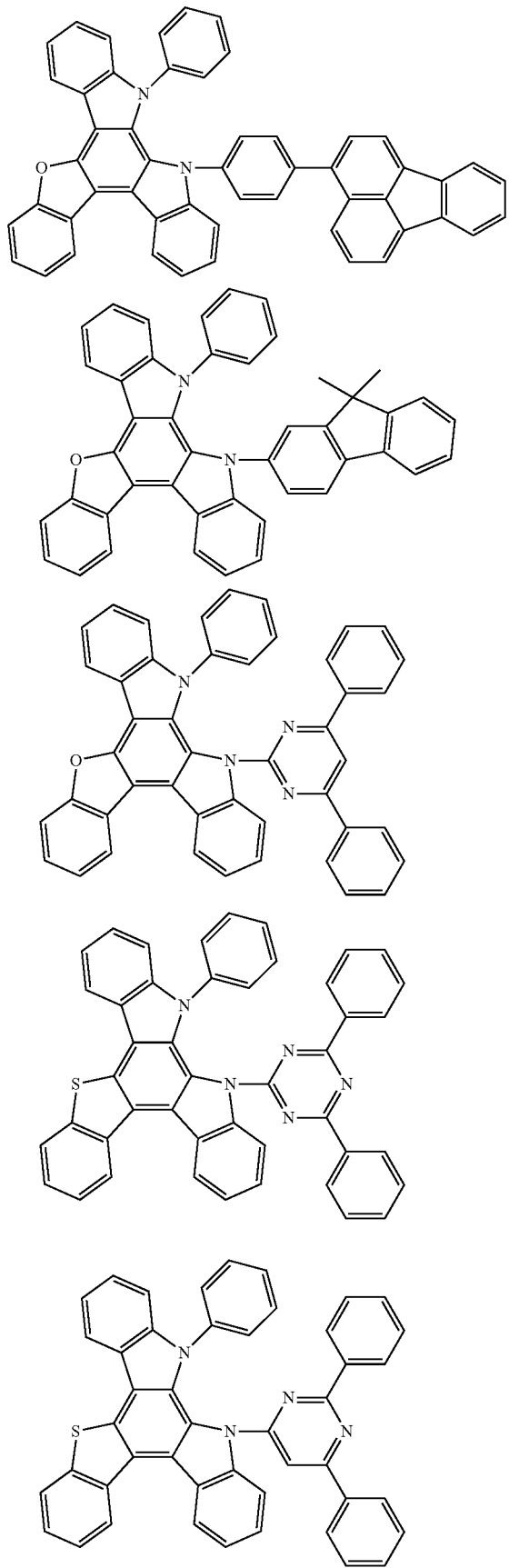
262
-continued
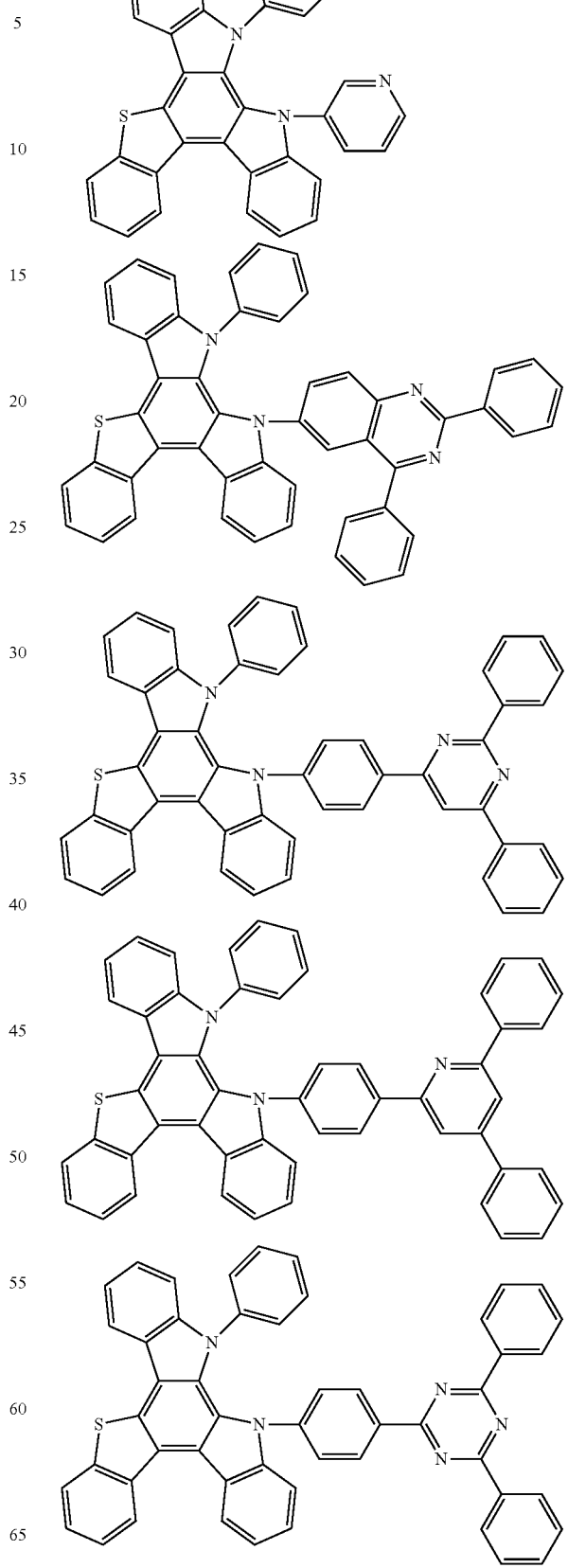

263
-continued
264
-continued
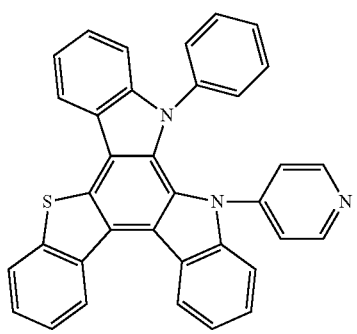
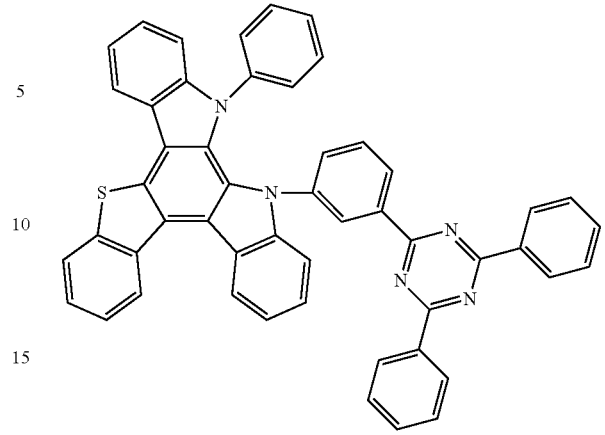
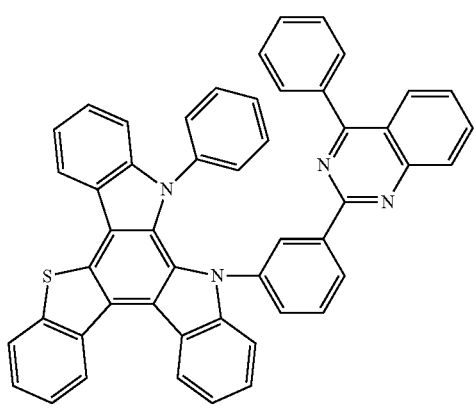
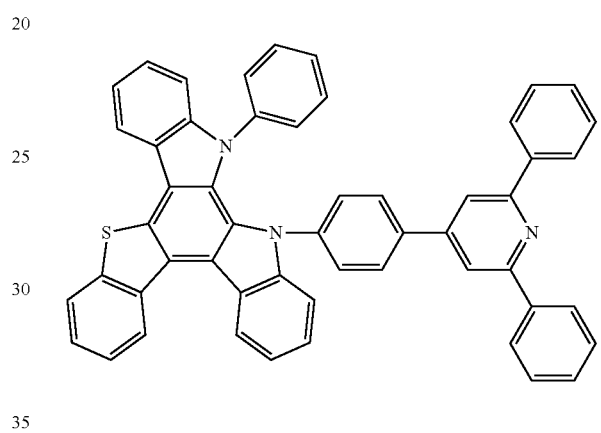
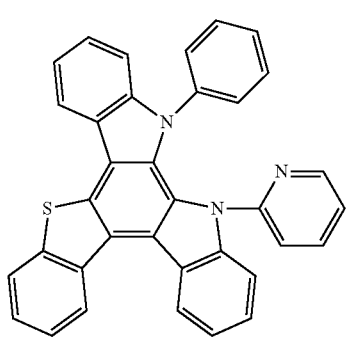
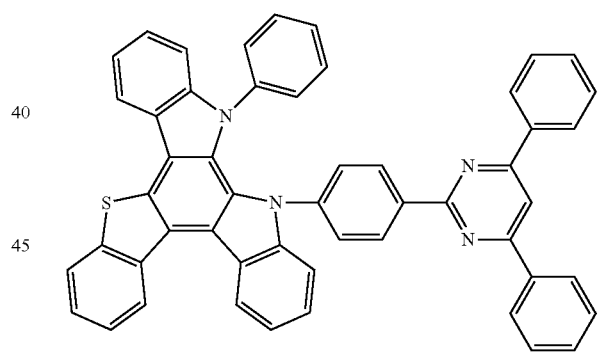
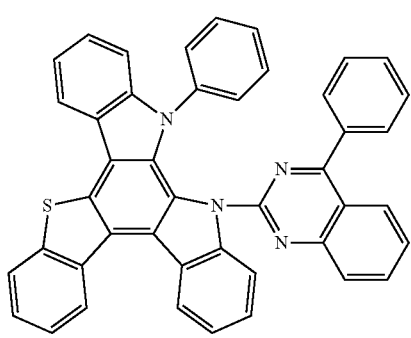
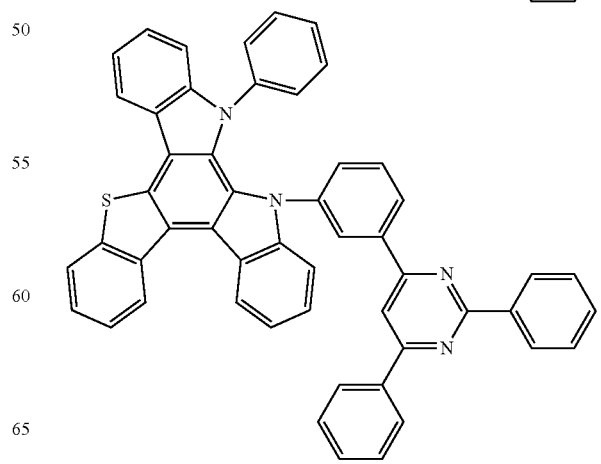

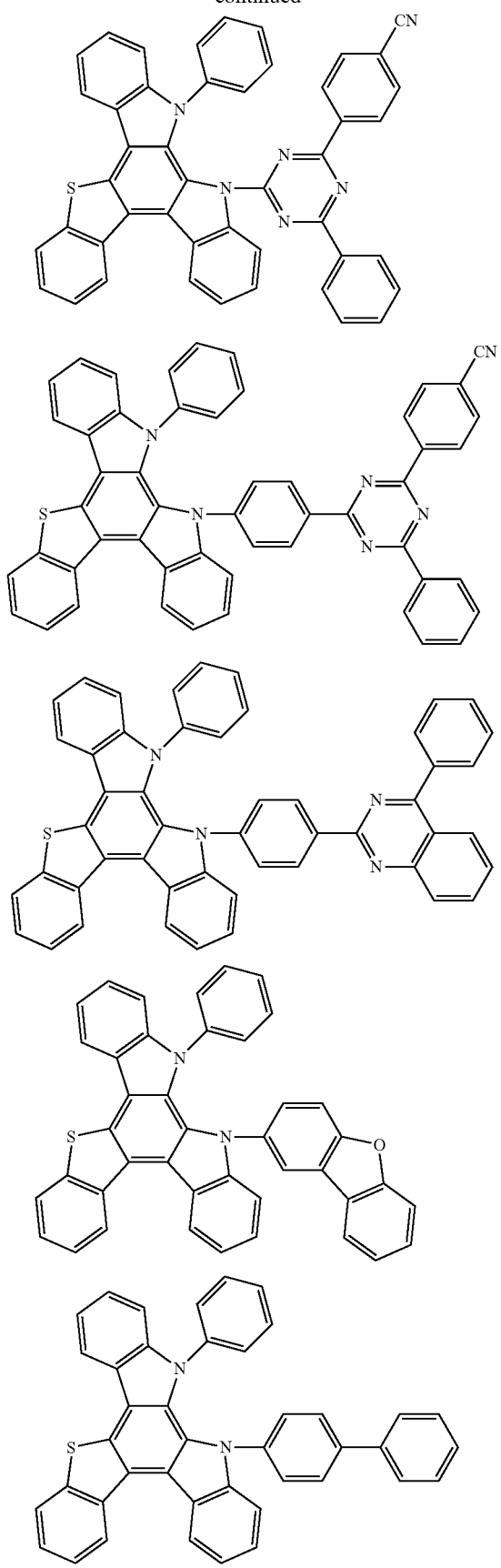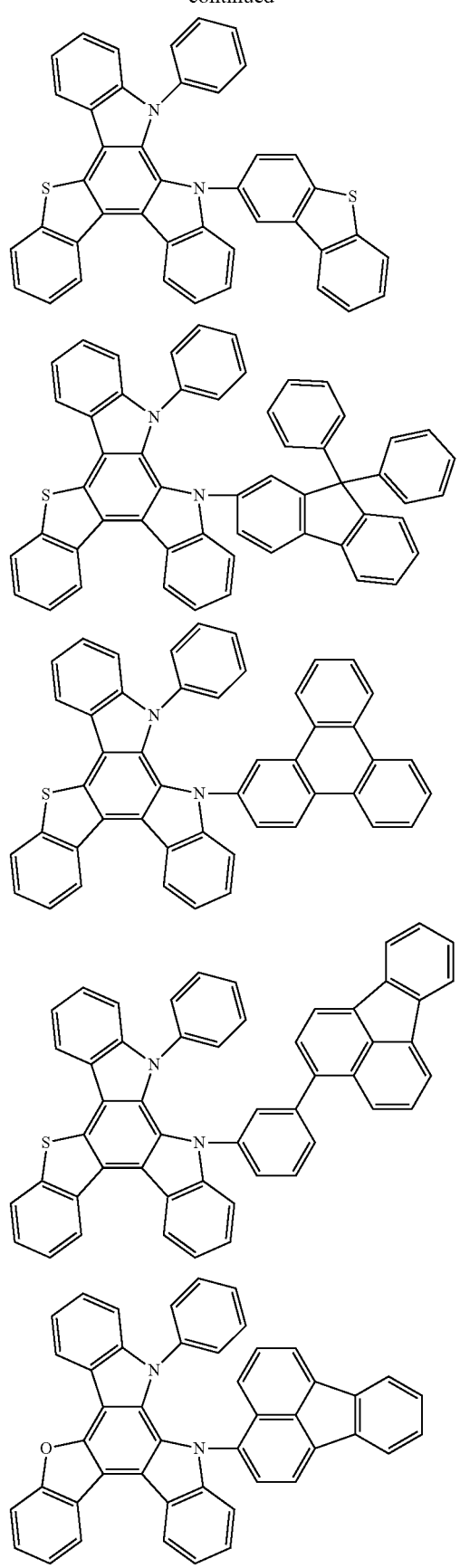

267
-continued
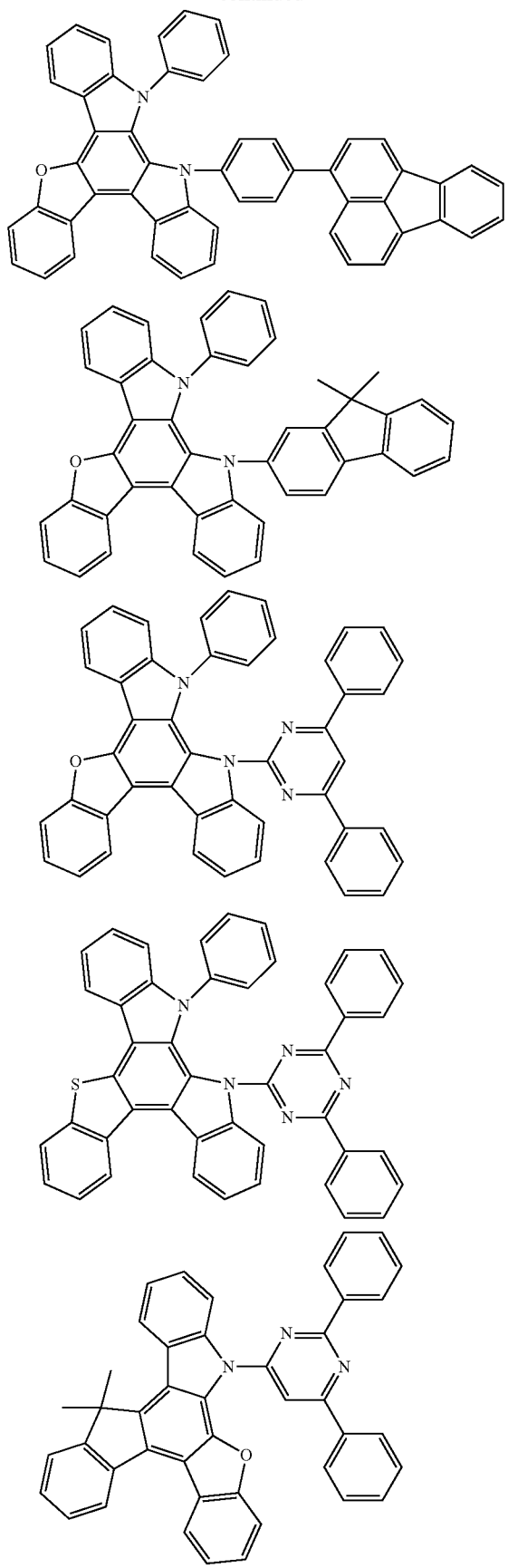
268
-continued
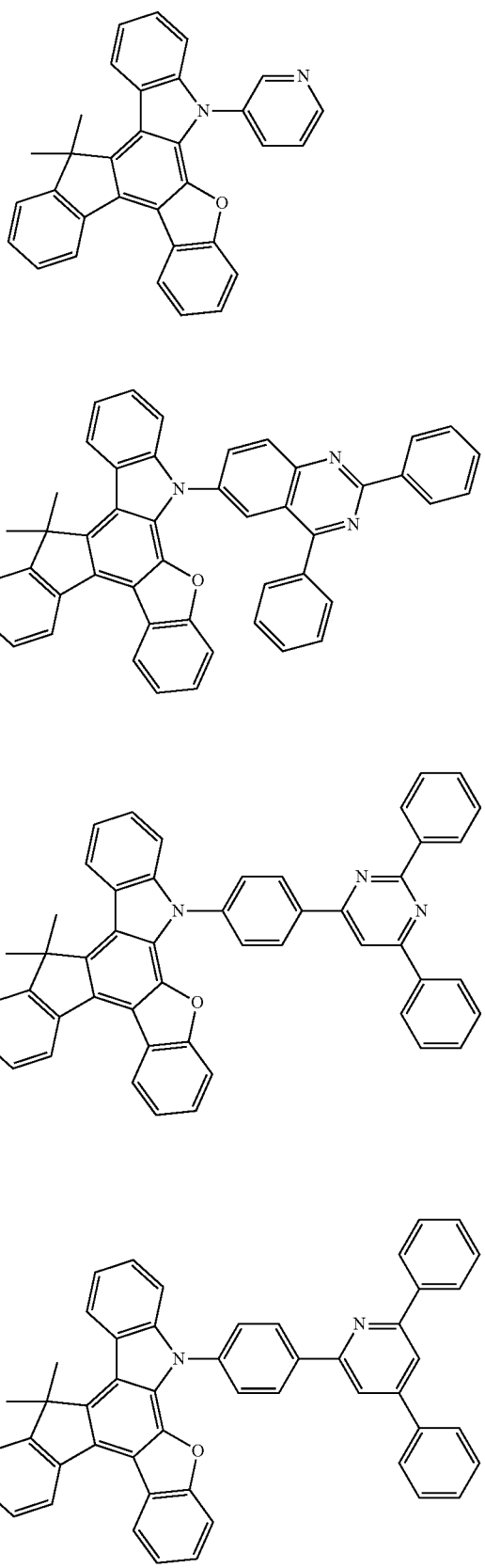

269
-continued
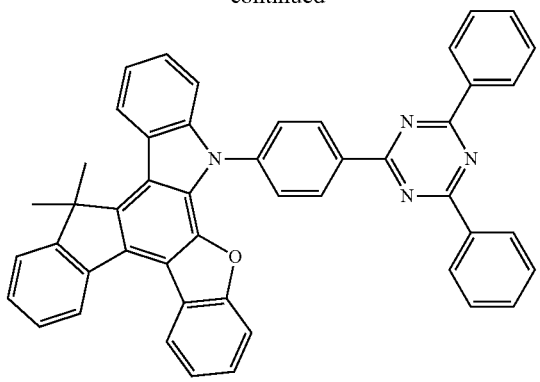
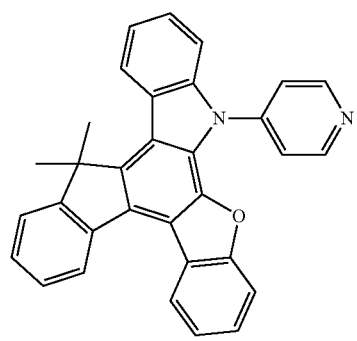
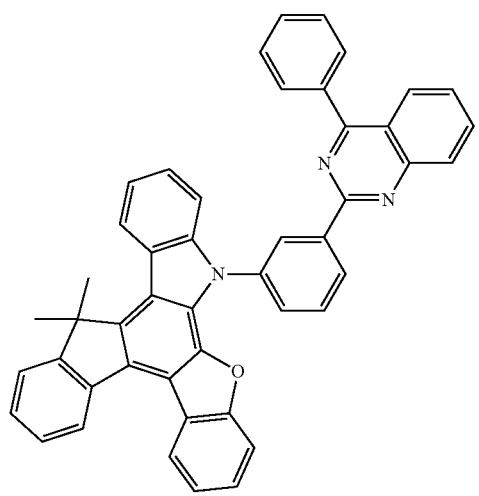
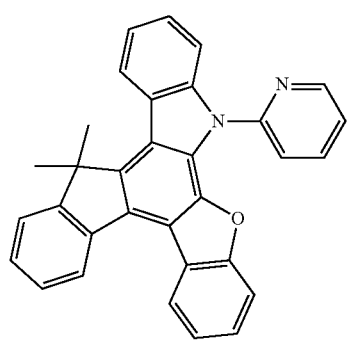
270
-continued
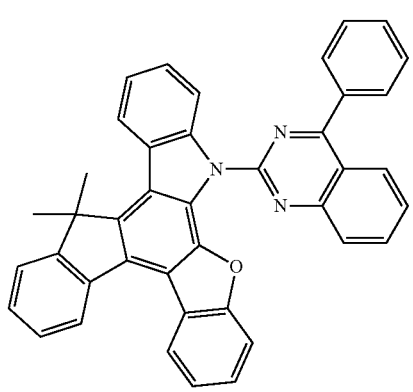
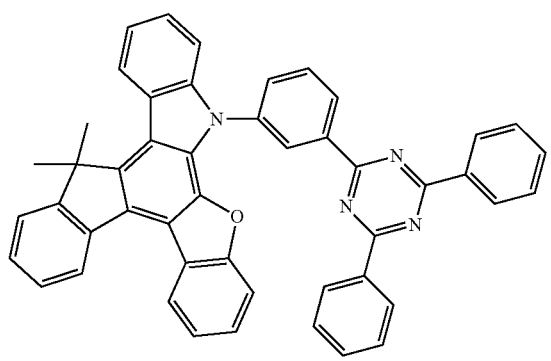
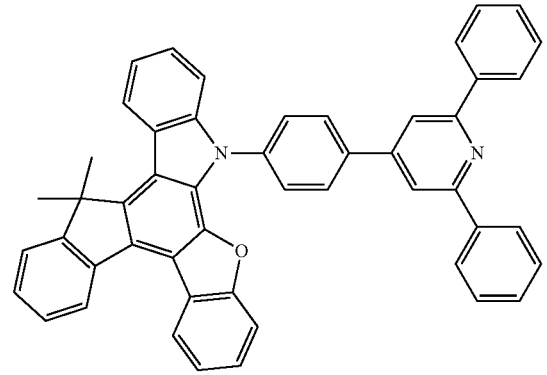
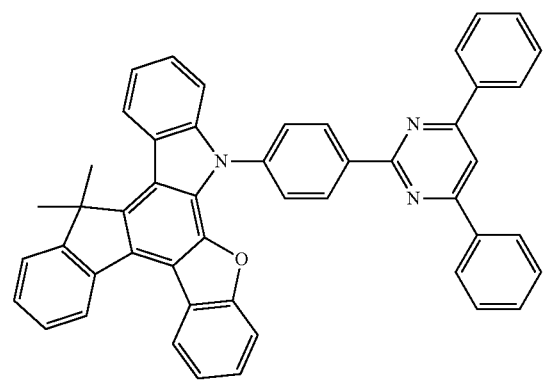

271
-continued
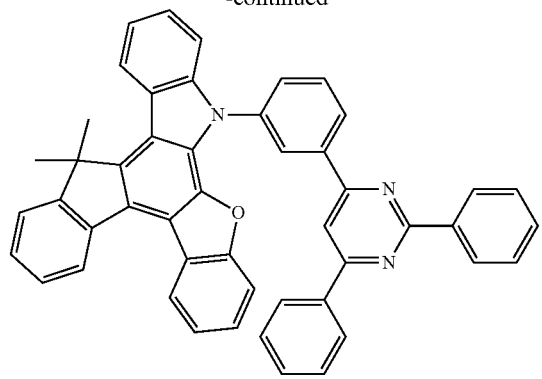
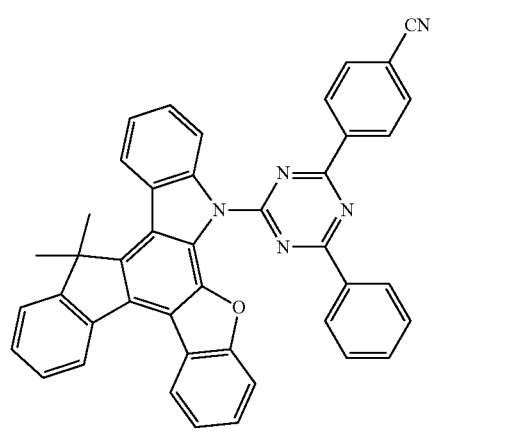
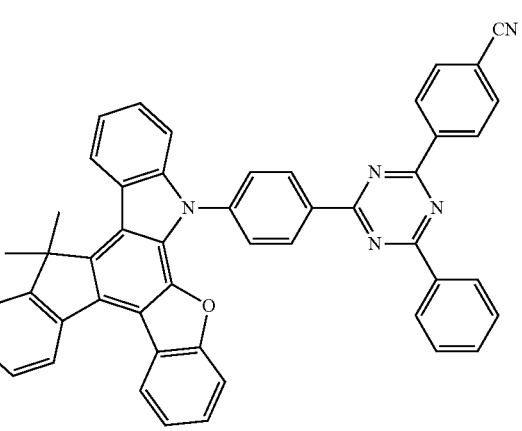
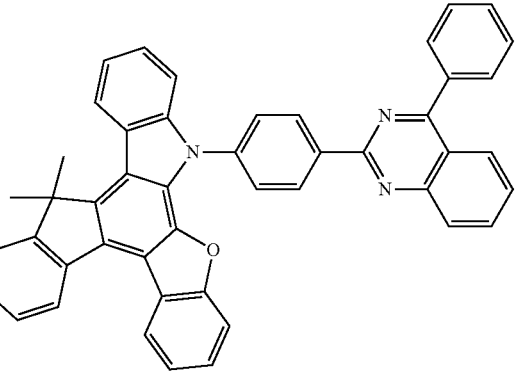
272
-continued
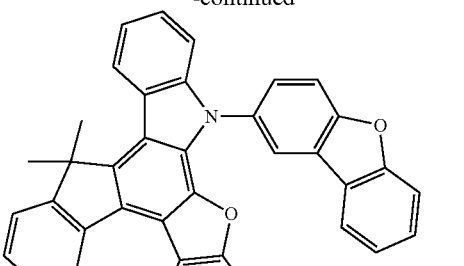
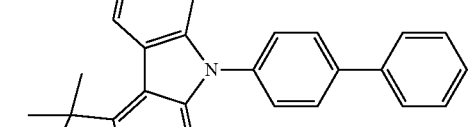
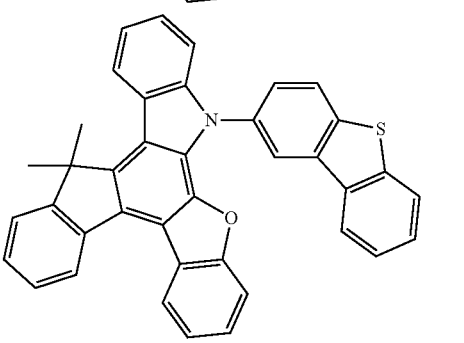
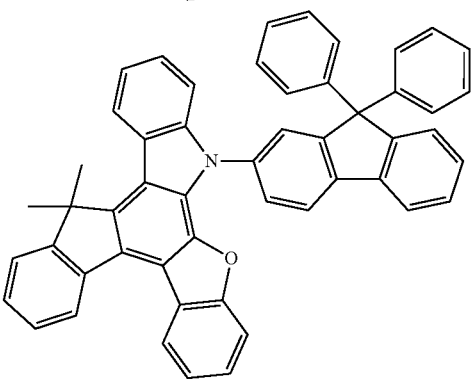
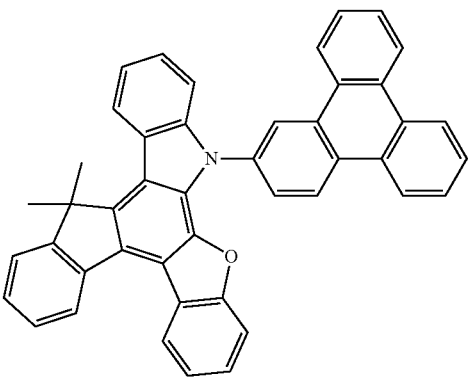

273
-continued
274
-continued
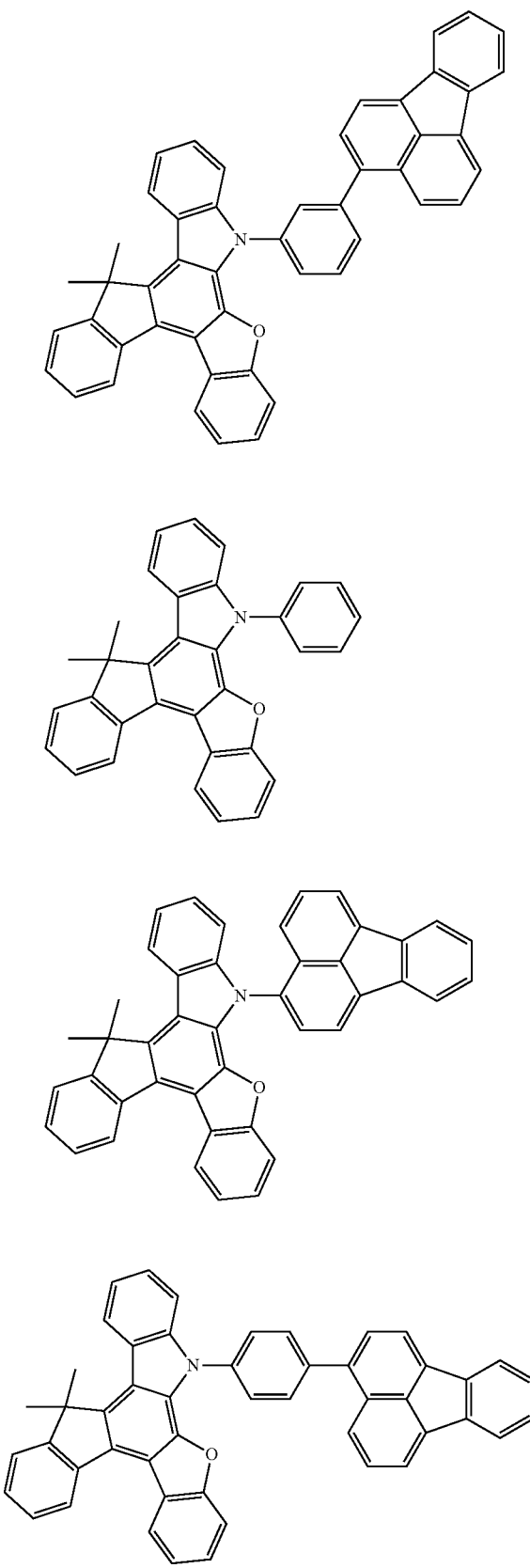
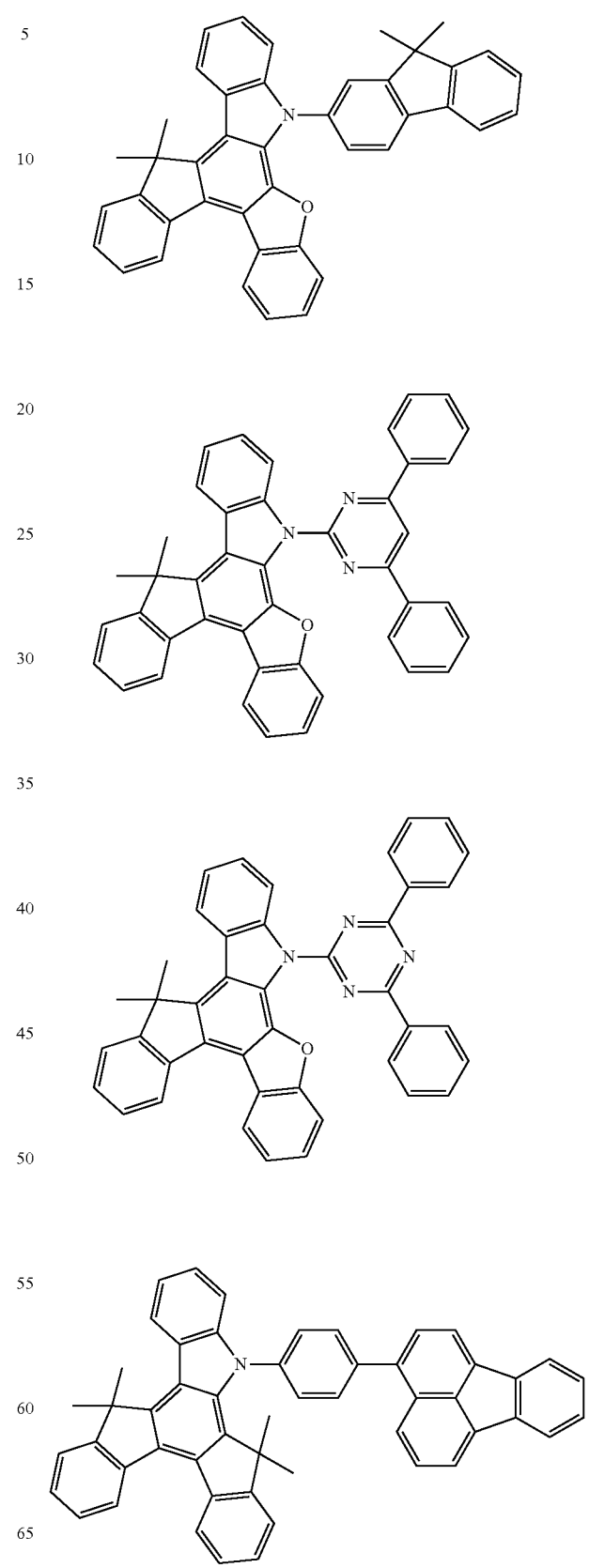

275
-continued
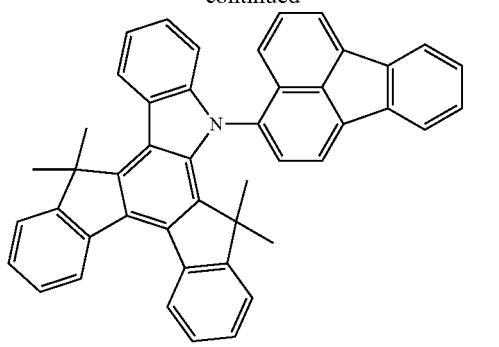
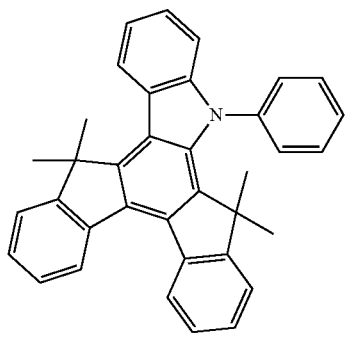
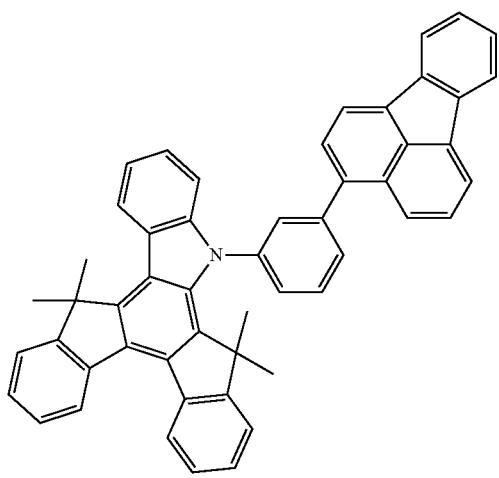
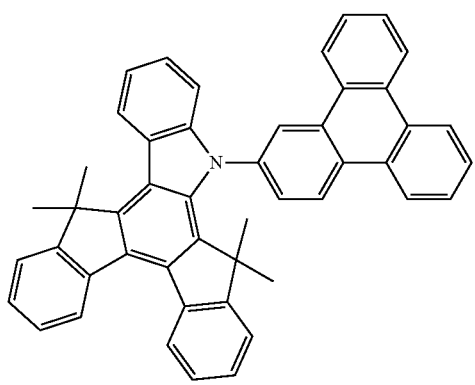
276
-continued
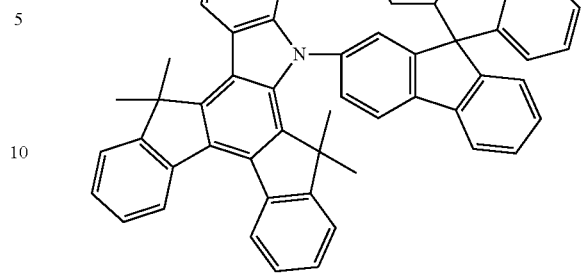
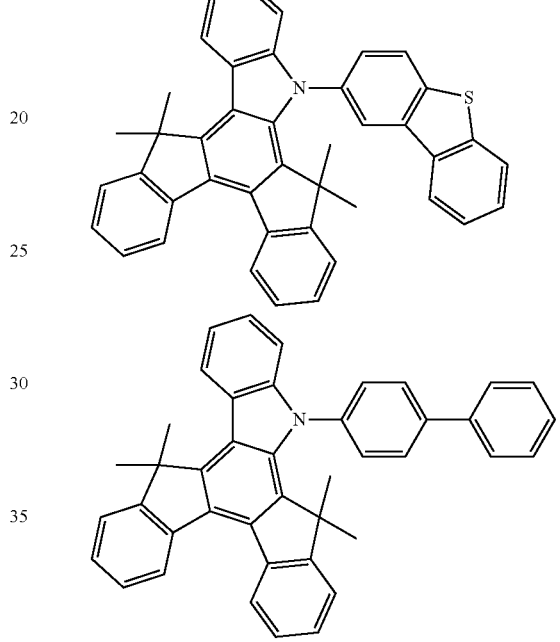
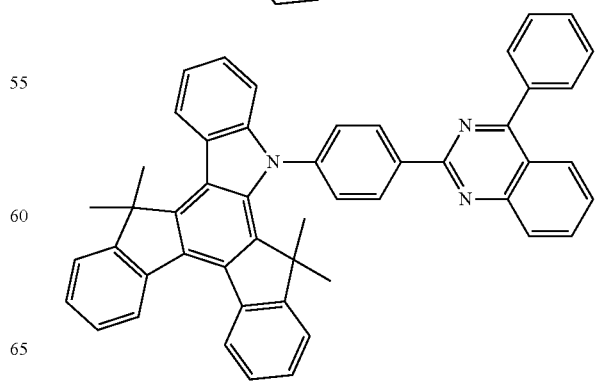

277
-continued
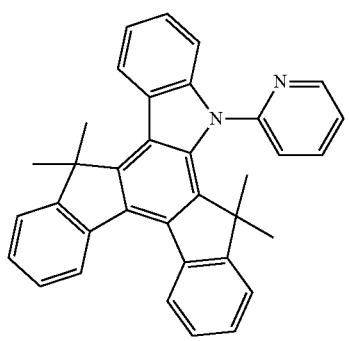
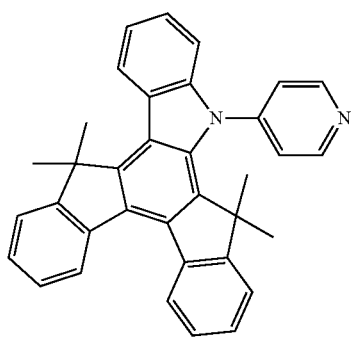
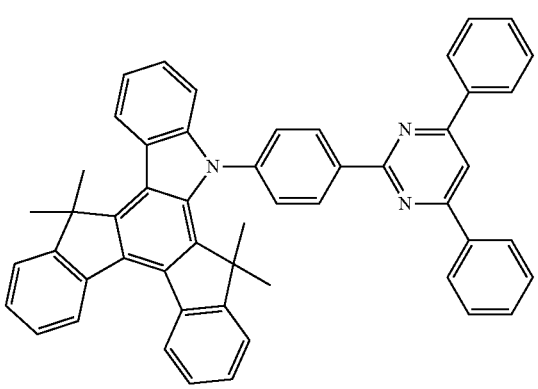
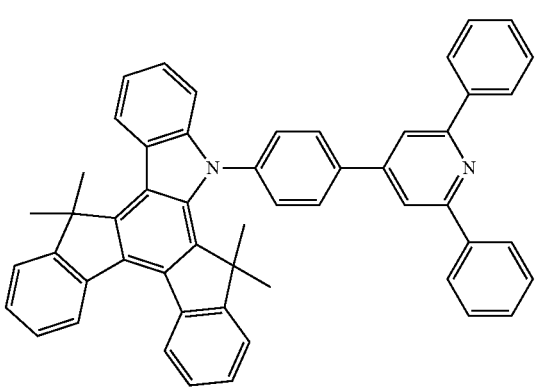
278
-continued
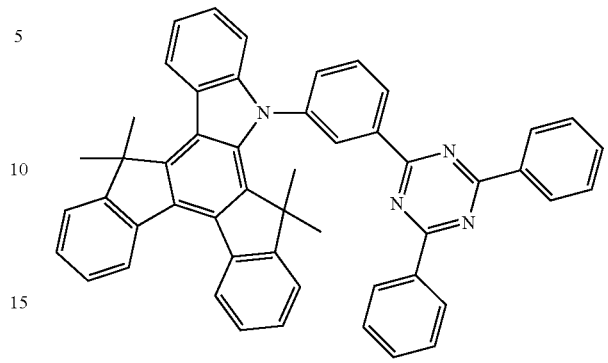
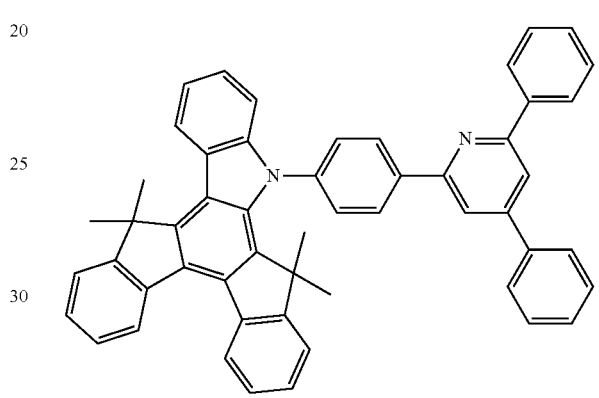
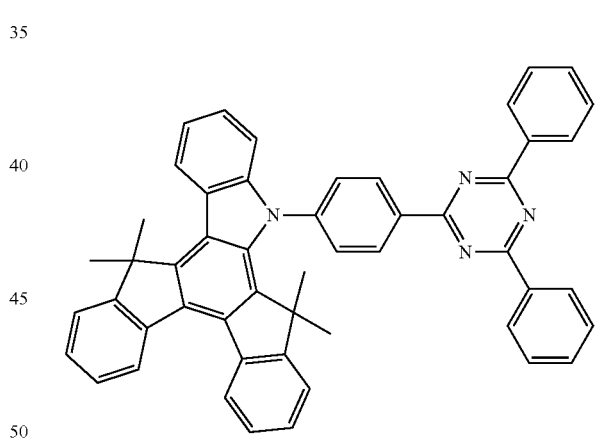
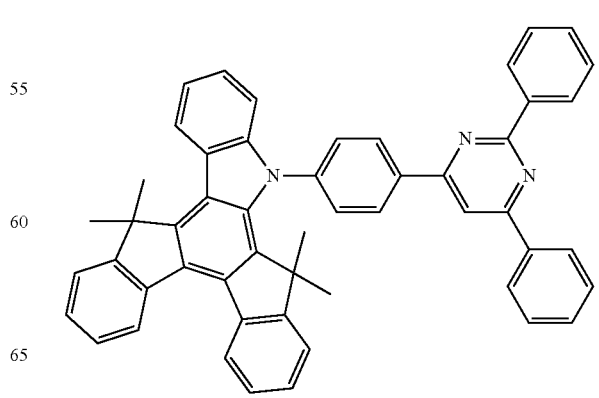

279
-continued
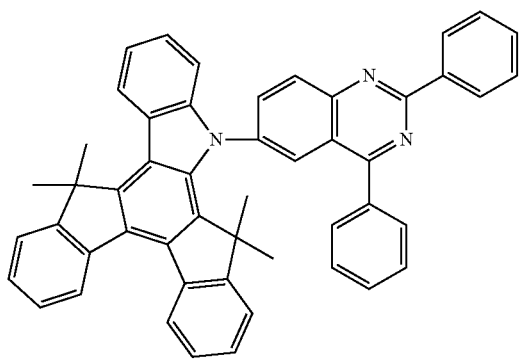
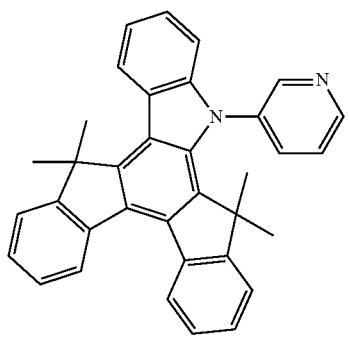
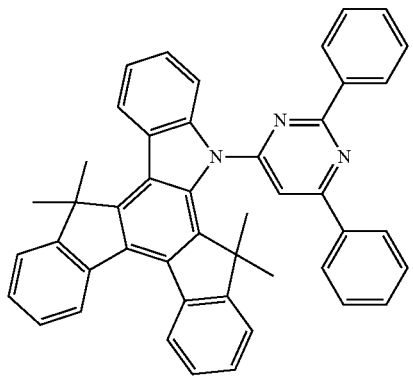
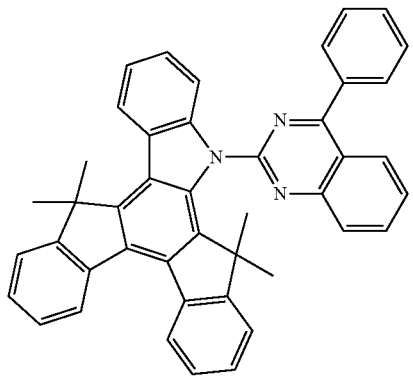
280
-continued
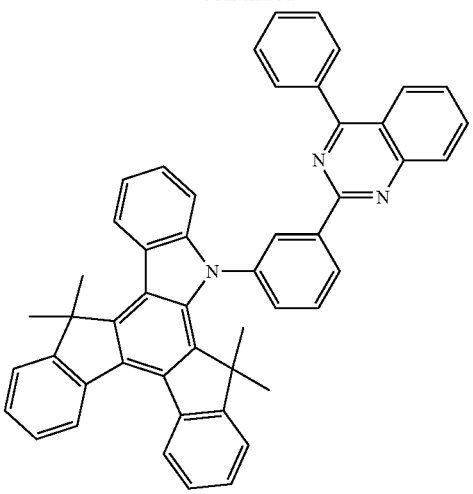
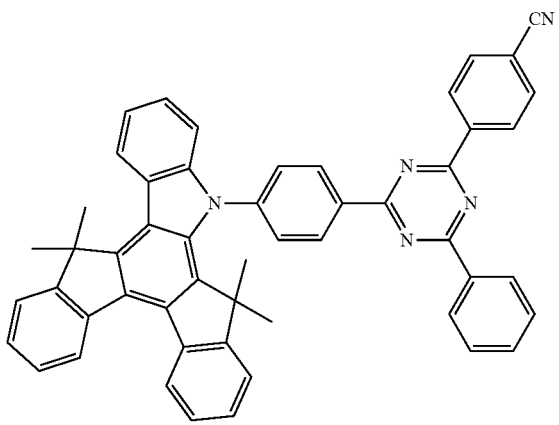
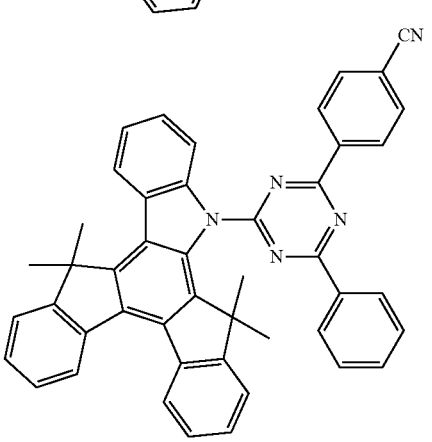
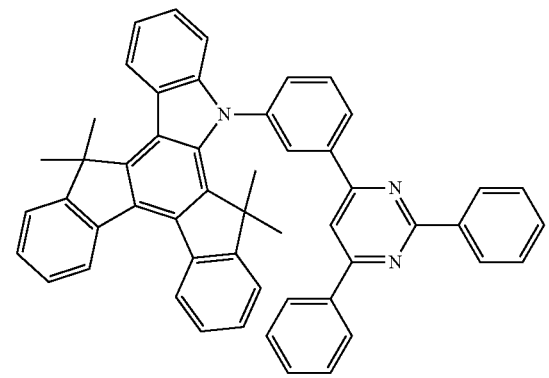

281
-continued
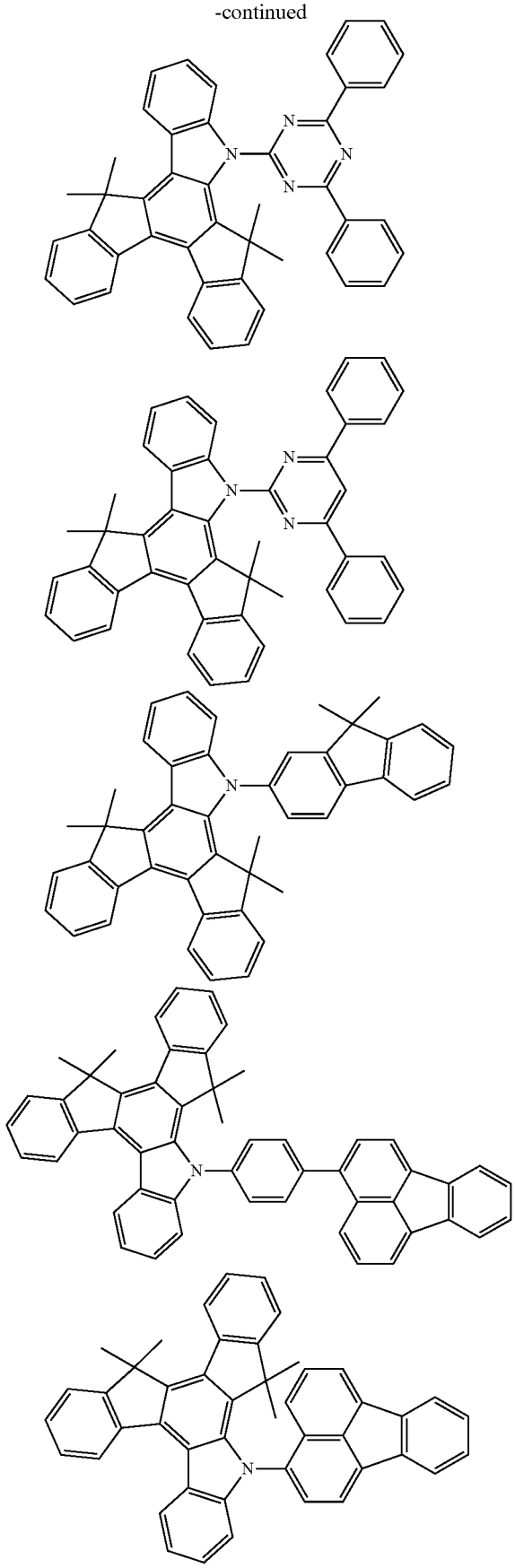
282
-continued
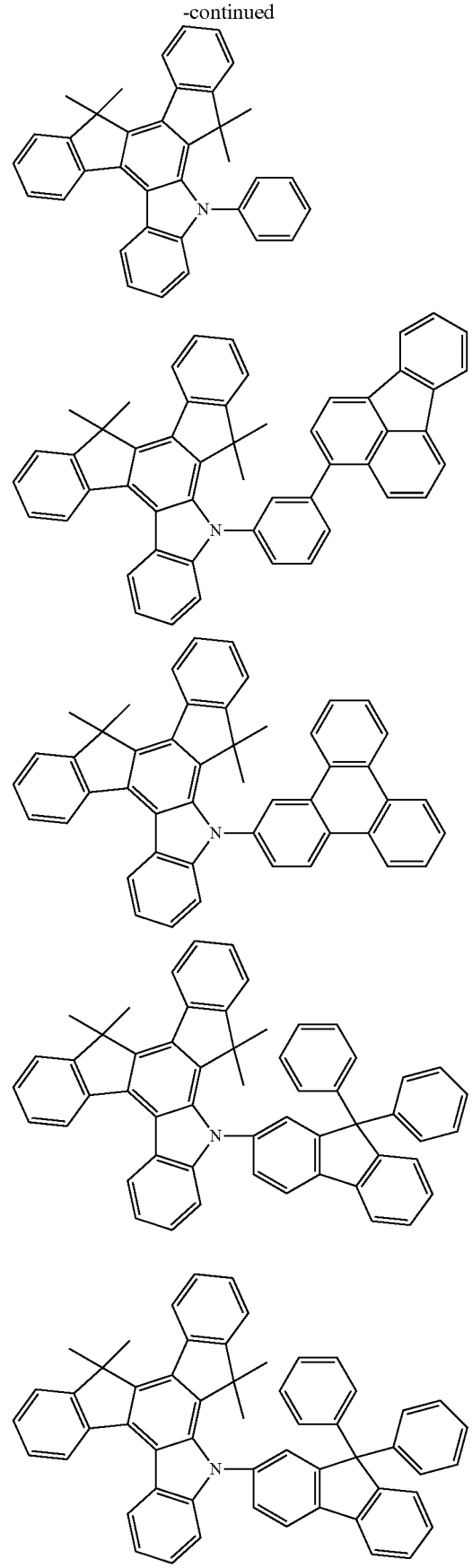

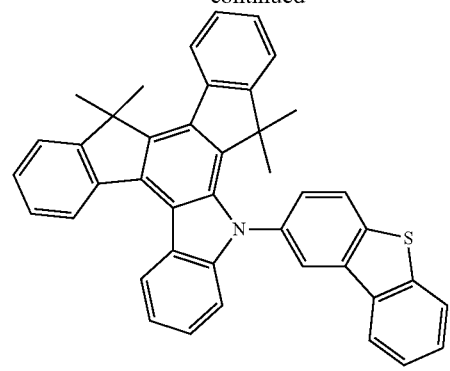
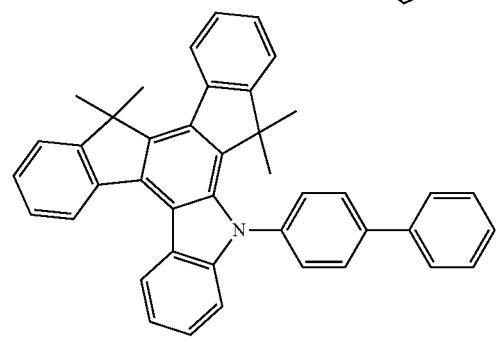
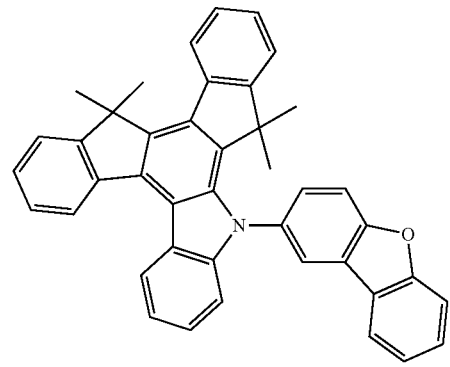
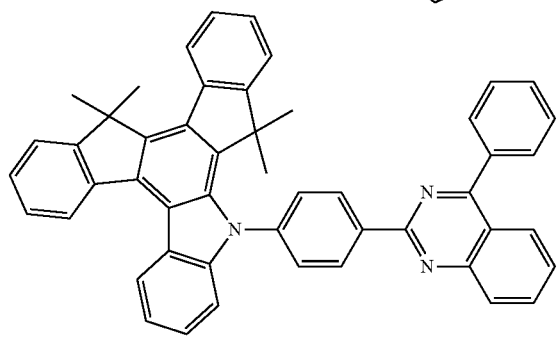
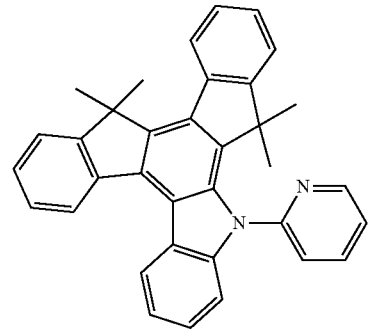
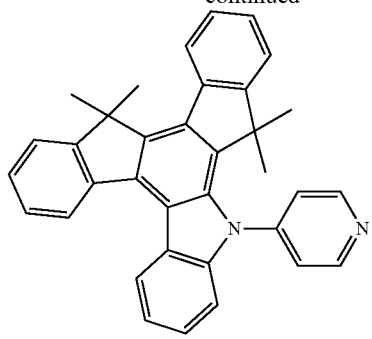
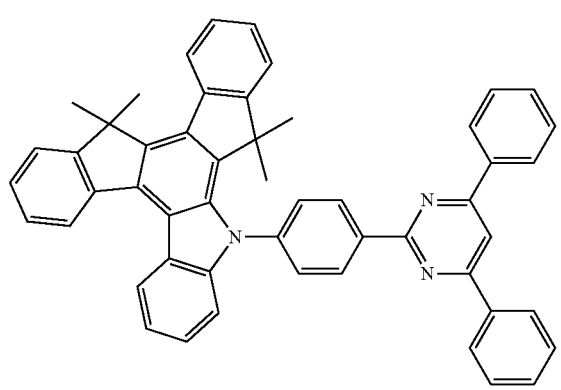
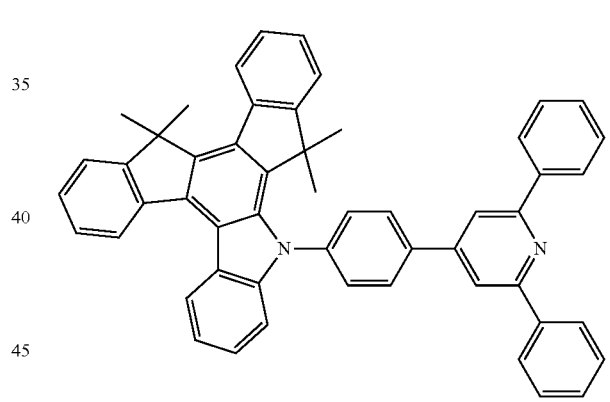
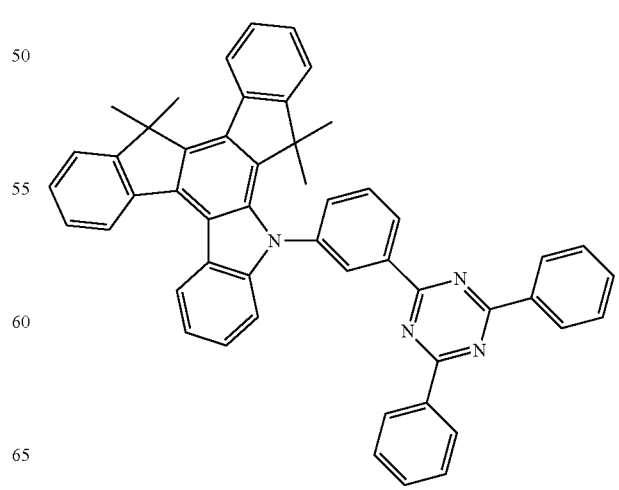

285
-continued
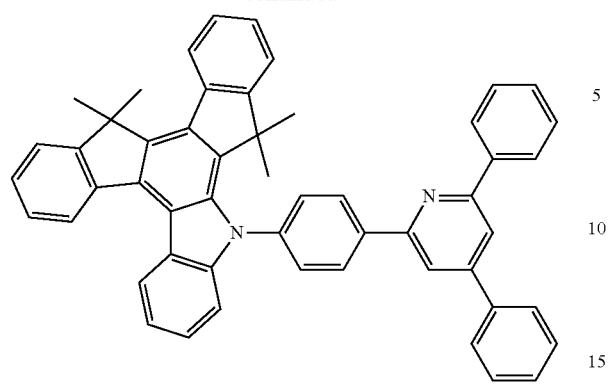
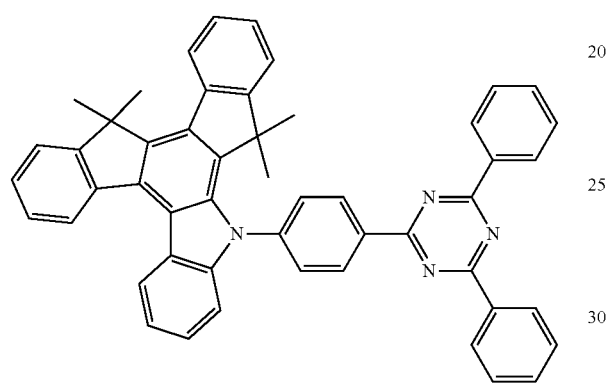
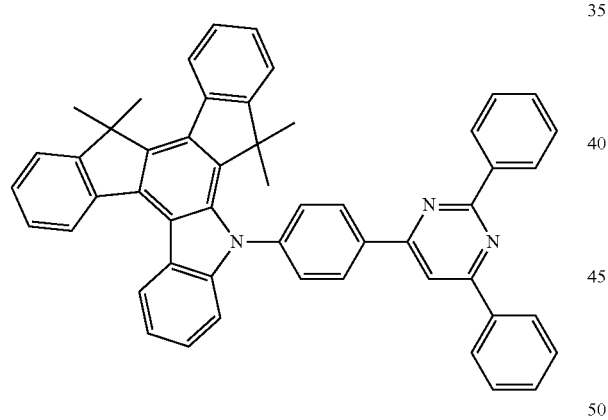
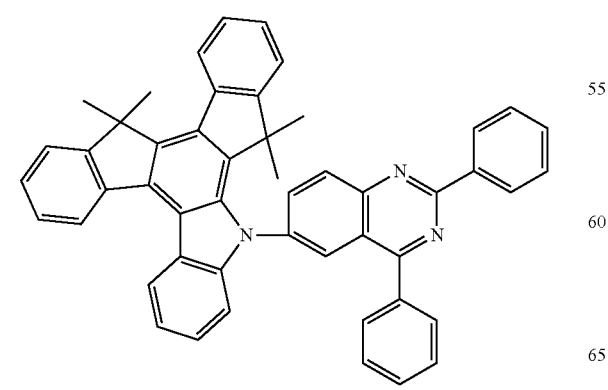
286
-continued
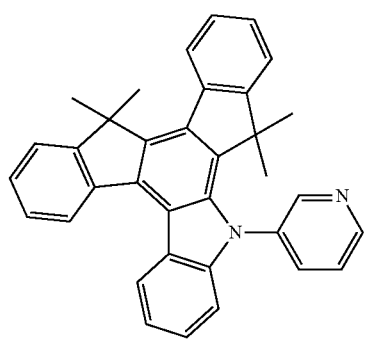
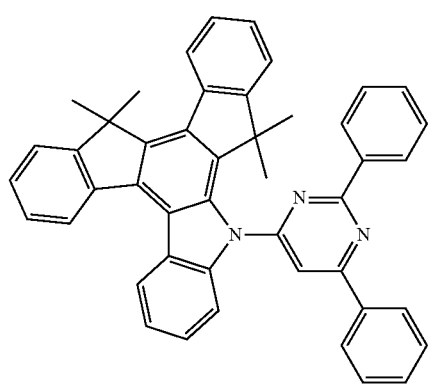
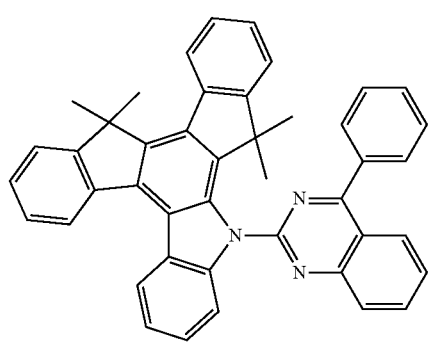
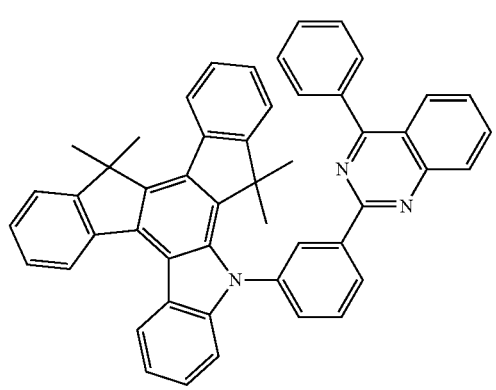

287
-continued
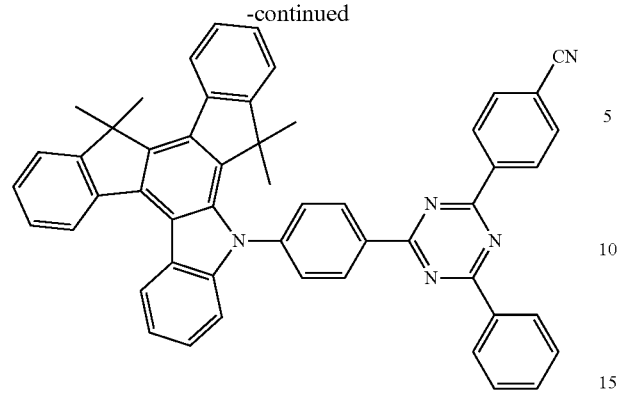
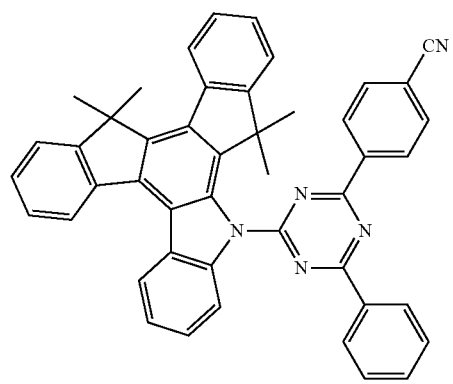
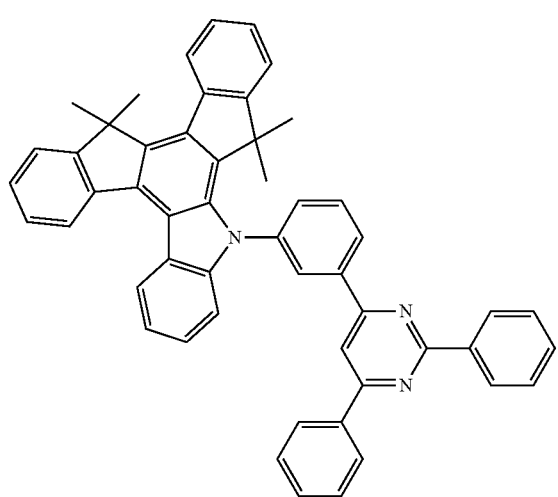
288
-continued
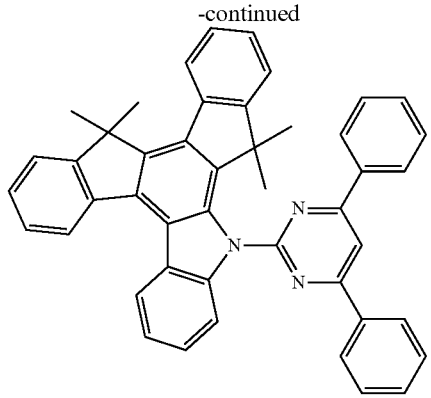
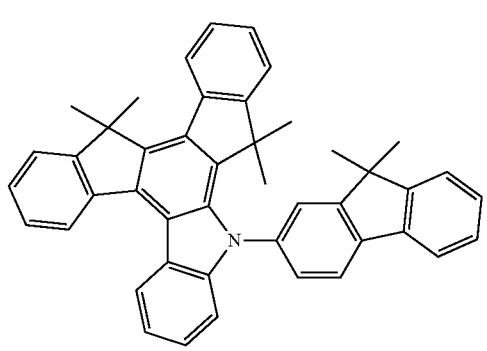
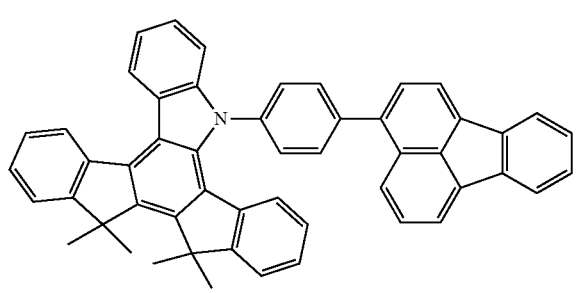
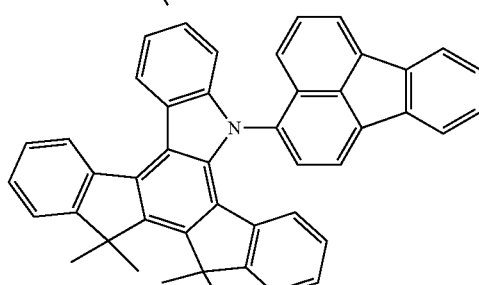
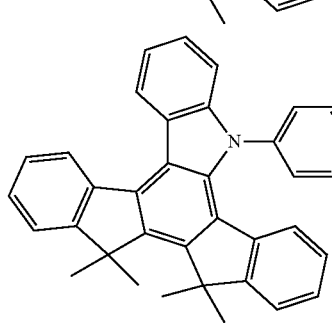

289
-continued
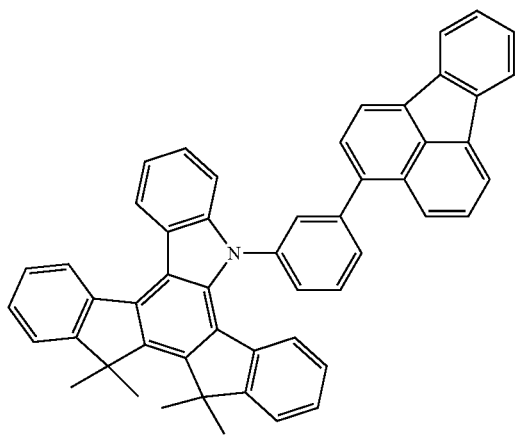
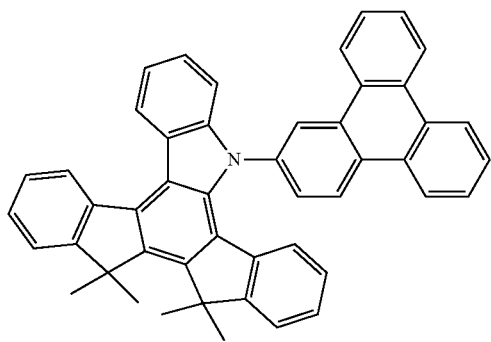
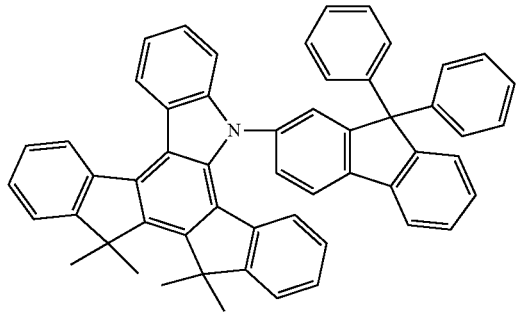
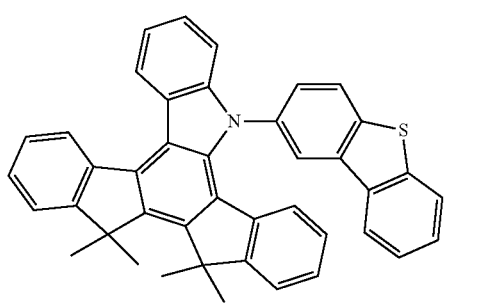
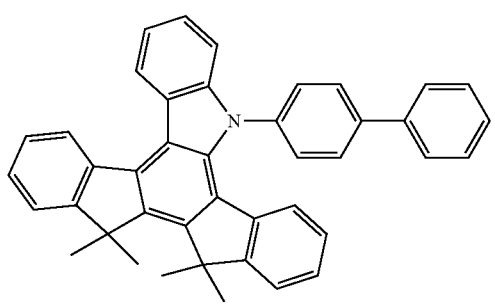
290
-continued
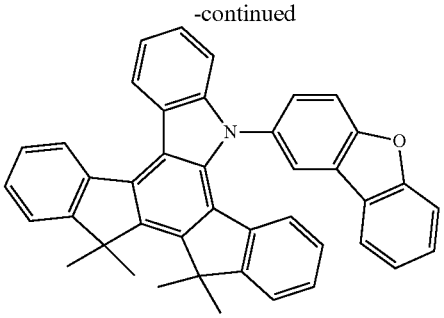
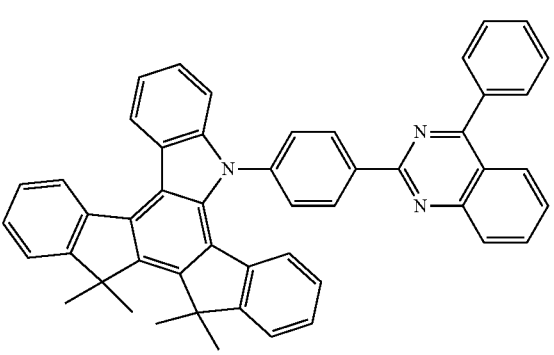
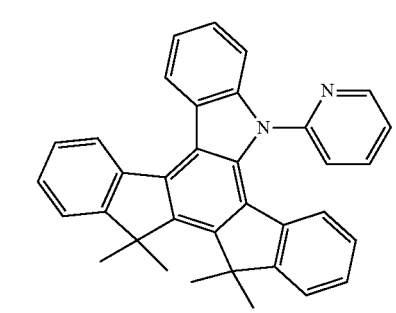
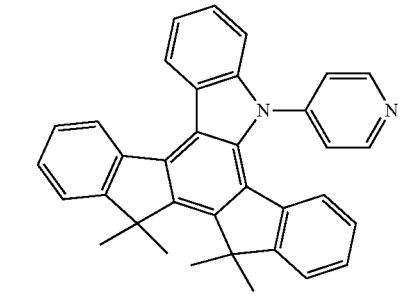
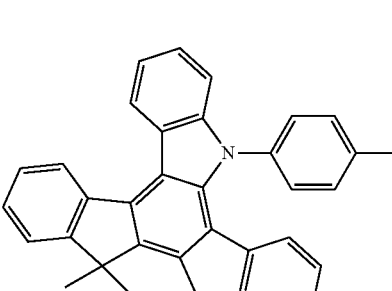

291
-continued
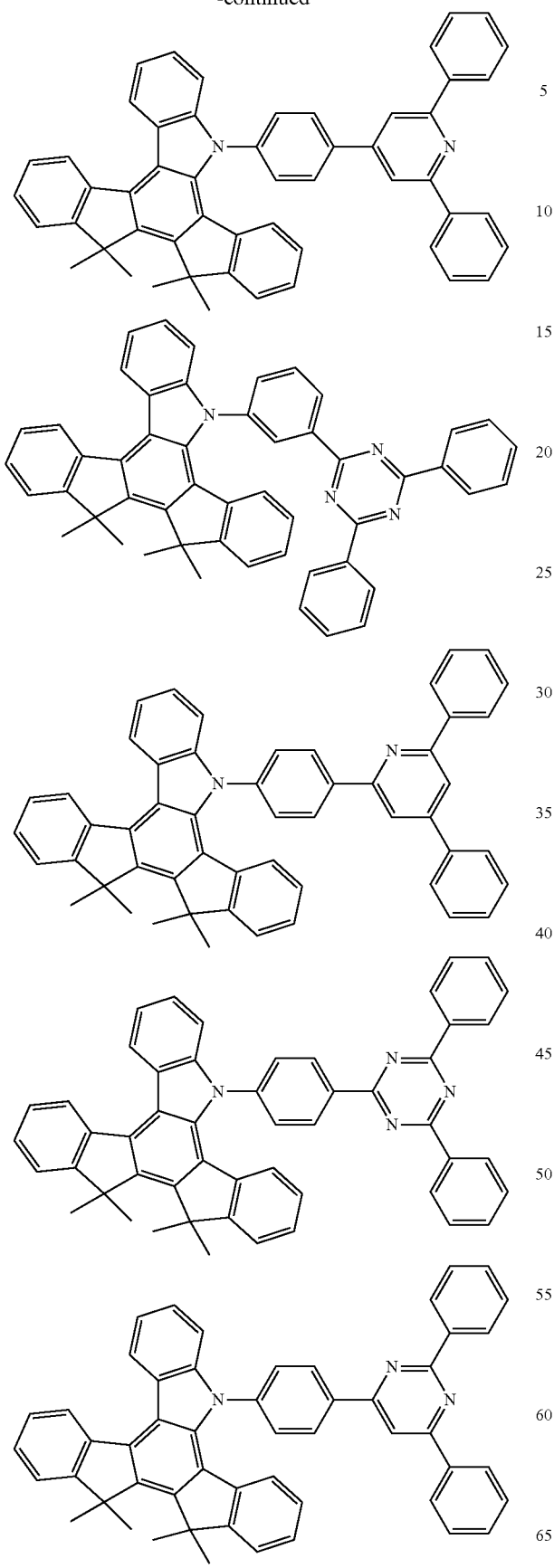
292
-continued
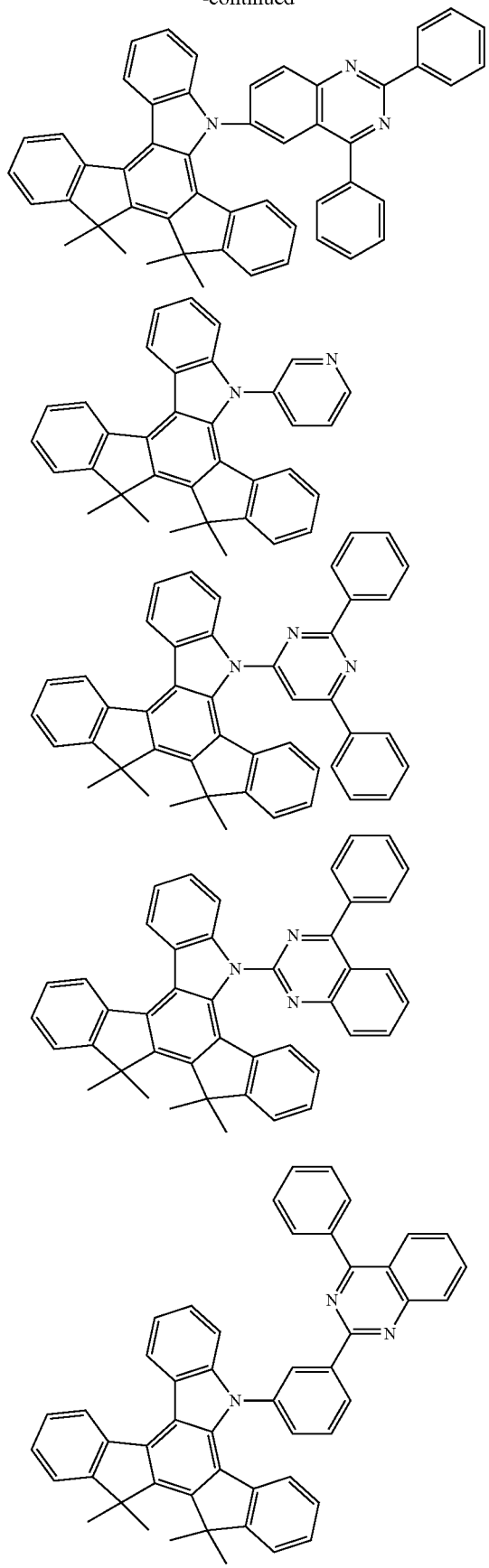

293
-continued
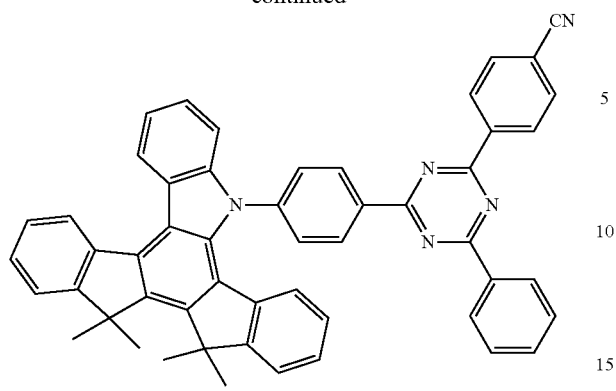
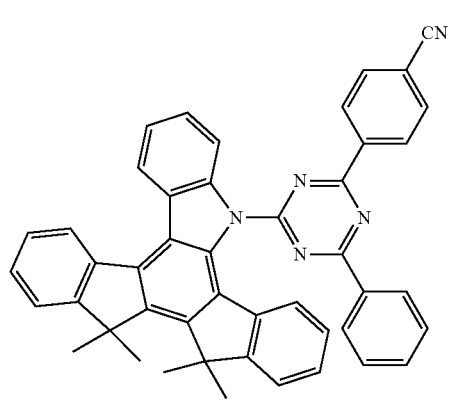
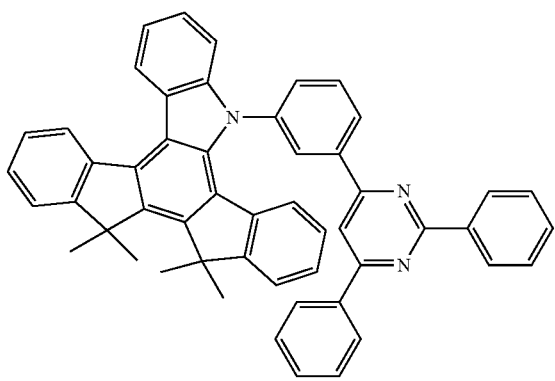
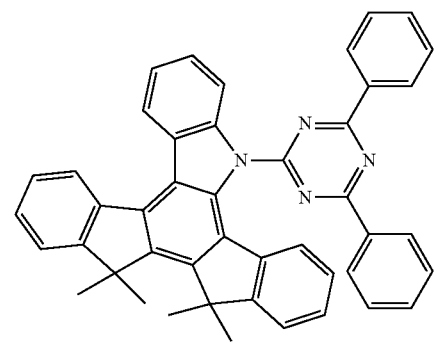
294
-continued
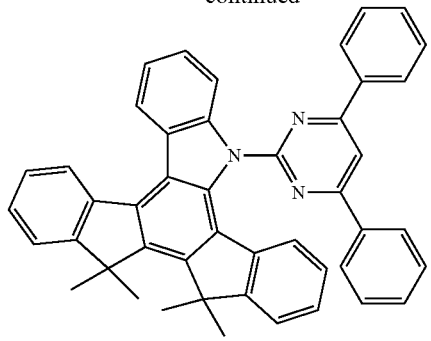
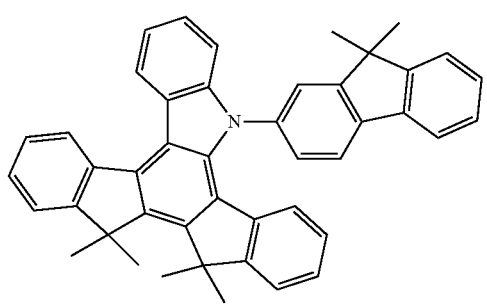
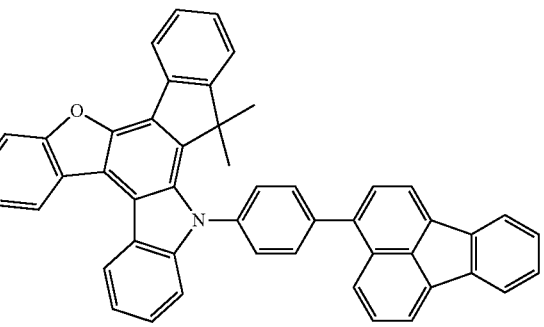
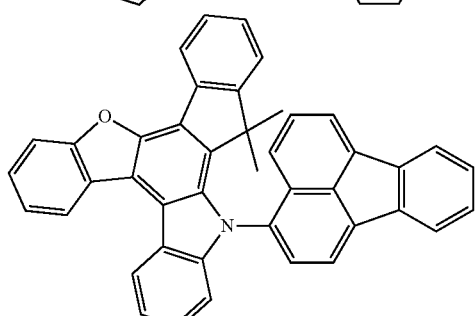
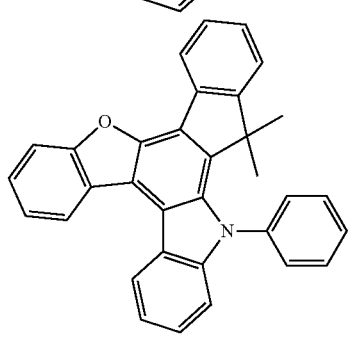

295
-continued
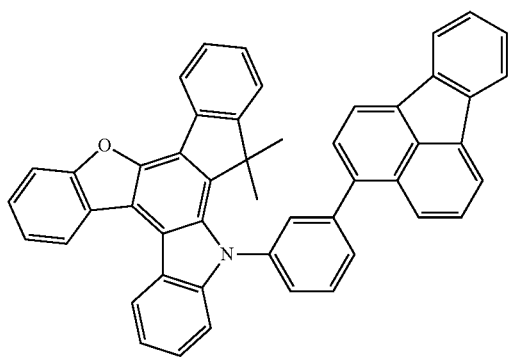
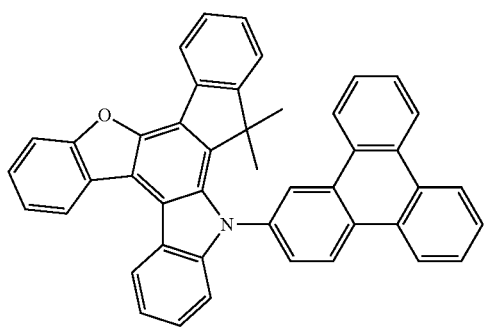
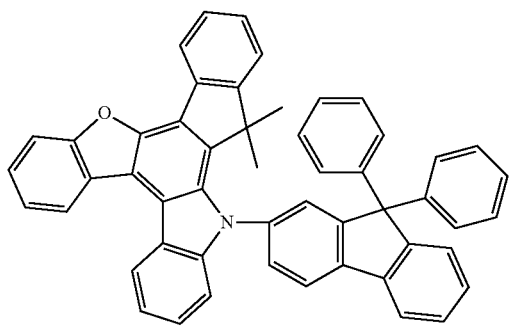
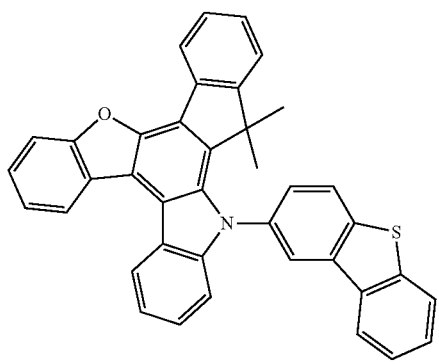
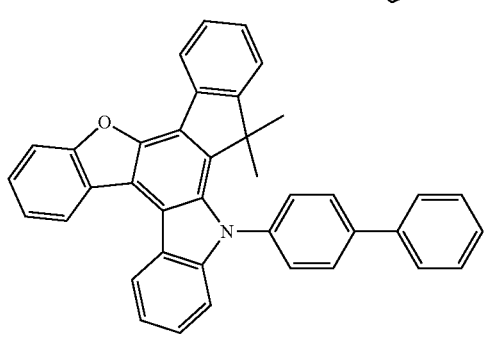
296
-continued
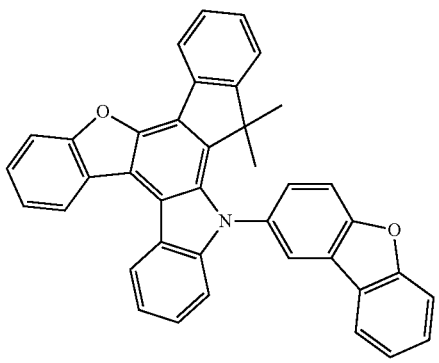
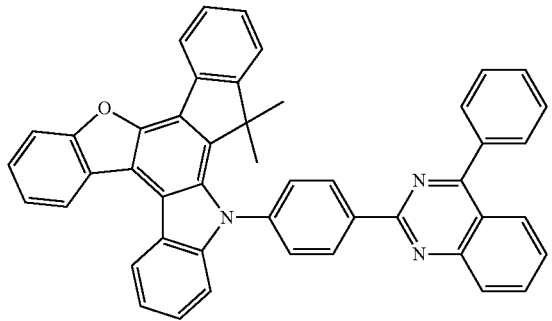
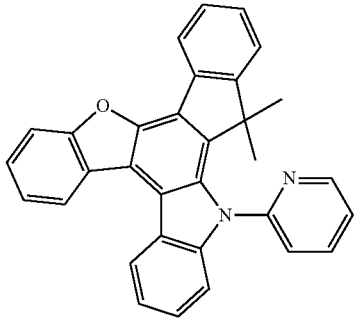
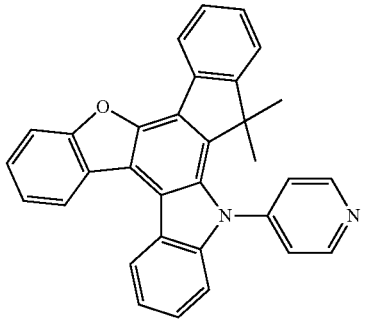
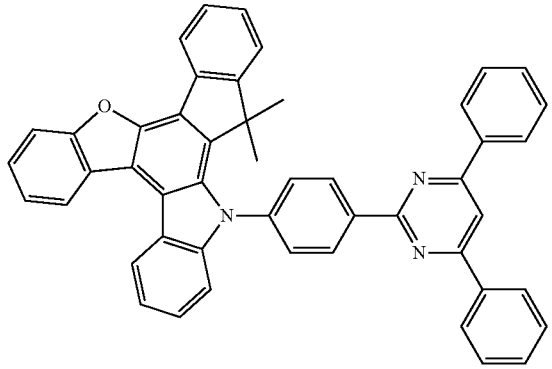

297
-continued
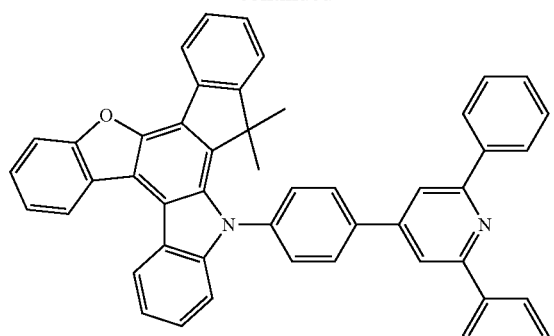
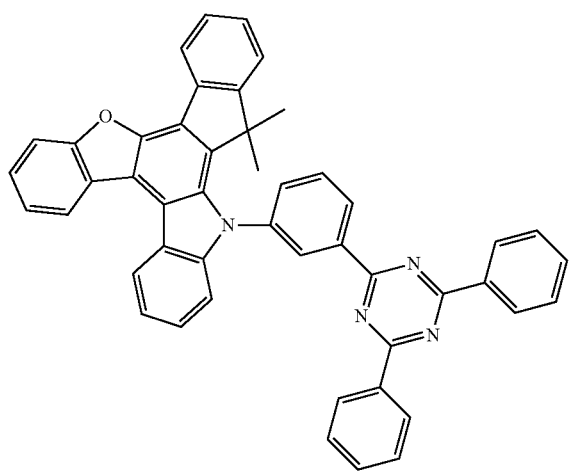
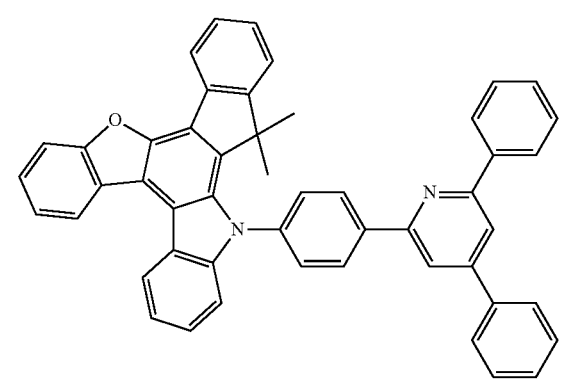
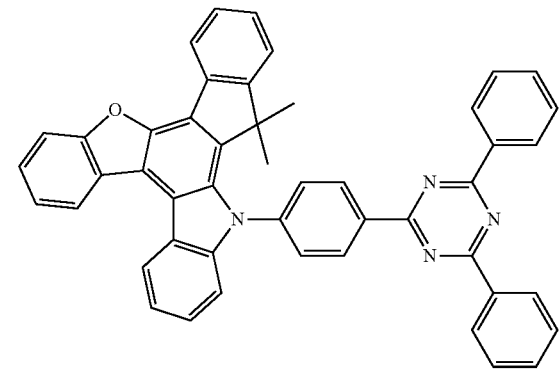
298
-continued
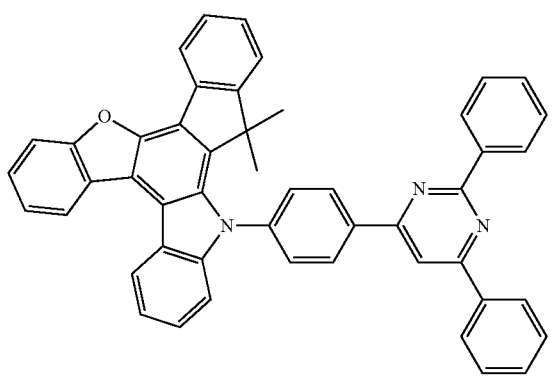
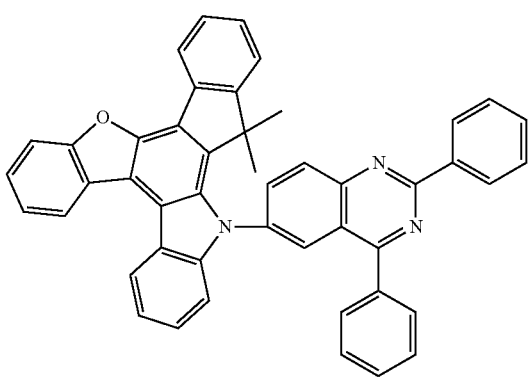
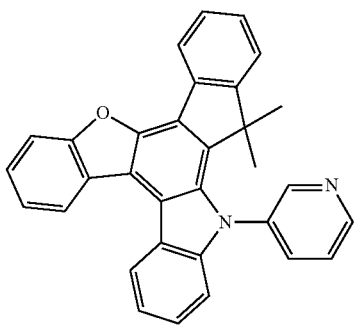
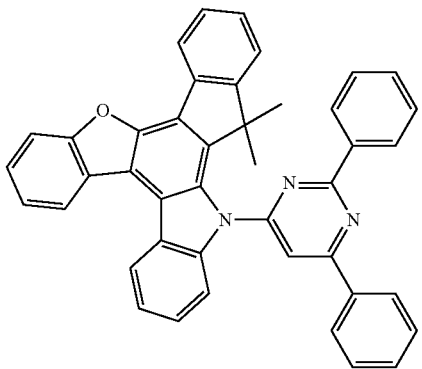

299
-continued
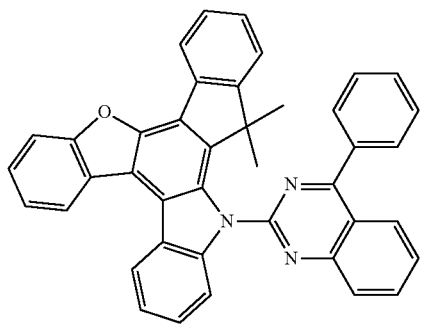
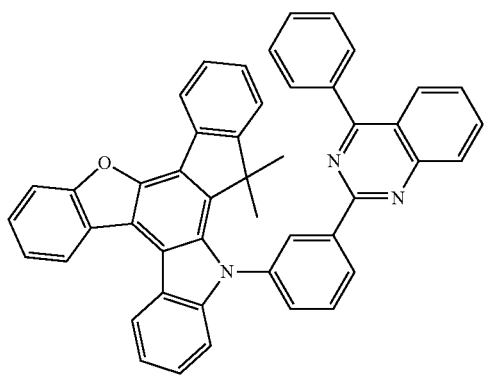
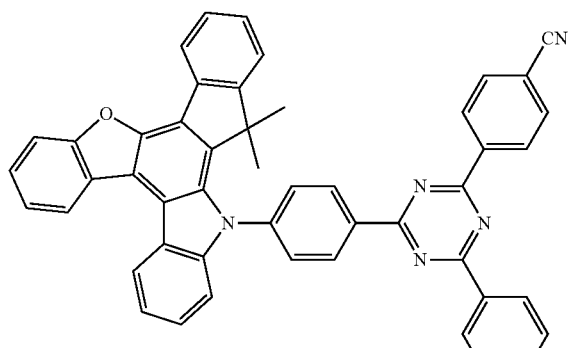
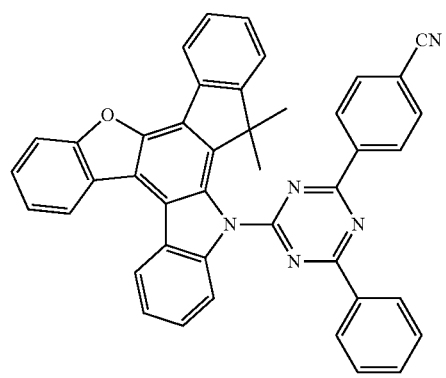
300
-continued
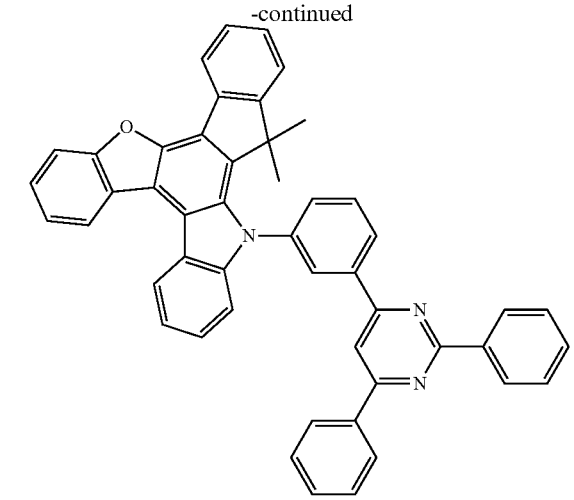
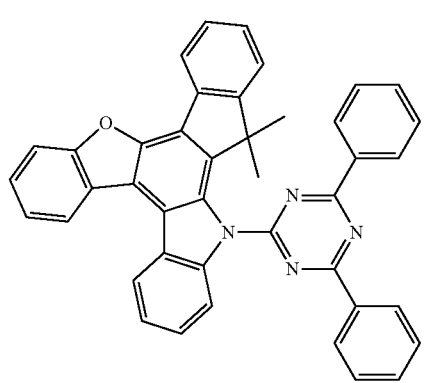
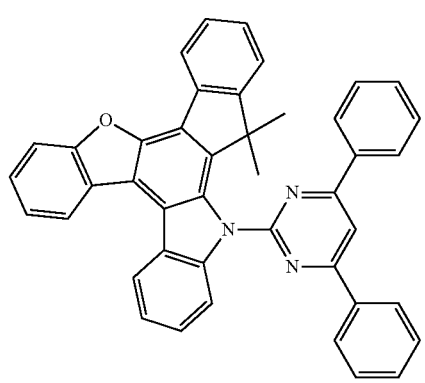
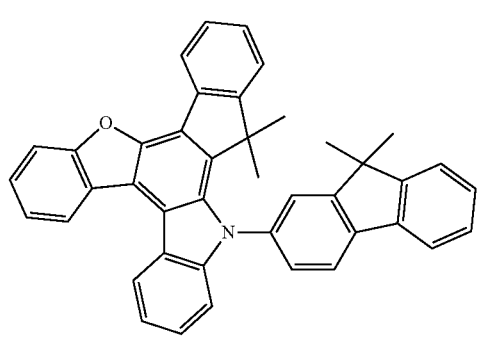

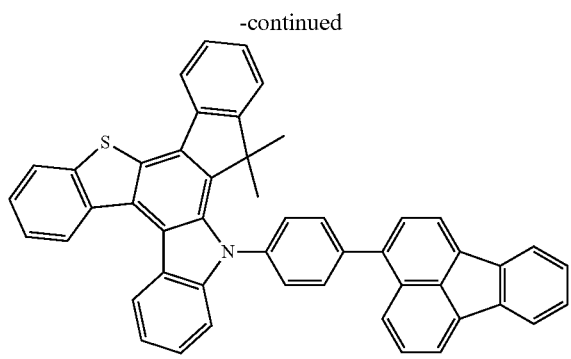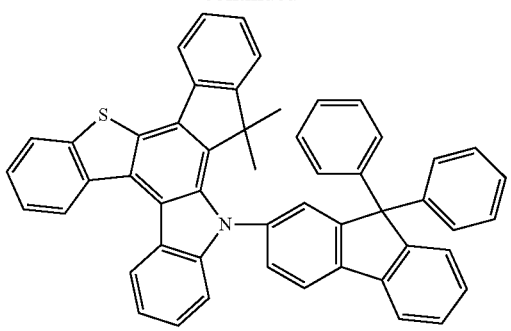

303
-continued
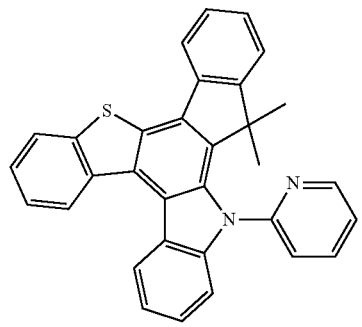
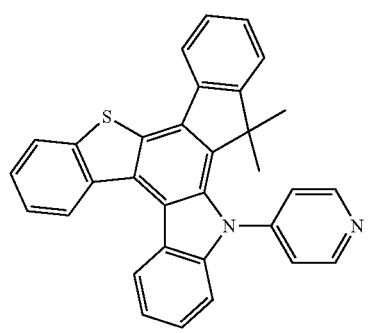
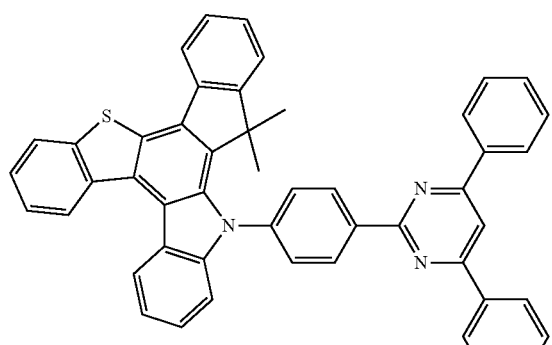
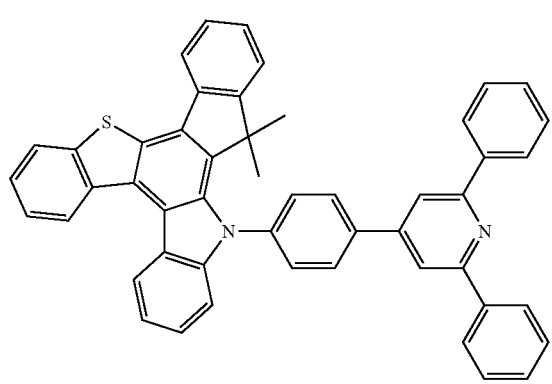
304
-continued
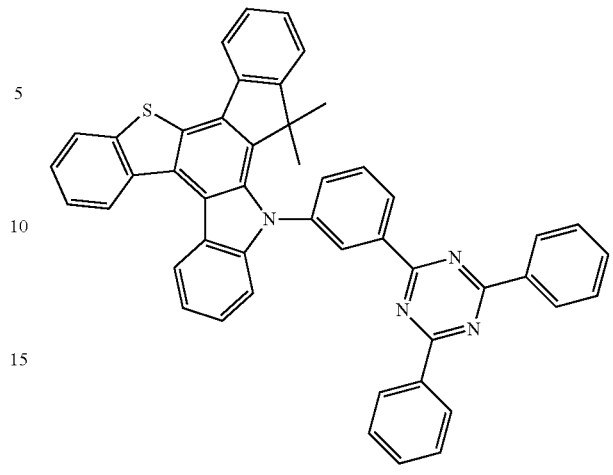
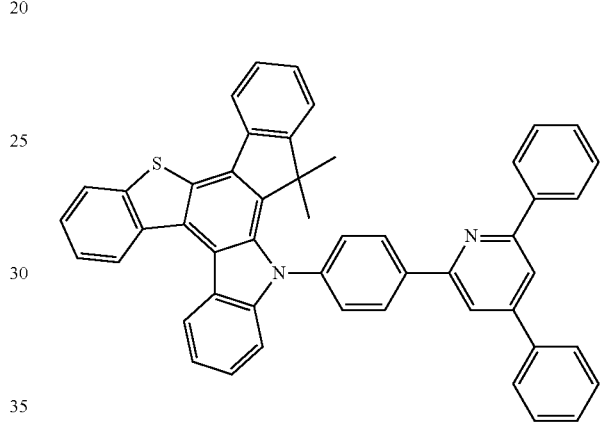
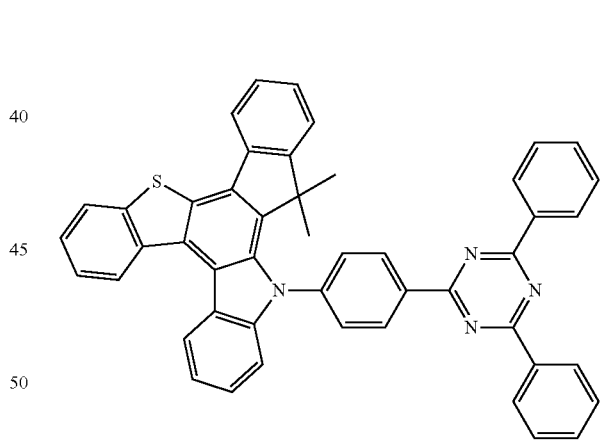
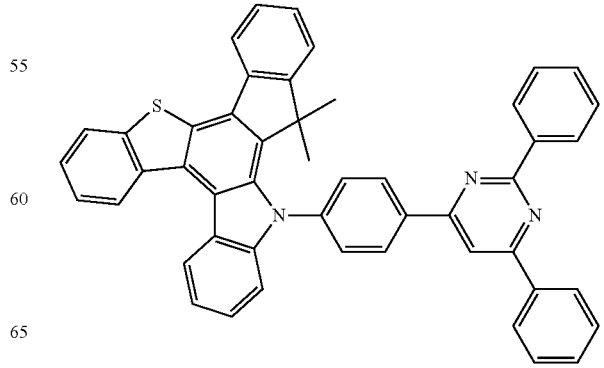

305
-continued
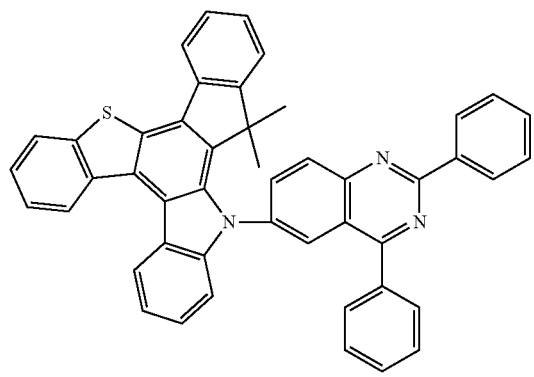
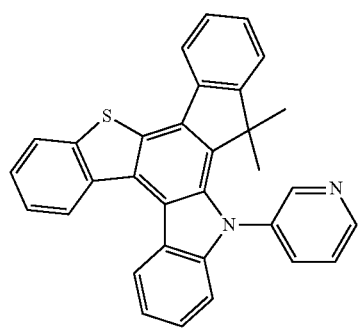
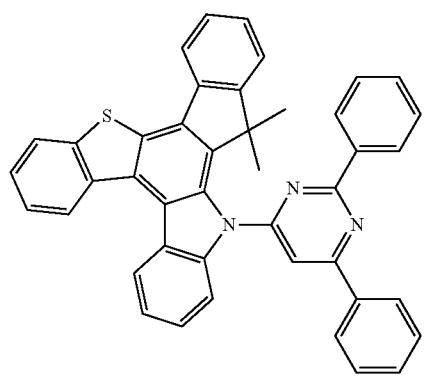
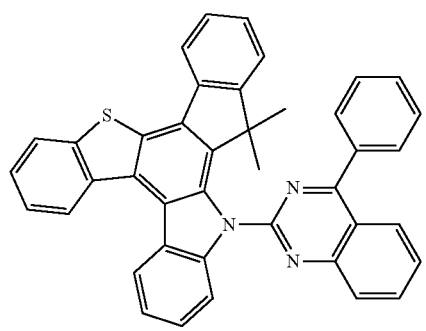
306
-continued
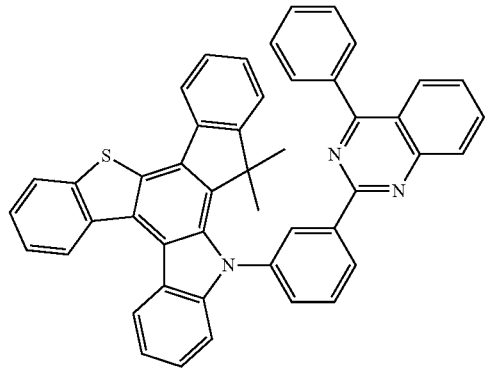
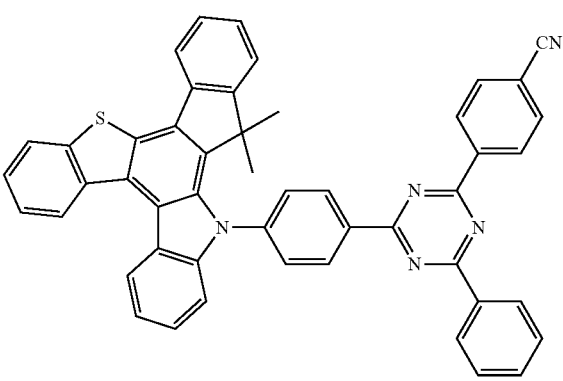
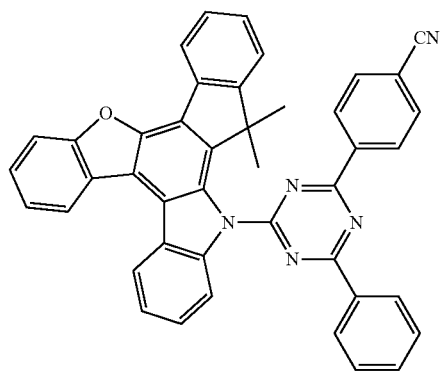
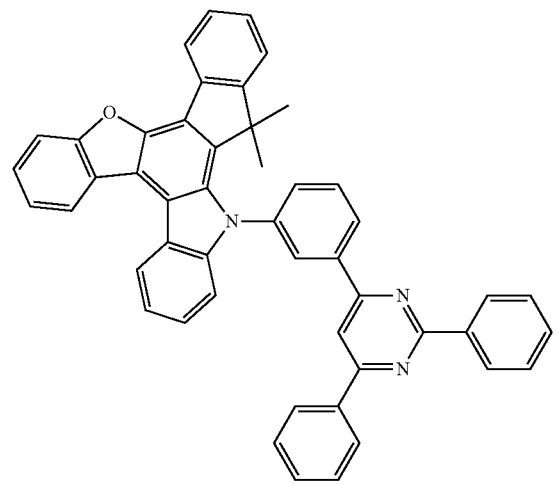

307
-continued
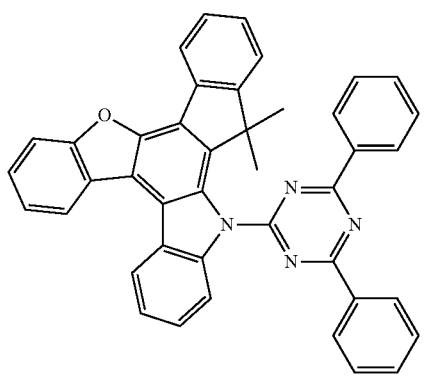
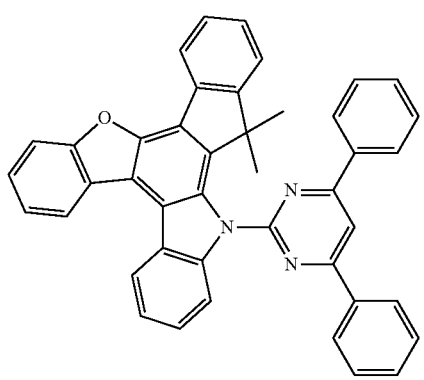
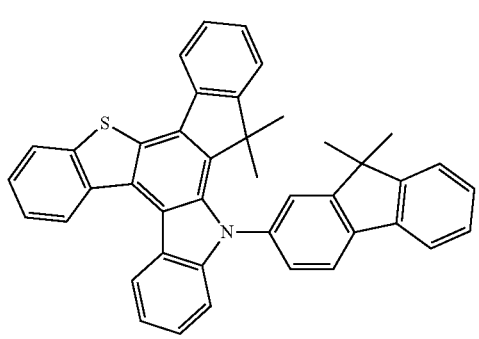
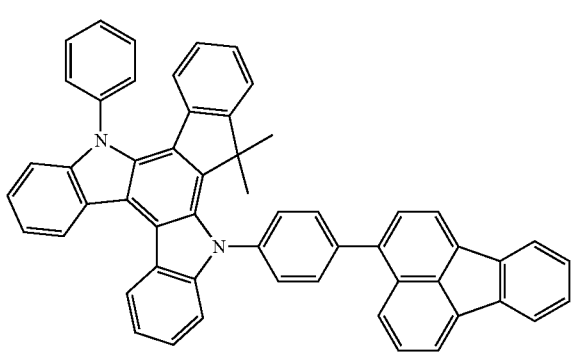
308
-continued
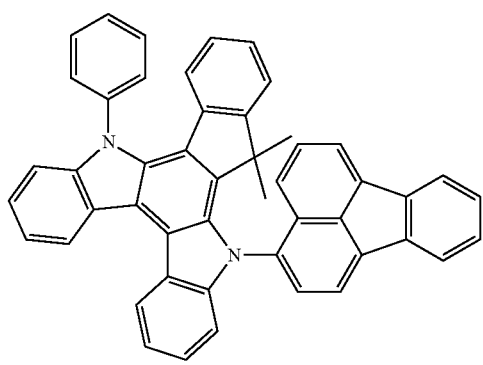
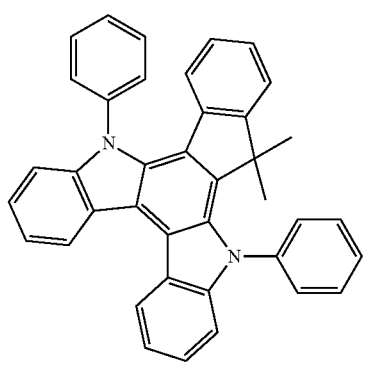
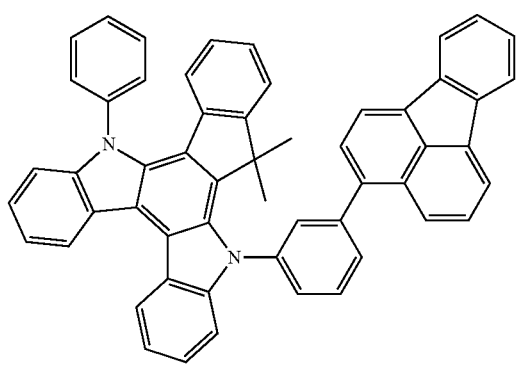
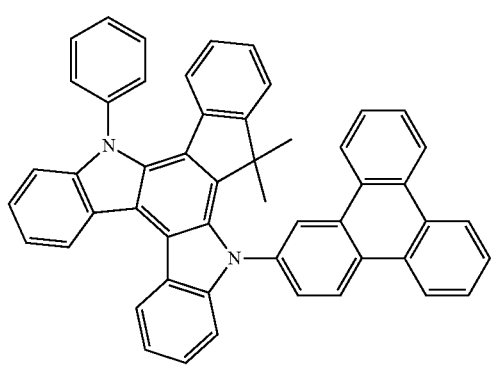

309
-continued
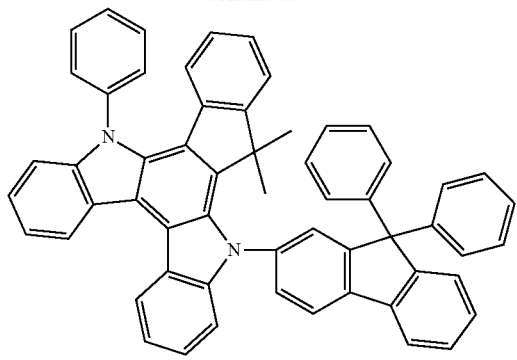
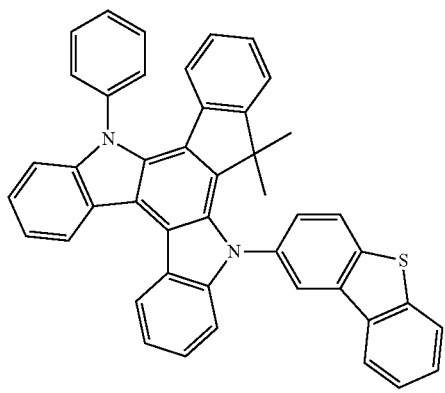
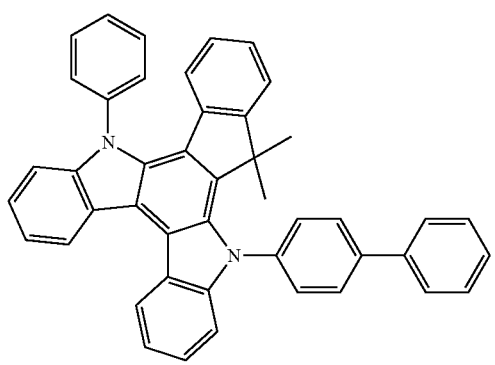
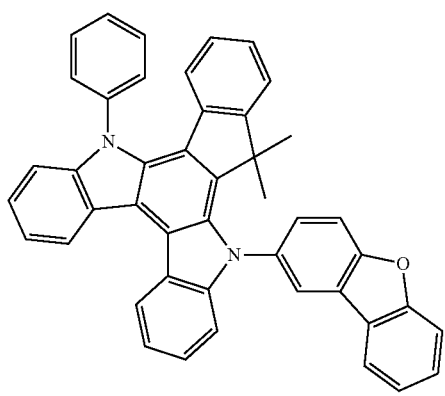
310
-continued
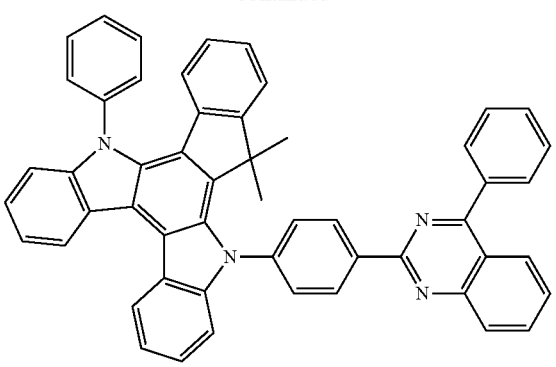
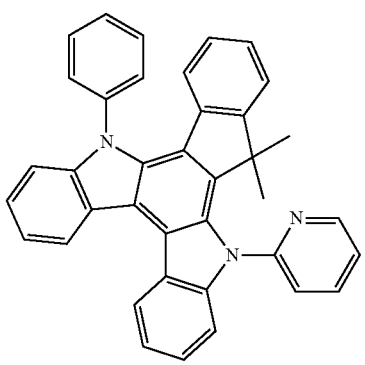
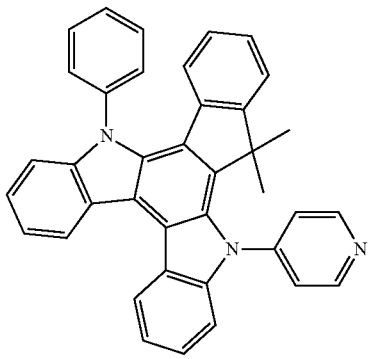
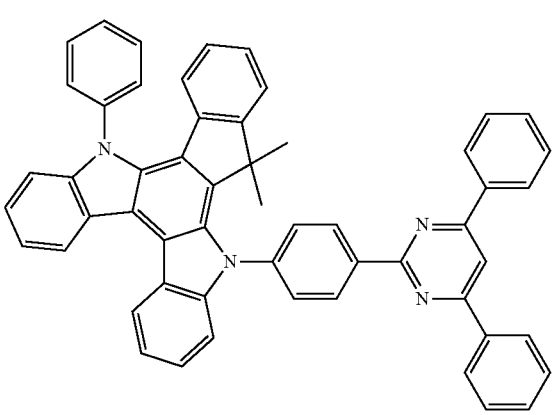

311
-continued
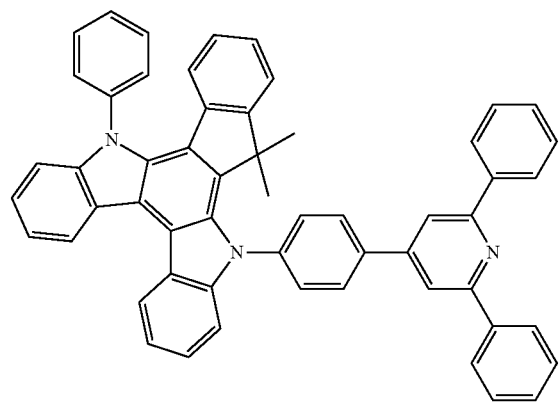
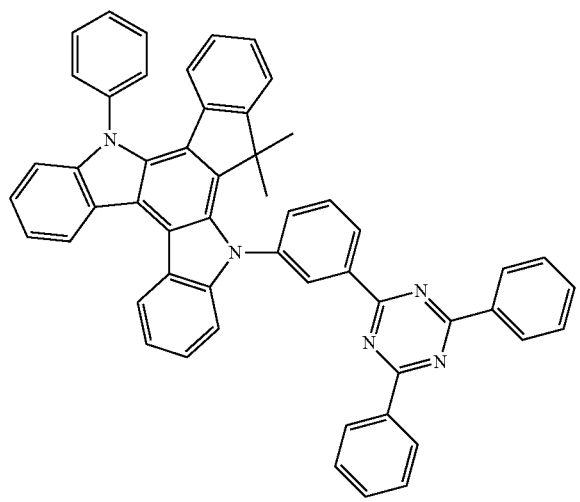
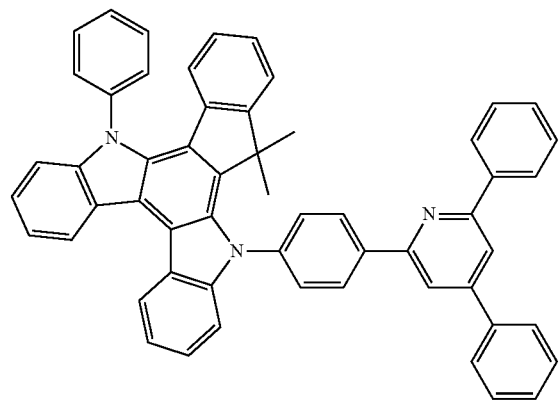
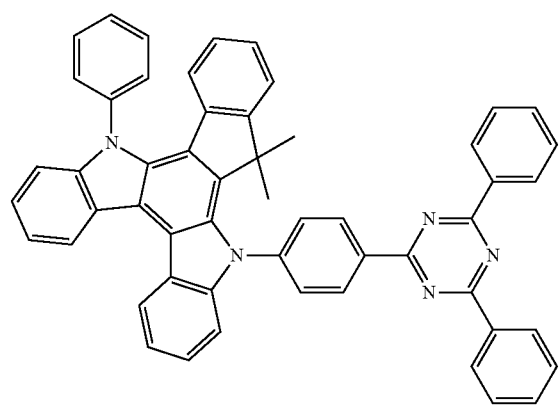
312
-continued
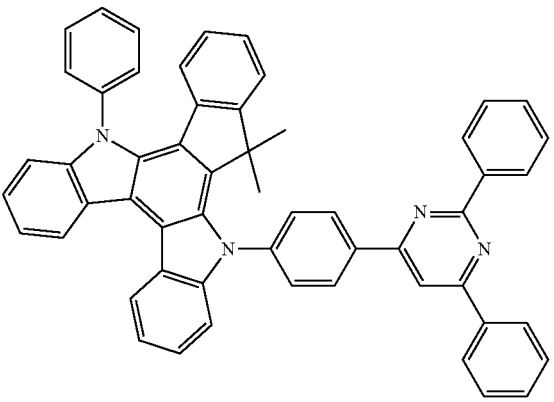
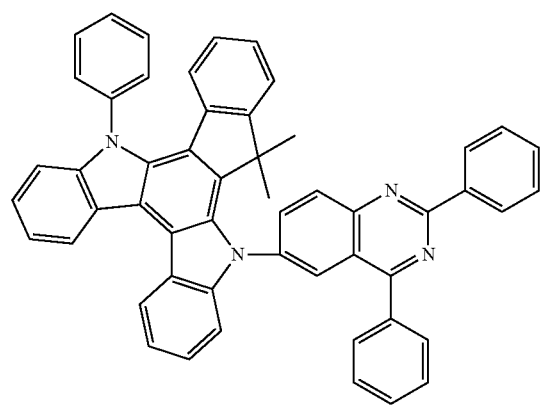
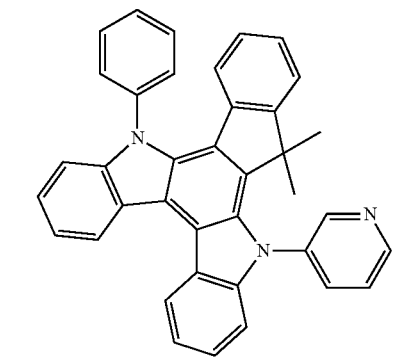
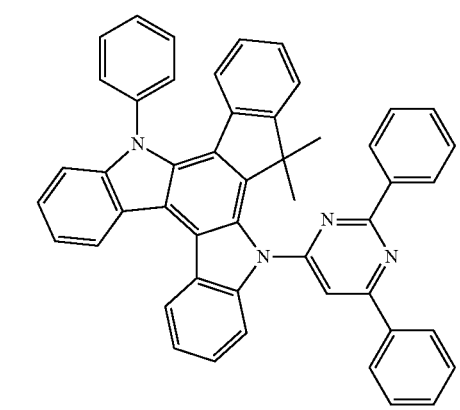

313
-continued
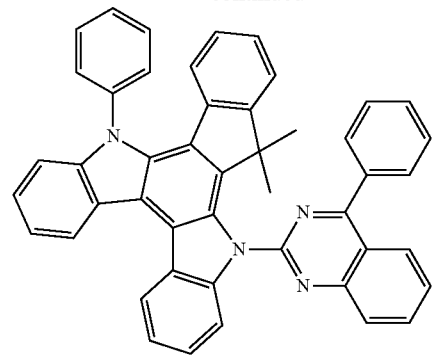
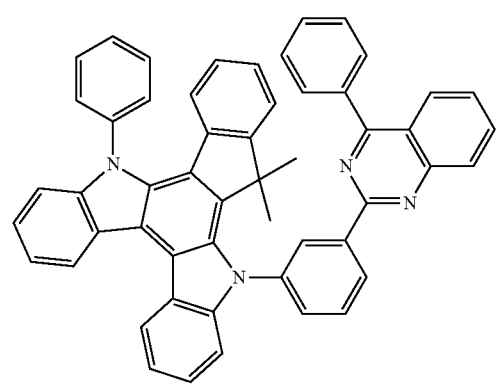
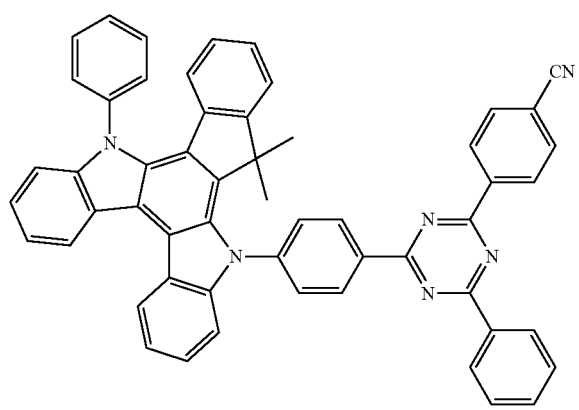
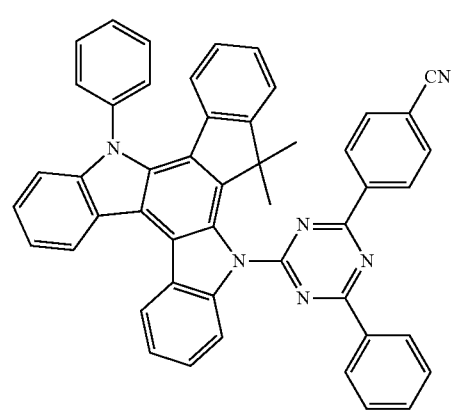
314
-continued
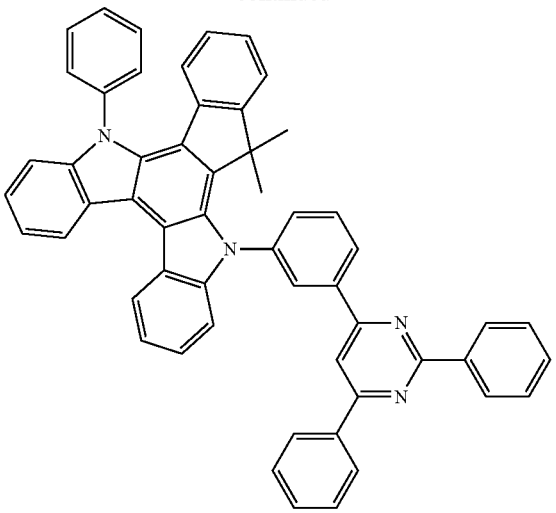
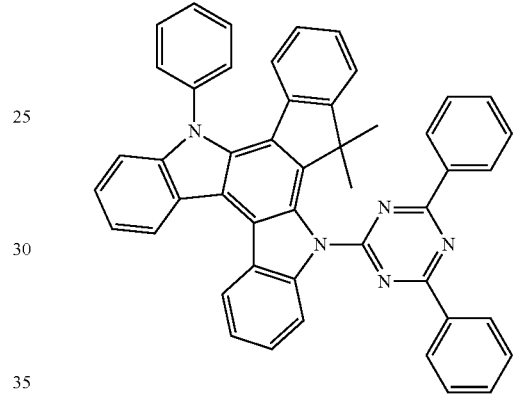
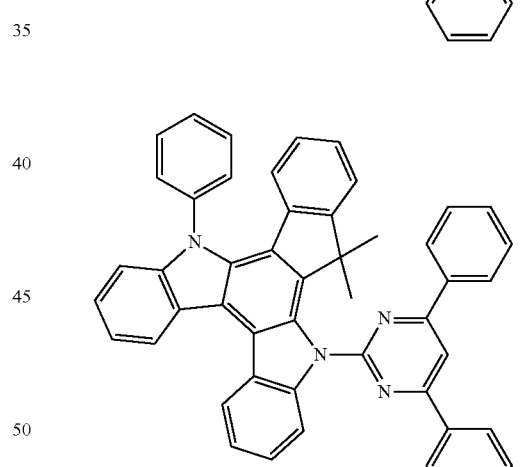
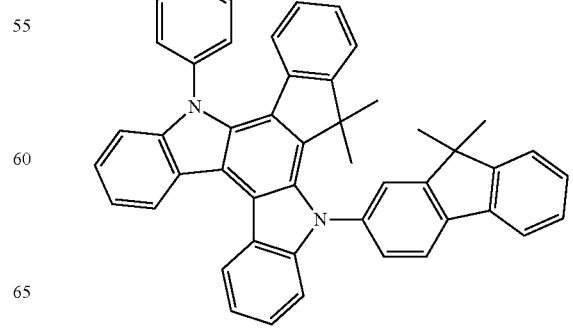

315
-continued
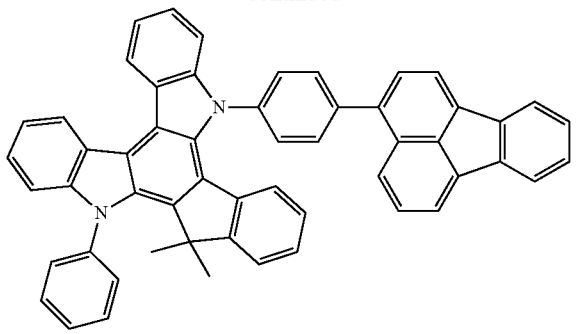
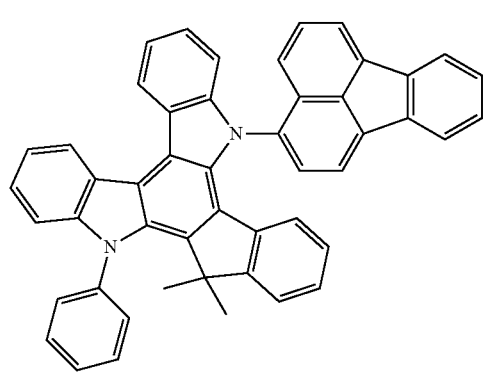
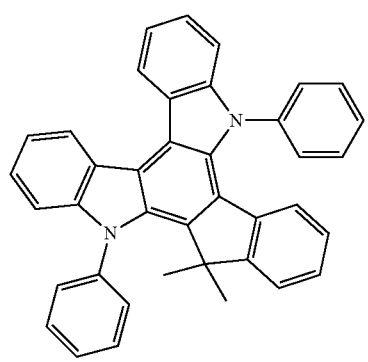
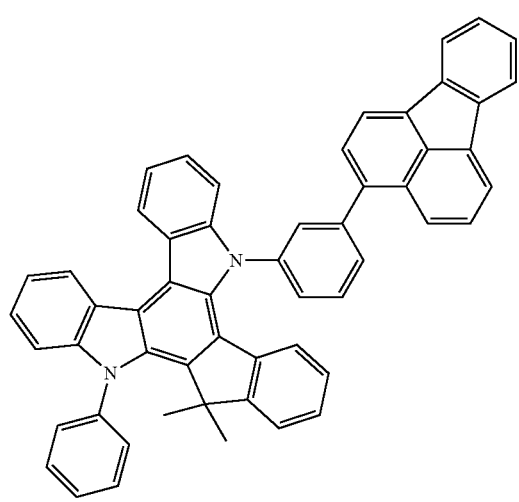
316
-continued
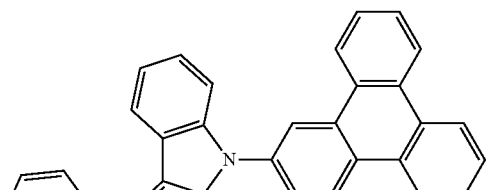
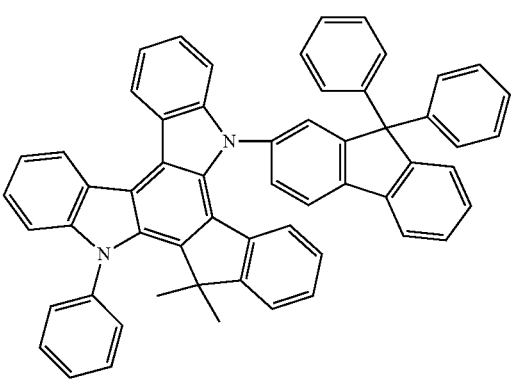
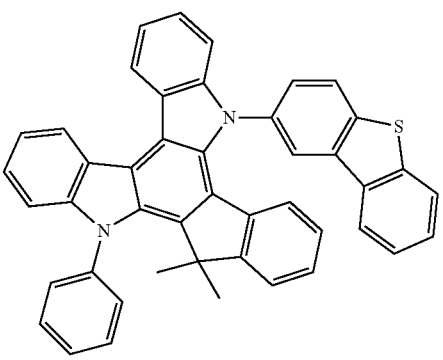
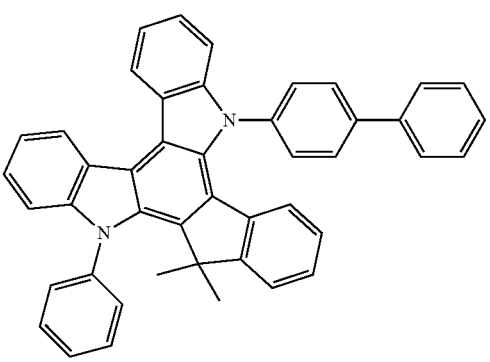

317
-continued
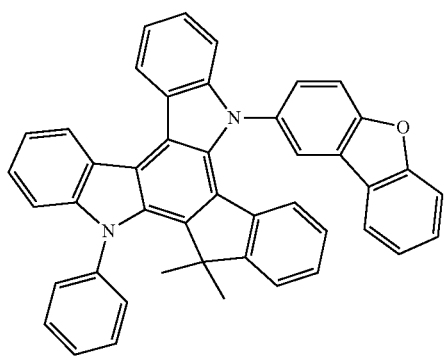
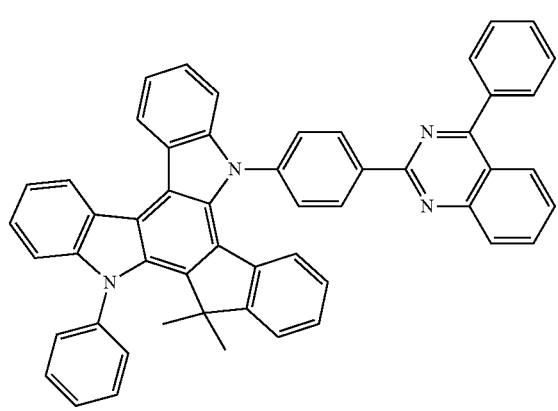
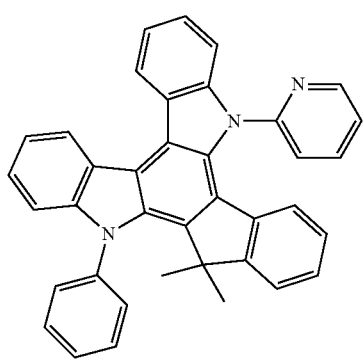
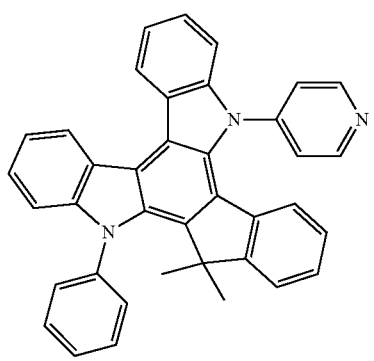
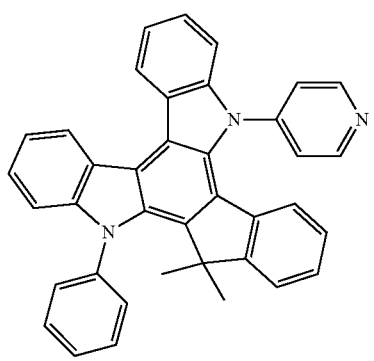
318
-continued
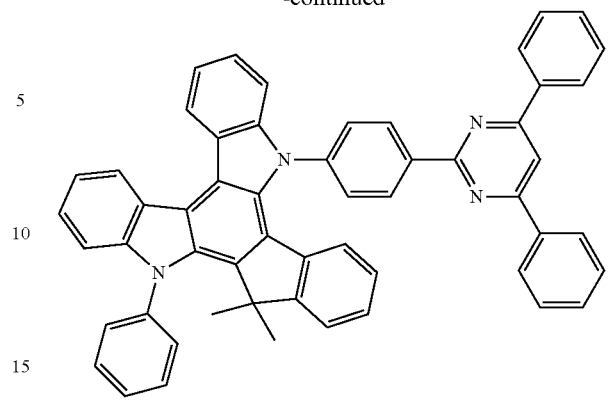
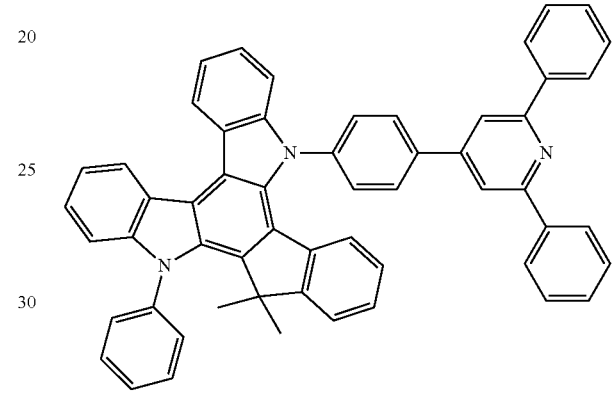
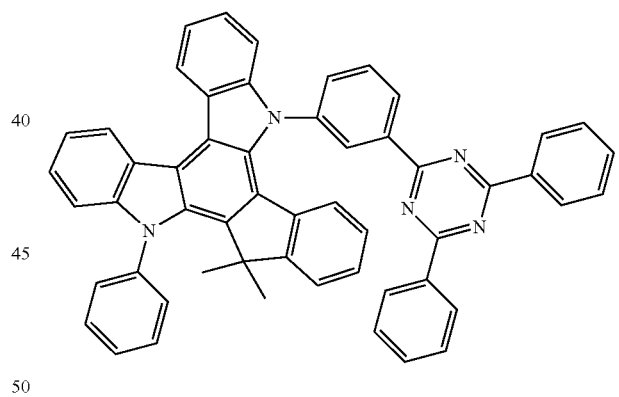
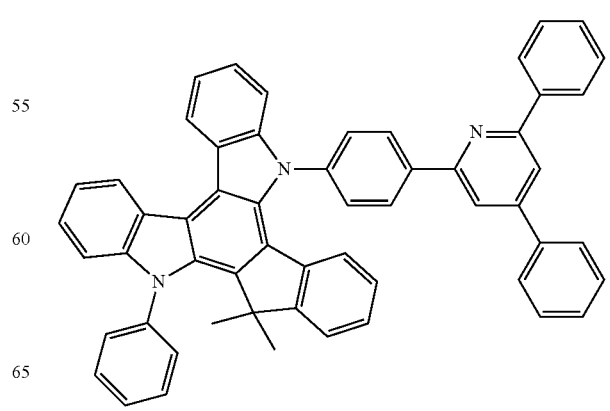
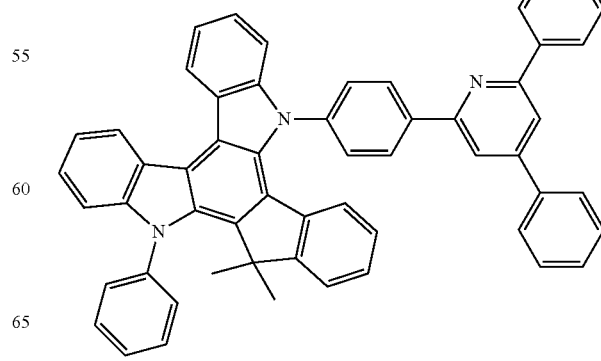

319
-continued
320
-continued
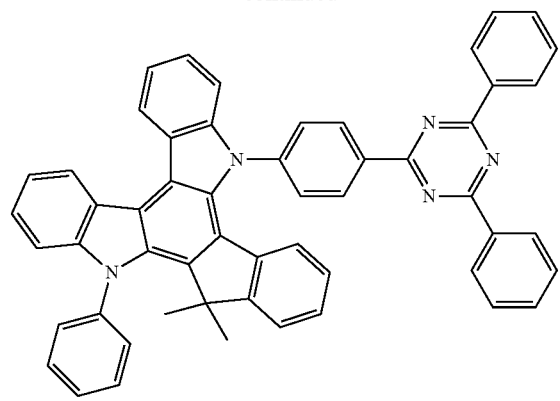
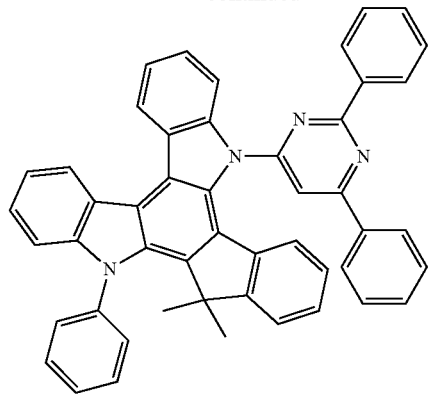
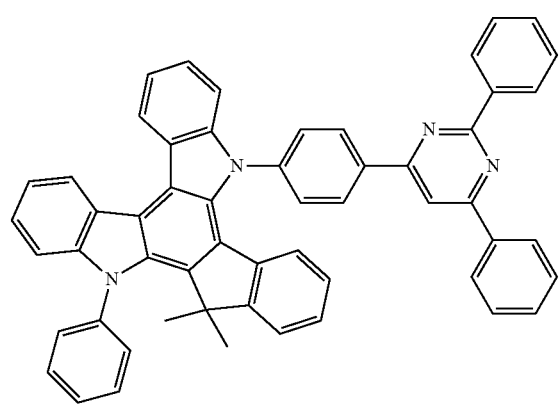
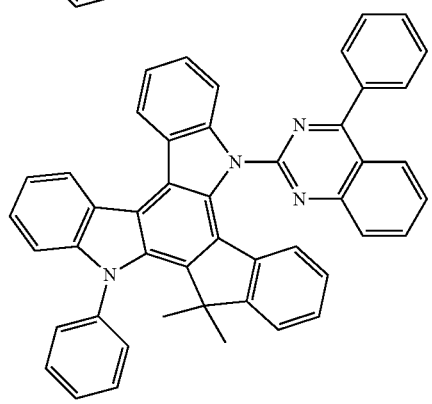
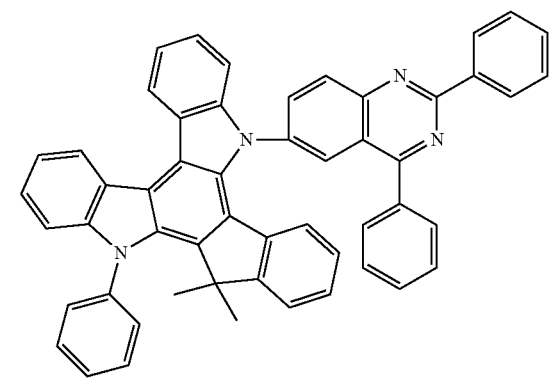
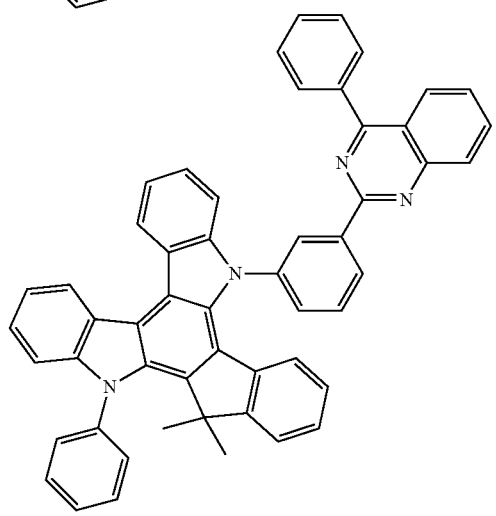
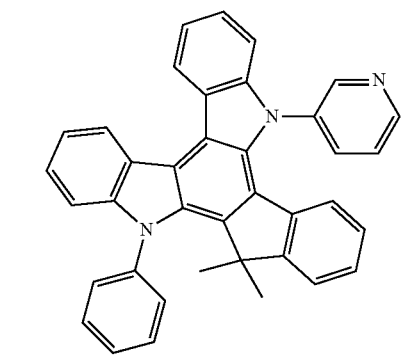
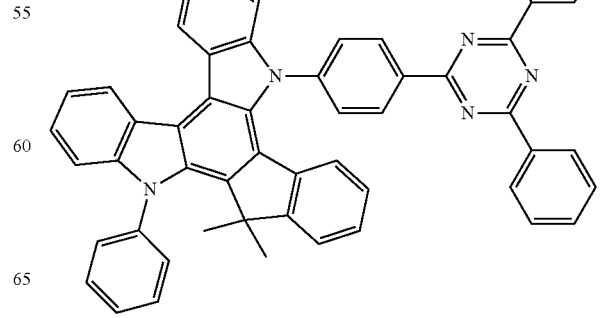

321
-continued
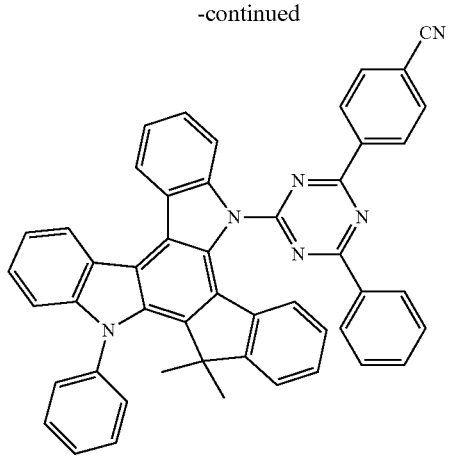
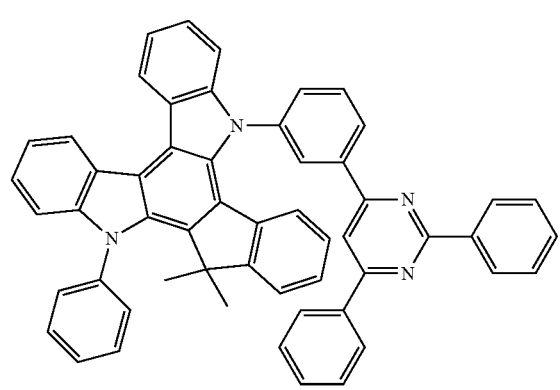
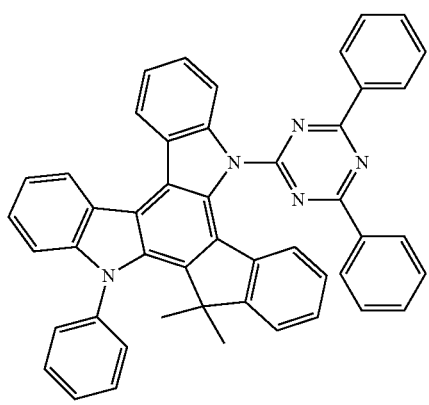
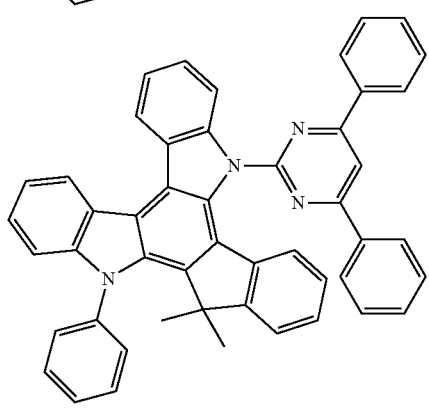
322
-continued
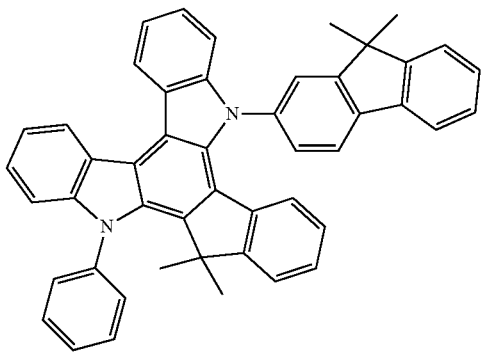
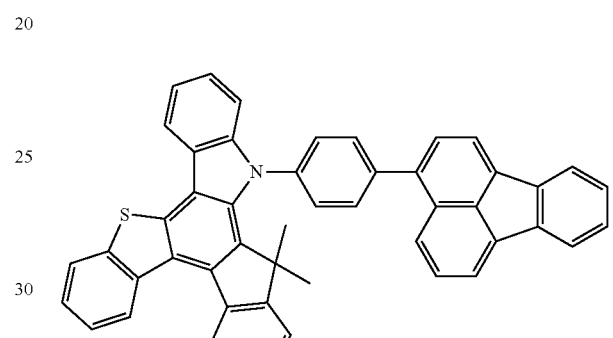
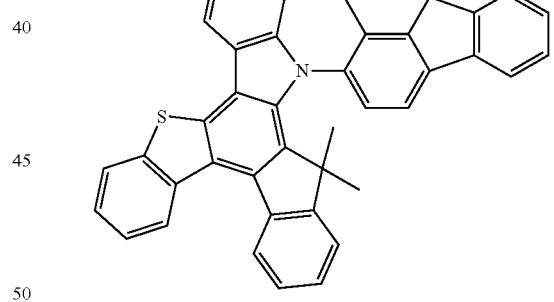
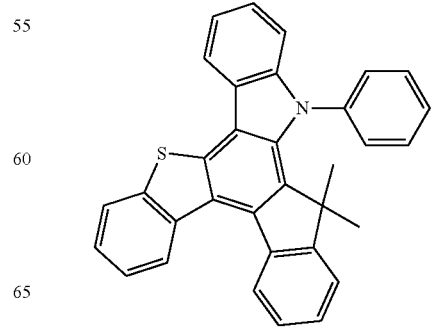

323
-continued
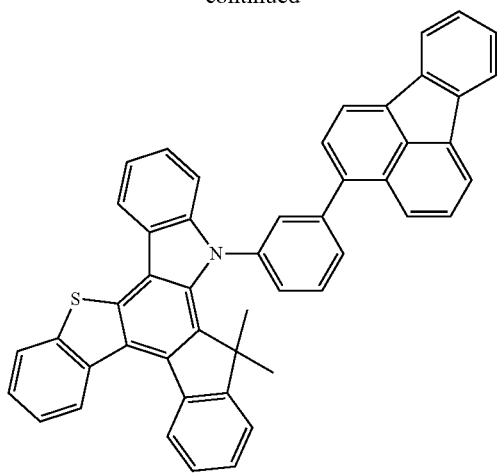
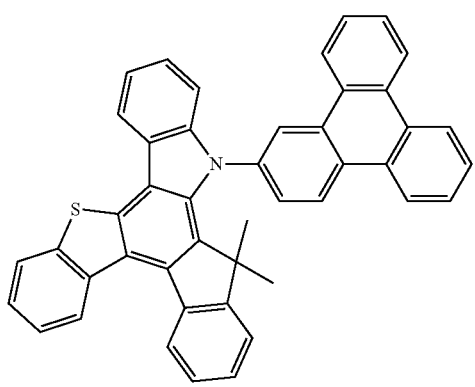
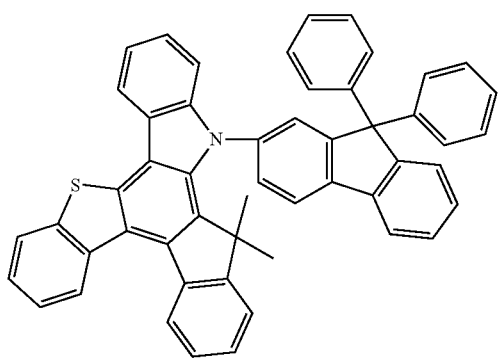
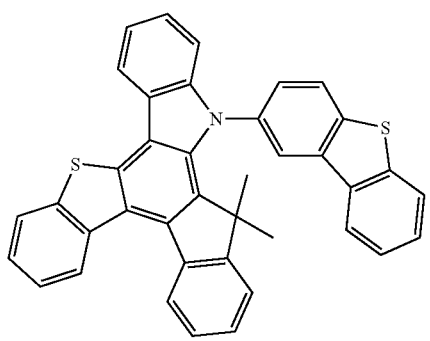
324
-continued
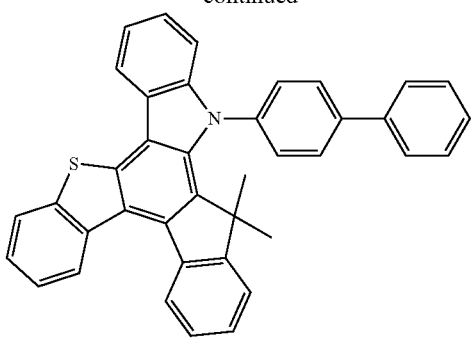
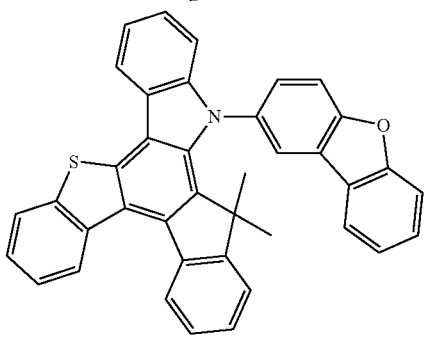
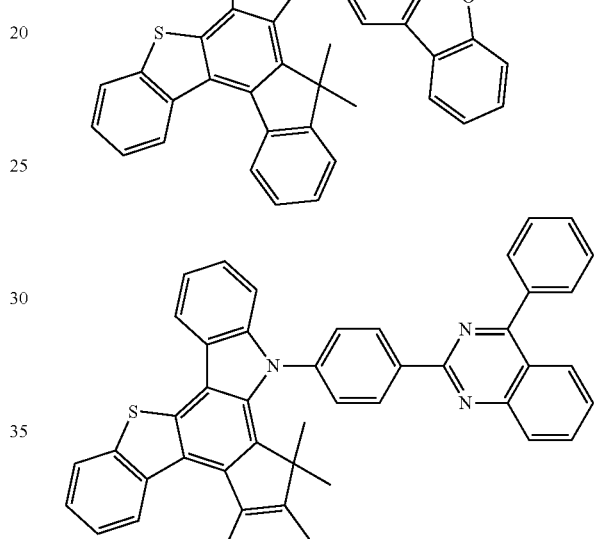
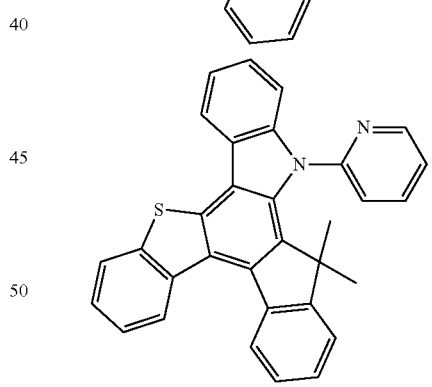
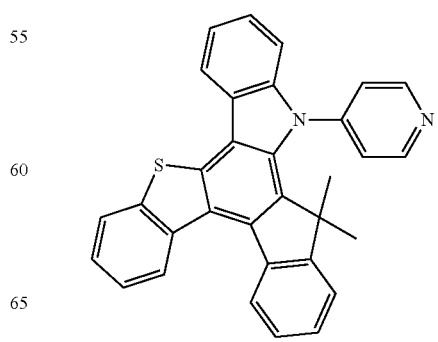

325
-continued
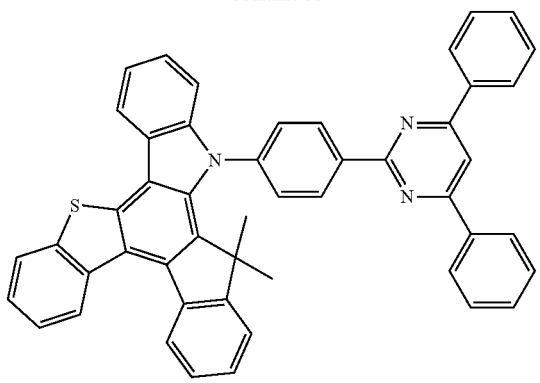
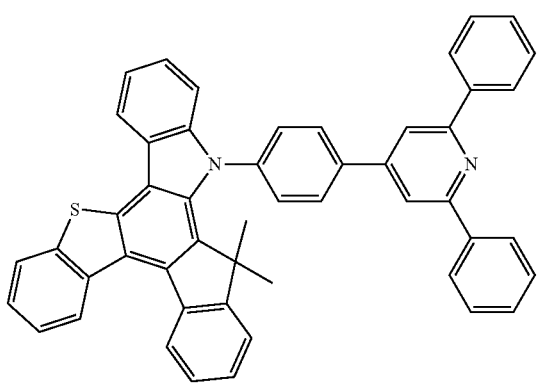
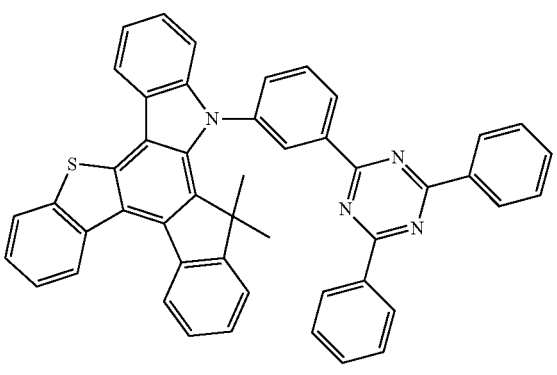
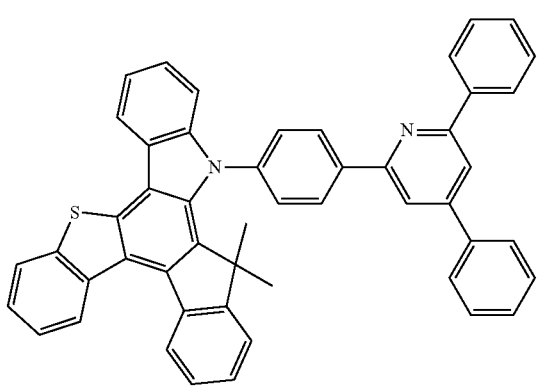
326
-continued
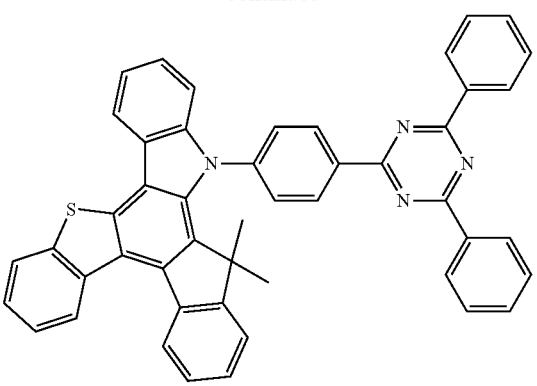
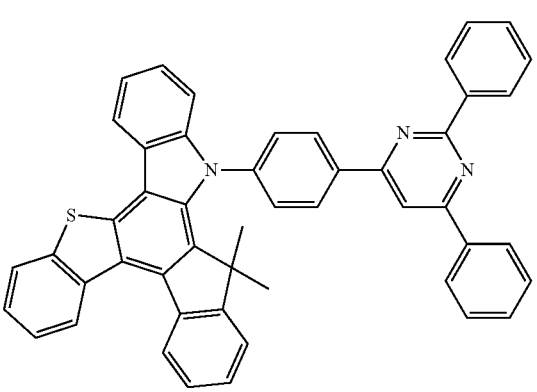
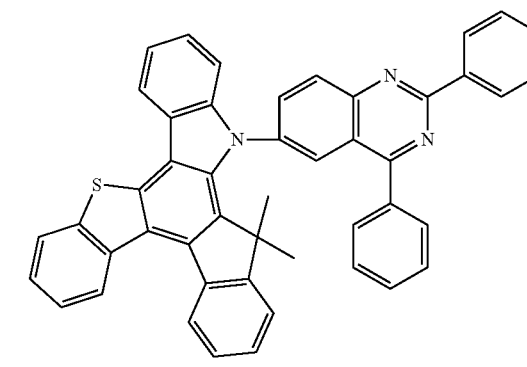
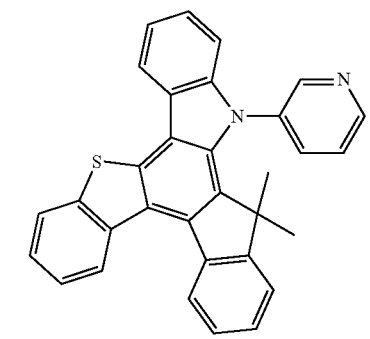

| 327 -continued | 328 -continued |
|---|---|
| 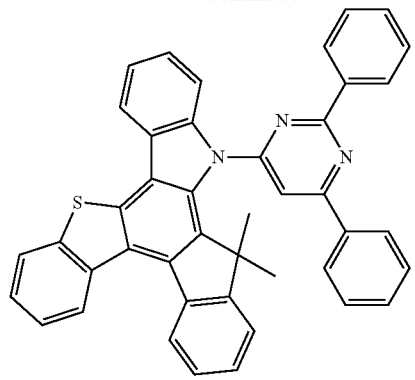 | 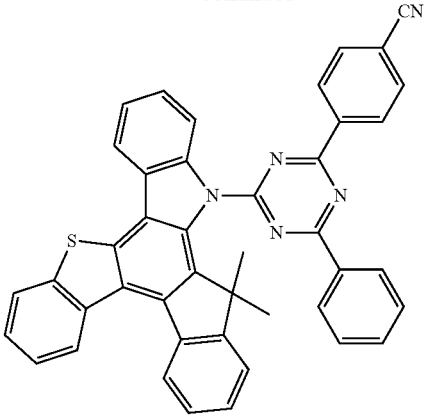 |
| 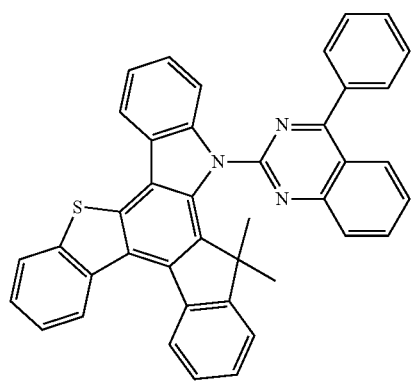 | 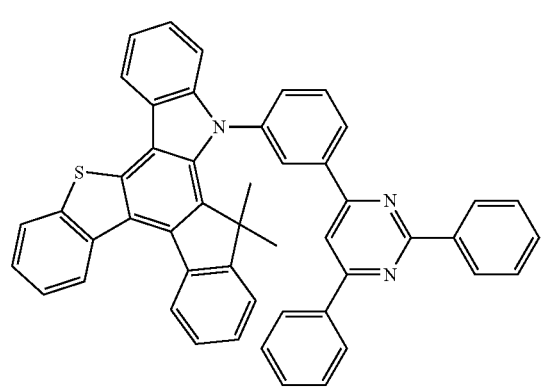 |
| 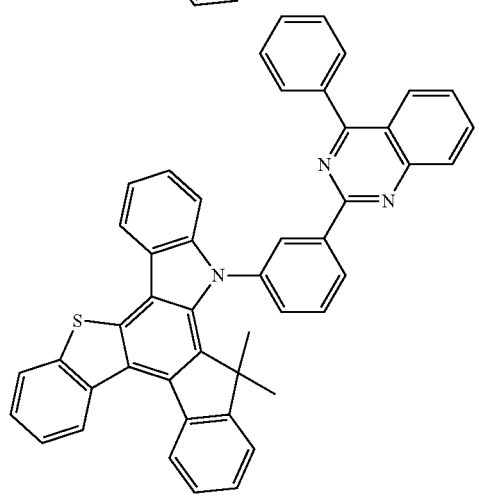 | 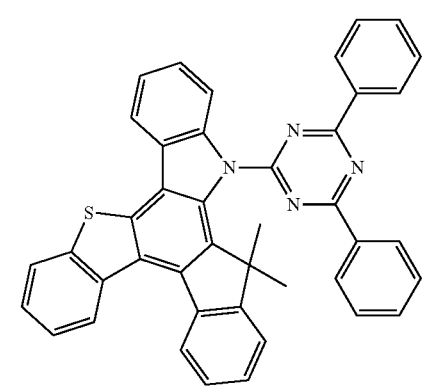 |
| 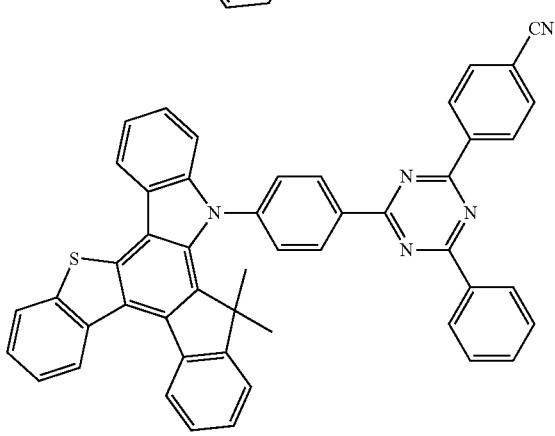 | 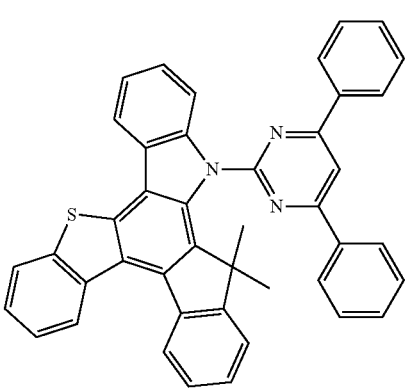 |

329
-continued
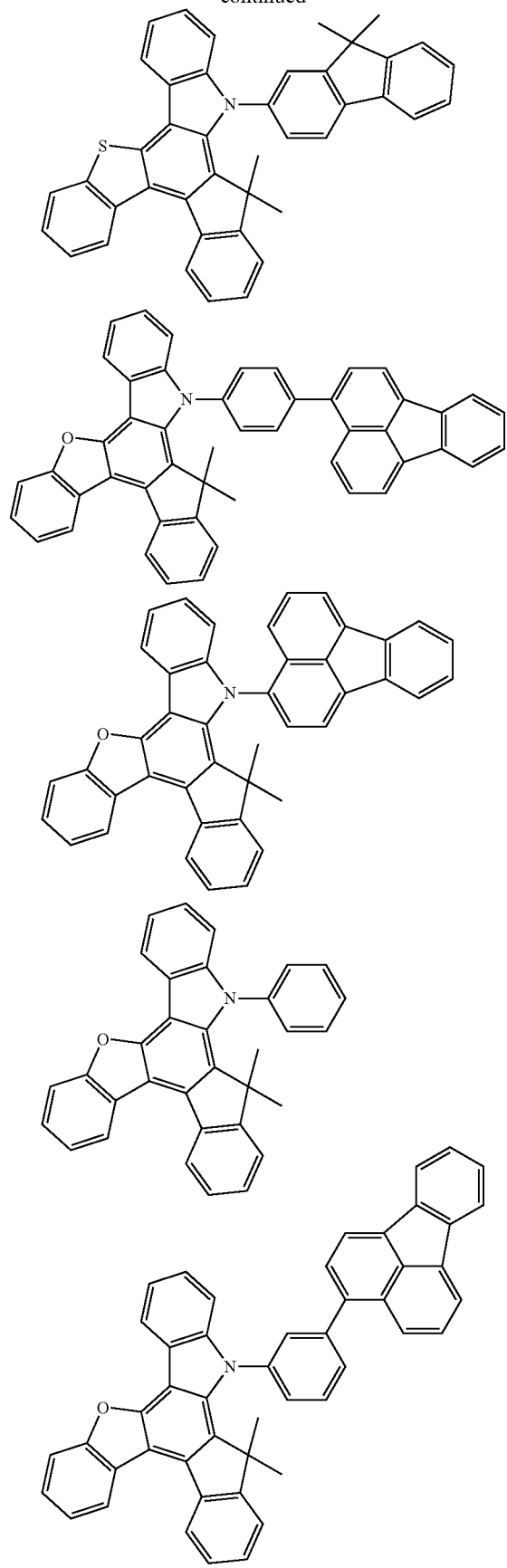
330
-continued
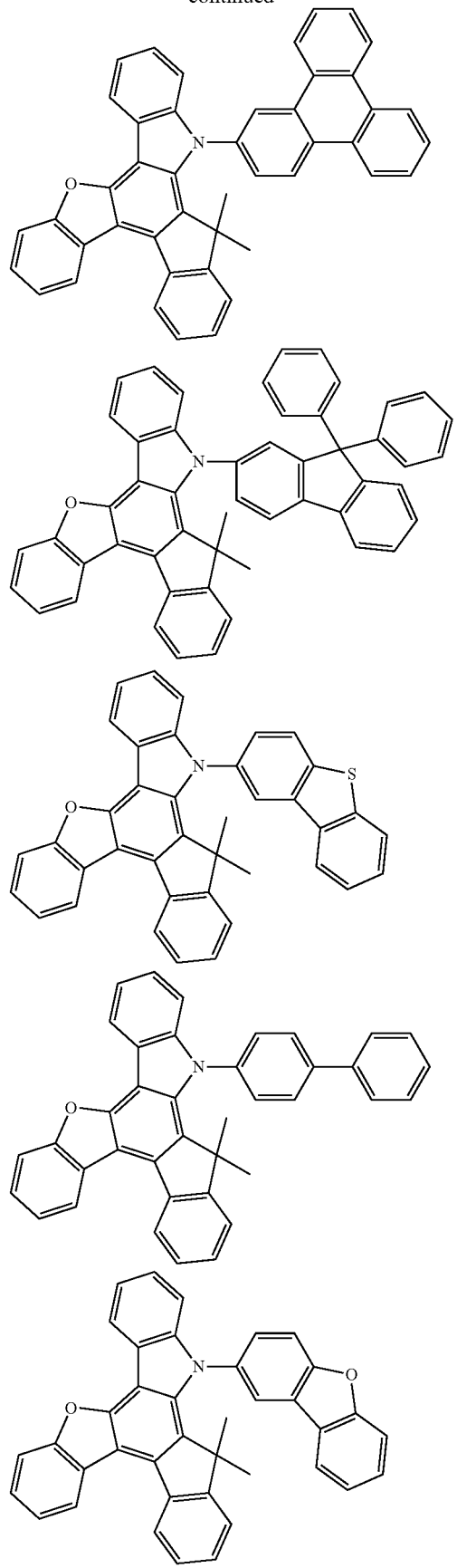

| 331 -continued | 332 -continued |
|---|---|
| 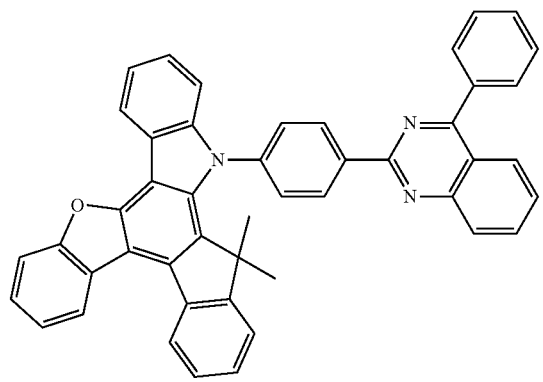 | 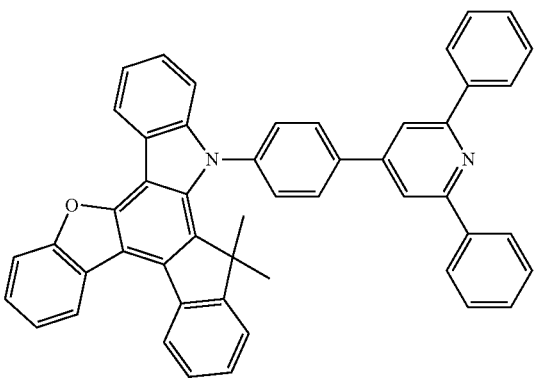 |
| 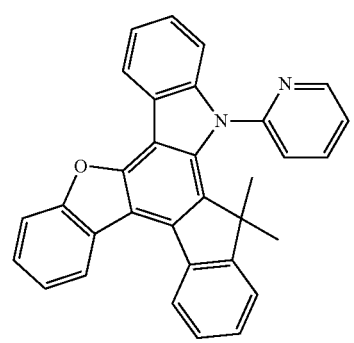 | 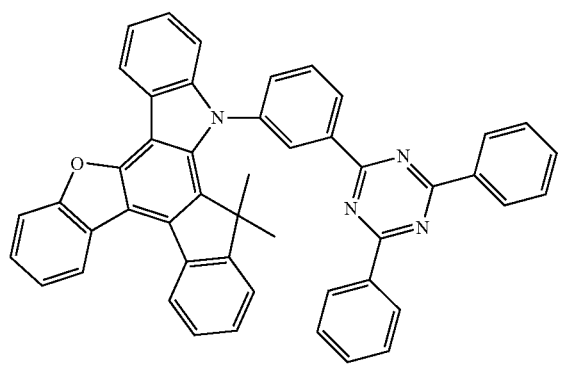 |
| 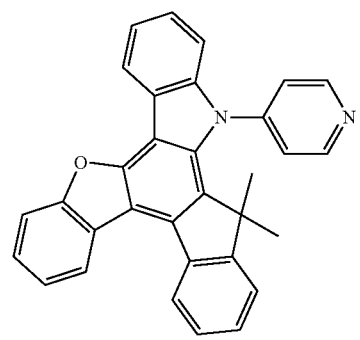 | |
| 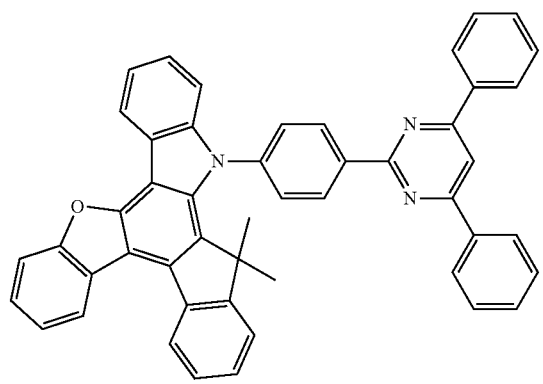 | 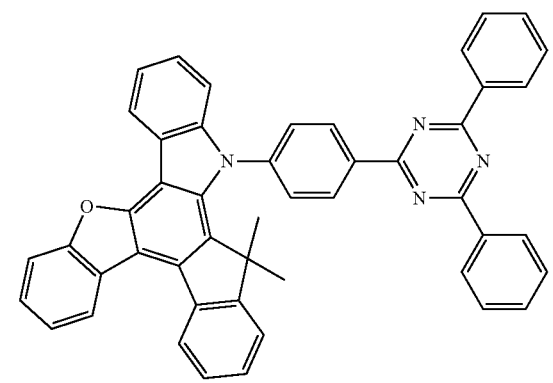 |

333
-continued
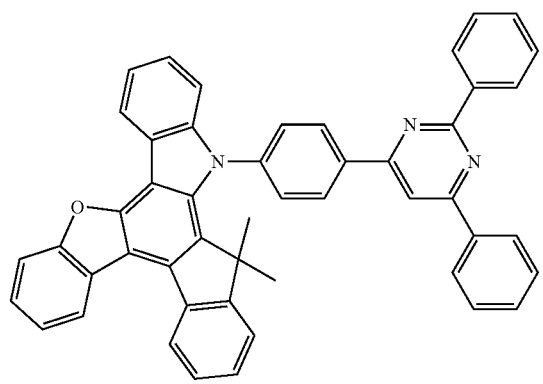
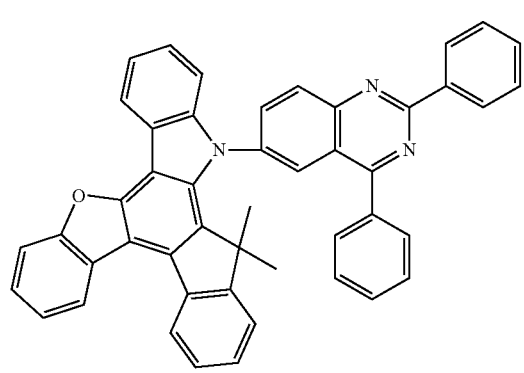
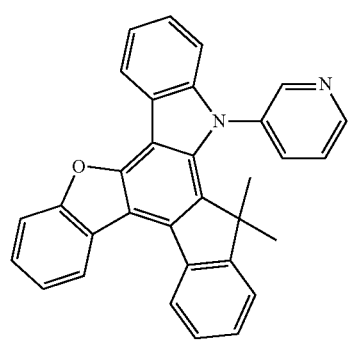
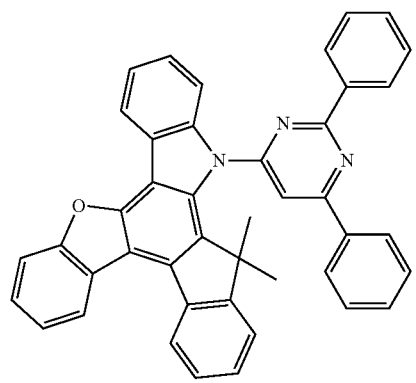
334
-continued
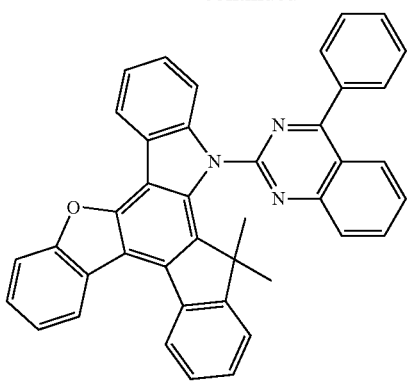
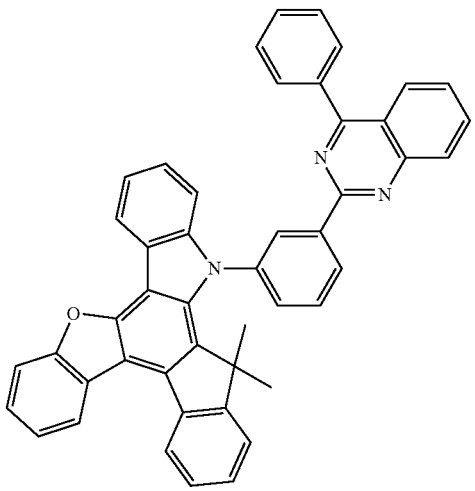
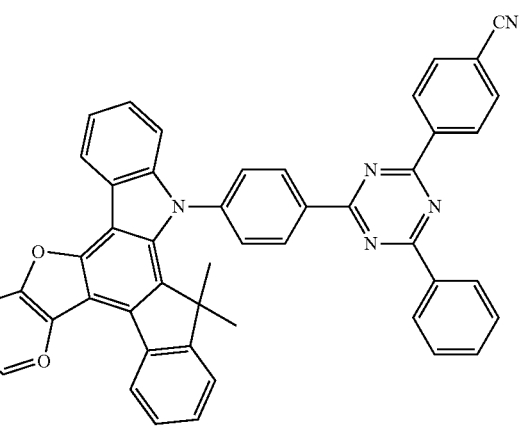
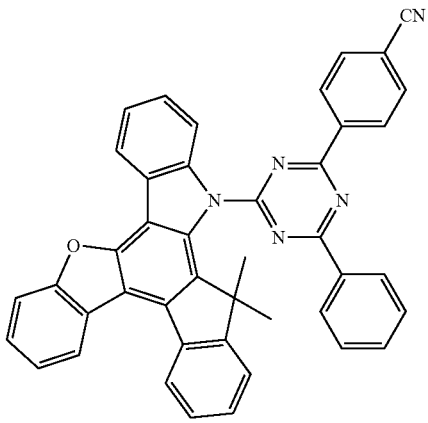

335
-continued
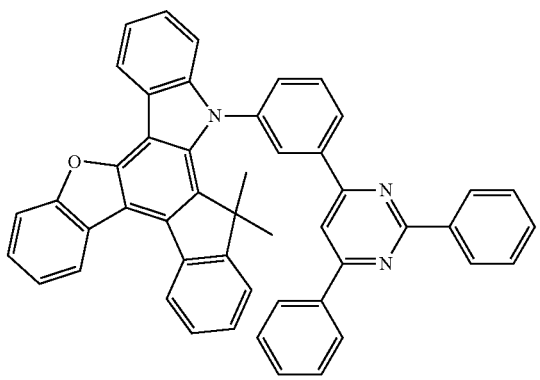
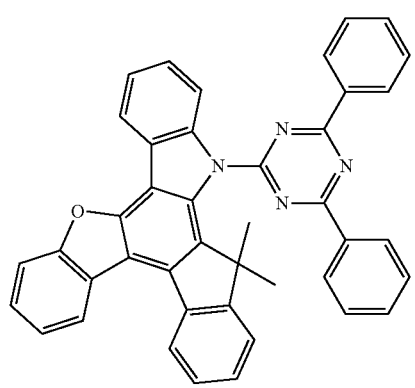
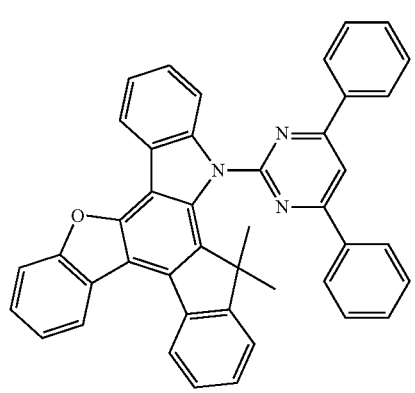
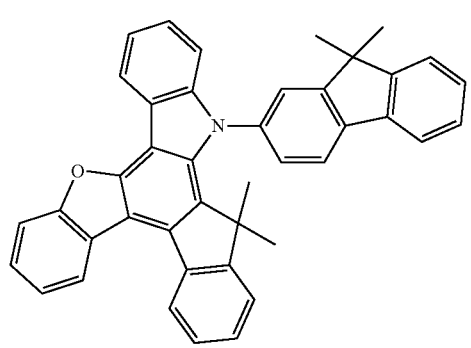
336
-continued
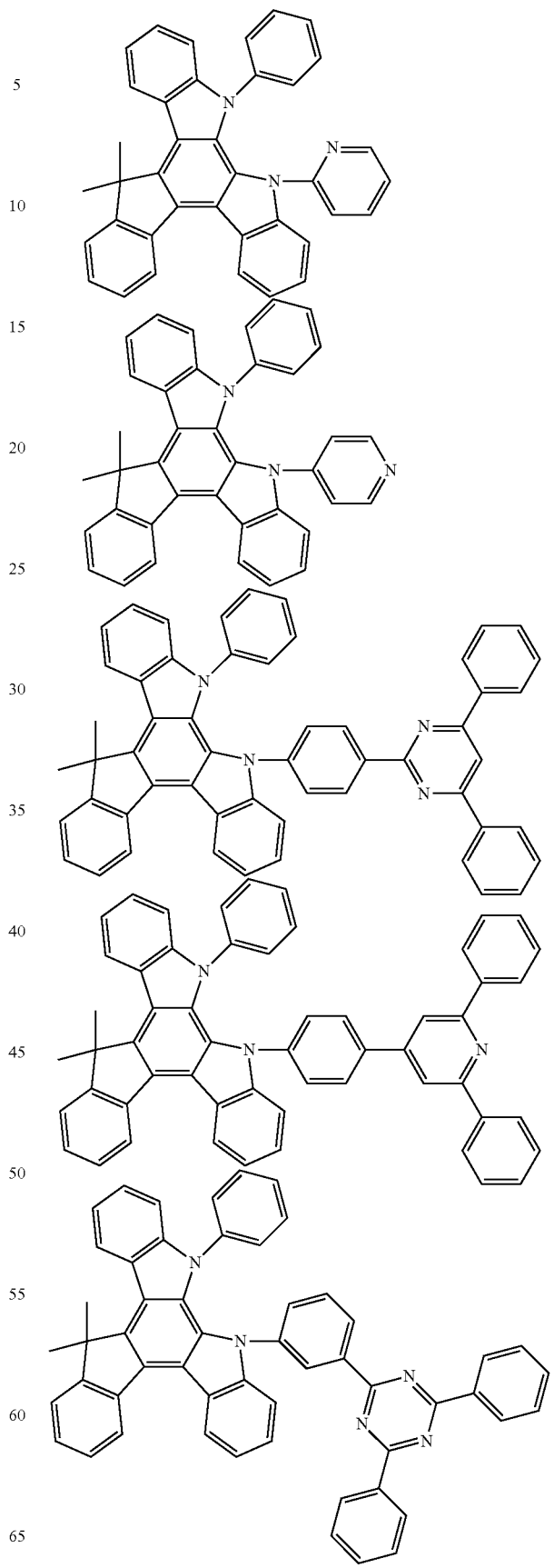

337
-continued
338
-continued
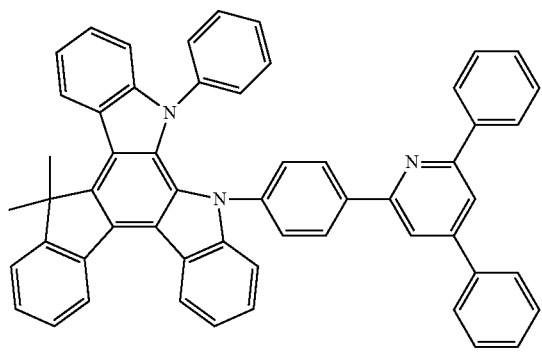
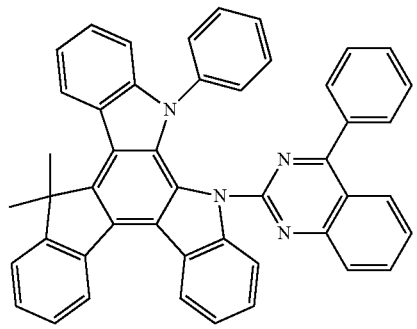
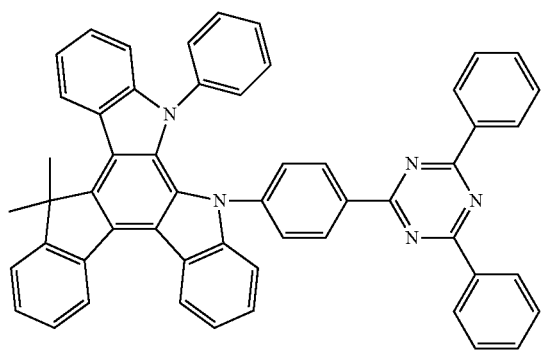
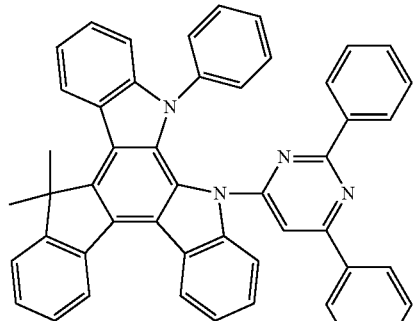
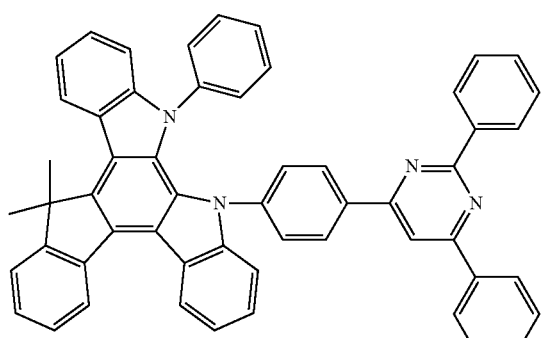
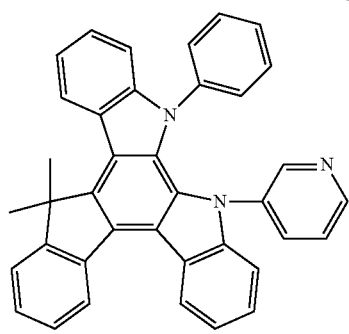
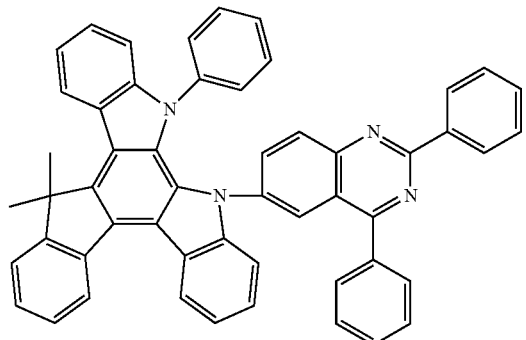
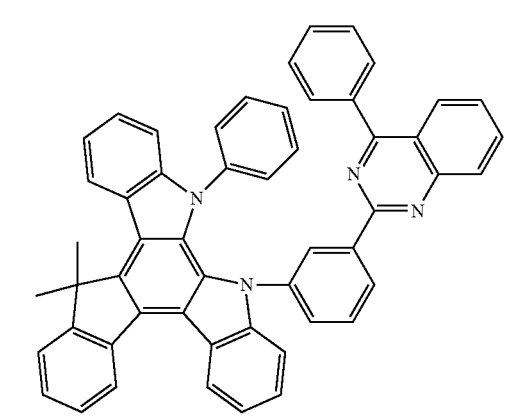
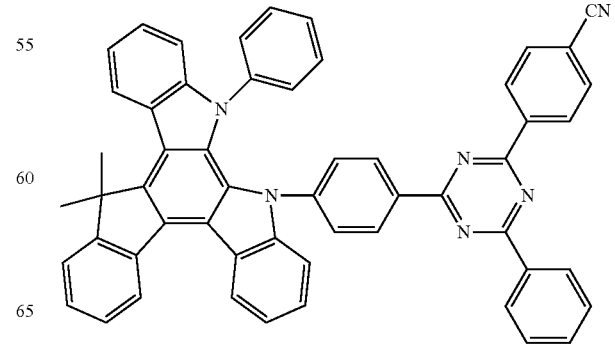

339
-continued
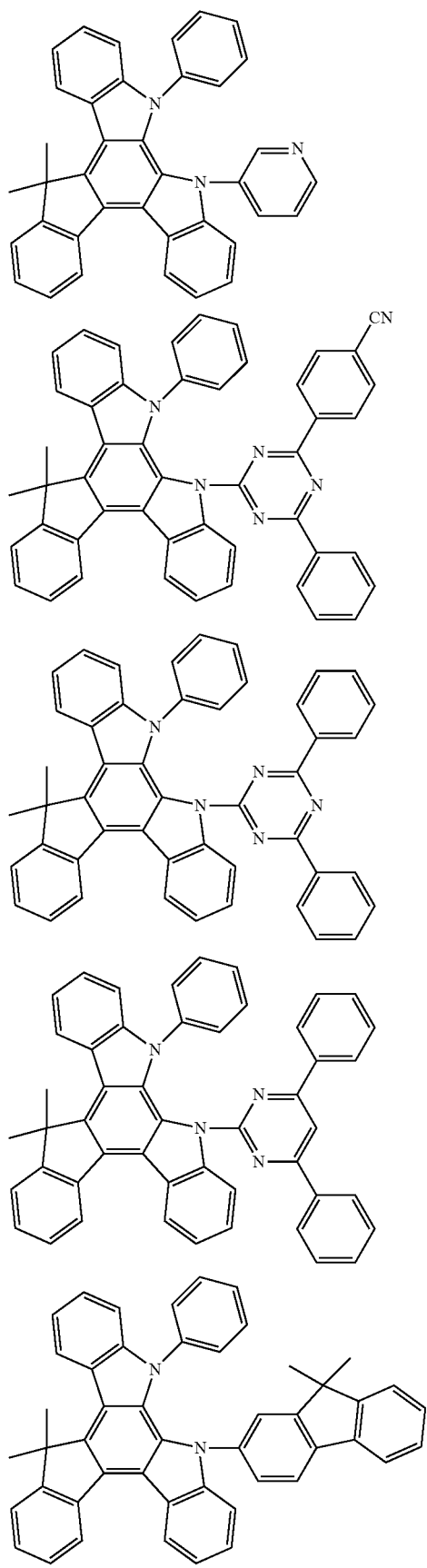
340
-continued
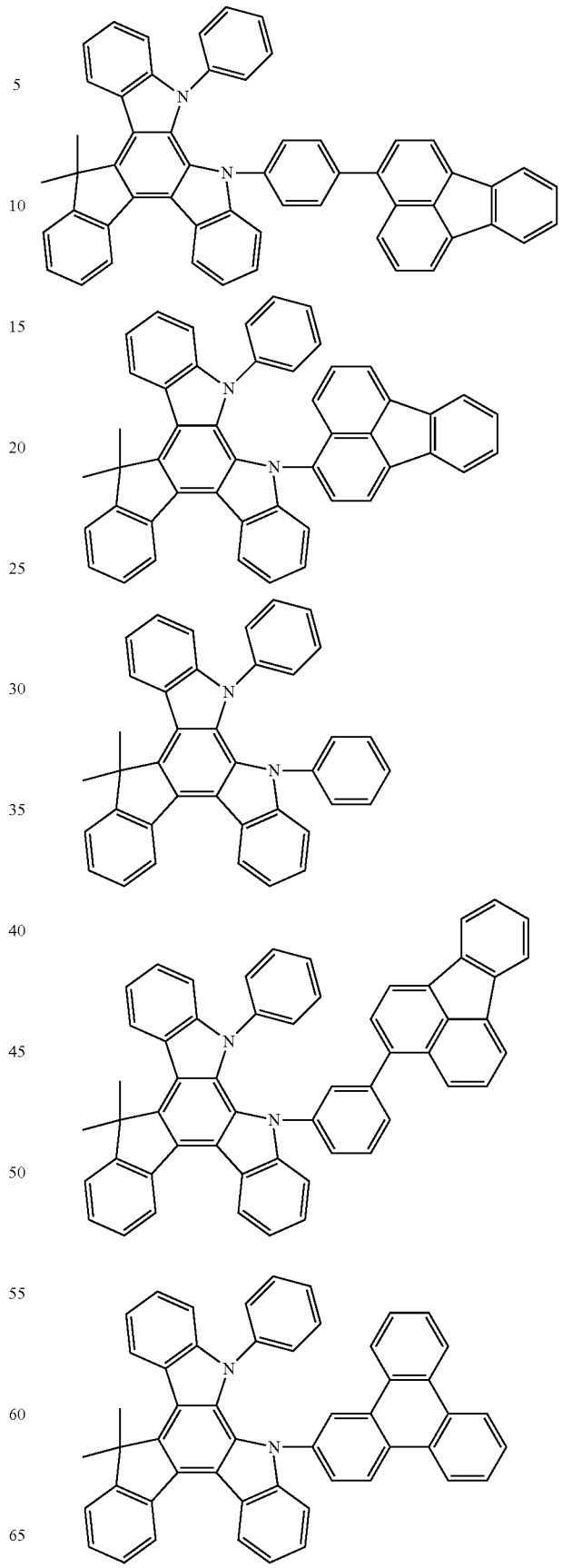

341
-continued
342
-continued
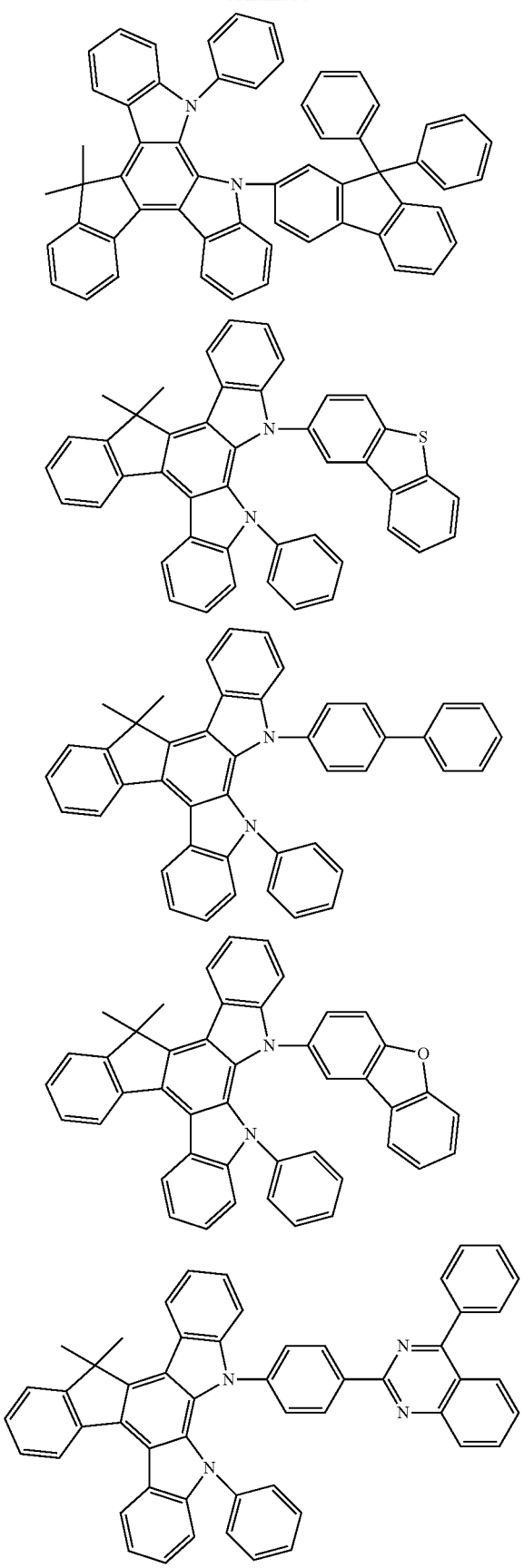
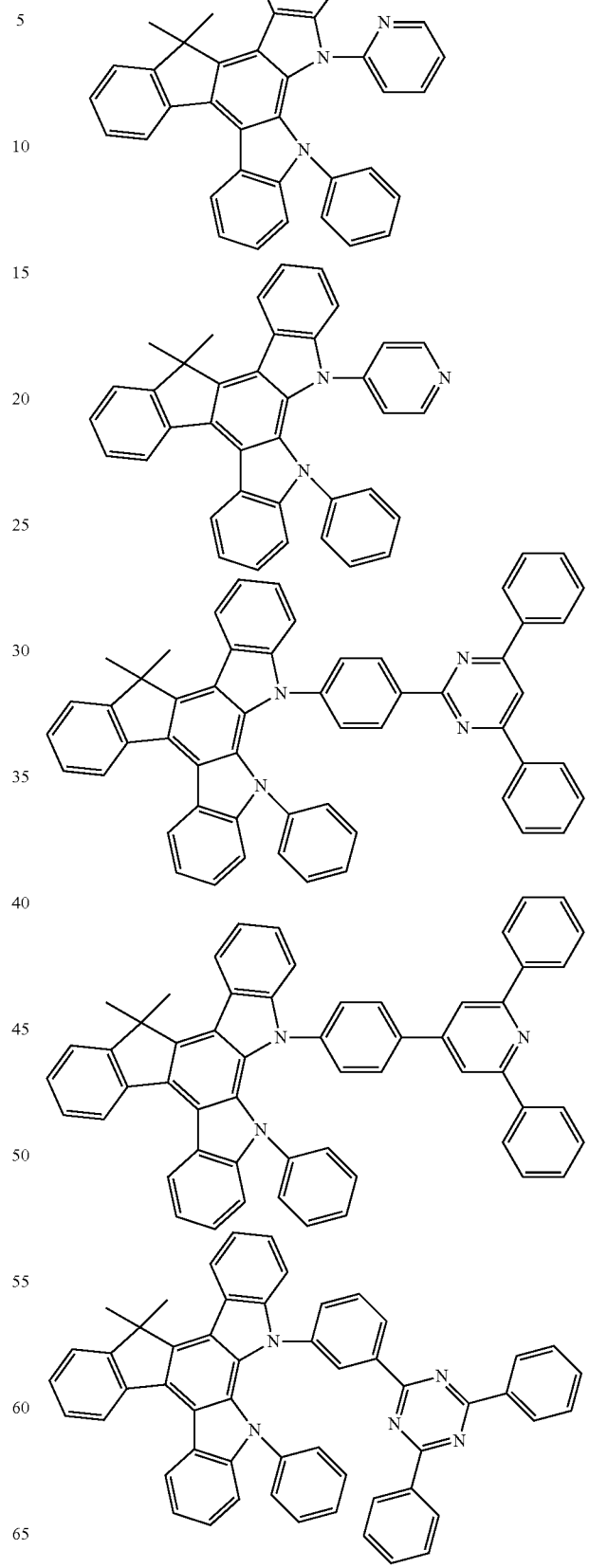

343
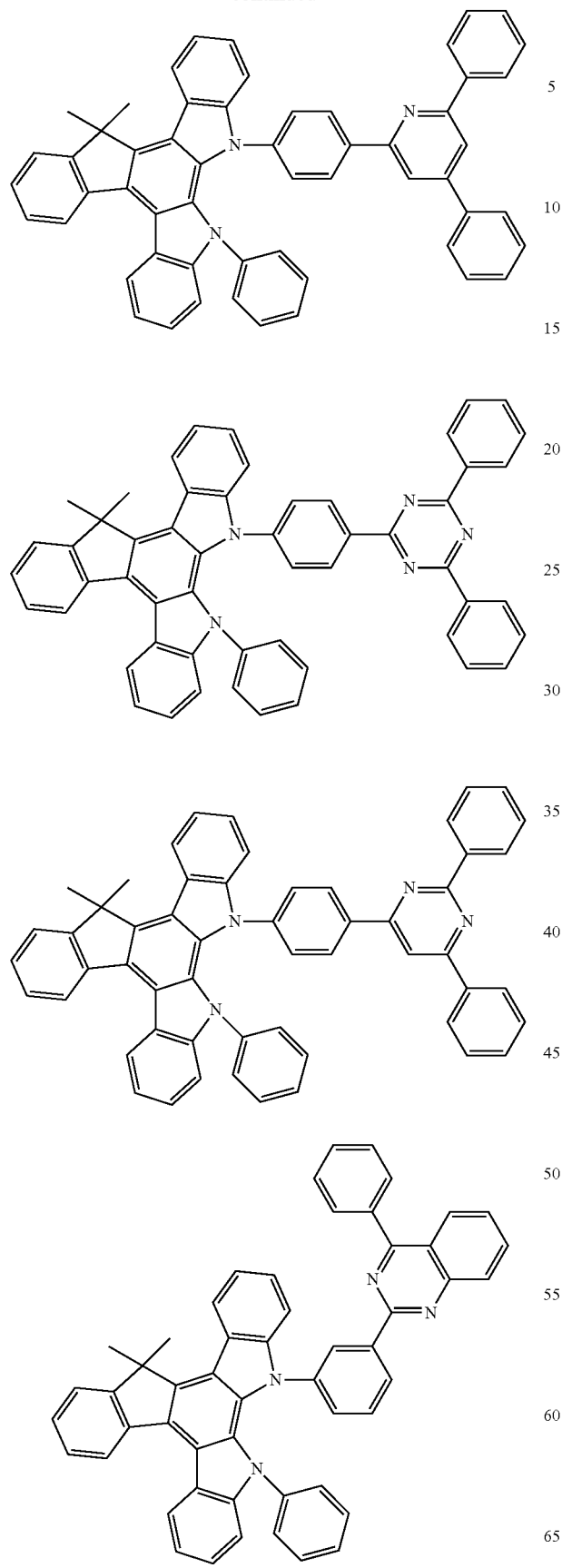
344
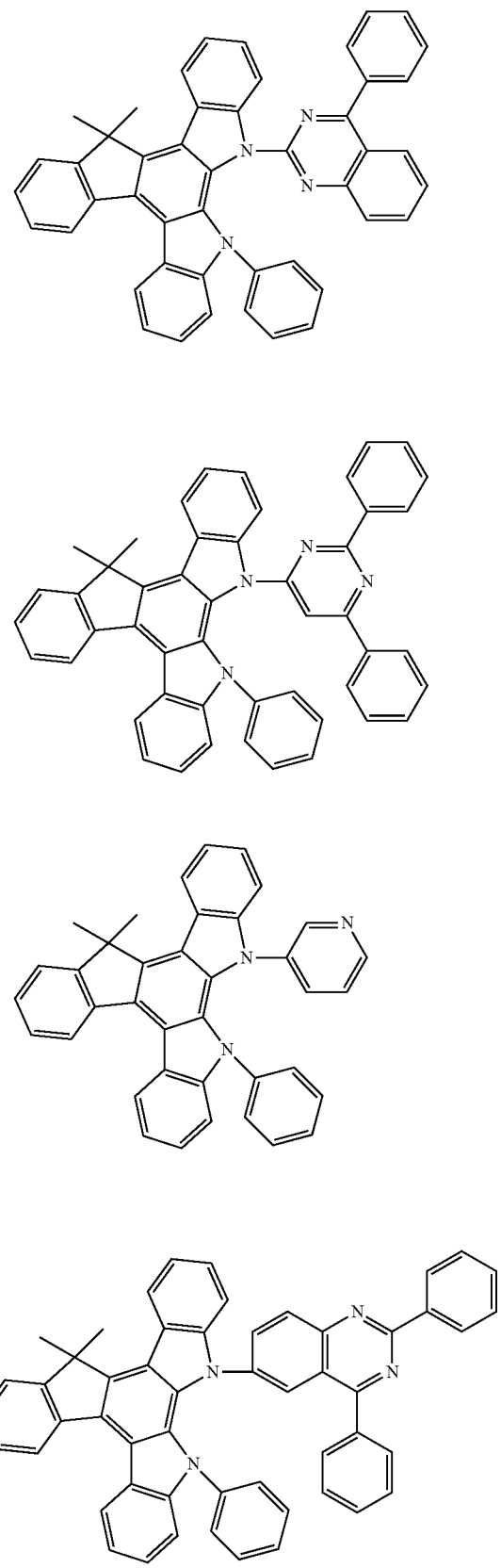

345
-continued
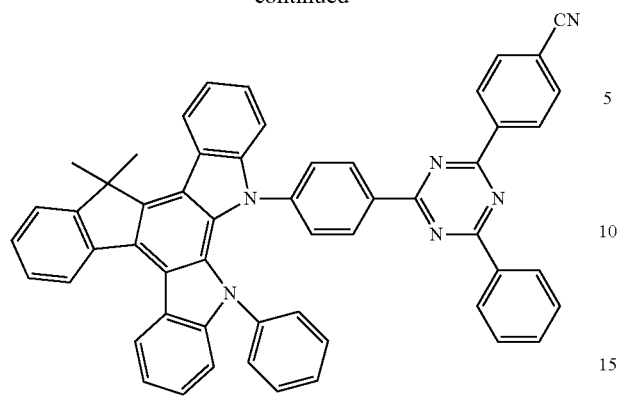
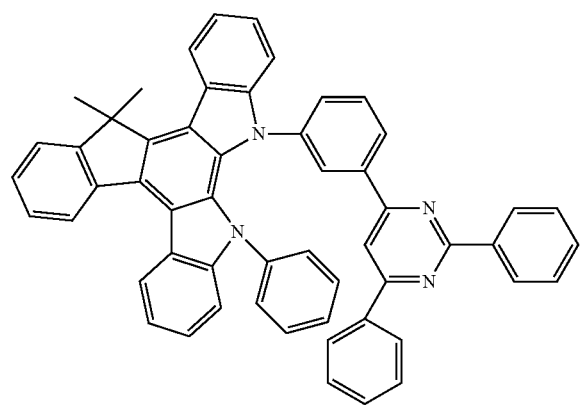
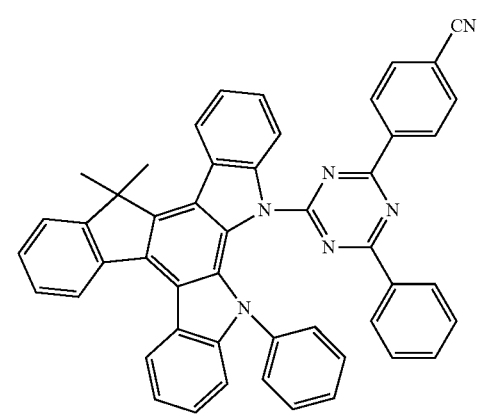
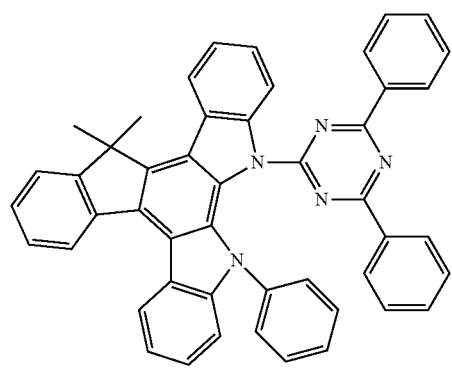
346
-continued
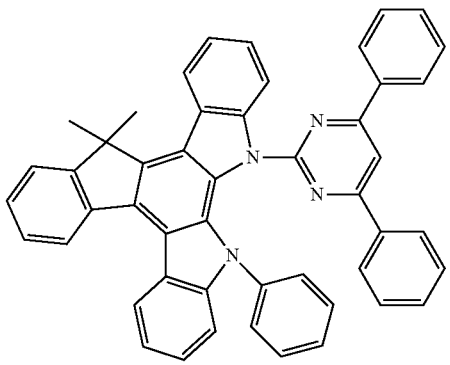
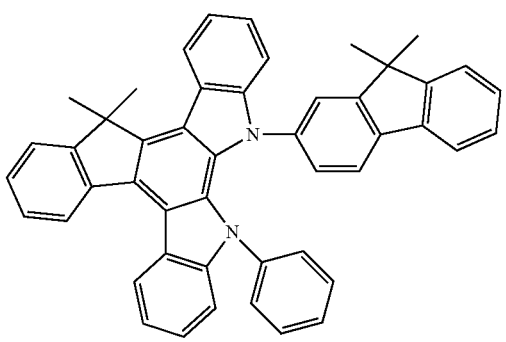
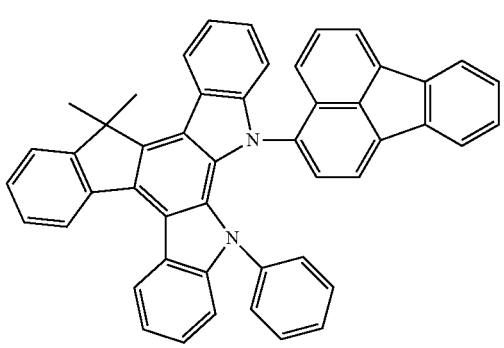

347
-continued
348
-continued
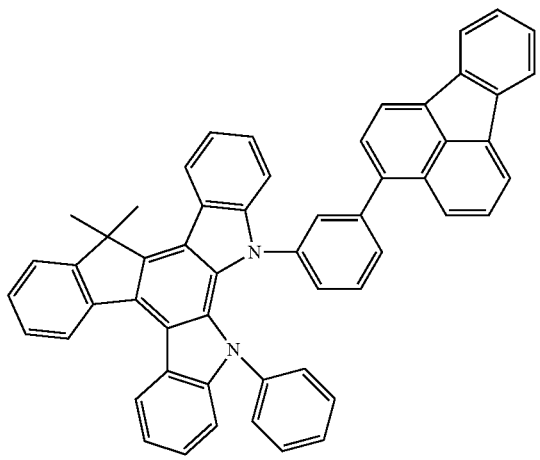
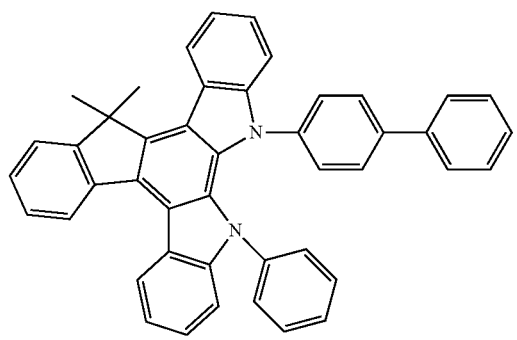
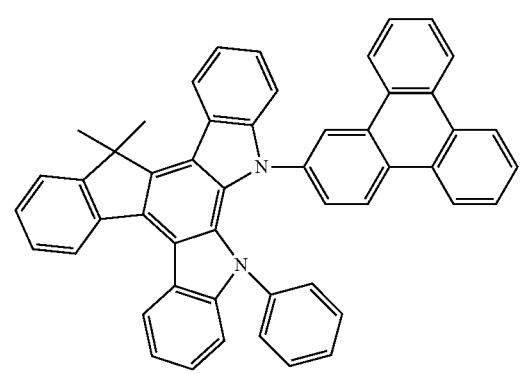
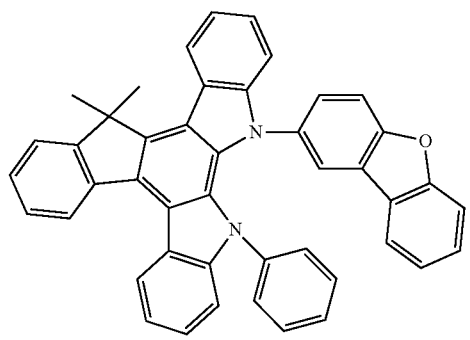
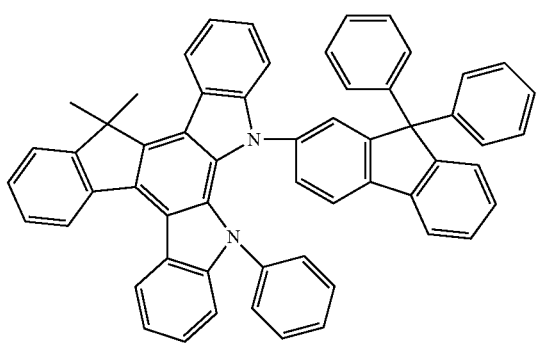
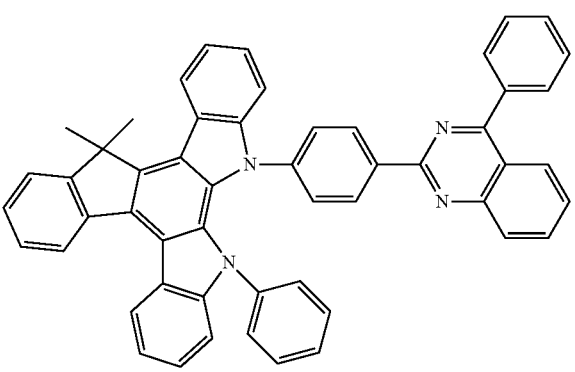
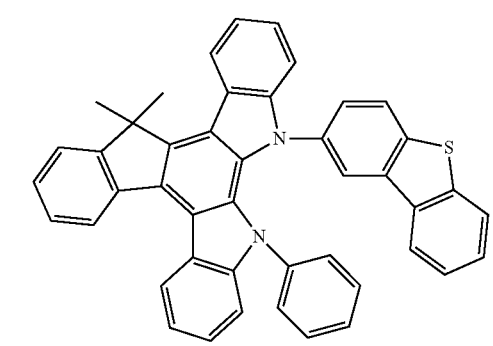
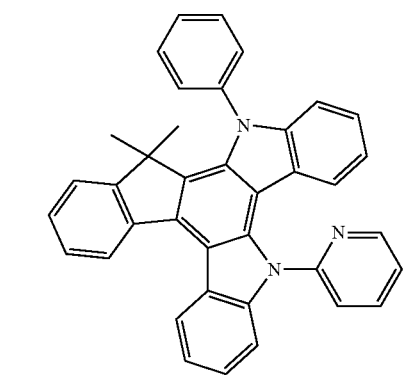

349
-continued
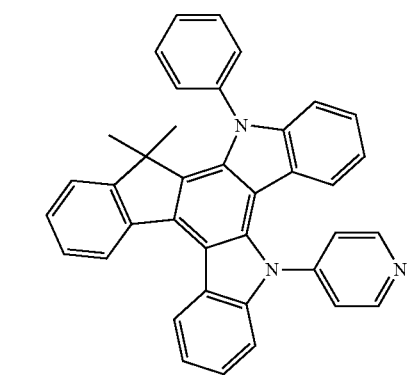
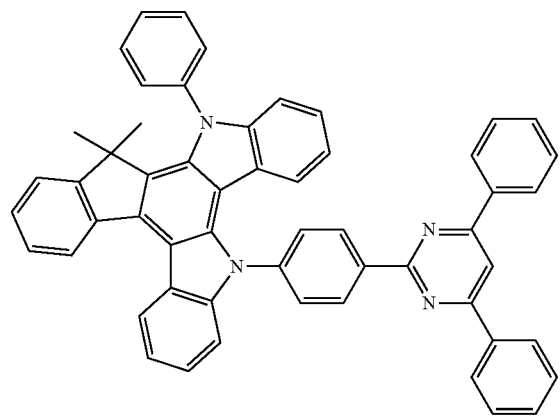
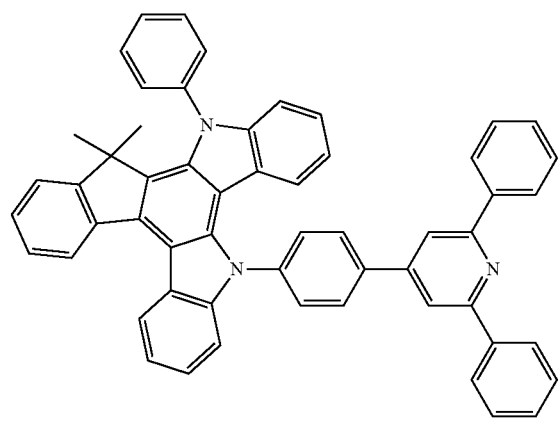
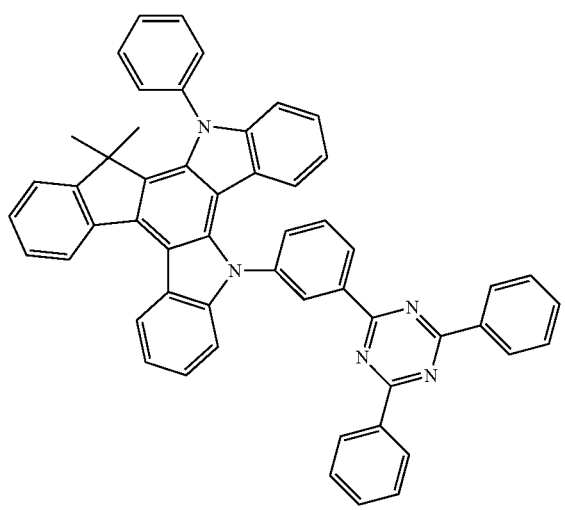
350
-continued
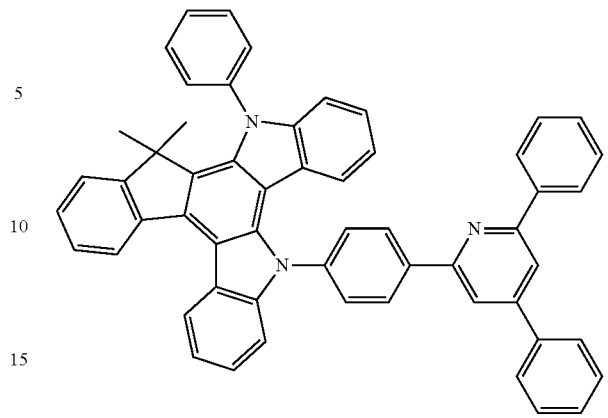
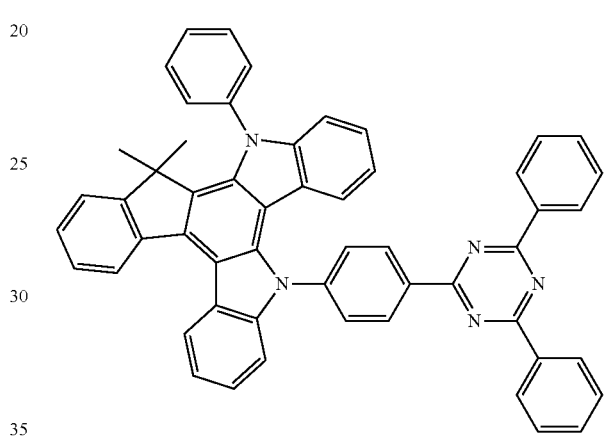
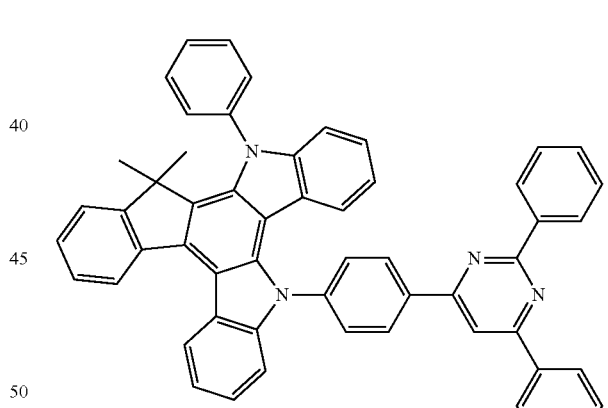
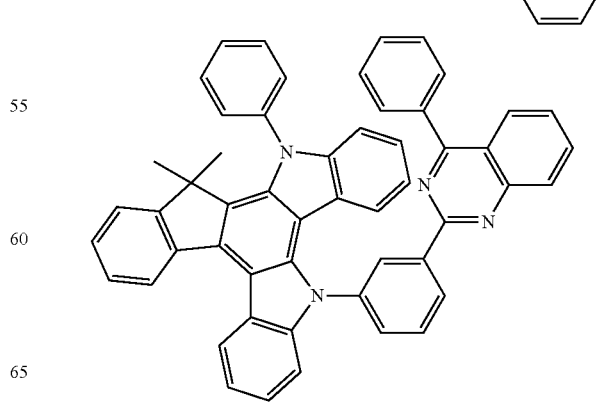

351
-continued
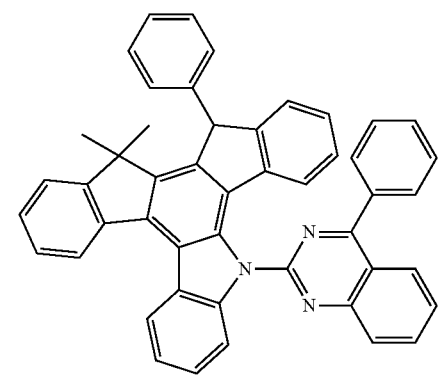
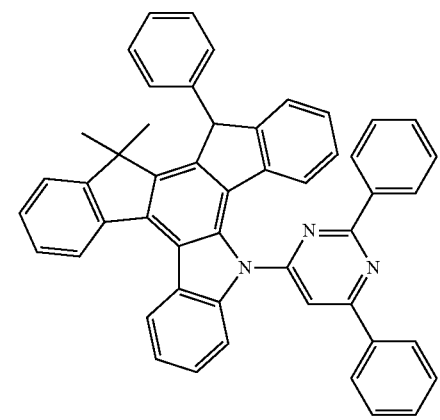
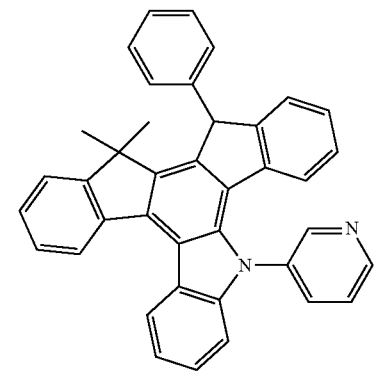
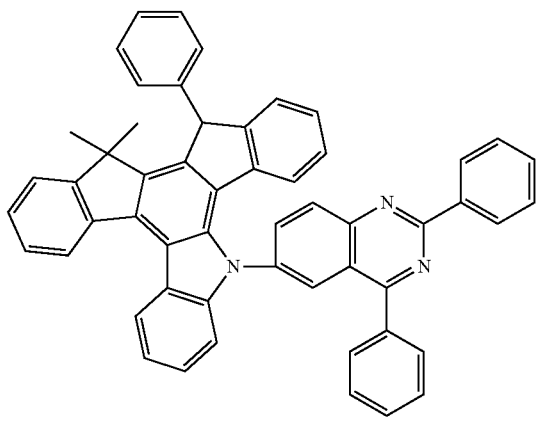
352
-continued
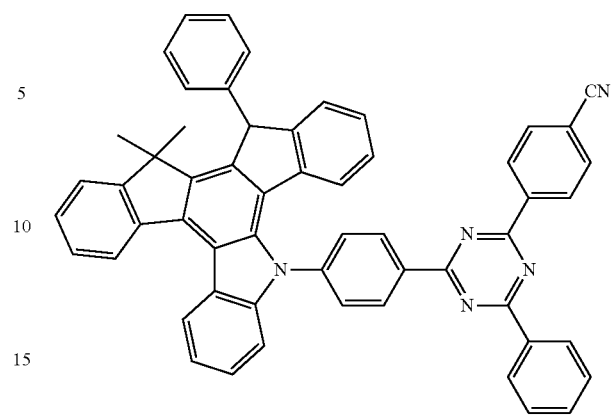
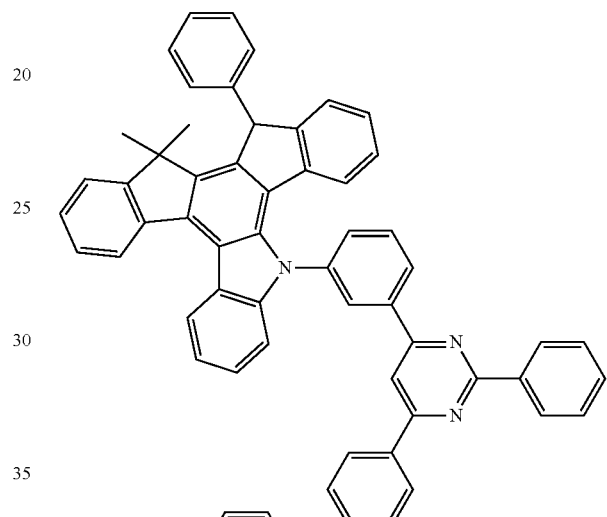
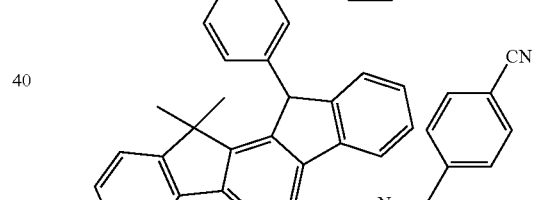
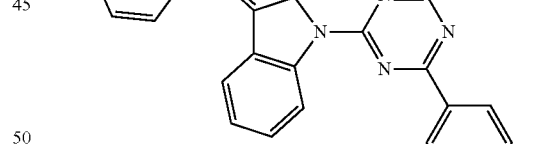
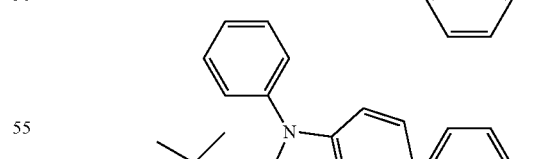
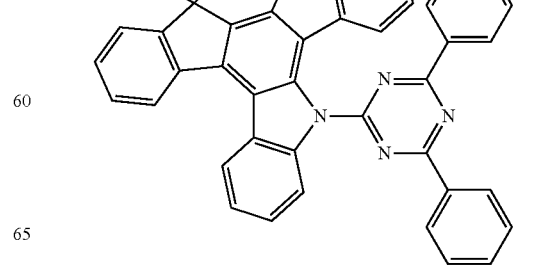

353
-continued
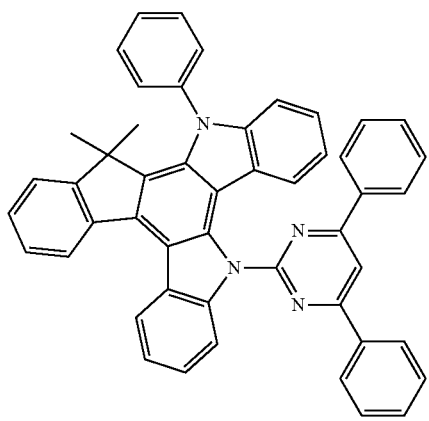
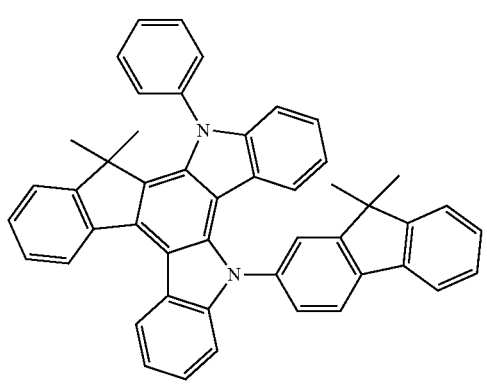
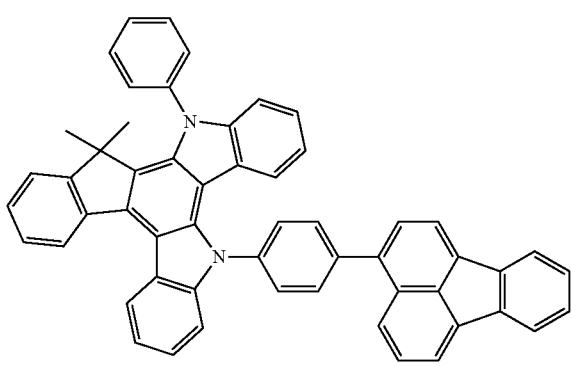
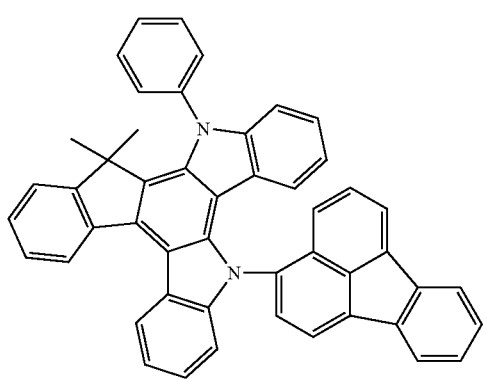
354
-continued
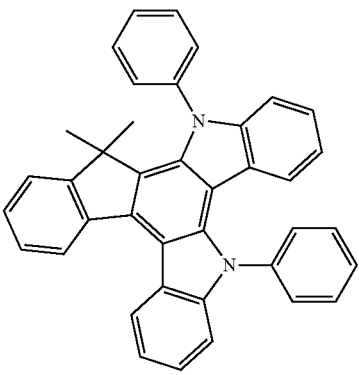
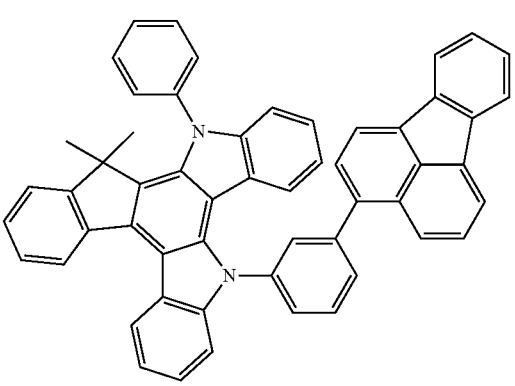
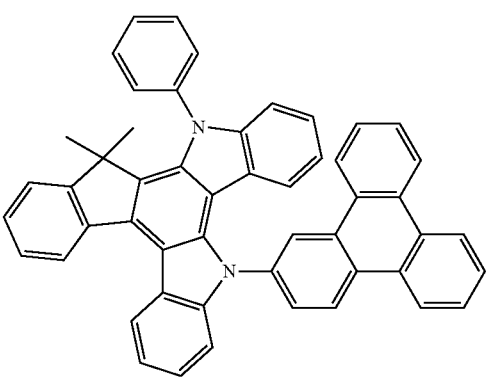
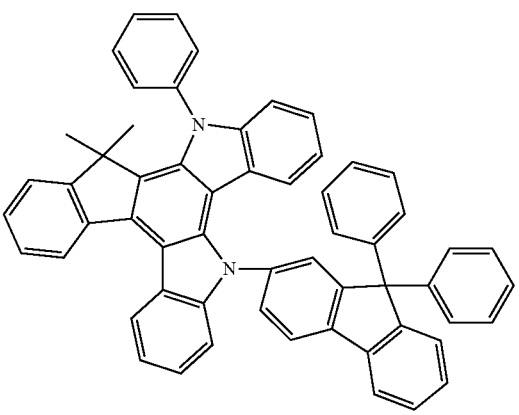

355
-continued
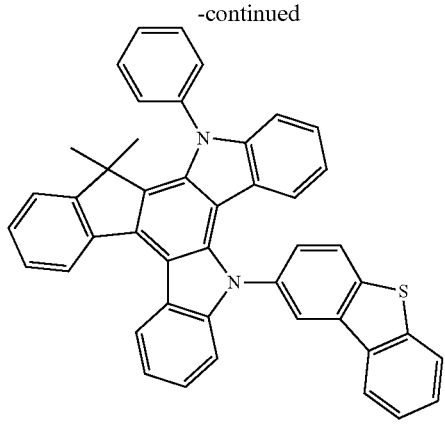
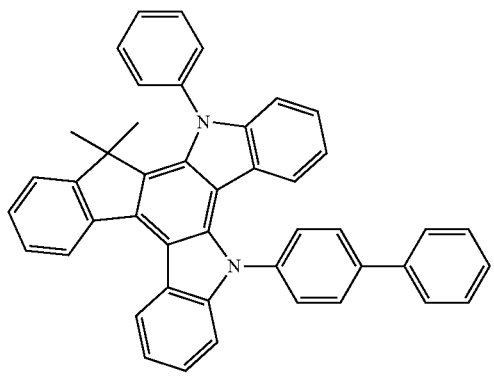
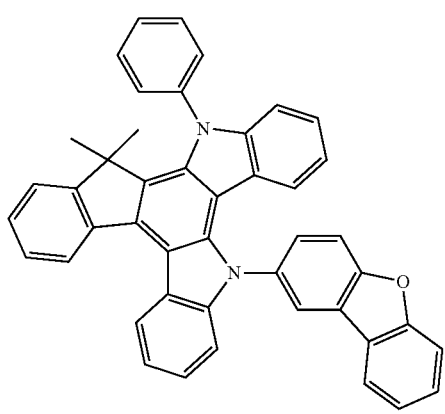
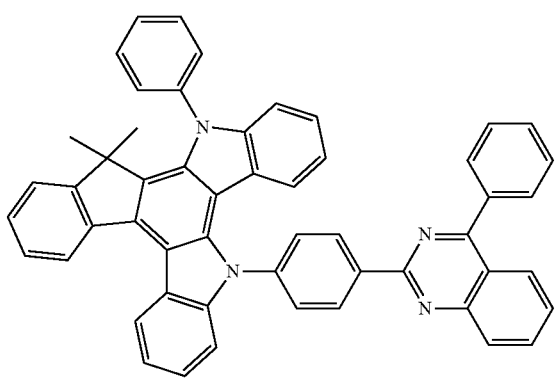
356
-continued
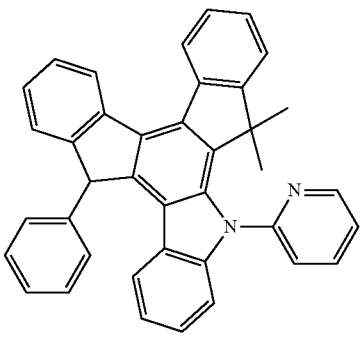
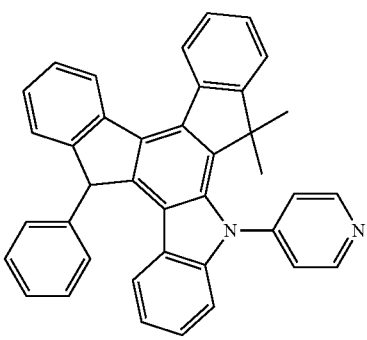
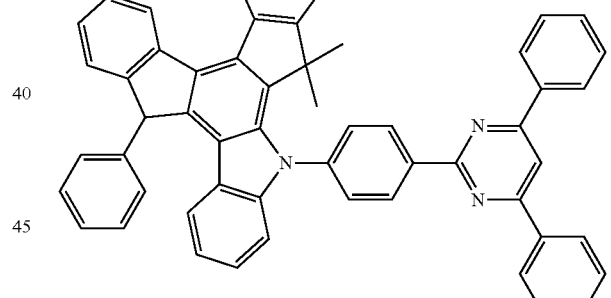
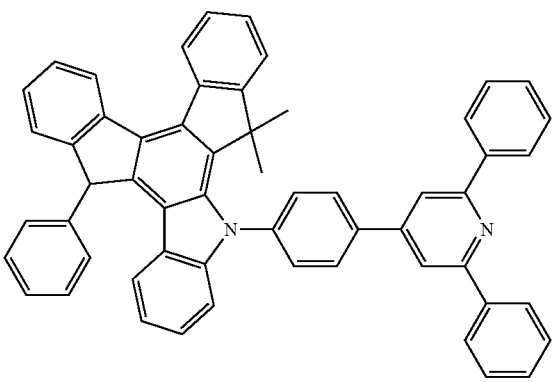

357
-continued
358
-continued
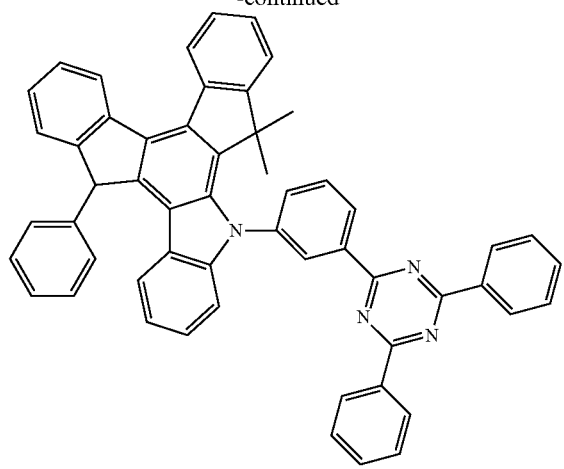
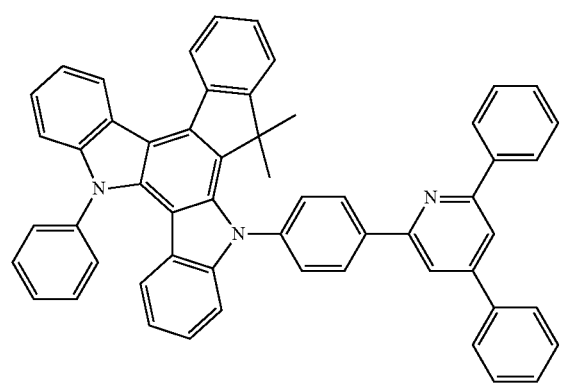
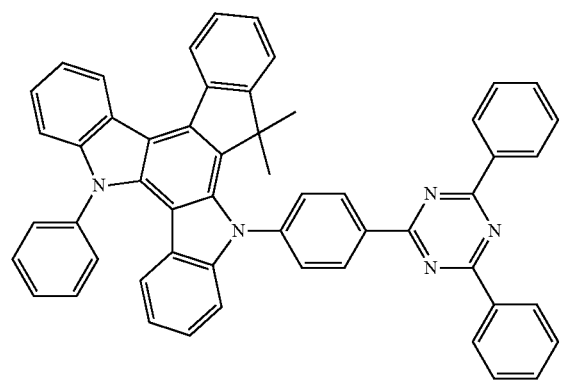
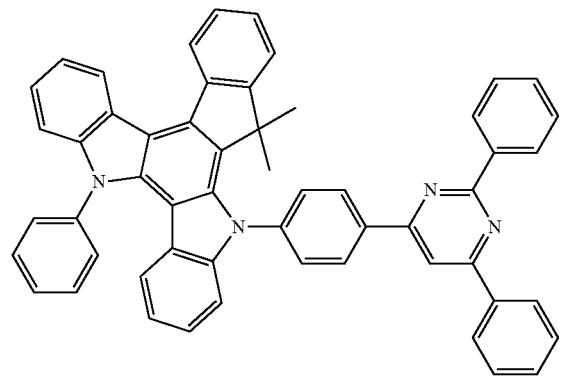
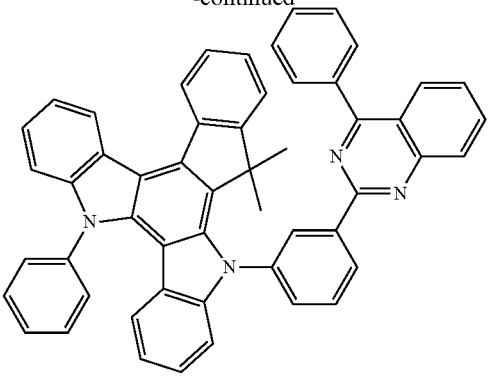
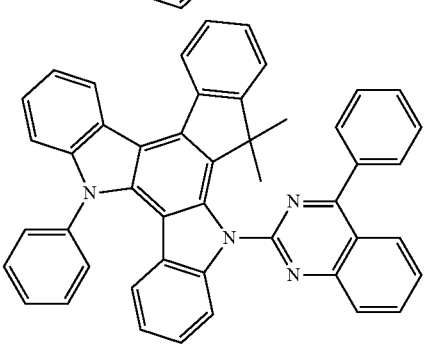
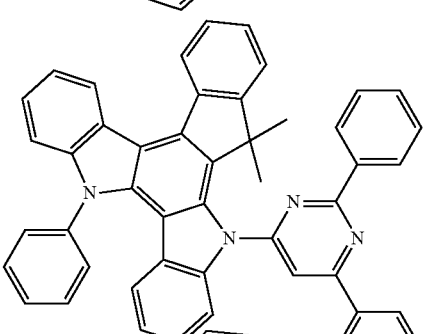
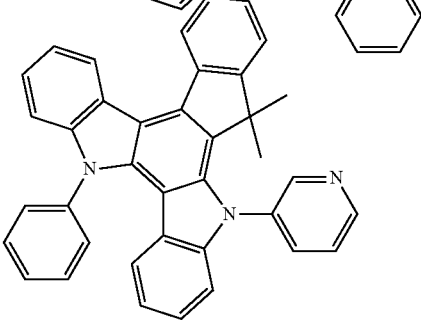
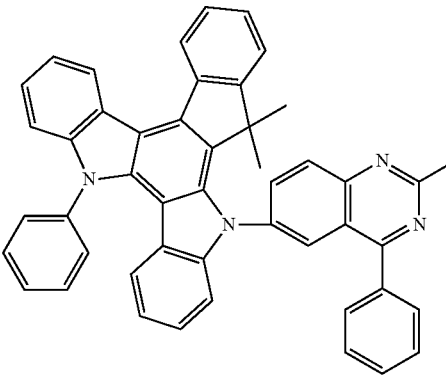

359
-continued
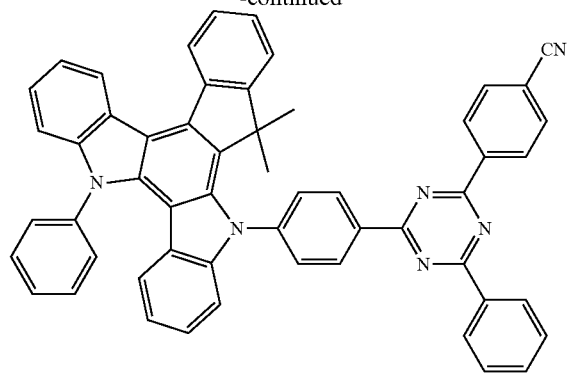
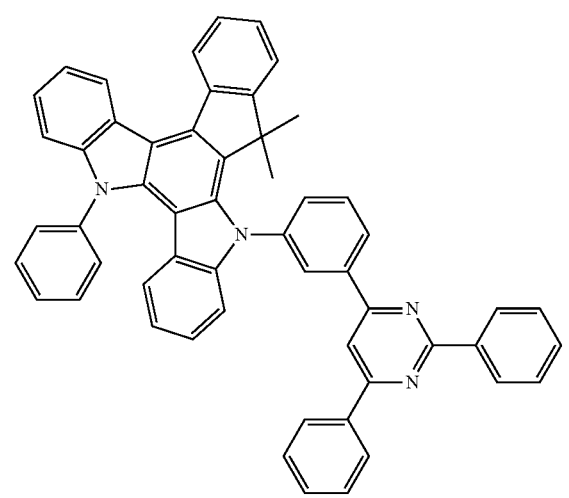
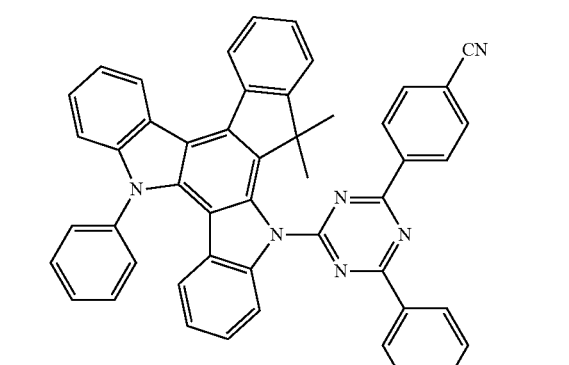
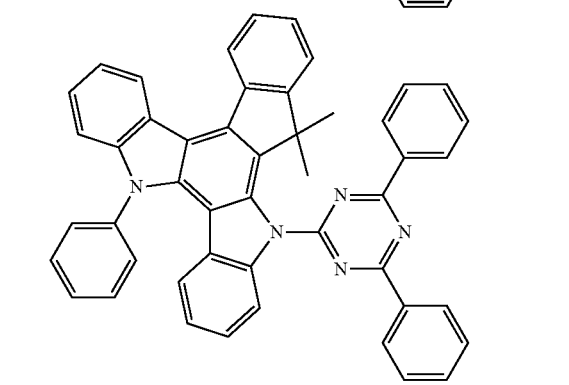
360
-continued
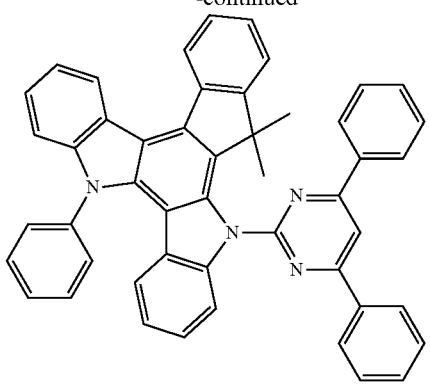
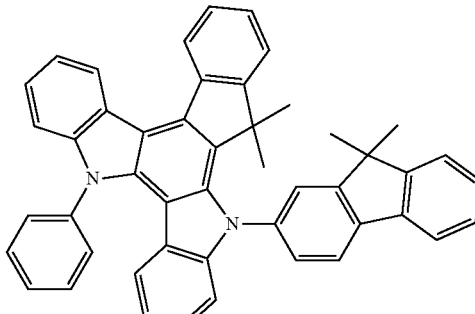
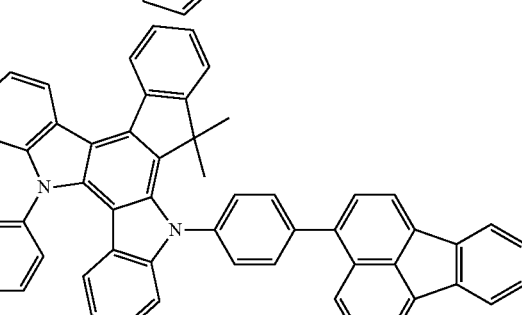
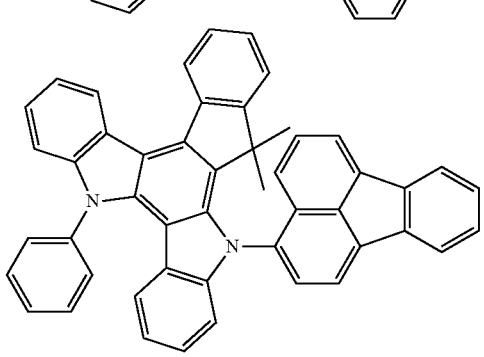
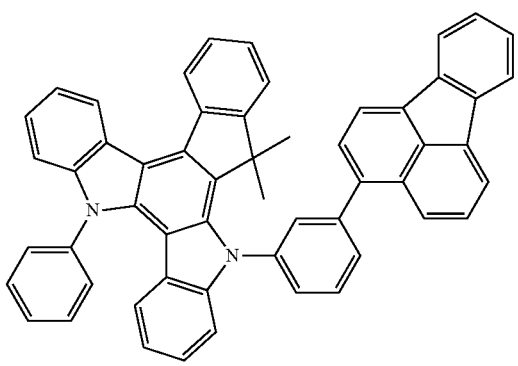

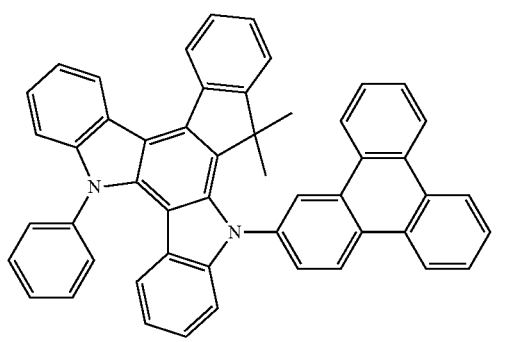
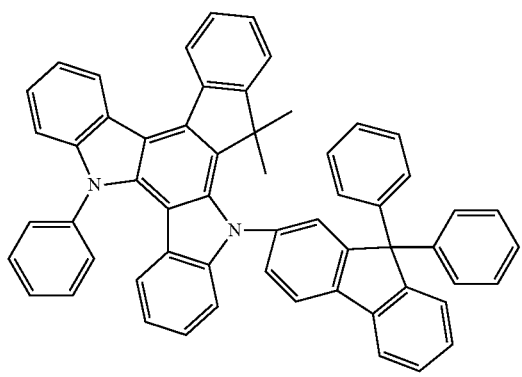
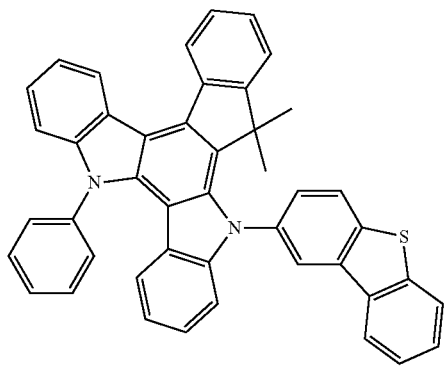
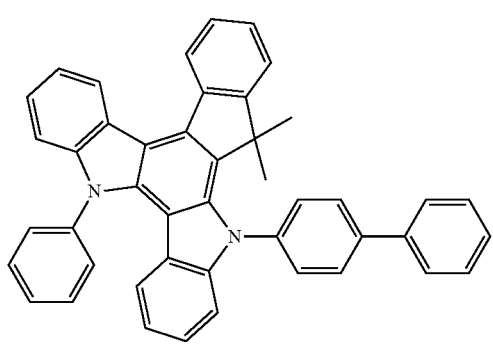
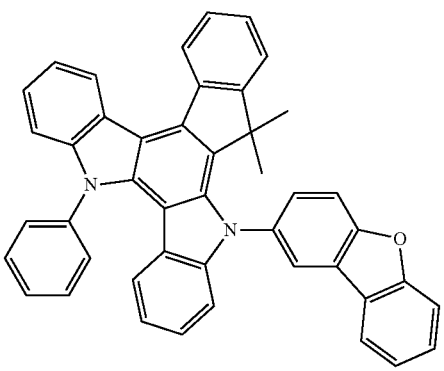
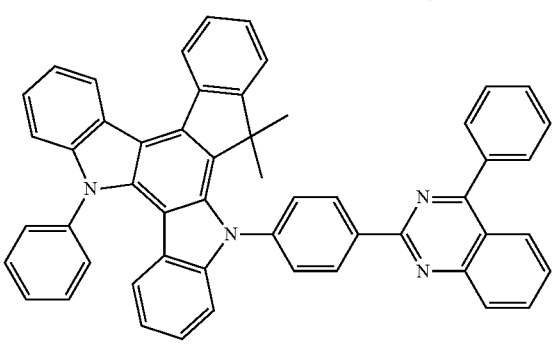
The heterocyclic compound is synthesized according to, for example, the following synthetic route.
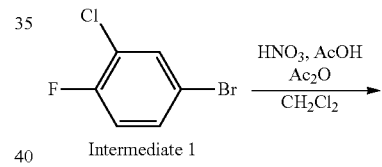
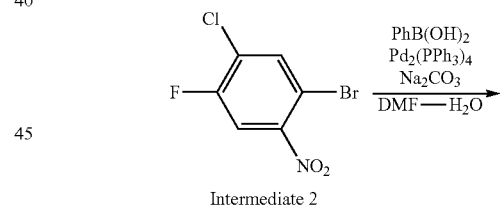
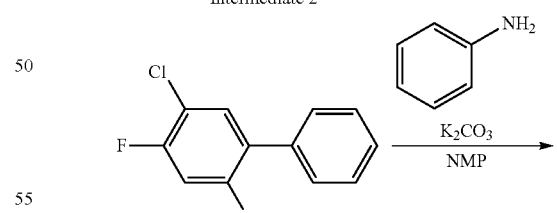
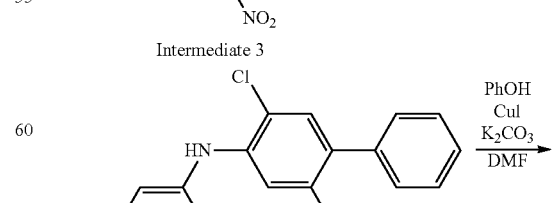
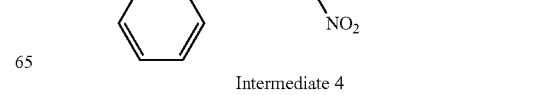

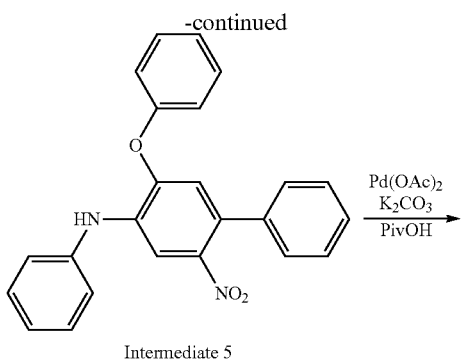

Intermediate 5

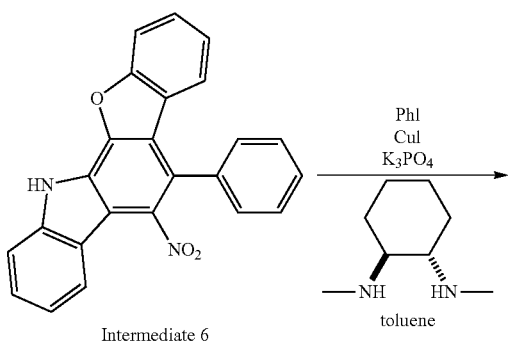

Intermediate 6

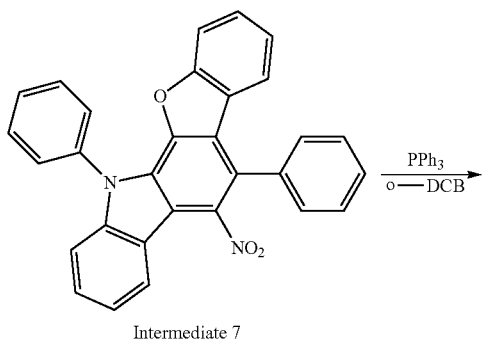

Intermediate 7

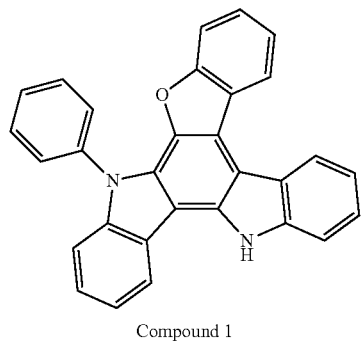

Compound 1 fluorine atom of intermediate 3 is treated with aniline under a basic condition to obtain a secondary amine (intermediate 4), which is then subjected to Ullmann reaction to synthesize an ether (intermediate 5). Intermediate 5 is subjected to a cyclization reaction in the presence of pivalic acid to synthesize a ladder compound (intermediate 6) in which a benzofuran and a indole are fused to the benzene at one step. Intermediate 7 obtained by introducing a phenyl group by amination is then subjected to a reductive cyclization reaction in the presence of a phosphorus reagent to synthesize a fused compound (compound 1).

Compound 1 thus obtained can be converted to another heterocyclic compound according to the following synthetic route:

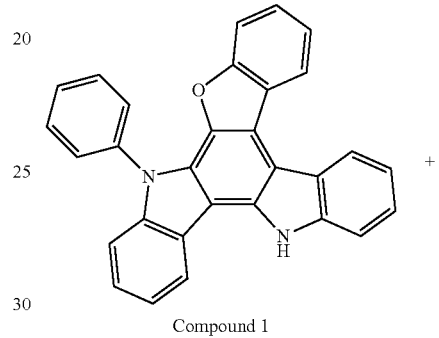

Compound 1

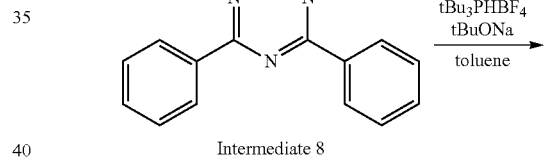

Intermediate 8

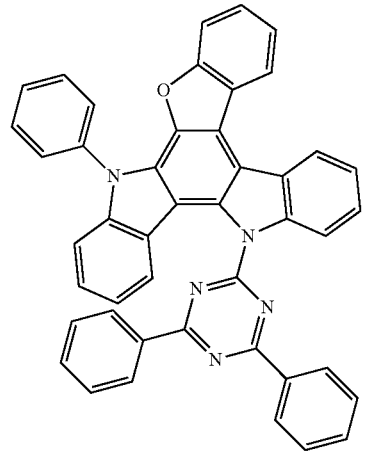

Compound 2 wherein a fused azine compound (compound 2) can be obtained by an amination reaction between compound 1 and a 1,3,5-trizaine compound (intermediate 8).

Alternatively, the heterocyclic compound can be synthesized by the following synthetic route.

In the above synthetic route, a starting trisubstituted benzene (intermediate 1) is regioselectively nitrated into a tetrasubstituted benzene (intermediate 2) in the presence of a mixed acid of fuming nitric acid and acetic acid. Using Suzuki-Miyaura coupling reaction, intermediate 2 is converted to intermediate 3 by introducing a phenyl group. The

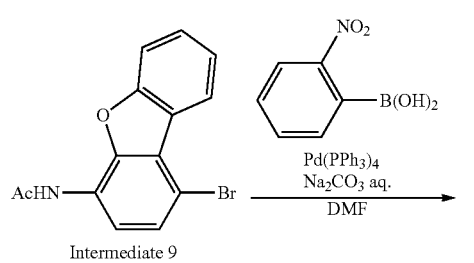

Intermediate 9

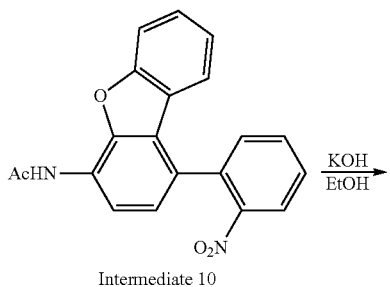

Intermediate 10

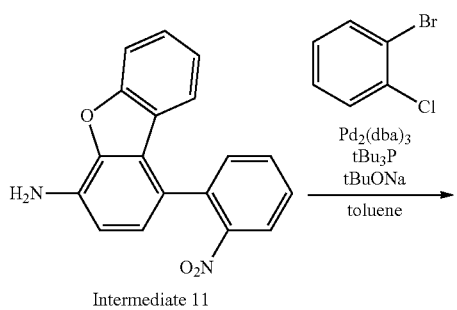

Intermediate 11

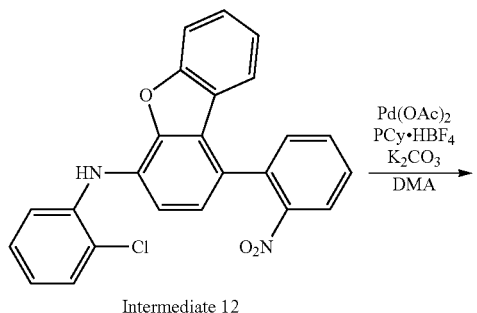

Intermediate 12

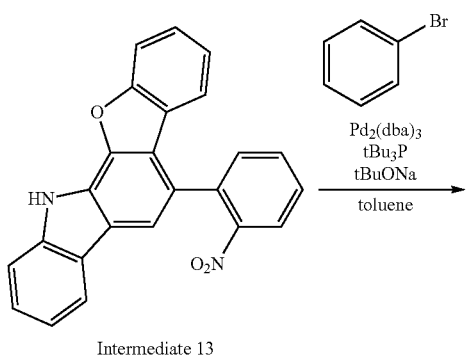

Intermediate 13

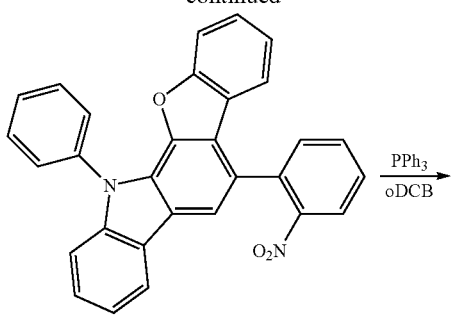

Intermediate 14

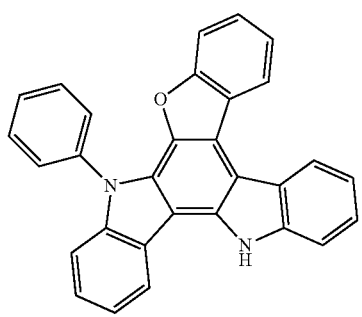

Compound 1

In the above synthetic route, a starting 1,4-disubstituted dibenzofuran (intermediate 9) is converted to intermediate 10 by Suzuki-Miyaura coupling reaction. By treating intermediate 10 with potassium hydroxide in an alcohol solvent, an amine compound (intermediate 11) is synthesized, which is then subjected to an amination reaction in the presence of a palladium catalyst to synthesize a chlorinated compound (intermediate 12). Intermediate 12 is subjected to a ring closure reaction by treating with a palladium catalyst in the presence of a base to synthesize an indole-fused ladder compound (intermediate 13), which is then subjected to an amination reaction to introduce a phenyl group into the nitrogen atom of the indole ring, thereby synthesizing intermediate 14. Finally, by a reductive cyclization reaction of intermediate 14 in the presence of a phosphorus reagent, a fused compound (compound 1) is synthesized.

The above synthetic method is one embodiment of the synthetic method for the heterocyclic compound of the invention. In another embodiment, the heterocyclic compound may be synthesized by appropriately modifying the above synthetic method.

For example, compound 19 can be synthesized in the same manner as in the above synthetic method except for changing intermediate 9 to intermediate 21.

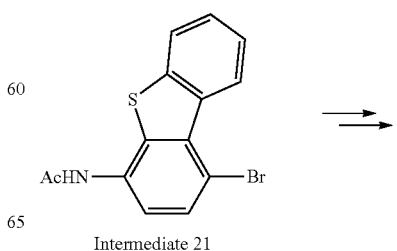

Intermediate 21

-continued

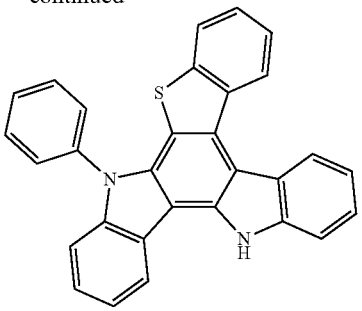

Compound 19

In addition, the heterocyclic compound of the invention can be obtained by the synthetic routes as shown in the examples described below.

Organic EL Device

The organic EL device in an aspect of the invention will be described below.

The organic EL device comprises an organic thin film layer between a cathode and an anode. The organic thin film layer comprises a light emitting layer and at least one layer of the organic thin film layer comprises the material for organic EL devices.

Examples of the organic thin film layer comprising the material for organic EL devices include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto. The material for organic EL devices may be used in any of the above layers and preferably used in a light emitting layer of a fluorescent emitting unit as a host material or a dopant material, in a light emitting layer of a phosphorescent emitting unit as a host material, or in a hole transporting layer or a electron transporting layer of an emission unit.

The organic EL device may be any of a single color emitting device of fluorescent or phosphorescent type, a white-emitting device of fluorescent-phosphorescent hybrid type, an emitting device of a simple type having a single emission unit, and an emitting device of a tandem type having two or more emission units, with the phosphorescent device being preferred. The "emission unit" referred to herein is the smallest unit for emitting light by the recombination of injected holes and injected electrons, which comprises one or more organic layers wherein at least one layer is a light emitting layer.

Representative device structures of the simple-type organic EL device are shown below.

(1) Anode/Emission Unit/Cathode

The emission unit may be a laminate comprising two or more layers selected from a phosphorescent light emitting layer and a fluorescent light emitting layer. A space layer may be disposed between the light emitting layers to prevent the diffusion of excitons generated in the phosphorescent light emitting layer into the fluorescent light emitting layer. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer);
(g) hole transporting layer/electron blocking layer/light emitting layer (/electron transporting layer);
(h) hole transporting layer/light emitting layer/hole blocking layer (/electron transporting layer); and
(i) hole transporting layer/fluorescent light emitting layer/triplet blocking layer (/electron transporting layer).

The emission color of the phosphorescent light emitting layer and that of the fluorescent light emitting layer may be different. For example, the layered structure of the laminated light emitting layer (d) may be hole transporting layer/first phosphorescent light emitting layer (red emission)/second phosphorescent light emitting layer (green emission)/space layer/fluorescent light emitting layer (blue emission)/electron transporting layer.

An electron blocking layer may be disposed between the light emitting layer and the hole transporting layer or between the light emitting layer and the space layer, if necessary. Also, a hole blocking layer may be disposed between the light emitting layer and the electron transporting layer, if necessary. With such an electron blocking layer or a hole blocking layer, electrons and holes are confined in the light emitting layer to increase the degree of charge recombination in the light emitting layer, thereby improving the lifetime.

Representative device structure of the tandem-type organic EL device is shown below.

(2) Anode/First Emission Unit/Intermediate Layer/Second Emission Unit/Cathode

The layered structure of the first emission unit and the second emission unit may be selected from those described above with respect to the emission unit.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

A schematic structure of an example of the organic EL device is shown in the FIGURE wherein the organic EL device 1 comprises a substrate 2, an anode 3, a cathode 4, and an emission unit 10 disposed between the anode 3 and the cathode 4. The emission unit 10 comprises a light emitting layer 5 which comprises at least one phosphorescent emitting layer containing a phosphorescent host material and a phosphorescent dopant material (phosphorescent material). An anode-side organic thin film layer 6, such as a hole injecting layer and a transporting layer, may be disposed between the light emitting layer 5 and the anode 3, and a cathode-side thin film layer 7, such as an electron injecting layer and a transporting layer, may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the degree of exciton generation in the light emitting layer 5.

In the present invention, a host is referred to as a fluorescent host when combinedly used with a fluorescent dopant (fluorescent material) and as a phosphorescent host when combinedly used with a phosphorescent dopant. Therefore, the fluorescent host and the phosphorescent host are not distinguished from each other merely by the difference in their molecular structures. Namely, in the present invention, the term "phosphorescent host" means a material for constituting a phosphorescent emitting layer containing a phosphorescent dopant and does not mean a material that cannot be utilized as a material for a fluorescent emitting layer. The same applies to the fluorescent host.

Substrate

The organic EL device in an aspect of the invention is formed on a light-transmissive substrate. The light-transmissive substrate serves as a support for the organic EL device and preferably a flat substrate having a transmittance of 50% or more to 400 to 700 nm visible light. Examples of the substrate include a glass plate and a polymer plate. The glass plate may include a plate made of soda-lime glass, barium-strontium-containing glass, lead glass, aluminosilicate glass, borosilicate glass, barium borosilicate glass, or quartz. The polymer plate may include a plate made of polycarbonate, acryl, polyethylene terephthalate, polyether sulfide, or polysulfone.

Anode

The anode of the organic EL device injects holes to the hole transporting layer or the light emitting layer, and an anode having a work function of 4.5 eV or more is effective. Examples of the material for anode include indium tin oxide alloy (ITO), tin oxide (NESA), indium zinc oxide alloy, gold, silver, platinum, and cupper. The anode is formed by making the electrode material into a thin film by a method, such as a vapor deposition method or a sputtering method. When getting the light emitted from the light emitting layer through the anode, the transmittance of anode to visible light is preferably 10% or more. The sheet resistance of anode is preferably several hundreds $\Omega/\square$ or less. The film thickness of anode depends upon the kind of material and generally 10 nm to 1 µm, preferably 10 to 200 nm.

Cathode

The cathode injects electrons to the electron injecting layer, the electron transporting layer or the light emitting layer, and formed preferably by a material having a small work function. Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy. Like the anode, the cathode is formed by making the material into a thin film by a method, such as the vapor deposition method and the sputtering method. The emitted light may be taken through the cathode, if necessary.

Light Emitting Layer

The light emitting layer is an organic layer having a light emitting function and contains a host material and a dopant material when a doping system is employed. The major function of the host material is to promote the recombination of electrons and holes and confine excitons in the light emitting layer. The dopant material causes the excitons generated by recombination to emit light efficiently.

In case of a phosphorescent device, the major function of the host material is to confine the excitons generated on the dopant in the light emitting layer.

To control the carrier balance in the light emitting layer, the light emitting layer may be made into a double host (host/co-host) layer, for example, by combinedly using an electron transporting host and a hole transporting host.

The light emitting layer may be made into a double dopant layer, in which two or more kinds of dopant materials having high quantum yield are combinedly used and each dopant material emits light with its own color. For example, to obtain a yellow emission, a light emitting layer formed by co-depositing a host, a red-emitting dopant and a green-emitting dopant is used.

In a laminate of two or more light emitting layers, electrons and holes are accumulated in the interface between the light emitting layers, and therefore, the recombination region is localized in the interface between the light emitting layers, to improve the quantum efficiency.

The easiness of hole injection to the light emitting layer and the easiness of electron injection to the light emitting layer may be different from each other. Also, the hole transporting ability and the electron transporting ability each being expressed by mobility of holes and electrons in the light emitting layer may be different from each other.

The light emitting layer is formed, for example, by a known method, such as a vapor deposition method, a spin coating method, and LB method. The light emitting layer can be formed also by making a solution of a binder, such as resin, and the material for the light emitting layer in a solvent into a thin film by a method such as spin coating.

The light emitting layer is preferably a molecular deposit film. The molecular deposit film is a thin film formed by depositing a vaporized material or a film formed by solidifying a material in the state of solution or liquid. The molecular deposit film can be distinguished from a thin film formed by LB method (molecular build-up film) by the differences in the assembly structures and higher order structures and the functional difference due to the structural differences.

The phosphorescent dopant (phosphorescent material) used in the light emitting layer is a compound which emits light by releasing the energy of excited triplet state and preferably a organometallic complex comprising at least one metal selected from Ir, Pt, Os, Au, Cu, Re, and Ru and a ligand, although not particularly limited thereto as long as emitting light by releasing the energy of excited triplet state. The ligand is preferably ortho-metallated. In view of obtaining a high phosphorescent quantum yield and further improving the external quantum efficiency of luminescent device, a metal complex comprising a metal selected from Ir, Os, and Pt is preferred, a metal complex, such as an iridium complex, an osmium complex and a platinum complex, particularly an ortho-metallated complex is more preferred, an iridium complex and a platinum complex are still more preferred, and an ortho-metallated iridium complex is particularly preferred.

The content of the phosphorescent dopant in the light emitting layer is not particularly limited and selected according to the use of the device, and preferably 0.1 to 70% by mass, and more preferably 1 to 30% by mass. If being 0.1% by mass or more, the amount of light emission is sufficient. If being 70% by mass or less, the concentration quenching can be avoided.
Preferred examples of the organometallic complex for the phosphorescent dopant are shown below.
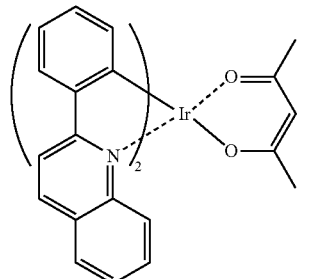
PQIr
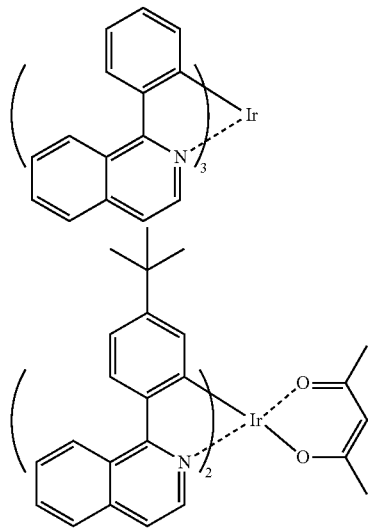
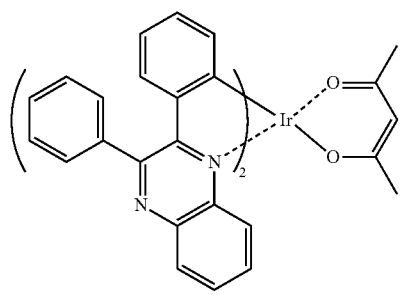
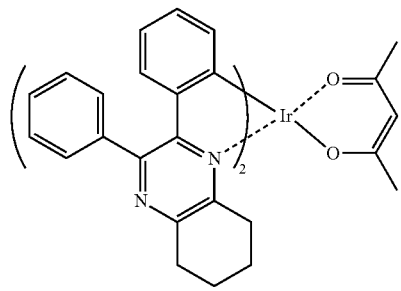
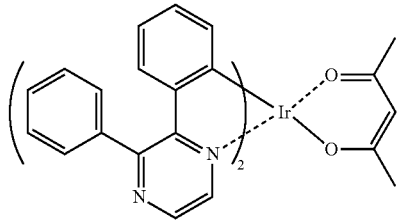
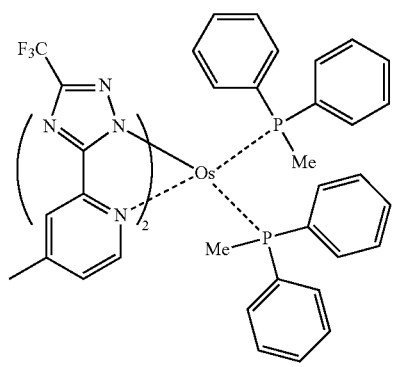
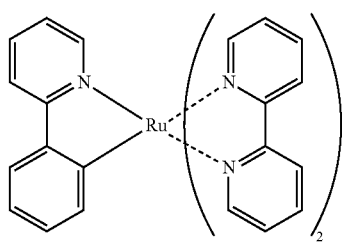
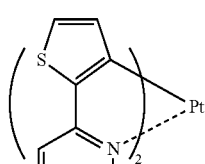
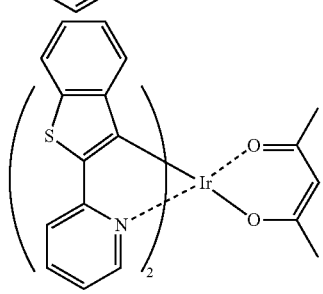
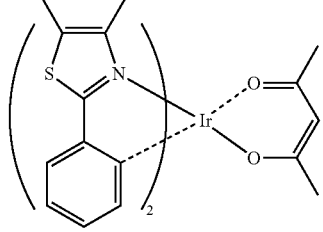

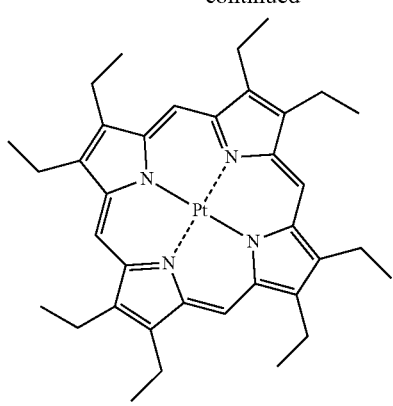
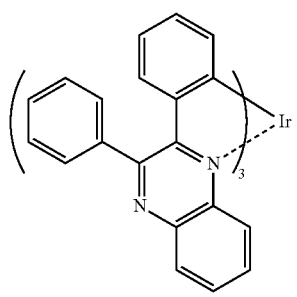
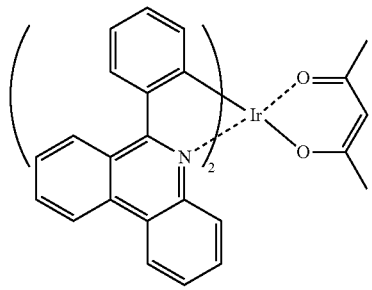
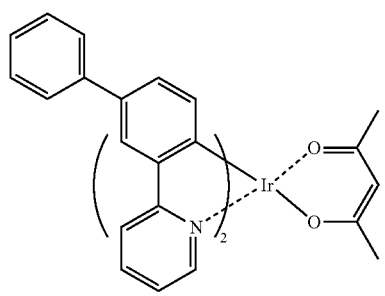
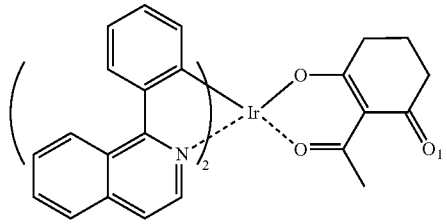
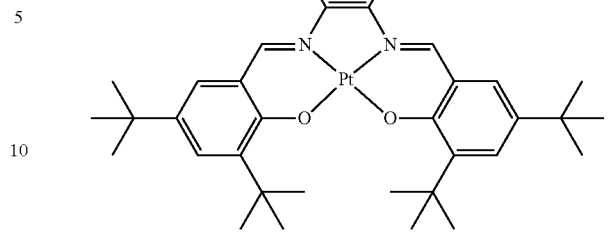
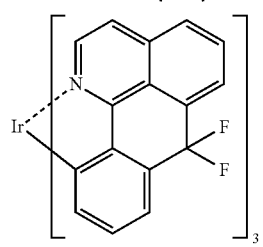
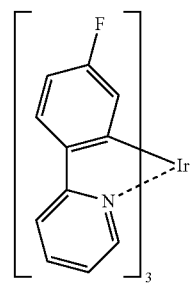
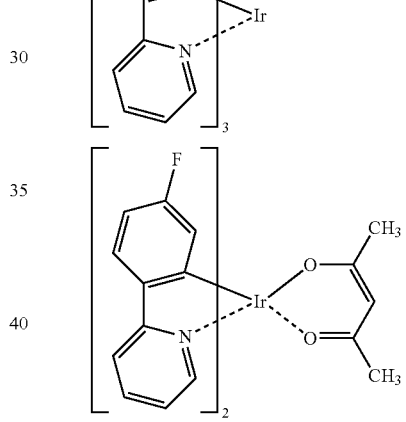
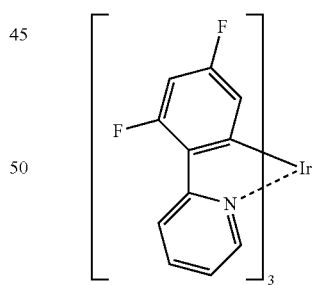
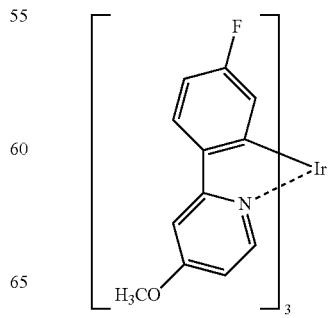

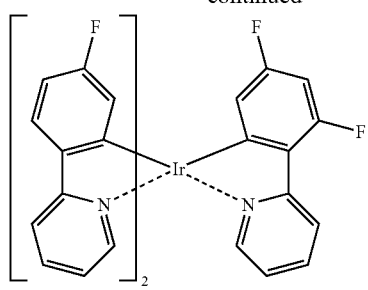
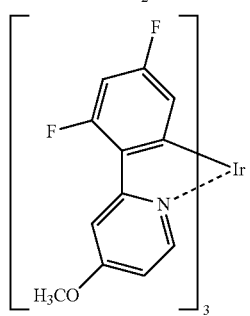
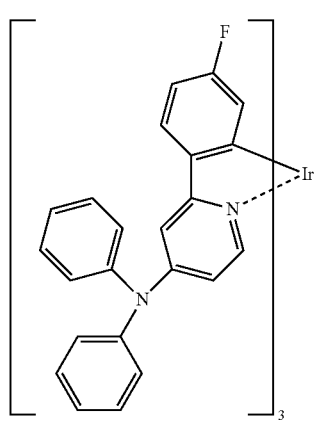
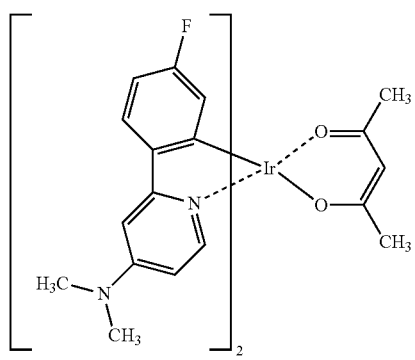
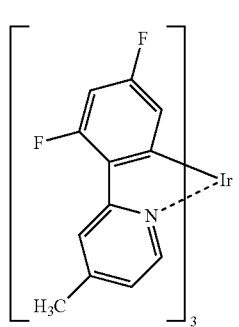
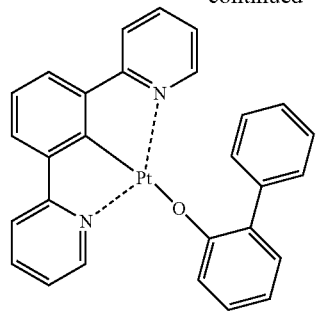
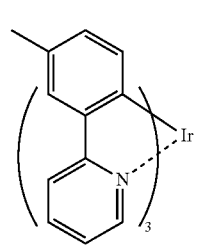
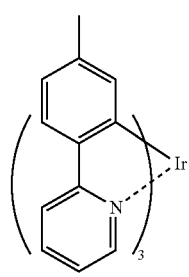
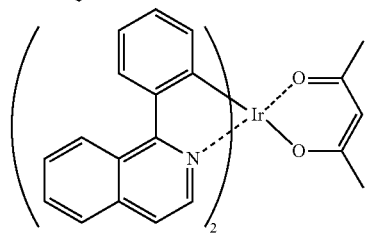
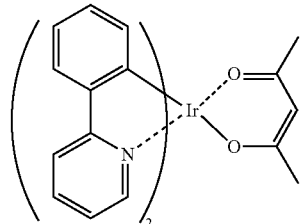
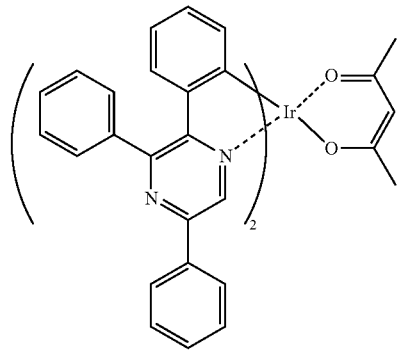

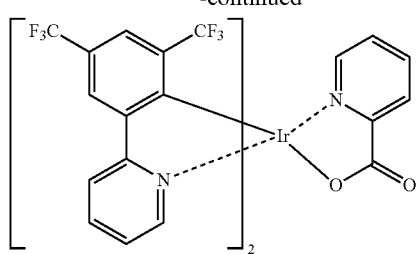
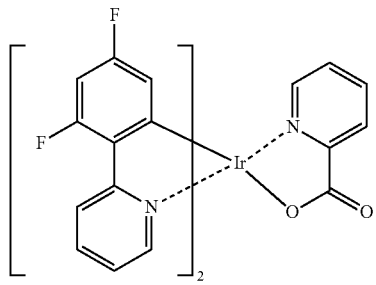
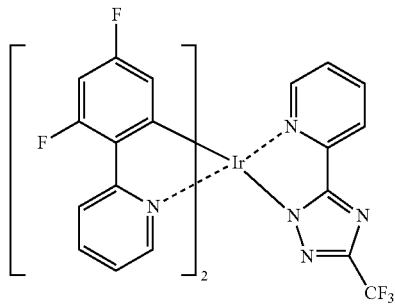
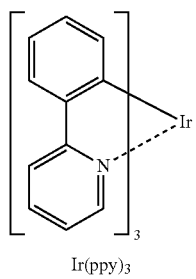
Ir(ppy)₃
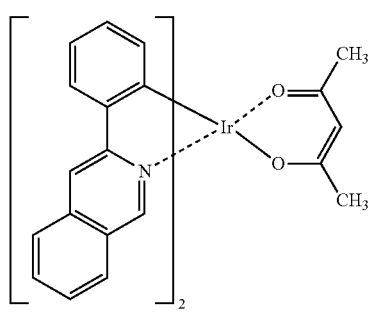
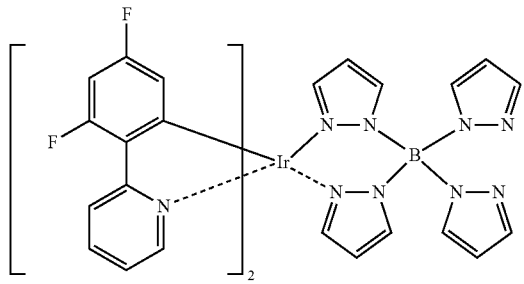
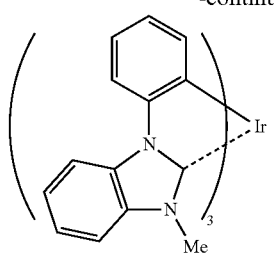
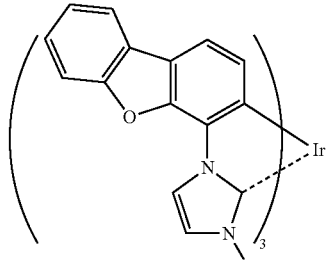
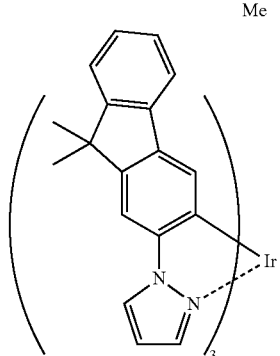
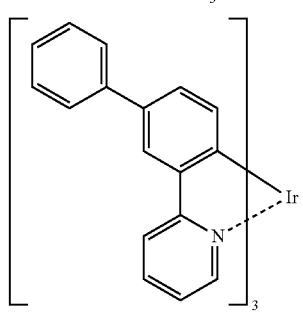
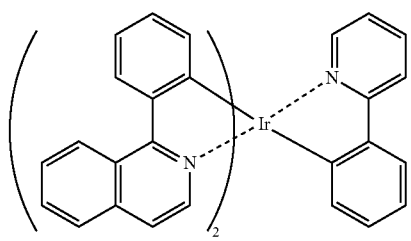
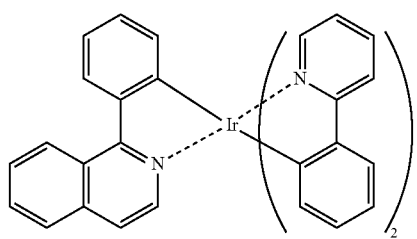

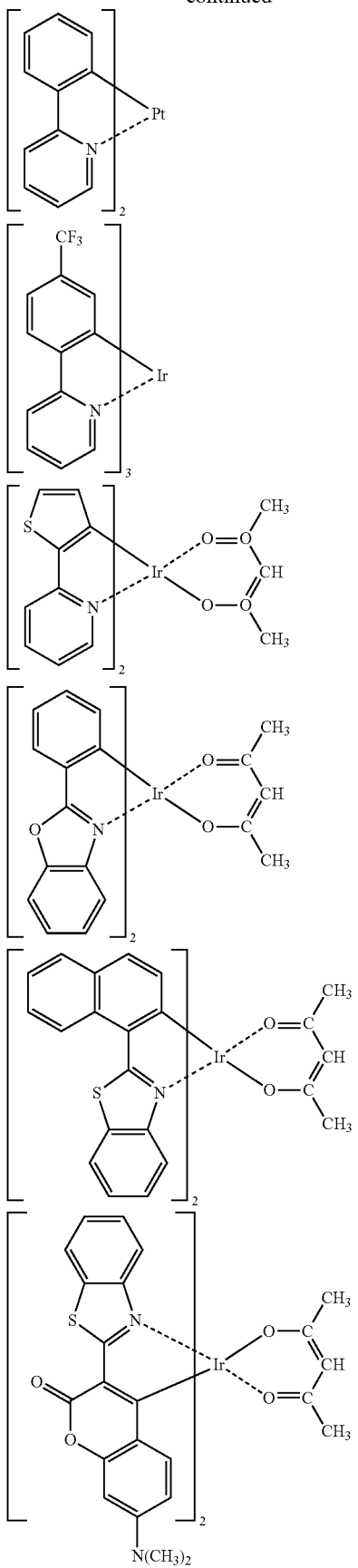
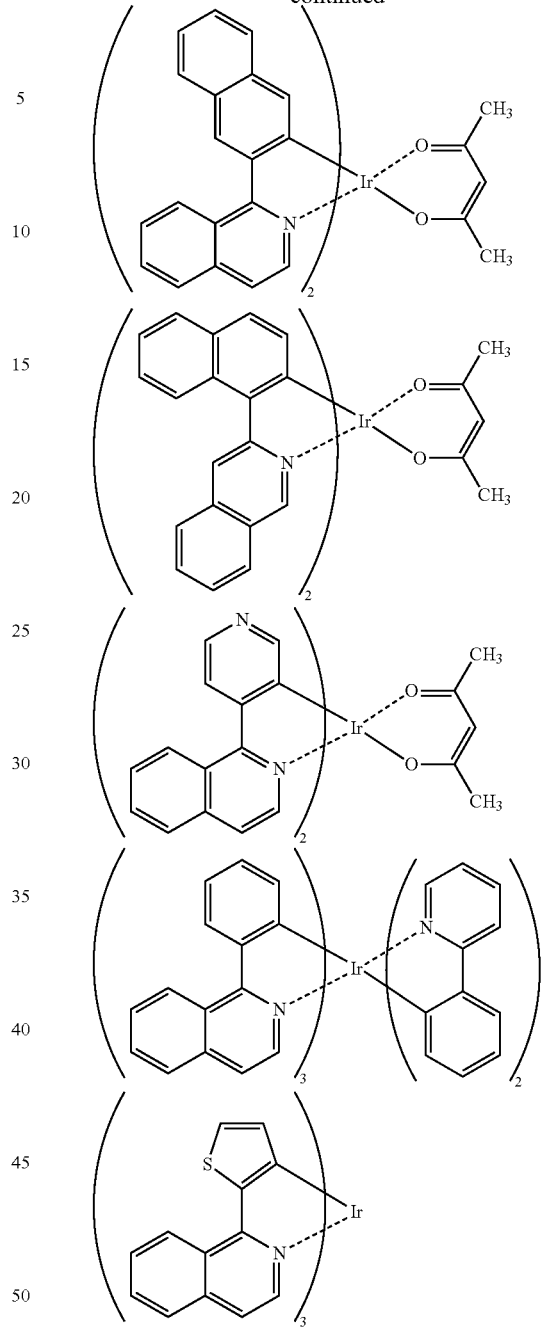

The phosphorescent host is a compound which confines the triplet energy of the phosphorescent dopant efficiently in the light emitting layer to cause the phosphorescent dopant to emit light efficiently. Although the material for organic EL device is useful as a phosphorescent host, a compound other than the material for organic EL device may be used as the phosphorescent host according to the use of the device.

The material for organic EL device and the compound other than it may be combinedly used in the same light emitting layer as the phosphorescent host material. If two or more light emitting layers are formed, the material for organic EL device can be used in one of the light emitting layers as the phosphorescent host material and a compound other than the material for organic EL device can be used in another light emitting layer as the phosphorescent host material. The material for organic EL device may be used in an organic layer other than the light emitting layer. In this case, a compound other than the material for organic EL device may be used as a phosphorescent host of the light emitting layer.

Examples of the preferred phosphorescent host other than the material for organic EL device include a carbazole derivative, a triazole derivative, a oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic methylidene compound, a porphyrin compound, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, a tetracarboxylic anhydride of fused ring such as naphthalene and perylene, a phthalocyanine derivative, a metal complex of 8-quinolinol derivative, metal phthalocyanine, metal complexes having a ligand such as benzoxazole and benzothiazole, an electroconductive oligomer, such as a polysilane compound, a poly(N-vinylcarbazole) derivative, an aniline copolymer, thiophene oligomer, and a polythiophene, and a polymer such as a polythiophene derivative, a polyphenylene derivative, a polyphenylenevinylene derivative, and a polyfluorene derivative. These phosphorescent hosts may be used alone or in combination of two or more. Examples thereof are shown below.

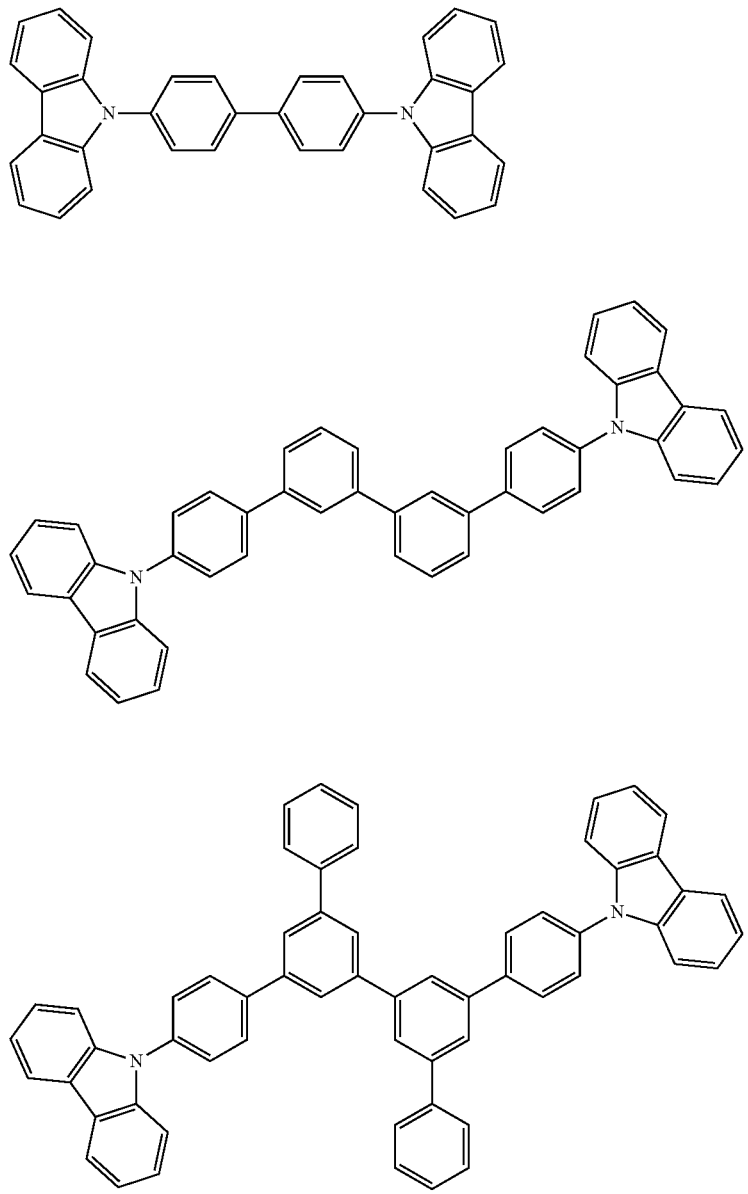

-continued

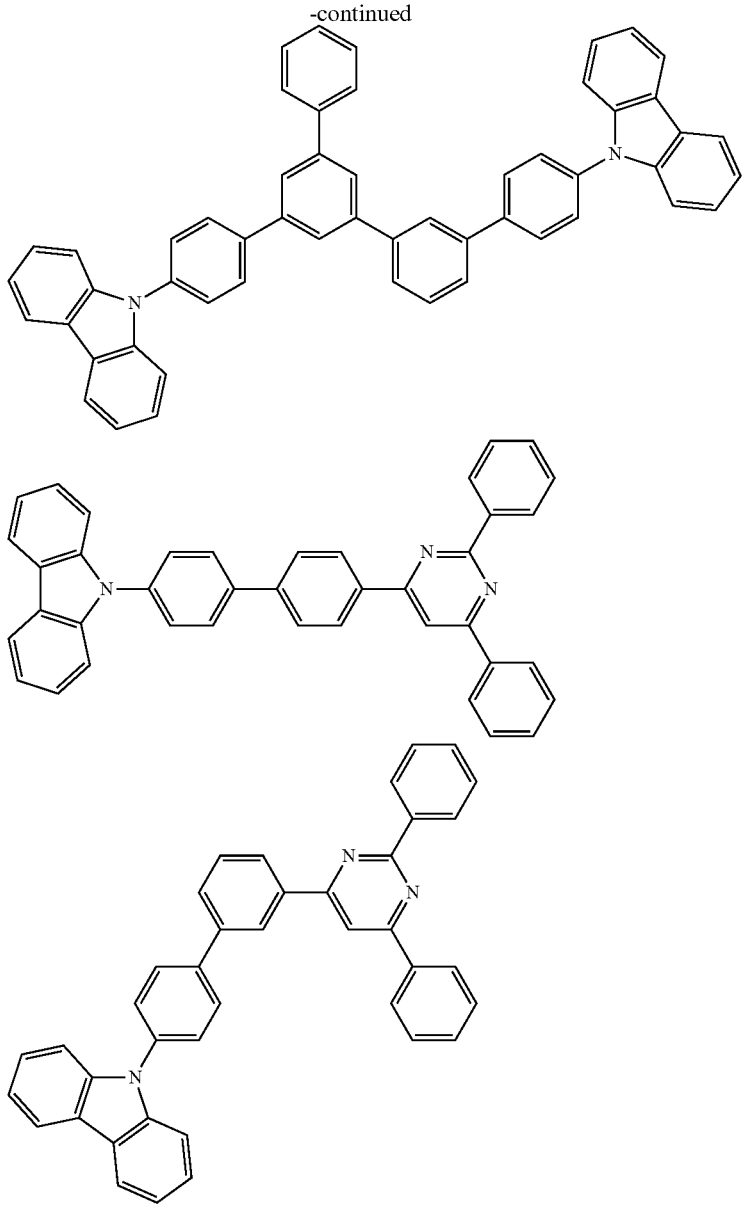

The organic EL device may comprise a light emitting layer comprising a fluorescent material, i.e., a fluorescent emitting layer. The fluorescent emitting layer may be formed from a known fluorescent material, for example, at least one material selected from an anthracene derivative, a fluoranthene derivative, a styrylamine derivative, and an arylamine derivative, with the anthracene derivative and the arylamine derivative being more preferred. In particular, the anthracene derivative is preferably used as the host material and the arylamine derivative is preferably used as the dopant. The materials described in WO 2010/134350 and WO 2010/134352 are preferably used. The material for organic EL device may be used in a fluorescent emitting layer as a fluorescent emitting material or a host material.

The anthracene derivative for use as a fluorescent material has preferably 26 to 100, more preferably 26 to 80, and still more preferably 26 to 60 ring carbon atoms. The anthracene derivative is preferably represented by formula (10):

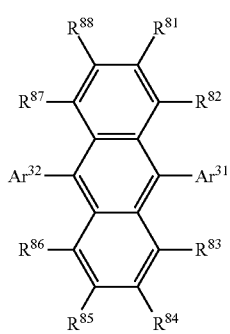

(10)

wherein:

each of $Ar^{31}$ and $Ar^{32}$ independently represents a substituted or unsubstituted aryl group having 6 to 50 ring carbon atoms or a substituted or unsubstituted heteroaryl group having 5 to 50 ring atoms; and each of $R^{81}$ to $R^{88}$ independently represents a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group, or a hydroxyl group.

The aryl group having 6 to 50 ring carbon atoms is preferably an aryl group having 6 to 40 ring carbon atoms and more preferably an aryl group having 6 to 30 ring carbon atoms.

The heterocyclic group having 5 to 50 ring atoms is preferably a heterocyclic group having 5 to 40 ring atoms and more preferably a heterocyclic group having 5 to 30 ring atoms.

The alkyl group having 1 to 50 carbon atoms is preferably an alkyl group having 1 to 30 carbon atoms, more preferably an alkyl group having 1 to 10 carbon atoms, and still more preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, and still more preferably an alkoxy group having 1 to 5 carbon atoms.

The aralkyl group having 7 to 50 carbon atoms is preferably an aralkyl group having 7 to 30 carbon atoms and more preferably an aralkyl group having 7 to 20 carbon atoms.

The aryloxy group having 6 to 50 ring carbon atoms is preferably an aryloxy group having 6 to 40 ring carbon atoms and more preferably an aryloxy group having 6 to 30 ring carbon atoms.

The arylthio group having 6 to 50 ring carbon atoms is preferably an arylthio group having 6 to 40 ring carbon atoms and more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, and still more preferably an alkoxycarbonyl group having 2 to 5 carbon atoms.

Examples of the halogen atom include a fluorine atom, a chlorine atom, and a bromine atom.

Each of $Ar^{31}$ and $Ar^{32}$ particularly preferably represents a substituted or unsubstituted aryl group having 6 to 50 ring carbon atoms.

The anthracene derivative represented by formula (10) is preferably represented by formula (10-1):

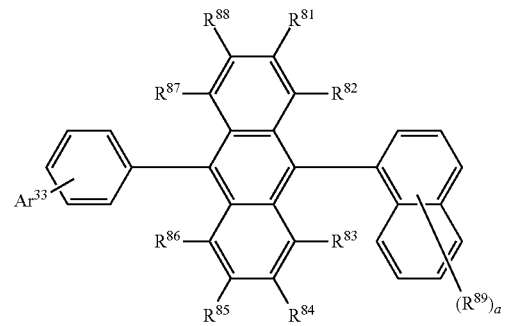

(10-1)

wherein:

$Ar^{33}$ represents a substituted or unsubstituted aryl group having 6 to 50 ring carbon atoms or a substituted or unsubstituted heterocyclic group having 5 to 50 ring atoms;

each of $R^{81}$ to $R^{88}$ is as defined above;

$R^{89}$ is defined in the same manner as in $R^{81}$ to $R^{88}$; and a is an integer of 1 to 7.

Preferred examples of $R^{81}$ to $R^{88}$ are as described above. Preferred examples of $R^{89}$ are the same as those of $R^{81}$ to $R^{88}$. The subscript a is preferably an integer of 1 to 3 and more preferably 1 or 2.

The aryl group having 6 to 50 ring carbon atoms for $Ar^{33}$ is preferably an aryl group having 6 to 40 ring carbon atoms, more preferably an aryl group having 6 to 30 ring carbon atoms, still more preferably an aryl group having 6 to 20 ring carbon atoms, and particularly preferably an aryl group having 6 to 12 ring carbon atoms.

The arylamine derivative for use as the fluorescent material is preferably an aryldiamine derivative, more preferably an aryldiamine derivative comprising a pyrene skeleton, and still more preferably an aryldiamine derivative having a pyrene skeleton and a dibenzofuran skeleton.

The aryldiamine derivative is preferably an aryldiamine derivative represented by formula (11):

(11)

wherein:

each of $Ar^{34}$ to $Ar^{37}$ independently represents a substituted or unsubstituted aryl group having 6 to 50 ring carbon atoms or a substituted or unsubstituted heteroaryl group having 5 to 50 ring atoms; and $L^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, still more preferably an aryl group having 6 to 12 ring carbon atoms, with a phenyl group and a naphthyl group being particularly preferred.

The heteroaryl group having 5 to 50 ring atoms is preferably a heteroaryl group having 5 to 40 ring atoms, more preferably a heteroaryl group having 5 to 30 ring atoms, and still more preferably a heteroaryl group having 5 to 20 ring atoms, for example, a carbazolyl group, a dibenzofuranyl group and dibenzothiophenyl group, with a dibenzofuranyl group being preferred. Preferred examples of the substituent for the heteroaryl group include an aryl group having 6 to 30, preferably 6 to 20, and more preferably 6 to 12 ring carbon atoms, with a phenyl group and a naphthyl group being more preferred.

The arylene group having 6 to 50 ring carbon atoms is preferably an arylene group having 6 to 40 ring carbon atoms, more preferably an arylene group having 6 to 30 ring carbon atoms, and still more preferably an arylene group having 6 to 20 ring carbon atoms, with a pyrenyl group being particularly preferred.

A double host (host/co-host) system may be used for the light emitting layer. For example, to control the carrier balance in the light emitting layer, an electron transporting host and a hole transporting host may be combinedly used.

The light emitting layer may be also made into a double dopant layer. When two or more kinds of dopant materials having high quantum yield are used in the light emitting layer, each dopant emits light with its own color. For example, a yellow light emitting layer can be obtained by co-depositing a host, a red-emitting dopant and a green-emitting dopant.

The light emitting layer may further comprise a hole transporting material, an electron transporting material, and a polymer binder, if necessary.

The thickness of the light emitting layer is preferably 5 to 50 nm, more preferably 7 to 50 nm and most preferably 10 to 50 nm. If less than 5 nm, the light emitting layer may be difficult to form and the color may be difficult to control. If exceeding 50 nm, the driving voltage is likely to increase.

Electron-donating Dopant

The organic EL device preferably comprises an electron-donating dopant at an interfacial region between the cathode and the emitting unit. With such a construction, the organic EL device has an improved luminance and an elongated lifetime. The electron-donating dopant comprises a metal having a work function of 3.8 eV or less and examples thereof include at least one selected from alkali metal, alkali metal complex, alkali metal compound, alkaline earth metal, alkaline earth metal complex, alkaline earth metal compound, rare earth metal, rare earth metal complex, and rare earth metal compound.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs. Examples of the alkaline earth metal include Ca (work function: 2.9 eV), Sr (work function: 2.0 to 2.5 eV), and Ba (work function: 2.52 eV), with those having a work function of 2.9 eV or less being particularly preferred. Examples of the rare earth metal include Sc, Y, Ce, Tb, and Yb, with those having a work function of 2.9 eV or less being particularly preferred.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred. Examples of the alkaline earth metal compound include BaO, SrO, CaO, and mixture thereof, such as $Ba_xSr_{1-x}O$ (0<x<1) and $Ba_xCA_{1-x}O$ (0<x<1), with BaO, SrO, and CaO being preferred. Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal are not particularly limited as long as containing at least one metal ion selected from alkali metal ions, alkaline earth metal ions, and rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The electron-donating dopant is added to the interfacial region preferably into a form of layer or island. The electron-donating dopant is added preferably by co-depositing the electron-donating dopant with the organic compound (light emitting material, electron injecting material) for forming the interfacial region by a resistance heating deposition method, thereby dispersing the electron-donating dopant into the organic material. The disperse concentration expressed by the molar ratio of the organic material and the electron-donating dopant is 100:1 to 1:100 and preferably 5:1 to 1:5.

When the electron-donating dopant is formed into a form of layer, a light emitting material or an electron injecting material is made into a layer which serves as an organic layer in the interface, and then, the electron-donating dopant alone is deposited by a resistance heating deposition method into a layer having a thickness preferably 0.1 to 15 nm. When the electron-donating dopant is formed into a form of island, a light emitting material or an electron injecting material is made into a form of island which serves as an organic layer in the interface, and then, the electron-donating dopant alone is deposited by a resistance heating deposition method into a form of island having a thickness preferably 0.05 to 1 nm.

The molar ratio of the main component and the electron-donating dopant in the organic electroluminescence device is preferably 5:1 to 1:5 and more preferably 2:1 to 1:2.

Electron Transporting Layer

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer injects electrons from the cathode to the organic layer unit efficiently. The material for organic EL devices of the invention may be used in the electron transporting layer as the electron transporting material.

An aromatic heterocyclic compound having one or more heteroatoms in a molecule thereof is preferably used as an electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring, or a fused aromatic ring compound having a nitrogen-containing, 6- or 5-membered ring.

The nitrogen-containing ring derivative is preferably, for example, a metal chelate complex of a nitrogen-containing ring represented by formula (A):

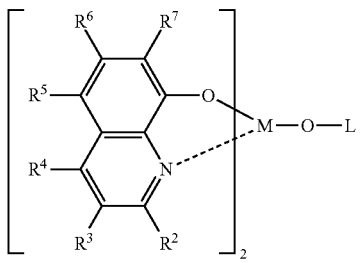
(A)

wherein each of $R^2$ to $R^7$ independently represents a hydrogen atom, a heavy hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or an aromatic heterocyclic group having 5 to 50 ring carbon atoms, each being optionally substituted.

The halogen atom may include fluorine, chlorine, bromine, and iodine.

The substituted amino group may include an alkylamino group, an arylamino group, and an aralkylamino group.

The alkylamino group and the aralkylamino group are represented by —$NQ^1Q^2$. Each of $Q^1$ and $Q^2$ independently represents an alkyl group having 1 to 20 carbon atoms or an aralkyl group having 1 to 20 carbon atoms. One of $Q^1$ and $Q^2$ may be a hydrogen atom or a heavy hydrogen atom.

The arylamino group is represented by —$NAr^1Ar^2$, wherein each of $Ar^1$ and $Ar^2$ independently represents a non-fused aromatic hydrocarbon groups or a fused aromatic hydrocarbon groups, each having 6 to 50 carbon atoms. One of $Ar^1$ and $Ar^2$ may be a hydrogen atom or a heavy hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by —COOY', wherein Y' is an alkyl group having 1 to 20 carbon atoms.

M is aluminum (Al), gallium (Ga), or indium (In), with In being preferred.

L is a group represented by formula (A') or (A"):

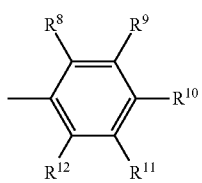
(A')

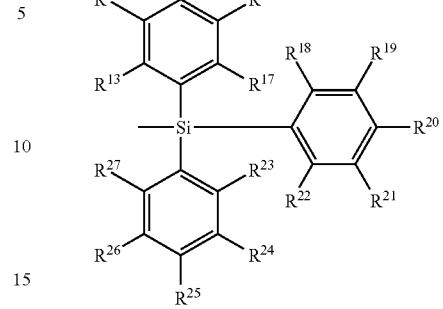
(A")

wherein each $R^8$ to $R^{12}$ independently represents a hydrogen atom, a heavy hydrogen atom or a substituted or unsubstituted hydrocarbon group having 1 to 40 carbon atoms. Two neighboring groups may form a ring structure. Each of $R^{13}$ to $R^{27}$ independently represents a hydrogen atom, a heavy hydrogen atom or a substituted or unsubstituted hydrocarbon group having 1 to 40 carbon atoms. Two neighboring groups may form a ring structure.

Examples of the hydrocarbon group having 1 to 40 carbon atoms for $R^8$ to $R^{12}$ and $R^{13}$ to $R^{27}$ in formulae (A') and (A") are the same as those described above with respect to $R^2$ to $R^7$ of formula (A). Examples of the divalent group formed by two neighboring groups of $R^8$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

The electron transporting compound for use in the electron transporting layer is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid including a chelated oxine (generally, 8-quinolinol or 8-hydroxyquinoline), for example, tris(8-quinolinol) aluminum. Examples of the oxadiazole derivative are shown below:

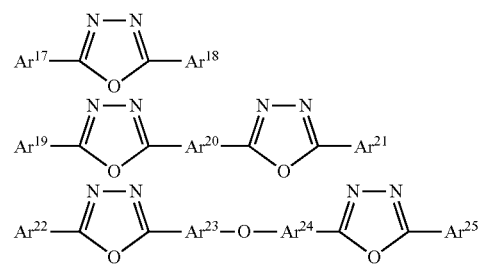

wherein each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted fused aromatic hydrocarbon group each having 6 to 50 carbon atoms, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the fused aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

Each of Ar²⁰, Ar²³, and Ar²⁴ is a substituted or unsubstituted bivalent aromatic hydrocarbon group or a substituted or unsubstituted bivalent fused aromatic hydrocarbon group each having 6 to 50 carbon atoms, and Ar²³ and Ar²⁴ may be the same or different. Examples of the bivalent aromatic hydrocarbon group or the bivalent fused aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

Electron transporting compounds which have a good thin film-forming property are preferably used. Examples of the electron transporting compound are shown below.

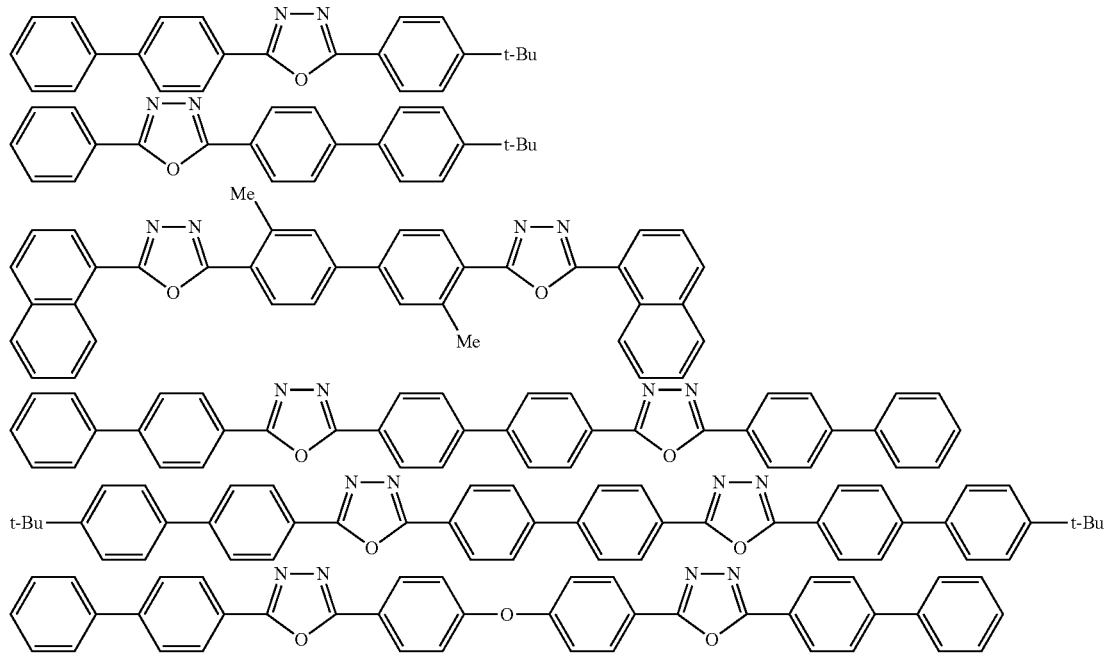

Examples of the nitrogen-containing heterocyclic derivative for use as the electron transporting compound include a nitrogen-containing heterocyclic derivative having the following formulae but exclusive of metal complex, for example, a compound having a 5- or 6-membered ring which has the skeleton represented by formula (B) or having the structure represented by formula (C):

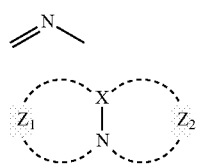

wherein X is a carbon atom or a nitrogen atom and each of $Z_1$ and $Z_2$ independently represents a group of atoms for completing the nitrogen-containing heterocyclic ring.

The nitrogen-containing heterocyclic derivative is more preferably an organic compound which has a nitrogen-containing aromatic polycyclic ring comprising a 5-membered ring or a 6-membered ring. If two or more nitrogen atoms are included, the nitrogen-containing aromatic polycyclic compound preferably has a skeleton of a combination of (B) and (C) or a combination of (B) and (D):

The nitrogen-containing group of the nitrogen-containing aromatic polycyclic compound is selected, for example, from the nitrogen-containing heterocyclic groups shown below:

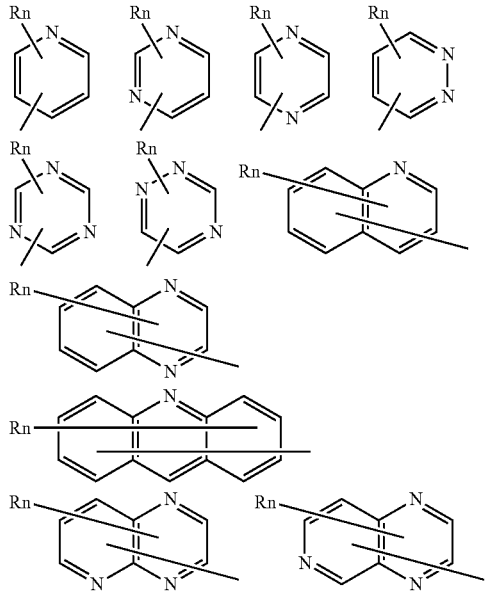

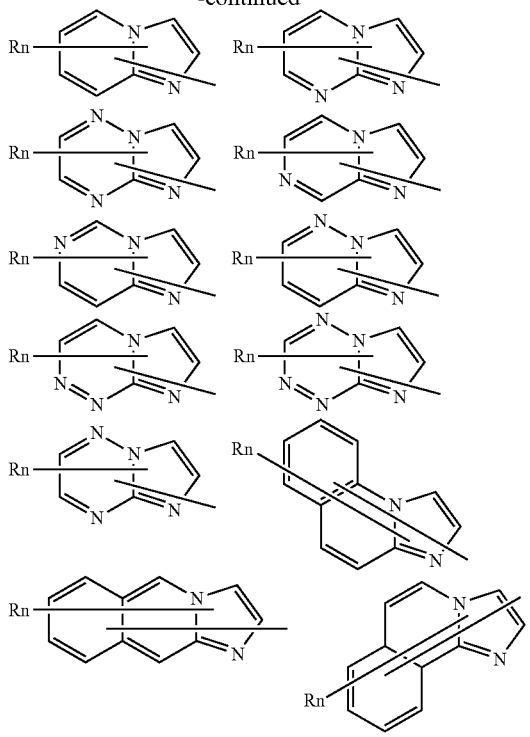

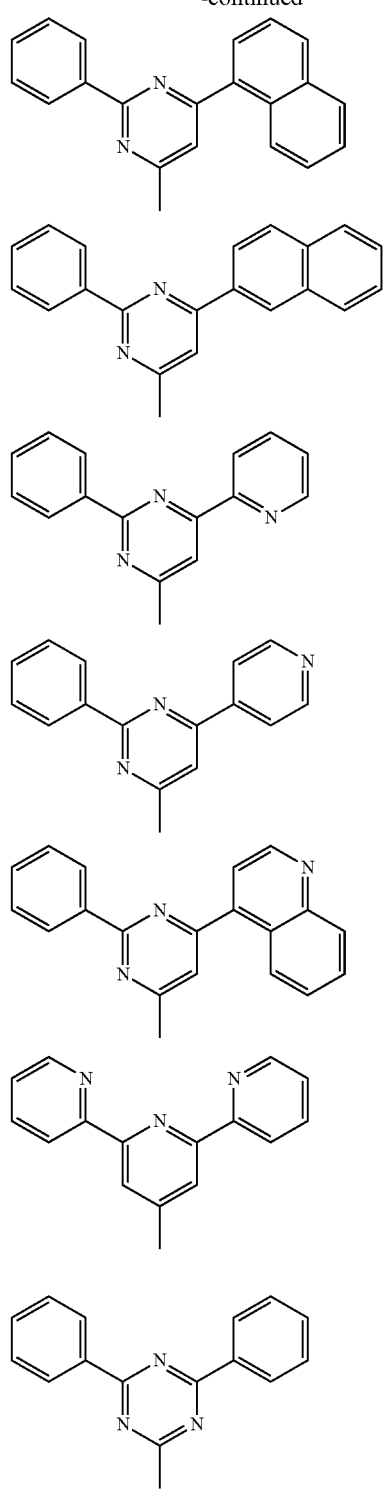

wherein R is an aromatic hydrocarbon group or a fused aromatic hydrocarbon group each having 6 to 40 carbon atoms, an aromatic heterocyclic group or a fused aromatic heterocyclic group each having 3 to 40 carbon atoms, an alkyl group having 1 to 20 carbon atoms, or an alkoxy group having 1 to 20 carbon atoms; and n is an integer of 0 to 5. If n is an integer of 2 or more, groups R may be the same or different.

More preferred is a nitrogen-containing heterocyclic derivative represented by formula (D1):

$$HAr\text{-}L^1\text{-}Ar^1\text{—}Ar^2 \quad (D1)$$

wherein HAr is a substituted or unsubstituted nitrogen-containing heterocyclic group having 3 to 40 carbon atoms; $L^1$ is a single bond, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; $Ar^1$ is a substituted or unsubstituted divalent aromatic hydrocarbon group having 6 to 40 carbon atoms; and $Ar^2$ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms.

HAr is selected, for example, from the following groups:

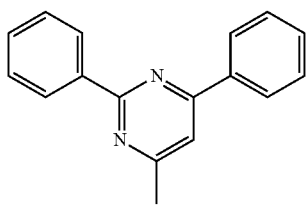

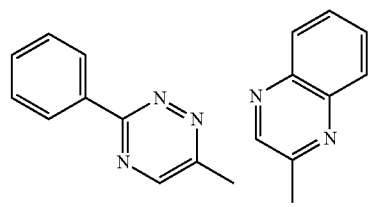

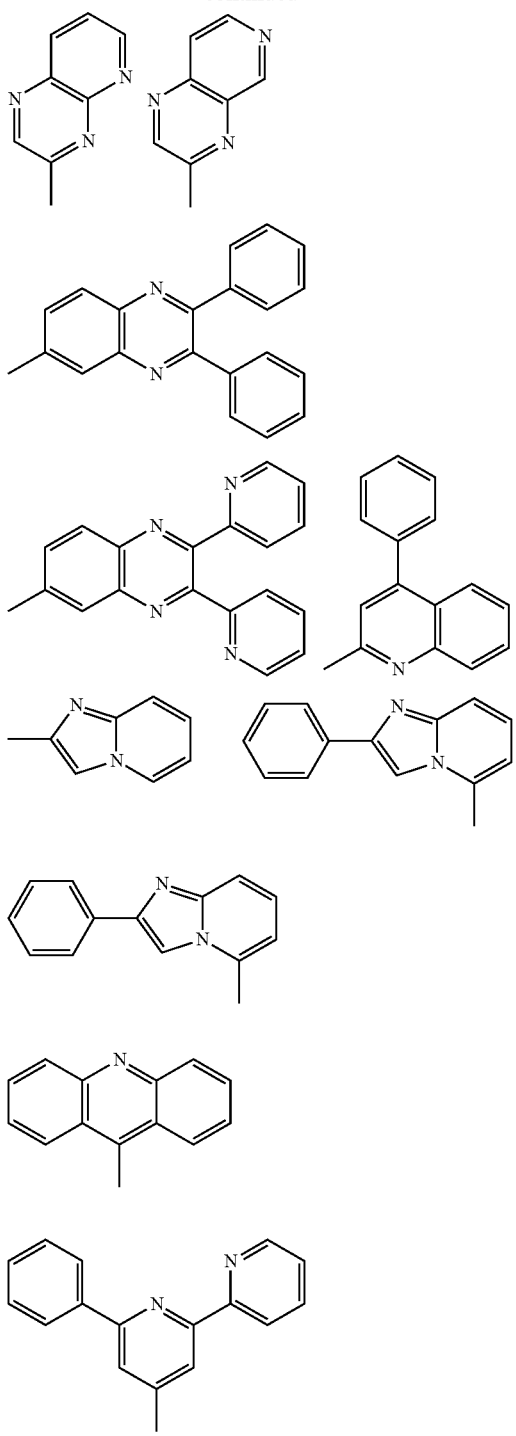

L¹ is selected, for example, from the following groups:

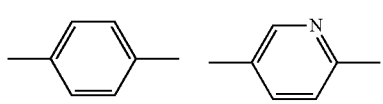

Ar¹ is selected, for example, from the following arylanthranyl group represented by formula (D2) or (D3):

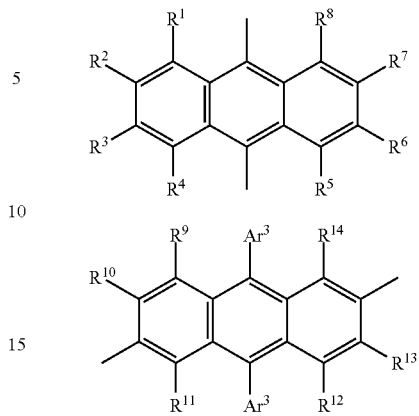

wherein R¹ to R¹⁴ are each independently a hydrogen atom, a halogen atom, an alkyl group having 1 to 20 carbon atoms, an alkoxy group having 1 to 20 carbon atoms, an aryloxy group having 6 to 40 carbon atoms, a substituted or unsubstituted aromatic hydrocarbon group or fused aromatic hydrocarbon group each having 6 to 40 carbon atoms, or a substituted or unsubstituted aromatic heterocyclic group or fused aromatic heterocyclic group each having 3 to 40 carbon atoms; and Ar³ is a substituted or unsubstituted aromatic hydrocarbon group or fused aromatic hydrocarbon group each having 6 to 40 carbon atoms or a substituted or unsubstituted aromatic heterocyclic group or fused aromatic heterocyclic group each having 3 to 40 carbon atoms. Each of R¹ to R⁸ may be selected from a hydrogen atom and a heavy hydrogen atom.

Ar² is selected, for example, from the following groups:

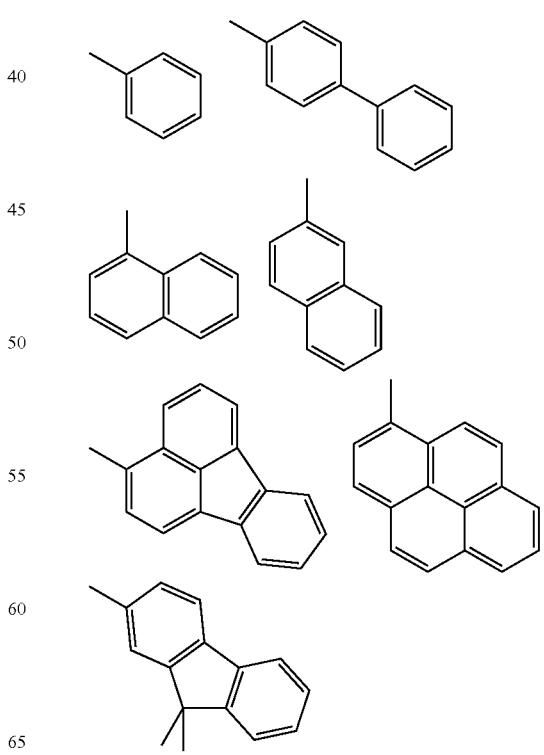

In addition, the following compound is preferably used as the nitrogen-containing aromatic polycyclic compound for use as the electron transporting compound:

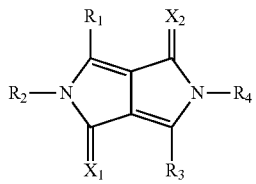
(D4)

wherein $R^1$ to $R^4$ each independently represent a hydrogen atom, a heavy hydrogen atom, a substituted or unsubstituted aliphatic group having 1 to 20 carbon atoms, a substituted or unsubstituted alicyclic group having 3 to 20 carbon atoms, a substituted or unsubstituted aromatic ring group having 6 to 50 carbon atoms, or a substituted or unsubstituted heterocyclic group having 3 to 50 carbon atoms; and $X_1$ and $X_2$ each independently represent an oxygen atom, a sulfur atom, or dicyanomethylene group.

Further, the following compound is also suitable as the electron transporting compound:

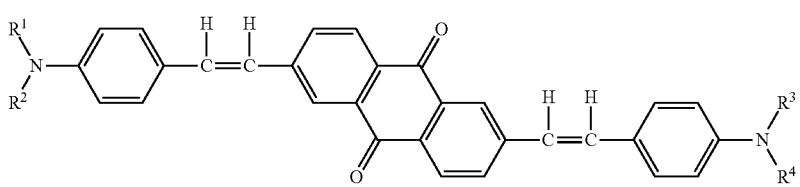
(D5)

wherein $R^1$, $R^2$, $R^3$, and $R^4$ may be the same or different and each represents an aromatic hydrocarbon group or a fused aromatic hydrocarbon group each represented by formula (D6):

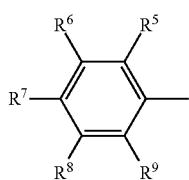
(D6)

wherein $R^5$, $R^6$, $R^7$, $R^8$, and $R^9$ may be the same or different and each represents a hydrogen atom, a heavy hydrogen atom, a saturated or unsaturated alkoxyl group having 1 to 20 carbon atoms, a saturated or unsaturated alkyl group having 1 to 20 carbon atoms, an amino group, or an alkylamino group having 1 to 20 carbon atoms. At least one of $R^5$, $R^6$, $R^7$, $R^8$, and $R^9$ represents a group other than a hydrogen atom and a heavy hydrogen atom.

Further, a polymer including the nitrogen-containing heterocyclic group or the nitrogen-containing heterocyclic derivative is also usable as the electron transporting compound.

The electron transporting layer in the organic EL device of the invention preferably comprises at least one compound selected from the nitrogen-containing heterocyclic derivatives represented by formulae (E) to (G):

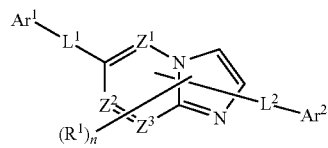
(E)

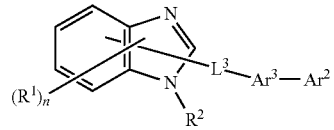
(F)

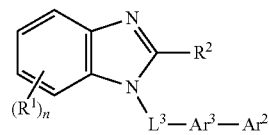
(G)

wherein $Z^1$, $Z^2$, and $Z^3$ each independently represent a nitrogen atom or a carbon atom;

$R^1$ and $R^2$ each independently represent a substituted or unsubstituted aryl group having 6 to 50 ring carbon atoms, a substituted or unsubstituted heteroaryl group having 5 to 50 ring atoms, a substituted or unsubstituted alkyl group having 1 to 20 carbon atoms, a substituted or unsubstituted haloalkyl group having 1 to 20 carbon atoms, or a substituted or unsubstituted alkoxyl group having 1 to 20 carbon atoms;

n is an integer of 0 to 5, when n is an integer of 2 or more, groups $R^1$ may be the same or different, and neighboring two groups $R^1$ may bond to each other to form a substituted or unsubstituted hydrocarbon ring;

$Ar^1$ represents a substituted or unsubstituted aryl group having 6 to 50 ring carbon atoms or a substituted or unsubstituted heteroaryl group having 5 to 50 ring atoms;

$Ar^2$ represents a hydrogen atom, a substituted or unsubstituted alkyl group having 1 to 20 carbon atoms, a substituted or unsubstituted haloalkyl group having 1 to 20 carbon atoms, a substituted or unsubstituted alkoxyl group having 1 to 20 carbon atoms, a substituted or unsubstituted aryl group having 6 to 50 ring carbon atoms, or a substituted or unsubstituted heteroaryl group having 5 to 50 ring atoms;

provided that one of $Ar^1$ and $Ar^2$ is a substituted or unsubstituted condensed aromatic hydrocarbon ring group having 10 to 50 ring carbon atoms or a substituted or unsubstituted condensed aromatic heterocyclic group having 9 to 50 ring atoms;

$Ar^3$ represents a substituted or unsubstituted arylene group having 6 to 50 ring carbon atoms or a substituted or unsubstituted heteroarylene group having 5 to 50 ring atoms; and $L^1$, $L^2$, and $L^3$ each independently represent a single bond, a substituted or unsubstituted arylene group having 6 to 50 ring carbon atoms or a substituted or unsubstituted divalent condensed aromatic heterocyclic group having 9 to 50 ring atoms.

Examples of the aryl group having 6 to 50 ring carbon atoms include a phenyl group, a naphthyl group, an anthryl group, a phenanthryl group, a naphthacenyl group, a chrysenyl group, pyrenyl group, a biphenyl group, a terphenyl group, a tolyl group, a fluoranthenyl group, and a fluorenyl group.

Examples of the heteroaryl group having 5 to 50 ring atoms include a pyrrolyl group, a furyl group, a thiophenyl group, a silolyl group, a pyridyl group, a quinolyl group, an isoquinolyl group, a benzofuryl group, an imidazolyl group, a pyrimidyl group, a carbazolyl group, a selenophenyl group, an oxadiazolyl group, a triazolyl group, a pyrazinyl group, a pyridazinyl group, a triazinyl group, a quinoxalinyl group, an acridinyl group, an imidazo[1,2-a]pyridinyl group, an imidazo[1,2-a]pyrimidinyl, and a dibenzo[c,h]acridinyl group.

Examples of the alkyl group having 1 to 20 carbon atoms include a methyl group, an ethyl group, a propyl group, a butyl group, a pentyl group, and a hexyl group.

Examples of the haloalkyl group having 1 to 20 carbon atoms include the groups obtained by replacing one or more hydrogen atoms of the alkyl group mentioned above with at least one halogen atom selected from fluorine, chlorine, iodine, and bromine.

Examples of the alkyl moiety of the alkoxyl group having 1 to 20 carbon atoms include the alkyl group mentioned above.

Examples of the arylene groups include the groups obtained by removing one hydrogen atom from the aryl group mentioned above.

Examples of the divalent condensed aromatic heterocyclic group having 9 to 50 ring atoms include the groups obtained by removing one hydrogen atom from the condensed aromatic heterocyclic group mentioned above as the heteroaryl group.

The thickness of the electron transporting layer is preferably, but not particularly limited to, 1 to 100 nm.

Preferred examples of the material for an electron injecting layer optionally formed adjacent to the electron transporting layer include, in addition to the nitrogen-containing ring derivative, an inorganic compound, such as an insulating material and a semiconductor. The electron injecting layer containing the insulating material or the semiconductor effectively prevents the leak of electric current to enhance the electron injecting properties.

The insulating material is preferably at least one metal compound selected from the group consisting of alkali metal chalcogenides, alkaline earth metal chalcogenides, alkali metal halides and alkaline earth metal halides. The alkali metal chalcogenide, etc. mentioned above are preferred because the electron injecting properties of the electron injecting layer are further enhanced. Examples of preferred alkali metal chalcogenide include $Li_2O$, $K_2O$, $Na_2S$, $Na_2Se$ and $Na_2O$, and examples of preferred alkaline earth metal chalcogenide include CaO, BaO, SrO, BeO, BaS and CaSe. Examples of preferred alkali metal halide include LiF, NaF, KF, LiCl, KCl and NaCl. Examples of the alkaline earth metal halide include fluorides, such as $CaF_2$, $BaF_2$, $SrF_2$, $MgF_2$ and $BeF_2$, and halides other than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer may contain the electron-donating dopant mentioned above.

Hole Transporting Layer

The hole injecting/transporting layer is an organic layer formed between the light emitting layer and the anode and has a function of transporting holes from the anode to the light emitting layer. When the hole transporting layer is formed by two or more layers, the layer closer to the anode may be defined as the hole injecting layer in some cases. The hole injecting layer has a function of efficiently injecting holes from the anode to the organic layer unit. The material for organic EL devices of the invention may be used in the hole transporting layer as a hole transporting material.

Another preferred material for the hole transporting layer may include an aromatic amine compound, for example, an aromatic amine derivative represented by formula (H):

(H)

wherein:

each of $Ar^1$ to $Ar^4$ represents a substituted or unsubstituted aromatic hydrocarbon group or fused aromatic hydrocarbon group having 6 to 50 ring carbon atoms, a substituted or unsubstituted aromatic heteroaryl group or fused aromatic heteroaryl group having 5 to 50 ring atoms, or a group wherein the aromatic hydrocarbon group or fused aromatic hydrocarbon group is bonded to the aromatic heteroaryl group or fused aromatic heteroaryl group; and L represents a substituted or unsubstituted aromatic hydrocarbon group or fused aromatic hydrocarbon group having 6 to 50 ring carbon atoms or a substituted or unsubstituted aromatic heteroaryl group or fused aromatic heteroaryl group having 5 to 50 ring atoms.

Examples of the compound represented by formula (H) are shown below.

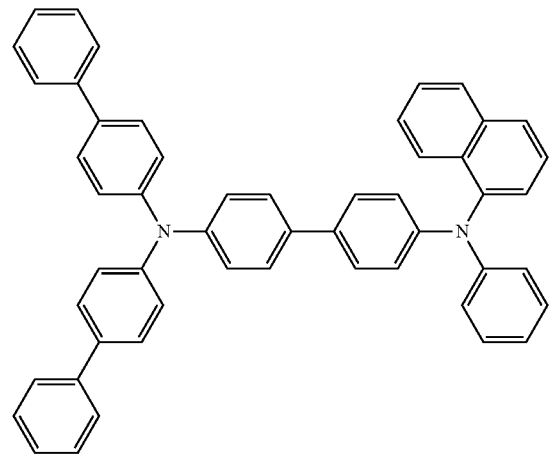

401
-continued
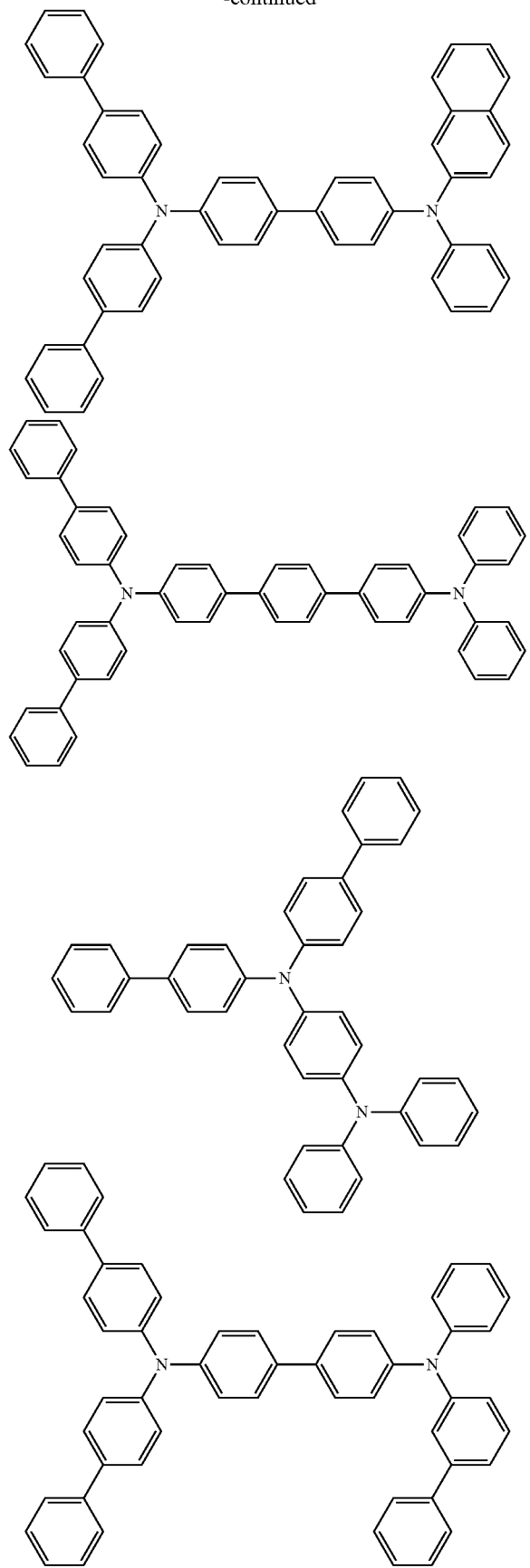
402
-continued
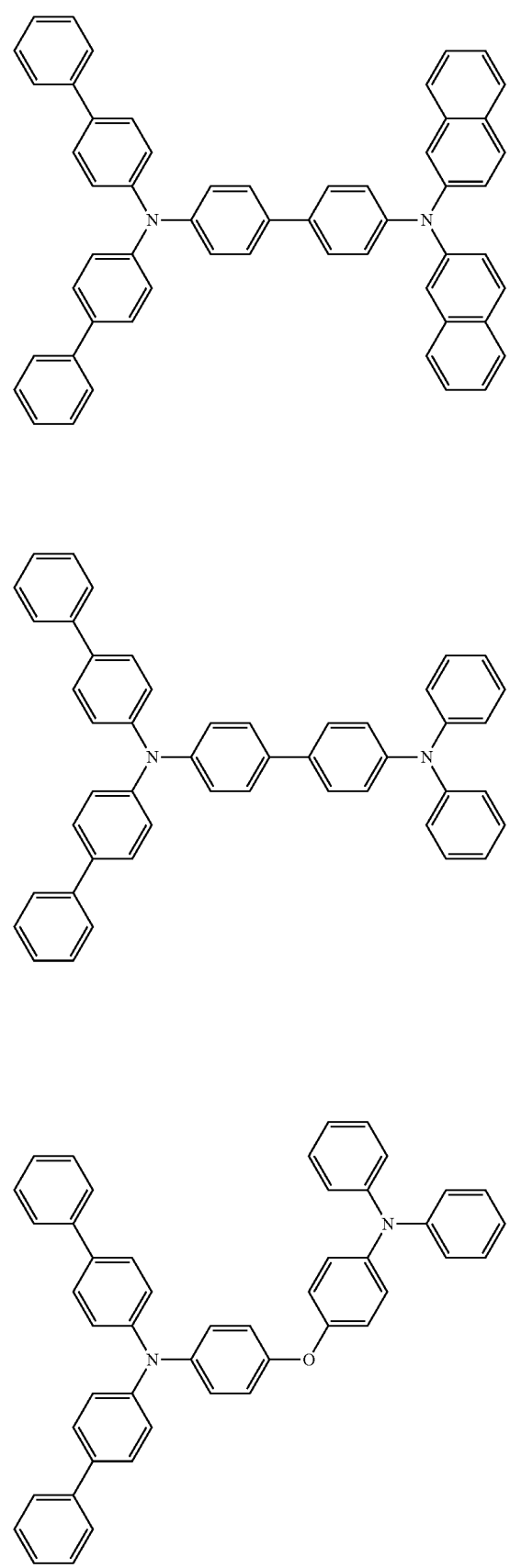

403
-continued
404
-continued
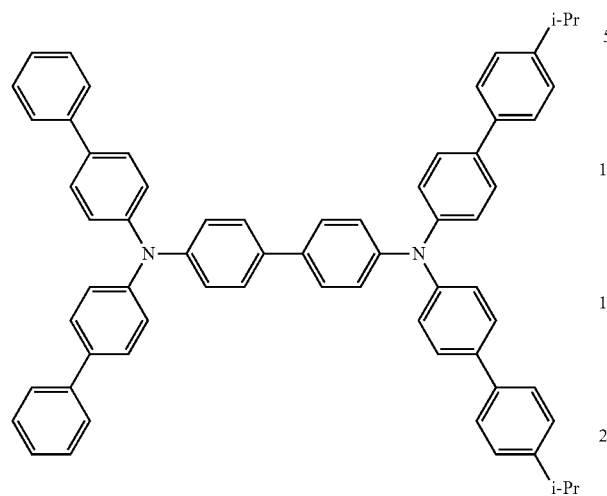
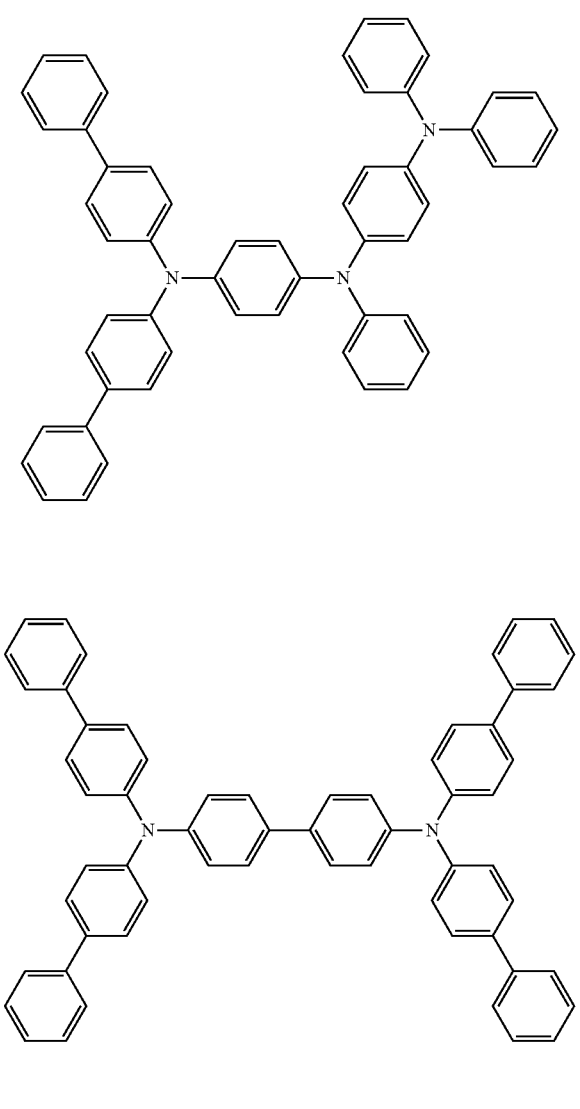
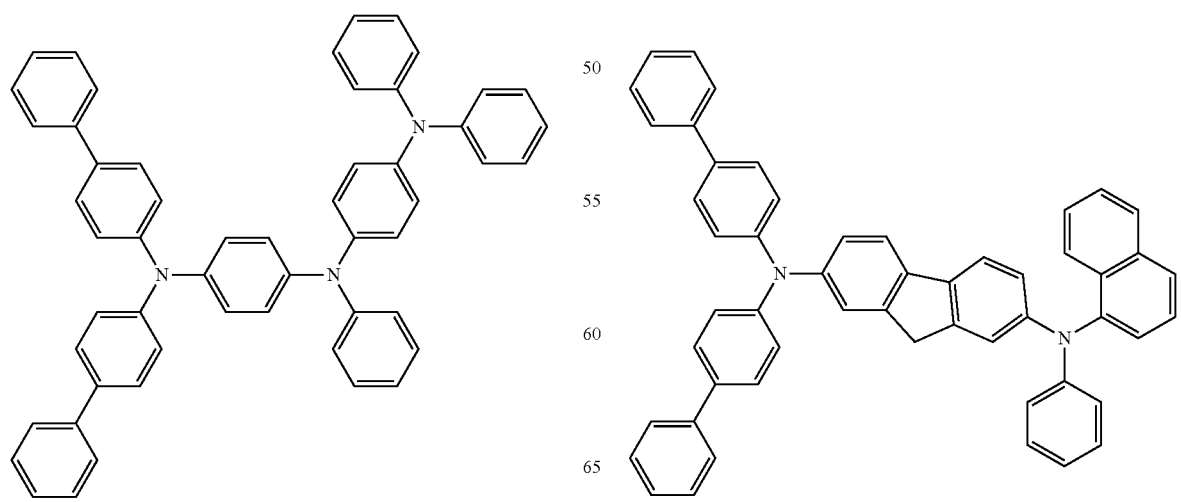

405
-continued
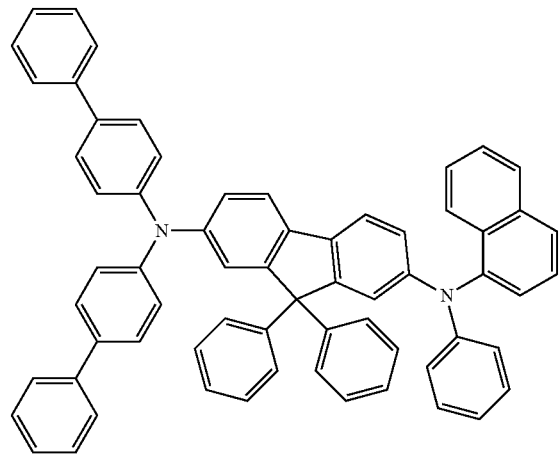
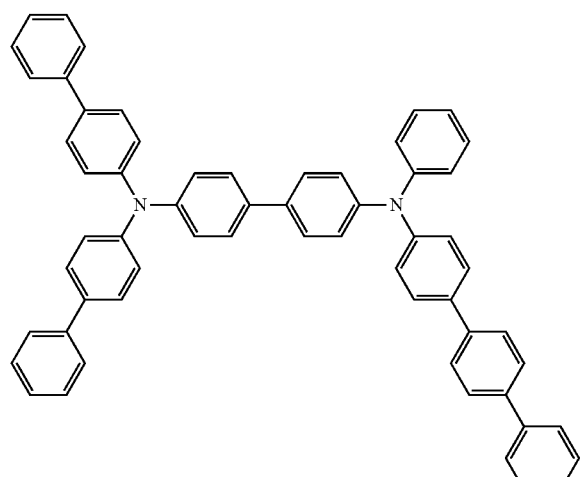
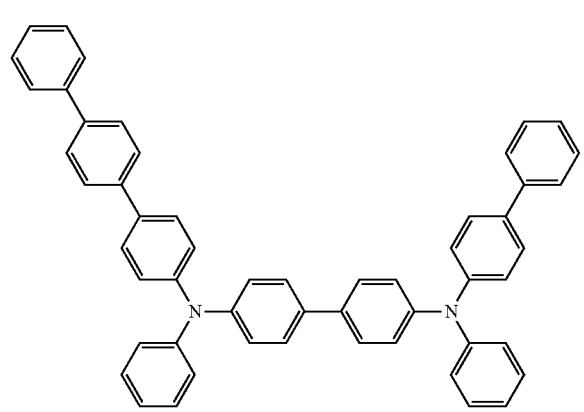
406
-continued
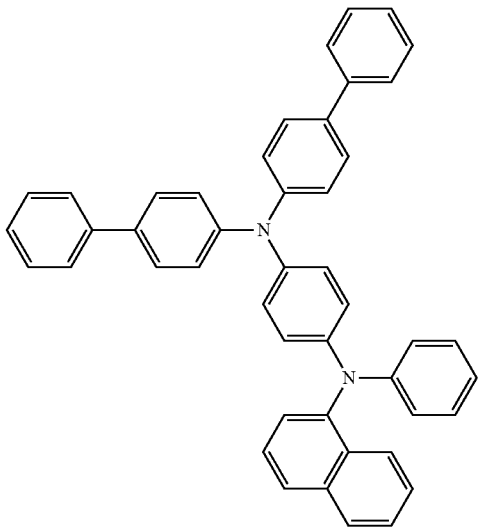
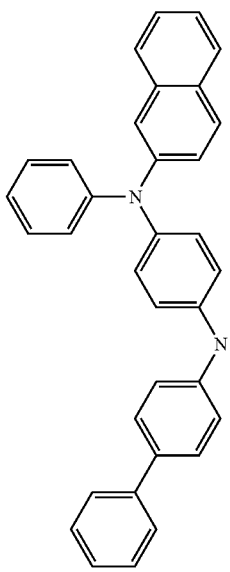
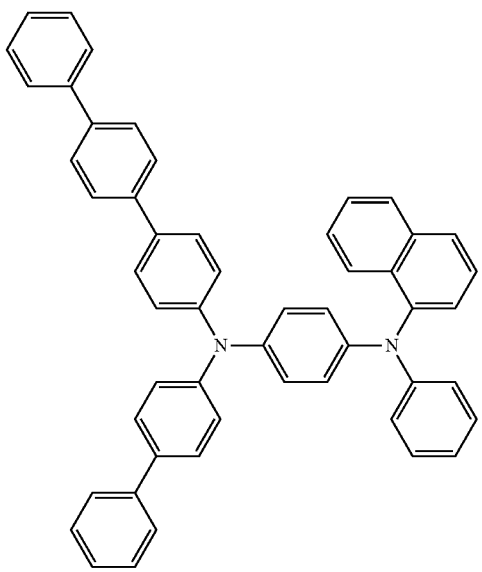

407
-continued
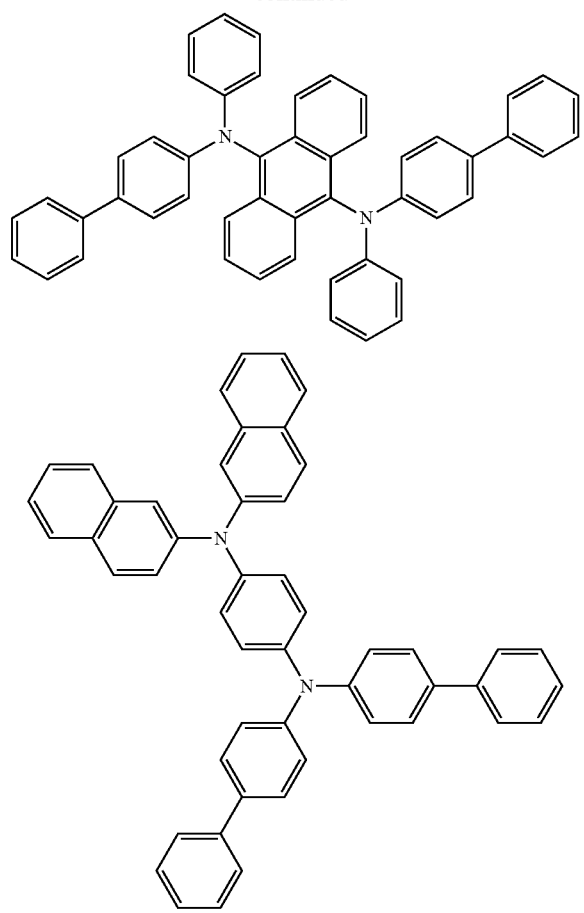
408
-continued
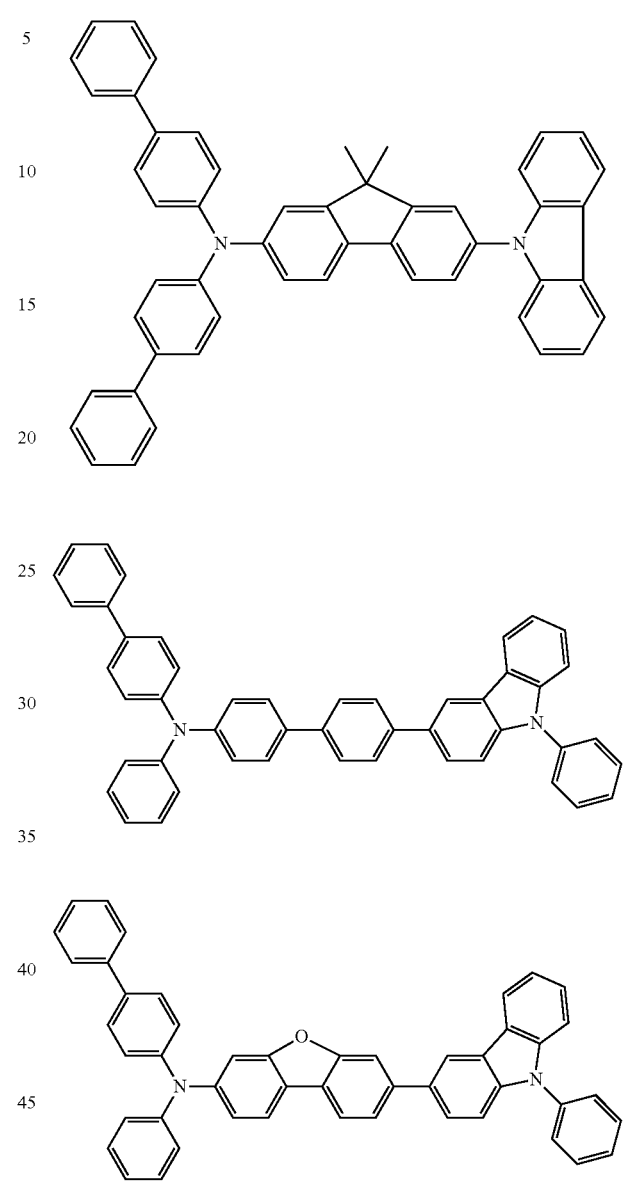
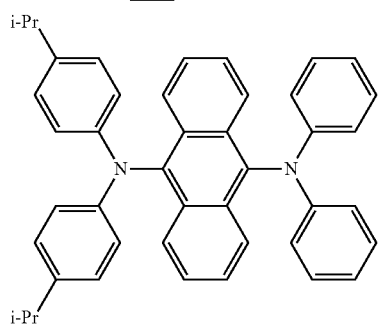
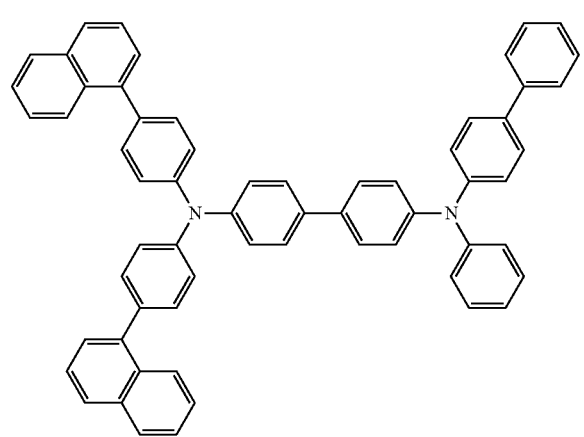
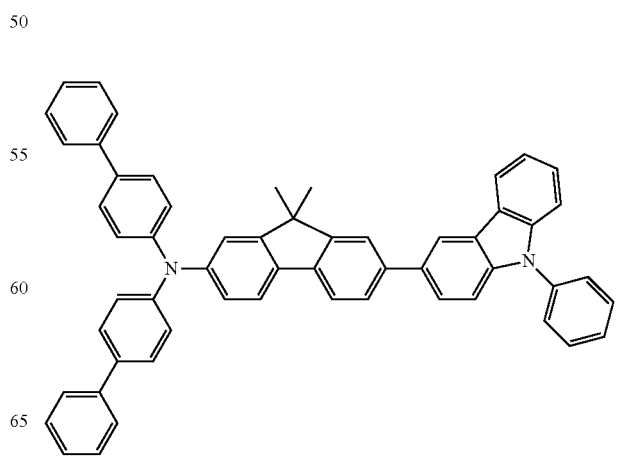

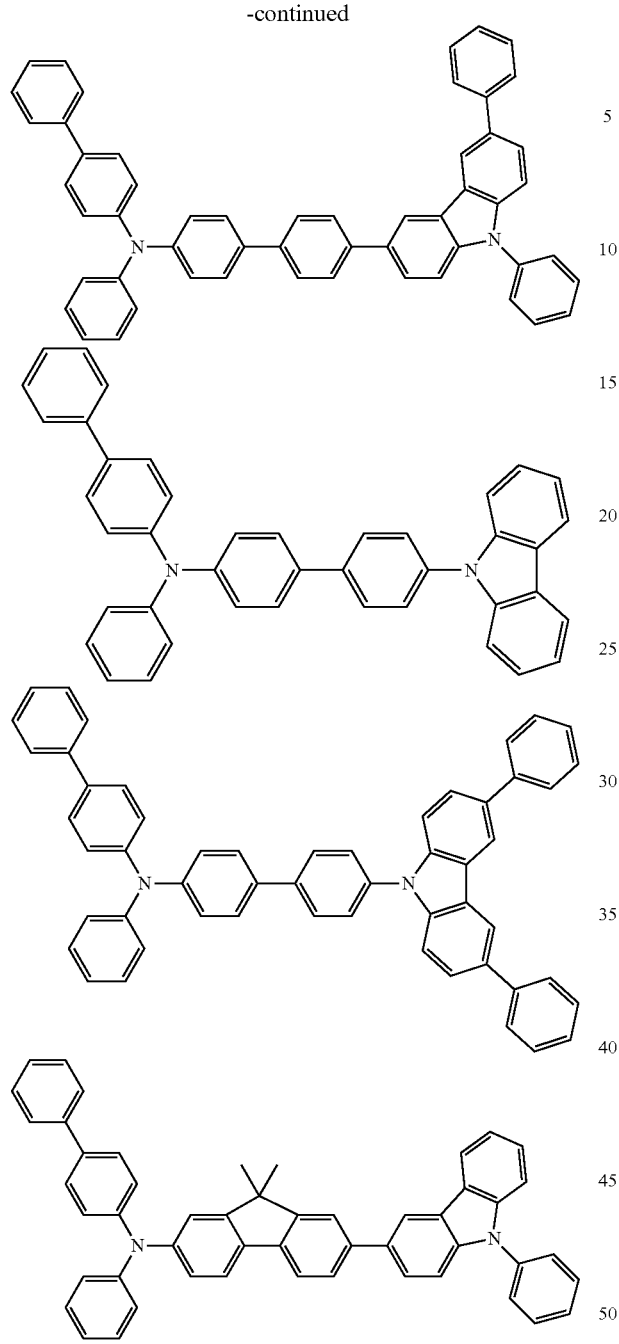
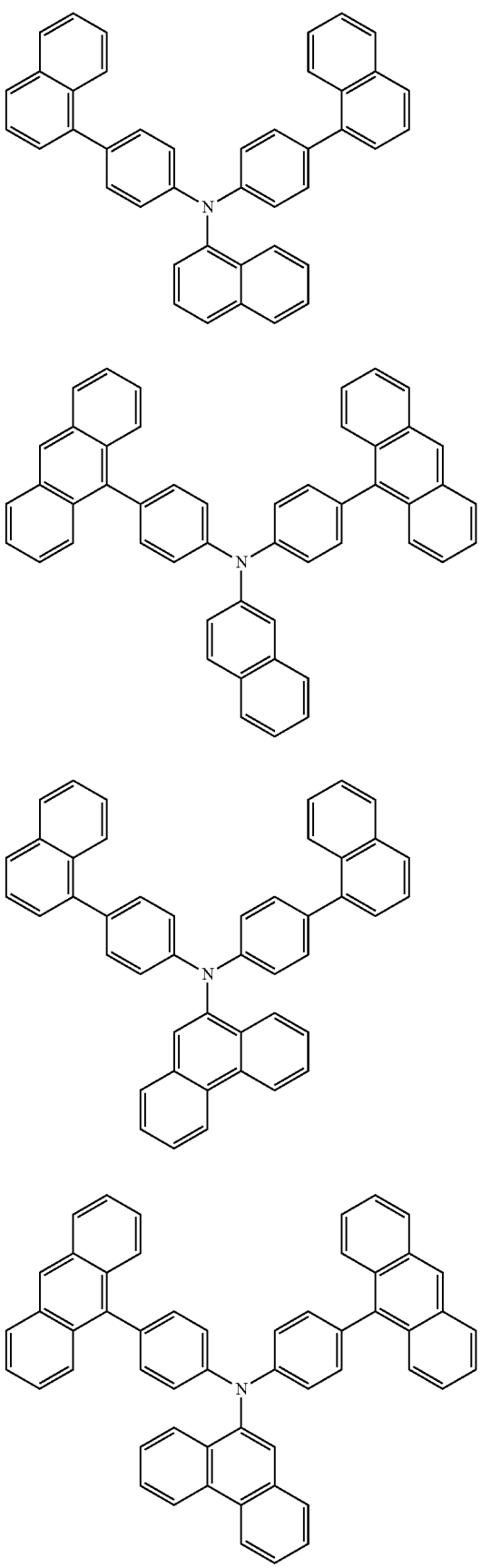
An aromatic amine represented by formula (J) is also preferably used to form the hole transporting layer:
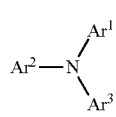
(J)
wherein $Ar^1$ to $Ar^3$ are the same as defined with respect to $Ar^1$ to $Ar^4$ of formula (H). Examples of the compound represented by formula (J) are shown below, although not limited thereto.

411
-continued
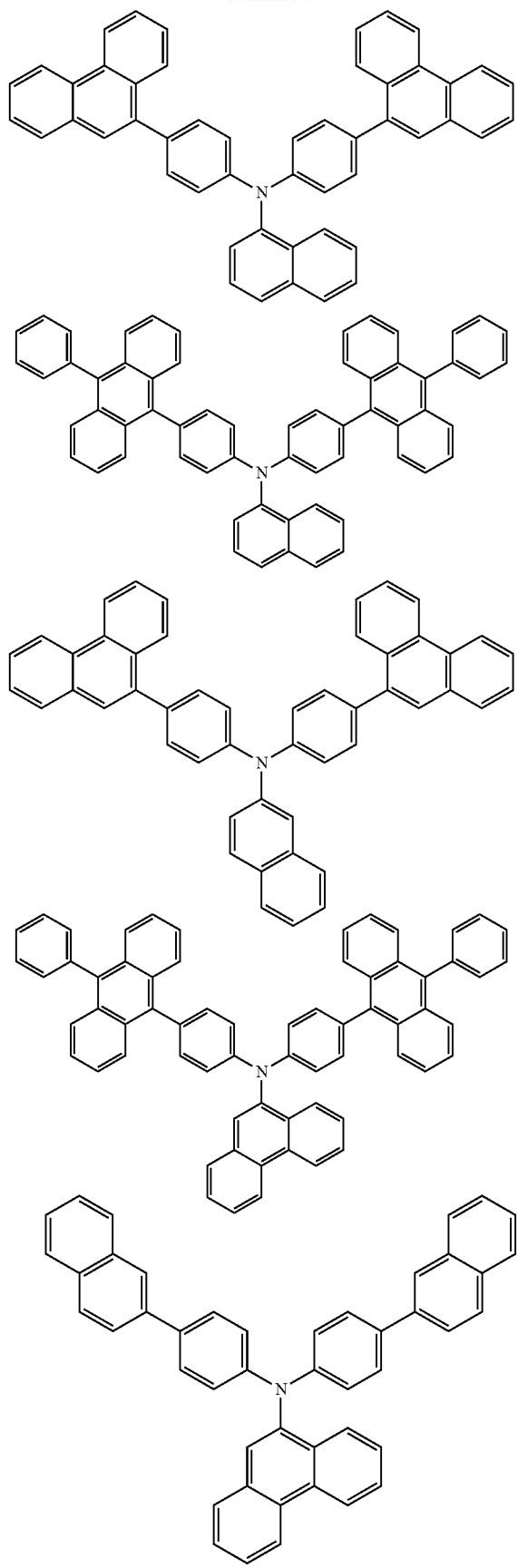
412
-continued
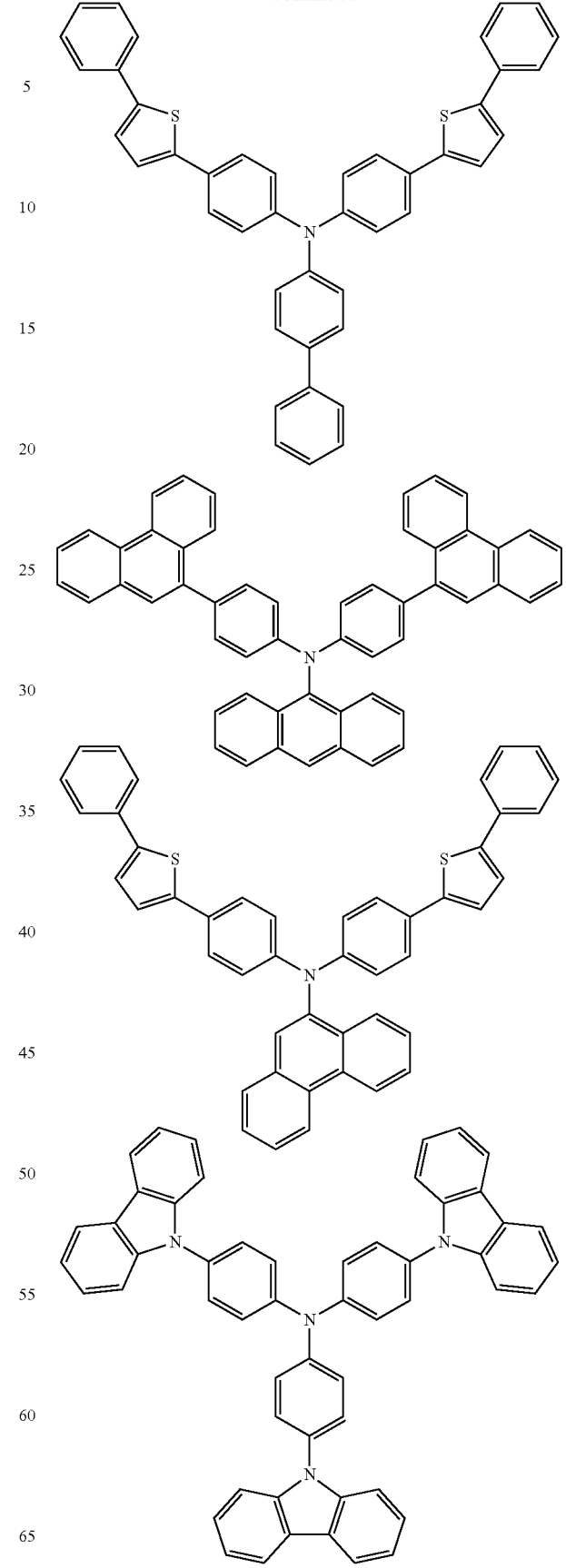

-continued

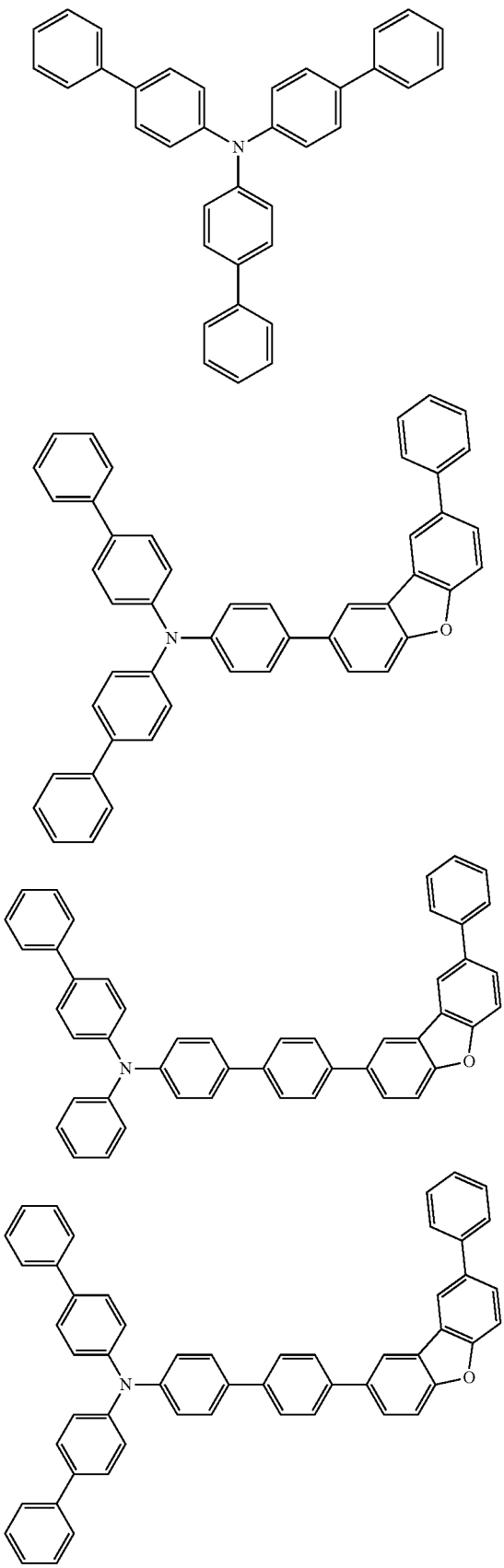

The hole transporting layer may be made into two-layered structure of a first hole transporting layer (anode side) and a second hole transporting layer (cathode side).

The thickness of the hole transporting layer is preferably 10 to 200 nm, although not particularly limited thereto.

The organic EL device of the invention may have a layer comprising an acceptor material which is disposed in contact with the anode side of each of the hole transporting layer and the first hole transporting layer. With such a layer, it is expected that the driving voltage is lowered and the production cost is reduced.

The acceptor material is preferably a compound represented by formula (K):

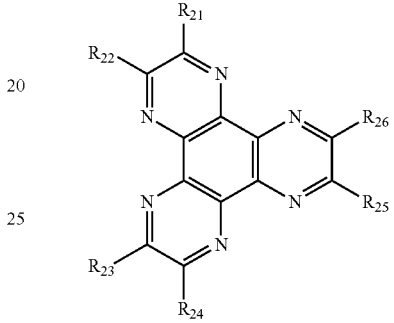

(K)

wherein $R_{21}$ to $R_{26}$ may be the same or different and each independently represent a cyano group, —$CONH_2$, a carboxyl group, or —$COOR_{27}$ wherein $R_{27}$ represents an alkyl group having 1 to 20 carbon atoms or a cycloalkyl group having 3 to 20 carbon atoms. One or more of a pair of $R_{21}$ and $R_{22}$, a pair of $R_{23}$ and $R_{24}$, and a pair of $R_{25}$ and $R_{26}$ may bond to each other to form a group represented by —CO—O—CO—.

Examples of $R_{27}$ include a methyl group, an ethyl group, a n-propyl group, an isopropyl group, a n-butyl group, an isobutyl group, a t-butyl group, a cyclopentyl group, and a cyclohexyl group.

The thickness of the layer comprising the acceptor material is preferably 5 to 20 nm, although not particularly limited thereto.

N/P Doping

The carrier injecting properties of the hole transporting layer and the electron transporting layer can be controlled, as described in JP 3695714B, by the doping (n) with a donor material or the doping (p) with an acceptor material.

A typical example of the n-doping is an electron transporting material doped with a metal, such as Li and Cs, and a typical example of the p-doping is a hole transporting material doped with an acceptor material, such as $F_4TCNQ$ (2,3,5,6-Tetrafluoro-7,7,8,8-tetracyanoquinodimethane).

Space Layer

For example, in an organic EL device wherein a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material combining the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described with respect to the hole transporting layer are usable as the material for the space layer. The material for organic EL device in an aspect of the invention may be used as the material for the space layer.

Blocking Layer

The organic EL device of the invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. The material for organic EL device of the invention may be used as the material for the hole blocking layer.

The triplet blocking layer prevents the diffusion of triplet excitons generated in the light emitting layer to adjacent layers and has a function of confining the triplet excitons in the light emitting layer, thereby preventing the deactivation of energy on molecules other than the emitting dopant of triplet excitons, for example, on molecules in the electron transporting layer.

If a phosphorescent device having a triplet blocking layer satisfies the following energy relationship:

$$E^T_d < E^T_{TB}$$

wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device of the invention is usable as the material for triplet blocking layer of the TTF device described in WO 2010/134350A1.

The electron mobility of the material for the triplet blocking layer is preferably $10^{-6}$ cm$^2$/Vs or more at an electric field strength in a range of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength in a range of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The organic electroluminescence device of the invention is usable in electronic equipment, for example, as display parts, such as organic EL panel module, display devices of television sets, mobile phones, personal computer, etc., and light emitting sources of lighting equipment and vehicle lighting equipment.

EXAMPLES

The present invention will be described below in more detail with reference to the following examples. However, it should be noted that the scope of the invention is not limited thereto.

Example 1

Synthesis of Compound 1

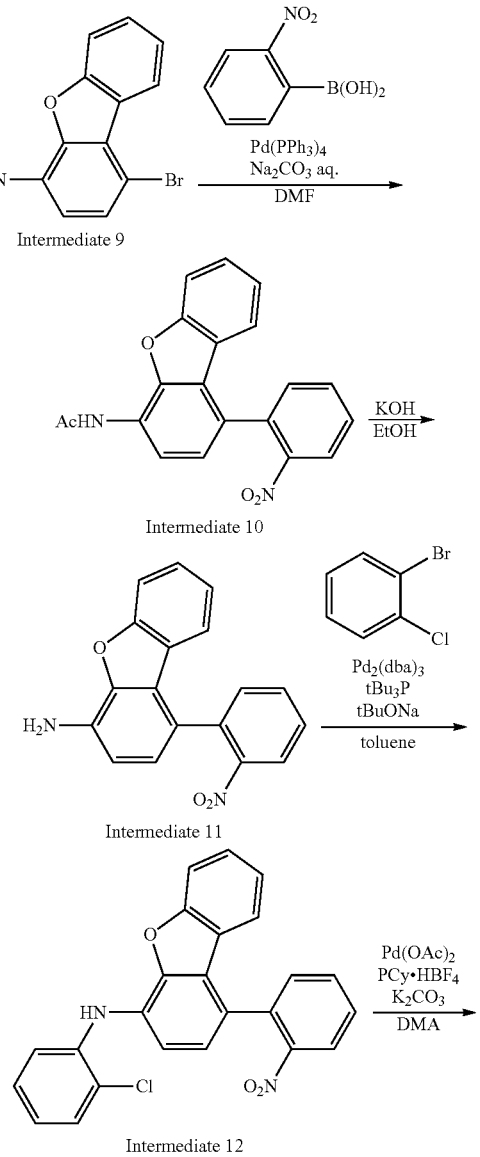

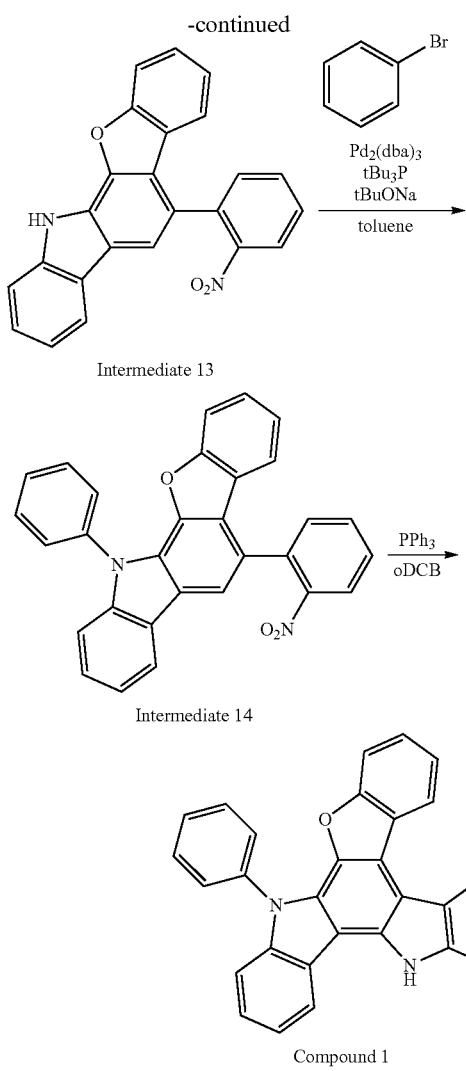

Intermediate 13

Intermediate 14

Compound 1

Synthesis of Intermediate 10

Under an argon atmosphere, a mixture of a known intermediate 9 (17.5 g), 2-nitrophenylboronic acid (10.57 g), tetrakis(triphenylphosphine) palladium(0) (2.05 g), a 2 M aqueous solution of sodium carbonate (58 ml), and DMF (250 ml) was stirred at 100° C. for 18 h. The obtained reaction mixture was cooled to room temperature, filtered through celite, and extracted with toluene. The toluene layer was washed with a saturated saline and dried over anhydrous sodium sulfate, and then the solvent was evaporated off under reduced pressure. The obtained residue was purified by silica gel column chromatography to obtain intermediate 10 (12.35 g). The yield was 62%.

Synthesis of Intermediate 11

A mixture of intermediate 10 (3.2 g) and potassium hydroxide (2.6 g) in 100 ml of ethanol was stirred at room temperature for 48 h. The obtained reaction mixture was neutralized by hydrochloric acid under ice-cooling and extracted with toluene. The toluene layer was washed with a saturated saline and dried over anhydrous sodium sulfate, and then the solvent was evaporated off under reduced pressure. The obtained residue was purified by silica gel column chromatography to obtain intermediate 11 (1.97 g). The yield was 70%.

Synthesis of Intermediate 12

Under an argon atmosphere, a mixture of intermediate 11 (8.34 g), 1-bromo-2-chlorobenzene (6.36 ml), tris(dibenzylideneacetone) dipalladium(0) (247 mg), tri-t-butylphosphine (111.3 mg), sodium t-butoxide (3.7 g), and toluene (140 ml) was stirred at 40° C. for 7 h. The obtained reaction mixture was cooled to room temperature and filtered through celite, and then the solvent was evaporated off under reduced pressure. The obtained residue was purified by silica gel column chromatography and recrystallization to obtain intermediate 12 (5.57 g). The yield was 49%.

Synthesis of Intermediate 13

Under an argon atmosphere, intermediate 12 (6.28 g), palladium acetate (102 mg), potassium carbonate (4.17 g), tricyclohexylphosphine tetrafluorohydroborate (334 mg), and N,N-dimethylacetamide (75 mL) were charged in a flask, and the resultant mixture was stirred at 130° C. for 24 h. The obtained reaction mixture was cooled to room temperature and extracted with toluene. The extract was filtered to remove the insolubles and the filtrate was evaporated off under reduced pressure. The obtained residue was purified by silica gel column chromatography to obtain intermediate 13 (2.17 g). The yield was 38%.

Synthesis of Intermediate 14

Under an argon atmosphere, a mixture of intermediate 13 (1.26 g), bromobenzene (386 µl), tris(dibenzylideneacetone) dipalladium(0) (61 mg), tri-t-butylphosphine (27 mg), sodium t-butoxide (448 mg), and toluene (15 mL) was stirred for 7 h under heat-refluxing. The obtained reaction mixture was cooled to room temperature and filtered through celite, and then the solvent was evaporated off under reduced pressure. The obtained residue was purified by silica gel column chromatography and recrystallization to obtain intermediate 14 (999 mg). The yield was 66%.

Synthesis of Compound 1

Under an argon atmosphere, a mixture of intermediate 14 (27.8 g), triphenylphosphine (40.1 g), and o-dichlorobenzene (600 ml) was stirred for 16 h under heat-refluxing. The obtained reaction mixture was cooled to room temperature and hexane was added. The precipitated crystal was collected by filtration, which was then recrystallized from toluene to obtain compound 1 (11.6 g). The yield was 45%. The obtained compound was identified by a mass spectrometric analysis, which showed m/e=422 to the molecular weight of 422.14.

The above synthetic method is one embodiment of the synthetic method for the heterocyclic compound of the invention. In another embodiment, the heterocyclic compound may be synthesized by appropriately modifying the above synthetic method.

Example 2

Synthesis of Compound 2

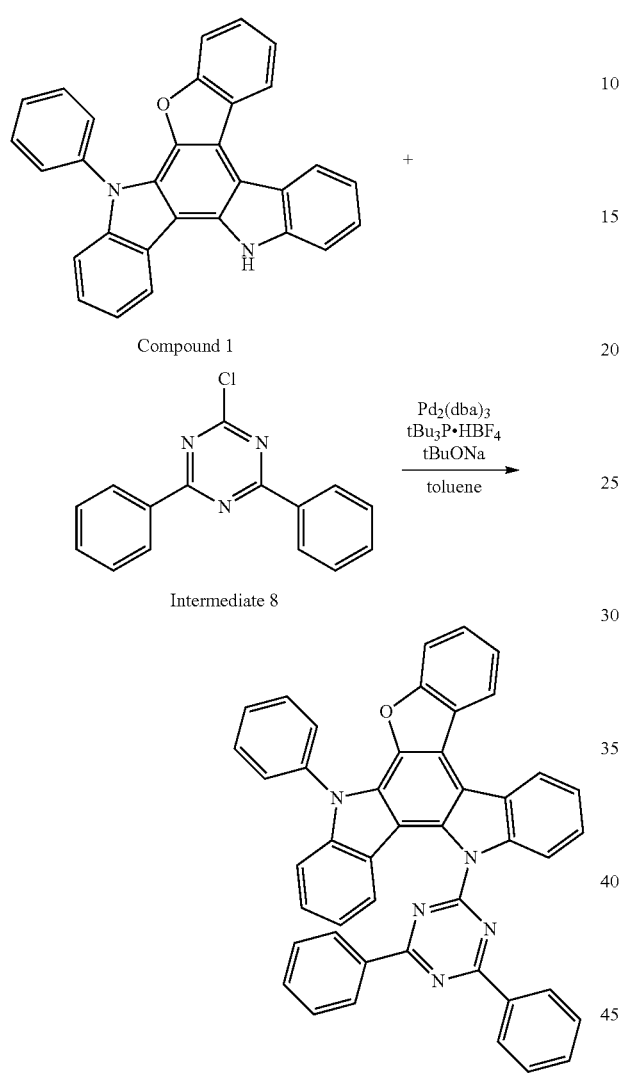

Compound 2

Under an argon atmosphere, a mixture of compound 1 (1.17 g), intermediate B synthesized by a known method (816 mg), trisdibenzylideneacetone dipalladium(0) (50 mg), tri-t-butylphosphine tetrafluorohydroborate (63 mg), sodium t-butoxide (373 mg), and dehydrated toluene (40 ml) was stirred for 8 h under heat-refluxing. The obtained reaction mixture was cooled to room temperature, filtered through celite, and extracted with toluene. The toluene layer was washed with a saturated saline and dried over anhydrous sodium sulfate, and then the solvent was evaporated off under reduced pressure. The obtained residue was purified by silica gel column chromatography and recrystallization to obtain compound 2 (1.19 g). The yield was 66%. The obtained compound was identified by a mass spectrometric analysis, which showed m/e=653 to the molecular weight of 653.22.

Example 3

Synthesis of Compound 3

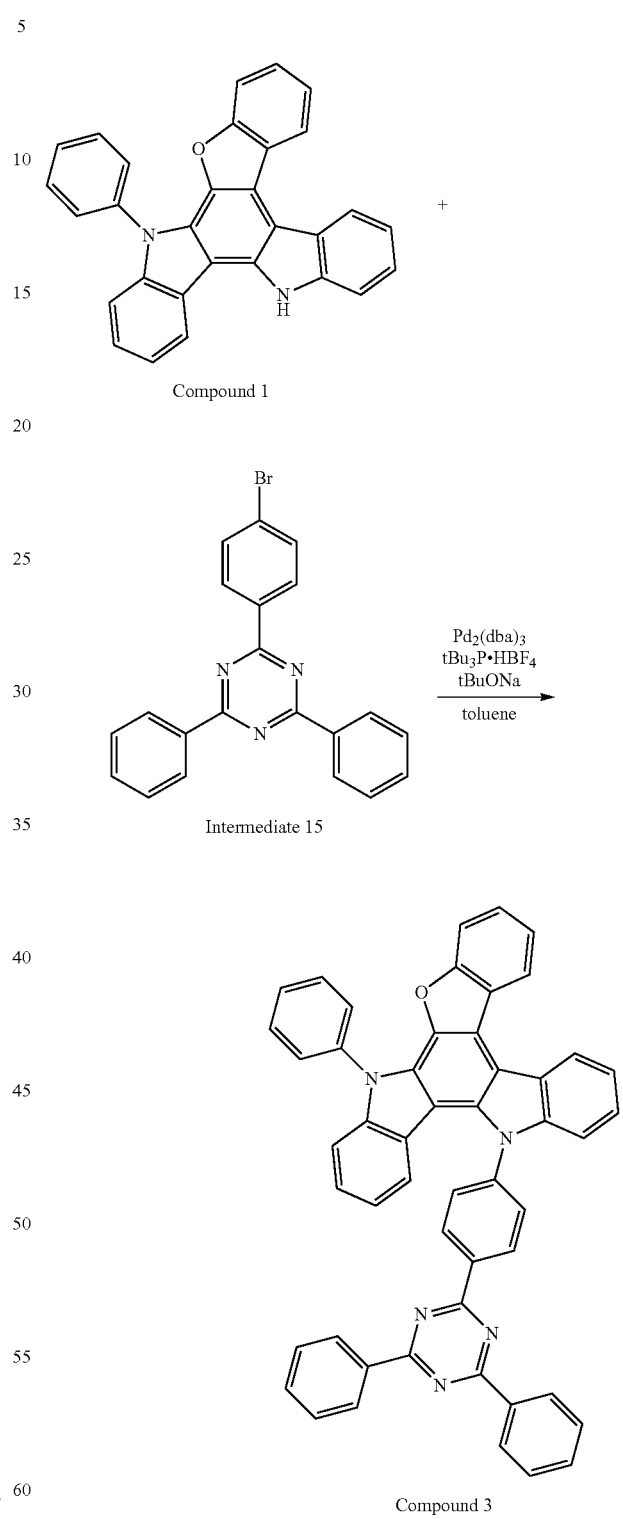

Compound 3

Compound 3 was obtained in the same manner as in Example 2 except for using intermediate 15 synthesized by a known method in place of intermediate B. The obtained compound was identified by a mass spectrometric analysis, which showed m/e=729 to the molecular weight of 729.25.

Example 4

Synthesis of Compound 4

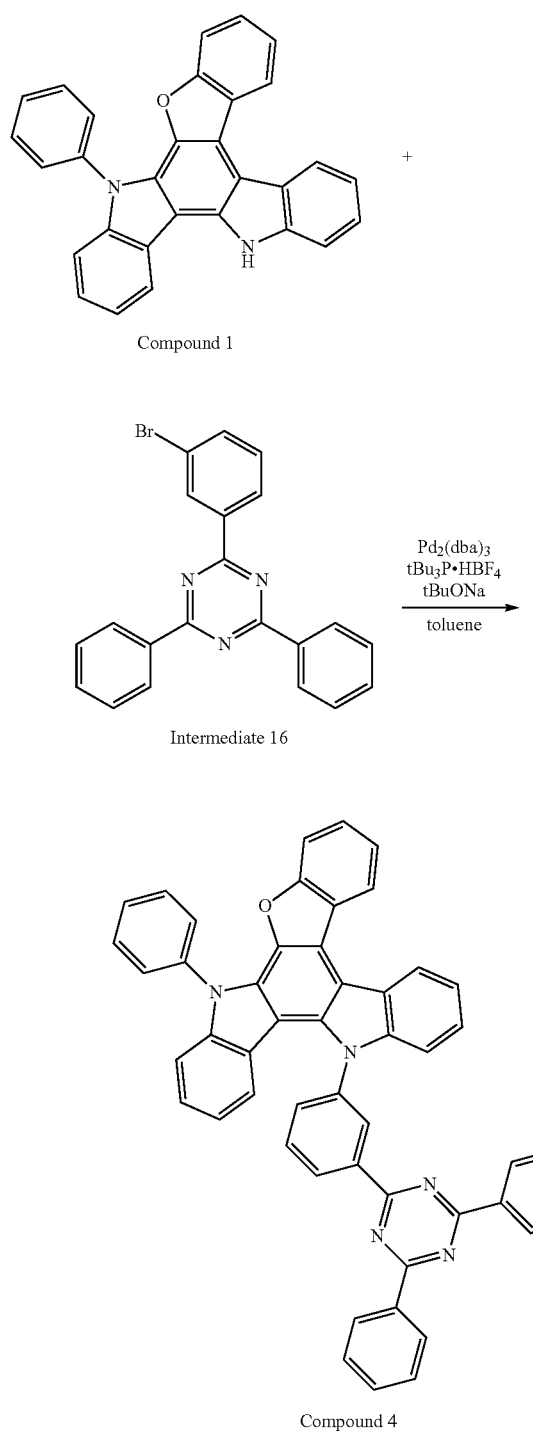

Compound 4 was obtained in the same manner as in Example 2 except for using intermediate 16 synthesized by a known method in place of intermediate B. The obtained compound was identified by a mass spectrometric analysis, which showed m/e=729 to the molecular weight of 729.25.

Example 5

Synthesis of Compound 5

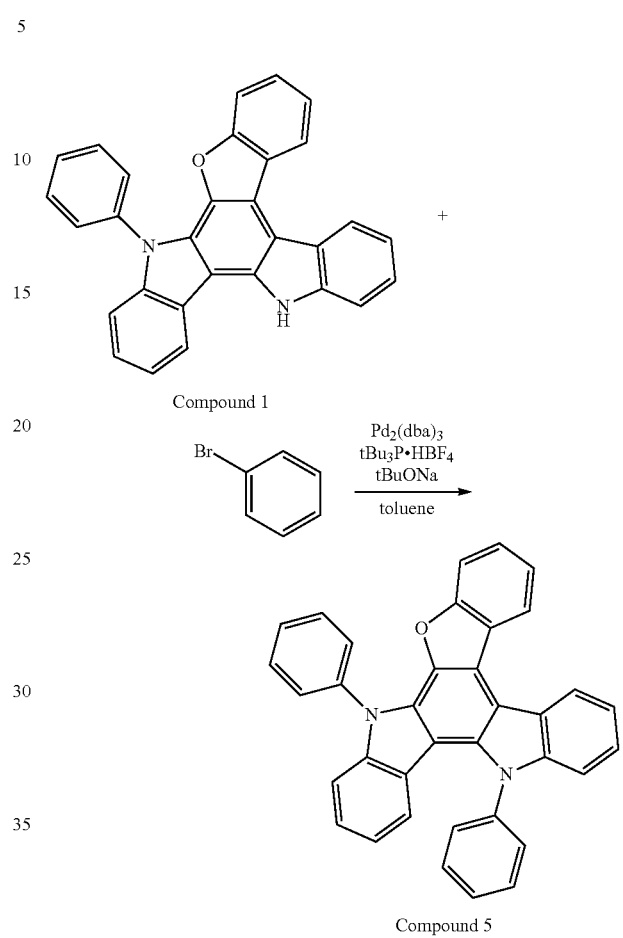

Compound 5 was obtained in the same manner as in Example 2 except for using bromobenzene in place of intermediate B. The obtained compound was identified by a mass spectrometric analysis, which showed m/e=498 to the molecular weight of 498.17.

Example 6

Synthesis of Compound 6

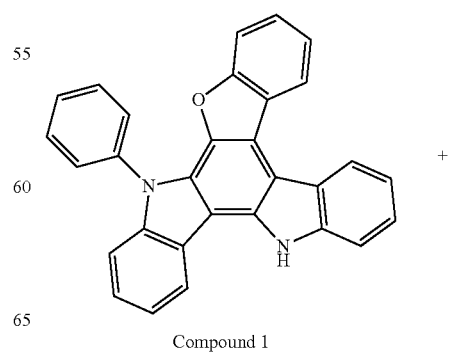

-continued

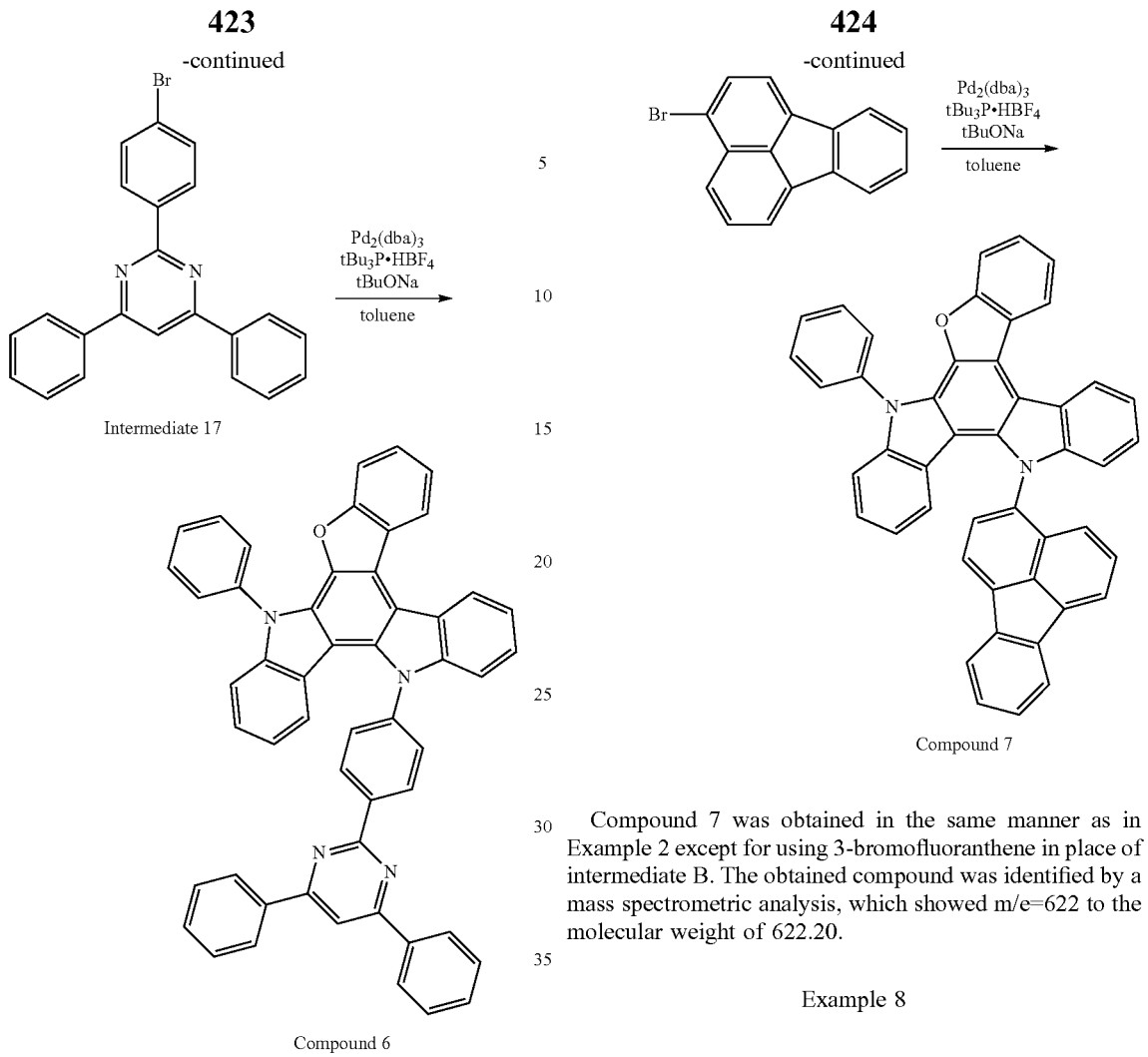

Compound 6 was obtained in the same manner as in Example 2 except for using intermediate 17 synthesized by a known method in place of intermediate B. The obtained compound was identified by a mass spectrometric analysis, which showed m/e=728 to the molecular weight of 728.26.

Example 7

Synthesis of Compound 7

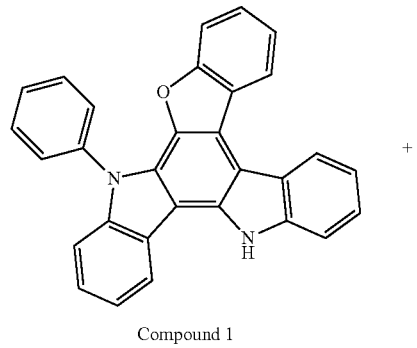

Compound 7 was obtained in the same manner as in Example 2 except for using 3-bromofluoranthene in place of intermediate B. The obtained compound was identified by a mass spectrometric analysis, which showed m/e=622 to the molecular weight of 622.20.

Example 8

Synthesis of Compound 8

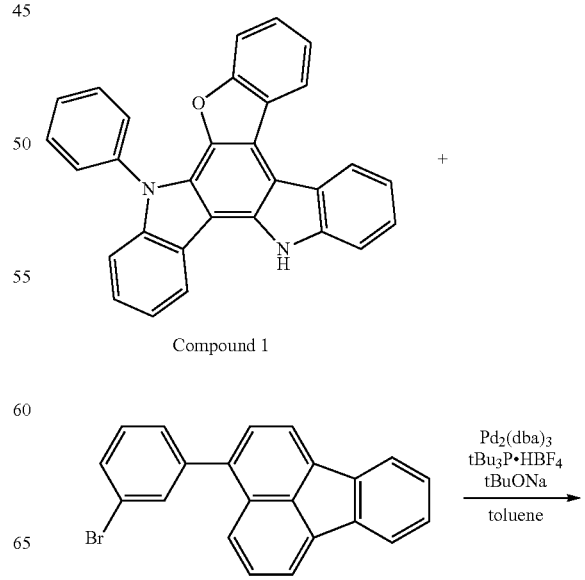

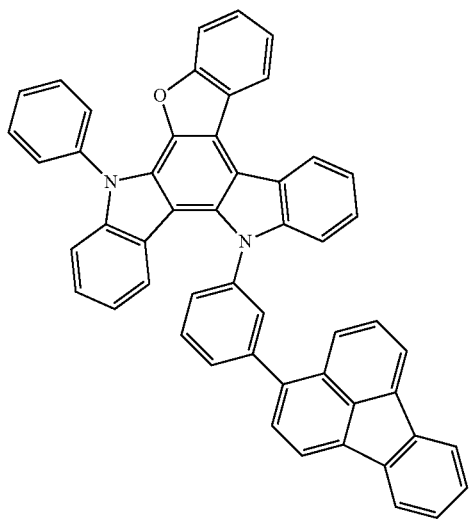

Compound 8

Compound 8 was obtained in the same manner as in Example 2 except for using 3-(3-bromophenyl)fluoranthene in place of intermediate B. The obtained compound was identified by a mass spectrometric analysis, which showed m/e=698 to the molecular weight of 698.24.

Example 9

Synthesis of Compound 9

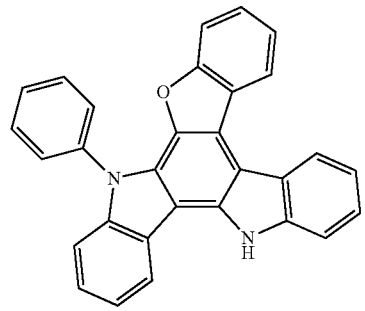

Compound 1

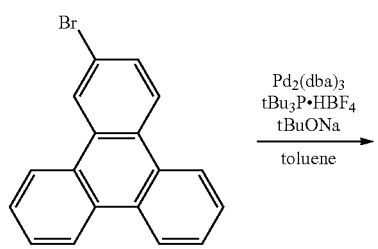

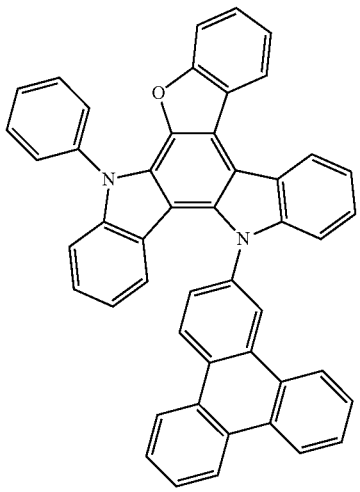

Compound 9

Compound 9 was obtained in the same manner as in Example 2 except for using 2-bromotriphenylene in place of intermediate B. The obtained compound was identified by a mass spectrometric analysis, which showed m/e=648 to the molecular weight of 648.22.

Example 10

Synthesis of Compound 10

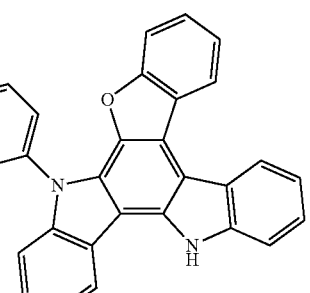

Compound 1

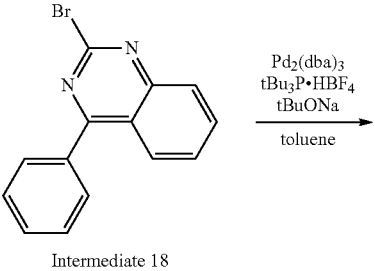

Intermediate 18

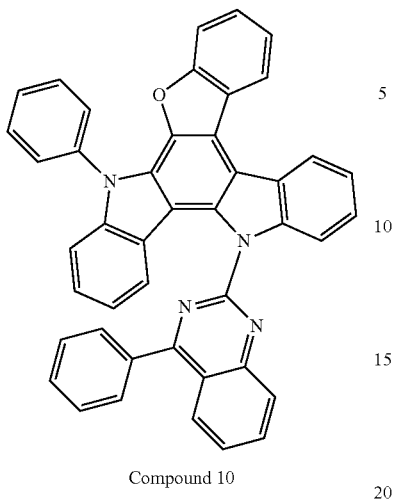

Compound 10

Compound 10 was obtained in the same manner as in Example 2 except for using intermediate 18 synthesized by a known method in place of intermediate B. The obtained compound was identified by a mass spectrometric analysis, which showed m/e=626 to the molecular weight of 626.21.

Example 11

Synthesis of Compound 11

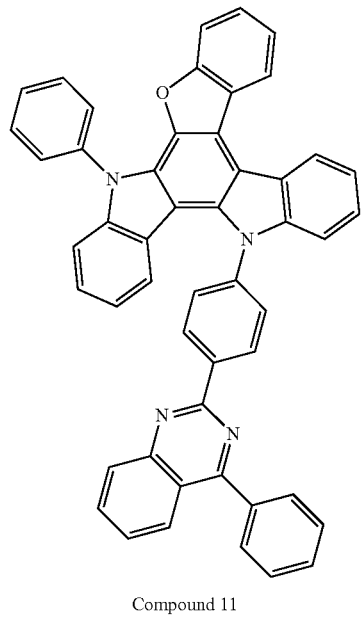

Compound 11

Compound 11 was obtained in the same manner as in Example 2 except for using intermediate 19 synthesized by a known method in place of intermediate B. The obtained compound was identified by a mass spectrometric analysis, which showed m/e=702 to the molecular weight of 702.24.

Example 12

Synthesis of Compound 12

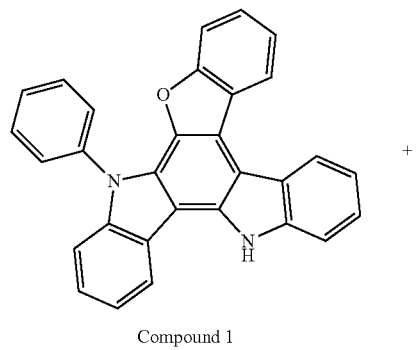

Compound 1

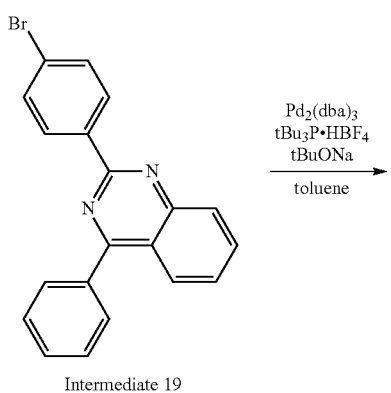

Intermediate 19

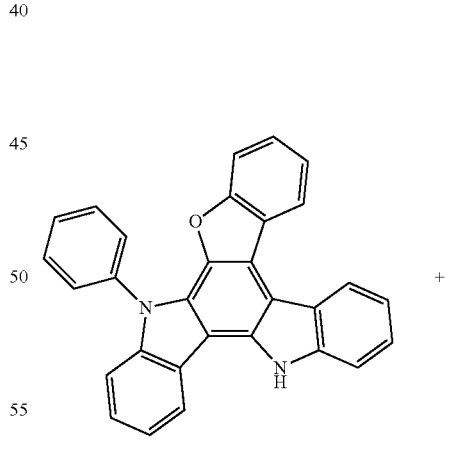

Compound 1

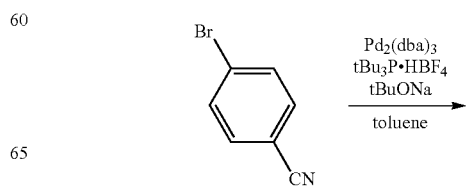

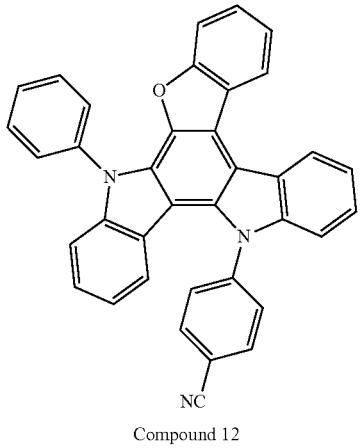

Compound 12

Compound 12 was obtained in the same manner as in Example 2 except for using 4-bromobenzonitrile in place of intermediate B. The obtained compound was identified by a mass spectrometric analysis, which showed m/e=523 to the molecular weight of 523.12.

Example 13

Synthesis of Compound 13

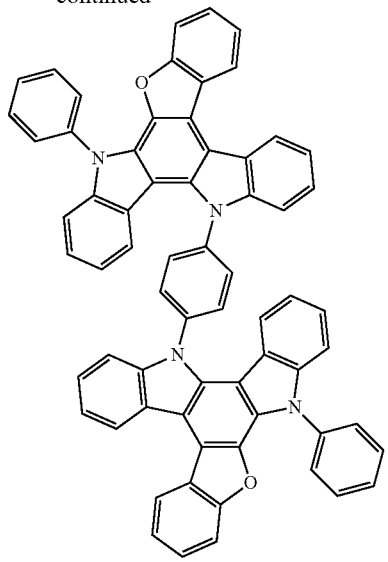

Compound 13

Under an argon atmosphere, a mixture of compound 1 (2.47 g), 1,4-dibromobenzene (690 mg), trisdibenzylideneacetone dipalladium(0) (107 mg), tri-t-butylphosphine tetrafluorohydroborate (136 mg), sodium t-butoxide (1.8 g), and dehydrated toluene (50 ml) was stirred for 24 h under heat-refluxing. The obtained reaction mixture was neutralized by hydrochloric acid under ice-cooling and extracted with toluene. The toluene layer was washed with a saturated saline and dried over anhydrous sodium sulfate, and then the solvent was evaporated off under reduced pressure. The obtained residue was purified by silica gel column chromatography and recrystallization to obtain compound 13 (1.72 g). The yield was 32%. The obtained compound was identified by a mass spectrometric analysis, which showed m/e=918 to the molecular weight of 918.30.

Example 14

Synthesis of Compound 14

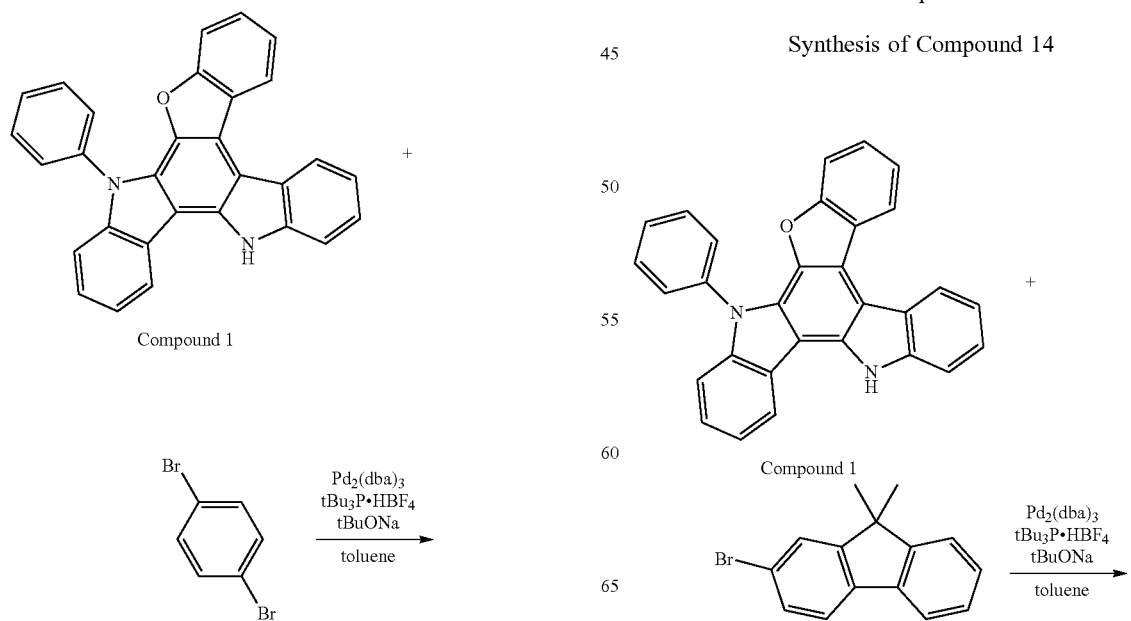

-continued

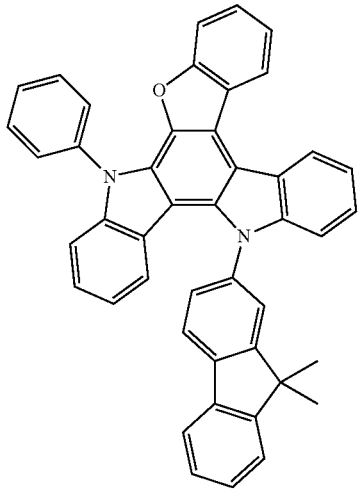

Compound 14

Compound 14 was obtained in the same manner as in Example 2 except for using 2-bromo-9,9-dimethylfluorene in place of intermediate B. The obtained compound was identified by a mass spectrometric analysis, which showed m/e=614 to the molecular weight of 614.24.

Example 15

Synthesis of Compound 15

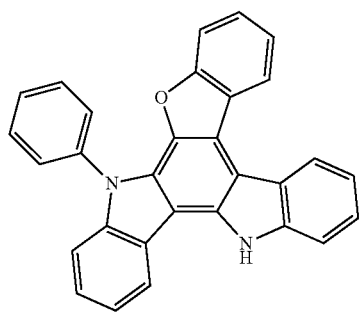

Compound 1

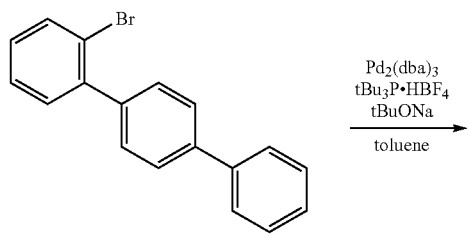

Intermediate 20

-continued

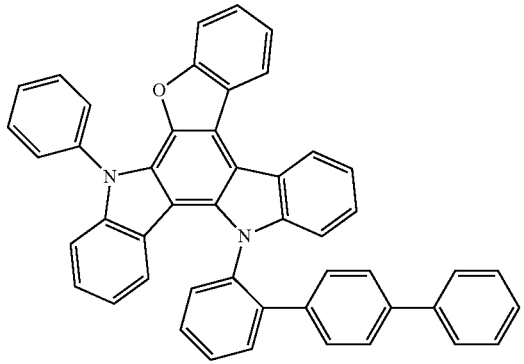

Compound 15

Compound 15 was obtained in the same manner as in Example 2 except for using 2-bromo-p-terphenyl in place of intermediate B. The obtained compound was identified by a mass spectrometric analysis, which showed m/e=650 to the molecular weight of 650.24.

Example 16

Synthesis of Compound 16

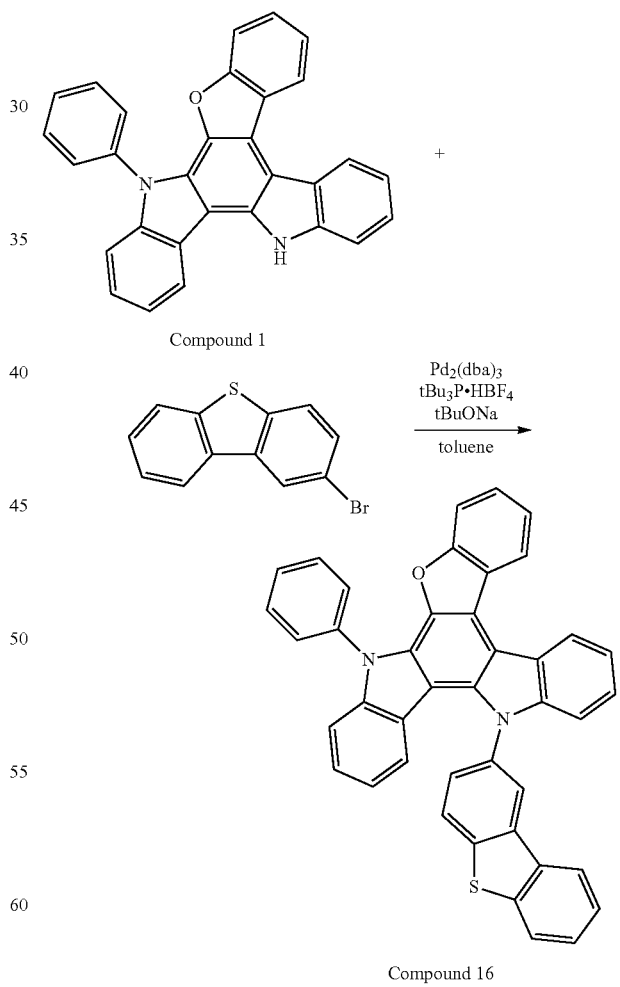

Compound 16

Compound 16 was obtained in the same manner as in Example 2 except for using 2-bromo-dibenzothiophene in place of intermediate B. The obtained compound was identified by a mass spectrometric analysis, which showed m/e=604 to the molecular weight of 604.16.

Example 17

Production of Organic EL Devices

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min.

The cleaned glass substrate having a transparent electrode line with a thickness of 130 nm was mounted to a substrate holder of a vacuum vapor deposition apparatus. The following compound HI as a hole injecting material was vapor-deposited so as to cover the transparent electrode to form a hole injecting layer with a thickness of 10 nm. Then, the following compound HT-1 as a first hole transporting material was vapor-deposited to form a first hole transporting layer with a thickness of 50 nm. Successively after forming the first hole transporting layer, the following compound HT-2 as a second hole transporting material was vapor-deposited to form a second hole transporting layer with a thickness of 15 nm.

On the second hole transporting layer, compound 2 (host material) obtained in Example 2, the following compound PG2-1 (co-host material), and Ir(ppy)$_3$ (phosphorescent material) were vapor co-deposited to form a phosphorescent light emitting layer with a thickness of 30 nm. The mass ratio of compound 2:PG2-1:Ir(ppy)$_3$ in the light emitting layer was 45%:45%:10%. The co-deposited film works as a light emitting layer.

Successively after forming the light emitting layer, the following compound ET was vapor-deposited into a film with a thickness of 30 nm. The film of compound ET works as an electron transporting layer.

Then, LiF was vapor-deposited into a film with a thickness of 1 nm at a film-forming speed of 0.01 nm/sec to form an electron injecting electrode (cathode). On the LiF film, metallic Al was vapor-deposited to form a metallic cathode with a thickness of 80 nm, thereby obtaining an organic EL device.

The compounds used in the examples and comparative example are shown below.

HI

-continued

HT-1

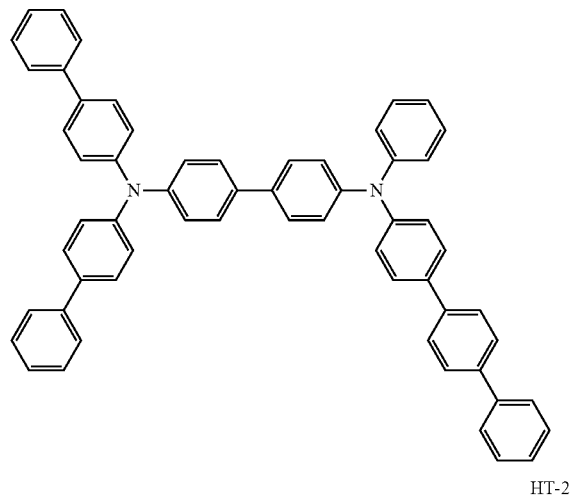

HT-2

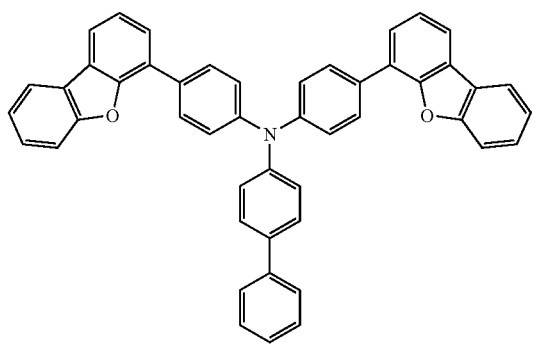

PG2-1

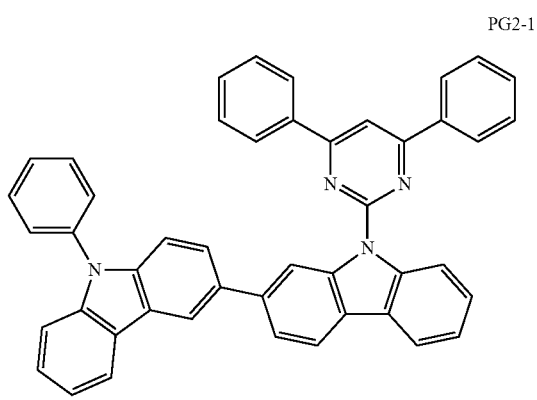

PG2-2

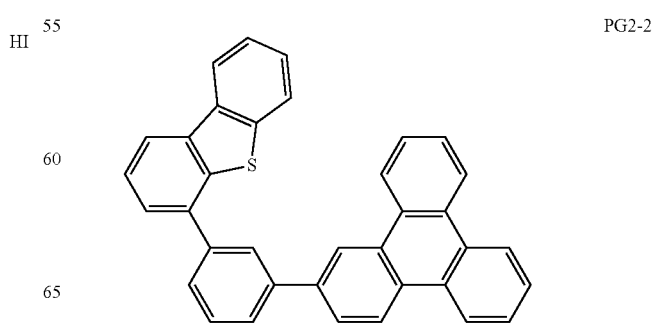

435
-continued
PG2-3
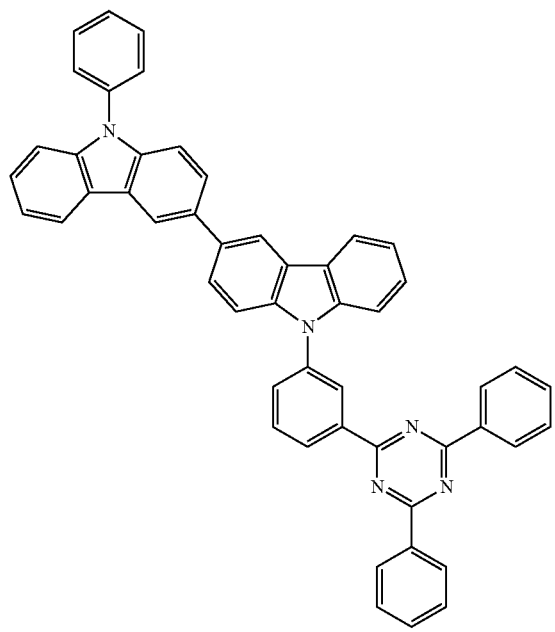
PG2-4
ET
Ir(ppy)3
436
-continued
PQIr(acac)
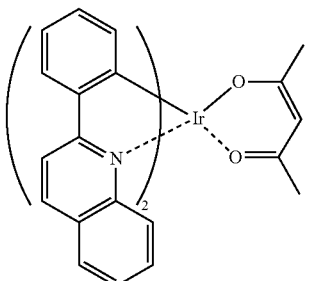
Ir(piq)3
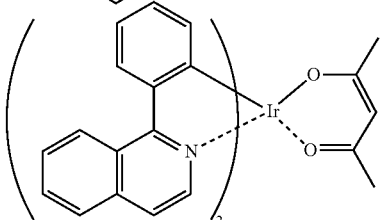
Ir(bzq)3
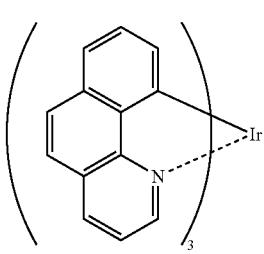
Comparative compound 1
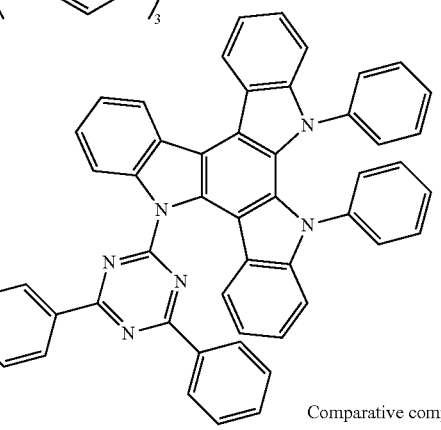
Comparative compound 2
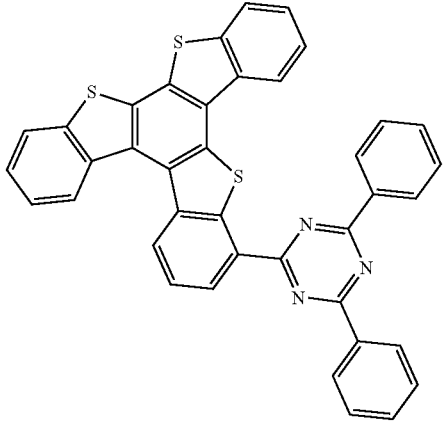
The organic EL device thus obtained was evaluated for an external quantum efficiency (%) and a lifetime in the following manners.

Evaluation of Emission Performance of Organic EL Devices

By driving the obtained organic EL device at room temperature at a constant direct current (current density: 10 mA/cm$^2$), the external quantum efficiency was measured using a spectroradiometer (CS-1000 manufactured by Minolta). The results are shown in Table 1.

Measurement of Lifetime

The obtained organic EL device was allowed to emit light by driving at room temperature at a constant direct current, thereby measuring the time (LT80) taken until the luminance was reduced to 80% of the initial luminance of 5000 cd/m$^2$. The results are shown in Table 1.

Examples 18 to 31

Each device having the following device structure was produced in the same manner as in Example 17 except for using each compound shown in Table 1. The results of the above measurements are shown in Table 1.

Device Structure
Dopant: Ir(ppy)$_3$
Host: each of Compounds 2 to 6, 9, 12, and 13
ITO/HI (10 nm)/HT-1 (50 nm)/HT-2 (15 nm)/host:co-host: Ir(ppy)$_3$ (30 nm, 45%:45%:10% by mass)/ET (30 nm)/LiF (1 nm)/Al (80 nm)
Dopant: Ir(piq)$_3$
Host: each of Compounds 7 and 8 and Comparative compounds 1 and 2
ITO/HI (10 nm)/HT-1 (30 nm)/HT-2 (10 nm)/host:Ir(piq)$_3$ (40 nm, 95%:5% by mass)/ET (40 nm)/LiF (1 nm)/Al (80 nm)
Dopant: PQIr(acac)
Host: each of Compounds 10 and 11
ITO/HI (10 nm)/HT-1 (30 nm)/HT-2 (15 nm)/host:PQIr(acac) (40 nm, 95%:5% by mass)/ET (30 nm)/LiF (1 nm)/Al (80 nm)
Dopant: Ir(bzq)$_3$
Host: each of Compounds 14 to 16
ITO/HI (10 nm)/HT-1 (40 nm)/HT-2 (15 nm)/host:co-host: Ir(bzq)$_3$ (40 nm, 45%:45%:10% by mass)/ET (30 nm)/LiF (1 nm)/Al (80 nm)

Comparative Example 1

An organic EL device was produced in the same manner as in Example 23 except for forming the light emitting layer by using comparative compound 1 as a host material in place of compound 8. The obtained organic EL device was measured for the external quantum efficiency and the lifetime (LT80) until the luminance was reduced to 80%. The results are shown in Table 1.

Comparative Example 2

An organic EL device was produced in the same manner as in Comparative Example 1 except for forming the light emitting layer by using Ir(ppy)$_3$ as a dopant material in place of Ir(piq)$_3$. The obtained organic EL device was measured for the external quantum efficiency and the lifetime (LT80) until the luminance was reduced to 80%. The results are shown in Table 1.

TABLE 1

|    | Host | Co-host | Dopant | Voltage (V) @10 mA/cm$^2$ | External quantum efficiency (%) @10 mA/cm$^2$ | LT80 (hrs) @ 50 mA/cm$^2$ |
|---|---|---|---|---|---|---|
| Examples ||||||| 
| 17 | compound 2 | PG2-1 | Ir(ppy)$_3$ | 3.3 | 18.1 | 103 |
| 18 | compound 3 | PG2-1 | Ir(ppy)$_3$ | 3.2 | 17.8 | 95 |
| 19 | compound 4 | PG2-2 | Ir(ppy)$_3$ | 3.5 | 19.0 | 117 |
| 20 | compound 5 | PG2-3 | Ir(ppy)$_3$ | 3.4 | 18.8 | 108 |
| 21 | compound 6 | PG2-1 | Ir(ppy)$_3$ | 3.1 | 17.8 | 90 |
| 22 | compound 7 | — | Ir(piq)$_3$ | 3.8 | 13.6 | 411 |
| 23 | compound 8 | — | Ir(piq)$_3$ | 3.5 | 14.3 | 398 |
| 24 | compound 9 | PG2-4 | Ir(ppy)$_3$ | 3.5 | 17.9 | 115 |
| 25 | compound 10 | — | PQIr(acac) | 3.5 | 14.5 | 338 |
| 26 | compound 11 | — | PQIr(acac) | 3.2 | 15.2 | 329 |
| 27 | compound 12 | PG2-3 | Ir(ppy)$_3$ | 3.5 | 19.1 | 110 |
| 28 | compound 13 | PG2-3 | Ir(ppy)$_3$ | 3.7 | 19.7 | 124 |
| 29 | compound 14 | PG2-3 | Ir(bzq)$_3$ | 3.3 | 20.1 | 387 |
| 30 | compound 15 | PG2-3 | Ir(bzq)$_3$ | 3.4 | 20.7 | 409 |
| 31 | compound 16 | PG2-3 | Ir(bzq)$_3$ | 3.3 | 21.5 | 376 |
| Comparative Examples ||||||| 
| 1 | comparative compound 1 | — | Ir(piq)$_3$ | 3.8 | 10.5 | 253 |
| 2 | comparative compound 2 | — | Ir(ppy)$_3$ | 4.1 | 13.1 | 34 |

Upon comparing Examples 17 to 31 with Comparative Examples 1 and 2, it can be seen that the organic EL device including the heterocyclic compound of the invention has a high external quantum efficiency as compared with the device including the fused heterocyclic compound of Comparative Example 1 or 2.

Upon comparing Examples 22 and 23 with Comparative Example 1, each including Ir(piq)$_3$ as a dopant, it can be seen that each organic EL device of Examples 22 and 23 including the heterocyclic compound of the invention exhibits a longer emission lifetime.

In addition, upon comparing Examples 17 to 21, 24, 27, and 28 with Comparative Example 2, each including Ir(ppy)$_3$ as a dopant, it can be seen that each organic EL device of Examples 17 to 21, 24, 27, and 28 including the heterocyclic compound of the invention exhibits a longer emission lifetime.

REFERENCE NUMERALS

1: Organic electroluminescence device
2: Substrate
3: Anode
4: Cathode
5: Light emitting layer
6: Anode-side organic thin film layer
7: Cathode-side organic thin film layer
10: Organic thin film layer

What is claimed is:

1. A heterocyclic compound represented by formula (1):

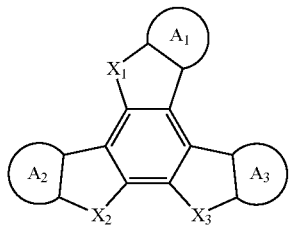

(1)

wherein:
each of $A_1$ to $A_3$ independently represents a saturated or unsaturated ring and each of $A_1$ to $A_3$ may independently have a substituent;
each of $X_1$ to $X_3$ independently represents a linking group represented by any of formulae (2) to (5), provided that one or two of $X_1$ to $X_3$ are represented by formula (2) and the rest is represented by any of formulae (3) to (5):

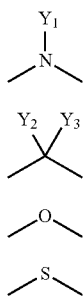

(2)

(3)

(4)

(5)

wherein each of $Y_1$ to $Y_3$ independently represents a hydrogen atom or a substituent; $Y_2$ and $Y_3$ may be bonded to each other to form a ring structure; each of $Y_1$ to $Y_3$ may be bonded to the substituent of each of $A_1$ to $A_3$ to form a ring structure; and when $X_2$ is represented by formula (2) or (3) and $X_3$ is represented by (2) or (3), $Y_1$ to $Y_3$ in $X_2$ and $X_3$ may be bonded to each other to form a ring structure.

2. The heterocyclic compound according to claim 1, wherein each of $A_1$ to $A_3$ independently represents a substituted or unsubstituted 5-, 6- or 7-membered ring.

3. The heterocyclic compound according to claim 1, wherein the heterocyclic compound is represented by formula (6):

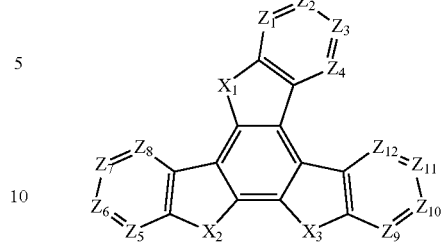

(6)

wherein:
$X_1$ to $X_3$ are as defined above;
each of $Z_1$ to $Z_{12}$ independently represents C(R) or a nitrogen atom;
each R independently represents a hydrogen atom or a substituent; and
when two or more of $Z_1$ to $Z_{12}$ have substituents, the substituents may be bonded to each other to form a ring structure.

4. The heterocyclic compound according to claim 1, wherein the substituent referred to in formulae (1) to (3) is independently selected from a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 ring carbon atoms; a disubstituted phosphoryl group having a substituent selected from a substituted or unsubstituted alkyl group having 1 to 50 carbon atoms and a substituted or unsubstituted aryl group having 6 to 50 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl- or aryl-substituted carbonyl group; a carboxyl group; a vinyl group; a (meth)acryloyl group; an epoxy group; and an oxetanyl group.

5. The heterocyclic compound according to claim 4, wherein R of formula (6) is independently selected from a hydrogen atom; a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 ring carbon atoms; a disubstituted phosphoryl group having a substituent selected from a substituted or unsubstituted alkyl group having 1 to 50 carbon atoms and a substituted or unsubstituted aryl group having 6 to 50 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl- or aryl-substituted carbonyl group; a carboxyl group; a vinyl group; a (meth)acryloyl group; an epoxy group; and an oxetanyl group.

6. The heterocyclic compound according to claim 5, wherein R of formula (6) is independently selected from a hydrogen atom; a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; a nitro group; a sulfonyl group having a substituent selected from a substituted or unsubstituted alkyl group having 1 to 50 carbon atoms and a substituted or unsubstituted aryl group having 6 to 50 ring carbon atoms; and a disubstituted phosphoryl group having a substituent selected from a substituted or unsubstituted alkyl group having 1 to 50 carbon atoms and a substituted or unsubstituted aryl group having 6 to 50 ring carbon atoms.

7. The heterocyclic compound according to claim 6, wherein R of formula (6) is independently selected from a hydrogen atom; a substituted or unsubstituted alkyl group having 1 to 50 carbon atoms; a substituted or unsubstituted cycloalkyl group having 3 to 50 ring carbon atoms; a substituted or unsubstituted aryl group having 6 to 50 ring carbon atoms; a substituted or unsubstituted aralkyl group having 7 to 51 carbon atoms; an amino group; a mono- or disubstituted amino group having a substituent selected from a substituted or unsubstituted alkyl group having 1 to 50 carbon atoms and a substituted or unsubstituted aryl group having 6 to 50 ring carbon atoms; a substituted or unsubstituted alkoxy group having 1 to 50 carbon atoms; a substituted or unsubstituted aryloxy group having 6 to 50 ring carbon atoms; a mono-, di-, or trisubstituted silyl group having a substituent selected from a substituted or unsubstituted alkyl group having 1 to 50 carbon atoms and a substituted or unsubstituted aryl group having 6 to 50 ring carbon atoms; a substituted or unsubstituted heteroaryl group having 5 to 50 ring atoms; a substituted or unsubstituted haloalkyl group having 1 to 50 carbon atoms; a halogen atom; a cyano group; and a nitro group.

8. The heterocyclic compound according to claim 1, wherein each of $Y_2$ and $Y_3$ of formula (3) is independently selected from a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heteroaryl group having 5 to 50 ring atoms.

9. The heterocyclic compound according to claim 1, wherein $Y_1$ of formula (2) is selected from a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, and a substituted or unsubstituted heteroaryl group having 5 to 50 ring atoms.

10. The heterocyclic compound according to claim 1, wherein one of $X_1$ to $X_3$ is represented by formula (2), and the other two are represented by any of formulae (3) to (5).

11. The heterocyclic compound according to claim 1, wherein two of $X_1$ to $X_3$ are represented by formula (2), and the other one is represented by any of formulae (3) to (5).

12. The heterocyclic compound according to claim 1, wherein at least one of $X_1$ to $X_3$ is represented by formula (4).

13. The heterocyclic compound according to claim 1, wherein at least one of $X_1$ to $X_3$ is represented by formula (5).

14. A material for organic electroluminescence devices which comprises the heterocyclic compound according to claim 1.

15. An organic electroluminescence device which comprises an organic thin film layer between a cathode and an anode, wherein the organic thin film layer comprises one or more layers and comprises a light emitting layer, and at least one layer of the organic thin film layer comprises the heterocyclic compound according to claim 1.

16. The organic electroluminescence device according to claim 15, wherein the light emitting layer comprises the heterocyclic compound.

17. The organic electroluminescence device according to claim 15, wherein the organic electroluminescence device further comprises an anode-side organic thin film layer between the anode and the light emitting layer, and the anode-side organic thin film layer comprises the heterocyclic compound.

18. The organic electroluminescence device according to claim 15, wherein the organic electroluminescence device further comprises a cathode-side organic thin film layer between the cathode and the light emitting layer, and the cathode-side organic thin film layer comprises the heterocyclic compound.

19. The organic electroluminescence device according to claim 15, wherein the light emitting layer comprises a phosphorescent material.

20. The organic electroluminescence device according to claim 15, wherein the light emitting layer comprises a fluorescent material.

21. The organic electroluminescence device according to claim 19, wherein the phosphorescent material is an ortho-metallated complex comprising a metal atom selected from iridium (Ir), osmium (Os) and platinum (Pt).

22. An electronic equipment comprising the organic electroluminescence device according to claim 15.

* * * * *